US009034798B2

(12) United States Patent
Köster et al.

(10) Patent No.: US 9,034,798 B2
(45) Date of Patent: *May 19, 2015

(54) CAPTURE COMPOUNDS, COLLECTIONS THEREOF AND METHODS FOR ANALYZING THE PROTEOME AND COMPLEX COMPOSITIONS

(75) Inventors: Hubert Köster, Figino (CH); Daniel Paul Little, Winchester, MA (US); Suhaib Mahmood Siddiqi, San Diego, CA (US); Matthew Peter Grealish, Citrus Heights, CA (US); Subramanian Marappan, San Diego, CA (US); Chester Frederick Hassman, III, Oceanside, CA (US); Ping Yip, San Diego, CA (US)

(73) Assignee: CAPROTEC BIOANALYTICS GMBH, Berlin (DE)

( * ) Notice: Subject to any disclaimer, the term of this patent is extended or adjusted under 35 U.S.C. 154(b) by 121 days.

This patent is subject to a terminal disclaimer.

(21) Appl. No.: 12/660,511

(22) Filed: Feb. 26, 2010

(65) Prior Publication Data

US 2010/0248264 A1    Sep. 30, 2010

Related U.S. Application Data

(63) Continuation of application No. 10/760,085, filed on Jan. 16, 2004, now abandoned.

(60) Provisional application No. 60/441,398, filed on Jan. 16, 2003.

(51) Int. Cl.

| G01N 33/68 | (2006.01) |
| C07D 495/04 | (2006.01) |
| C07C 69/76 | (2006.01) |
| C07C 69/96 | (2006.01) |
| C07D 207/404 | (2006.01) |
| C07D 207/46 | (2006.01) |
| C07D 209/48 | (2006.01) |
| C07D 211/60 | (2006.01) |
| C07D 211/78 | (2006.01) |
| C07D 213/79 | (2006.01) |
| C07D 215/48 | (2006.01) |
| C07D 239/54 | (2006.01) |
| C07D 239/545 | (2006.01) |
| C07D 241/44 | (2006.01) |
| C07D 261/12 | (2006.01) |
| C07D 271/07 | (2006.01) |
| C07D 303/14 | (2006.01) |
| C07D 303/16 | (2006.01) |
| C07D 317/36 | (2006.01) |
| C07D 401/12 | (2006.01) |
| C07D 405/10 | (2006.01) |
| C07D 405/12 | (2006.01) |
| C07D 417/12 | (2006.01) |
| C07D 417/14 | (2006.01) |
| C07D 519/00 | (2006.01) |

(52) U.S. Cl.
CPC .............. *C07D 495/04* (2013.01); *C07C 69/76* (2013.01); *C07C 69/96* (2013.01); *C07C 2103/74* (2013.01); *C07D 207/404* (2013.01); *C07D 207/46* (2013.01); *C07D 209/48* (2013.01); *C07D 211/60* (2013.01); *C07D 211/78* (2013.01); *C07D 213/79* (2013.01); *C07D 215/48* (2013.01); *C07D 239/54* (2013.01); *C07D 239/545* (2013.01); *C07D 241/44* (2013.01); *C07D 261/12* (2013.01); *C07D 271/07* (2013.01); *C07D 303/14* (2013.01); *C07D 303/16* (2013.01); *C07D 317/36* (2013.01); *C07D 401/12* (2013.01); *C07D 405/10* (2013.01); *C07D 405/12* (2013.01); *C07D 417/12* (2013.01); *C07D 417/14* (2013.01); *C07D 519/00* (2013.01); *G01N 33/6803* (2013.01); *G01N 33/6842* (2013.01); *G01N 33/6845* (2013.01); *G01N 33/6848* (2013.01)

(58) Field of Classification Search
None
See application file for complete search history.

(56) References Cited

U.S. PATENT DOCUMENTS

| 4,415,732 A | 11/1983 | Caruthers et al. ................ 536/27 |
| 4,725,677 A | 2/1988 | Koster et al. ..................... 536/27 |
| 5,143,854 A | 9/1992 | Pirrung et al. ................. 436/518 |
| 5,198,540 A | 3/1993 | Koster ......................... 536/25.3 |
| 5,252,707 A * | 10/1993 | Ozaki et al. ................... 530/345 |
| RE34,609 E | 5/1994 | Mueller ........................ 318/254 |
| 5,410,068 A | 4/1995 | Coull et al. .................... 548/545 |

(Continued)

FOREIGN PATENT DOCUMENTS

| EP | 0 124 561 | 11/1984 |
| EP | 0 124 562 | 11/1984 |

(Continued)

OTHER PUBLICATIONS

Alley et al (2000 JACS 122:6126-6127).*
Alley et al (1999 JBC 274:24485-89).*
Morgan et al (1955 Plant Disease Report 39:487-490).*
Geselowitz et al (1995 Bioconjugate Chem 6:502-506).*
"PAMAM Dendrimers," retrieved from the Internet:<URL: dendritech.com/pamam.htm. (Accessed on Apr. 25, 2003).
Aaserud et al., "Distinguishing N- and C-terminus ions for mass spectrometry sequencing of proteins without prior degradation," Rapid Comm. Mass Spec. 9(10):871-876 (1995).
Adams et al., "A new caged CA$^{2+}$, azid-1, is far more photosensitive than nitrobenzyl-based chelators," Chem. Biol. 4:867-878 (1997).
Aebersold et al., "Mass spectrometry-based proteomics," Nature 422:198-206 (2003).
Aebersold et al., "Proteomics—advances, applications and the challenges that remain," Trends Biotechnol. 20(12): S1-S2 (2002).

(Continued)

*Primary Examiner* — Christopher M Gross
(74) *Attorney, Agent, or Firm* — JMB Davis Ben-David

(57) ABSTRACT

Capture compounds and collections thereof and methods using the compounds for the analysis of biomolecules are provided. In particular, collections, compounds and methods are provided for analyzing complex protein mixtures, such as the proteome. The compounds are multifunctional reagents that provide for the separation and isolation of complex protein mixtures. Automated systems for performing the methods also are provided.

20 Claims, 132 Drawing Sheets

(56) References Cited

U.S. PATENT DOCUMENTS

| | | | |
|---|---|---|---|
| 5,432,018 A | 7/1995 | Dower et al. | 435/5 |
| 5,512,473 A | 4/1996 | Brent et al. | 435/240.2 |
| 5,532,379 A | 7/1996 | Fujimoto | 548/304.1 |
| 5,547,835 A | 8/1996 | Koster | 435/6 |
| 5,547,839 A | 8/1996 | Dower et al. | 435/6 |
| 5,580,721 A | 12/1996 | Brent et al. | 435/6 |
| 5,580,736 A | 12/1996 | Brent et al. | 435/6 |
| 5,605,798 A | 2/1997 | Koster | 435/6 |
| 5,622,824 A | 4/1997 | Koster | 435/6 |
| 5,641,959 A | 6/1997 | Holle et al. | 250/287 |
| 5,654,545 A | 8/1997 | Holle et al. | 250/287 |
| 5,691,141 A | 11/1997 | Koster | 435/6 |
| 5,695,941 A | 12/1997 | Brent et al. | 435/6 |
| 5,741,462 A | 4/1998 | Nova et al. | 422/68.1 |
| 5,742,049 A | 4/1998 | Holle et al. | 250/282 |
| 5,751,629 A | 5/1998 | Nova et al. | 365/151 |
| 5,760,393 A | 6/1998 | Vestal et al. | 250/282 |
| 5,770,625 A | 6/1998 | Nakanishi et al. | 514/616 |
| 5,777,325 A | 7/1998 | Weinberger et al. | 250/287 |
| 5,807,525 A | 9/1998 | Allen et al. | 422/131 |
| 5,812,272 A | 9/1998 | King et al. | 356/445 |
| 5,851,765 A | 12/1998 | Koster | 435/6 |
| 5,872,003 A | 2/1999 | Koster | 435/283.1 |
| 5,874,214 A | 2/1999 | Nova et al. | 435/6 |
| 5,900,481 A | 5/1999 | Lough et al. | 536/55.3 |
| 5,922,617 A | 7/1999 | Wang et al. | 436/518 |
| 5,925,562 A | 7/1999 | Nova et al. | 435/287.1 |
| 5,928,906 A | 7/1999 | Koster et al. | 435/91.2 |
| 5,955,280 A | 9/1999 | Vidal et al. | 435/6 |
| 5,961,923 A | 10/1999 | Nova et al. | 422/68.1 |
| 5,972,639 A | 10/1999 | Parandoosh | 435/29 |
| 6,017,496 A | 1/2000 | Nova et al. | 422/68.1 |
| 6,022,688 A | 2/2000 | Jurinke et al. | 435/6 |
| 6,024,925 A | 2/2000 | Little et al. | 422/100 |
| 6,025,129 A | 2/2000 | Nova et al. | 435/6 |
| 6,043,031 A | 3/2000 | Koster et al. | 435/6 |
| 6,074,823 A | 6/2000 | Koster | 435/6 |
| 6,110,687 A | 8/2000 | Nilsen et al. | 435/5 |
| 6,117,631 A | 9/2000 | Nilsen et al. | 435/6 |
| 6,133,436 A | 10/2000 | Koster et al. | 536/24.3 |
| 6,140,053 A | 10/2000 | Koster | 435/6 |
| 6,146,854 A | 11/2000 | Koster et al. | 435/91.1 |
| 6,168,914 B1 | 1/2001 | Campbell et al. | 435/4 |
| 6,191,280 B1 * | 2/2001 | Hamprecht et al. | 546/294 |
| 6,194,144 B1 | 2/2001 | Koster | 435/6 |
| 6,197,498 B1 | 3/2001 | Koster | 435/5 |
| 6,207,370 B1 | 3/2001 | Little et al. | 435/6 |
| 6,221,601 B1 | 4/2001 | Koster | 435/6 |
| 6,221,605 B1 | 4/2001 | Koster | 435/6 |
| 6,225,061 B1 | 5/2001 | Becker et al. | 435/6 |
| 6,225,450 B1 | 5/2001 | Koster | 536/22.1 |
| 6,235,478 B1 | 5/2001 | Koster | 435/6 |
| 6,238,871 B1 | 5/2001 | Koster | 435/6 |
| 6,258,538 B1 | 7/2001 | Koster et al. | 435/6 |
| 6,268,131 B1 | 7/2001 | Kang et al. | 435/6 |
| 6,268,144 B1 | 7/2001 | Koster | 435/6 |
| 6,274,337 B1 | 8/2001 | Parce et al. | 435/29 |
| 6,277,573 B1 | 8/2001 | Koster | 435/6 |
| 6,300,076 B1 | 10/2001 | Koster | 435/6 |
| 6,303,309 B1 | 10/2001 | Jurinke et al. | 435/6 |
| 6,322,970 B1 | 11/2001 | Little et al. | 435/6 |
| 6,329,209 B1 | 12/2001 | Wagner et al. | 436/518 |
| 6,387,628 B1 | 5/2002 | Little et al. | 435/6 |
| 6,391,649 B1 | 5/2002 | Chait et al. | 436/173 |
| 6,428,955 B1 | 8/2002 | Koster et al. | 435/6 |
| 6,436,635 B1 | 8/2002 | Fu et al. | 435/6 |
| 6,455,071 B1 | 9/2002 | Shchepinov et al. | 424/486 |
| 6,485,913 B1 | 11/2002 | Becker et al. | 435/6 |
| 6,500,621 B2 | 12/2002 | Koster | 435/6 |
| 6,629,040 B1 | 9/2003 | Goodlett et al. | 702/23 |
| 6,654,545 B2 | 11/2003 | Nishi et al. | 250/287 |
| 6,670,194 B1 | 12/2003 | Aebersold et al. | 436/173 |
| 6,680,178 B2 | 1/2004 | Harris et al. | 435/23 |
| 6,818,394 B1 | 11/2004 | O'Donnell-Maloney et al. | 435/6 |
| 6,872,574 B2 | 3/2005 | Cravatt et al. | 436/119 |
| 7,179,655 B2 | 2/2007 | Patricelli | 436/173 |
| 7,858,560 B2 * | 12/2010 | Koster et al. | 506/13 |
| 2001/0008615 A1 | 7/2001 | Little et al. | 422/102 |
| 2002/0040275 A1 | 4/2002 | Cravatt et al. | 702/19 |
| 2002/0042112 A1 | 4/2002 | Koster | 435/174 |
| 2002/0045194 A1 | 4/2002 | Cravatt et al. | 435/7.9 |
| 2002/0045269 A1 | 4/2002 | Shcepinov | 436/173 |
| 2002/0064799 A1 | 5/2002 | Cravatt et al. | 435/7.1 |
| 2002/0076739 A1 | 6/2002 | Aebersold et al. | 435/7.92 |
| 2002/0146684 A1 | 10/2002 | Meldal et al. | 435/5 |
| 2002/0168644 A1 | 11/2002 | Aebersold et al. | 435/6 |
| 2002/0182652 A1 | 12/2002 | Cravatt et al. | 435/7.9 |
| 2002/0192720 A1 | 12/2002 | Parker et al. | 435/7.9 |
| 2003/0119021 A1 | 6/2003 | Koster et al. | 435/6 |
| 2003/0166007 A1 * | 9/2003 | Climie et al. | 435/7.1 |
| 2004/0023306 A1 | 2/2004 | Aebersold et al. | 435/7.1 |
| 2004/0033625 A1 | 2/2004 | Aebersold et al. | 436/518 |
| 2004/0038319 A1 | 2/2004 | Aebersold et al. | 435/7.5 |
| 2004/0062911 A1 | 4/2004 | Lauf et al. | 428/138 |
| 2004/0209255 A1 | 10/2004 | Koster et al. | 435/6 |
| 2005/0042771 A1 | 2/2005 | Koster et al. | 436/518 |
| 2006/0079476 A1 | 4/2006 | Keasling et al. | 514/44 |

FOREIGN PATENT DOCUMENTS

| | | |
|---|---|---|
| EP | 0 149 634 | 7/1985 |
| EP | 0 285 675 | 10/1988 |
| EP | 0 305 929 | 3/1989 |
| EP | 0 353 460 | 2/1990 |
| EP | 0 424 819 | 5/1991 |
| EP | 0 689 610 | 1/1996 |
| EP | 0 698 792 | 2/1996 |
| EP | 0 901 531 | 3/1999 |
| EP | 0 914 471 | 5/1999 |
| EP | 0 937 097 | 8/1999 |
| EP | 1 138 781 | 10/2001 |
| EP | 1 164 203 | 12/2001 |
| EP | 1 262 564 | 12/2002 |
| EP | 1 296 143 | 6/2009 |
| JP | 64-55181 | 3/1989 |
| JP | 6-222058 | 8/1994 |
| JP | A-11-44647 | 2/1999 |
| JP | 2001-321199 | 11/2001 |
| JP | 2004-531207 | 10/2004 |
| WO | WO 85/00621 | 2/1985 |
| WO | WO 85/00816 | 2/1985 |
| WO | WO 89/03041 | 4/1989 |
| WO | WO 94/16101 | 7/1994 |
| WO | WO 94/21822 | 9/1994 |
| WO | WO 96/29431 | 9/1996 |
| WO | WO 96/32504 | 10/1996 |
| WO | WO 97/07126 | 2/1997 |
| WO | WO 97/08306 | 3/1997 |
| WO | WO 97/42348 | 5/1997 |
| WO | WO 97/33169 | 9/1997 |
| WO | WO 97/37041 | 10/1997 |
| WO | WO 97/37953 | 10/1997 |
| WO | WO 97/40385 | 10/1997 |
| WO | WO 97/42507 | 11/1997 |
| WO | WO 97/43617 | 11/1997 |
| WO | WO 98/06874 | 2/1998 |
| WO | WO 98/20019 | 5/1998 |
| WO | WO 98/20020 | 5/1998 |
| WO | WO 98/20166 | 5/1998 |
| WO | WO 98/33808 | 8/1998 |
| WO | WO 98/59360 | 12/1998 |
| WO | WO 99/32618 | 12/1998 |
| WO | WO 99/02733 | 1/1999 |
| WO | WO 99/05320 | 2/1999 |
| WO | WO 99/12040 | 3/1999 |
| WO | WO 99/31278 | 6/1999 |
| WO | WO 99/51773 | 10/1999 |
| WO | WO 99/55718 | 11/1999 |
| WO | WO 99/57318 | 11/1999 |
| WO | WO 99/60007 | 11/1999 |
| WO | WO 00/11208 | 3/2000 |
| WO | WO 00/56446 | 9/2000 |
| WO | WO 00/60361 | 10/2000 |

(56) References Cited

FOREIGN PATENT DOCUMENTS

| WO | WO 01/18234 | 3/2001 |
|---|---|---|
| WO | WO 01/18627 | 3/2001 |
| WO | WO 01/27857 | 4/2001 |
| WO | WO 01/96607 | 6/2001 |
| WO | WO 01/77668 | 10/2001 |
| WO | WO 01/77684 | 10/2001 |
| WO | WO 02/34922 | 5/2002 |
| WO | WO 02/48403 | 6/2002 |
| WO | WO 02/058533 | 8/2002 |
| WO | WO 02/063271 | 8/2002 |
| WO | WO 02/063301 | 8/2002 |
| WO | WO 02/071066 | 9/2002 |
| WO | WO 02/081752 | 10/2002 |
| WO | WO 03/005026 | 1/2003 |
| WO | WO 03/050544 | 6/2003 |
| WO | WO 03/064704 | 8/2003 |
| WO | WO 03/077851 | 9/2003 |
| WO | WO 03/092581 | 11/2003 |
| WO | WO 2004/008151 * | 1/2004 |
| WO | WO 2004/064972 | 8/2004 |
| WO | WO 2006/138571 | 12/2006 |

OTHER PUBLICATIONS

Alley et al., "Mapping protein-protein interactions in the bacteriophage T4 DNA polymerase holoenzyme using a novel trifunctional photo-cross-linking and affinity reagent," J. Am. Chem. Soc. 122:6126-6127 (2000).

Altschul et al., "Basic local alignment search tool," J. Mol. Biol. 215:403-410 (1990).

Beck, S. and H. Koster, "Perspective: Analytical biotechnology. Applications of dioxetane chemiluminescent probes to molecular biology," Anal. Chem. 62:2258-2270 (1990); Erratum: Anal. Chem. 63(8):848 (1991).

Behrens et al., "Synthesis of achiral linker reagents for direct labeling of oligonucleotides on solid supports," Nucleos. Nucleot. 18(2):291-305 (1999).

Bogyo et al., "Covalent modification of the active site threonine of proteasomal beta subunits and the *Escherichia coli* homolog HsIV by a new class of inhibitors," Proc. Natl. Acad. Sci. U.S.A. 94(13):6629-6634 (1997).

Bogyo et al., "Substrate binding and sequence preference of the proteasome revealed by active-site-directed affinity probes," Chem. Biol. 5(6):307-320 (1998).

Boring et al., "Trifunctional agents as a design strategy for tailoring ligand properties: irreversible inhibitors of A1 adenosine receptors," Bioconj. Chem. 2(2):77-88 (1991).

Braun et al., "Detecting CFTR gene mutations by using primer oligo base extension and mass spectrometry," Clin. Chem. 43(7):1151-1158 (1997).

Braun et al., "Improved analysis of microsatellites using mass spectrometry," Genomics 46:18-23 (1997).

Budavari et al., "The Merck Index, 11th edition," Merck & Co., Rahway, NJ (1989).

Buetow et al., "High-throughput development and characterization of a genomewide collection of gene-based single nucleotide polymorphism markers by chip-based matrix-assisted laser desorption/ionization time-of-flight mass spectrometry," Proc. Natl. Acad. Sci.U.S.A 98(2):581-584 (2001).

Cantor et al., "Massive attack on high-throughput biology," Nat. Gen. 20:5-6 (1998).

Carrillo et al., "The multiple sequence alignment problem in biology," SIAM J. Appl. Math. 48(5):1073-1082 (1988).

Chao et al., "Interaction of *Escherichia coli* heat-stable enterotoxin B with cultured human intestinal epithelial cells," Infect. Immun. 65(8):3209-3217 (1997).

Chiu et al., "Mass spectrometry of single-stranded restriction fragments captured by an undigested complementary sequence," Nucl. Acids Res. 28(8):e31(4 pages) (2000).

Coull et al., "Functionalized membrane supports for covalent protein microsequence analysis," Anal. Biochem. 194:110-120 (1991).

Crozet et al., "Synthesis and characterization of cyclic pseudopeptide libraries containing thiomethylene and thiomethylene-sulfoxide amide bond surrogates," Mol Divers. 3(4):261-276 (1998).

Damoiseaux et al., "Synthesis and applications of chemical probes for human O6-alkylguanine-DNA alkyltransferase," Chembiochem. 2(4):285-287 (2001).

Derwent English Abstract for European Patent Application EP 0 124 561, entitled, "Solid phase oligonucleoside phosphonate prodn.—using nucleoside monohalo phosphinite as reactant," Derwent Accession Number: 003969477.

Derwent English Abstract for European Patent Application EP 0 149 634 and PCT Patent Application WO 85/00621, entitled, "New oligonucleotide linker sequences—for cohesive end ligation of DNA fragments," Derwent Accession Number: 004205815.

Derwent English Abstract for European Patent Application EP 0 285 675 and Japanese Patent Application JP 1055181, entitled, "New synthetic DNA cassettes—used to code nutritionally useful artificial proteins," Derwent Accession Number: 007653017.

Devereux et al., "A comprehensive set of sequence analysis programs for the VAX," Nucl. Acids Res. 12(1):387-95 (1984).

Dormán et al., "Chemical library approaches to target validation in the post-genomic era," Curr. Drug Discov. Oct. 21-24 (2001).

Dormán et al., "Using photolabile ligands in drug discovery and development," Trends Biotechnol. 18:64-77 (2000).

Fang et al., "A bifunctional photoaffinity probe for ligand/receptor interaction studies," J. Am. Chem. Soc. 120: 8543-8544 (1998).

Flory et al., "Advances in quantitative proteomics using stable isotope tags," Trends Biotechnol. 20(12): S23-S29 (2002).

Geysen et al., "Isotope or mass encoding of combinatorial libraries," Chem. Biol. 3:679-688 (1996).

Gildea et al., "A versatile acid-labile linker for modification of synthetic biomolecules," Tetrahedron Lett. 31:7095-7098 (1990).

Glasner et al., "Metal ion requirements for structure and catalysis of an RNA ligase ribozyme," Biochemistry 41:8103-8112 (2002).

Gribskov et al., "Sigma factors from *E. coli*, *B. subtilis*, phage SP01, and phage T4 are homologous proteins," Nucl. Acids Res. 14(16):6745-63 (1986).

Griffin et al., "Advances in proteome analysis by mass spectrometry," J. Biol. Chem. 276(49): 45497-45500 (2001).

Griffin et al., "Toward a high-throughput approach to quantitative proteomic analysis: expression-dependent protein identification by mass spectrometry," J. Am. Soc. Mass. Spectrom. 12: 1238-1246 (2001).

Gygi et al., "Quantitative analysis of complex protein mixture using isotope-coded affinity tags," Nature Biotech. 17:994-999 (1999).

Gygi et al., "Proteome analysis of low-abundance proteins using multidimensional chromatography and isotope-coded affinity tags," J. Proteome Res. 1:47-54 (2002).

Hagenstein et al., "Affinity-based tagging of protein families with reversible inhibitors: a concept for functional proteomics," Angew. Chem. Int. Ed. 42: 5635-5638 (2003).

Hasegawa et al., "Determination of the binding site on the extracellular domain of guanyl cyclase C to heat-stable enterotoxin," J. Biol. Chem. 274(44):31713-31719 (1999).

Hasegawa et al., "Expression and characterization of the extracellular domain of guanylyl cyclase C from a baculovirus and Sf21 insect cells," Protein Express. Purif. 15:271-281 (1999).

Hashimoto et al., "Cell-surface recognition of biotinylated membrane proteins requires very long spacer arms: an example from glucose-transporter probes," Chembiochem. 2:52-59 (2001).

Hashimoto et al., "Synthesis of biotinylated bis(D-glucose) derivatives for glucose transporter photoaffinity labelling," Carbohydrate Res. 331:119-127 (2001).

Hatanaka et al., "A carbene-generating biotinylated lactosylceramide analog as novel photoreactive substrate for GM3 synthase," Bioorg. Med. Chem. Lett. 5(23):2859-2862 (1995).

Hatanaka et al., "A novel biotinylated heterobifunctional cross-linking reagent bearing an aromatic diazirine," Bioorg. Med. Chem. 2(12):1367-1373 (1994).

Hatanaka et al., "A novel family of aromatic diazirines for photoaffinity labeling," J. Org. Chem. 59:383-387 (1994).

(56) References Cited

OTHER PUBLICATIONS

Hatanaka et al., "A rapid and efficient method for identifying photoaffinity biotinylated sites within proteins," J. Am. Chem. Soc. 120: 453-454 (1998).
Hatanaka et al., "Photoaffinity labeling in drug discovery and developments: chemical gateway for entering proteomic frontier," Curr. Top. Med. Chem. 2: 271-288 (2002).
Herman, B., "Chapter 8. Resonance Energy Transfer Microscopy," Meth. Cell Biol. 30:219-243 (1989).
Hesselberth et al., "In vitro selection of nucleic acids for diagnostic applications," Reviews in Molecular Biotechnology 74:15-25 (2000).
Hessler et al., "Molecular Engineering in Nanotechnology IV: Atomic Force Microscopy Characterization of Dendrimer Drug Delivery Agents," Ninth Foresight Conference on Molecular Nanotechnology (Abstract) (http://www.foresight.org/Conferences/MNT9/Abstracts/Hessler/index.html (accessed on Dec. 6, 2002).
Higgins et al., "Competitive oligonucleotide single-base extension combined with mass spectrometric detection for mutation screening," Biotechniques 23(4):710-714 (1997).
Homey et al., "Synthesis and characterization of Insulin-like Growth Factor (IGF)-1 photoprobes selective for the IGF-binding proteins (IGFBPs)," J. Biol. Chem. 276(4):2880-2889 (2001).
Ilver et al., "*Heliobacter pylori* adhesin binding fucosylated histo-blood group antigens revealed by retagging," Science 279:373-377 (1998).
IUPAC-IUB Commission on Biochemical Nomenclature, "A one-letter notation for amino acid sequences: tentative rules," J. Biol. Chem. 243(13):3557-3559 (1968).
IUPAC-IUB Commission on Biochemical Nomenclature, "Abbreviated nomenclature of synthetic polypeptides (polymerized amino acids): revised recommendations (1971)," Biochem. 11(5):942-944 (1972).
Jaschke et al., "Synthesis and properties of oligodeoxyribonucleotide-polyethelene glycol conjugates," Nucleic Acids Res. 22(22):4810-4817 (1994).
Jeffery et al., "Chemical proteomics and its application to drug discovery," Curr. Opin. Biotechnol. 14: 87-95 (2003).
Juhasz et al., "Applications of delayed extraction matrix-assisted laser desorption ionization time-of-flight mass spectrometry to oligonucleotide analysis," Anal. Chem. 68:941-946 (1996).
Jurinke et al., "Analysis of ligase chain reaction products via matrix-assisted laser desorption/ionization time-of-flight-mass spectrometry," Anal. Biochem. 237(2):174-181 (1996).
Jurinke et al., "Automated genotyping using the DNA MassArray™ technology," Methods Mol. Biol. 187:179-192 (2002).
Jurinke et al., "Recovery of nucleic acids from immobilized biotin-streptavidin complexes using ammonium hydroxide and applications in MALDI-TOF mass spectrometry," Anal. Chem. 69(5):904-910 (1997).
Jurinke et al., "The use of MassARRAY technology for high throughput genotyping," Adv. Biochem. Eng. Biotechnol. 77:57-74 (2002).
Kahne et al., "Hydrolysis of a peptide bond in neutral water," J. Am. Chem. Soc. 110:7529-7534 (1998).
Kam et al., "Biotinylated isocoumarins, new inhibitors and reagents for detection, localization and isolation of serine proteases," Bioconjugate Chem. 4(6):560-567 (1993).
Konoki et al., "Development of biotin-avidin technology to investigate okadaic acid-promoted cell signaling pathway," Tetrahedron 56:9003-9014 (2000).
Köster et al., "A strategy for rapid and efficient DNA sequencing by mass spectrometry," Nature Biotechnol. 14(9):1123-1128 (19961.
Köster et al., "Oligonucleotide synthesis and multiplex DNA sequencing using chemiluminescent detection," Nucleic Acids Res., Symposium Series 24:318-321 (1991).
Koumanov et al., "Cell-surface biotinylation of GLUT4 using bis-mannose photolabels," Biochem. J. 330:1209-1215 (1998).
Kwon et al., "DNA sequencing and genotyping by transcriptional synthesis of chain-terminated RNA ladders and MALDI-TOF mass spectrometry," Nucleic Acids Res. 29(3):ell (2001).

Laktionov et al., "Characterization of membrane oligonucleotide-binding proteins and oligonucleotide uptake in keratinocytes," Nucleic Acids. Res. 27(11):2315-2324 (1999).
Laktionov et al., "Interaction of oligonucleotides with cellular proteins," Nucleos. Nucleot. Nucl. 20(4-7):859-862 (2001).
Larsson et al., "Use of an affinity proteomics approach for the identification of low-abundant bacterial adhesins as applied on the Lewis$^b$-binding adhesin of *Helicobacter pylori*," FEBS Lett. 469:155-158 (2000).
Leanna, C. and M. Hannink, "The reverse two-hybrid system: a genetic scheme for selection against specific protein/protein interactions," Nucleic Acids Res. 24(17):3341-3347 (1996).
Leikauf et al., "Heterobifunctional trityl derivatives as linking reagents for the recovery of nucleic acids after labeling and immobilization," Tetrahedron 51:3793-3802 (1995).
Lin et al., "Deign and synthesis of a novel photoaffinity taxoid as a potential probe for the study of paclitaxel-microtubules interactions," Tetrahedron Lett. 41:4287-4290 (2000).
Little et al., "Detection of RET proto-oncogene codon 634 mutations using mass spectrometry," J. Mol. Med. 75(10):745-750 (1997).
Little et al., "Identification of apolipoprotein E polymorphisms using temperature cycled primer oligo base extension and mass spectrometry," Eur. J. Clin. Chem. Clin. Biochem. 35(7):545-548 (1997).
Little et al., "Infrared multiphoton dissociation of large multiply charged ions for biomolecule sequencing," Anal. Chem. 66(18):2809-2815 (1994).
Little et al., "Mass spectrometry from miniaturized arrays for full comparative DNA analysis," Nature Med. 3(12):1413-1416 (1997).
Little et al., "Verification of 50- to 100-mer DNA and RNA sequences with high-resolution mass spectrometry", Proc. Natl. Acad. Sci. USA, 92(6):2318-2322 (1995).
Liu et al., "Activity-based protein profiling: the serine hydrolases," Proc. Natl. Acad. Sci. U.S.A. 96(26):14694-14699 (1999).
Manning et al., "Facile, efficient conjugation of a trifunctional lanthanide chelate to a peripheral benzodiazepine receptor ligand," Org. Lett. 4(7):1075-1078 (2002).
Marshall et al., "Training ribozymes to switch," Nature 6(11):992-994 (1999).
Müller et al., "Retention of imprinting of the human apoptosis-related gene TSSC3 in human brain tumors," Hum. Mol. Genet. 9(5):757-763 (2000).
Musiani et al., "Chemiluminescence: a sensitive detection system in in situ hybridization," Histol. Histopathol. 13:243-248 (1998).
Nazif et al., "Global analysis of proteasomal substrate specificity using positional-scanning libraries of covalent inhibitors," Proc. Natl. Acad. Sci. U.S.A. 98(6):2967-2972 (2001).
Needleman et al., "A general method applicable to the search for similarities in the amino acid sequence of two proteins," J. Mol. Biol. 48:443-453 (1970).
Nesnas et al., "Synthesis of biotinylated retinoids for cross-linking and isolation of retinol binding proteins," Tetrahedron 58:6577-6584 (2002).
Niemeyer et al., "Oligonucleotide-directed self-assembly of proteins: semisynthetic DNA—strepavidin hybrid molecules as connectors for the generation of macroscopic arrays and the construction of supramolecular bioconjugates," Nucleic Acids Res. 22:5530-5539 (1994).
O'Connor et al., "Isotopic assignment in large-molecule mass spectra by fragmentation of a selected isotopic peak," Anal. Chem. 68(3):542-545 (1996).
O'Day et al., "*Aristostomias scintillans* (Malacosteidae): a deep-sea fish with visual pigments apparently adapted to its own bioluminescence," Vision Res. 14:545-550 (1974).
O'Donnell-Maloney et al., "Microfabrication and array technologies for DNA sequencing and diagnostics," Gen. Anal. Biomol. Engin. 13:151-157 (1996).
Pappin et al., "Solid-phase sequence analysis of proteins electroblotted or spottted onto polyvinylidene difluoride membranes," Anal. Biochem. 187(1):10-19 (1990).
Pearson et al., "Improved tools for biological sequence comparison," Proc. Natl. Acad. Sci. U.S.A. 85:2444-2448 (1988).

(56) References Cited

OTHER PUBLICATIONS

Qu et al., "Synthesis, characterization, and cytotoxicity of trifunctional dinulear platinum complexes: comparison of effects of geometry and polyfunctionality on biological activity," J. Med. Chem. 43(16):3189-3192 (2000).

Reddy et al., "Analysis of synthetic oligodeoxynucleotides containing modified components by electrospray ionization mass spectrometry," Anal. Biochem. 220:200-207 (1994).

Robbins et al., "Forskolin carbamates: binding and activiation studies with type I adenylyl cyclase," J. Med. Chem. 39(14):2745-2752 (1996).

Rühl et al., "A trifunctional reagent for photoaffinity labeling," Tet. Lett. 41: 4555-4558 (2000).

Rühmann et al., "Synthesis and characterization of a photoactivatable analog of corticotrophinreleasing factor for specific receptor labeling," Proc. Natl. Acad. Sci. U.S.A. 93:10609-10613 (1996).

Samanta et al., "*Escherichia coli* heat stable enterotoxin receptors & guanylyl cyclase activity in the intestinal brush border membrane of hamsters & guinea pigs," Indian J. Med. Res. pp. 1-6 (2001) (downloaded from http://findarticles.com/p/articles/mi-qa3867/is_200101/ai_n8947273/pg_1 on Nov. 12, 2007).

Santhoshkumar et al., "Identification of a region in alcohol dehydrogenase that binds to alpha-crystallin during chaperone action," Biochim. Biophys. Acta 1598:115-121 (2002).

Sapan et al., "Colorimetric protein assay techniques," Biotechnol. Appl. Biochem. 29:99-108 (1999).

Savige et al., "Cleavage of the tryptophanyl peptide bond by dimethyl sulfoxide-hydroboromic acid," Method. Enzymol. 47:459-469 (1977).

Schwartz et al., "Matrices for Detecting Distant Relationships," Chapter 23 of: Atlas of Protein Sequence and Structure, Dayhoff, M.O., Ed., National Biomedical Research Foundation, pp. 353-358 (1978).

Shchepinov et al., "Matrix-induced fragmentation of P3'-N5' phosphoramidate-containing DNA: high-throughput MALDI-TOF analysis of genomic sequence polymorphisms," Nucleic Acids Res. 29(18):3864-3872 (2001).

Shchepinov et al., "Oligonucleotide dendrimers: stable nano-structures," Nucleic Acids Res. 27(15):3035-3041 (1999).

Shchepinov et al., "Oligonucleotide dendrimers: synthesis and use as polylabelled DNA probes," Nucleic Acids Res. 25:4447-4454 (1997).

Shchepinov et al., "Rapid detection of point mutations with biotinylated selectively cleavable synthetic oligonucleotides," Russian J. Bioorg. Chem. 21(1):68-69 (1995) [Translated from Bioorganicheskaya Khimiya, 21(1):77-79 (1995)].

Shchepinov et al., "Specifically cleavable oligodeoxyribonucleotides for reversible immobilization of DNA," Russian J. Bioorg. Chem. 20(8-9):520-528 (1994) [Translated from Bioorganicheskaya Khimiya, 20(8-9):955-966 (1994)].

Shchepinov et al., "Steric factors influencing hybridisation of nucleic acids to oligonucleotide arrays," Nucleic Acids Res. 25(6):1155-1161 (1997).

Shchepinov et al., "Trityl mass-tags for encoding in combinatorial oligonucleotide synthesis," Nucleic Acids Symp. Ser. 42:107-108 (1999).

Shchepinov et al., "Trityl tags for encoding in combinatorial synthesis," Tetrahedron 56(17):2713-2724 (2000).

Shchepinov, M.S. and V.A. Korshun, "Design of multidye systems for FRET-based applications," Nucleosides Nucleotides Nucleic Acids 20(4-7):369-374 (2001).

Shilo et al., "DNA sequences homologous to vertebrate oncogenes are conserved in *Drosophila melanogaster*," Proc. Natl. Acad. Sci. U.S.A. 78(11):6789-6792 (1981).

Siegert et al., "Matrix-assisted laser desorption/ionization time-of-flight mass spectrometry for the detection of polymerase chain reaction products containing 7-deazapurine moieties," Anal. Biochem. 243(1):55-65 (1996).

Sinha et al., "Polymer support oligonucleotide synthesis XVIII: use of beta-cyanoethyl-N, N-dialkylamino-/N-morpholino phosphoramidite of deoxynucleosides for the synthesis of DNA fragments simplifying deprotection and isolation of the final product," Nucleic Acids Res. 12(11):4539-4557 (1984).

Sittampalam et al., "High-throughput screening: advances in assay technologies," Curr. Opin. Chem. Biol. 1(3):384-391 (1997).

Smith et al., "Comparison of biosequences," Adv. Applied Mathem. 2:482-489 (1981).

Southern et al., "Molecular interactions on microarrays," Nat Genet. 21(1 Suppl):5-9 (1999).

Souto et al., "Synthesis of a photoaffinity-labeled (11Z)-retinal: identification of retinol/rhodopsin cross-linked sites along the visual-transduction path," Helv. Chim. Acta 83:2617-2628 (2000).

Stahl et al., "Solid phase DNA sequencing using the biotin-avidin system," Nucleic Acids Res. 16(7):3025-3038 (1988).

Sugimoto et al., "Syntheses of novel photoaffinity probes for bioorganic studies on nyctinasty of leguminous plants," Tet. Lett. 43:6529-6532 (2002).

Tang et al., "Chip-based genotyping by mass spectrometry," Proc. Natl. Acad. Sci. U.S.A. 96(18):10016-10020 (1999).

Tang et al., "Matrix-assisted laser desorpton/ionization mass spectrometry of immobilized duplex DNA probes," Nucleic Acids Res. 23(16):3126-3131 (1995).

Turro, N.J., (Ed.), "Modem Molecular Photochemistry," Menlo Park, California: The Benjamin/Cummings Publishing Co., Inc., pp. 297-361 (1978).

Valaskovic et al., "Attomole-sensitivity electrospray source for large-molecule mass spectrometry," Anal. Chem. 67(20):3802-3805 (1995).

van den Boom et al., "Combined amplification and sequencing in a single reaction using two DNA polymerases with differential incorporation rates for dideoxynucleotides," J. Biochem. Biophys. Methods 35(2):69-79 (1997).

van den Boom et al., "Forward and reverse DNA sequencing in a single reaction," Anal. Biochem. 256(1):127-129 (1998).

Watson et al., Eds., "Molecular Biology of the Gene, vol. I," 4th ed., Menlo Park, California: The Benjamin/Cummings Publishing Company, Inc., p. 224 (1987).

Weiler et al., "Hybridisation based DNA screening on peptide nucleic acid (PNA) oligomer arrays," Nucliec Acids Res. 25(14):2792-2799 (1997).

Wood et al., "Direct sequence data from heterogeneous creatine kinase (43 kDa) by high-resolution tandem mass spectrometry," Biochemistry 34(50):16251-16254 (1995).

Yang et al., "Development of high-affinity ligands and photoaffinity labels for the D-fructose transporter GLUT5," Biochem. J. 367-533-539 (2002).

Zhou et al., "Quantitative proteome analysis by solid-phase isotope tagging and mass spectrometry," Nat. Biotechnol. 19: 512-515 (2002).

* cited by examiner

SMALL MOLECULES $CH_3$, $C_2H_5$, and longer chain alkyl groups

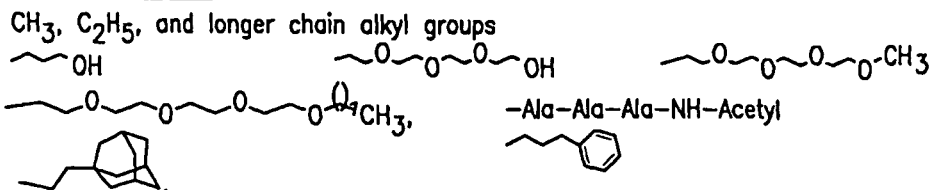

—Ala—Ala—Ala—NH—Acetyl

NATURAL PRODUCTS

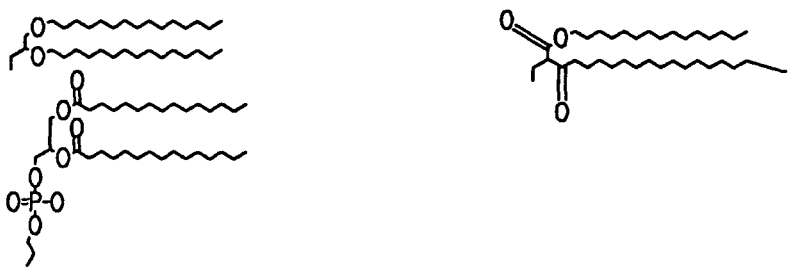

Cholesterol, Steroids, alkaloids, flavonoids, prostaglandin, peptides, EGF, rapamycin

PROTEIN AGONISTS AND ANTAGONISTS 1,1,1-Trifluoro-6Z,9Z,12Z,15Z-heneicosateraen-2-one, trans-4-[3-Methyl-6-(1-methylethenyl)-2-cyclohexen-1-yl]-5-pentyl-1,3-benzenediol, Arachidonyl-2'-chloroethylamide/
(all Z)-N-(2-cycloethyl)-5,8,11,14-eicosatetraenamide, Arachidonylcyclopropylamide/(all Z)-N-(cyclopropyl)-5,8,11,14-eicosatetraenamide, N-(Piperidin-1-yl)-5-(4-iodophenyl)-1-(2,4-dichlorophenyl)-4-methyl-1H-pyrazole-3-carboxamide, 1-(2,4-Dichlorophenyl)-5-(4-iodophenyl)-4-methyl-N-4-morpholinyl-1H-pyrazole-3-carboxamide, (all Z)-N-(4-Hydroxyphenyl)-5,8,11,14-eicosatetraenamide, 6-Iodo-2-methyl-1-[2-(4-morpholinyl)ethyl]-1H-indol-3-yl](4-methoxyphenyl)
methanone, Arachidonylethanolamide/(all Z)-N-(2-Hydroxyethyl)-5,8,11,14-eicosatetraenamide,

FIG. 17a

Arachidonylethanolamide/(all Z)-N-(2-Hydroxyethyl)-5,8,11,14-
eicosatetraenamide, N-(2-Hydroxyethyl)-[5,6,8,9,11,12,14,15-H]-5Z,8Z,11Z,14Z-eicosatetraenamide, 2-AG/(5Z,8Z,11Z,14Z)-5,8,11,14-Eicosatetraenoic acid, 2-hydroxy-1-
(hydroxymethyl)ethyl ester, (-)-cis-3-[2-Hydroxy-4-(1,1-dimethylheptyl)phenyl]-trans-4-(3-
hydroxypropyl)cyclohexanol, Docosatetraenylethanolamide/N-(2-Hydroxyethyl)-7Z,10Z,13Z,16Z-
docosatetraenamide, (6aR)-trans-3-(1,1-Dimethylheptyl)-6a,7,10,10a-tetrahydro-1-hydroxy-6,6-
dimethyl-6H-dibenzo[b,d]pyran-9-methanol,

[6aR-(6aα,9α,10aβ)]-3-(1,1-Dimethylheptyl)-6a,7,8,9,10,10a-hexahydro-1-
hydroxy-6,6-dimethyl-6H-dibenzo[b,d]pyran-[7,8-H]-9-methanol, (2-Methyl-1-propyl-1H-indol-3-yl)-1-naphthalenylmethanone, (6aR,10aR)-3-(1,1-dimethylbutyl)-6a,7,10,10a-tetrahydro-6,6,9-trimethyl-6H-
dibenzo[b,d]pyran, Methyl arachidonyl fluorophosphonate/(5Z,8Z,11Z,14Z)-5,8,11,14-
eicosatetraenyl-methyl ester phosphonofluoridic acid,

[R-(all-Z)]-N-(2-Hydroxy-1-methylethyl)-5,8,11,14-eicosatetraenamide, 2-
[(5Z,8Z,11Z,14Z)-Eicosatetraenyloxy]-1,3-propanediol, N-(bis-3-chloro-4-hydroxybenzyl)-5Z,8Z,11Z,14Z-eicosatetraenamide, (9Z)-N-(2-Hydroxyethyl)-9-octadecenamide, N-(2-Hydroxyethyl)hexadecanamide, (5Z,8Z,11Z,14Z)-N-(4-Hydroxy-2-methylphenyl)-5,8,11,14-eicosatetraenamide, (R)-(+)-[2,3-Dihydro-5-methyl-3-(4-morpholinylmethyl)pyrrolo[1,2,3-de]-1,4-
benzoxazin-6-yl]-1-naphthalenylmethanone

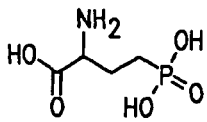

FIG. 17b

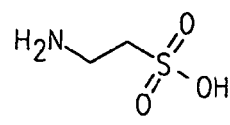
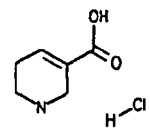
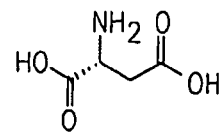
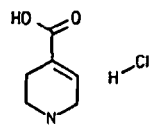
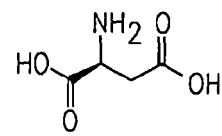
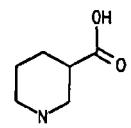
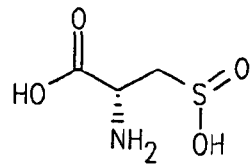
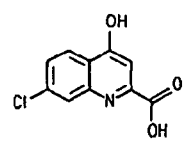
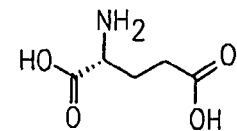
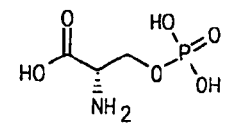
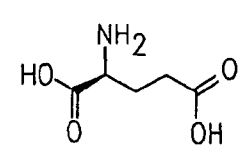
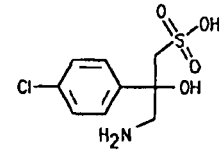
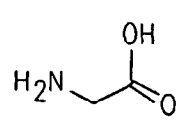
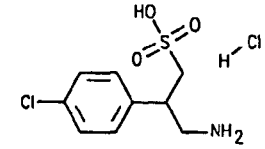
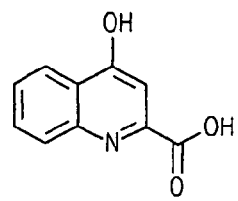
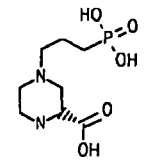
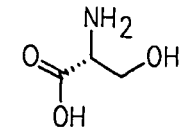
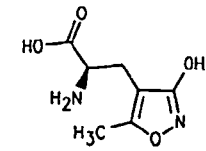
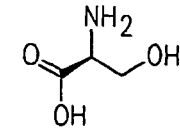
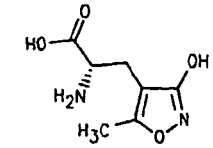
FIG. 17g FIG. 17h

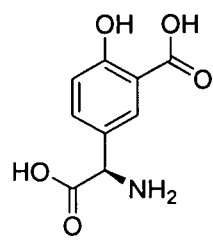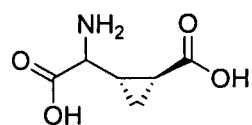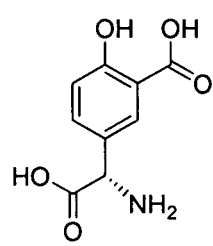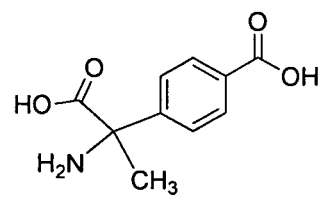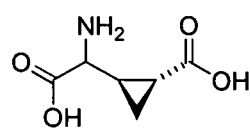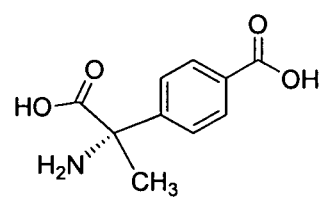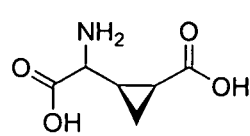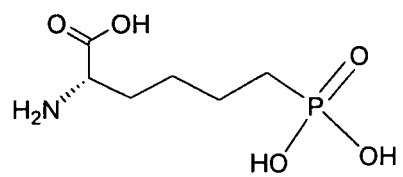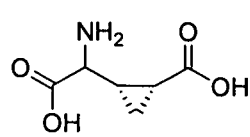
FIG. 17I

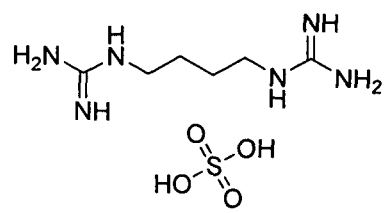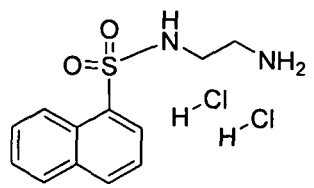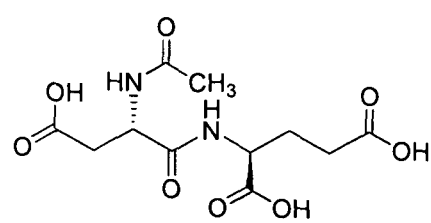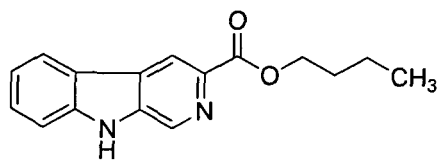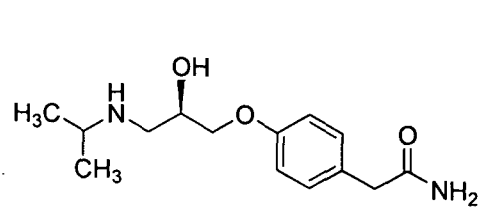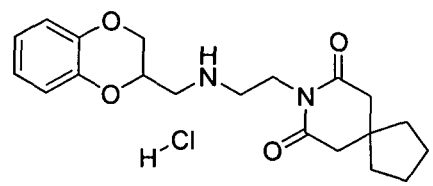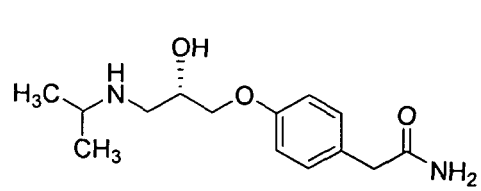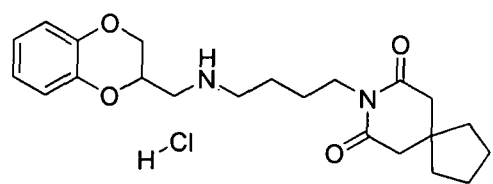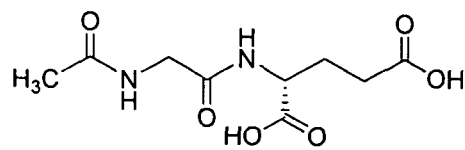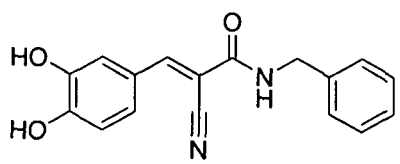
FIG. 17p

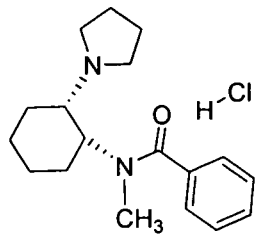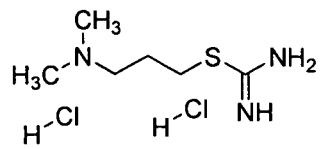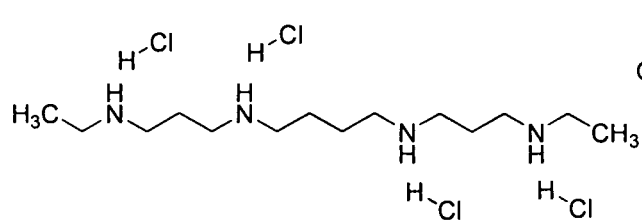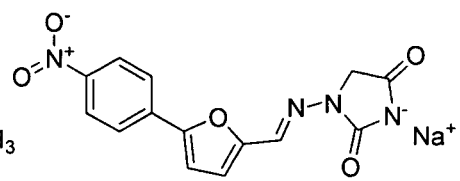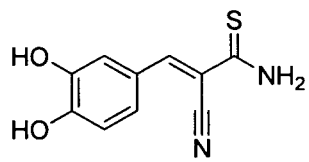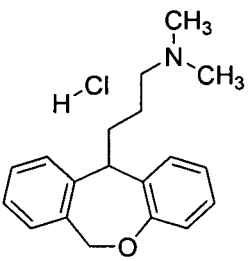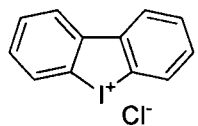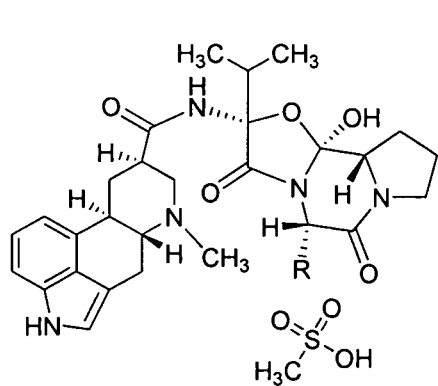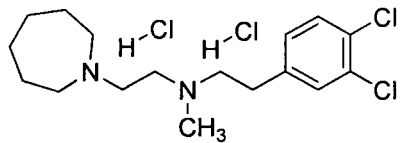
FIG. 17w

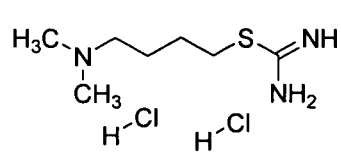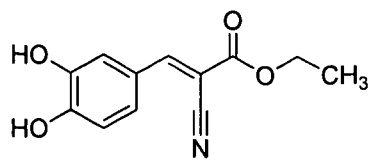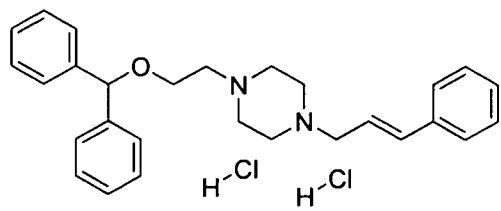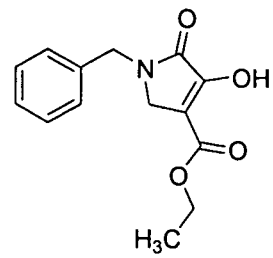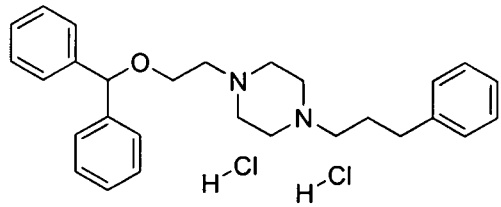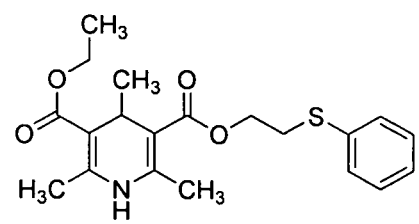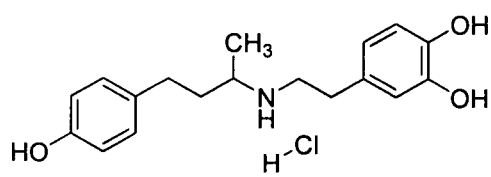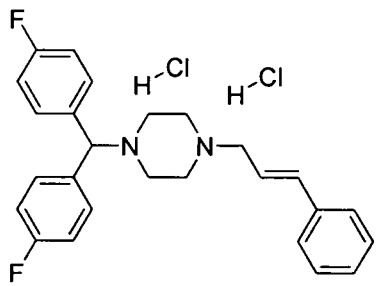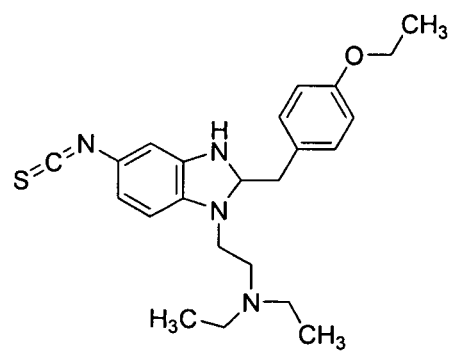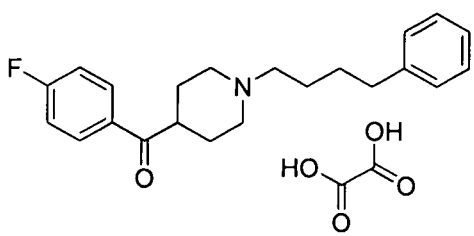
FIG. 17x

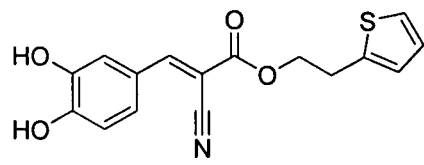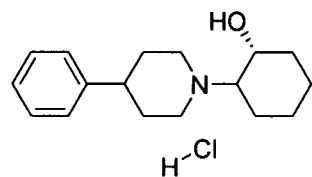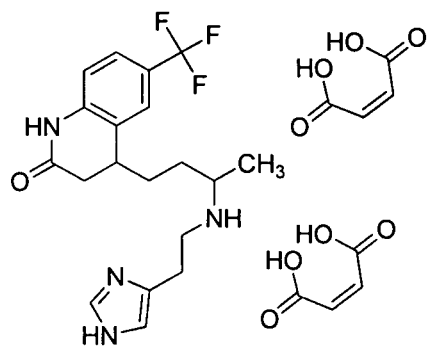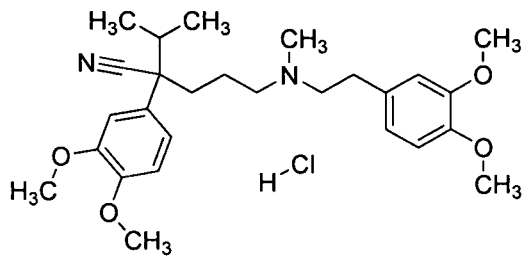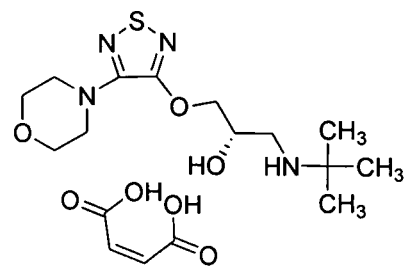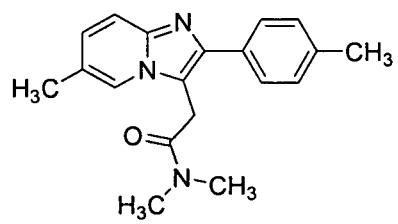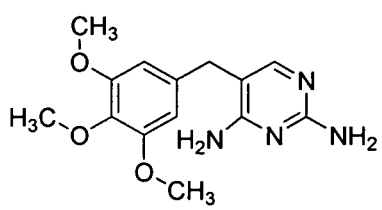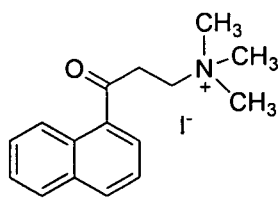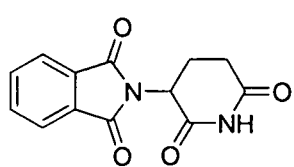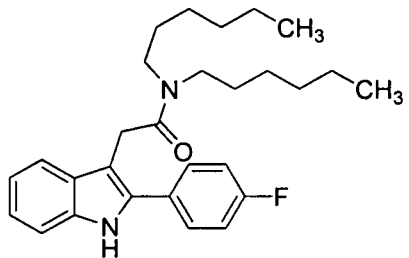
FIG. 17hh

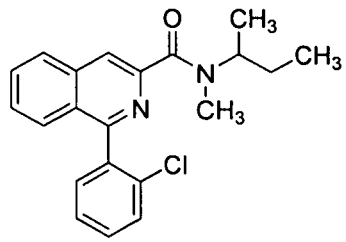
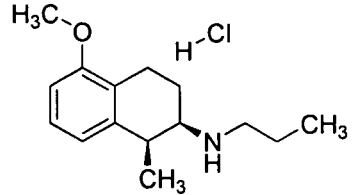
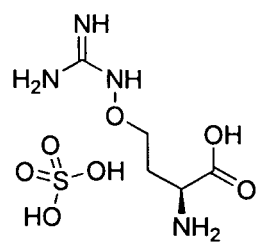
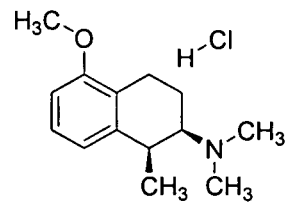
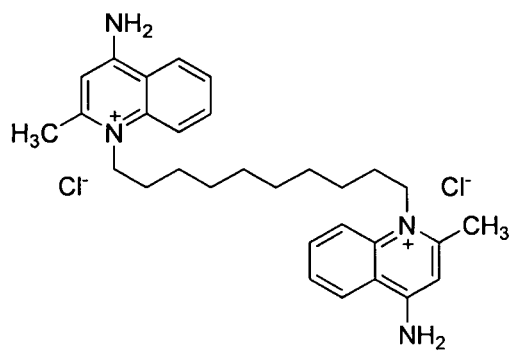
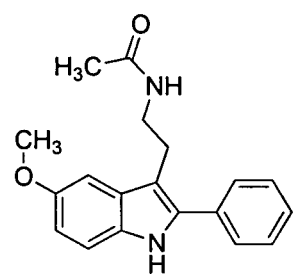
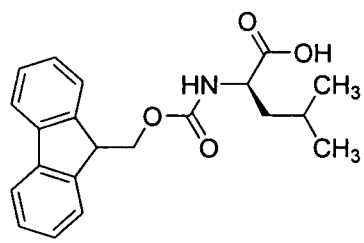
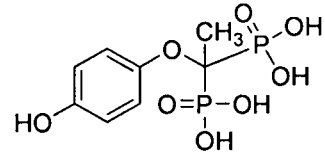
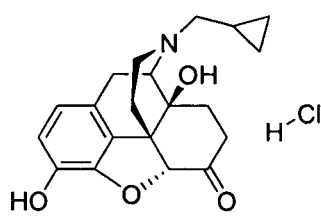
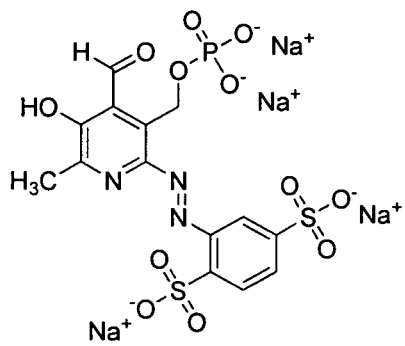
FIG. 17jj

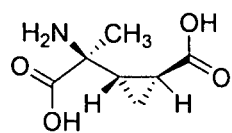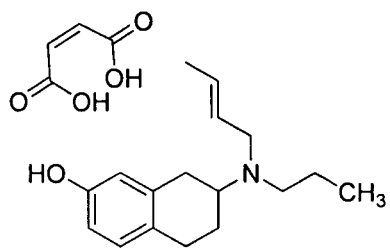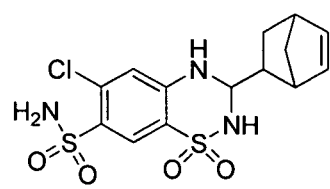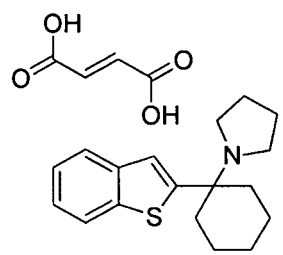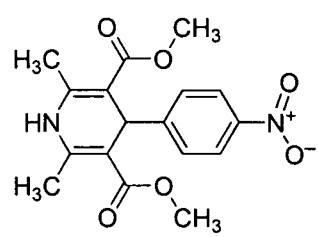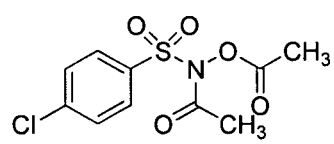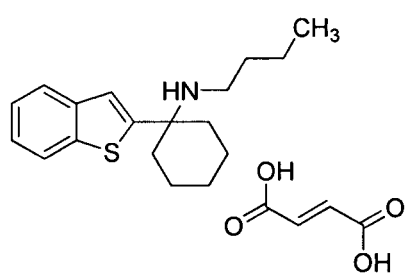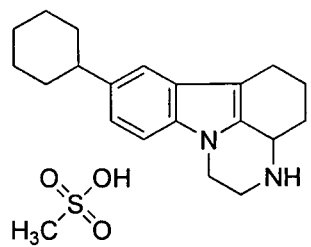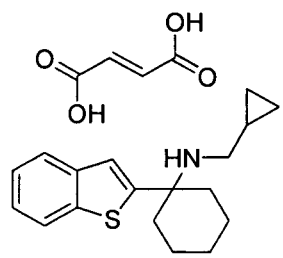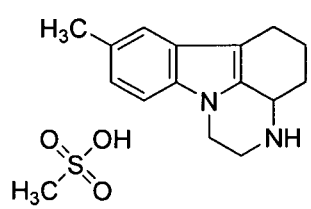
FIG. 17mm

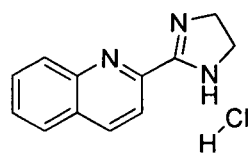 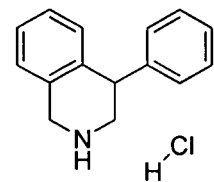
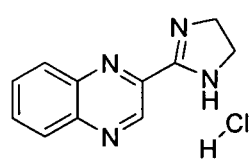 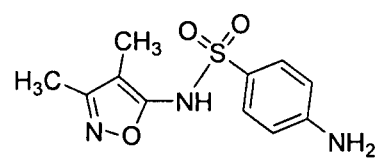
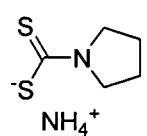 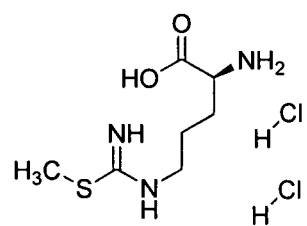
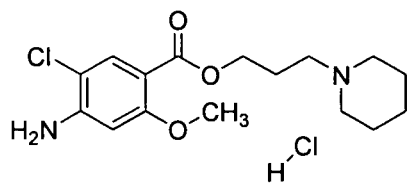 
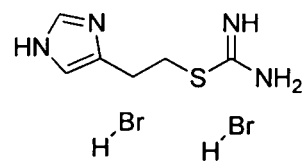 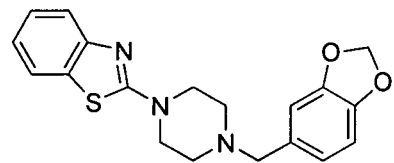
FIG. 17nn

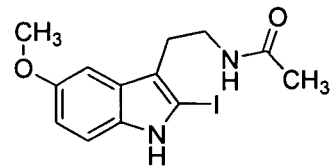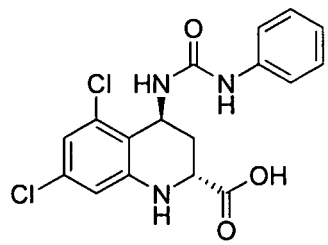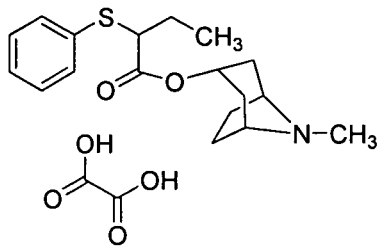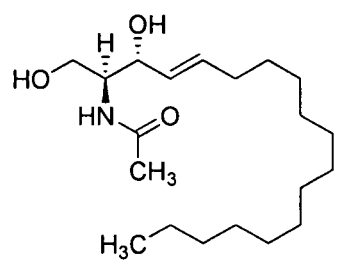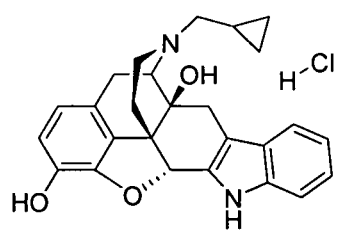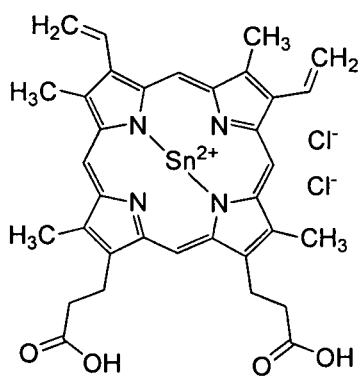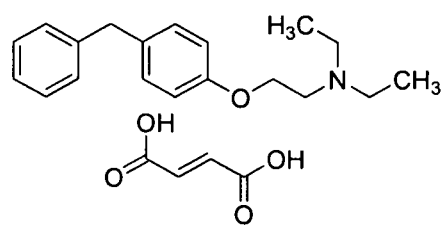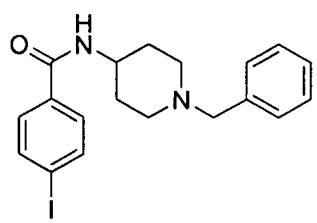
FIG. 17oo

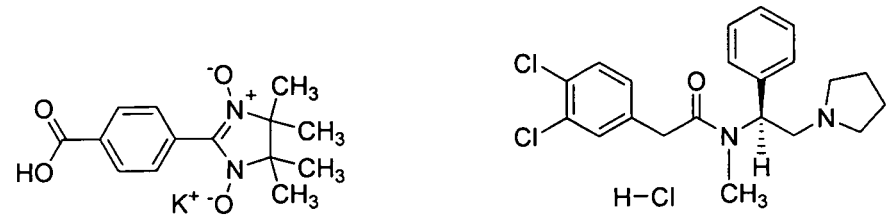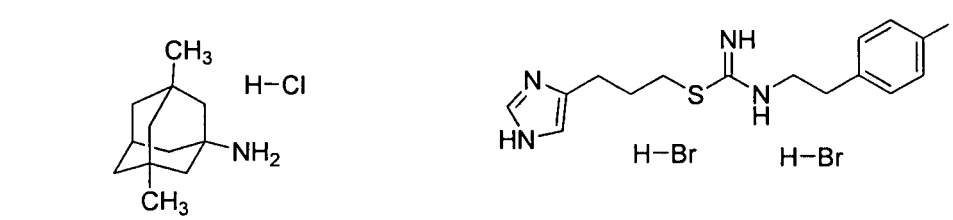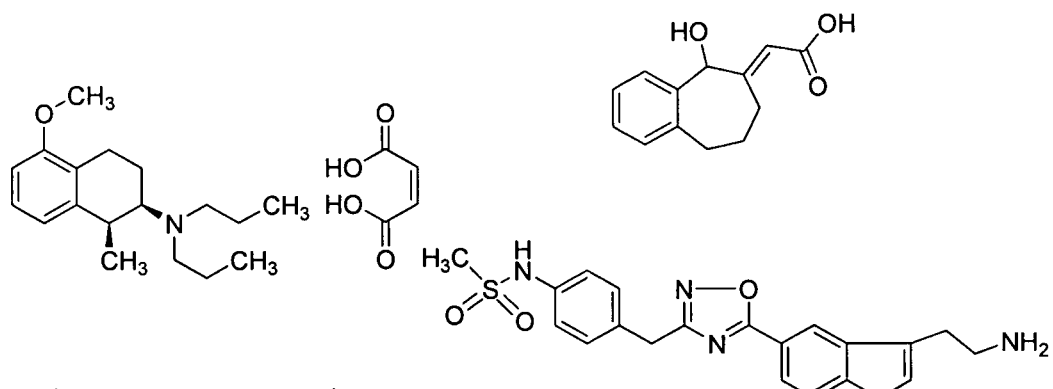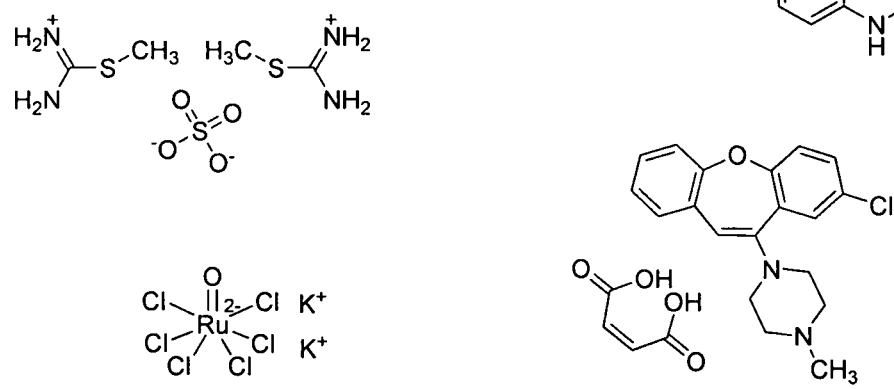
FIG. 17rr

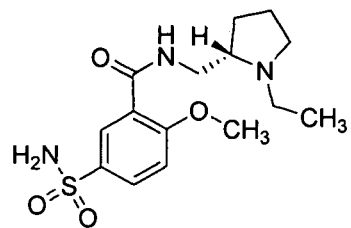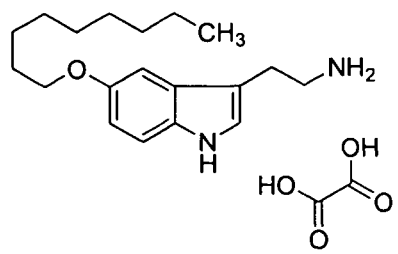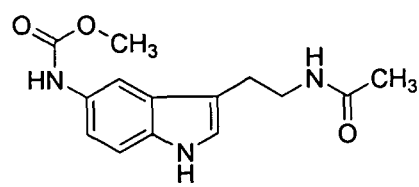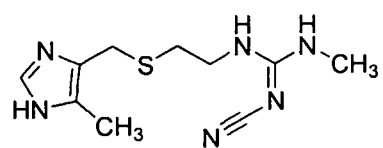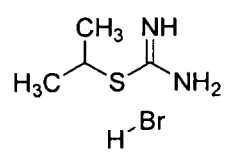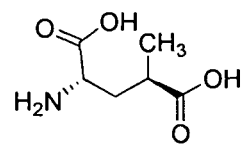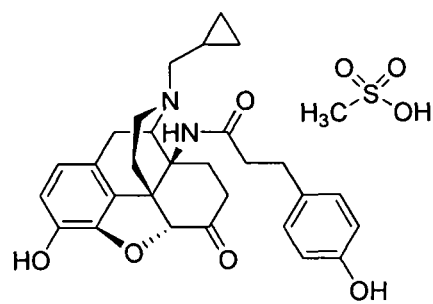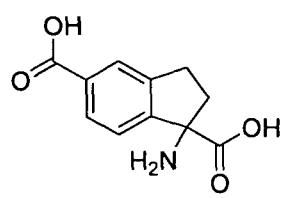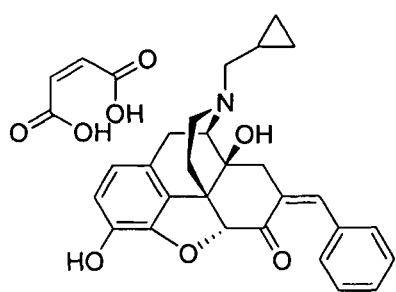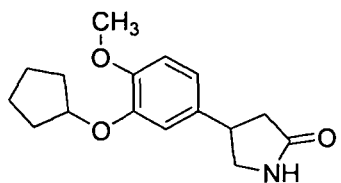
FIG. 17aaa

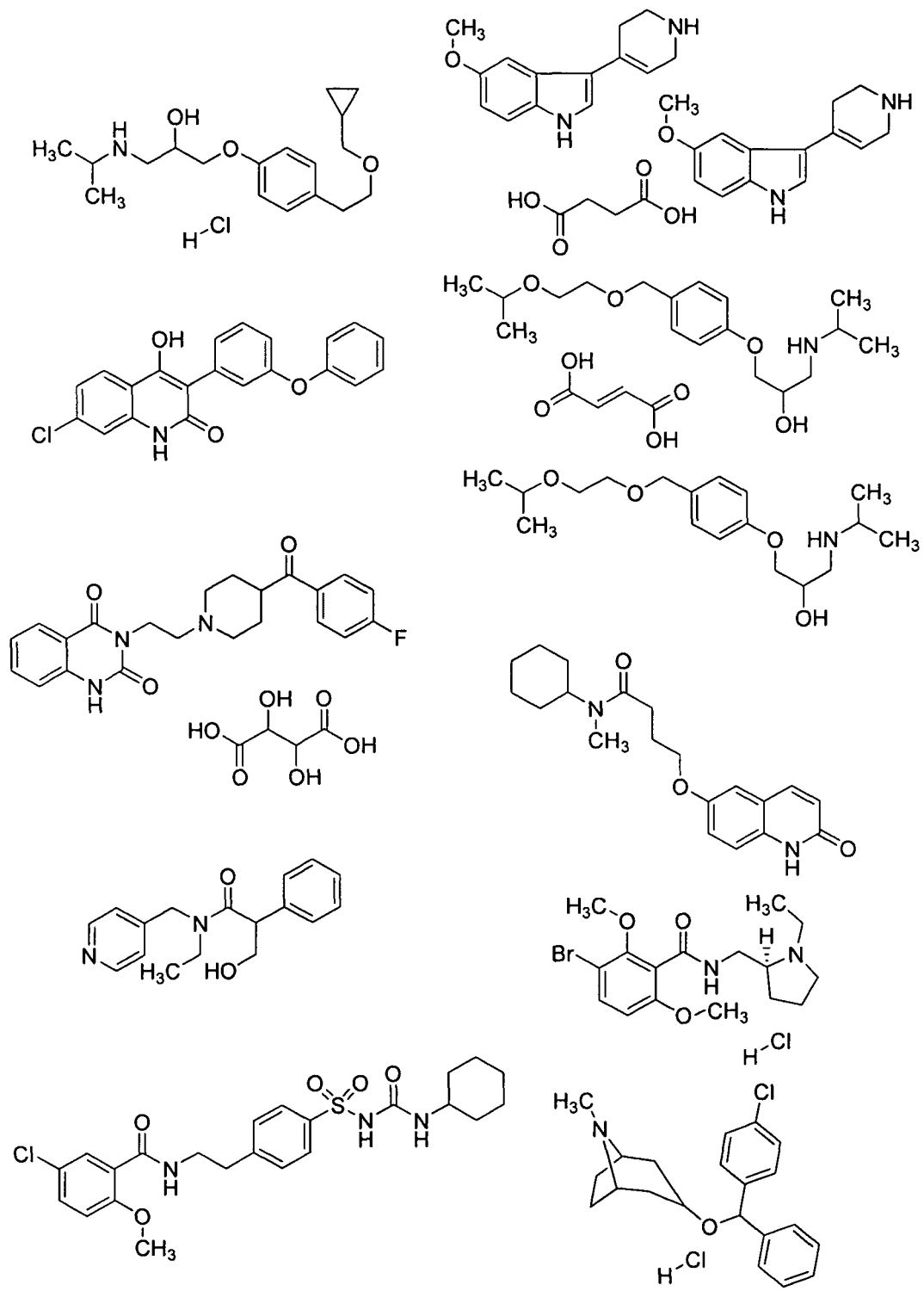
FIG. 17bbb

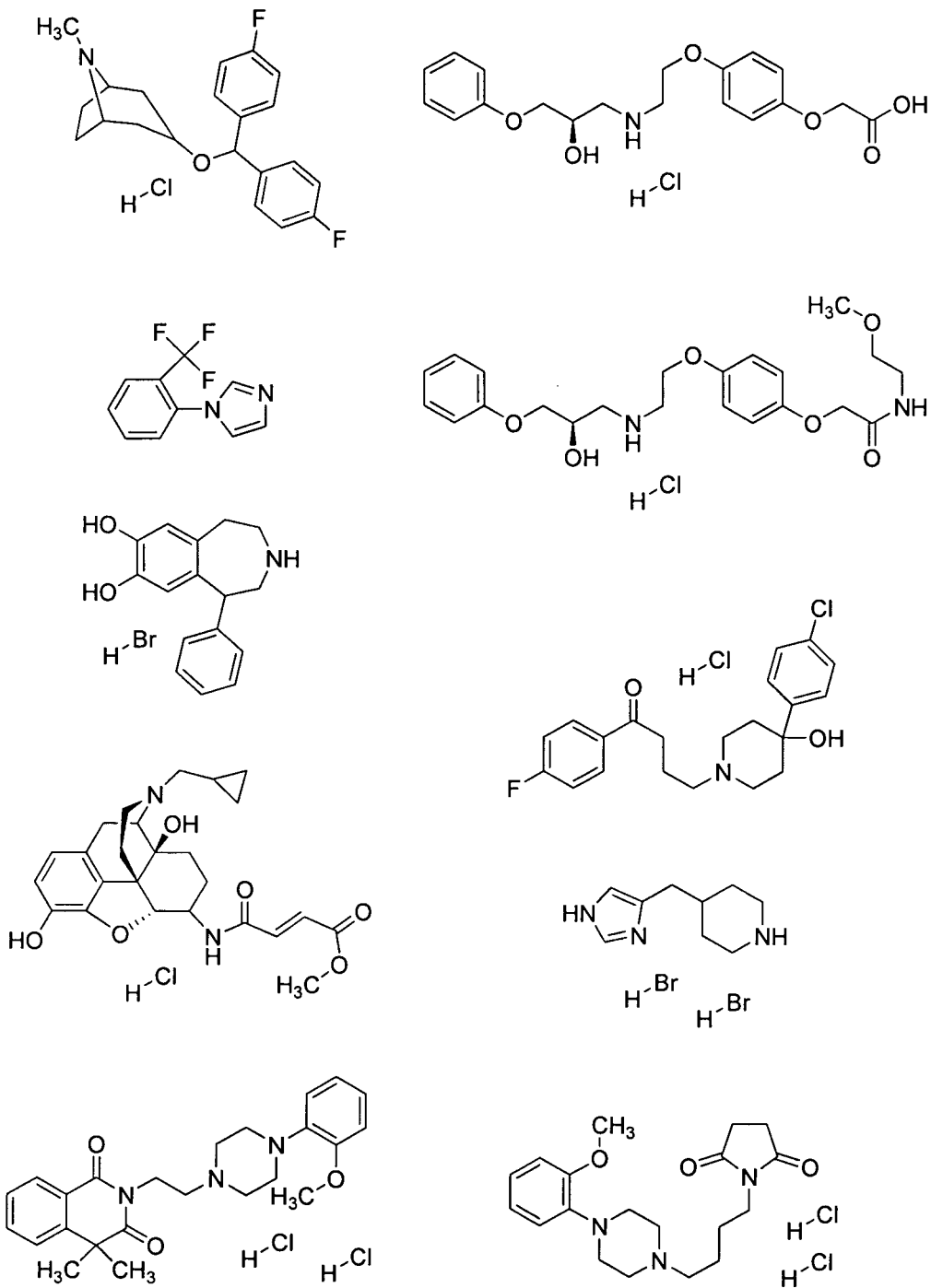
FIG. 17ccc

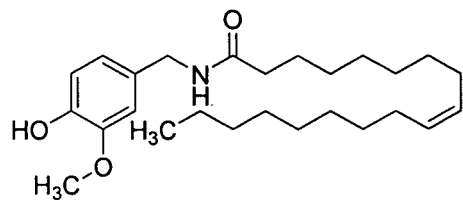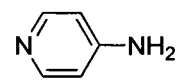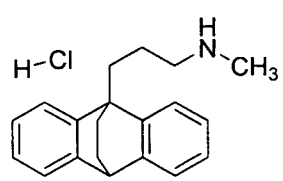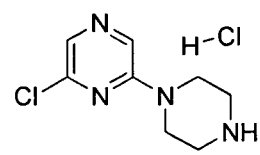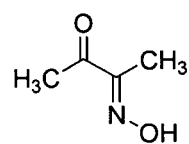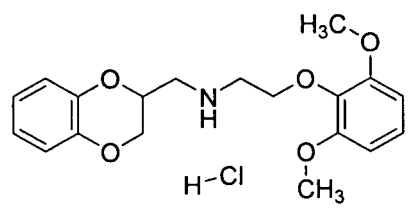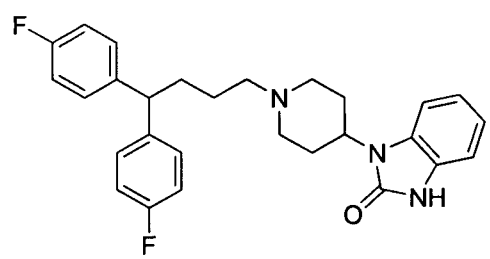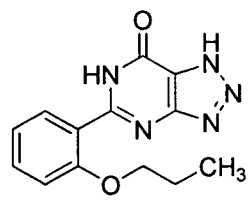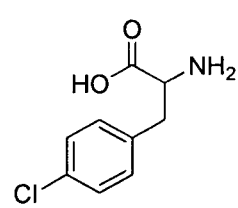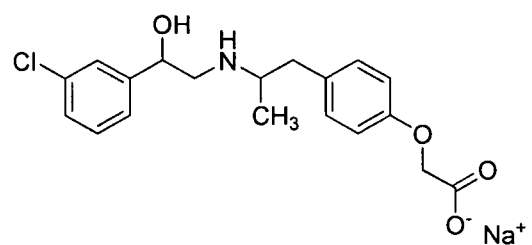
FIG. 17ddd

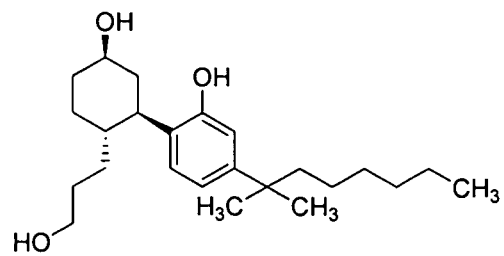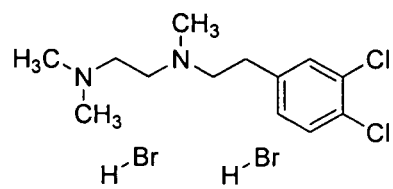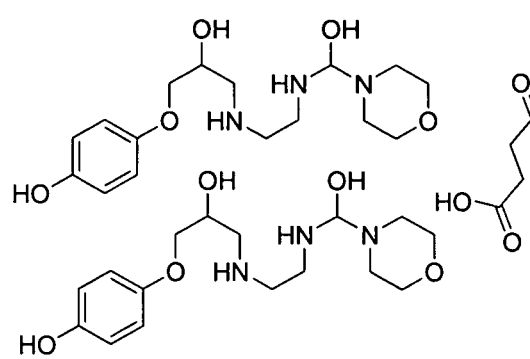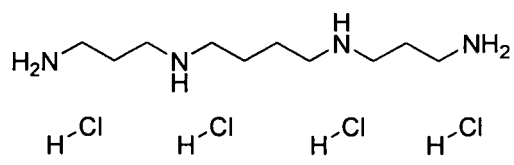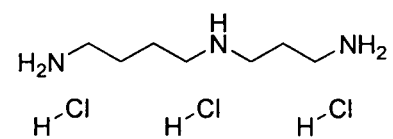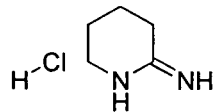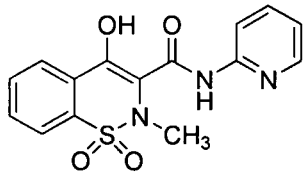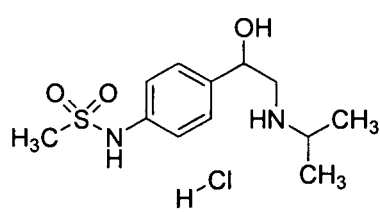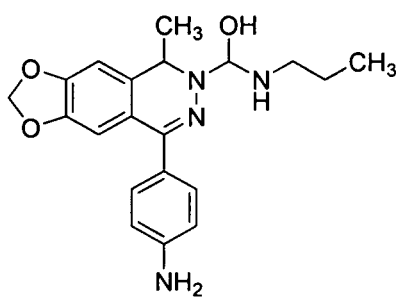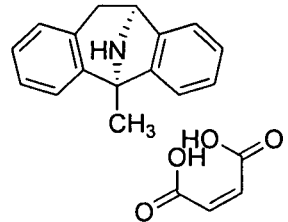
FIG. 17eee

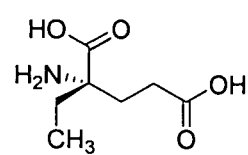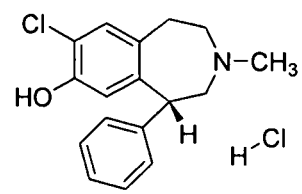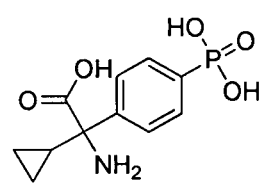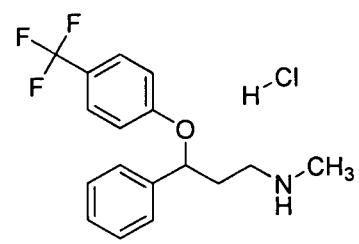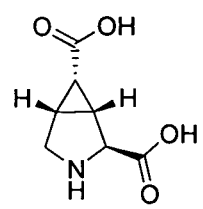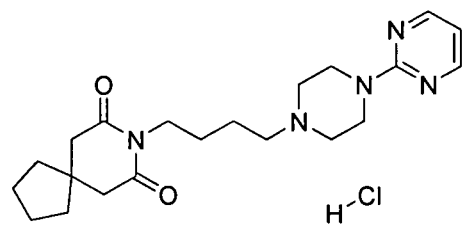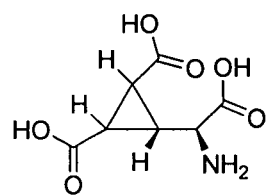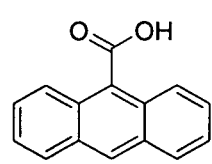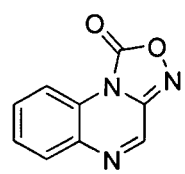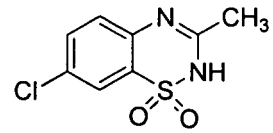
FIG. 17fff

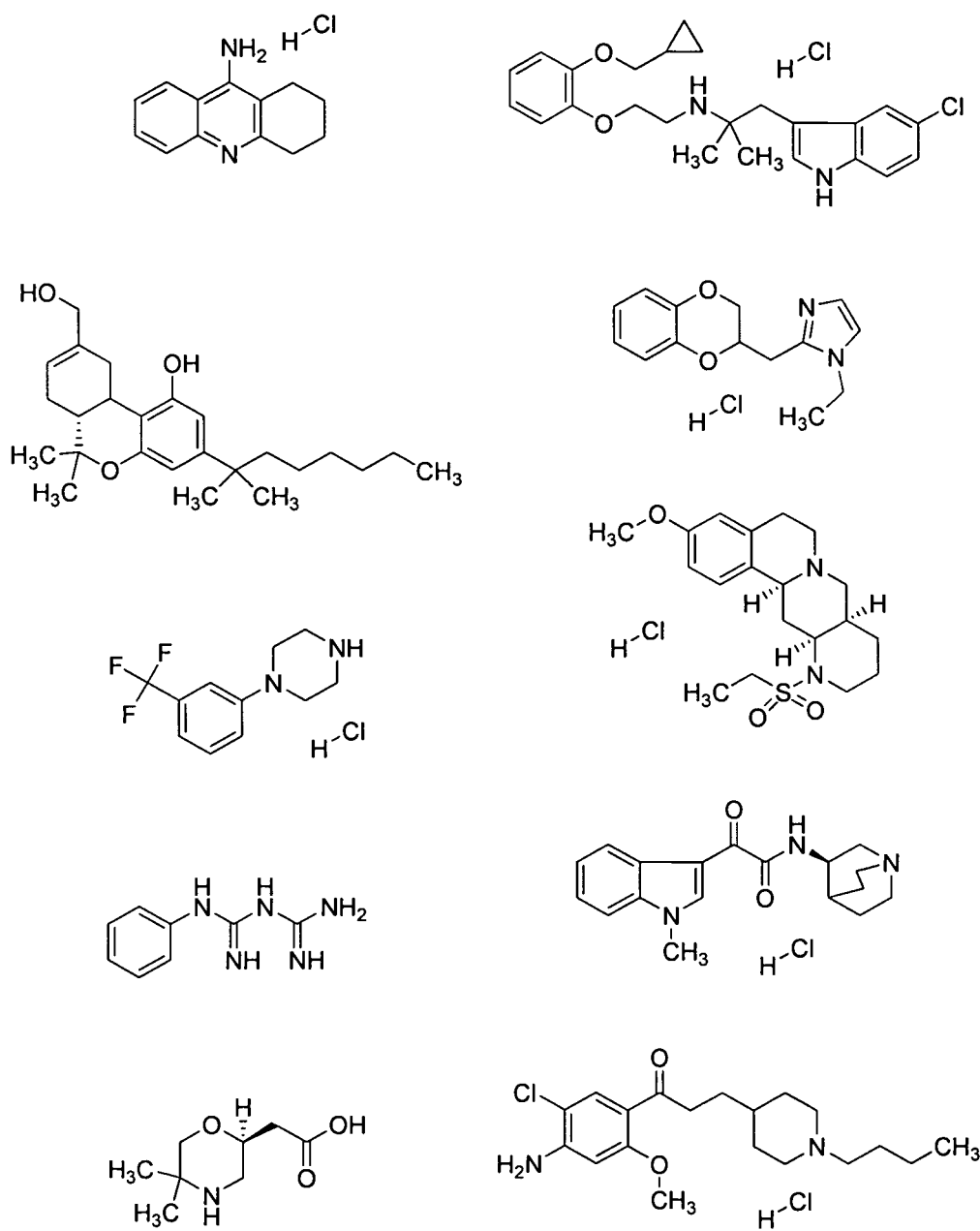
FIG. 17ggg

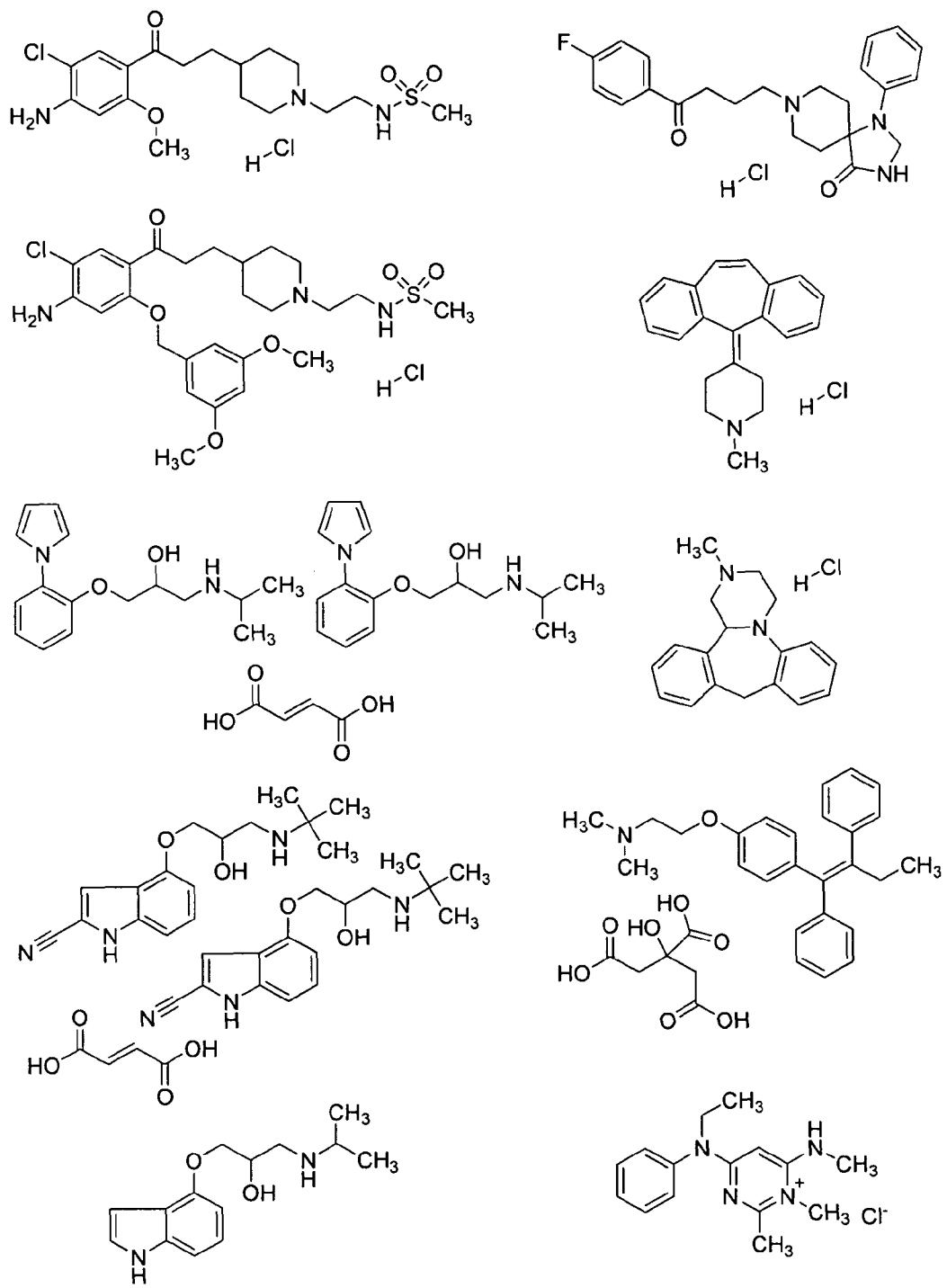
FIG. 17hhh

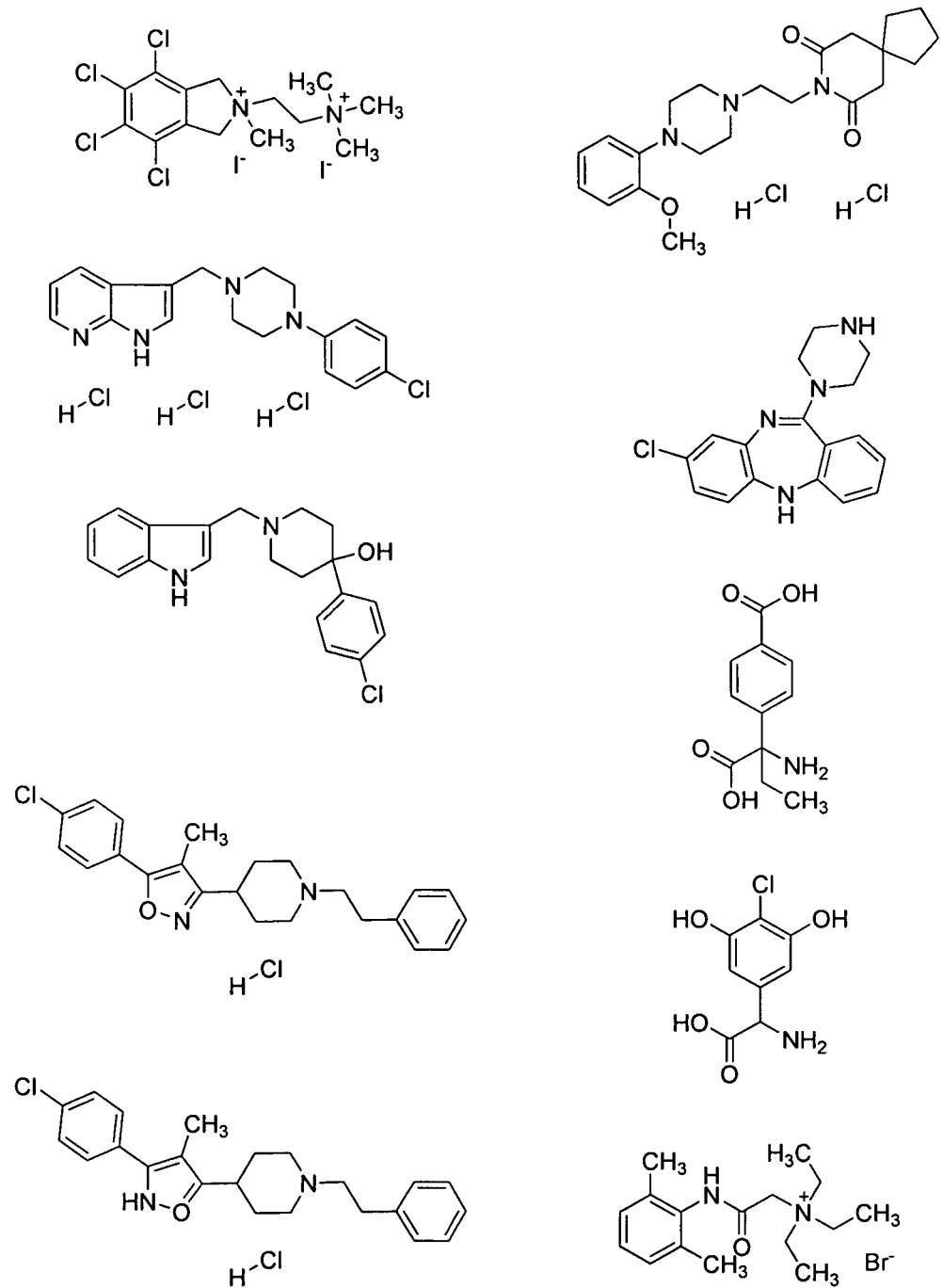
FIG. 17iii

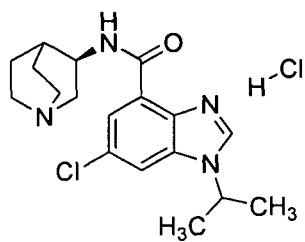
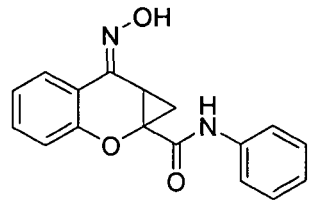
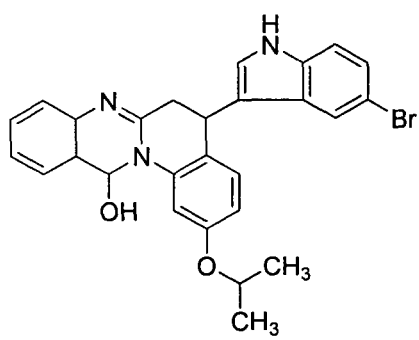
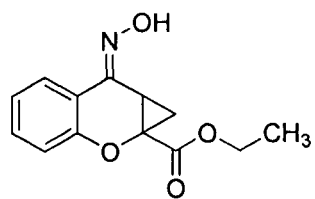
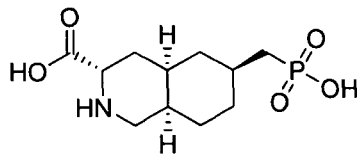
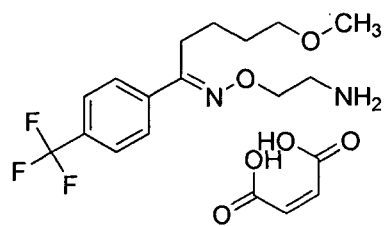
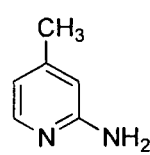
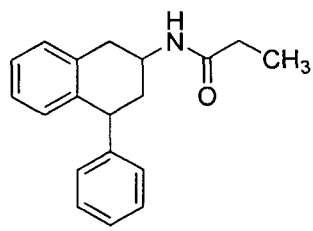
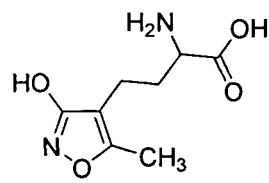
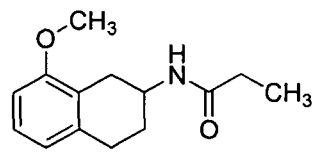
FIG. 17jjj

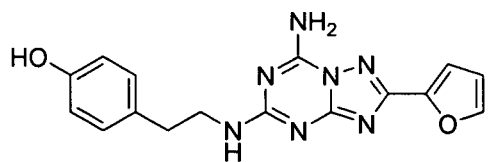
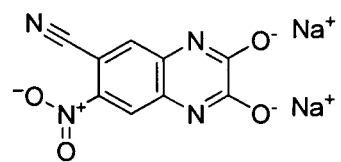
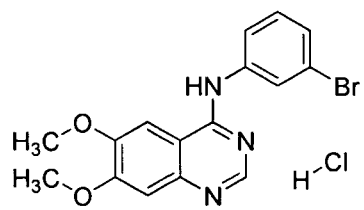
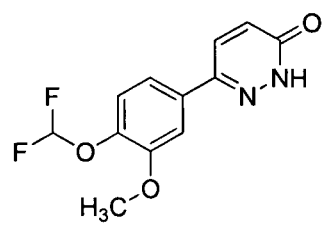
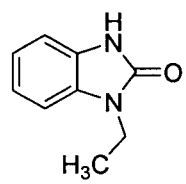
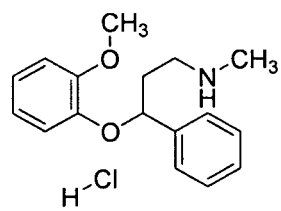
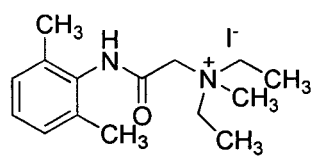
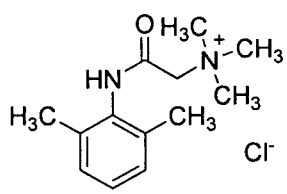
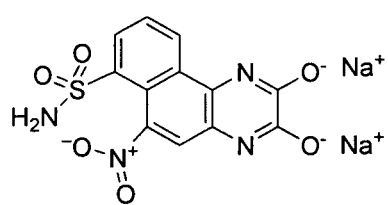
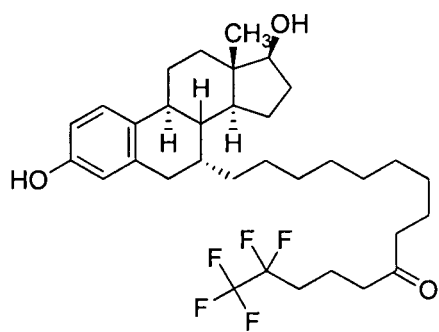
FIG. 17kkk

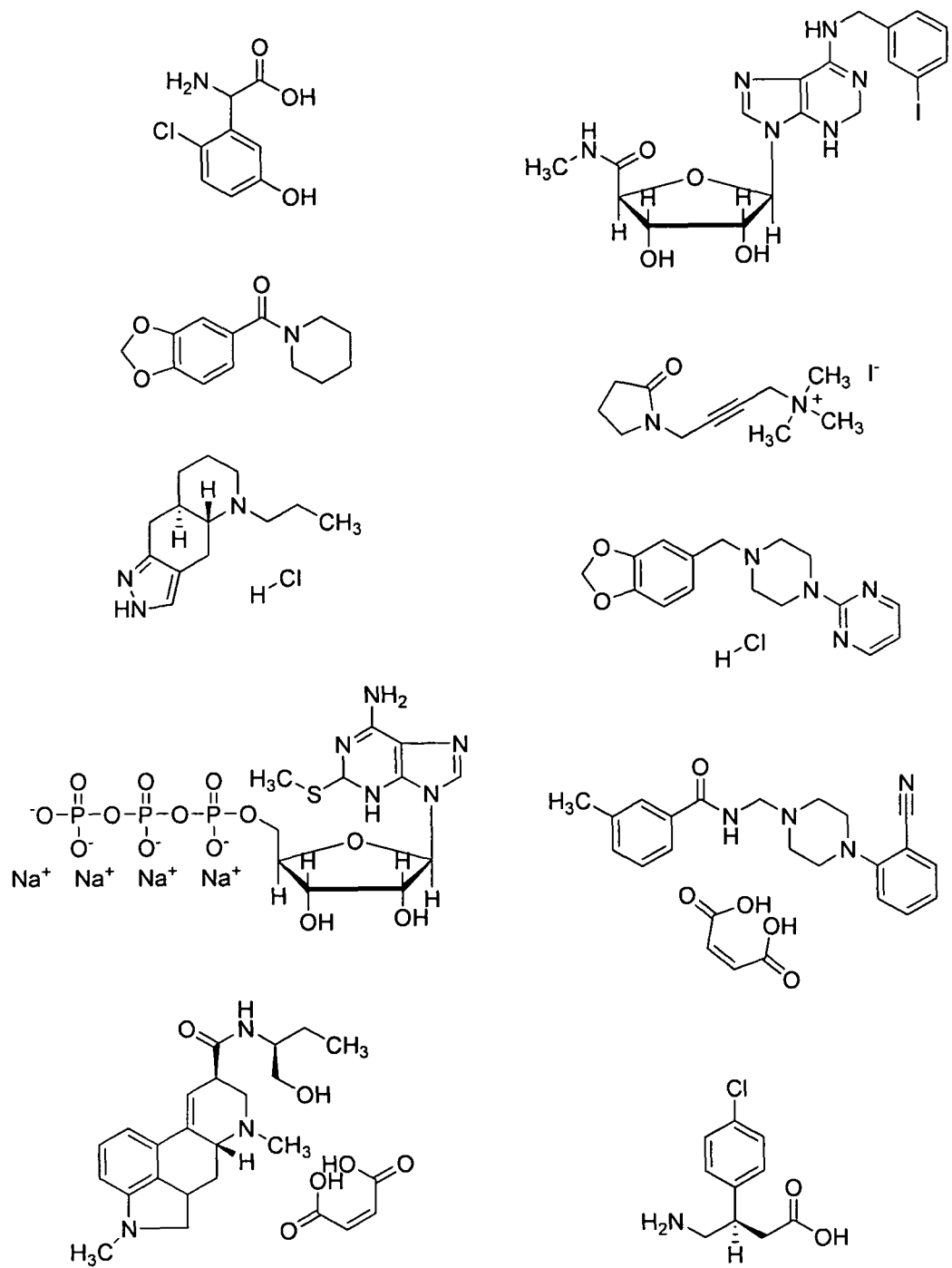
FIG. 17III

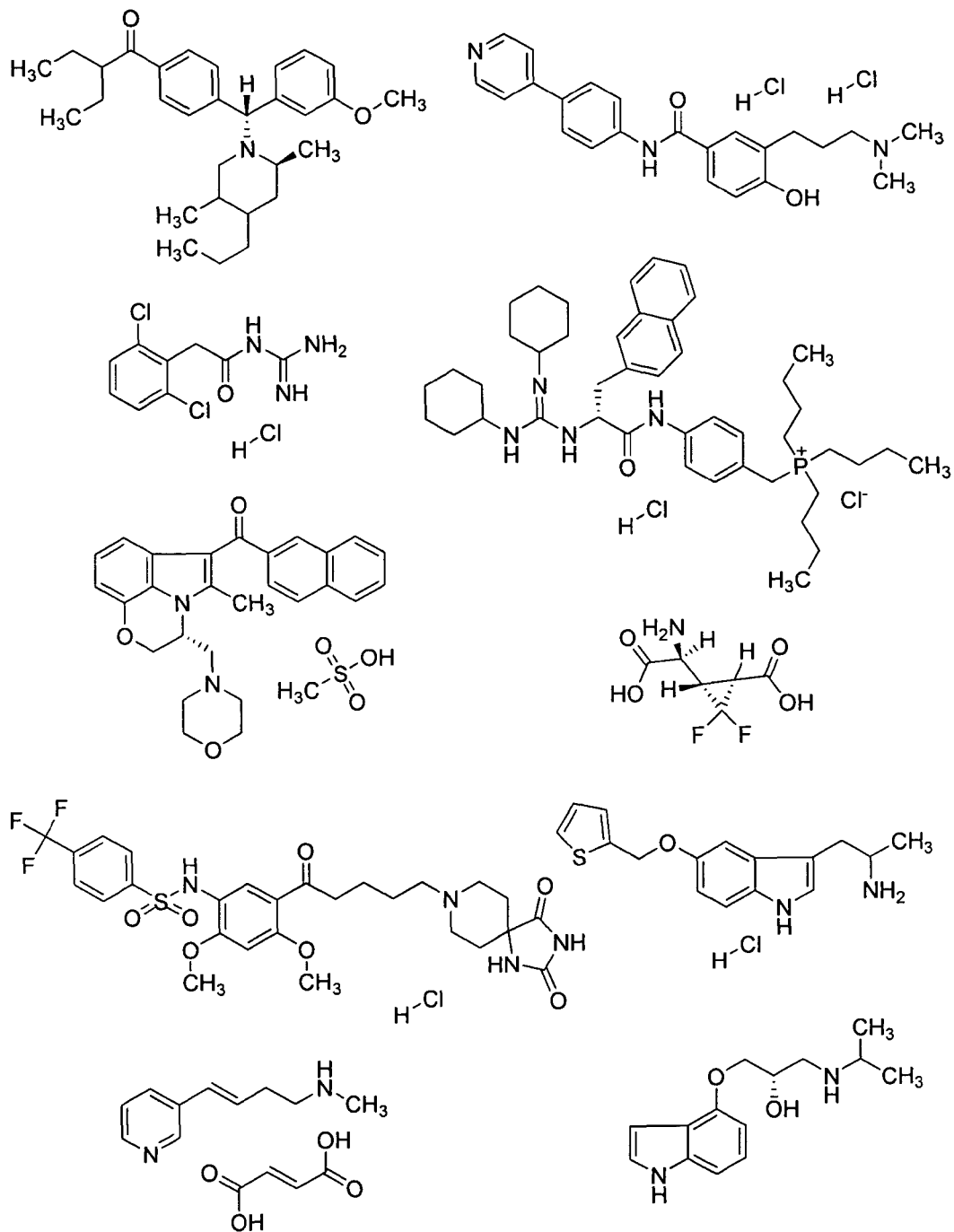
FIG. 17mmm

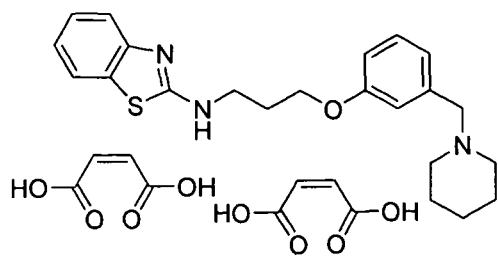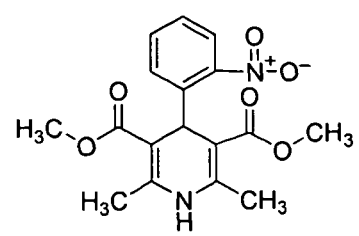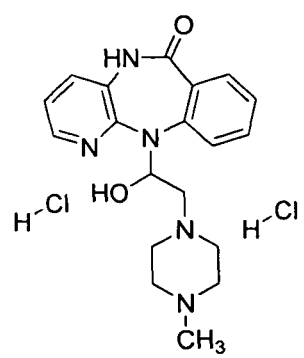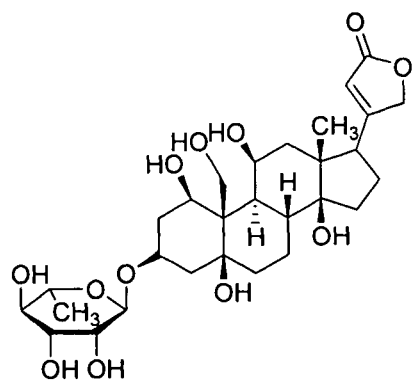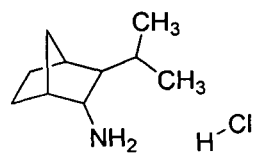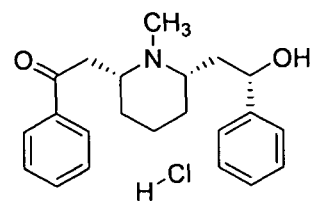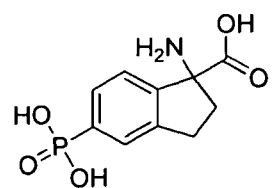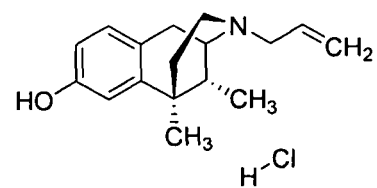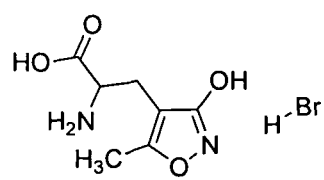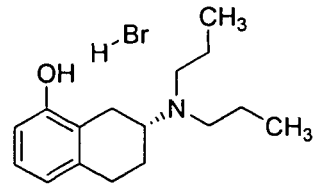
FIG. 17nnn

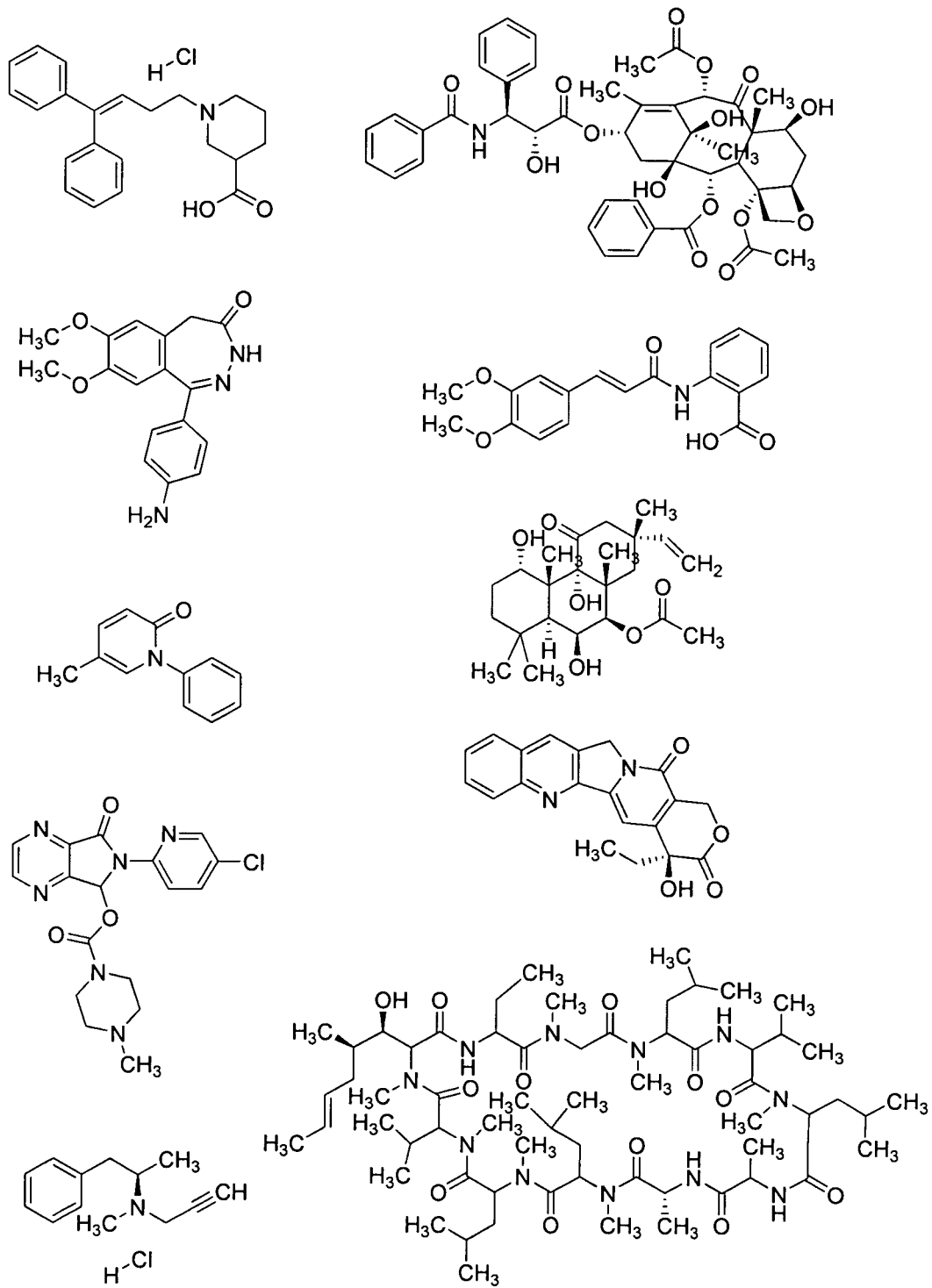
FIG. 17ooo

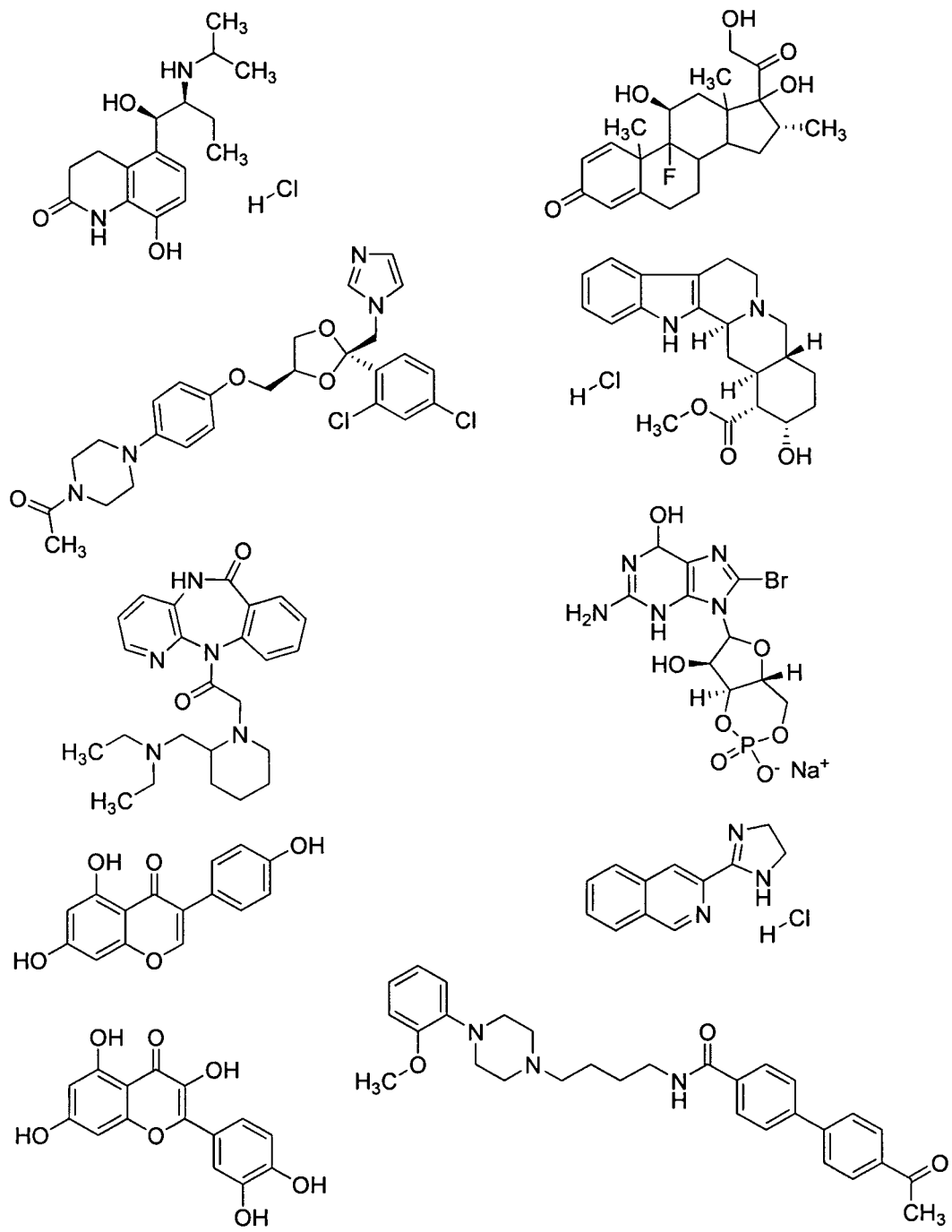
FIG. 17ppp

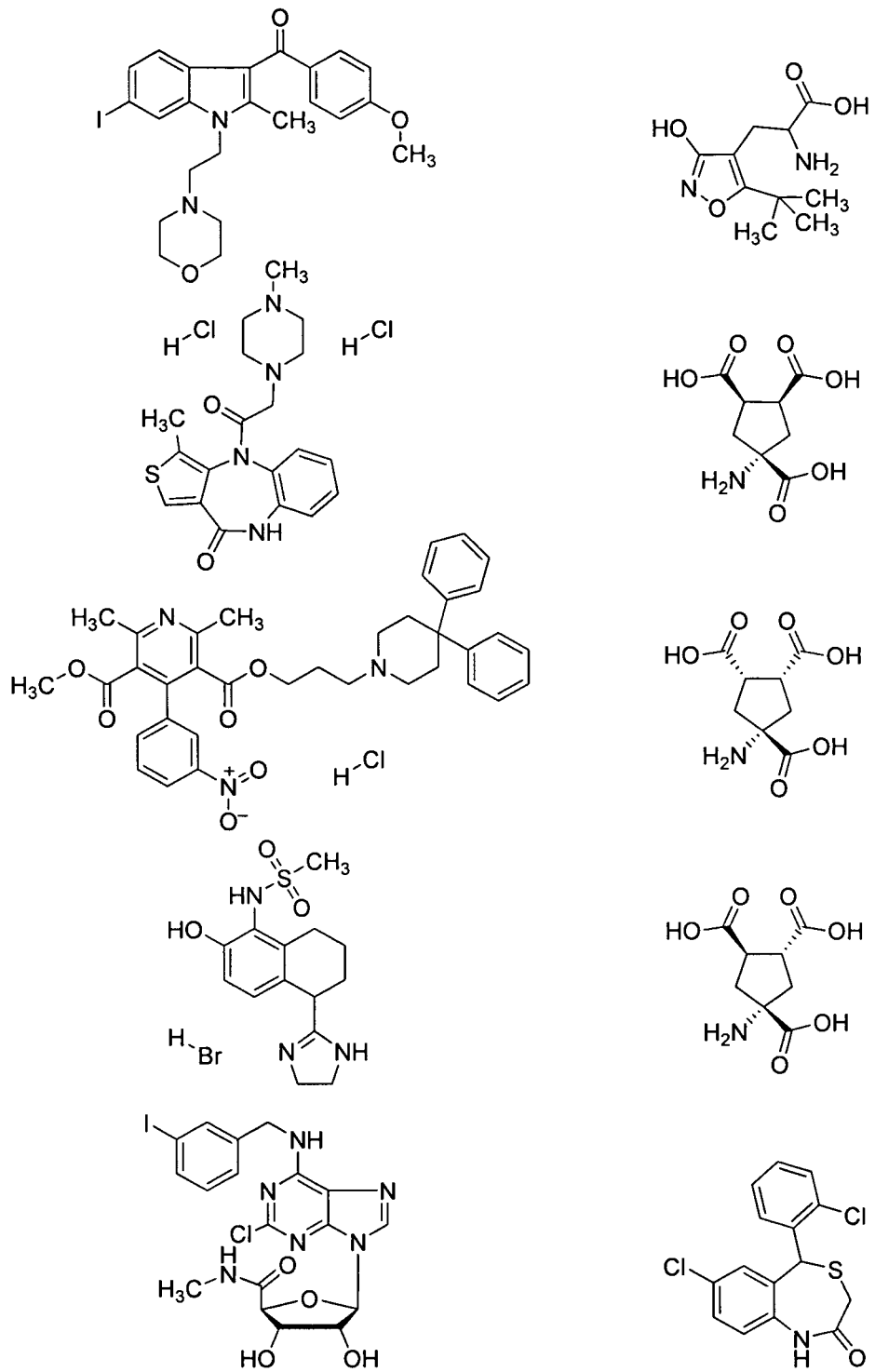
FIG. 17qqq

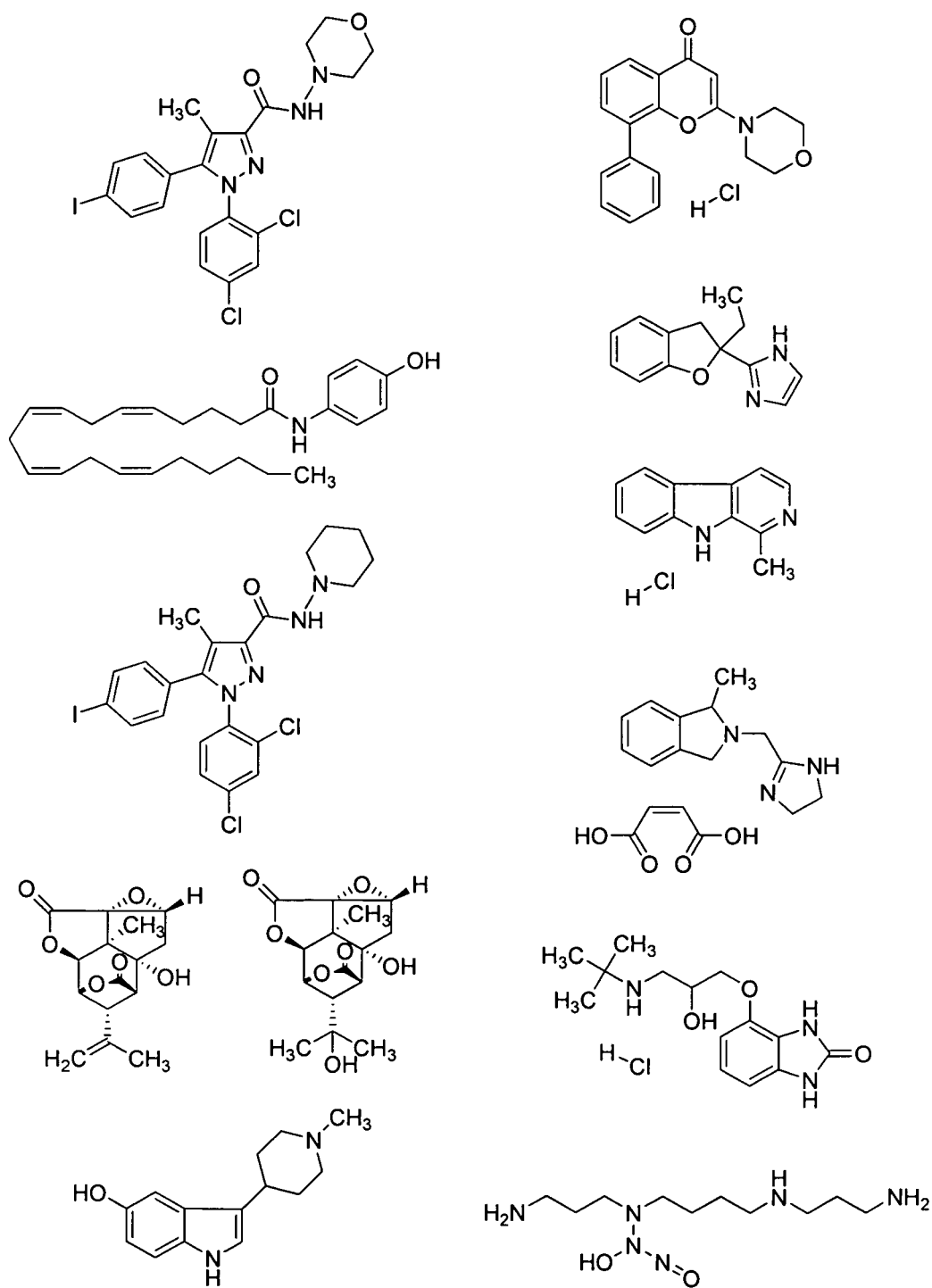
FIG. 17rrr

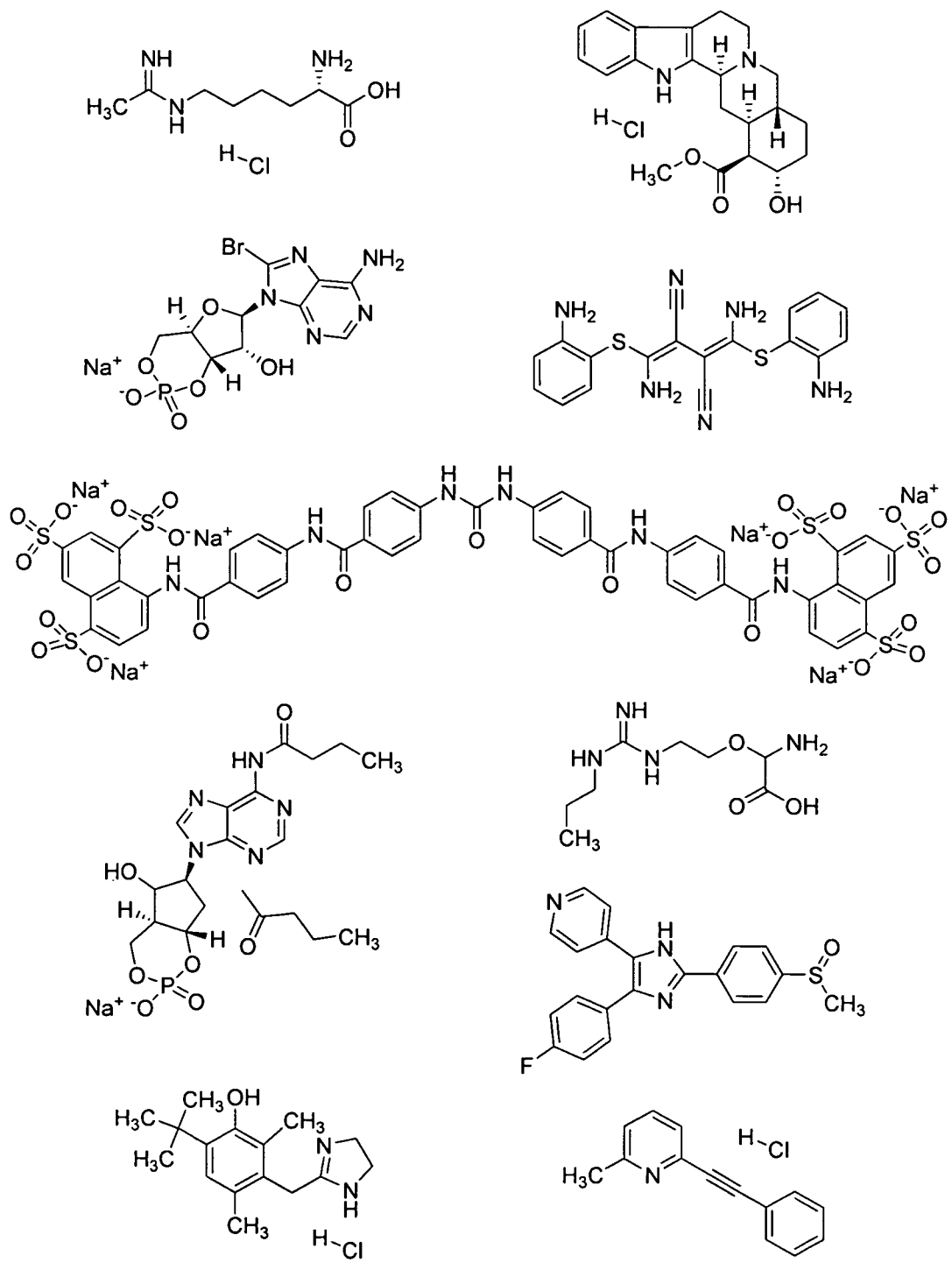
FIG. 17sss

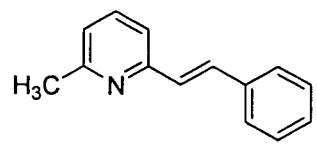
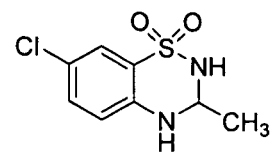
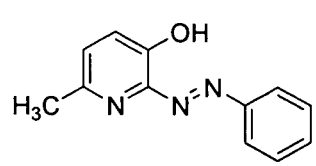
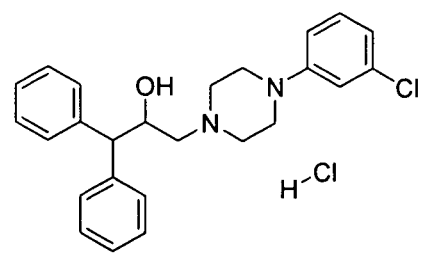
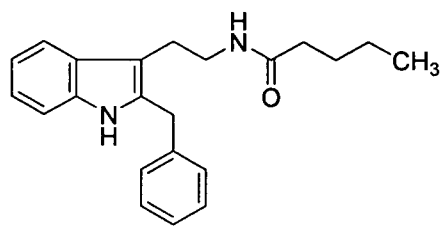
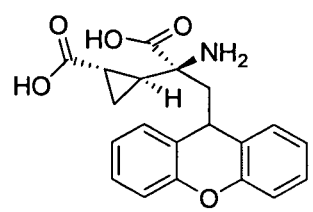
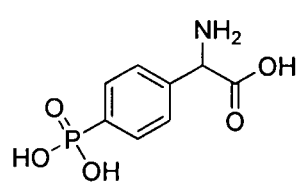
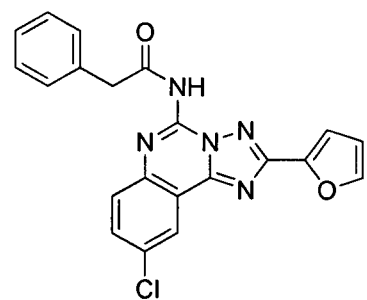
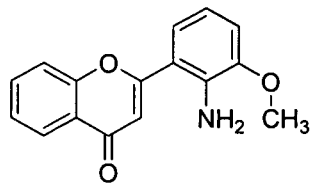
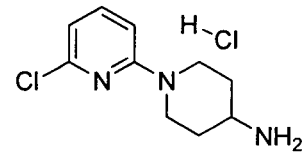
FIG. 17ttt

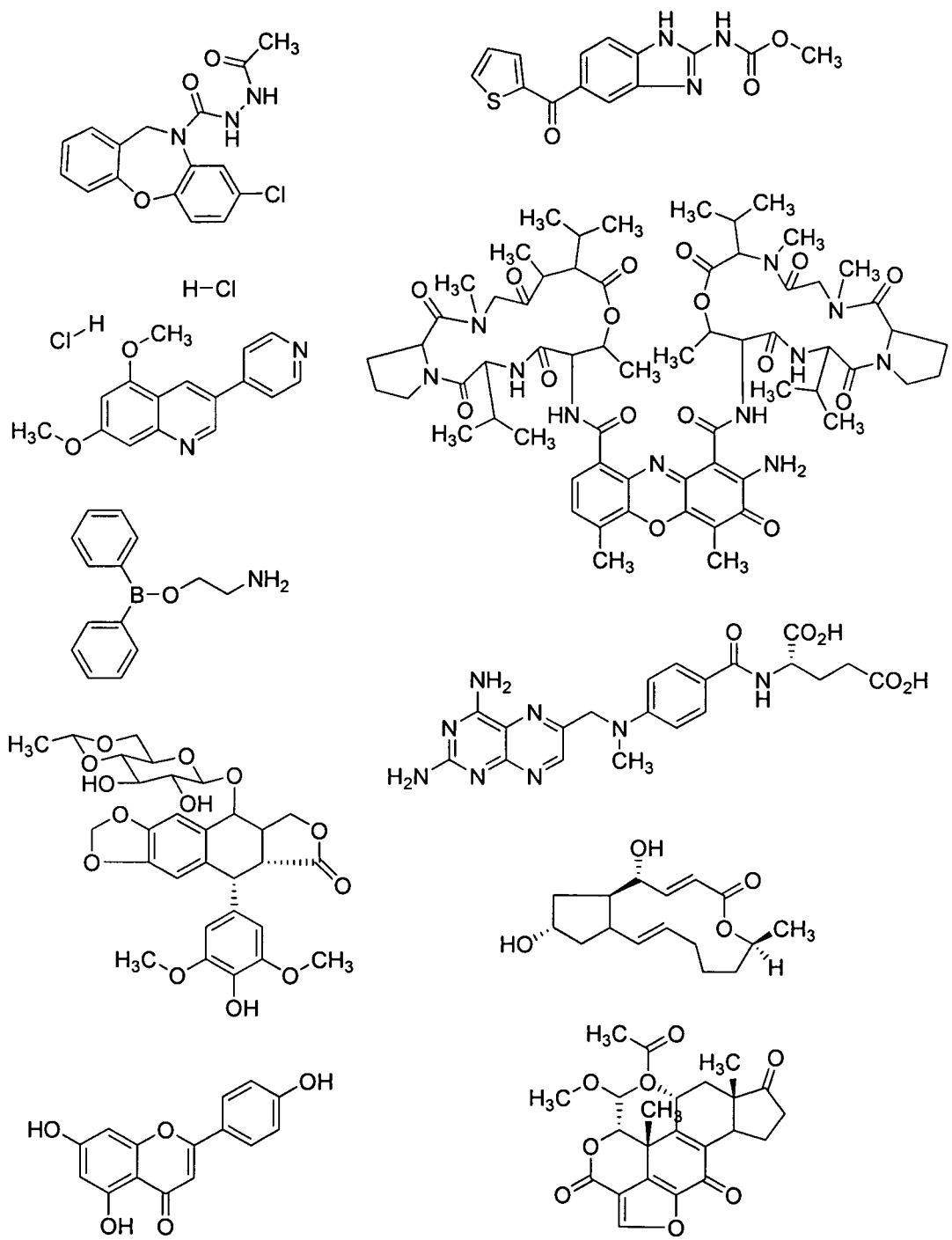
FIG. 17uuu

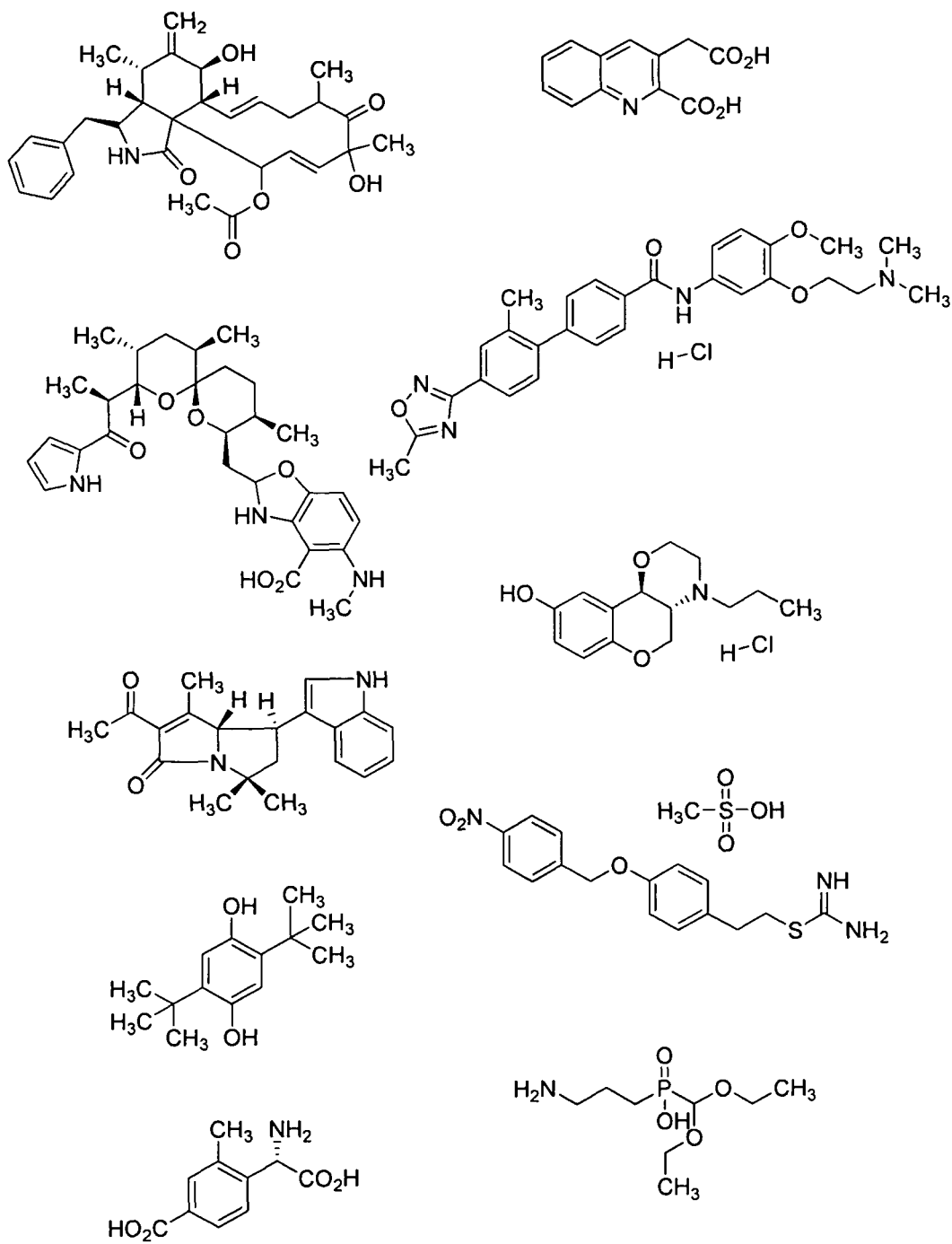
FIG. 17vvv

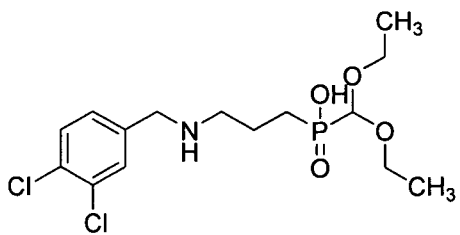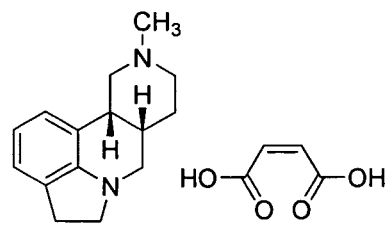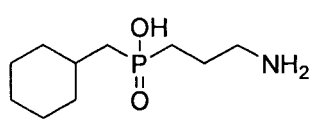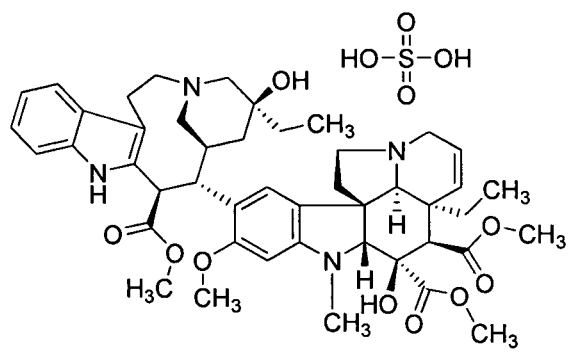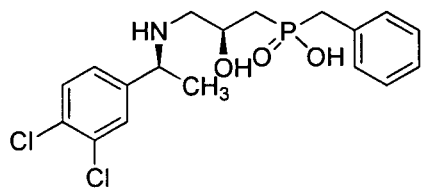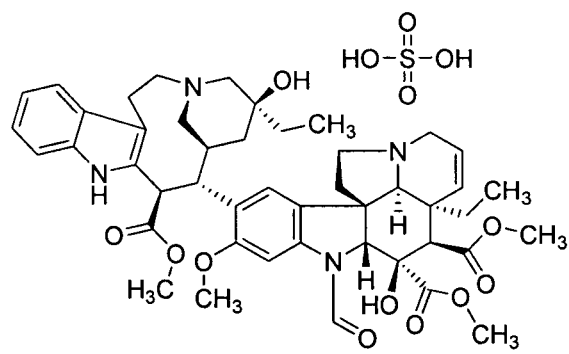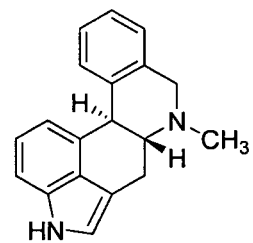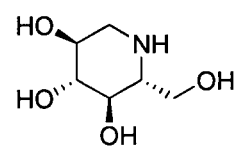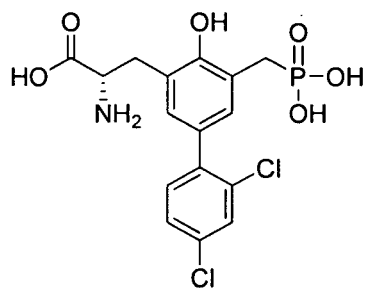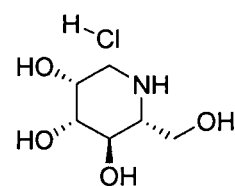
FIG. 17www

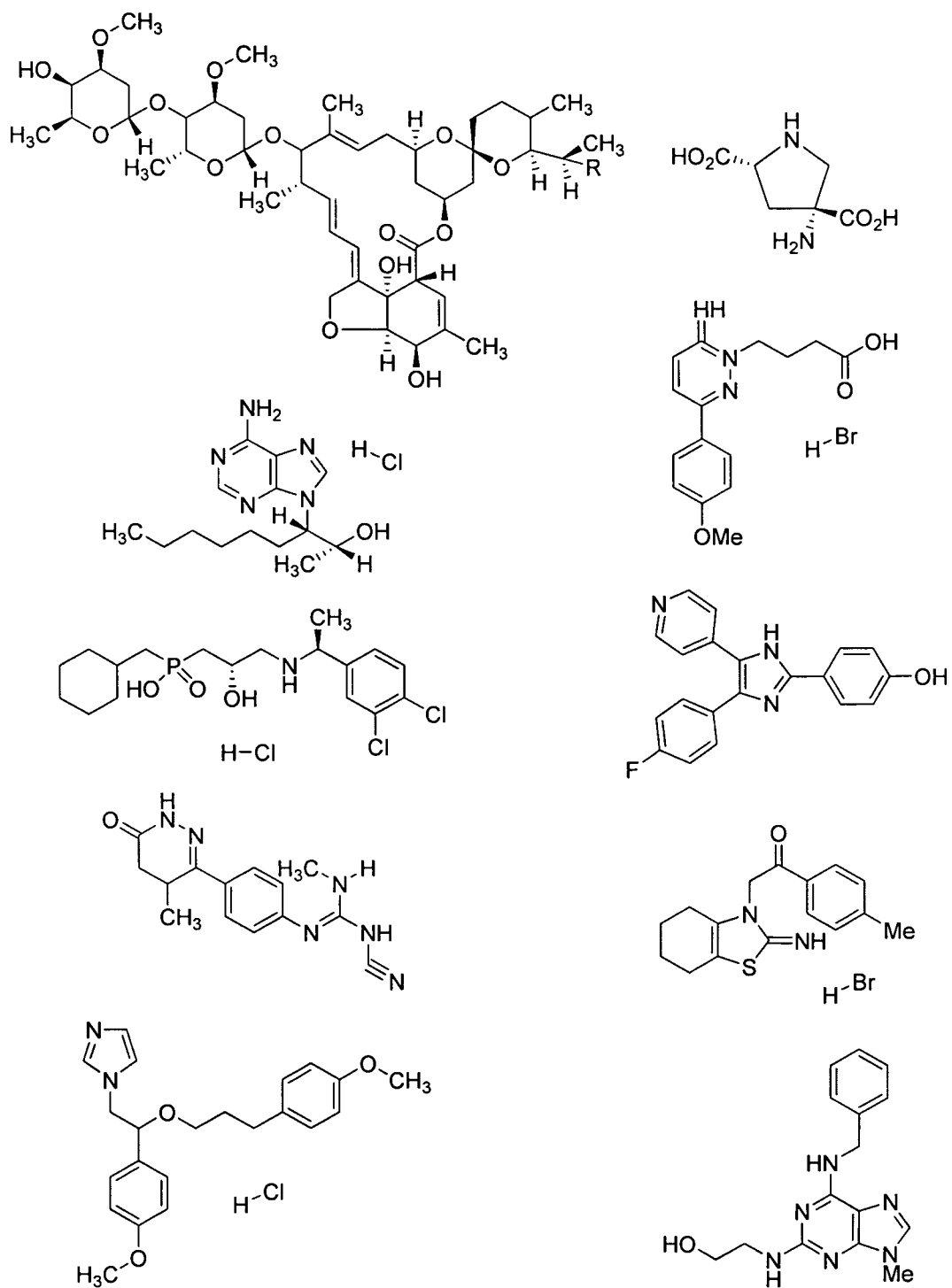
FIG. 17xxx

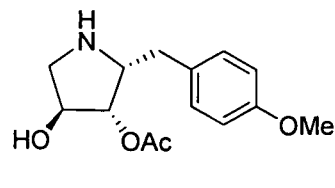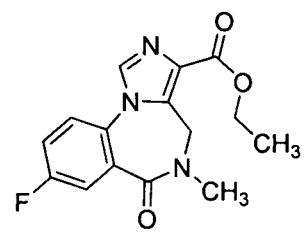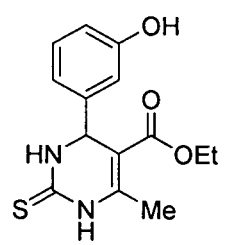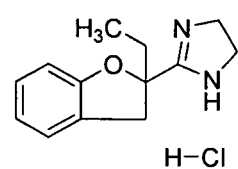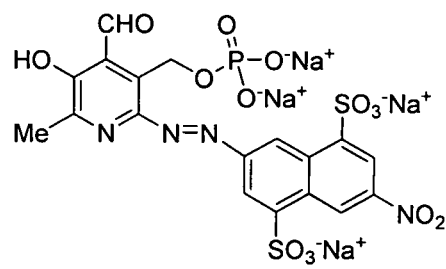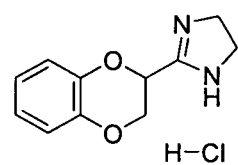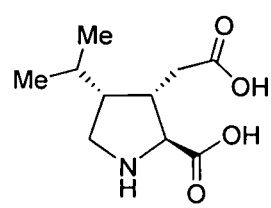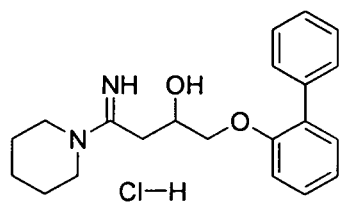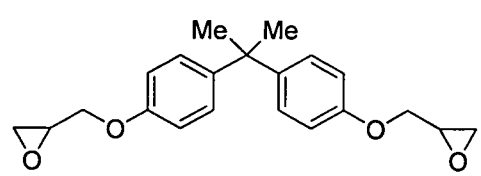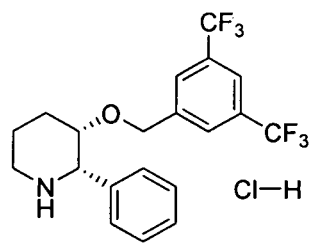
FIG. 17yyy

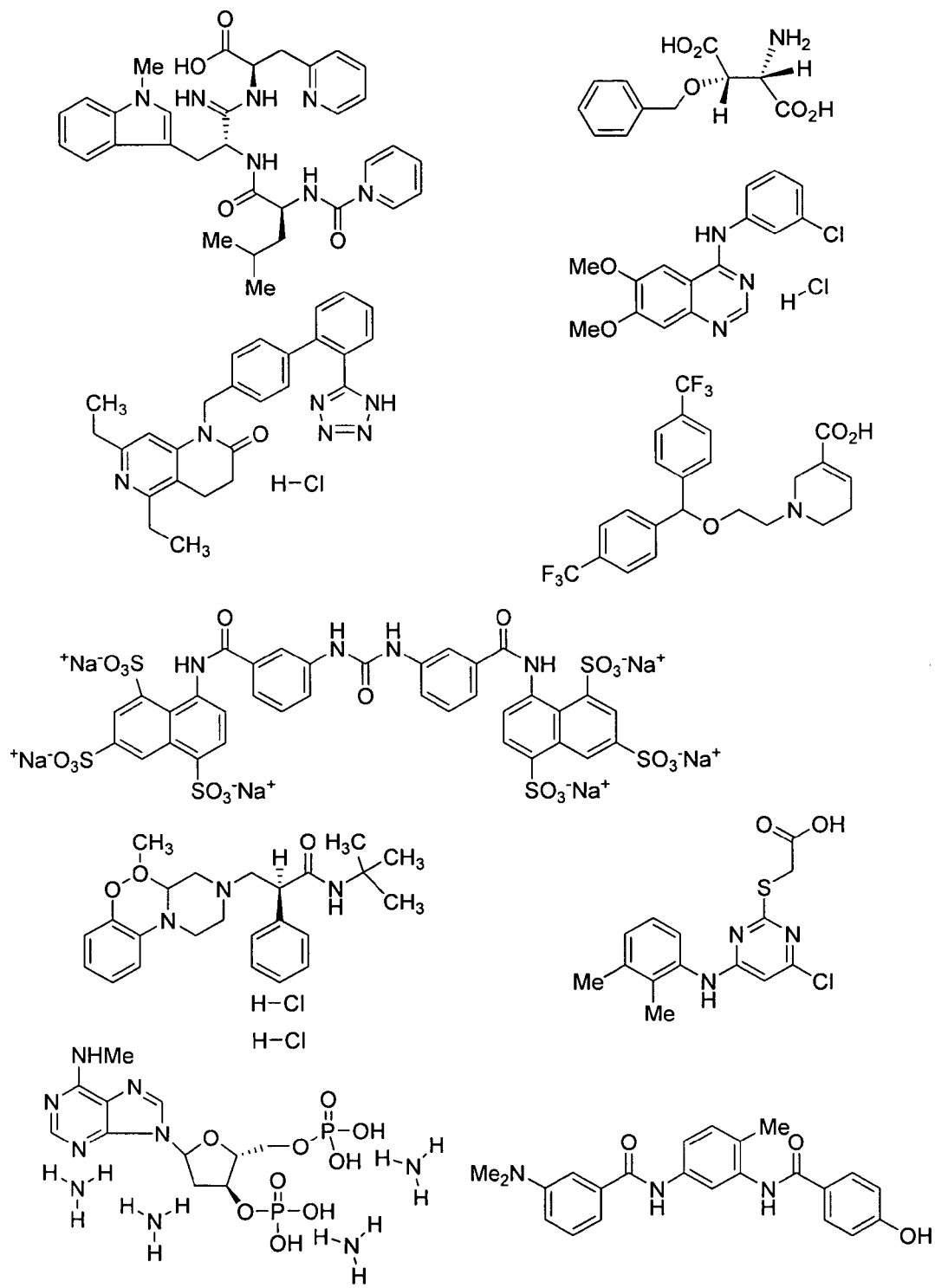
FIG. 17zzz

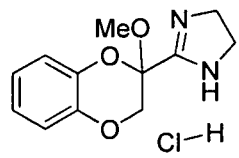
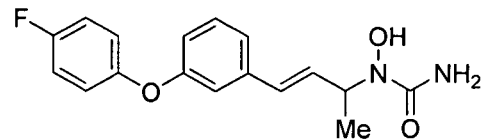
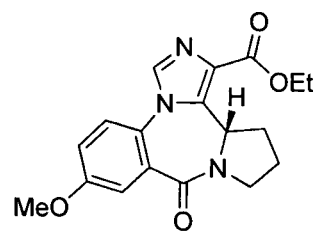
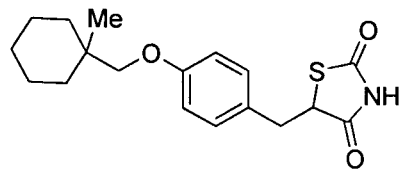
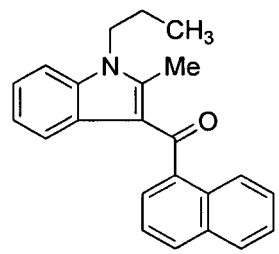
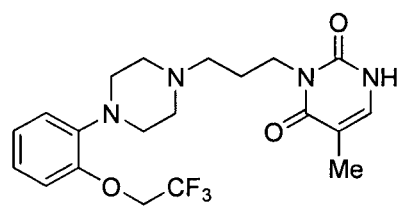
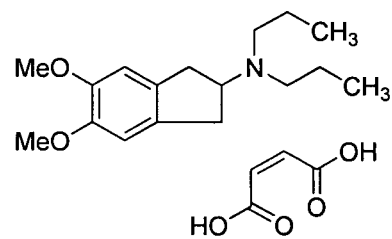
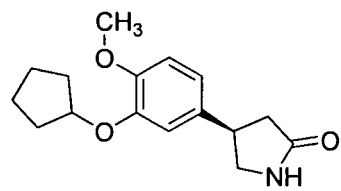
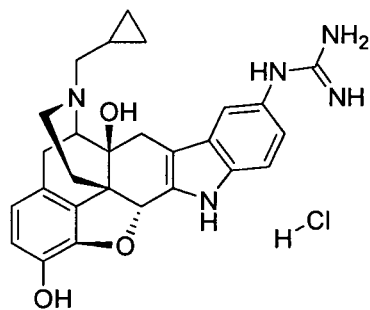
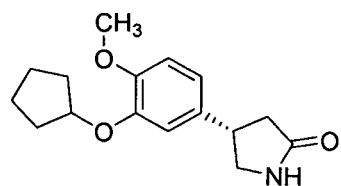
FIG. 17aaaa

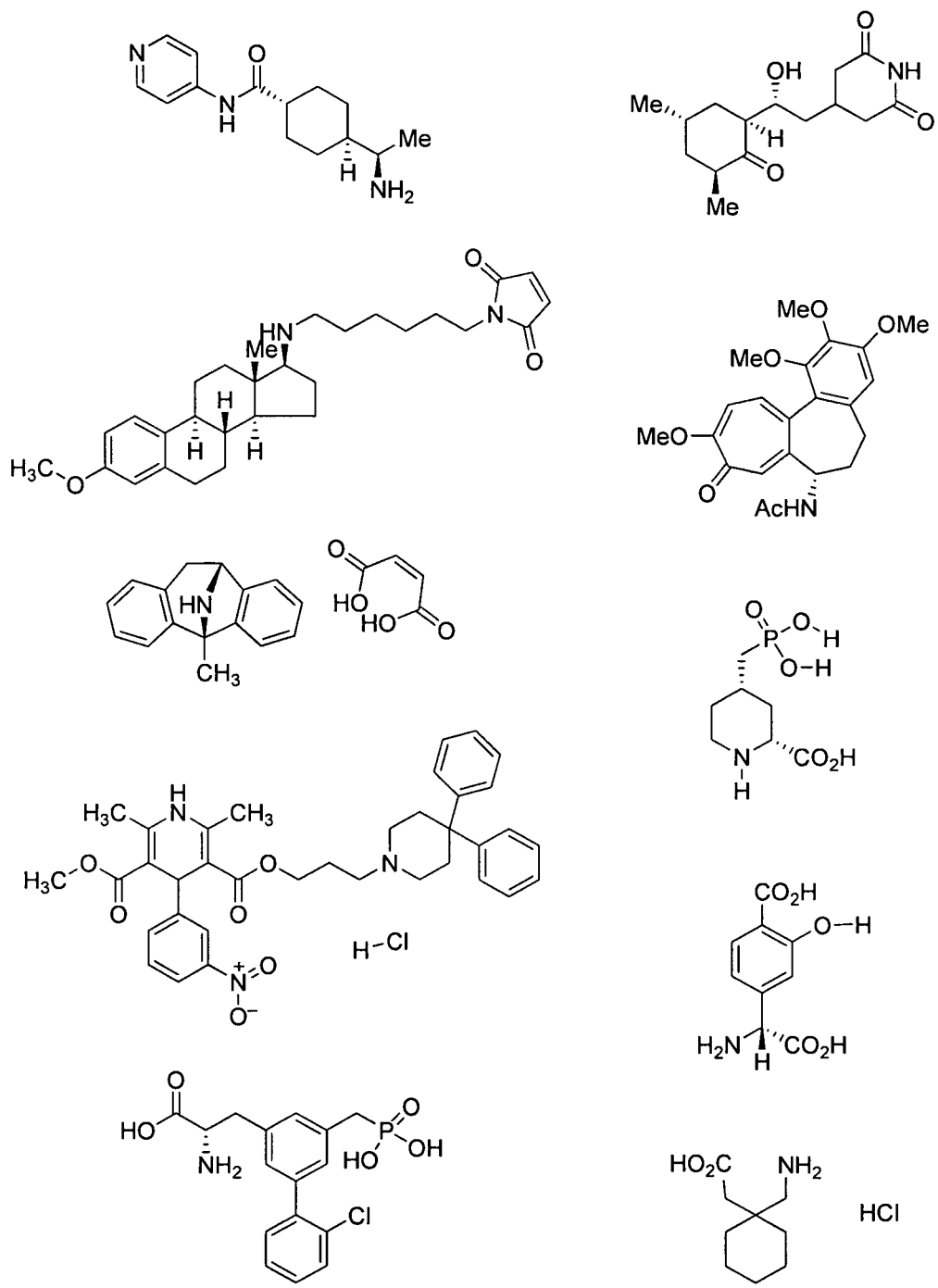
FIG. 17bbbb

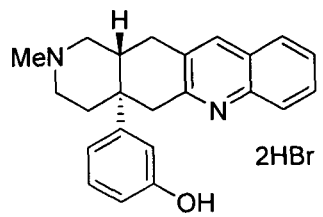
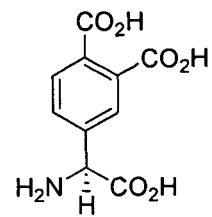
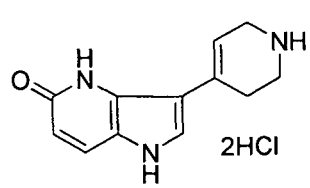
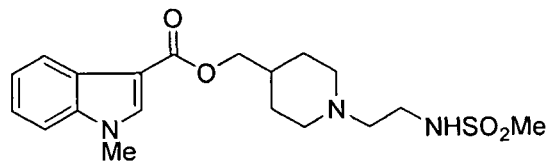
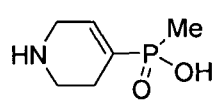
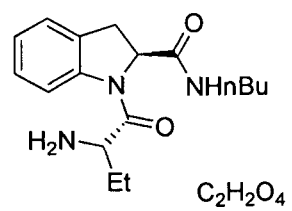
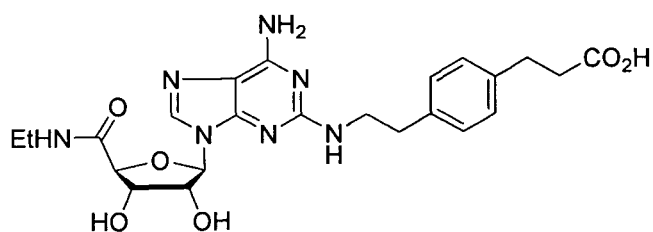
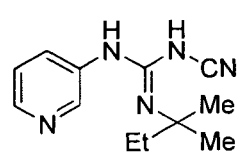
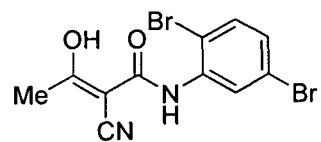
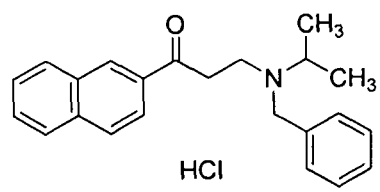
FIG. 17cccc

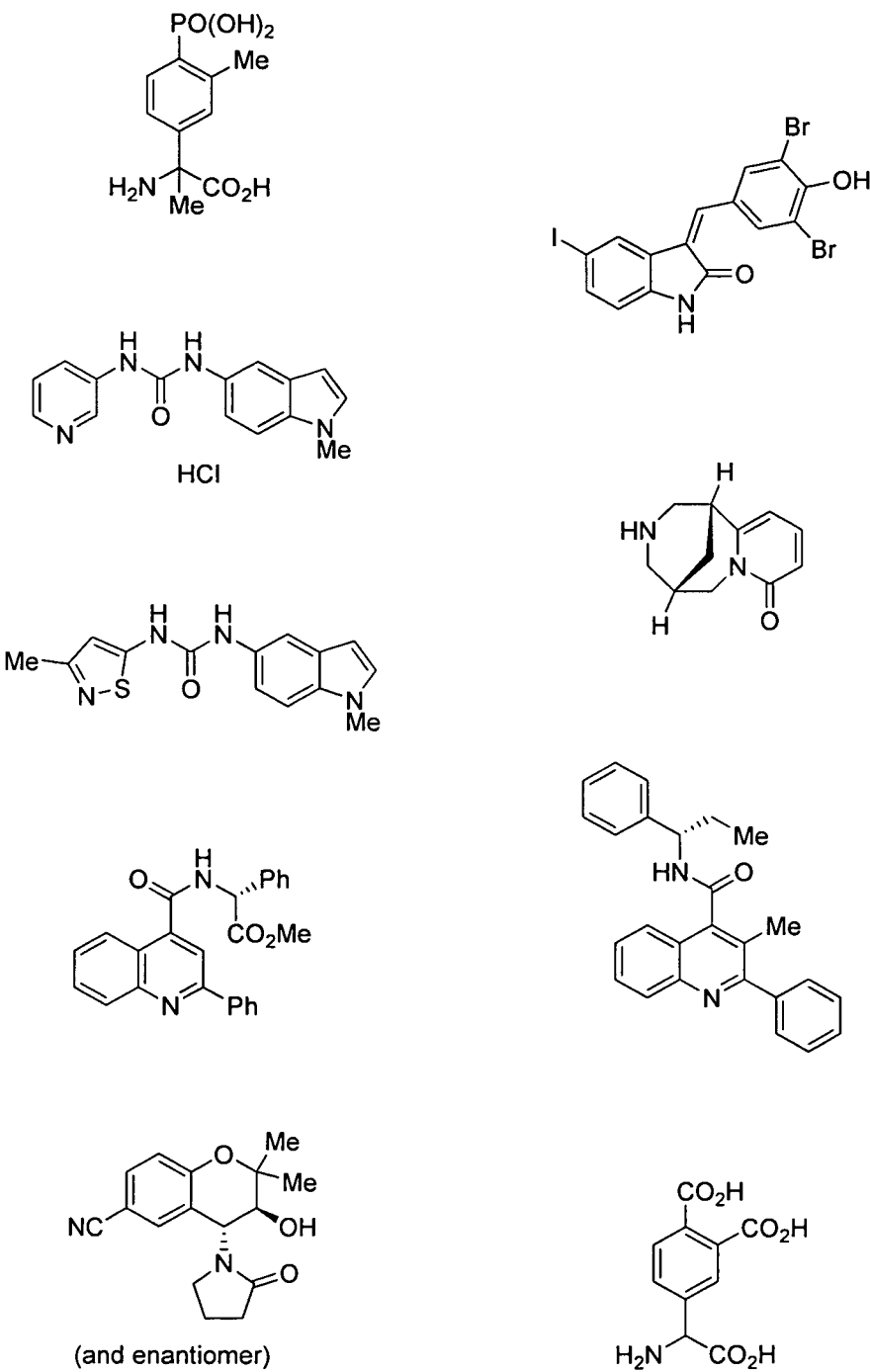
FIG. 17dddd

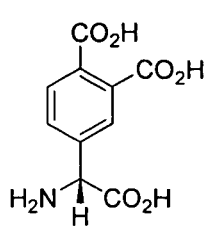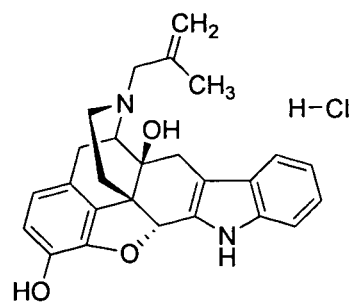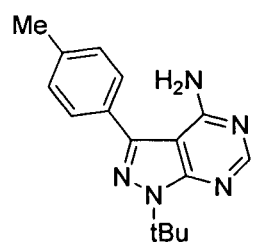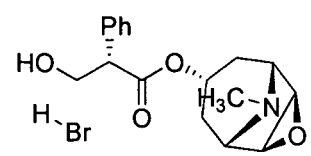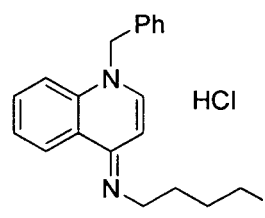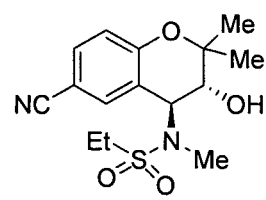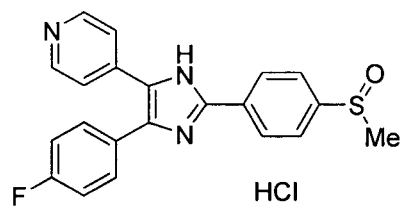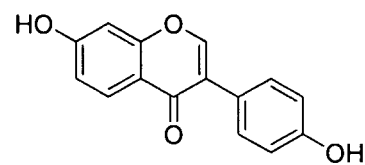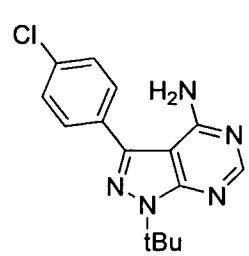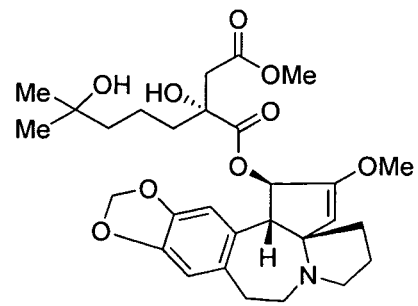
FIG. 17eeee

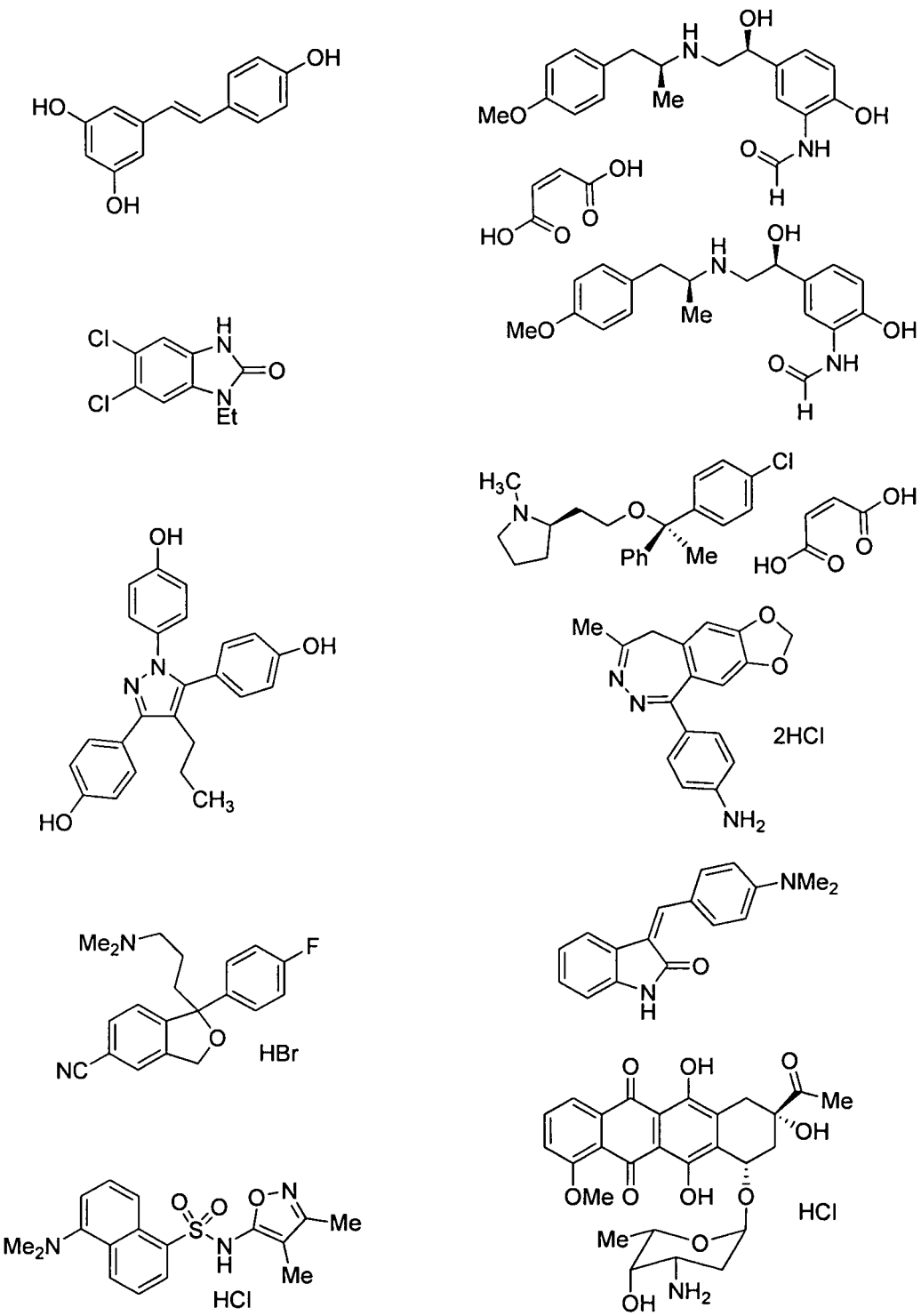
FIG. 17ffff

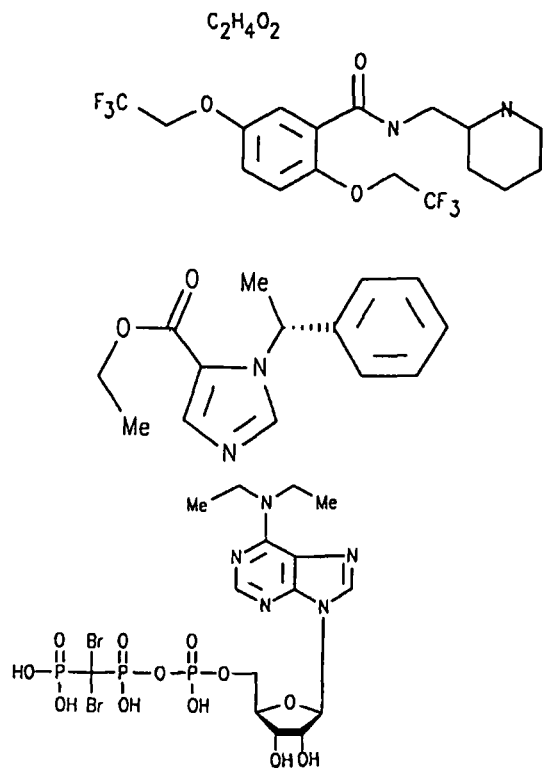

FIG. 17gggg

PEPTIDES AND ANTIBODIES PROBES FOR CENTRAL NERVOUS SYSTEM DISEASES

β-Amyloid Precursor Protein
β-Secretase Inhibitor III
γ-Secretase Inhibitor XII
(±)-Ibuprofen
(S)-(+)-Ibuprofen
Anti-β-Amyloid(1-43)
Anti-BACE1, C-Terminal(485-501)
Anti-Nicastrin, C-Terminal
Anti-Nicastrin, N-Terminal
Anti-Reelin

PEPTIDES FOR ANGIOGENESIS

MT1-MMp Hemopexin Domain, His•Tag®, Human, Recombinant
MT2-MMp Hemopexin Domain, His•Tag®, Human, Recombinant
VEGF Inhibitor

FIG. 17hhhh

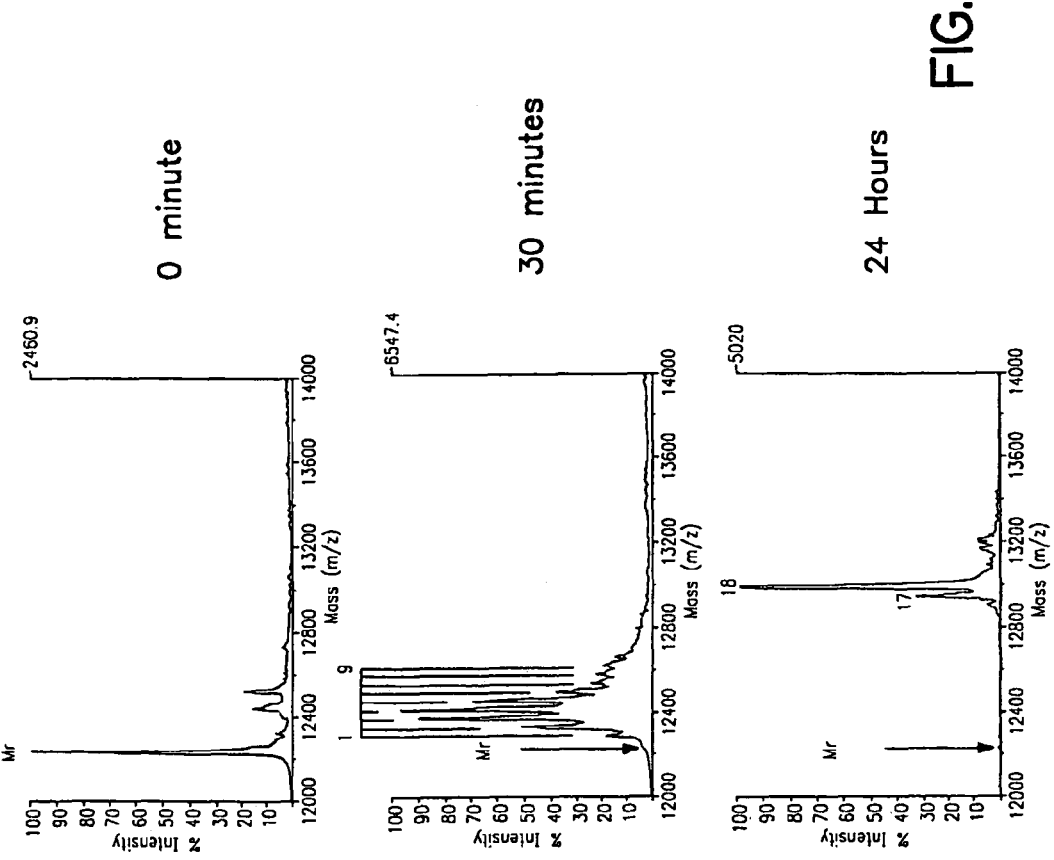
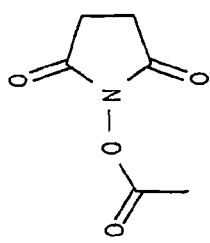
FIG. 20f

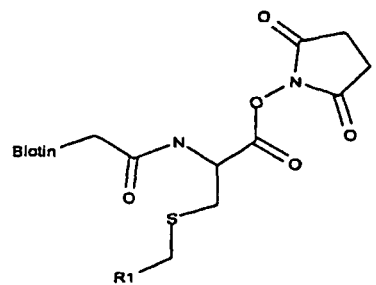
R1 (Selectivity Function)
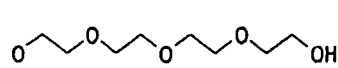 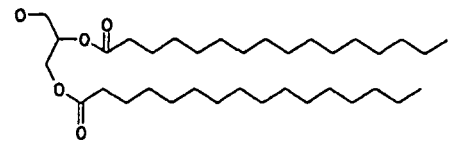
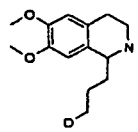 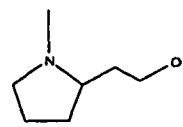
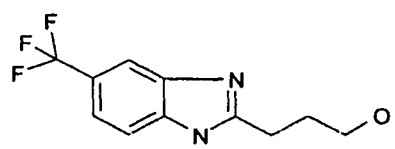 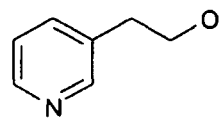
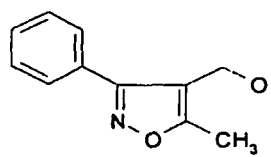 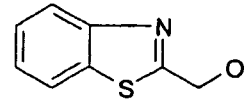
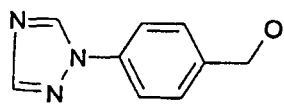 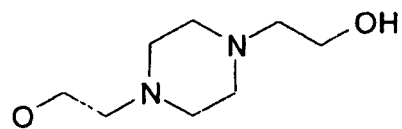
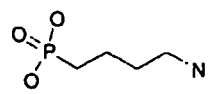 
FIG. 21A

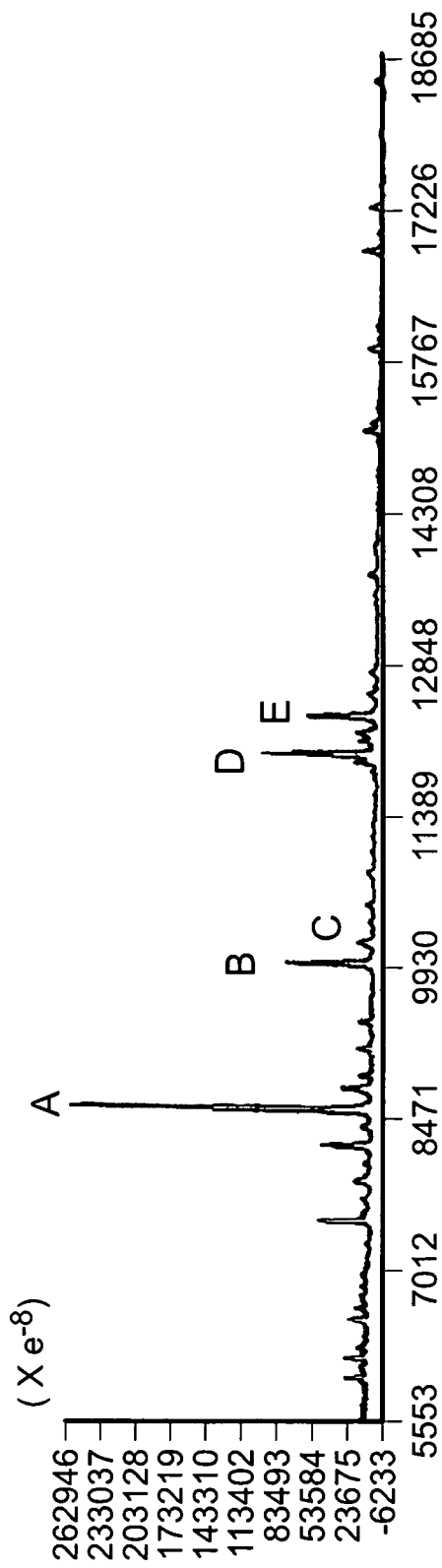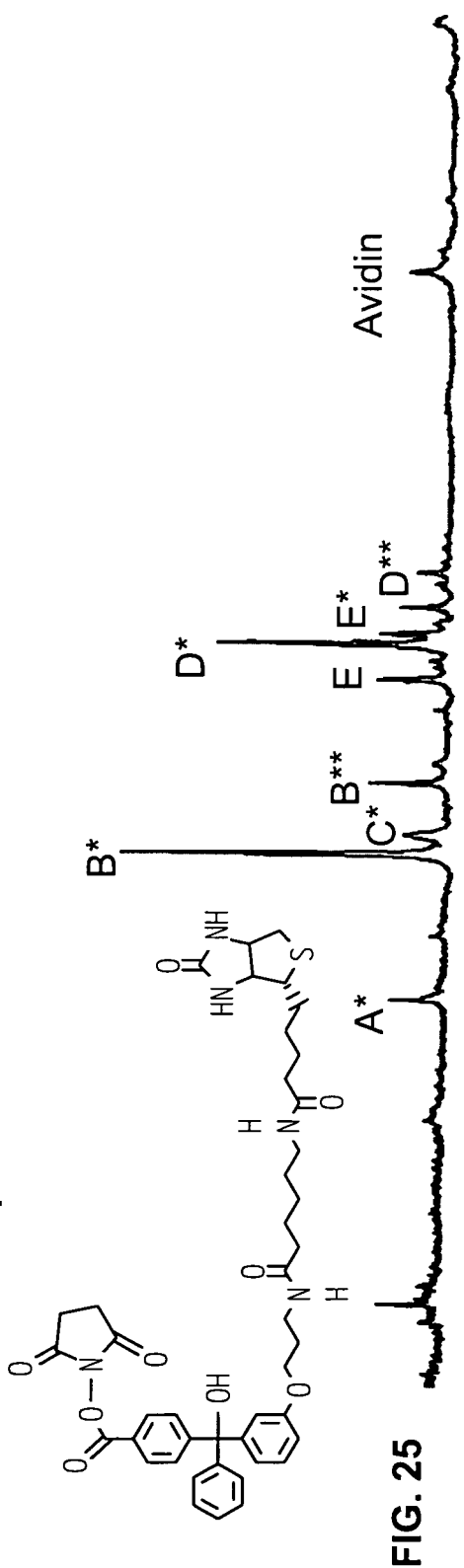
FIG. 25

```
                              SEQUENCE LISTING

<160> NUMBER OF SEQ ID NOS: 158

<210> SEQ ID NO 1
<211> LENGTH: 39
<212> TYPE: PRT
<213> ORGANISM: Homo Sapien

<400> SEQUENCE: 1

Ser Tyr Ser Met Glu His Phe Arg Trp Gly Lys Pro Val Gly Lys Lys
1               5                   10                  15

Arg Arg Pro Val Lys Val Tyr Pro Asn Gly Ala Glu Asp Glu Ser Ala
            20                  25                  30

Glu Ala Phe Pro Leu Glu Phe
        35

<210> SEQ ID NO 2
<211> LENGTH: 52
<212> TYPE: PRT
<213> ORGANISM: Homo Sapien

<400> SEQUENCE: 2

Tyr Arg Gln Ser Met Asn Asn Phe Gln Gly Leu Arg Ser Phe Gly Cys
1               5                   10                  15

Arg Phe Gly Thr Cys Thr Val Gln Lys Leu Ala His Gln Ile Tyr Gln
            20                  25                  30

Phe Thr Asp Lys Asp Lys Asp Asn Val Ala Pro Arg Ser Lys Ile Ser
        35                  40                  45

Pro Gln Gly Tyr
    50

<210> SEQ ID NO 3
<211> LENGTH: 13
<212> TYPE: PRT
<213> ORGANISM: Homo Sapien

<400> SEQUENCE: 3

Ala Pro Ser Gly Ala Gln Arg Leu Tyr Gly Phe Gly Leu
1               5                   10

<210> SEQ ID NO 4
<211> LENGTH: 13
<212> TYPE: PRT
<213> ORGANISM: Homo Sapien

<400> SEQUENCE: 4

Trp Gly Lys Pro Val Ser Tyr Ser Met Glu His Phe Arg
1               5                   10

<210> SEQ ID NO 5
<211> LENGTH: 9
<212> TYPE: PRT
<213> ORGANISM: Homo Sapien

<400> SEQUENCE: 5

Ala Pro Arg Glu Arg Phe Tyr Ser Glu
1               5
```

```
<210> SEQ ID NO 6
<211> LENGTH: 10
<212> TYPE: PRT
<213> ORGANISM: Homo Sapien

<400> SEQUENCE: 6

Tyr Gly Gly Phe Leu Arg Lys Tyr Pro Lys
1               5                   10

<210> SEQ ID NO 7
<211> LENGTH: 14
<212> TYPE: PRT
<213> ORGANISM: Homo Sapien
<220> FEATURE:
<221> NAME/KEY: MOD_RES
<222> LOCATION: 14
<223> OTHER INFORMATION: AMIDATION
<220> FEATURE:
<221> NAME/KEY: MOD_RES
<222> LOCATION: 1
<223> OTHER INFORMATION: PYRROLIDONE CARBOXYLIC ACID

<400> SEQUENCE: 7

Glu Gly Arg Leu Gly Thr Gln Trp Ala Val Gly His Leu Met
1               5                   10

<210> SEQ ID NO 8
<211> LENGTH: 37
<212> TYPE: PRT
<213> ORGANISM: Homo Sapien

<400> SEQUENCE: 8

Lys Cys Asn Thr Ala Thr Cys Ala Thr Asn Arg Leu Ala Asn Phe Leu
1               5                   10                  15

Val His Ser Ser Asn Asn Phe Gly Ala Ile Leu Ser Ser Thr Asn Val
            20                  25                  30

Gly Ser Asn Thr Tyr
        35

<210> SEQ ID NO 9
<211> LENGTH: 10
<212> TYPE: PRT
<213> ORGANISM: Homo Sapien

<400> SEQUENCE: 9

Asp Arg Val Tyr Ile His Pro Phe His Leu
1               5                   10

<210> SEQ ID NO 10
<211> LENGTH: 8
<212> TYPE: PRT
<213> ORGANISM: Homo Sapien

<400> SEQUENCE: 10

Asp Arg Val Tyr Ile His Pro Phe
1               5

<210> SEQ ID NO 11
<211> LENGTH: 7
<212> TYPE: PRT
<213> ORGANISM: Homo Sapien

<400> SEQUENCE: 11

Arg Val Tyr Ile His Pro Phe
1               5
```

```
<210> SEQ ID NO 12
<211> LENGTH: 13
<212> TYPE: PRT
<213> ORGANISM: Homo Sapien

<400> SEQUENCE: 12

Asn Arg Pro Arg Leu Ser His Leu Gly Pro Met Pro Phe
1               5                   10

<210> SEQ ID NO 13
<211> LENGTH: 29
<212> TYPE: PRT
<213> ORGANISM: Homo Sapien
<220> FEATURE:
<221> NAME/KEY: MOD_RES
<222> LOCATION: 1
<223> OTHER INFORMATION: Xaa is D-Phe
<220> FEATURE:
<221> NAME/KEY: MOD_RES
<222> LOCATION: 10
<223> OTHER INFORMATION: Nle
<220> FEATURE:
<221> NAME/KEY: MOD_RES
<222> LOCATION: 26
<223> OTHER INFORMATION: Nle

<400> SEQUENCE: 13

Xaa His Leu Leu Arg Glu Val Leu Glu Leu Ala Arg Ala Glu Gln Leu
1               5                   10                  15

Ala Gln Glu Ala His Lys Asn Arg Leu Leu Glu Ile Ile
            20                  25

<210> SEQ ID NO 14
<211> LENGTH: 28
<212> TYPE: PRT
<213> ORGANISM: Homo Sapien

<400> SEQUENCE: 14

Ser Leu Arg Arg Ser Ser Cys Phe Gly Gly Arg Met Asp Arg Ile Gly
1               5                   10                  15

Ala Gln Ser Gly Leu Gly Cys Asn Ser Phe Arg Tyr
            20                  25

<210> SEQ ID NO 15
<211> LENGTH: 13
<212> TYPE: PRT
<213> ORGANISM: Homo Sapien

<400> SEQUENCE: 15

Lys Lys Ala Leu Arg Arg Gln Glu Thr Val Asp Ala Leu
1               5                   10

<210> SEQ ID NO 16
<211> LENGTH: 12
<212> TYPE: PRT
<213> ORGANISM: Homo Sapien

<400> SEQUENCE: 16

Tyr Gly Gly Phe Met Arg Arg Val Gly Arg Pro Glu
1               5                   10

<210> SEQ ID NO 17
<211> LENGTH: 14
<212> TYPE: PRT
<213> ORGANISM: Homo Sapien
```

<400> SEQUENCE: 17

Tyr Gly Gly Phe Met Arg Arg Val Gly Arg Pro Glu Trp Trp
1               5                   10

<210> SEQ ID NO 18
<211> LENGTH: 12
<212> TYPE: PRT
<213> ORGANISM: Homo Sapien

<400> SEQUENCE: 18

Tyr Gly Gly Phe Met Arg Arg Val Gly Arg Pro Glu
1               5                   10

<210> SEQ ID NO 19
<211> LENGTH: 31
<212> TYPE: PRT
<213> ORGANISM: Homo Sapien

<400> SEQUENCE: 19

Tyr Gly Gly Phe Met Thr Ser Glu Lys Ser Gln Thr Pro Leu Val Thr
1               5                   10                  15

Leu Phe Lys Asn Ala Ile Ile Lys Asn Ala Tyr Lys Lys Gly Glu
            20                  25                  30

<210> SEQ ID NO 20
<211> LENGTH: 22
<212> TYPE: PRT
<213> ORGANISM: Homo Sapien

<400> SEQUENCE: 20

Ala Glu Lys Lys Asp Glu Gly Pro Tyr Arg Met Glu His Phe Arg Trp
1               5                   10                  15

Gly Ser Pro Pro Lys Asp
            20

<210> SEQ ID NO 21
<211> LENGTH: 9
<212> TYPE: PRT
<213> ORGANISM: Homo Sapien

<400> SEQUENCE: 21

Tyr Gly Gly Phe Leu Arg Lys Tyr Pro
1               5

<210> SEQ ID NO 22
<211> LENGTH: 43
<212> TYPE: PRT
<213> ORGANISM: Homo Sapien

<400> SEQUENCE: 22

Asp Ala Glu Phe Arg His Ala Ser Gly Tyr Glu Val His His Gln Lys
1               5                   10                  15

Leu Val Phe Phe Ala Glu Asp Val Gly Ser Asn Leu Gly Ala Ile Ile
            20                  25                  30

Gly Leu Met Val Gly Gly Val Val Ile Ala Thr
            35                  40

<210> SEQ ID NO 23
<211> LENGTH: 5
<212> TYPE: PRT
<213> ORGANISM: Homo Sapien

```
<400> SEQUENCE: 23

Arg Leu Arg Phe His
1               5

<210> SEQ ID NO 24
<211> LENGTH: 32
<212> TYPE: PRT
<213> ORGANISM: Homo Sapien

<400> SEQUENCE: 24

Ser Pro Lys Met Val Gln Gly Ser Gly Cys Phe Gly Arg Lys Met Asp
1               5                   10                  15

Arg Ile Ser Ser Ser Ser Gly Leu Gly Cys Lys Val Leu Arg Arg His
            20                  25                  30

<210> SEQ ID NO 25
<211> LENGTH: 9
<212> TYPE: PRT
<213> ORGANISM: Homo Sapien

<400> SEQUENCE: 25

Arg Pro Pro Gly Phe Ser Pro Phe Arg
1               5

<210> SEQ ID NO 26
<211> LENGTH: 11
<212> TYPE: PRT
<213> ORGANISM: Homo Sapien
<220> FEATURE:
<221> NAME/KEY: MOD_RES
<222> LOCATION: 11
<223> OTHER INFORMATION: AMIDATION

<400> SEQUENCE: 26

Gly Met Asp Ser Leu Ala Phe Ser Gly Gly Leu
1               5                   10

<210> SEQ ID NO 27
<211> LENGTH: 3
<212> TYPE: PRT
<213> ORGANISM: Homo Sapien
<220> FEATURE:
<221> NAME/KEY: MOD_RES
<222> LOCATION: 3
<223> OTHER INFORMATION: AMIDATION

<400> SEQUENCE: 27

Lys His Gly
1

<210> SEQ ID NO 28
<211> LENGTH: 11
<212> TYPE: PRT
<213> ORGANISM: Homo Sapien

<400> SEQUENCE: 28

Ala Ser Lys Lys Pro Lys Arg Asn Ile Lys Ala
1               5                   10

<210> SEQ ID NO 29
<211> LENGTH: 10
<212> TYPE: PRT
<213> ORGANISM: Homo Sapien
<220> FEATURE:
<221> NAME/KEY: MOD_RES
<222> LOCATION: 4
```

```
<223> OTHER INFORMATION: SULFATATION
<220> FEATURE:
<221> NAME/KEY: MOD_RES
<222> LOCATION: 1
<223> OTHER INFORMATION: PYRROLIDONE CARBOXYLIC ACID

<400> SEQUENCE: 29

Glu Gln Asp Tyr Thr Gly Trp Met Asp Phe
1               5                   10

<210> SEQ ID NO 30
<211> LENGTH: 28
<212> TYPE: PRT
<213> ORGANISM: Homo Sapien

<400> SEQUENCE: 30

Ala Ile Pro Ile Thr Ser Phe Glu Glu Ala Lys Gly Leu Asp Arg Ile
1               5                   10                  15

Asn Glu Arg Met Pro Pro Arg Arg Asp Ala Met Pro
            20                  25

<210> SEQ ID NO 31
<211> LENGTH: 32
<212> TYPE: PRT
<213> ORGANISM: Homo Sapien

<400> SEQUENCE: 31

Cys Gly Asn Leu Ser Thr Cys Met Leu Gly Thr Tyr Thr Gln Asp Phe
1               5                   10                  15

Asn Lys Phe His Thr Phe Pro Gln Thr Ala Ile Gly Val Gly Ala Pro
            20                  25                  30

<210> SEQ ID NO 32
<211> LENGTH: 27
<212> TYPE: PRT
<213> ORGANISM: Homo Sapien

<400> SEQUENCE: 32

Asp Pro Met Ser Ser Thr Tyr Ile Glu Glu Leu Gly Lys Arg Glu Val
1               5                   10                  15

Thr Ile Pro Pro Lys Tyr Arg Glu Leu Leu Ala
            20                  25

<210> SEQ ID NO 33
<211> LENGTH: 25
<212> TYPE: PRT
<213> ORGANISM: Homo Sapien

<400> SEQUENCE: 33

Asn Gln Gly Arg His Phe Cys Gly Gly Ala Glu Ile His Ala Arg Phe
1               5                   10                  15

Val Met Thr Ala Ala Ser Cys Phe Asn
            20                  25

<210> SEQ ID NO 34
<211> LENGTH: 30
<212> TYPE: PRT
<213> ORGANISM: Homo Sapien

<400> SEQUENCE: 34

Asn Pro Met Tyr Asn Ala Val Ser Asn Ala Asp Leu Met Asp Phe Lys
1               5                   10                  15

Asn Leu Leu Asp His Leu Glu Glu Lys Met Pro Leu Glu Asp
```

<210> SEQ ID NO 35
<211> LENGTH: 18
<212> TYPE: PRT
<213> ORGANISM: Homo Sapien

<400> SEQUENCE: 35

Cys Asn Leu Ala Val Ala Ala Ser His Ile Tyr Gln Asn Gln Phe
1               5                   10                  15

Val Gln

<210> SEQ ID NO 36
<211> LENGTH: 35
<212> TYPE: PRT
<213> ORGANISM: Homo Sapien

<400> SEQUENCE: 36

Lys Trp Lys Val Phe Lys Lys Ile Glu Lys Met Gly Arg Asn Ile Arg
1               5                   10                  15

Asn Gly Ile Val Lys Ala Gly Pro Ala Ile Ala Val Leu Gly Glu Ala
            20                  25                  30

Lys Ala Leu
        35

<210> SEQ ID NO 37
<211> LENGTH: 16
<212> TYPE: PRT
<213> ORGANISM: Homo Sapien

<400> SEQUENCE: 37

Ser Gly Ser Ala Lys Val Ala Phe Ser Ala Ile Arg Ser Thr Asn His
1               5                   10                  15

<210> SEQ ID NO 38
<211> LENGTH: 37
<212> TYPE: PRT
<213> ORGANISM: Homo Sapien

<400> SEQUENCE: 38

Ala Cys Asp Thr Ala Thr Cys Val Thr His Arg Leu Ala Gly Leu Leu
1               5                   10                  15

Ser Arg Ser Gly Gly Val Val Lys Asn Asn Phe Val Pro Thr Asn Val
            20                  25                  30

Gly Ser Lys Ala Phe
        35

<210> SEQ ID NO 39
<211> LENGTH: 37
<212> TYPE: PRT
<213> ORGANISM: Homo Sapien

<400> SEQUENCE: 39

Ala Cys Asn Thr Ala Thr Cys Val Thr His Arg Leu Ala Gly Leu Leu
1               5                   10                  15

Ser Arg Ser Gly Gly Met Val Lys Ser Asn Phe Val Pro Thr Asn Val
            20                  25                  30

Gly Ser Lys Ala Phe
        35

<210> SEQ ID NO 40

```
<211> LENGTH: 17
<212> TYPE: PRT
<213> ORGANISM: Homo Sapien

<400> SEQUENCE: 40

Leu Gln Asn Arg Arg Gly Leu Asp Leu Leu Phe Leu Lys Glu Gly Gly
1               5                   10                  15

Leu

<210> SEQ ID NO 41
<211> LENGTH: 29
<212> TYPE: PRT
<213> ORGANISM: Homo Sapien

<400> SEQUENCE: 41

Gln Glu Gly Ala Pro Pro Gln Gln Ser Ala Arg Arg Asp Arg Met Pro
1               5                   10                  15

Cys Arg Asn Phe Phe Trp Lys Thr Phe Ser Ser Cys Lys
            20                  25

<210> SEQ ID NO 42
<211> LENGTH: 2
<212> TYPE: PRT
<213> ORGANISM: Homo Sapien

<400> SEQUENCE: 42

Trp Gly
1

<210> SEQ ID NO 43
<211> LENGTH: 30
<212> TYPE: PRT
<213> ORGANISM: Homo Sapien

<400> SEQUENCE: 43

Ala Cys Tyr Cys Arg Ile Pro Ala Cys Ile Ala Gly Glu Arg Arg Tyr
1               5                   10                  15

Gly Thr Cys Ile Tyr Gln Gly Arg Leu Trp Ala Phe Cys Cys
            20                  25                  30

<210> SEQ ID NO 44
<211> LENGTH: 29
<212> TYPE: PRT
<213> ORGANISM: Homo Sapien

<400> SEQUENCE: 44

Cys Tyr Cys Arg Ile Pro Ala Cys Ile Ala Gly Glu Arg Arg Tyr Gly
1               5                   10                  15

Thr Cys Ile Tyr Gln Gly Arg Leu Trp Ala Phe Cys Cys
            20                  25

<210> SEQ ID NO 45
<211> LENGTH: 33
<212> TYPE: PRT
<213> ORGANISM: Homo Sapien

<400> SEQUENCE: 45

Ala Leu Trp Lys Thr Met Leu Lys Lys Leu Gly Thr Met Ala Leu His
1               5                   10                  15

Ala Gly Lys Ala Ala Leu Gly Ala Ala Ala Asp Thr Ile Ser Gln Thr
            20                  25                  30

Gln
```

```
<210> SEQ ID NO 46
<211> LENGTH: 17
<212> TYPE: PRT
<213> ORGANISM: Homo Sapien

<400> SEQUENCE: 46

Tyr Gly Gly Phe Leu Arg Arg Ile Arg Pro Lys Leu Lys Trp Asp Asn
 1               5                  10                  15

Gln

<210> SEQ ID NO 47
<211> LENGTH: 13
<212> TYPE: PRT
<213> ORGANISM: Homo Sapien

<400> SEQUENCE: 47

Tyr Gly Gly Phe Leu Arg Arg Gln Phe Lys Val Val Thr
 1               5                  10

<210> SEQ ID NO 48
<211> LENGTH: 11
<212> TYPE: PRT
<213> ORGANISM: Homo Sapien
<220> FEATURE:
<221> NAME/KEY: MOD_RES
<222> LOCATION: 11
<223> OTHER INFORMATION: AMIDATION
<220> FEATURE:
<221> NAME/KEY: MOD_RES
<222> LOCATION: 1
<223> OTHER INFORMATION: PYRROLIDONE CARBOXYLIC ACID

<400> SEQUENCE: 48

Glu Pro Ser Lys Asp Ala Phe Ile Gly Leu Met
 1               5                  10

<210> SEQ ID NO 49
<211> LENGTH: 4
<212> TYPE: PRT
<213> ORGANISM: Homo Sapien

<400> SEQUENCE: 49

Tyr Pro Trp Phe
 1

<210> SEQ ID NO 50
<211> LENGTH: 4
<212> TYPE: PRT
<213> ORGANISM: Homo Sapien

<400> SEQUENCE: 50

Tyr Pro Phe Phe
 1

<210> SEQ ID NO 51
<211> LENGTH: 21
<212> TYPE: PRT
<213> ORGANISM: Homo Sapien

<400> SEQUENCE: 51

Cys Ser Cys Ser Ser Leu Met Asp Lys Glu Cys Val Tyr Phe Cys His
 1               5                  10                  15

Leu Asp Ile Ile Trp
            20
```

```
<210> SEQ ID NO 52
<211> LENGTH: 39
<212> TYPE: PRT
<213> ORGANISM: Homo Sapien
<220> FEATURE:
<221> NAME/KEY: MOD_RES
<222> LOCATION: 39
<223> OTHER INFORMATION: AMIDATION

<400> SEQUENCE: 52

His Ser Asp Gly Thr Phe Thr Ser Asp Leu Ser Lys Gln Met Glu Glu
 1               5                  10                  15

Glu Ala Val Arg Leu Phe Ile Glu Trp Leu Lys Asn Gly Gly Pro Ser
            20                  25                  30

Ser Gly Ala Pro Pro Ser
        35

<210> SEQ ID NO 53
<211> LENGTH: 17
<212> TYPE: PRT
<213> ORGANISM: Homo Sapien

<400> SEQUENCE: 53

Ala Ala Asp Ser Gly Glu Gly Asp Phe Leu Ala Glu Gly Gly Gly Val
 1               5                  10                  15

Arg

<210> SEQ ID NO 54
<211> LENGTH: 15
<212> TYPE: PRT
<213> ORGANISM: Homo Sapien

<400> SEQUENCE: 54

Asx Gln Gly Val Asn Asp Asn Glu Glu Gly Phe Phe Ser Ala Arg
 1               5                  10                  15

<210> SEQ ID NO 55
<211> LENGTH: 8
<212> TYPE: PRT
<213> ORGANISM: Homo Sapien

<400> SEQUENCE: 55

Glu Ile Leu Asp Val Pro Ser Thr
 1               5

<210> SEQ ID NO 56
<211> LENGTH: 4
<212> TYPE: PRT
<213> ORGANISM: Homo Sapien

<400> SEQUENCE: 56

Phe Met Arg Phe
 1

<210> SEQ ID NO 57
<211> LENGTH: 30
<212> TYPE: PRT
<213> ORGANISM: Homo Sapien

<400> SEQUENCE: 57

Gly Trp Thr Leu Asn Ser Ala Gly Tyr Leu Leu Gly Pro His Ala Val
 1               5                  10                  15
```

Gly Asn His Arg Ser Phe Ser Asp Lys Asn Gly Leu Thr Ser
             20                  25                  30

<210> SEQ ID NO 58
<211> LENGTH: 20
<212> TYPE: PRT
<213> ORGANISM: Homo Sapien
<220> FEATURE:
<221> NAME/KEY: MOD_RES
<222> LOCATION: 20
<223> OTHER INFORMATION: AMIDATION

<400> SEQUENCE: 58

Gly Trp Thr Leu Asn Ser Ala Gly Tyr Leu Leu Gly Pro Gln Gln Phe
 1               5                  10                  15

Phe Gly Leu Met
             20

<210> SEQ ID NO 59
<211> LENGTH: 5
<212> TYPE: PRT
<213> ORGANISM: Homo Sapien

<400> SEQUENCE: 59

Arg Leu Arg Phe Asp
 1               5

<210> SEQ ID NO 60
<211> LENGTH: 17
<212> TYPE: PRT
<213> ORGANISM: Homo Sapien

<400> SEQUENCE: 60

Glu Gly Pro Trp Leu Glu Glu Glu Glu Ala Tyr Gly Trp Met Asp
 1               5                  10                  15

Phe

<210> SEQ ID NO 61
<211> LENGTH: 27
<212> TYPE: PRT
<213> ORGANISM: Homo Sapien

<400> SEQUENCE: 61

Val Pro Leu Pro Ala Gly Gly Gly Thr Val Leu Thr Lys Met Tyr Pro
 1               5                  10                  15

Arg Gly Asn His Trp Ala Val Gly His Leu Met
             20                  25

<210> SEQ ID NO 62
<211> LENGTH: 28
<212> TYPE: PRT
<213> ORGANISM: Homo Sapien

<400> SEQUENCE: 62

Gly Ser Ser Phe Leu Ser Pro Glu His Gln Arg Val Gln Gln Arg Lys
 1               5                  10                  15

Glu Ser Lys Lys Pro Pro Ala Lys Leu Gln Pro Arg
             20                  25

<210> SEQ ID NO 63
<211> LENGTH: 42
<212> TYPE: PRT
<213> ORGANISM: Homo Sapien

```
<400> SEQUENCE: 63

Tyr Ala Glu Gly Thr Phe Ile Ser Asp Tyr Ser Ile Ala Met Asp Lys
1               5                   10                  15

Ile His Gln Gln Asp Phe Val Asn Trp Leu Leu Ala Gln Lys Gly Lys
            20                  25                  30

Lys Asn Asp Trp Lys His Asn Ile Thr Gln
            35                  40

<210> SEQ ID NO 64
<211> LENGTH: 29
<212> TYPE: PRT
<213> ORGANISM: Homo Sapien

<400> SEQUENCE: 64

His Ser Gln Gly Thr Phe Thr Ser Asp Tyr Ser Lys Tyr Leu Asp Ser
1               5                   10                  15

Arg Arg Ala Gln Asp Phe Val Asp Trp Leu Met Asn Thr
            20                  25

<210> SEQ ID NO 65
<211> LENGTH: 20
<212> TYPE: PRT
<213> ORGANISM: Homo Sapien

<400> SEQUENCE: 65

Arg Arg Phe Ala Cys Asp Pro Asp Gly Tyr Asp Asn Tyr Phe His Cys
1               5                   10                  15

Val Pro Gly Gly
            20

<210> SEQ ID NO 66
<211> LENGTH: 20
<212> TYPE: PRT
<213> ORGANISM: Homo Sapien

<400> SEQUENCE: 66

Thr Gly Ser Trp Cys Gly Leu Met His Tyr Asp Asn Ala Trp Leu Cys
1               5                   10                  15

Asn Thr Gln Gly
            20

<210> SEQ ID NO 67
<211> LENGTH: 20
<212> TYPE: PRT
<213> ORGANISM: Homo Sapien

<400> SEQUENCE: 67

Arg Ser Lys Trp Cys Arg Asp Gly Tyr Tyr Ala Asn Tyr Pro Gln Cys
1               5                   10                  15

Trp Thr Gln Gly
            20

<210> SEQ ID NO 68
<211> LENGTH: 20
<212> TYPE: PRT
<213> ORGANISM: Homo Sapien

<400> SEQUENCE: 68

Arg Ser Thr Leu Cys Trp Phe Glu Gly Tyr Asp Asn Thr Phe Pro Cys
1               5                   10                  15

Lys Tyr Phe Arg
```

```
<210> SEQ ID NO 69
<211> LENGTH: 20
<212> TYPE: PRT
<213> ORGANISM: Homo Sapien

<400> SEQUENCE: 69

Arg Val Gln Glu Cys Lys Tyr Leu Tyr Tyr Asp Asn Asp Tyr Leu Cys
 1               5                  10                  15

Lys Asp Asp Gly
            20

<210> SEQ ID NO 70
<211> LENGTH: 20
<212> TYPE: PRT
<213> ORGANISM: Homo Sapien

<400> SEQUENCE: 70

Gly Leu Arg Arg Cys Leu Tyr Gly Pro Tyr Asp Asn Ala Trp Val Cys
 1               5                  10                  15

Asn Ile His Glu
            20

<210> SEQ ID NO 71
<211> LENGTH: 20
<212> TYPE: PRT
<213> ORGANISM: Homo Sapien

<400> SEQUENCE: 71

Lys Leu Phe Trp Cys Thr Tyr Glu Asp Tyr Ala Asn Glu Trp Pro Cys
 1               5                  10                  15

Pro Gly Tyr Ser
            20

<210> SEQ ID NO 72
<211> LENGTH: 20
<212> TYPE: PRT
<213> ORGANISM: Homo Sapien

<400> SEQUENCE: 72

Phe Cys Ala Val Cys Asn Glu Glu Leu Tyr Glu Asn Cys Gly Gly Cys
 1               5                  10                  15

Ser Cys Gly Lys
            20

<210> SEQ ID NO 73
<211> LENGTH: 20
<212> TYPE: PRT
<213> ORGANISM: Homo Sapien

<400> SEQUENCE: 73

Arg Thr Ser Pro Cys Gly Tyr Ile Gly Tyr Asp Asn Ile Phe Glu Cys
 1               5                  10                  15

Thr Tyr Leu Gly
            20

<210> SEQ ID NO 74
<211> LENGTH: 20
<212> TYPE: PRT
<213> ORGANISM: Homo Sapien

<400> SEQUENCE: 74
```

```
Thr Gly Glu Trp Cys Ala Gln Ser Val Tyr Ala Asn Tyr Asp Asn Cys
1               5                   10                  15

Lys Ser Ala Trp
            20

<210> SEQ ID NO 75
<211> LENGTH: 20
<212> TYPE: PRT
<213> ORGANISM: Homo Sapien

<400> SEQUENCE: 75

Asn Val Ser Arg Cys Thr Tyr Ile His Tyr Asp Asn Trp Ser Leu Cys
1               5                   10                  15

Gly Val Glu Val
            20

<210> SEQ ID NO 76
<211> LENGTH: 20
<212> TYPE: PRT
<213> ORGANISM: Homo Sapien

<400> SEQUENCE: 76

Gly Val Ser Asn Cys Val Phe Trp Gly Tyr Ala Asn Asp Trp Leu Cys
1               5                   10                  15

Ser Asp Tyr Ser
            20

<210> SEQ ID NO 77
<211> LENGTH: 44
<212> TYPE: PRT
<213> ORGANISM: Homo Sapien

<400> SEQUENCE: 77

Tyr Ala Asp Ala Ile Phe Thr Asn Ser Tyr Arg Lys Val Leu Gly Gln
1               5                   10                  15

Leu Ser Ala Arg Lys Leu Leu Gln Asp Ile Met Ser Arg Gln Gln Gly
            20                  25                  30

Glu Ser Asn Gln Glu Arg Gly Ala Arg Ala Arg Leu
            35                  40

<210> SEQ ID NO 78
<211> LENGTH: 15
<212> TYPE: PRT
<213> ORGANISM: Homo Sapien

<400> SEQUENCE: 78

Pro Gly Thr Cys Glu Ile Cys Ala Tyr Ala Ala Cys Thr Gly Cys
1               5                   10                  15

<210> SEQ ID NO 79
<211> LENGTH: 35
<212> TYPE: PRT
<213> ORGANISM: Homo Sapien
<220> FEATURE:
<221> NAME/KEY: MOD_RES
<222> LOCATION: 35
<223> OTHER INFORMATION: AMIDATION

<400> SEQUENCE: 79

His Ser Asp Ala Ile Phe Thr Glu Glu Tyr Ser Lys Leu Leu Ala Lys
1               5                   10                  15

Leu Ala Leu Gln Lys Tyr Leu Ala Ser Ile Leu Gly Ser Arg Thr Ser
```

```
                    20                  25                  30

Pro Pro Pro
        35

<210> SEQ ID NO 80
<211> LENGTH: 38
<212> TYPE: PRT
<213> ORGANISM: Homo Sapien

<400> SEQUENCE: 80

His Ser Asp Ala Thr Phe Thr Ala Glu Tyr Ser Lys Leu Leu Ala Lys
1               5                   10                  15

Leu Ala Leu Gln Lys Tyr Leu Glu Ser Ile Leu Gly Ser Ser Thr Ser
            20                  25                  30

Pro Arg Pro Pro Ser Ser
        35

<210> SEQ ID NO 81
<211> LENGTH: 37
<212> TYPE: PRT
<213> ORGANISM: Homo Sapien

<400> SEQUENCE: 81

His Ser Asp Ala Thr Phe Thr Ala Glu Tyr Ser Lys Leu Leu Ala Lys
1               5                   10                  15

Leu Ala Leu Gln Lys Tyr Leu Glu Ser Ile Leu Gly Ser Ser Thr Ser
            20                  25                  30

Pro Arg Pro Pro Ser
        35

<210> SEQ ID NO 82
<211> LENGTH: 24
<212> TYPE: PRT
<213> ORGANISM: Homo Sapien

<400> SEQUENCE: 82

Asp Ser His Ala Lys Arg His His Gly Tyr Lys Arg Lys Phe His Glu
1               5                   10                  15

Lys His His Ser His Arg Gly Tyr
            20

<210> SEQ ID NO 83
<211> LENGTH: 4
<212> TYPE: PRT
<213> ORGANISM: Homo Sapien
<220> FEATURE:
<221> NAME/KEY: MOD_RES
<222> LOCATION: 1
<223> OTHER INFORMATION: ACETYLATION
<220> FEATURE:
<221> NAME/KEY: MOD_RES
<222> LOCATION: 4
<223> OTHER INFORMATION: Xaa is Aspartic acid-fluroacetylmethylketone

<400> SEQUENCE: 83

Tyr Val Ala Xaa
1

<210> SEQ ID NO 84
<211> LENGTH: 6
<212> TYPE: PRT
<213> ORGANISM: Homo Sapien

<400> SEQUENCE: 84
```

Val Glu Pro Ile Pro Tyr
1               5

<210> SEQ ID NO 85
<211> LENGTH: 21
<212> TYPE: PRT
<213> ORGANISM: Homo Sapien

<400> SEQUENCE: 85

Gly Ile Val Glu Gln Cys Cys Thr Ser Ile Cys Ser Leu Tyr Gln Leu
1               5                   10                  15

Glu Asn Tyr Cys Asn
            20

<210> SEQ ID NO 86
<211> LENGTH: 30
<212> TYPE: PRT
<213> ORGANISM: Homo Sapien

<400> SEQUENCE: 86

Phe Val Asn Gln His Leu Cys Gly Ser His Leu Val Glu Ala Leu Tyr
1               5                   10                  15

Leu Val Cys Gly Glu Arg Gly Phe Phe Tyr Thr Pro Lys Thr
            20                  25                  30

<210> SEQ ID NO 87
<211> LENGTH: 51
<212> TYPE: PRT
<213> ORGANISM: Homo Sapien

<400> SEQUENCE: 87

Gly Ile Val Glu Gln Cys Cys Thr Ser Ile Cys Ser Leu Tyr Gln Leu
1               5                   10                  15

Glu Asn Tyr Cys Asn Phe Val Asn Gln His Leu Cys Gly Ser His Leu
            20                  25                  30

Val Glu Ala Leu Tyr Leu Val Cys Gly Glu Arg Gly Phe Phe Tyr Thr
        35                  40                  45

Pro Lys Thr
    50

<210> SEQ ID NO 88
<211> LENGTH: 9
<212> TYPE: PRT
<213> ORGANISM: Homo Sapien

<400> SEQUENCE: 88

Ile Ala Arg Arg His Pro Tyr Phe Leu
1               5

<210> SEQ ID NO 89
<211> LENGTH: 5
<212> TYPE: PRT
<213> ORGANISM: Homo Sapien

<400> SEQUENCE: 89

Tyr Gly Gly Phe Leu
1               5

<210> SEQ ID NO 90
<211> LENGTH: 9
<212> TYPE: PRT
<213> ORGANISM: Homo Sapien

```
<220> FEATURE:
<221> NAME/KEY: MOD_RES
<222> LOCATION: 9
<223> OTHER INFORMATION: AMIDATION
<220> FEATURE:
<221> NAME/KEY: MOD_RES
<222> LOCATION: 1
<223> OTHER INFORMATION: PYRROLIDONE CARBOXYLIC ACID

<400> SEQUENCE: 90

Glu Gln Trp Ala Val Gly His Phe Met
 1               5

<210> SEQ ID NO 91
<211> LENGTH: 14
<212> TYPE: PRT
<213> ORGANISM: Homo Sapien

<400> SEQUENCE: 91

Arg Thr Lys Arg Ser Gly Ser Val Tyr Glu Pro Leu Lys Ile
 1               5                  10

<210> SEQ ID NO 92
<211> LENGTH: 5
<212> TYPE: PRT
<213> ORGANISM: Homo Sapien

<400> SEQUENCE: 92

Tyr Gly Gly Phe Met
 1               5

<210> SEQ ID NO 93
<211> LENGTH: 9
<212> TYPE: PRT
<213> ORGANISM: Homo Sapien
<220> FEATURE:
<221> NAME/KEY: MOD_RES
<222> LOCATION: 9
<223> OTHER INFORMATION: AMIDATION

<400> SEQUENCE: 93

Tyr Gly Gly Gly Phe Met Arg Arg Val
 1               5

<210> SEQ ID NO 94
<211> LENGTH: 22
<212> TYPE: PRT
<213> ORGANISM: Homo Sapien

<400> SEQUENCE: 94

Phe Val Pro Ile Phe Thr Tyr Gly Glu Leu Gln Arg Met Gln Glu Lys
 1               5                  10                  15

Glu Arg Asn Lys Gly Gln
            20

<210> SEQ ID NO 95
<211> LENGTH: 9
<212> TYPE: PRT
<213> ORGANISM: Homo Sapien

<400> SEQUENCE: 95

Pro Met Ser Met Leu Arg Leu Asn His
 1               5

<210> SEQ ID NO 96
<211> LENGTH: 13
```

```
<212> TYPE: PRT
<213> ORGANISM: Homo Sapien

<400> SEQUENCE: 96

Ile Pro Lys Lys Arg Ala Ala Arg Ala Thr Ser Asn His
1               5                   10

<210> SEQ ID NO 97
<211> LENGTH: 6
<212> TYPE: PRT
<213> ORGANISM: Homo Sapien

<400> SEQUENCE: 97

Gly Ala Val Ser Thr Ala
1               5

<210> SEQ ID NO 98
<211> LENGTH: 10
<212> TYPE: PRT
<213> ORGANISM: Homo Sapien
<220> FEATURE:
<221> NAME/KEY: MOD_RES
<222> LOCATION: 10
<223> OTHER INFORMATION: AMIDATION

<400> SEQUENCE: 98

His Lys Thr Asp Ser Phe Val Gly Leu Met
1               5                   10

<210> SEQ ID NO 99
<211> LENGTH: 10
<212> TYPE: PRT
<213> ORGANISM: Homo Sapien
<220> FEATURE:
<221> NAME/KEY: MOD_RES
<222> LOCATION: 10
<223> OTHER INFORMATION: AMIDATION

<400> SEQUENCE: 99

Asp Met His Asp Phe Phe Val Gly Leu Met
1               5                   10

<210> SEQ ID NO 100
<211> LENGTH: 10
<212> TYPE: PRT
<213> ORGANISM: Homo Sapien
<220> FEATURE:
<221> NAME/KEY: MOD_RES
<222> LOCATION: 10
<223> OTHER INFORMATION: AMIDATION

<400> SEQUENCE: 100

Gly Asn Leu Trp Ala Thr Gly His Phe Met
1               5                   10

<210> SEQ ID NO 101
<211> LENGTH: 36
<212> TYPE: PRT
<213> ORGANISM: Homo Sapien
<220> FEATURE:
<221> NAME/KEY: MOD_RES
<222> LOCATION: 36
<223> OTHER INFORMATION: AMIDATION

<400> SEQUENCE: 101

Tyr Pro Ser Lys Pro Asp Asn Pro Gly Glu Asp Ala Pro Ala Glu Asp
1               5                   10                  15
```

```
Met Ala Arg Tyr Tyr Ser Ala Lys Arg His Tyr Ile Asn Leu Ile Thr
             20                  25                  30

Arg Gln Arg Tyr
        35

<210> SEQ ID NO 102
<211> LENGTH: 12
<212> TYPE: PRT
<213> ORGANISM: Homo Sapien
<220> FEATURE:
<221> NAME/KEY: MOD_RES
<222> LOCATION: 1
<223> OTHER INFORMATION: PYRROLIDONE CARBOXYLIC ACID

<400> SEQUENCE: 102

Glu Leu Tyr Glu Asn Lys Pro Arg Arg Pro Ile Leu
1               5                   10

<210> SEQ ID NO 103
<211> LENGTH: 17
<212> TYPE: PRT
<213> ORGANISM: Homo Sapien

<400> SEQUENCE: 103

Phe Gly Gly Phe Thr Gly Ala Arg Lys Ser Ala Arg Lys Leu Ala Asn
1               5                   10                  15

Gln

<210> SEQ ID NO 104
<211> LENGTH: 31
<212> TYPE: PRT
<213> ORGANISM: Homo Sapien

<400> SEQUENCE: 104

Phe Ala Glu Pro Leu Pro Ser Glu Glu Gly Glu Ser Tyr Ser Lys
1               5                   10                  15

Glu Val Pro Glu Met Glu Lys Arg Tyr Gly Gly Phe Met Arg Phe
             20                  25                  30

<210> SEQ ID NO 105
<211> LENGTH: 6
<212> TYPE: PRT
<213> ORGANISM: Homo Sapien

<400> SEQUENCE: 105

Glu Gln Lys Gln Leu Gln
1               5

<210> SEQ ID NO 106
<211> LENGTH: 33
<212> TYPE: PRT
<213> ORGANISM: Homo Sapien
<220> FEATURE:
<221> NAME/KEY: MOD_RES
<222> LOCATION: 33
<223> OTHER INFORMATION: AMIDATION
<220> FEATURE:
<221> NAME/KEY: MOD_RES
<222> LOCATION: 1
<223> OTHER INFORMATION: PYRROLIDONE CARBOXYLIC ACID

<400> SEQUENCE: 106

Glu Pro Leu Pro Asp Cys Cys Arg Gln Lys Thr Cys Ser Cys Arg Leu
1               5                   10                  15

Tyr Glu Leu Leu His Gly Ala Gly Asn His Ala Ala Gly Ile Leu Thr
```

```
                 20                  25                  30

Leu

<210> SEQ ID NO 107
<211> LENGTH: 28
<212> TYPE: PRT
<213> ORGANISM: Homo Sapien
<220> FEATURE:
<221> NAME/KEY: MOD_RES
<222> LOCATION: 28
<223> OTHER INFORMATION: AMIDATION

<400> SEQUENCE: 107

Arg Ser Gly Pro Pro Gly Leu Gln Gly Arg Leu Gln Arg Leu Leu Gln
1               5                   10                  15

Ala Ser Gly Asn His Ala Ala Gly Ile Leu Thr Met
            20                  25

<210> SEQ ID NO 108
<211> LENGTH: 49
<212> TYPE: PRT
<213> ORGANISM: Homo Sapien

<400> SEQUENCE: 108

Tyr Leu Tyr Gln Trp Leu Gly Ala Pro Val Pro Tyr Pro Asp Pro Leu
1               5                   10                  15

Glu Pro Arg Arg Glu Val Cys Glu Leu Asn Pro Asp Cys Asp Glu Leu
            20                  25                  30

Ala Asp His Ile Gly Phe Gln Glu Ala Tyr Arg Arg Phe Tyr Gly Pro
        35                  40                  45

Val

<210> SEQ ID NO 109
<211> LENGTH: 11
<212> TYPE: PRT
<213> ORGANISM: Homo Sapien

<400> SEQUENCE: 109

Cys Tyr Ile Gln Asn Cys Pro Leu Gly Asn His
1               5                   10

<210> SEQ ID NO 110
<211> LENGTH: 27
<212> TYPE: PRT
<213> ORGANISM: Homo Sapien

<400> SEQUENCE: 110

His Ser Asp Gly Ile Phe Thr Asp Ser Tyr Ser Arg Tyr Arg Lys Gln
1               5                   10                  15

Met Ala Val Lys Lys Tyr Leu Ala Ala Val Leu
            20                  25

<210> SEQ ID NO 111
<211> LENGTH: 29
<212> TYPE: PRT
<213> ORGANISM: Homo Sapien

<400> SEQUENCE: 111

Asp Val Ala His Gly Ile Leu Asn Glu Ala Tyr Arg Lys Val Leu Asp
1               5                   10                  15

Gln Leu Ser Ala Gly Lys His Leu Gln Ser Leu Val Ala
            20                  25
```

<210> SEQ ID NO 112
<211> LENGTH: 38
<212> TYPE: PRT
<213> ORGANISM: Homo Sapien

<400> SEQUENCE: 112

Ala Pro Leu Glu Pro Val Tyr Pro Gly Asp Asn Ala Thr Pro Glu Gln
1               5                   10                  15

Met Ala Gln Tyr Ala Ala Asp Leu Arg Arg Tyr Ile Asn Met Leu Thr
            20                  25                  30

Arg Pro Arg Tyr Asn His
        35

<210> SEQ ID NO 113
<211> LENGTH: 4
<212> TYPE: PRT
<213> ORGANISM: Homo Sapien

<400> SEQUENCE: 113

Gly Gly Tyr Arg
1

<210> SEQ ID NO 114
<211> LENGTH: 12
<212> TYPE: PRT
<213> ORGANISM: Homo Sapien

<400> SEQUENCE: 114

Tyr Gly Gly Phe Met Arg Arg Val Gly Arg Pro Glu
1               5                   10

<210> SEQ ID NO 115
<211> LENGTH: 36
<212> TYPE: PRT
<213> ORGANISM: Homo Sapien
<220> FEATURE:
<221> NAME/KEY: MOD_RES
<222> LOCATION: 36
<223> OTHER INFORMATION: AMIDATION

<400> SEQUENCE: 115

Tyr Pro Ile Lys Pro Glu Ala Pro Gly Glu Asp Ala Ser Pro Glu Glu
1               5                   10                  15

Leu Asn Arg Tyr Tyr Ala Ser Leu Arg His Tyr Leu Asn Leu Val Thr
            20                  25                  30

Arg Gln Arg Tyr
        35

<210> SEQ ID NO 116
<211> LENGTH: 9
<212> TYPE: PRT
<213> ORGANISM: Homo Sapien

<400> SEQUENCE: 116

Arg Arg Lys Ala Ser Gly Pro Pro Val
1               5

<210> SEQ ID NO 117
<211> LENGTH: 11
<212> TYPE: PRT
<213> ORGANISM: Homo Sapien
<220> FEATURE:
<221> NAME/KEY: MOD_RES

```
<222> LOCATION: 11
<223> OTHER INFORMATION: AMIDATION
<220> FEATURE:
<221> NAME/KEY: MOD_RES
<222> LOCATION: 1
<223> OTHER INFORMATION: PYRROLIDONE CARBOXYLIC ACID

<400> SEQUENCE: 117

Glu Ala Asp Pro Asn Lys Phe Tyr Gly Leu Met
1               5                   10

<210> SEQ ID NO 118
<211> LENGTH: 11
<212> TYPE: PRT
<213> ORGANISM: Homo Sapien
<220> FEATURE:
<221> NAME/KEY: MOD_RES
<222> LOCATION: 11
<223> OTHER INFORMATION: AMIDATION
<220> FEATURE:
<221> NAME/KEY: MOD_RES
<222> LOCATION: 1
<223> OTHER INFORMATION: PYRROLIDONE CARBOXYLIC ACID

<400> SEQUENCE: 118

Glu Val Pro Gln Trp Ala Val Gly His Phe Met
1               5                   10

<210> SEQ ID NO 119
<211> LENGTH: 5
<212> TYPE: PRT
<213> ORGANISM: Homo Sapien
<220> FEATURE:
<221> NAME/KEY: UNSURE
<222> LOCATION: 1,5
<223> OTHER INFORMATION: Xaa is a variable

<400> SEQUENCE: 119

Xaa Arg Gly Asp Xaa
1               5

<210> SEQ ID NO 120
<211> LENGTH: 4
<212> TYPE: PRT
<213> ORGANISM: Homo Sapien

<400> SEQUENCE: 120

Gly Gln Pro Arg
1

<210> SEQ ID NO 121
<211> LENGTH: 13
<212> TYPE: PRT
<213> ORGANISM: Homo Sapien

<400> SEQUENCE: 121

Arg Arg Leu Ile Glu Asp Ala Glu Tyr Ala Ala Arg Gly
1               5                   10

<210> SEQ ID NO 122
<211> LENGTH: 5
<212> TYPE: PRT
<213> ORGANISM: Homo Sapien

<400> SEQUENCE: 122

Arg Pro Thr Val Leu
1               5
```

```
<210> SEQ ID NO 123
<211> LENGTH: 27
<212> TYPE: PRT
<213> ORGANISM: Homo Sapien

<400> SEQUENCE: 123

His Ser Asp Gly Thr Phe Thr Ser Glu Leu Ser Arg Leu Arg Glu Gly
 1               5                  10                  15

Ala Arg Leu Gln Arg Leu Leu Gln Gly Leu Val
            20                  25

<210> SEQ ID NO 124
<211> LENGTH: 9
<212> TYPE: PRT
<213> ORGANISM: Homo Sapien
<220> FEATURE:
<221> NAME/KEY: MOD_RES
<222> LOCATION: 1
<223> OTHER INFORMATION: PYRROLIDONE CARBOXYLIC ACID

<400> SEQUENCE: 124

Glu Ala Lys Ser Gln Gly Gly Ser Asn
 1               5

<210> SEQ ID NO 125
<211> LENGTH: 19
<212> TYPE: PRT
<213> ORGANISM: Homo Sapien

<400> SEQUENCE: 125

Pro Gln Cys Gly Lys Cys Arg Ile Cys Lys Asn Pro Glu Ser Asn Tyr
 1               5                  10                  15

Cys Leu Lys

<210> SEQ ID NO 126
<211> LENGTH: 19
<212> TYPE: PRT
<213> ORGANISM: Homo Sapien

<400> SEQUENCE: 126

Pro Gln Cys Gly Lys Cys Arg Val Cys Lys Asn Pro Glu Ser Asn Tyr
 1               5                  10                  15

Cys Leu Lys

<210> SEQ ID NO 127
<211> LENGTH: 19
<212> TYPE: PRT
<213> ORGANISM: Homo Sapien

<400> SEQUENCE: 127

Pro Gln Cys Gly Lys Cys Arg Ile Cys Lys Asn Pro Glu Ser Asn Tyr
 1               5                  10                  15

Cys Leu Lys

<210> SEQ ID NO 128
<211> LENGTH: 19
<212> TYPE: PRT
<213> ORGANISM: Homo Sapien

<400> SEQUENCE: 128

Pro Leu Cys Arg Lys Cys Lys Phe Cys Leu Ser Pro Leu Thr Asn Leu
 1               5                  10                  15
```

Cys Gly Lys

<210> SEQ ID NO 129
<211> LENGTH: 18
<212> TYPE: PRT
<213> ORGANISM: Homo Sapien

<400> SEQUENCE: 129

Pro Gln Gly Glu Cys Lys Phe Cys Leu Asn Pro Lys Thr Asn Leu Cys
1               5                   10                  15

Gln Lys

<210> SEQ ID NO 130
<211> LENGTH: 11
<212> TYPE: PRT
<213> ORGANISM: Homo Sapien
<220> FEATURE:
<221> NAME/KEY: MOD_RES
<222> LOCATION: 11
<223> OTHER INFORMATION: AMIDATION

<400> SEQUENCE: 130

Arg Pro Lys Pro Gln Gln Phe Phe Gly Leu Met
1               5                   10

<210> SEQ ID NO 131
<211> LENGTH: 15
<212> TYPE: PRT
<213> ORGANISM: Homo Sapien

<400> SEQUENCE: 131

Pro Leu Ala Arg Thr Leu Ser Val Ala Gly Leu Pro Gly Lys Lys
1               5                   10                  15

<210> SEQ ID NO 132
<211> LENGTH: 18
<212> TYPE: PRT
<213> ORGANISM: Homo Sapien

<400> SEQUENCE: 132

Ala Val Gln Ser Lys Pro Pro Ser Lys Arg Asp Pro Pro Lys Met Gln
1               5                   10                  15

Thr Asp

<210> SEQ ID NO 133
<211> LENGTH: 36
<212> TYPE: PRT
<213> ORGANISM: Homo Sapien

<400> SEQUENCE: 133

Thr Phe Gly Ser Gly Glu Ala Asp Cys Gly Leu Arg Pro Leu Phe Glu
1               5                   10                  15

Lys Lys Ser Leu Glu Asp Lys Thr Glu Arg Glu Leu Leu Glu Ser Tyr
                20                  25                  30

Ile Asp Gly Arg
            35

<210> SEQ ID NO 134
<211> LENGTH: 5
<212> TYPE: PRT
<213> ORGANISM: Homo Sapien

<400> SEQUENCE: 134

```
Arg Lys Asp Val Tyr
 1               5

<210> SEQ ID NO 135
<211> LENGTH: 9
<212> TYPE: PRT
<213> ORGANISM: Homo Sapien

<400> SEQUENCE: 135

Gln Ala Lys Ser Gln Gly Gly Ser Asn
 1               5

<210> SEQ ID NO 136
<211> LENGTH: 3
<212> TYPE: PRT
<213> ORGANISM: Homo Sapien
<220> FEATURE:
<221> NAME/KEY: MOD_RES
<222> LOCATION: 1
<223> OTHER INFORMATION: PYRROLIDONE CARBOXYLIC ACID

<400> SEQUENCE: 136

Glu His Pro
 1

<210> SEQ ID NO 137
<211> LENGTH: 4
<212> TYPE: PRT
<213> ORGANISM: Homo Sapien

<400> SEQUENCE: 137

Thr Lys Pro Arg
 1

<210> SEQ ID NO 138
<211> LENGTH: 11
<212> TYPE: PRT
<213> ORGANISM: Homo Sapien
<220> FEATURE:
<221> NAME/KEY: MOD_RES
<222> LOCATION: 11
<223> OTHER INFORMATION: AMIDATION
<220> FEATURE:
<221> NAME/KEY: MOD_RES
<222> LOCATION: 1
<223> OTHER INFORMATION: PYRROLIDONE CARBOXYLIC ACID

<400> SEQUENCE: 138

Glu Pro Asp Pro Asn Ala Phe Tyr Gly Leu Met
 1               5                  10

<210> SEQ ID NO 139
<211> LENGTH: 5
<212> TYPE: PRT
<213> ORGANISM: Homo Sapien

<400> SEQUENCE: 139

Asp Leu Trp Gln Lys
 1               5

<210> SEQ ID NO 140
<211> LENGTH: 40
<212> TYPE: PRT
<213> ORGANISM: Homo Sapien

<400> SEQUENCE: 140

Asp Asn Pro Ser Leu Ser Ile Asp Leu Thr Phe His Leu Leu Arg Thr
```

```
                1               5                      10                      15
Leu Leu Glu Leu Ala Arg Thr Gln Ser Gln Arg Glu Arg Ala Glu Gln
                   20                      25                      30

Asn Arg Ile Ile Phe Asp Ser Val
                   35                      40
```

<210> SEQ ID NO 141
<211> LENGTH: 16
<212> TYPE: PRT
<213> ORGANISM: Homo Sapien

<400> SEQUENCE: 141

```
Asn Asp Asp Cys Glu Leu Cys Val Asn Val Ala Cys Thr Gly Cys Leu
 1               5                      10                      15
```

<210> SEQ ID NO 142
<211> LENGTH: 27
<212> TYPE: PRT
<213> ORGANISM: Homo Sapien

<400> SEQUENCE: 142

```
Gly Leu Ser Lys Gly Cys Phe Gly Leu Lys Leu Asp Arg Ile Gly Ser
 1               5                      10                      15

Met Ser Gly Leu Gly Cys Asn Ser Phe Arg Tyr
                   20                      25
```

<210> SEQ ID NO 143
<211> LENGTH: 9
<212> TYPE: PRT
<213> ORGANISM: Homo Sapien

<400> SEQUENCE: 143

```
Cys Tyr Phe Gln Asn Cys Pro Arg Gly
 1               5
```

<210> SEQ ID NO 144
<211> LENGTH: 9
<212> TYPE: PRT
<213> ORGANISM: Homo Sapien

<400> SEQUENCE: 144

```
Cys Tyr Ile Gln Asn Cys Pro Arg Gly
 1               5
```

<210> SEQ ID NO 145
<211> LENGTH: 28
<212> TYPE: PRT
<213> ORGANISM: Homo Sapien

<400> SEQUENCE: 145

```
His Ser Asp Ala Val Phe Thr Asp Asn Tyr Thr Arg Leu Arg Lys Gln
 1               5                      10                      15

Met Ala Val Lys Lys Tyr Leu Asn Ser Ile Leu Asn
                   20                      25
```

<210> SEQ ID NO 146
<211> LENGTH: 25
<212> TYPE: PRT
<213> ORGANISM: Homo Sapien

<400> SEQUENCE: 146

```
Met Leu Thr Lys Phe Glu Thr Lys Ser Ala Arg Val Lys Gly Leu Ser
 1               5                      10                      15
```

-continued

```
Phe His Pro Lys Arg Pro Trp Ile Leu
            20                  25

<210> SEQ ID NO 147
<211> LENGTH: 3
<212> TYPE: PRT
<213> ORGANISM: Homo Sapien
<220> FEATURE:
<221> NAME/KEY: UNSURE
<222> LOCATION: 2
<223> OTHER INFORMATION: Xaa is a variable

<400> SEQUENCE: 147

Tyr Xaa Asn
 1

<210> SEQ ID NO 148
<211> LENGTH: 9
<212> TYPE: PRT
<213> ORGANISM: Homo Sapien

<400> SEQUENCE: 148

Phe Gln Phe His Phe His Trp Gly Ser
 1               5

<210> SEQ ID NO 149
<211> LENGTH: 11
<212> TYPE: PRT
<213> ORGANISM: Homo Sapien

<400> SEQUENCE: 149

Ile Ile Ile Gln Phe His Phe His Trp Gly Ser
 1               5                  10

<210> SEQ ID NO 150
<211> LENGTH: 11
<212> TYPE: DNA
<213> ORGANISM: Artificial Sequence
<220> FEATURE:
<221> NAME/KEY: variation
<222> LOCATION: (5)..(7)
<223> OTHER INFORMATION: "n" stands for a, g, c or t.
<220> FEATURE:
<223> OTHER INFORMATION: Chemically synthesized oligonucleotide

<400> SEQUENCE: 150
gtgcnnngtg c                                                           11

<210> SEQ ID NO 151
<211> LENGTH: 12
<212> TYPE: DNA
<213> ORGANISM: Artificial Sequence
<220> FEATURE:
<221> NAME/KEY: variation
<222> LOCATION: (5)..(8)
<223> OTHER INFORMATION: "n" stands for a, g, c or t.
<220> FEATURE:
<223> OTHER INFORMATION: Chemically synthesized oligonucleotide

<400> SEQUENCE: 151
gtccnnnnct ac                                                          12

<210> SEQ ID NO 152
<211> LENGTH: 23
<212> TYPE: DNA
<213> ORGANISM: Artificial Sequence
<220> FEATURE:
```

```
<221> NAME/KEY: variation
<222> LOCATION: (8)..(15)
<223> OTHER INFORMATION: "n" stands for a, g, c or t.
<220> FEATURE:
<223> OTHER INFORMATION: Chemically synthesized oligonucleotide

<400> SEQUENCE: 152
gctgcccnnn nnnnngcctg ccc                                              23

<210> SEQ ID NO 153
<211> LENGTH: 11
<212> TYPE: DNA
<213> ORGANISM: Artificial Sequence
<220> FEATURE:
<221> NAME/KEY: variation
<222> LOCATION: (5)..(7)
<223> OTHER INFORMATION: "n" stands for a, g, c or t.
<220> FEATURE:
<223> OTHER INFORMATION: Chemically synthesized oligonucleotide

<400> SEQUENCE: 153
ctgcnnngtg c                                                           11

<210> SEQ ID NO 154
<211> LENGTH: 11
<212> TYPE: DNA
<213> ORGANISM: Artificial Sequence
<220> FEATURE:
<221> NAME/KEY: variation
<222> LOCATION: (5)..(7)
<223> OTHER INFORMATION: "n" stands for a, g, c or t.
<220> FEATURE:
<223> OTHER INFORMATION: Chemically synthesized oligonucleotide

<400> SEQUENCE: 154
gcacnnngca c                                                           11

<210> SEQ ID NO 155
<211> LENGTH: 23
<212> TYPE: DNA
<213> ORGANISM: Artificial Sequence
<220> FEATURE:
<223> OTHER INFORMATION: Chemically synthesized oligonucleotide

<400> SEQUENCE: 155
acgttttgcg ttgtagtcaa tcg                                              23

<210> SEQ ID NO 156
<211> LENGTH: 23
<212> TYPE: DNA
<213> ORGANISM: Artificial Sequence
<220> FEATURE:
<223> OTHER INFORMATION: Chemically synthesized oligonucleotide

<400> SEQUENCE: 156
cgattgacta caacgcaaaa cgt                                              23

<210> SEQ ID NO 157
<211> LENGTH: 23
<212> TYPE: DNA
<213> ORGANISM: Artificial Sequence
<220> FEATURE:
<223> OTHER INFORMATION: Chemically synthesized oligonucleotide

<400> SEQUENCE: 157
cggccccatt tttgggcgct acg                                              23
```

```
<210> SEQ ID NO 158
<211> LENGTH: 23
<212> TYPE: DNA
<213> ORGANISM: Artificial Sequence
<220> FEATURE:
<223> OTHER INFORMATION: Chemically synthesized oligonucleotide

<400> SEQUENCE: 158
cgtagcgccc aaaaatgggg ccg                                          23
```

CAPTURE COMPOUNDS, COLLECTIONS THEREOF AND METHODS FOR ANALYZING THE PROTEOME AND COMPLEX COMPOSITIONS

RELATED APPLICATIONS

This application is a continuation of and claims priority under 35 U.S.C. §120 to U.S. application Ser. No. 10/760,085, filed Jan. 16, 2004 now abandoned, to Hubert Koster, Daniel Paul Little, Suhaib Mahmood Siddiqi, Matthew Peter Grealish, Subramanian Marappan, Chester Frederick Hassman III, and Ping Yip entitled "CAPTURE COMPOUNDS, COLLECTIONS THEREOF AND METHODS FOR ANALYZING THE PROTEOME AND COMPLEX COMPOSITIONS," which claims benefit of priority under 35 U.S.C. §119(e) to U.S. Provisional Application No. 60/441,398, filed Jan. 16, 2003, to Hubert Koster, Daniel Paul Little, Suhaib Mahmood Siddiqi, Matthew Peter Grealish, Subramanian Marappan, and Chester Frederick Hassman III entitled "CAPTURE COMPOUNDS, COLLECTIONS THEREOF AND METHODS FOR ANALYZING THE PROTEOME AND COMPLEX COMPOSITIONS." The subject matter of each of the above-noted US applications is incorporated by reference in its entirety.

FIELD

Provided herein are compounds and methods using the compounds to specifically and selectively analyze biomolecules. In particular, the compounds and methods are useful for analyzing the proteome.

BACKGROUND

Understanding the basis of disease and the development of therapeutic and preventative treatments has evolved over the last century from empirical observation and experimentation to genome wide mutation scanning. The revolution in genomics has provided researchers with the tools to look for a genomic basis for disease. The Human Genome effort has generated a raw sequence of the 3 billion base pairs of the human genome and revealed about 35,000 genes. Genetic variations amongst different individuals and in and in between populations are being studied in order to determine the association with the predisposition to disease or the correlation to drug efficacy and/or side effects. The promise of personalized medicine based on a panel of genetic markers has tantalized the healthcare community and provides an important goal for those focused on providing diagnostic and treatment options for healthcare providers and patients.

With the development of a variety of tools in molecular biology, such as nucleic amplification methods, cloning and expression systems and methods, disease analysis has been based on a genomics, or bottom up, approach. This approach presumes that a genetic change or set of changes will have a long reaching effect on protein function by affecting mRNA transcription or protein structure and function.

Technologies have been developed to analyze single nucleotide polymorphisms (SNPs) in an industrial scale (e.g., MassARRAY™ and the MassARRAY® system, Sequenom, Inc., San Diego, Calif.) and in pooled samples to study the frequency of SNPs in populations of various gender, ethnicity, age and health condition. The ultimate goal of these efforts is to understand the etiology of disease on the molecular level (e.g., based on genetic variances (pharmacogenomics)), to develop diagnostic assays and effective drugs with few or no side-effects.

Genomics has fallen short of the original expectation that this strategy could be used to stratify a population relative to a defined phenotype, including differences between normal and disease patient population or populations. Although single genetic markers have been found to be associated with or cause or predict a specific disease state, genomic information may not be sufficient to stratify individual populations by of the association of an SNP (or SNPs) with a given disease, drug side-effect or other target phenotype. Because of the large number of potential targets and regulatory signals that affect protein translation, it is not sufficient to establish the differential expression profiles of messenger RNA in comparing phenotypes or populations, such as healthy and disease states, or such as the analyses using expression DNA chips (e.g., GeneChip™ technology, Affymetrix, Inc., Santa Clara, Calif.; LifeArray™ technology, Incyte Genomics, Inc., Palo Alto, Calif.). The metabolic activities in a cell are not performed by mRNA but rather by the translated proteins and subsequently posttranslationally modified products, such as the alkylated, glycosylated and phosphorylated products.

The study of proteomics encompasses the study of individual proteins and how these proteins function within a biochemical pathway. Proteomics also includes the study of protein interactions, including how they form the architecture that constitutes living cells. In many human diseases such as cancer, Alzheimer's disease, diabetes as well as host responses to infectious diseases, the elucidation of the complex interactions between regulatory proteins, which can cause diseases, is a critical step to finding effective treatment. Often, SNPs and other nucleic acid mutations occur in genes whose products are such proteins as (1) growth related hormones, (2) membrane receptors for growth hormones, (3) components of the trans-membrane signal pathway and (4) DNA binding proteins that act on transcription and the inactivation of suppressor genes (e.g. p53) causing the onset of disease.

Complex protein mixtures are analyzed by two-dimensional (2D) gel electrophoresis and subsequent image processing to identify changes in the pattern (structural changes) or intensity of various protein spots. Two-dimensional gel electrophoresis is a laborious, error-prone method with low reproducibility and cannot be effectively automated. This gel technology is unable to effectively analyze membrane proteins. Further, the resolution of 2D gels is insufficient to analyze the profile of all proteins present in a mixture.

Available protein chips are limited by their ability to specifically capture hydrophobic and membrane proteins, which are frequently targets of drug development. Once bound to the chip, proteins are highly unstable and their structures often do not reflect the true conformation found under physiological conditions.

Proteins form the important structural and functional machinery of the cell, and are the molecular entities with which nearly all of today's marketed drugs interact. Proteins are thus drug targets. Most pharma companies are investing heavily to extract truly promising drug targets from their sea of unvalidated targets derived from gene-based approaches. Typically the mechanism of action defining how drugs act upon their targets is poorly understood; for some marketed drugs the target is not even known. Furthermore, identifying "non-target" proteins with which the drug interacts to trigger side effects has been especially elusive. It is believed that side effects of many drugs could be diminished with a greater understanding of the mechanism of action involving their target and the non-target proteins.

Drug programs are discontinued for a variety of reasons (e.g., lack of efficacy compared to placebo), but about half of the terminations relate to clinical safety and toxicity. As a result, the developments of many ill-chosen lead drug compounds are halted late in clinical trials after many years and millions of dollars have been spent. Compounding the financial problems caused by toxicity, the long duration of drug development also substantially reduces the length of patent protection.

Adverse side effects from drugs result in more than two million hospitalizations and more than 100,000 deaths each year. Many major drugs have severe toxic side effects.

The widely prescribed psoriasis drugs methoxetrate and cyclosporine can cause severe liver and kidney damage and are thus rarely prescribed for more than one year.

Approximately $13 billion has been spent so far in product injury and class action litigation connected with the withdrawal of the fen-phen weight loss drug combination.

Substantial liabilities were also associated with the hepatotoxicity of the diabetes drug Rezulin (Troglitazone), which was prescribed 2 million times and resulted in 398 deaths before its withdrawal from the market; 8700 law suits are being filed.

Baycol, a cholesterol-lowering statin taken by 700,000 Americans, was removed from the market due to reports of a sometimes fatal muscle-related adverse reaction (rhabdomyolysis) and 31 deaths in the USA. Projected annual Baycol revenues prior to the recall were approximately $1 billion.

Sales growth of Celebrex and Vioxx, blockbusters for the treatment of arthritis, has also been negatively affected by reports of a potential link to heart problems.

Thus, there is a need to reduce time and costs of drug development by (a) accelerating the hit-to-drug selection process by filtering out those hits likely to trigger side effects and (b) re-engineering drug chemical structure based on the knowledge of drug-target and drug-non-target interactions, reducing or eliminating the undesired interactions.

There is also a need to develop technologies for analysis of the proteome that allow scaling up to industrial levels with the features of an industrial process: high accuracy, reproducibility and flexibility in that the process is high-throughput, automatable and cost-effective. There is a need to develop technologies that permit probing and identification of proteins and other biomolecules in their native conformation using automated protocols and systems therefor. In particular, there is a need to develop strategies and technologies for identification and characterization of hydrophobic proteins under physiological conditions.

SUMMARY

Provided herein are methods, capture compounds (also referred to herein as capture agents) and collections thereof for analysis of the proteome on an industrial level in a high-throughput format. The methods, capture compounds and collections permit sorting of complex mixtures of biomolecules. In addition, they permit identification of protein structures predicative or indicative of specific of phenotypes, such as disease states, thereby eliminating the need for random SNP analysis, expression profiling and protein analytical methods. The capture compounds, collections and methods sort complex mixtures by providing a variety of different capture agents. In addition, they can be used to identify structural "epitopes" that serve as markers for specific disease states, stratify individual populations relative to specific phenotypes, permit a detailed understanding of the proteins underlying molecular function, and provide targets for drug development. The increased understanding of target proteins permit the design of higher efficiency therapeutics.

The capture compounds, collections and methods provided herein also permit screening of biomolecules, including but not limited to receptor proteins and enzymes, which are drug targets and non-targets, as defined herein, that interact with pharmaceutical drugs under physiological conditions. The screening of biomolecules provides increased understanding of the mechanism of action of the pharmaceutical drugs or drug fragments, metabolites or synthetic intermediates in the drug syntheses, thereby helping the design of more target specific drugs. The methods also provide for identification of non-target biomolecules, such as proteins including but not limited to receptors and enzymes, that interact with pharmaceutical drugs, thereby causing side effects and other undesired therapeutic effects. In one embodiment, various attachments of the drugs or drug fragments, metabolites or synthetic intermediates in the drug syntheses to the capture compounds are used to determine which functionalities of the drugs or drug fragments, metabolites or synthetic intermediates in the drug syntheses interact with the target and non-target biomolecules. In one embodiment, the non-target functionalities are then eliminated from the drug, resulting in an improved drug that exhibits fewer side effects. In another embodiment, a drug is included in the capture compound, proteins that interact with the drug are isolated and identified, the proteins are related to function, and the drug is re-engineered to eliminate or reduce interactions with non-target proteins. The method may be repeated on the re-engineered drug, as desired.

Capture compounds, collections of the compounds and methods that use the compounds, singly or in collections thereof, provided herein are designed to capture, separate and analyze biomolecules, including, but not limited to, mixtures of biomolecules, including biopolymers and macromolecules, individual biomolecules, such as proteins, including individual or membrane proteins. The capture and separation of biomolecules in the methods provided herein, is based on the unique surface features of the biomolecules or mixtures thereof, including but not limited to chemically reactive amino acid residues on the surface of a protein or a mixture of proteins. Thus, the capture compounds provided herein are designed not to target any specific biomolecule, but to capture the biomolecules based on the reactive groups present on the surface of the biomolecules or mixtures thereof.

The collections of the compounds provided herein contain a plurality, generally at least two, three, typically at least 10, 50, 100, 1000 or more different capture compounds. The compounds and collections are designed to permit probing of a mixture of biomolecules by virtue of interaction of the capture compounds in the collection with the components of the a mixture under conditions that preserve their three-dimensional configuration. Each member of the collection is designed 1) to bind, either covalently or via some other chemical interaction with high binding affinity ($k_a$) such that the binding is irreversible or stable under conditions of mass spectrometric analysis to fewer than all, typically about 5 to 20 or more component biomolecules in a mixture, depending upon complexity and diversity of the mixture, under physiological conditions, including hydrophobic conditions, and 2) distinguish among biomolecules based upon topological features. In addition, the capture compounds generally include a group, such as a single-stranded oligonucleotide or partially single-stranded oligonucleotide, that permits separation of each set of capture compounds.

The capture compounds and collections are used in a variety of methods, but are particularly designed for assessing biomolecules, such as biopolymers or components in mixtures from biological samples. The collections are used in top-down unbiased methods that assess structural changes, including post-translational structural changes and, for example, are used to compare patterns, particularly post-translational protein patterns, in diseased versus healthy cells from primary cells generally from the same individual. The cells that serve as the sources of biomolecules can be frozen into a selected metabolic state or synchronized to permit direct comparison and identification of phenotype-specific, such as disease-specific biomolecules, generally proteins.

A capture compound includes at a chemical reactivity group X (also referred to herein as a function or a functionality), which effects the covalent or a high binding affinity (high $k_a$) binding, and least one of three other groups (also referred to herein as functions or functionalities). The other groups are selected from among a selectivity function Y that modulates the interaction of a biomolecule with the reactivity function, a sorting function Q for addressing the components of the collection, and a solubility function W that alters solubility of the capture compound, such as by increasing the solubility of the capture compound under selected conditions, such as various physiological conditions, including hydrophobic conditions of cell membranes. Hence, for example, if membrane proteins are targeted, then the capture compounds in the collection are designed with solubility functions that increase or provide for solubility in such environment.

For example, the reactivity group (reactivity function) includes groups that specifically react or interact with functionalities on the surface of a protein such as hydroxyl, amine, amide, sulfide and carboxylic acid groups, or that recognize specific surface areas, such as an antibody, a lectin or a receptor-specific ligand, or interacts with the active site of enzymes. Those skilled in the art can select from a library of functionalities to accomplish this interaction. While this interaction can be highly reaction-specific, these compounds can react multiple times within the same protein molecule depending on the number of surface-accessible functional groups. Modification of the reaction conditions allows the identification of surface accessible functional groups with differing reactivity, thereby permitting identification of one or more highly reactive sites used to separate an individual protein from a mixture. Available technologies do not separate species in the resulting reaction mixture. The collections and compounds provided herein solve that problem through a second functionality, the selectivity group, which alters binding of the reactivity groups to the biomolecule.

Selectivity functions include a variety of groups, as well as the geometric spacing of the second functionality, a single stranded unprotected or suitably protected oligonucleotide or oligonucleotide analog. The selective functionality can be separate from the compound and include the solid or semi-solid support. The selective functionality in this embodiment can be porosity, hydrophobicity, charge and other chemical properties of the material. For example, selectivity functions interact noncovalently with target proteins to alter the specificity or binding of the reactivity function. Such functions include chemical groups and biomolecules that can sterically hinder proteins of specific size, hydrophilic compounds or proteins (e.g., PEG and trityls), hydrophobic compounds or proteins (e.g., polar aromatic, lipids, glycolipids, phosphotriester, oligosaccharides), positive or negatively charged groups, groups or biomolecules which create defined secondary or tertiary structure.

The capture compounds can also include a sorting function for separation or addressing of each capture compound according to its structure. The sorting function, for example, can be a single-stranded (or partially single-stranded) unprotected or suitably protected oligonucleotide or oligonucleotide analog, typically containing between at least about 5 and up to 25, 35, 50, 100 or any desired number of nucleotides (or analogs thereof) containing a sequence-permuted region and optionally flanking regions. Each such block has a multitude of sequence permutations with or without flanking conserved regions, which is capable of hybridizing with a base-complementary single stranded nucleic acid molecule or a nucleic acid analog. The sorting function can also be a label, such as a symbology, including a bar code, particularly a machine-readable bar code, a color coded-label, such as small colored bead that can be sorted by virtue of its color, a radio-frequency tag or other electronic label or a chemical label. Any functionality that permits sorting of each set of capture compounds to permit separate analysis of bound biomolecules is contemplated.

In certain embodiments, each biomolecule to be captured is derivatized with more than one capture compound provided herein, where each tagged compound provides an additional level of sorting capability. In other embodiments, each of the plurality of compounds that derivatize a single biomolecule is different, allowing for specific and efficient sorting of the biomolecule mixture (see, e.g., FIG. 3). The capture compound also can be multifunctional containing other functionalities that can be used to reduce the complexity of biomolecule mixtures.

Some of the capture compounds include at least a reactivity function and a selectivity function. These capture compounds optionally include sorting functionalities, which are one or more additional moieties that bind either covalently or noncovalently to a specific molecule to permit addressing of the compounds, such as by separation at discrete loci on a solid support, separation of the compounds on discrete loci. These capture compounds also optionally include one or more solubility functions, which are moieties that influence the solubility of the resulting compound, to attenuate or alter the hydrophobicity/hydrophilicity of the compounds (solubility function).

Others of the capture compounds (or capture agents) include at least two functional portions: a reactivity function and a sorting function. The reactive group that specifically interacts with proteins or other biomolecules (reactivity function); and the other is an entity (sorting functions) that binds either covalently or noncovalently to a specific molecule(s). This entity can be a nucleic acid portion or nucleic acid analog portion that includes a single-stranded region that can specifically hybridize to a complementary single-stranded oligonucleotide or analog thereof.

The capture compounds are provided as collections, generally as collections of sets of different compounds that differ in all functionalities. For sorting of complex mixtures of biopolymers the collection includes diverse capture compound members so that, for example, when they are arrayed, each locus of the array contains 0 to 100, generally, 5 to 50 and desirably 1 to 20, typically 5 to 20, different biomolecules at each locus in the array.

In practice in one embodiment, a collection of capture compounds is contacted with a biomolecule mixture and the bound molecules are assessed using, for example, mass spectrometry, followed by optional application of tagging, such as fluorescence tagging, after arraying to identify low abundance proteins. In other embodiments, a single capture compound is contacted with one or plurality of biomolecules, and the bound molecules are assessed.

Also provided herein are methods for the discovery and identification of proteins, which are selected based on a defined phenotype. The methods allow proteins to bind to the target molecules under physiological conditions while maintaining the correct secondary and tertiary conformation of the target. The methods can be performed under physiological and other conditions that permit discovery of biologically important proteins, including membrane proteins, that are selected based upon a defined phenotype.

Before, during or after exposure of one or a plurality of capture compounds to a mixture of biomolecules, including, but not limited to, a mixture of proteins, the oligonucleotide portion, or analog thereof, of these compounds is allowed to hybridize to a complementary strand of immobilized oligonucleotide(s), or analog(s) thereof, to allow separation, isolation and subsequent analysis of bound biomolecules, such as proteins, by, for example, mass spectrometry, such as matrix assisted laser desorption ionization-time of flight (MALDI-TOF) mass spectrometry, colorimetric, fluorescent or chemiluminescent tagging, or to allow for increased resolution by mass spectrometry, including MALDI-TOF mass spectrometry.

The collections of capture compounds can be used to generate compound arrays to capture target proteins or groups of related proteins that can mimic biological structures such as nuclear and mitochondrial transmembrane structures, artificial membranes or intact cell walls. Thus, the compounds and compound arrays provided herein are capable of mimicking biological entities and biological surfaces, thereby allowing for capture of biomolecules, including but not limited to proteins, which would otherwise be difficult or impossible to capture, such as those found in transmembrane regions of a cell.

Samples for analysis include any biomolecules, particularly protein-containing samples, such as protein mixtures, including, but not limited to, natural and synthetic sources. Proteins can be prepared by translation from isolated chromosomes, genes, cDNA and genomic libraries. Proteins can be isolated from cells, and other sources. In certain embodiments, the capture compounds provided herein are designed to selectively capture different post-translational modifications of the same protein (i.e., phosphorylation patterns (e.g., oncogenes), glycosylation and other post-translational modifications).

Other methods that employ the collections are also provided. In one method, the collections of one or more member capture compounds are used to distinguish between or among different conformations of a protein and, for example, can be used for phenotypic identification, such as for diagnosis. For example, for diseases of protein aggregation, which are diseases involving a conformationally altered protein, such as amyloid diseases, the collections can distinguish between the disease-involved form of the protein from the normal protein and thereby diagnose the disease in a sample.

BRIEF DESCRIPTION OF THE FIGURES

FIG. 19a depicts methods for separation of cells from blood from a single patient to separate them by phenotype; FIG. 19b shows the results of flow cytometry separation of blood cells without labeling; FIG. 19c shows an example in which synchronized cells in culture are sorted according to DNA content as a way to separate cells by phase of the cell cycle.

FIG. 20a-f shows a schematic of a biomolecule capture assay and results using exemplary capture compounds and proteins.

FIG. 21a-b shows exemplary selectivity functions for use in the capture compounds provided herein.

FIG. 23A-1 to FIG. 23D-3 shows exemplary capture compounds provided herein.

FIG. 25 shows mass spectrometric results of the reaction of a capture compound provided herein with Burkitt's lymphoma cytosol. As shown in the Figure, the proteins labeled A-E are captured by the indicated capture compound.

DETAILED DESCRIPTION

A. Definitions

Figure 1:
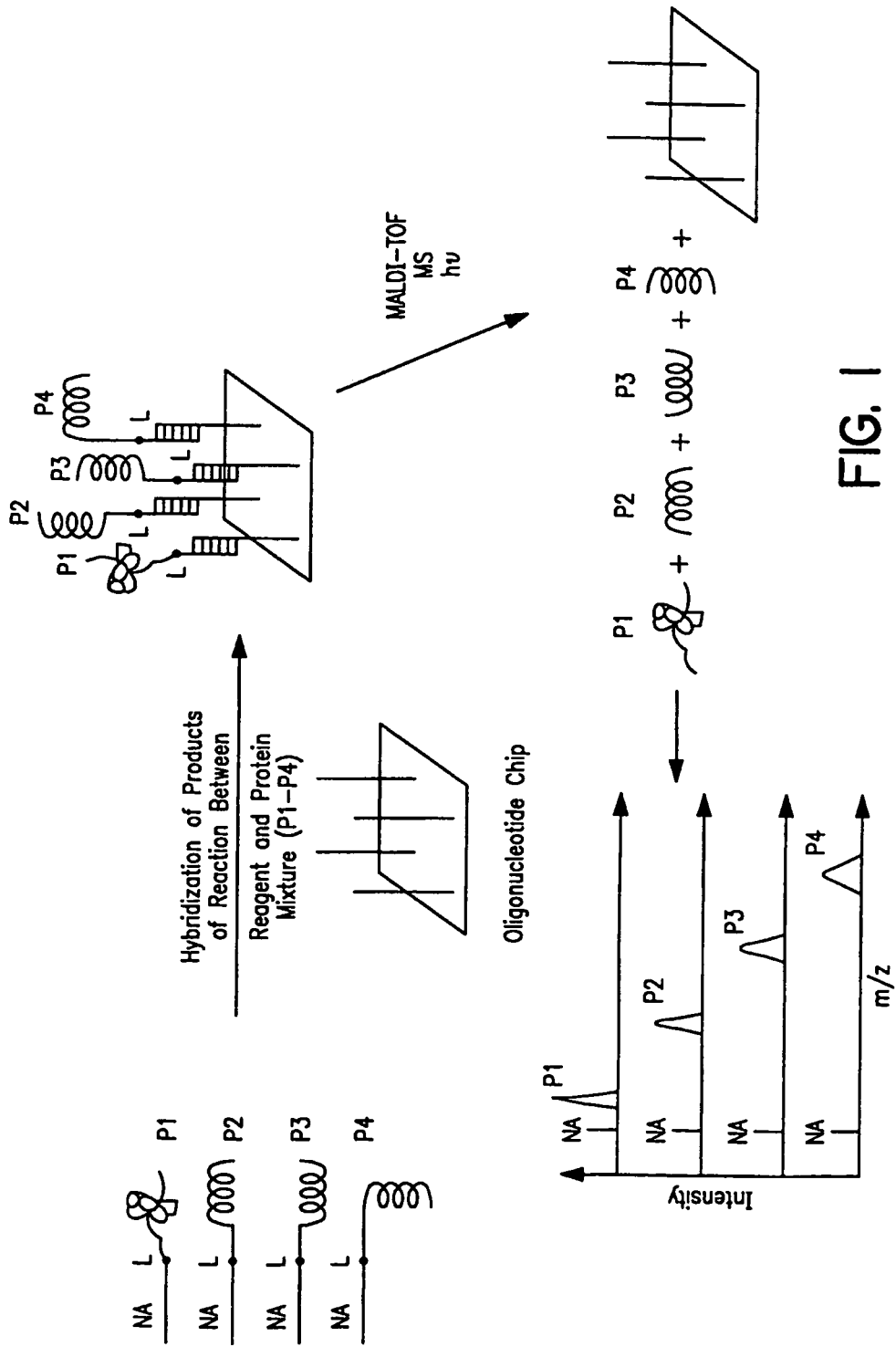
FIG. 1 shows the hybridization, separation and mass spectral analysis of a mixture of proteins.

Unless defined otherwise, all technical and scientific terms used herein have the same meaning as is commonly understood by one of skill in the art to which the invention(s) belong. All patents, patent applications, published applications and publications, Genbank sequences, websites and other published materials referred to throughout the entire disclosure herein, unless noted otherwise, are incorporated by reference in their entirety. In the event that there are a plurality of definitions for terms herein, those in this section prevail. Where reference is made to an URL or other such indentifier or address, it is understood that such identifiers can change and particular information on the internet can come and go, but equivalent information can be found by searching the internet. Reference thereto evidences the availability and public dissemination of such information.

As used herein, an oligonucleotide means a linear sequence of up to about 20, about 50, or about 100, nucleotides joined by phosphodiester bonds. Above this length the term polynucleotide begins to be used.

As used herein, an oligonucleotide analog means a linear sequence of up to about 20, about 50, or about 100, nucleotide analogs, or linear sequence of up to about 20, about 50, or about 100 nucleotides linked by a "backbone" bond other than a phosphodiester bond, for example, a phosphotriester bond, a phosphoramidate bond, a phophorothioate bond, a methylphosphonate diester bond, a thioester bond, or a peptide bond (peptide nucleic acid).

As used herein, peptide nucleic acid (PNA) refers to nucleic acid analogs in that the ribose-phosphate backbone is replaced by a backbone held together by amide bonds.

As used herein, proteome means all the proteins present within a cell.

As used herein, a biomolecule is any compound found in nature, or derivatives thereof. Biomolecules include, but are not limited to oligonucleotides, oligonucleosides, proteins, peptides, amino acids, lipids, steroids, peptide nucleic acids (PNAs), oligosaccharides and monosaccharides.

As used herein, MALDI-TOF refers to matrix assisted laser desorption ionization-time of flight mass spectrometry.

As used herein, the term "conditioned" or "conditioning," when used in reference to a protein thereof, means that the polypeptide is modified to decrease the laser energy required to volatilize the protein, to minimize the likelihood of fragmentation of the protein, or to increase the resolution of a mass spectrum of the protein or of the component amino acids. Resolution of a mass spectrum of a protein can be increased by conditioning the protein prior to performing mass spectrometry. Conditioning can be performed at any stage prior to mass spectrometry and, in one embodiment, is performed while the protein is immobilized. A protein can be conditioned, for example, by treating it with a cation exchange material or an anion exchange material, which can reduce the charge heterogeneity of the protein, thereby for eliminating peak broadening due to heterogeneity in the number of cations (or anions) bound to the various proteins in a population. In one embodiment, removal of all cations by ion exchange, except for $H^+$ and ammonium ions, is performed. By contacting a polypeptide with an alkylating agent such as alkyliodide, iodoacetamide, iodoethanol, or 2,3epoxy-1-propanol, the formation of disulfide bonds, for example, in a protein can be prevented. Likewise, charged amino acid side chains can be converted to uncharged derivatives employing trialkylsilyl chlorides.

Since the capture compounds contain protein and nucleic acid portions, conditioning suitable for one or both portions is also contemplated. Hence, a prepurification to enrich the biomolecules to be analyzed and the removal of all cations, such as by ion exchange, except for H+ and ammonium, or other conditioning treatment to improve resolution is advantageous for analysis of the nucleic acid portion as well as the protein portion.

Conditioning of proteins is generally unnecessary because proteins are relatively stable under acidic, high energy conditions so that proteins do not require conditioning for mass spectrometric analyses. There are means of improving resolution, however, in one embodiment for shorter peptides, such as by incorporating modified amino acids that are more basic than the corresponding unmodified residues. Such modification in general increases the stability of the polypeptide during mass spectrometric analysis. Also, cation exchange chromatography, as well as general washing and purification procedures that remove proteins and other reaction mixture components away from the protein can be used to increase the resolution of the spectrum resulting from mass spectrometric analysis of the protein.

As used herein, capture efficiency is the peak area of the captured biomolecule/(peak area captured biomolecule+peak area uncaptured biomolecule) as measured by HPLC analysis.

As used herein, "matrix" refers to the material with which the capture compound biomolecule conjugates are combined for MALDI mass spectrometric analysis. Any matrix material, such as solid acids, including 3-hydroxypicolinic acid, liquid matrices, such as glycerol, known to those of skill in the art for nucleic acid and/or protein analyses is contemplated. Since the compound biomolecule conjugates contain nucleic acid and protein a mixture (optimal for nucleic acids and proteins) of matrix molecules can be used.

As used herein, macromolecule refers to any molecule having a molecular weight from the hundreds up to the millions. Macromolecules include, but are not limited to, peptides, proteins, nucleotides, nucleic acids, carbohydrates, and other such molecules that are generally synthesized by biological organisms, but can be prepared synthetically or using recombinant molecular biology methods.

As used herein, the term "biopolymer" is refers to a biological molecule, including macromolecules, composed of two or more monomeric subunits, or derivatives thereof, which are linked by a bond or a macromolecule. A biopolymer can be, for example, a polynucleotide, a polypeptide, a carbohydrate, or a lipid, or derivatives or combinations thereof, for example, a nucleic acid molecule containing a peptide nucleic acid portion or a glycoprotein. The methods and collections herein, though described with reference to biopolymers, can be adapted for use with other synthetic schemes and assays, such as organic syntheses of pharmaceuticals, or inorganics and any other reaction or assay performed on a solid support or in a well in nanoliter or smaller volumes.

As used herein, biomolecule includes biopolymers and macromolecules and all molecules that can be isolated from living organisms and viruses, including, but are not limited to, cells, tissues, prions, animals, plants, viruses, bacteria and other organisms.

As used herein, a biological particle refers to a virus, such as a viral vector or viral capsid with or without packaged nucleic acid, phage, including a phage vector or phage capsid, with or without encapsulated nucleotide acid, a single cell, including eukaryotic and prokaryotic cells or fragments thereof, a liposome or micellar agent or other packaging particle, and other such biological materials. For purposes herein, biological particles include molecules that are not typically considered macromolecules because they are not generally synthesized, but are derived from cells and viruses.

As used herein, a drug refers to any compound that is a candidate for use as a therapeutic or as a lead compound for designing a therapeutic or that is a known pharmaceutical. Such compounds can be small molecules, including small organic molecules, peptides, peptide mimetics, antisense molecules, antibodies, fragments of antibodies or recombinant antibodies. Of particular interest are "drugs" that have specific binding properties so that they can be used as selectivity groups or can be used as for sorting of the capture compounds, either a sorting functionality that binds to a target on a support, or linked to a solid support, where the sorting functionality is the drug target.

As used herein, a drug metabolite refers to any compound that is formed after transformation of a drug following its metabolism in the body that results in a different molecule that may be more or less active than the parent drug.

As used herein, a drug fragment refers to a molecule that is a portion or moiety of a drug.

As used herein, a drug synthetic intermediate is a compound that is used as an intermediate in the chemical synthesis of a drug.

As used herein, the term "a" is singular or plural.

As used herein, a "drug target" is a biomolecule, such as a protein including but not limited to receptors and enzymes, that the drug is intended to interact with in vivo, thereby exerting the desired therapeutic effects.

As used herein, a "drug non-target" is a biomolecule, such as a protein including but not limited to receptors and enzymes, that the drug is not intended to interact with in vivo. The interaction of a drug with drug non-targets may result in undesired therapeutic effects such as side effects.

As used herein, the term "nucleic acid" refers to single-stranded and/or double-stranded polynucleotides such as deoxyribonucleic acid (DNA), and ribonucleic acid (RNA) as well as analogs or derivatives of either RNA or DNA. Nucleic acid molecules are linear polymers of nucleotides, linked by 3',5' phosphodiester linkages. In DNA, deoxyribonucleic acid, the sugar group is deoxyribose and the bases of the nucleotides are adenine, guanine, thymine and cytosine.

RNA, ribonucleic acid, has ribose as the sugar and uracil replaces thymine. Also included in the term "nucleic acid" are analogs of nucleic acids such as peptide nucleic acid (PNA), phosphorothioate DNA, and other such analogs and derivatives or combinations thereof.

As used herein, the term "polynucleotide" refers to an oligomer or polymer containing at least two linked nucleotides or nucleotide derivatives, including a deoxyribonucleic acid (DNA), a ribonucleic acid (RNA), and a DNA or RNA derivative containing, for example, a nucleotide analog or a "backbone" bond other than a phosphodiester bond, for example, a phosphotriester bond, a phosphoramidate bond, a methylphosphonate diester bond, a phophorothioate bond, a thioester bond, or a peptide bond (peptide nucleic acid). The term "oligonucleotide" also is used herein essentially synonymously with "polynucleotide," although those in the art recognize that oligonucleotides, for example, PCR primers, generally are less than about fifty to one hundred nucleotides in length.

Nucleotide analogs contained in a polynucleotide can be, for example, mass modified nucleotides, which allows for mass differentiation of polynucleotides; nucleotides containing a detectable label such as a fluorescent, radioactive, colorometric, luminescent or chemiluminescent label, which allows for detection of a polynucleotide; or nucleotides containing a reactive group such as biotin or a thiol group, which facilitates immobilization of a polynucleotide to a solid support. A polynucleotide also can contain one or more backbone bonds that are selectively cleavable, for example, chemically, enzymatically or photolytically. For example, a polynucleotide can include one or more deoxyribonucleotides, followed by one or more ribonucleotides, which can be followed by one or more deoxyribonucleotides, such a sequence being cleavable at the ribonucleotide sequence by base hydrolysis. A polynucleotide also can contain one or more bonds that are relatively resistant to cleavage, for example, a chimeric oligonucleotide primer, which can include nucleotides linked by peptide nucleic acid bonds and at least one nucleotide at the 3' end, which is linked by a phosphodiester bond, or the like, and is capable of being extended by a polymerase. Peptide nucleic acid sequences can be prepared using well known methods (see, for example, Weiler et al. (1997) *Nucleic acids Res.* 25:2792-2799).

A polynucleotide can be a portion of a larger nucleic acid molecule, for example, a portion of a gene, which can contain a polymorphic region, or a portion of an extragenic region of a chromosome, for example, a portion of a region of nucleotide repeats such as a short tandem repeat (STR) locus, a variable number of tandem repeats (VNTR) locus, a microsatellite locus or a minisatellite locus. A polynucleotide also can be single stranded or double stranded, including, for example, a DNA-RNA hybrid, or can be triple stranded or four stranded. Where the polynucleotide is double stranded DNA, it can be in an A, B, L or Z configuration, and a single polynucleotide can contain combinations of such configurations.

As used herein, a "mass modification," with respect to a biomolecule to be analyzed for mass spectrometry, refers to the inclusion of changes in constituent atoms or groups that change the molecular weight of the resulting molecule in defined increments detectable by mass spectrometric analysis. Mass modifications do not include radiolabels, such as isotope labels or fluorescent groups or other such tags normally used for detection by means other than mass spectrometry.

As used herein, the term "polypeptide" means at least two amino acids, or amino acid derivatives, including mass modified amino acids and amino acid analogs, which are linked by a peptide bond and which can be a modified peptide bond. A polypeptide can be translated from a polynucleotide, which can include at least a portion of a coding sequence or a portion of a nucleotide sequence that is not naturally translated due, for example, to it being located in a reading frame other than a coding frame, or it being an intron sequence, a 3' or 5' untranslated sequence, a regulatory sequence such as a promoter. A polypeptide also can be chemically synthesized and can be modified by chemical or enzymatic methods following translation or chemical synthesis. The terms "polypeptide," "peptide" and "protein" are used essentially synonymously herein, although the skilled artisan recognizes that peptides generally contain fewer than about fifty to one hundred amino acid residues, and that proteins often are obtained from a natural source and can contain, for example, post-translational modifications. A polypeptide can be posttranslationally modified by, for example, phosphorylation (phosphoproteins) or glycosylation (glycoproteins, proteoglycans), which can be performed in a cell or in a reaction in vitro.

As used herein, the term "conjugated" refers to stable attachment, typically by virtue of a chemical interaction, including ionic and/or covalent attachment. Among the conjugation means are streptavidin- or avidin- to biotin interaction; hydrophobic interaction; magnetic interaction (e.g., using functionalized magnetic beads, such as DYNABEADS, which are streptavidin-coated magnetic beads sold by Dynal, Inc. Great Neck, NY and Oslo Norway); polar interactions, such as "wetting" associations between two polar surfaces or between oligo/polyethylene glycol; formation of a covalent bond, such as an amide bond, disulfide bond, thioether bond, or via crosslinking agents; and via an acid-labile or photocleavable linker.

As used herein, "sample" refers to a composition containing a material to be detected. For the purposes herein, sample refers to anything which can contain an biomolecule. The sample can be a biological sample, such as a biological fluid or a biological tissue obtained from any organism or a cell of or from an organism or a viral particle or portions thereof. Examples of biological fluids include urine, blood, plasma, serum, saliva, semen, stool, sputum, cerebral spinal fluid, tears, mucus, sperm, amniotic fluid or the like. Biological tissues are aggregates of cells, usually of a particular kind together with their intercellular substance that form one of the structural materials of a human, animal, plant, bacterial, fungal or viral structure, including connective, epithelium, muscle and nerve tissues. Examples of biological tissues also include organs, tumors, lymph nodes, arteries and individual cell(s).

Thus, samples include biological samples (e.g., any material obtained from a source originating from a living being (e.g., human, animal, plant, bacteria, fungi, protist, virus). The biological sample can be in any form, including solid materials (e.g., tissue, cell pellets and biopsies, tissues from cadavers) and biological fluids (e.g., urine, blood, saliva, amniotic fluid and mouth wash (containing buccal cells)). In certain embodiments, solid materials are mixed with a fluid. In embodiments herein, the a sample for mass spectrometric analysis includes samples that contain a mixture of matrix used for mass spectrometric analyses and the capture compound/biomolecule complexes.

As used herein, the term "solid support" means a non-gaseous, non-liquid material having a surface. Thus, a solid support can be a flat surface constructed, for example, of glass, silicon, metal, plastic or a composite; or can be in the form of a bead such as a silica gel, a controlled pore glass, a magnetic or cellulose bead; or can be a pin, including an array of pins suitable for combinatorial synthesis or analysis.

As used herein, a collection refers to combination of two or more members, generally 3, 5, 10, 50, 100, 500, 1000 or more members. In particular a collection refers to such combination of the capture compounds as provided herein.

As used herein, an array refers to a collection of elements, such as the capture compounds, containing three or more members. An addressable array is one in that the members of the array are identifiable, typically by position on a solid phase support but also by virtue of an identifier or detectable label. Hence, in general the members of an array are be immobilized to discrete identifiable loci on the surface of a solid phase. A plurality of the compounds are attached to a support, such as an array (i.e., a pattern of two or more) on the surface of a support, such as a silicon chip or other surface, generally through binding of the sorting functionality with a group or compound on the surface of the support. Addressing can be achieved by labeling each member electronically, such as with an radio-frequency (RF) tag, through the use of color coded beads or other such identifiable and color coded labels and through molecular weight. These labels for addressing serve as sorting functions "Q." Hence, in general the members of the array are immobilized to discrete identifiable loci on the surface of a solid phase or directly or indirectly linked to or otherwise associated with the identifiable label, such as affixed to a microsphere or other particulate support (herein referred to as beads) and suspended in solution or spread out on a surface.

As used herein, "substrate" refers to an insoluble support onto which a sample and/or matrix is deposited. Support can be fabricated from virtually any insoluble or solid material. For example, silica gel, glass (e.g., controlled-pore glass (CPG)), nylon, Wang resin, Merrifield resin, dextran cross—linked with epichlorohydrin (e.g., Sephadex®), agarose (e.g., Sepharose®), cellulose, magnetic beads, Dynabeads, a metal surface (e.g., steel, gold, silver, aluminum, silicon and copper), a plastic material (e.g., polyethylene, polypropylene, polyamide, polyester, polyvinylidenedifluoride (PVDF)) Exemplary substrate include, but are not limited to, beads (e.g., silica gel, controlled pore glass, magnetic, dextran cross—linked with epichlorohydrin (e.g., Sephadex®), agarose (e.g., Sepharose®), cellulose, capillaries, flat supports such as glass fiber filters, glass surfaces, metal surfaces (steel, gold, silver, aluminum, copper and silicon), plastic materials including multiwell plates or membranes (e.g., of polyethylene, polypropylene, polyamide, polyvinylidenedifluoride), pins (e.g., arrays of pins suitable for combinatorial synthesis or analysis or beads in pits of flat surfaces such as wafers (e.g., silicon wafers) with or without filter plates. The solid support is in any desired form, including, but not limited to, a bead, capillary, plate, membrane, wafer, comb, pin, a wafer with pits, an array of pits or nanoliter wells and other geometries and forms known to those of skill in the art. Supports include flat surfaces designed to receive or link samples at discrete loci. In one embodiment, flat surfaces include those with hydrophobic regions surrounding hydrophilic loci for receiving, containing or binding a sample.

The supports can be particulate or can be in the form of a continuous surface, such as a microtiter dish or well, a glass slide, a silicon chip, a nitrocellulose sheet, nylon mesh, or other such materials. When particulate, typically the particles have at least one dimension in the 510 mm range or smaller. Such particles, referred collectively herein as "beads", are often, but not necessarily, spherical. Reference to "bead," however, does not constrain the geometry of the matrix, which can be any shape, including random shapes, needles, fibers, and elongated. "Beads", particularly microspheres that are sufficiently small to be used in the liquid phase, are also contemplated. The "beads" can include additional components, such as magnetic or paramagnetic particles (see, e.g., Dyna beads (Dynal, Oslo, Norway)) for separation using magnets, as long as the additional components do not interfere with the methods and analyses herein.

As used herein, "polymorphism" refers to the coexistence of more than one form of a gene or portion thereof. A portion of a gene of which there are at least two different forms, e.g., two different nucleotide sequences, is referred to as a "polymorphic region of a gene". A polymorphic region can be a single nucleotide, e.g., a single nucleotide polymorphism (SNP), the identity of which differs in different alleles. A polymorphic region also can be several nucleotides in length.

As used herein, "polymorphic gene" refers to a gene having at least one polymorphic region.

As used herein, "allele", which is used interchangeably herein with "allelic variant" refers to alternative forms of a gene or portions thereof. Alleles occupy the same locus or position on homologous chromosomes. When a subject has two identical alleles of a gene, the subject is said to be homozygous for the gene or allele. When a subject has two different alleles of a gene, the subject is said to be heterozygous for the gene. Alleles of a specific gene can differ from each other in a single nucleotide, or several nucleotides, and can include substitutions, deletions, and insertions of nucleotides. An allele of a gene also can be a form of a gene containing a mutation.

As used herein, "predominant allele" refers to an allele that is represented in the greatest frequency for a given population. The allele or alleles that are present in lesser frequency are referred to as allelic variants.

As used herein, "associated" refers to coincidence with the development or manifestation of a disease, condition or phenotype. Association can be due to, but is not limited to, genes responsible for housekeeping functions whose alteration can provide the foundation for a variety of diseases and conditions, those that are part of a pathway that is involved in a specific disease, condition or phenotype and those that indirectly contribute to the manifestation of a disease, condition or phenotype.

As used herein, the term "subject" refers to a living organism, such as a mammal, a plant, a fungi, an invertebrate, a fish, an insect, a pathogenic organism, such as a virus or a bacterium, and, includes humans and other mammals.

As used herein, the term "gene" or "recombinant gene" refers to a nucleic acid molecule containing an open reading frame and including at least one exon and (optionally) an intron sequence. A gene can be either RNA or DNA. Genes can include regions preceding and following the coding region.

As used herein, "intron" refers to a DNA fragment present in a given gene that is spliced out during mRNA maturation.

As used herein, "nucleotide sequence complementary to the nucleotide sequence set forth in SEQ ID NO: x" refers to the nucleotide sequence of the complementary strand of a nucleic acid strand having SEQ ID NO: x. The term "complementary strand" is used herein interchangeably with the term "complement". The complement of a nucleic acid strand can be the complement of a coding strand or the complement of a noncoding strand. When referring to double stranded nucleic acids, the complement of a nucleic acid having SEQ ID NO: x refers to the complementary strand of the strand having SEQ ID NO: x or to any nucleic acid having the nucleotide sequence of the complementary strand of SEQ ID NO: x.

When referring to a single stranded nucleic acid having the nucleotide sequence SEQ ID NO: x, the complement of this nucleic acid is a nucleic acid having a nucleotide sequence that is complementary to that of SEQ ID NO: x.

As used herein, the term "coding sequence" refers to that portion of a gene that encodes a amino acids that constitute a polypeptide or protein.

As used herein, the term "sense strand" refers to that strand of a double-stranded nucleic acid molecule that has the sequence of the mRNA that encodes the amino acid sequence encoded by the double-stranded nucleic acid molecule.

As used herein, the term "antisense strand" refers to that strand of a double-stranded nucleic acid molecule that is the complement of the sequence of the mRNA that encodes the amino acid sequence encoded by the double-stranded nucleic acid molecule.

As used herein, the amino acids, which occur in the various amino acid sequences appearing herein, are identified according to their well-known, three-letter or one-letter abbreviations. The nucleotides, which occur in the various DNA fragments, are designated with the standard single-letter designations used routinely in the art (see, Table 1).

As used herein, amino acid residue refers to an amino acid formed upon chemical digestion (hydrolysis) of a polypeptide at its peptide linkages. The amino acid residues described herein are, in certain embodiments, in the "L" isomeric form. Residues in the "D" isomeric form can be substituted for any Lamino acid residue, as long as the a desired functional property is retained by the polypeptide. $NH_2$ refers to the free amino group present at the amino terminus of a polypeptide. COOH refers to the free carboxy group present at the carboxyl terminus of a polypeptide. In keeping with standard polypeptide nomenclature described in *J. Biol. Chem.*, 243: 355259 (1969) and adopted at 37 C.F.R. §§1.821-1.822, abbreviations for amino acid residues are shown in the following Table:

TABLE 1

Table of Correspondence

SYMBOL

| 1 Letter | 3 Letter | AMINO ACID |
|---|---|---|
| Y | Tyr | tyrosine |
| G | Gly | glycine |
| F | Phe | phenylalanine |
| M | Met | methionine |
| A | Ala | alanine |
| S | Ser | serine |
| I | Ile | isoleucine |
| L | Leu | leucine |
| T | Thr | threonine |
| V | Val | valine |
| P | Pro | proline |
| K | Lys | lysine |
| H | His | histidine |
| Q | Gln | glutamine |
| E | Glu | glutamic acid |
| Z | Glx | Glu and/or Gln |
| W | Trp | tryptophan |
| R | Arg | arginine |
| D | Asp | aspartic acid |
| N | Asn | asparagine |
| B | Asx | Asn and/or Asp |
| C | Cys | cysteine |
| X | Xaa | Unknown or other |

It should be noted that all amino acid residue sequences represented herein by formulae have a left to right orientation in the conventional direction of aminoterminus to carboxyl-terminus. In addition, the phrase "amino acid residue" is broadly defined to include the amino acids listed in the Table of Correspondence and modified and unusual amino acids, such as those referred to in 37 C.F.R. §§1.821-1.822, and incorporated herein by reference. Furthermore, it should be noted that a dash at the beginning or end of an amino acid residue sequence indicates a peptide bond to a further sequence of one or more amino acid residues or to an amino-terminal group such as $NH_2$ or to a carboxylterminal group such as COOH.

In a peptide or protein, suitable conservative substitutions of amino acids are known to those of skill in this art and can be made generally without altering the biological activity of the resulting molecule. Those of skill in this art recognize that, in general, single amino acid substitutions in non-essential regions of a polypeptide do not substantially alter biological activity (see, e.g., Watson et al. *Molecular Biology of the Gene*, 4th Edition, 1987, The Benjamin/Cummings Pub. co., p. 224).

Such substitutions can be made in accordance with those set forth in TABLE 2 as follows:

TABLE 2

| Original residue | Conservative substitution |
|---|---|
| Ala (A) | Gly; Ser |
| Arg (R) | Lys |
| Asn (N) | Gln; His |
| Asp (D) | Glu |
| Cys (C) | Ser |
| Gln (Q) | Asn |
| Glu (E) | Asp |
| Gly (G) | Ala; Pro |
| His (H) | Asn; Gln |
| Ile (I) | Leu; Val |
| Leu (L) | Ile; Val |
| Lys (K) | Arg; Gln |
| Met (M) | Leu; Tyr; Ile |
| Phe (F) | Met; Leu; Tyr |
| Ser (S) | Thr |
| Thr (T) | Ser |
| Trp (W) | Tyr |
| Tyr (Y) | Trp; Phe |
| Val (V) | Ile; Leu |

Other substitutions are also permissible and can be determined empirically or in accord with known conservative substitutions.

As used herein, a DNA or nucleic acid homolog refers to a nucleic acid that includes a preselected conserved nucleotide sequence, such as a sequence encoding a therapeutic polypeptide. By the term "substantially homologous" is meant having at least 80%, at least 90% or at least 95% homology therewith or a less percentage of homology or identity and conserved biological activity or function.

The terms "homology" and "identity" are often used interchangeably. In this regard, percent homology or identity can be determined, for example, by comparing sequence information using a GAP computer program. The GAP program uses the alignment method of Needleman and Wunsch (*J. Mol. Biol.* 48:443 (1970), as revised by Smith and Waterman (*Adv. Appl. Math.* 2:482 (1981). Briefly, the GAP program defines similarity as the number of aligned symbols (e.g., nucleotides or amino acids) that are similar, divided by the total number of symbols in the shorter of the two sequences. The default parameters for the GAP program can include: (1) a unary comparison matrix (containing a value of 1 for identities and 0 for nonidentities) and the weighted comparison matrix of Gribskov and Burgess, *Nucl. Acids Res.* 14:6745

(1986), as described by Schwartz and Dayhoff, eds., *ATLAS OF PROTEIN SEQUENCE AND STRUCTURE*, National Biomedical Research Foundation, pp. 353358 (1979); (2) a penalty of 3.0 for each gap and an additional 0.10 penalty for each symbol in each gap; and (3) no penalty for end gaps.

Whether any two nucleic acid molecules have nucleotide sequences that are at least 80%, 85%, 90%, 95%, 96%, 97%, 98% or 99% "identical" can be determined using known computer algorithms such as the "FASTA" program, using for example, the default parameters as in Pearson and Lipman, *Proc. Natl. Acad. Sci. USA* 85:2444 (1988). Alternatively the BLAST function of the National Center for Biotechnology Information database can be used to determine identity.

In general, sequences are aligned so that the highest order match is obtained. "Identity" per se has an art-recognized meaning and can be calculated using published techniques. (See, e.g.: *Computational Molecular Biology*, Lesk, A. M., ed., Oxford University Press, New York, 1988; *Biocomputing: Informatics and Genome Projects*, Smith, D. W., ed., Academic Press, New York, 1993; *Computer Analysis of Sequence Data, Part I*, Griffin, A. M., and Griffin, H. G., eds., Humana Press, New Jersey, 1994; *Sequence Analysis in Molecular Biology*, von Heinje, G., Academic Press, 1987; and *Sequence Analysis Primer*, Gribskov, M. and Devereux, J., eds., M Stockton Press, New York, 1991). While there exist a number of methods to measure identity between two polynucleotide or polypeptide sequences, the term "identity" is well known to skilled artisans (Carillo, H. & Lipton, D., *SIAM J Applied Math* 48:1073 (1988)). Methods commonly employed to determine identity or similarity between two sequences include, but are not limited to, those disclosed in Guide to Huge Computers, Martin J. Bishop, ed., Academic Press, San Diego, 1994, and Carillo, H. & Lipton, D., *SIAM J Applied Math* 48:1073 (1988). Methods to determine identity and similarity are codified in computer programs. Computer program methods to determine identity and similarity between two sequences include, but are not limited to, GCG program package (Devereux, J., et al., *Nucleic Acids Research* 12(I):387 (1984)), BLASTP, BLASTN, FASTA (Atschul, S.F., et al., *J Molec Biol* 215:403 (1990)).

Therefore, as used herein, the term "identity" represents a comparison between a test and a reference polypeptide or polynucleotide. For example, a test polypeptide can be defined as any polypeptide that is 90% or more identical to a reference polypeptide.

As used herein, the term at least "90% identical to" refers to percent identities from 90 to 99.99 relative to the reference polypeptides. Identity at a level of 90% or more is indicative of the fact that, assuming for exemplification purposes a test and reference polypeptide length of 100 amino acids are compared. No more than 10% (e.g., 10 out of 100) amino acids in the test polypeptide differs from that of the reference polypeptides. Similar comparisons can be made between a test and reference polynucleotides. Such differences can be represented as point mutations randomly distributed over the entire length of an amino acid sequence or they can be clustered in one or more locations of varying length up to the maximum allowable, e.g., 10/100 amino acid difference (approximately 90% identity). Differences are defined as nucleic acid or amino acid substitutions, or deletions.

As used herein: stringency of hybridization in determining percentage mismatch is as follows:
1) high stringency: 0.1×SSPE, 0.1% SDS, 65° C.
2) medium stringency: 0.2×SSPE, 0.1% SDS, 50° C.
3) low stringency: 1.0×SSPE, 0.1% SDS, 50° C.

Those of skill in this art know that the washing step selects for stable hybrids and also know the ingredients of SSPE (see, e.g., Sambrook, E. F. Fritsch, T. Maniatis, in: *Molecular Cloning, A Laboratory Manual*, Cold Spring Harbor Laboratory Press (1989), vol. 3, p. B.13, see also numerous catalogs that describe commonly used laboratory solutions). SSPE is pH 7.4 phosphate-buffered, 0.18M NaCl. Further, those of skill in the art recognize that the stability of hybrids is determined by $T_m$, which is a function of the sodium ion concentration and temperature ($T_m$=81.5° C.-16.6($\log_{10}$[Na$^+$])+0.41(% G+C)-600/1)), so that the only parameters in the wash conditions critical to hybrid stability are sodium ion concentration in the SSPE (or SSC) and temperature.

It is understood that equivalent stringencies can be achieved using alternative buffers, salts and temperatures. By way of example and not limitation, procedures using conditions of low stringency are as follows (see also Shilo and Weinberg, *Proc. Natl. Acad. Sci. USA* 78:67896792 (1981)): Filters containing DNA are pretreated for 6 hours at 40° C. in a solution containing 35% formamide, 5×SSC, 50 mM TrisHCl (pH 7.5), 5 mM EDTA, 0.1% PVP, 0.1% Ficoll, 1% BSA, and 500 µg/ml denatured salmon sperm DNA (10×SSC is 1.5 M sodium chloride, and 0.15 M sodium citrate, adjusted to a pH of 7).

Hybridizations are carried out in the same solution with the following modifications: 0.02% PVP, 0.02% Ficoll, 0.2% BSA, 100 µg/ml salmon sperm DNA, 10% (wt/vol) dextran sulfate, and 520×10$^6$ cpm $^{32}$P-labeled probe is used. Filters are incubated in hybridization mixture for 1820 hours at 40° C., and then washed for 1.5 hours at 55° C. in a solution containing 2×SSC, 25 mM TrisHCl (pH 7.4), 5 mM EDTA, and 0.1% SDS. The wash solution is replaced with fresh solution and incubated an additional 1.5 hours at 60° C. Filters are blotted dry and exposed for autoradiography. If necessary, filters are washed for a third time at 6568° C. and re-exposed to film. Other conditions of low stringency which can be used are well known in the art (e.g., as employed for cross-species hybridizations).

By way of example and not way of limitation, procedures using conditions of moderate stringency include, for example, but are not limited to, procedures using such conditions of moderate stringency are as follows: filters containing DNA are pretreated for 6 hours at 55° C. in a solution containing 6×SSC, 5× Denhart's solution, 0.5% SDS and 100 µg/ml denatured salmon sperm DNA. Hybridizations are carried out in the same solution and 520×10$^6$ cpm $^{32}$P-labeled probe is used. Filters are incubated in hybridization mixture for 18-20 hours at 55° C., and then washed twice for 30 minutes at 60° C. in a solution containing 1×SSC and 0.1% SDS. Filters are blotted dry and exposed for autoradiography. Other conditions of moderate stringency which can be used are well-known in the art. Washing of filters is done at 37° C. for 1 hour in a solution containing 2×SSC, 0.1% SDS.

By way of example and not way of limitation, procedures using conditions of high stringency are as follows: Prehybridization of filters containing DNA is carried out for 8 hours to overnight at 65° C. in buffer composed of 6×SSC, 50 mM TrisHCl (pH 7.5), 1 mM EDTA, 0.02% PVP, 0.02% Ficoll, 0.02% BSA, and 500 µg/ml denatured salmon sperm DNA. Filters are hybridized for 48 hours at 65° C. in prehybridization mixture containing 100 µg/ml denatured salmon sperm DNA and 520×10$^6$ cpm of $^{32}$Plabeled probe. Washing of filters is done at 37° C. for 1 hour in a solution containing 2×SSC, 0.01% PVP, 0.01% Ficoll, and 0.01% BSA. This is followed by a wash in 0.1×SSC at 50° C. for 45 minutes before autoradiography. Other conditions of high stringency which can be used are well known in the art.

The term substantially identical or substantially homologous or similar varies with the context as understood by those skilled in the relevant art and generally means at least 60% or 70%, preferably means at least 80%, 85% or more preferably at least 90%, and most preferably at least 95% identity.

It is to be understood that the compounds provided herein can contain chiral centers. Such chiral centers can be of either the (R) or (S) configuration, or can be a mixture thereof. Thus, the compounds provided herein can be enantiomerically pure, or be stereoisomeric or diastereomeric mixtures. In the case of amino acid residues, such residues can be of either the L- or D-form. In one embodiment, the configuration for naturally occurring amino acid residues is L.

As used herein, substantially pure means sufficiently homogeneous to appear free of readily detectable impurities as determined by standard methods of analysis, such as thin layer chromatography (TLC), gel electrophoresis, high performance liquid chromatography (HPLC) and mass spectrometry (MS), used by those of skill in the art to assess such purity, or sufficiently pure such that further purification would not detectably alter the physical and chemical properties, such as enzymatic and biological activities, of the substance. Methods for purification of the compounds to produce substantially chemically pure compounds are known to those of skill in the art. A substantially chemically pure compound can, however, be a mixture of stereoisomers. In such instances, further purification might increase the specific activity of the compound.

As used herein, a cleavable bond or moiety refers to a bond or moiety that is cleaved or cleavable under the specific conditions, such as chemically, enzymatically or photolytically. Where not specified herein, such bond is cleavable under conditions of MALDI-MS analysis, such as by a UV or IR laser.

As used herein, a "selectively cleavable" moiety is a moiety that can be selectively cleaved without affecting or altering the composition of the other portions of the compound of interest. For example, a cleavable moiety L of the compounds provided herein is one that can be cleaved by chemical, enzymatic, photolytic, or other means without affecting or altering composition (e.g., the chemical composition) of the conjugated biomolecule, including a protein. "Non-cleavable" moieties are those that cannot be selectively cleaved without affecting or altering the composition of the other portions of the compound of interest.

As used herein, binding with high affinity refers to a binding that has an association constant $k_a$ of at least $10^9$ and generally $10^{10}$, $10^{11}$ liters/mole or greater) or a $K_{eq}$ of $10^9$, $10^{10}$, $10^{11}$, $10^{12}$ or greater. For purposes herein, high affinity bonds formed by the reactivity groups are those that are stable to the laser (UV and IR) used in MALDI-MS analyses.

As used herein, "alkyl", "alkenyl" and "alkynyl", if not specified, contain from 1 to 20 carbons, or 1 to 16 carbons, and are straight or branched carbon chains. Alkenyl carbon chains are from 2 to 20 carbons, and, in certain embodiments, contain 1 to 8 double bonds. Alkenyl carbon chains of 1 to 16 carbons, in certain embodiments, contain 1 to 5 double bonds. Alkynyl carbon chains are from 2 to 20 carbons, and, in one embodiment, contain 1 to 8 triple bonds. Alkynyl carbon chains of 2 to 16 carbons, in certain embodiments, contain 1 to 5 triple bonds. Exemplary alkyl, alkenyl and alkynyl groups include, but are not limited to, methyl, ethyl, propyl, isopropyl, isobutyl, n-butyl, sec-butyl, tert-butyl, isopentyl, neopentyl, tert-penytyl and isohexyl. The alkyl, alkenyl and alkynyl groups, unless otherwise specified, can be optionally substituted, with one or more groups, including alkyl group substituents that can be the same or different.

As used herein, "lower alkyl", "lower alkenyl", and "lower alkynyl" refer to carbon chains having less than about 6 carbons.

As used herein, "alk(en)(yn)yl" refers to an alkyl group containing at least one double bond and at least one triple bond.

As used herein, an "alkyl group substituent" includes, but is not limited to, halo, haloalkyl, including halo lower alkyl, aryl, hydroxy, alkoxy, aryloxy, alkyloxy, alkylthio, arylthio, aralkyloxy, aralkylthio, carboxy alkoxycarbonyl, oxo and cycloalkyl.

As used herein, "aryl" refers to aromatic groups containing from 5 to 20 carbon atoms and can be a mono-, multicyclic or fused ring system. Aryl groups include, but are not limited to, phenyl, naphthyl, biphenyl, fluorenyl and others that can be unsubstituted or are substituted with one or more substituents.

As used herein, "aryl" also refers to aryl-containing groups, including, but not limited to, aryloxy, arylthio, arylcarbonyl and arylamino groups.

As used herein, an "aryl group substituent" includes, but is not limited to, alkyl, alkenyl, alkynyl, cycloalkyl, cycloalkylalkyl, aryl, heteroaryl optionally substituted with 1 or more, including 1 to 3, substituents selected from halo, halo alkyl and alkyl, aralkyl, heteroaralkyl, alkenyl containing 1 to 2 double bonds, alkynyl containing 1 to 2 triple bonds, alk(en)(yn)yl groups, halo, pseudohalo, cyano, hydroxy, haloalkyl and polyhaloalkyl, including halo lower alkyl, especially trifluoromethyl, formyl, alkylcarbonyl, arylcarbonyl that is optionally substituted with 1 or more, including 1 to 3, substituents selected from halo, halo alkyl and alkyl, heteroarylcarbonyl, carboxy, alkoxycarbonyl, aryloxycarbonyl, aminocarbonyl, alkylaminocarbonyl, dialkylaminocarbonyl, arylaminocarbonyl, diarylaminocarbonyl, aralkylaminocarbonyl, alkoxy, aryloxy, perfluoroalkoxy, alkenyloxy, alkynyloxy, arylalkoxy, aminoalkyl, alkylaminoalkyl, dialkylaminoalkyl, arylaminoalkyl, amino, alkylamino, dialkylamino, arylamino, alkylarylamino, alkylcarbonylamino, arylcarbonylamino, azido, nitro, mercapto, alkylthio, arylthio, perfluoroalkylthio, thiocyano, isothiocyano, alkylsulfinyl, alkylsulfonyl, arylsulfinyl, arylsulfonyl, aminosulfonyl, alkylaminosulfonyl, dialkylaminosulfonyl and arylaminosulfonyl.

As used herein, "aralkyl" refers to an alkyl group in that one of the hydrogen atoms of the alkyl is replaced by an aryl group.

As used herein, "heteroaralkyl" refers to an alkyl group in that one of the hydrogen atoms of the alkyl is replaced by a heteroaryl group.

As used herein, "cycloalkyl" refers to a saturated mono- or multicyclic ring system, in one embodiment, of 3 to 10 carbon atoms, or 3 to 6 carbon atoms; cycloalkenyl and cycloalkynyl refer to mono- or multicyclic ring systems that respectively include at least one double bond and at least one triple bond. Cycloalkenyl and cycloalkynyl groups can contain, in one embodiment, 3 to 10 carbon atoms, with cycloalkenyl groups, in other embodiments, containing 4 to 7 carbon atoms and cycloalkynyl groups, in other embodiments, containing 8 to 10 carbon atoms. The ring systems of the cycloalkyl, cycloalkenyl and cycloalkynyl groups can be composed of one ring or two or more rings that can be joined together in a fused, bridged or spiro-connected fashion, and can be optionally substituted with one or more alkyl group substituents. "Cycloalk(en)(yn)yl" refers to a cycloalkyl group containing at least one double bond and at least one triple bond.

As used herein, "heteroaryl" refers to a monocyclic or multicyclic ring system, in one embodiment of about 5 to about 15 members where one or more, or 1 to 3, of the atoms in the ring system is a heteroatom, which is, an element other than carbon, for example, nitrogen, oxygen and sulfur atoms. The heteroaryl can be optionally substituted with one or more, including 1 to 3, aryl group substituents. The heteroaryl group can be optionally fused to a benzene ring. Exemplary heteroaryl groups include, but are not limited to, pyrroles, porphyrines, furans, thiophenes, selenophenes, pyrazoles, imidazoles, triazoles, tetrazoles, oxazoles, oxadiazoles, thiazoles, thiadiazoles, indoles, carbazoles, benzofurans, benzothiophenes, indazoles, benzimidazoles, benzotriazoles, benzoxatriazoles, benzothiazoles, benzoselenozoles, benzothiadiazoles, benzoselenadiazoles, purines, pyridines, pyridazines, pyrimidines, pyrazines, pyrazines, triazines, quinolines, acridines, isoquinolines, cinnolines, phthalazines, quinazolines, quinoxalines, phenazines, phenanthrolines, imidazinyl, pyrrolidinyl, pyrimidinyl, tetrazolyl, thienyl, pyridyl, pyrrolyl, N-methylpyrrolyl, quinolinyl and isoquinolinyl.

As used herein, "heteroaryl" also refers to heteroaryl-containing groups, including, but not limited to, heteroaryloxy, heteroarylthio, heteroarylcarbonyl and heteroarylamino.

As used herein, "heterocyclic" refers to a monocyclic or multicyclic ring system, in one embodiment of 3 to 10 members, in another embodiment 4 to 7 members, including 5 to 6 members, where one or more, including 1 to 3 of the atoms in the ring system is a heteroatom, which is, an element other than carbon, for example, nitrogen, oxygen and sulfur atoms. The heterocycle can be optionally substituted with one or more, or 1 to 3 aryl group substituents. In certain embodiments, substituents of the heterocyclic group include hydroxy, amino, alkoxy containing 1 to 4 carbon atoms, halo lower alkyl, including trihalomethyl, such as trifluoromethyl, and halogen. As used herein, the term heterocycle can include reference to heteroaryl.

As used herein, the nomenclature alkyl, alkoxy, carbonyl, etc., are used as is generally understood by those of skill in this art. For example, as used herein alkyl refers to saturated carbon chains that contain one or more carbons; the chains can be straight or branched or include cyclic portions or be cyclic.

Where the number of any given substituent is not specified (e.g., "haloalkyl"), there can be one or more substituents present. For example, "haloalkyl" can include one or more of the same or different halogens. As another example, "$C_{1-3}$ alkoxyphenyl" can include one or more of the same or different alkoxy groups containing one, two or three carbons.

Where named substituents such as carboxy or substituents represented by variables such as W are separately enclosed in parentheses, yet possess no subscript outside the parentheses indicating numerical value and that follow substituents not in parentheses, e.g., "$C_{1-4}$alkyl(W)(carboxy)", "W" and "carboxy" are each directly attached to $C_{1-4}$alkyl.

As used herein, "halogen" or "halide" refers to F, Cl, Br or I.

As used herein, pseudohalides are compounds that behave substantially similar to halides. Such compounds can be used in the same manner and treated in the same manner as halides (X, in that X is a halogen, such as Cl or Br). Pseudohalides include, but are not limited to, cyanide, cyanate, isocyanate, thiocyanate, isothiocyanate, selenocyanate, trifluoromethoxy, and azide.

As used herein, "haloalkyl" refers to a lower alkyl radical in that one or more of the hydrogen atoms are replaced by halogen including, but not limited to, chloromethyl, trifluoromethyl, 1 chloro2fluoroethyl and the like.

As used herein, "haloalkoxy" refers to RO in that R is a haloalkyl group. As used herein, "sulfinyl" or "thionyl" refers to S(O). As used herein, "sulfonyl" or "sulfuryl" refers to $S(O)_2$. As used herein, "sulfo" refers to $S(O)_2O$.

As used herein, "carboxy" refers to a divalent radical, C(O)O.

As used herein, "aminocarbonyl" refers to $C(O)NH_2$.

As used herein, "alkylaminocarbonyl" refers to C(O)NHR in that R is hydrogen or alkyl, including lower alkyl.

As used herein "dialkylaminocarbonyl" as used herein refers to C(O)NR'R in that R and R are independently selected from hydrogen or alkyl, including lower alkyl.

As used herein, "carboxamide" refers to groups of formula NR'COR.

As used herein, "diarylaminocarbonyl" refers to C(O)NRR' in that R and R' are independently selected from aryl, including lower aryl, such as phenyl.

As used herein, "aralkylaminocarbonyl" refers to C(O)NRR' in that one of R and R' is aryl, including lower aryl, such as phenyl, and the other of R and R' is alkyl, including lower alkyl.

As used herein, "arylaminocarbonyl" refers to C(O)NHR in that R is aryl, including lower aryl, such as phenyl.

As used herein, "alkoxycarbonyl" refers to C(O)OR in that R is alkyl, including lower alkyl.

As used herein, "aryloxycarbonyl" refers to C(O)OR in that R is aryl, including lower aryl, such as phenyl.

As used herein, "alkoxy" and "alkylthio" refer to RO and RS, in that R is alkyl, including lower alkyl.

As used herein, "aryloxy" and "arylthio" refer to RO and RS, in that R is aryl, including lower aryl, such as phenyl.

As used herein, "alkylene" refers to a straight, branched or cyclic, in one embodiment straight or branched, divalent aliphatic hydrocarbon group, in certain embodiments having from 1 to about 20 carbon atoms, in other embodiments 1 to 12 carbons, including lower alkylene. The alkylene group is optionally substituted with one or more "alkyl group substituents." There can be optionally inserted along the alkylene group one or more oxygen, sulphur or substituted or unsubstituted nitrogen atoms, where the nitrogen substituent is alkyl as previously described. Exemplary alkylene groups include methylene ($CH_2$), ethylene ($CH_2CH_2$), propylene ($—(CH_2)_3$), cyclohexylene ($C_6H_{10}$), methylenedioxy ($OCH_2O$) and ethylenedioxy ($O(CH_2)_2O$). The term "lower alkylene" refers to alkylene groups having 1 to 6 carbons. In certain embodiments, alkylene groups are lower alkylene, including alkylene of 1 to 3 carbon atoms.

As used herein, "alkenylene" refers to a straight, branched or cyclic, in one embodiment straight or branched, aliphatic hydrocarbon group, in certain embodiments having from 2 to about 20 carbon atoms and at least one double bond, in other embodiments 1 to 12 carbons, including lower alkenylene. The alkenylene group is optionally substituted with one or more "alkyl group substituents." There can be optionally inserted along the alkenylene group one or more oxygen, sulphur or substituted or unsubstituted nitrogen atoms, where the nitrogen substituent is alkyl as previously described. Exemplary alkenylene groups include —CH=CH— CH=CH— and CH=$CHCH_2$. The term "lower alkenylene" refers to alkenylene groups having 2 to 6 carbons. In certain embodiments, alkenylene groups are lower alkenylene, including alkenylene of 3 to 4 carbon atoms.

As used herein, "alkynylene" refers to a straight, branched or cyclic, in one embodiment straight or branched, divalent aliphatic hydrocarbon group, in certain embodiments having from 2 to about 20 carbon atoms and at least one triple bond, in other embodiments 1 to 12 carbons, including lower alkynylene. The alkynylene group is optionally substituted with one or more "alkyl group substituents." There can be optionally inserted along the alkynylene group one or more oxygen, sulphur or substituted or unsubstituted nitrogen atoms, where the nitrogen substituent is alkyl as previously described. Exemplary alkynylene groups include —C≡C—C≡C—, C≡C and C≡CCH$_2$. The term "lower alkynylene" refers to alkynylene groups having 2 to 6 carbons. In certain embodiments, alkynylene groups are lower alkynylene, including alkynylene of 3 to 4 carbon atoms.

As used herein, "alk(en)(yn)ylene" refers to a straight, branched or cyclic, in one embodiment straight or branched, divalent aliphatic hydrocarbon group, in certain embodiments having from 2 to about 20 carbon atoms and at least one triple bond, and at least one double bond; in other embodiments 1 to 12 carbons, including lower alk(en)(yn)ylene. The alk(en)(yn)ylene group is optionally substituted with one or more "alkyl group substituents." There can be optionally inserted along the alkynylene group one or more oxygen, sulphur or substituted or unsubstituted nitrogen atoms, where the nitrogen substituent is alkyl as previously described. Exemplary alk(en)(yn)ylene groups include —C═C— (CH$_2$)$_n$C═C—, where n is 1 or 2. The term "lower alk(en)(yn)ylene" refers to alk(en)(yn)ylene groups having up to 6 carbons. In certain embodiments, alk(en)(yn)ylene groups are lower alk(en)(yn)ylene, including alk(en)(yn)ylene of 4 carbon atoms.

As used herein, "arylene" refers to a monocyclic or polycyclic, in one embodiment monocyclic, divalent aromatic group, in certain embodiments having from 5 to about 20 carbon atoms and at least one aromatic ring, in other embodiments 5 to 12 carbons, including lower arylene. The arylene group is optionally substituted with one or more "alkyl group substituents." There can be optionally inserted around the arylene group one or more oxygen, sulphur or substituted or unsubstituted nitrogen atoms, where the nitrogen substituent is alkyl as previously described. Exemplary arylene groups include 1,2, 1,3- and 1,4-phenylene. The term "lower arylene" refers to arylene groups having 5 or 6 carbons. In certain embodiments, arylene groups are lower arylene.

As used herein, "heteroarylene" refers to a divalent monocyclic or multicyclic ring system, in one embodiment of about 5 to about 15 members where one or more, or 1 to 3 of the atoms in the ring system is a heteroatom, which is, an element other than carbon, for example, nitrogen, oxygen and sulfur atoms. The heteroarylene group can be optionally substituted with one or more, or 1 to 3, aryl group substituents.

As used herein, "alkylidene" refers to a divalent group, such as ═CR'R", which is attached to one atom of another group, forming a double bond. Exemplary alkylidene groups are methylidene (═CH$_2$) and ethylidene (═CHCH$_3$). As used herein, "aralkylidene" refers to an alkylidene group in that either R' or R" is and aryl group.

As used herein, "amido" refers to the divalent group C(O)NH. "Thioamido" refers to the divalent group C(S)NH. "Oxyamido" refers to the divalent group OC(O)NH. "Thiaamido" refers to the divalent group SC(O)NH. "Dithiaamido" refers to the divalent group SC(S)NH. "Ureido" refers to the divalent group HNC(O)NH. "Thioureido" refers to the divalent group HNC(S)NH.

As used herein, "semicarbazide" refers to NHC(O)NHNH. "Carbazate" refers to the divalent group OC(O)NHNH. "Isothiocarbazate" refers to the divalent group SC(O)NHNH. "Thiocarbazate" refers to the divalent group OC(S)NHNH. "Sulfonylhydrazide" refers to the group SO$_2$NHNH. "Hydrazide" refers to the divalent group C(O)NHNH. "Azo" refers to the divalent group N═N. "Hydrazinyl" refers to the divalent group NHNH.

As used herein, the term "amino acid" refers to α-amino acids that are racemic, or of either the D- or L-configuration. The designation "d" preceding an amino acid designation (e.g., dAla, dSer, dVal, etc.) refers to the D-isomer of the amino acid. The designation "dl" preceding an amino acid designation (e.g., dlAla) refers to a mixture of the L- and D-isomers of the amino acid.

As used herein, when any particular group, such as phenyl or pyridyl, is specified, this means that the group is unsubstituted or is substituted. Substituents where not specified are halo, halo lower alkyl, and lower alkyl.

As used herein, conformationally altered protein disease (or a disease of protein aggregation) refers to diseases associated with a protein or polypeptide that has a disease-associated conformation. The methods and collections provided herein permit detection of a conformer associated with a disease to be detected. Diseases and associated proteins that exhibit two or more different conformations in which at least one conformation is a conformationally altered protein include, but are not limited to, amyloid diseases and other neurodegenerative diseases known to those of skill in the art and set forth below.

As used herein, cell sorting refers to an assay in which cells are separated and recovered from suspension based upon properties measured in flow cytometry analysis. Most assays used for analysis can serve as the basis for sorting experiments, as long as gates and regions defining the subpopulation(s) to be sorted do not logically overlap. Maximum throughput rates are typically 5000 cells/second ($18 \times 10^6$ cells/hour). The rate of collection of the separated population(s) depends primarily upon the condition of the cells and the percentage of reactivity.

As used herein, the abbreviations for any protective groups, amino acids and other compounds, are, unless indicated otherwise, in accord with their common usage, recognized abbreviations, or the IUPAC-IUB Commission on Biochemical Nomenclature (see, *Biochem.* 1972, 11:942). For example, DMF=N,N-dimethylformamide, DMAc=N,N-dimethylacetamide; THF=tetrahydrofuran; TRIS=tris(hydroxymethyl)aminomethane; SSPE=saline-sodium phosphate-EDTA buffer; EDTA=ethylenediaminetetraacetic acid; SDS=sodium dodecyl sulfate.

B. Collections of Capture Compounds

Collections of capture compounds that selectively bind to biomolecules in samples, such as biomoelcules, particularly, although not exclusively, a cell lysate or in vitro translated polypeptides from a cell lysate are provided. Each capture compound in the collection can bind to specific groups or classes of biopolymers, and is designed to covalently or tightly (sufficient to sustain mass spectrometric analysis, for example) to a subset of all of the biomolecules in the sample. For example, a sample can contain 1000's of members, for example a cell lysate. The collections of compounds permit sufficient selectivity so that, for example, about 10-20 of the components of the sample bind to each member of the collection. The exact number is a small enough number for routine analyses to identify them, generally in one step, such as by mass spectrometry.

As described in greater detail below, the compounds provided herein are multifunctional synthetic small molecules that can select, covalently bind ("capture") and isolate proteins based on their unique surface features. The solubility of the compound may be modulated in the chemical synthesis process such that water soluble (cytosolic) or insoluble (membrane) protein mixtures may be analyzed. In one embodiment, the compound employs three critical functionalities: (1) a reactivity function; (2) a selectivity function; and (3) a sorting function.

Figure 27:
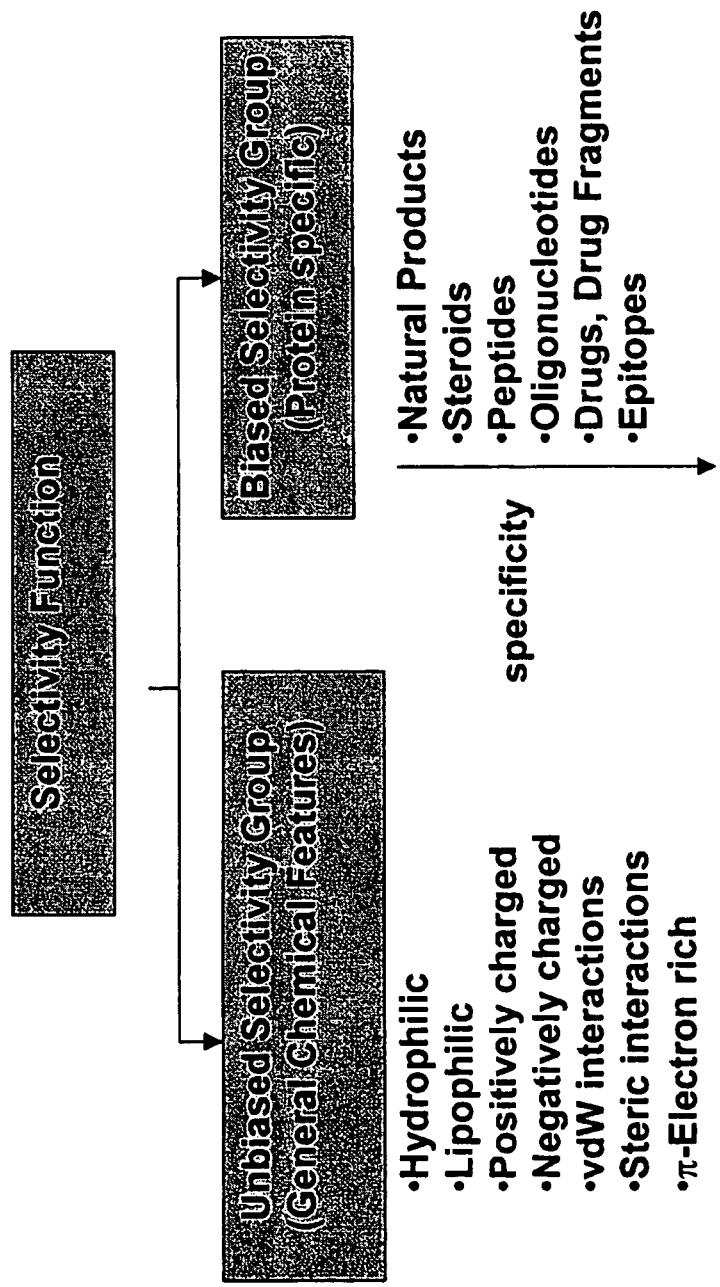
FIG. 27 shows exemplary features of the biased and unbiased selectivity groups in the selectivity function of the capture compounds.
Figure 28:
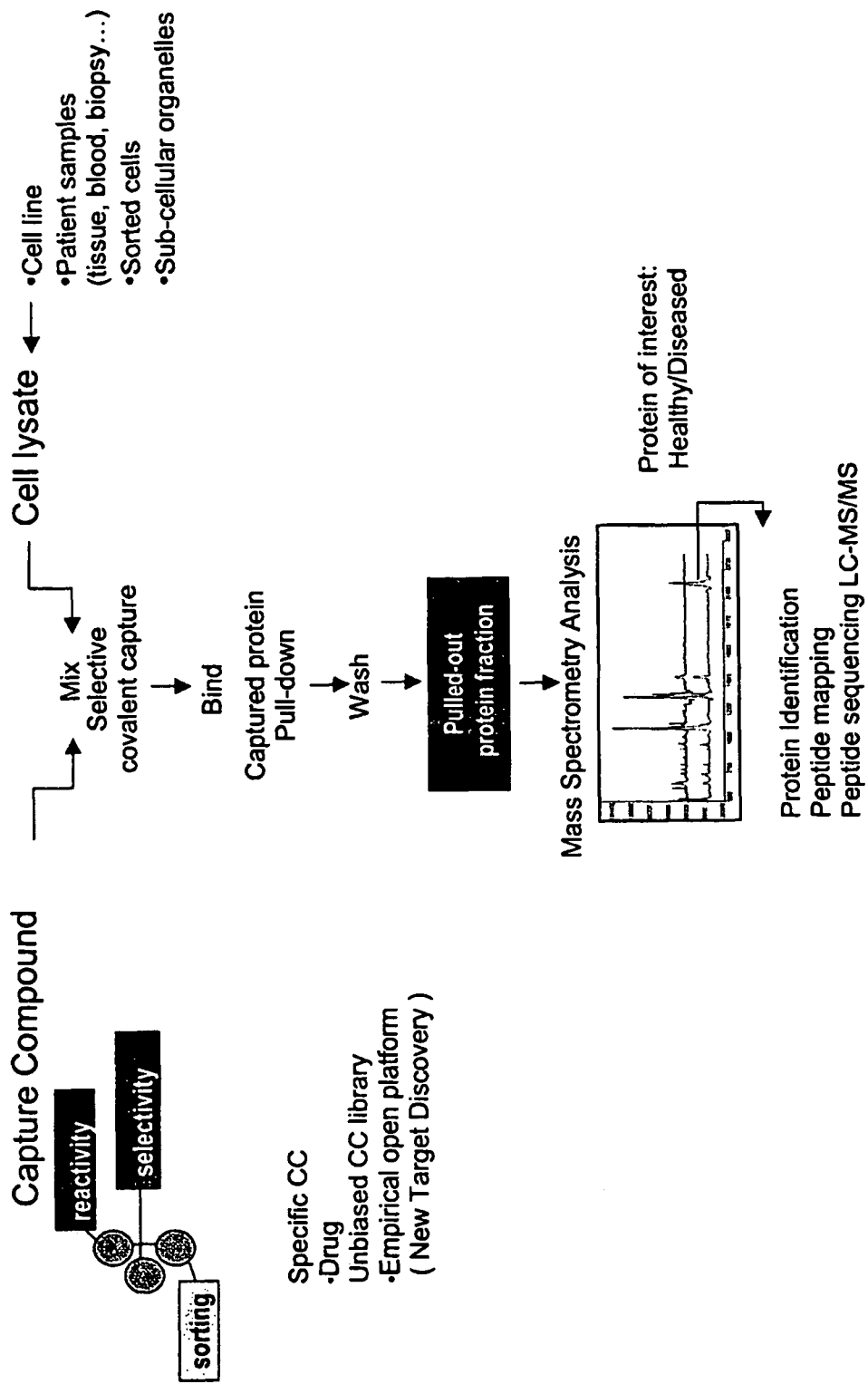
FIG. 28 illustrates an exemplary protocol for protein identification using capture compounds.
Figure 29:
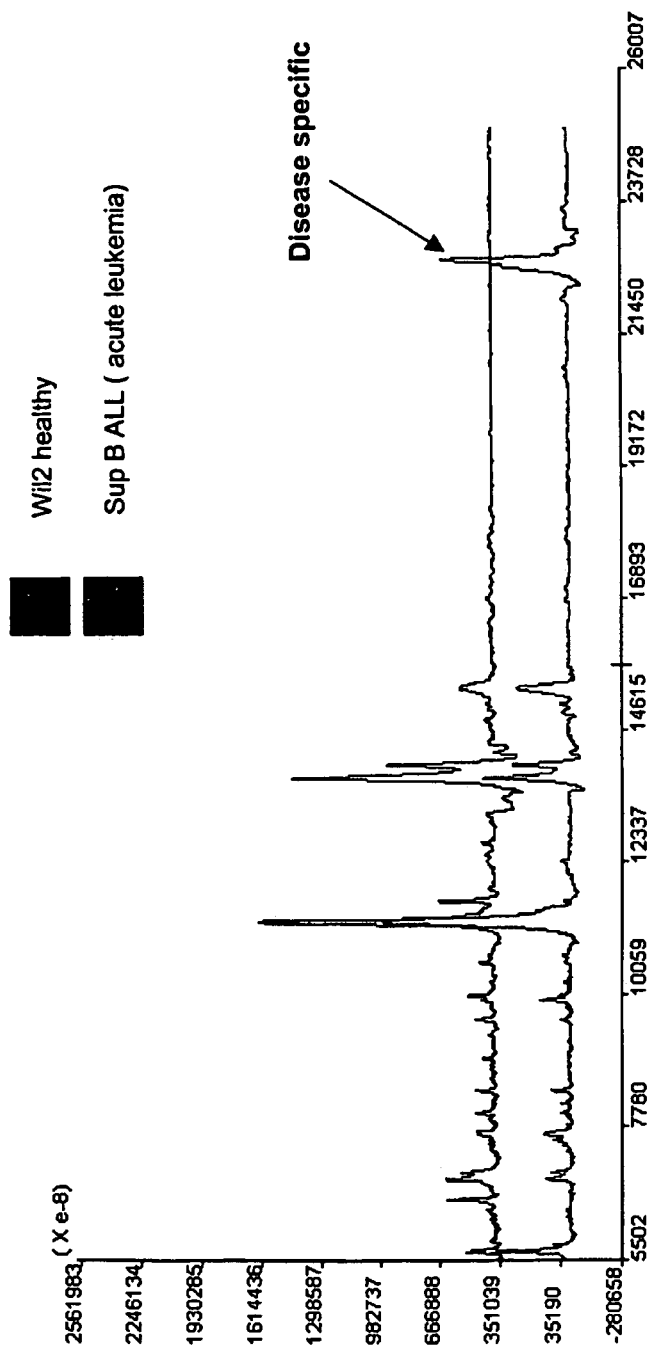
FIG. 29 shows mass spectrometric results of the reaction of an capture compound with a trityl scaffold, biotin, NHS reactivity function, OH selectivity function with the cytosolic fraction of cell lines from a 5 year old male acute lymphocytic leukemia (sup B ALL) and an age/gender matched control (wil2). The Figure shows that capture compound covalently captures many proteins which are similar in abundance. However a major protein is detected at ~22 kDa in the diseased cell line that is absent in the control. The protein is identified by tryptic digest and peptide database matching as HSP-27 (heat shock protein), which is implicated in other cancers in the literature.

As shown in FIG. 27, the selectivity function interacts via non-covalent interactions with a protein e.g. in the active site of enzymes or ligand binding site of receptors ("Biased approach" for e.g. non-target identification), or at a surface affinity motif (SAM) outside of the binding site ("Unbiased approach" for e.g. target discovery). A biased selectivity group enables isolation of specific proteins from complex mixtures. In one embodiment, the selectivity function is a drug (or metabolite thereof) known to cause side effects, attached in several different orientations to make different parts of the molecule accessible to proteins. An unbiased selectivity function utilizes chemical features underlying affinity interactions with the protein surface. The unbiased selectivity function tends to be less specific than the biased, since it is designed to interact with a broader set of proteins. Use of the unbiased capture compounds to screen for global protein profile differences between healthy and disease cells would require the development of a library of capture compounds which as a set interact with the majority of the proteins in the proteome. This approach enables monitoring of protein profile differences induced by the influence of a drug molecule, or discovering new potential drug targets or biomarkers based on the differences between healthy with disease cells.

In one embodiment, the reactivity function covalently "captures" or binds to the selected protein. While the selectivity function serves as the bait, the reactivity function serves as the hook. A protein thus captured will be able to survive downstream purification and analytical processes. Reactivity functions employed are chemically reactive with certain protein side chains (e.g. NHS forms bond with lysine amino function), or require an activation step (i.e., light) prior to forming covalent bond (e.g. photoactivated moiety such as azide which forms a nitrene radical).

In another embodiment, the sorting (pull-out) function isolates the specific protein from its complex cellular environment using a solid support (e.g. magnetic bead, DNA chip), enabling subsequent structural and functional characterization.

Figure 30:
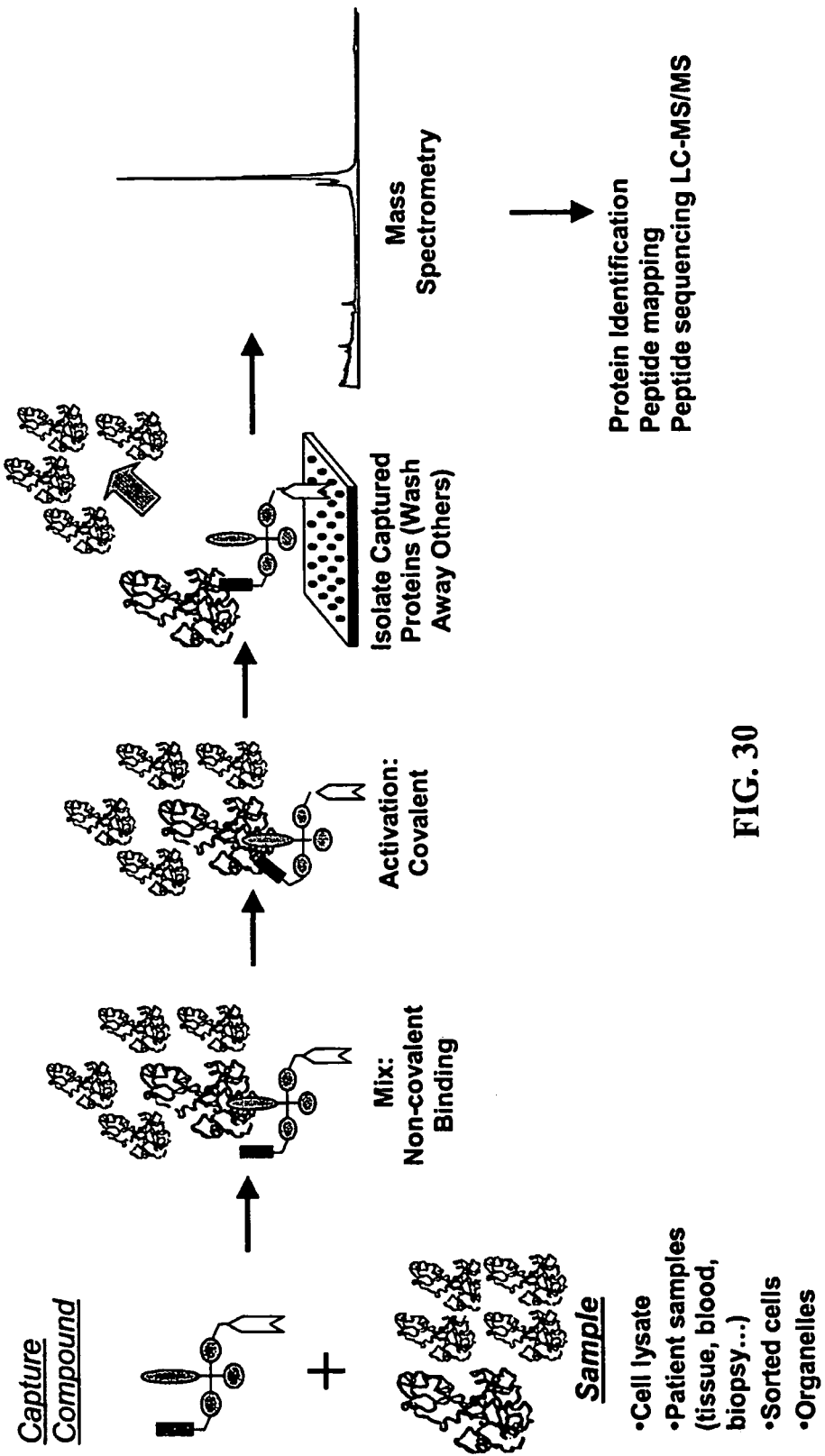
FIG. 30 illustrates a schematic diagram of the steps involved in protein capture and identification using a capture compound. The figure shows that a capture compound is mixed with a sample containing a mixture of proteins. Proteins with an affinity for the selectivity function (e.g. drug) are allowed to come to equilibrium with the selectivity function. The capture compound is then activated (for example, with hv) forming a radical which is shortlived and covalently captures the proteins for which there was an affinity. Other proteins are not captured if the capture compound was not in very close proximity due to the equilibrium between selectivity function and protein. The captured protein is isolated with biotin and identified using mass spectrometry.
Figure 31:
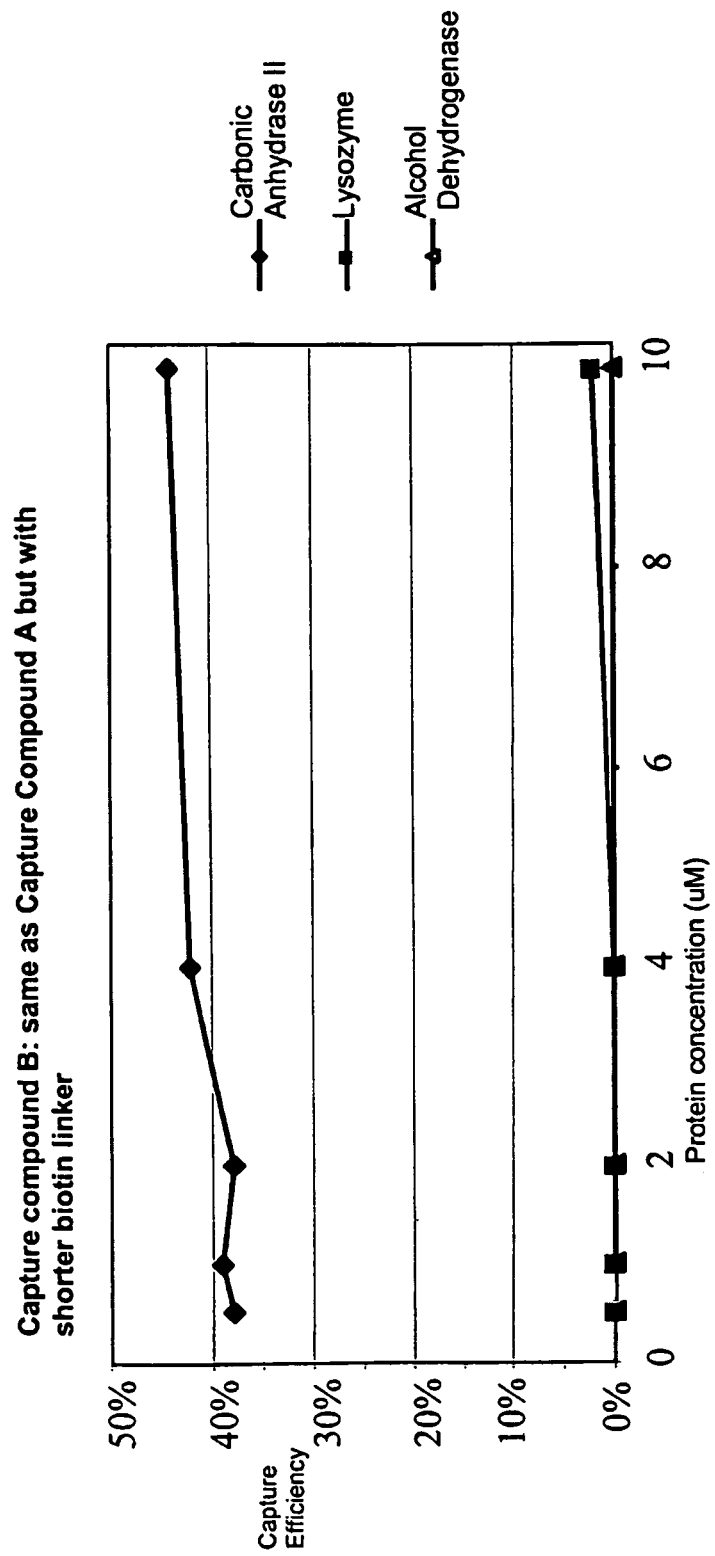
FIG. 31 shows selective protein capture using capture compounds. Capture compounds A and B containing sulfonamide interact with Carbonic Anhydrase. (According to literature, its Kd for CA II isoform is ~10 nM, and for CA I is ~1 µM (both values independently confirmed using activity assay)). Using purified proteins, affinity and capture efficiency is highest for Carbonic II, lower for CA I, and negligible for other purified proteins tested.
Figure 32:
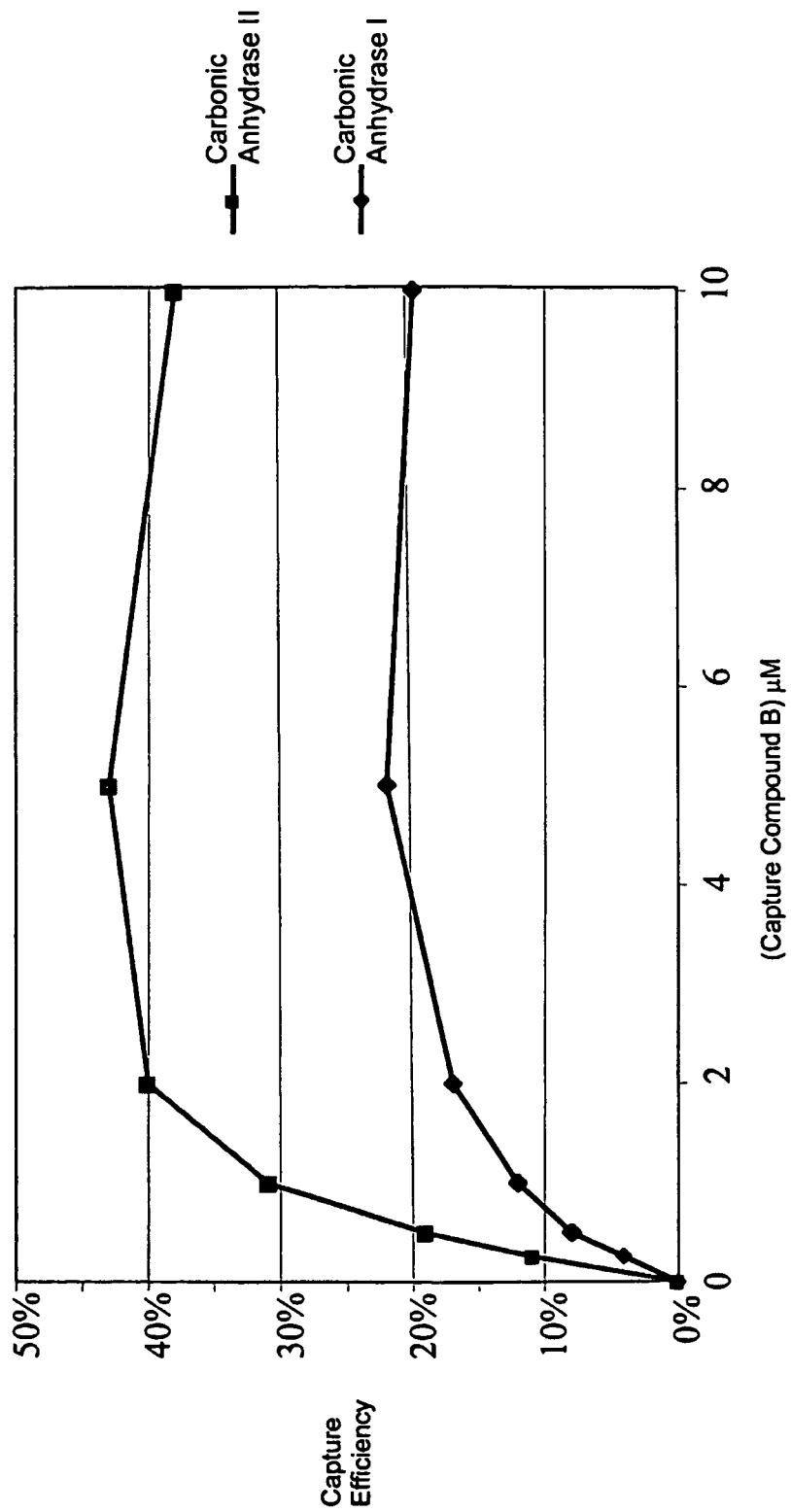
FIG. 32 shows relative binding strengths of protein isoforms to a known ligand for capture compound B.
Figure 33:
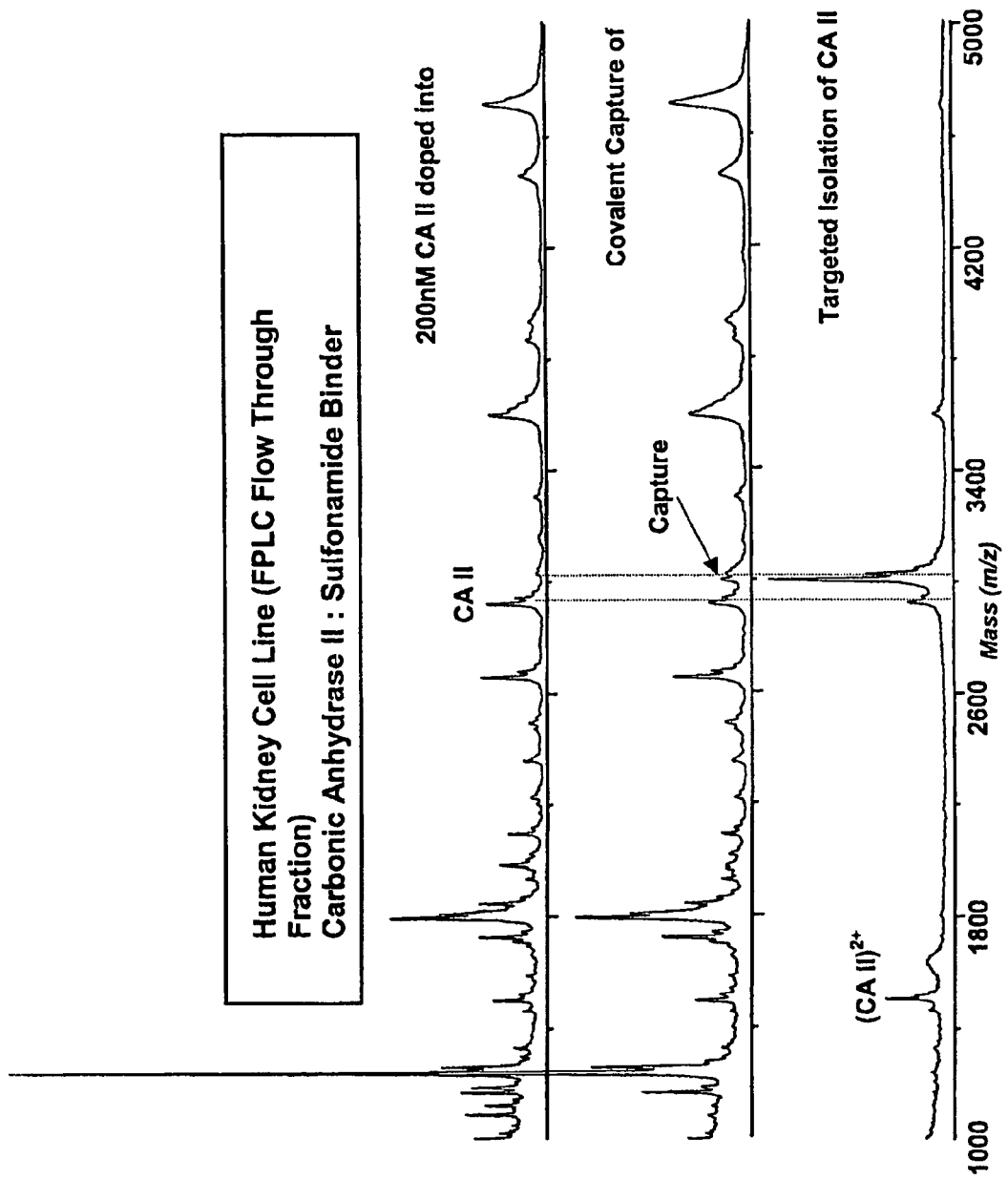
FIG. 33 shows isolation of Carbonic Anhydrase from complex protein mixtures using capture compound A. CA II was doped into a FPLC purified protein mixture from the human kidney cell line HEK293. The doped CAII was pulled out from all other proteins using avidin-coated (SoftLink) resin. Other proteins were discarded, yielding purified protein ready for further analysis.
Figure 34:
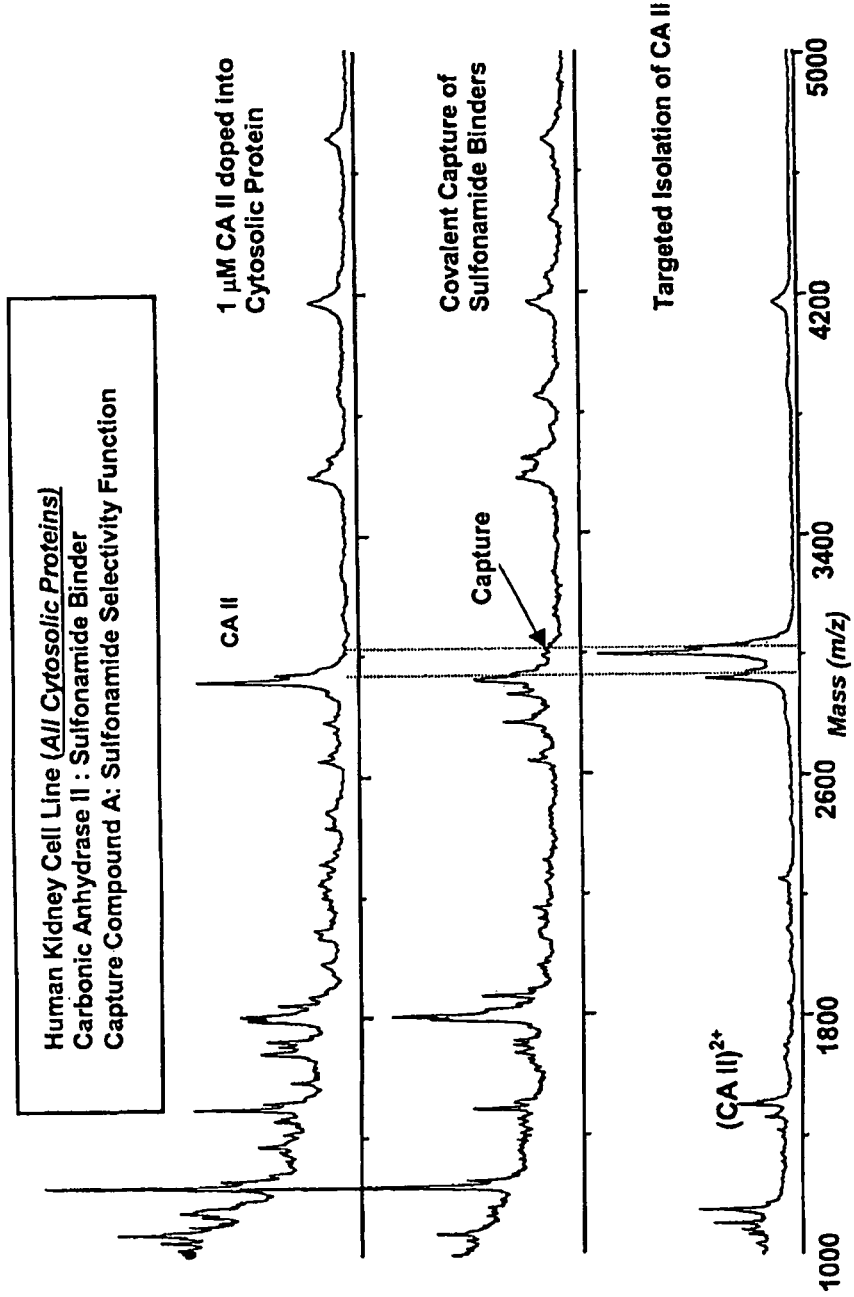
FIG. 34 shows isolation of Carbonic Anhydrase from highly complex protein mixtures using capture compound A. CA II was doped into the whole cytosolic extract from the human kidney cell line HEK293. The doped CAII was pulled out from all other proteins using avidin-coated (SoftLink) resin. Other proteins were discarded, yielding purified protein ready for further analysis.
Figure 35:
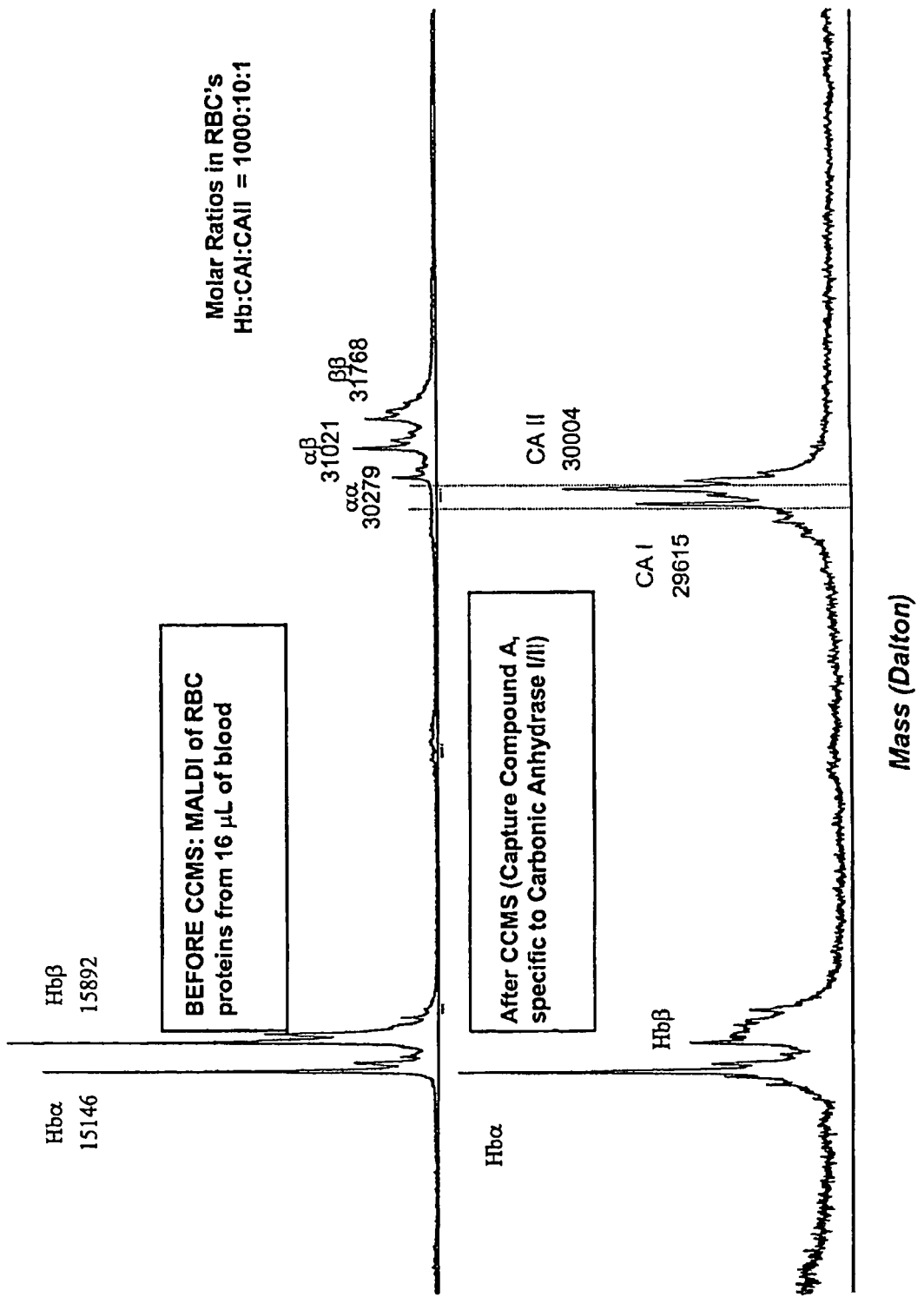
FIG. 35 shows capture and isolation of Carbonic Anhydrase from lysed red blood cells. The top spectrum in the figure shows direct MALDI of lysed red blood cells (no purification) wherein signal for Hemoglobin, which is in huge excess over all other proteins, can be seen. Signals are seen for the alpha and beta chains, and also for non-specific dimers (~30 kiloDaltons). Bottom spectrum in the figure is taken after capture compound A, containing a sulfonamide drug with an affinity for Carbonic Anhydrase, is mixed with the lysed red blood cells. The capture compound covalently captures the Carbonic Anhydrase isoforms I and II. All other proteins that are not covalently captured, including nearly all of the Hemoglobin which is in 2-3 log excess, are washed away prior to MALDI analysis. No gel or chromatographic cleanup is required to obtain this spectrum. The intensity of the CA II peak is higher than CAI (which is more ~100× more abundant in RBCs) because the sulfonamide drug has a higher affinity for CA II.
Figure 36:
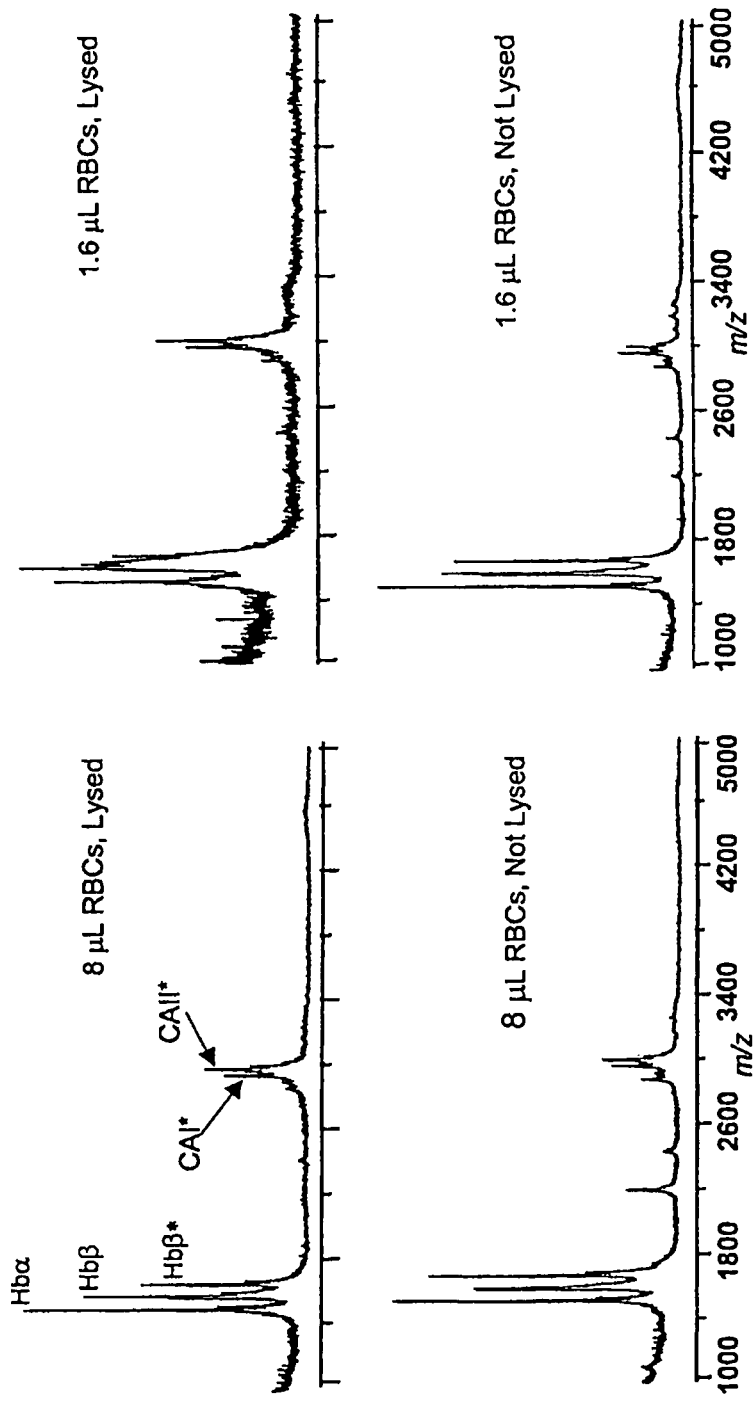
FIG. 36 shows direct capture of Carbonic Anhydrase from red blood cells, without pre-lysis of the cells.
Figure 37:
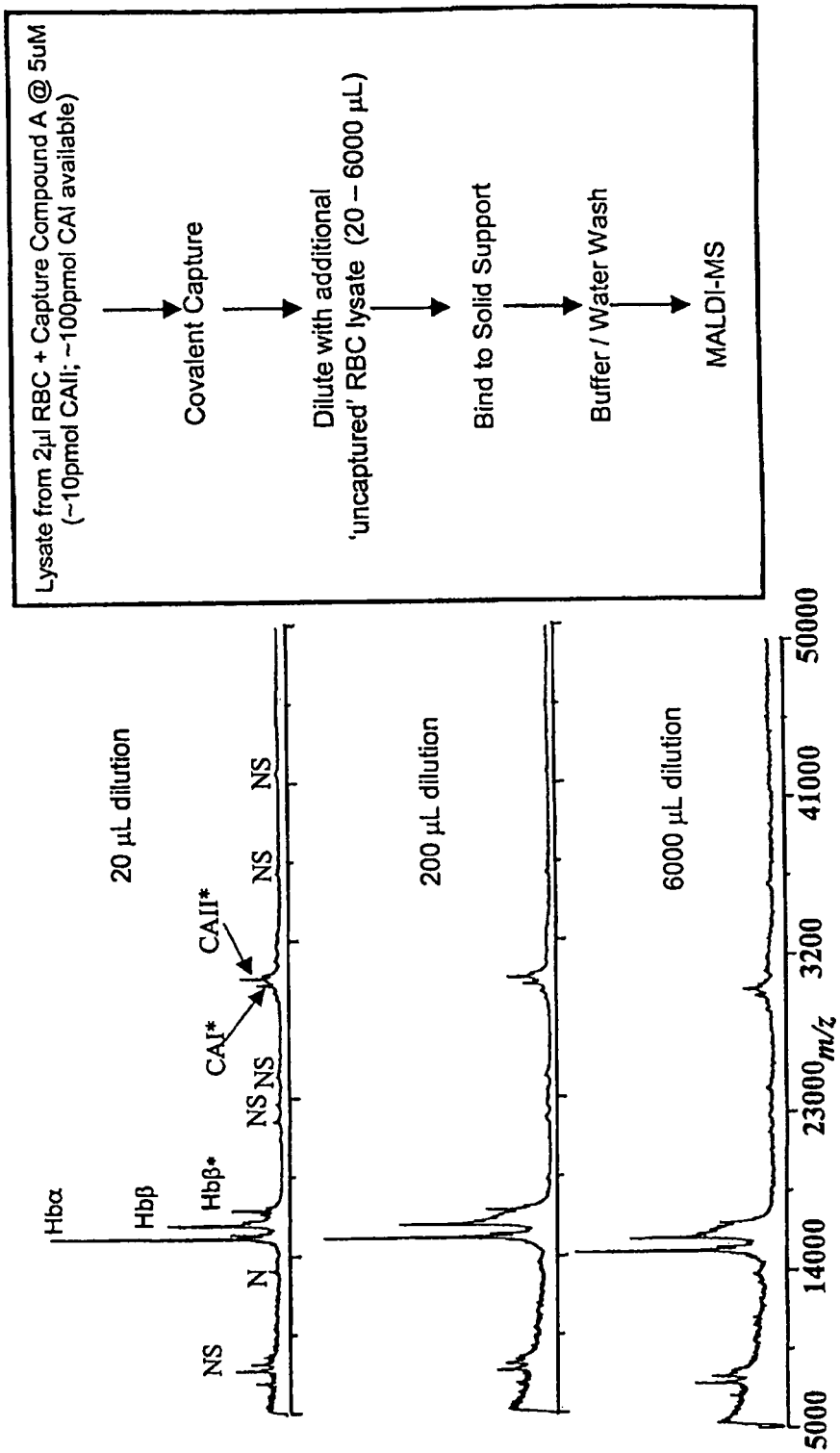
FIG. 37 shows capture of Carbonic Anhydrase from red blood cell lysate when unbiotinylated proteins including Carbonic Anhydrase are in huge excess.
Figure 38:
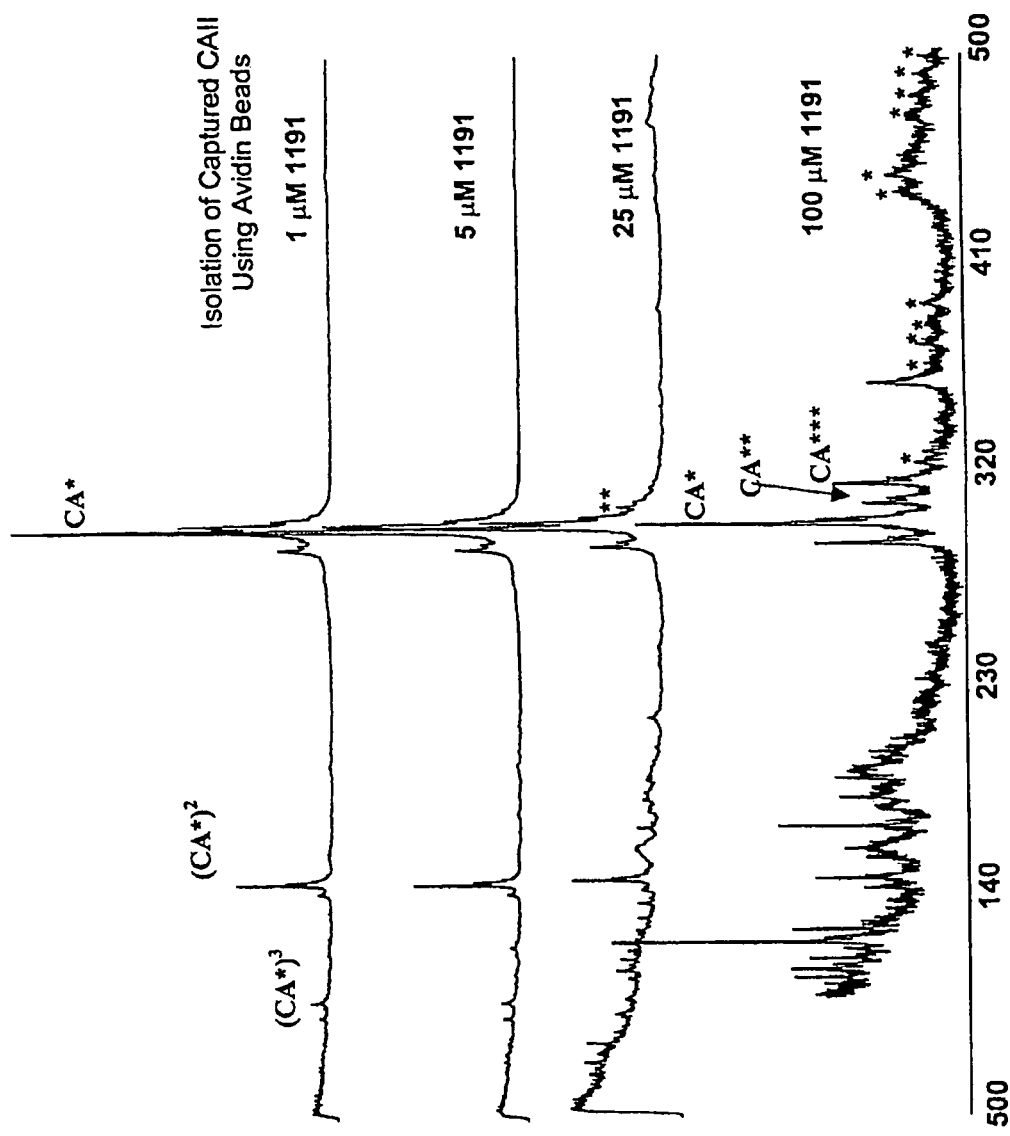
FIG. 38 shows capture of proteins with lower affinities using very high concentrations of capture compound A.

In another embodiment, the analytical process (FIG. 30) is simple and highly amenable to automation. First, a protein mixture from the cells of interest is incubated with a capture compound in buffer conditions which retain the native structural features of the proteins. The selectivity function reversibly interacts and comes to equilibrium with those proteins for which it has an affinity. The reactivity function then forms a covalent bond irreversibly linking the compound to those proteins for which there was an affinity. Our data indicates that the higher the affinity between the protein and the capture compound, the higher is the percentage covalently captured. Next, the covalently captured proteins are isolated onto a solid support and the uncaptured cellular components and proteins washed away. If the sorting function chosen is a biotin, then avidin or streptavidin beads are used as the solid support. Mass spectrometry (MS) is used to detect the captured proteins.

In certain embodiments, with its speed and precision ($M_r$ measured to 0.01%-0.10%), separating capabilities (even small structural variation lead to mass shift) and ability to multiplex (many proteins scanned simultaneously), MS is used for protein identification. This initial mass spectrum provides the molecular weights of all proteins captured. The identity of each can then be determined by conventional means (e.g. digestion and analysis or peptide fragments and genome/proteome database searches). Use of the capture compounds allows the researcher to further analyze and characterize the protein, since it is physically isolated from all others (e.g. mass spectrum identification, or x-ray crystallography after removal from beads). To do so, the protein is washed from the solid support (e.g., if using avidin/streptavidin beads, treat the beads with biotin to displace captured proteins) or make use of an incorporated photocleavable linker, or enzymatically or chemically cleavable linker, thereby releasing the captured purified protein from the solid support.

The collections permit a top down holistic approach to analysis of the proteome, including post-translationally modified proteins, and other biomolecules. Protein and other biomolecule patterns are the starting point for analyses that use these collections; rather than nucleic acids and the genome (bottom up). The collections can be used to assess the biomolecule components of a sample, such as a biological sample, to identify components specific to a particular phenotype, such as a disease state, to identify structural function, biochemical pathways and mechanisms of action. The collections and methods of use permit an unbiased analysis of biomolecules, since the methods do not necessarily assess specific classes of targets, instead, changes in samples are detected or identified. The collections permit the components of a complex mixture of biomolecules (i.e., a mixture of 50, 100, 500, 1000, 2000 and more) to be sorted into discrete loci containing reduced numbers, typically by 10%, 50% or greater reduction in complexity, or to about 1 to 50 different biomolecules per locus in an array, so that the components at each spot can be analyzed, such as by mass spectrometric analysis alone or in combination with other analyses. In some embodiments, such as for phenotypic analyses, homogeneity of the starting sample, such as cells, can be important. To provide homogeneity, cells, with different phenotypes, such as diseased versus healthy, from the same individual are compared. Methods for doing so are provided herein.

By virtue of the structure of compounds in the collections, the collections can be used to detect structural changes, such as those from the post-translational processing of proteins, and can be used to detect changes in membrane proteins, which are involved in the most fundamental processes, such as signal transduction, ion channels, receptors for ligand interaction and cell-to-cell interactions. When cells become diseased, changes associated with disease, such as transformation, often occur in membrane proteins.

The collections contain sets of member capture compounds. In general, members of each set differ in at least one functional group, and generally in two or three, from members of the other sets. Thus, for example, if the compounds include a reactivity function, a selectivity function and a sorting function, each set differs in at least the sorting function, typically in at least in the sorting and selectivity function, and generally in all three functions. The solubility functions, if present, which are selected to permit assaying in a selected environment, can differ among the compounds, or can be the same among all sets.

In practicing methods, the collections are contacted with a sample or partially purified or purified components thereof to effect binding of biomolecules to capture compounds in the collection. The capture compounds can be in an addressable array, such as bound to a solid support prior to contacting, or can be arrayed after contacting with the sample. The resulting array is optionally treated with a reagent that specifically cleaves the bound polymers, such as a protease, and is subjected to analysis, particularly mass spectrometric analysis to identify components of the bound biomolecules at each locus.

Once a molecular weight of a biomolecule, such as a protein or portion thereof of interest is determined, the biomolecule can be identified. Methods for identification include comparison of the molecular weights with databases, for example protein databases that include protease fragments and their molecular weights.

The capture compounds that include functional groups that confer reactivity, selective and separative properties, depending on the specificity of separation and analysis required (which depends on the complexity of the mixture to be analyzed). As more functional groups are added to the compounds, the compounds can exhibit increased selectivity and develop a signature for target molecules similar to an antigen (Ag) binding site on an antibody. In general, the compounds provided herein include at least two functional groups (functions) selected from four types of functions: a reactivity function, which binds to biopolymers either covalently or with a high $k_a$ (generally greater than about $10^9$, $10^{10}$, $10^{12}$ liters/mole and/or such that the binding is substantially irreversible or stable under conditions of mass spectrometric analyses, such as MALDI-MS conditions); a selectivity function, which by virtue of non-covalent interactions alters, generally increases, the specificity of the reactivity function; a sorting function, which permits the compounds to be addressed (arrayed or otherwise separated based according to the structure of the capture compound; and a solubility function, which when selected alters the solubility of the compounds depending upon the environment in which reactions are performed, permitting the conditions to simulate physiological conditions. In general, the reactivity function is the reactive group that specifically interacts, typically covalently or with high binding affinity ($k_a$), with particular biomolecules, such as proteins, or portions thereof; and the other functionality, the selectivity functions, alters, typically increasing, the specificity of the reactivity function. In general, the reactive function covalently interacts with groups on a particular biomolecule, such as amine groups on the surface of a protein. The reactivity function interacts with biomolecules to form a covalent bond or a non-covalent bond that is stable under conditions of analysis, generally with a $k_a$ of greater than $10^9$ liters/mole or greater than $10^{10}$ liters/mole. Conditions of analysis include, but are not limited to, mass spectrophotometric analysis, such as matrix assisted laser desorption ionization-time of flight (MALDI-TOF) mass spectrometry. The selectivity function influences the types of biomolecules that can interact with the reactivity function through a non-covalent interaction. The selectivity function alters the specificity for the particular groups, generally reducing the number of such groups with which the reactivity functions react. A goal is to reduce the number of proteins or biomolecules bound at a locus, so that the proteins can then be separated, such as by mass spectrometry.

Included among the capture compounds provided herein are those that can be classified in at least two sets: one for reactions in aqueous solution (e.g., for reaction with hydrophilic biomolecules), and the other for reaction in organic solvents (e.g., chloroform)(e.g., for reaction with hydrophobic biomolecules). Thus, in certain embodiments, the compounds provided herein discriminate between hydrophilic and hydrophobic biomolecules, including, but not limited to, proteins, and allow for analysis of both classes of biomolecules.

C. Capture Compounds

Capture compounds (also referred to as capture agents) are provided. The capture compounds include a core "Z" that presents one or more reactivity functions "X" and optionally at least a selectivity function "Y" and/or a sorting function "Q", and also optionally one or more solubility functions "W." Additionally, cleavable linkers and other functions are included in the molecules. The particular manner in which the functions are presented on the core or scaffold is a matter of design choice, but are selected such that the resulting molecule has the property that it captures biomolecules, particularly proteins, with sufficient specificity and either covalently or with bonds of sufficient stability or affinity to permit analysis, such as by mass spectrometry, including MALDI mass spectrometric analysis, so that at least a portion of bound biomolecules remain bound (generally a binding affinity of $10^9$, $10^{10}$, $10^{11}$ liters/mole or greater, or a $K_{eq}$ of $10^9$, $10^{10}$, $10^{11}$, $10^{12}$ or greater).

X, the reactivity functionality, is selected to be anything that forms such a covalent bond or a bond of high affinity that is stable under conditions of mass spectrometric analysis, particularly MALDI analysis. The selectivity functionality Y, is a group that "looks" at the topology of the protein around reactivity binding sites and functions to select particular groups on biomolecules from among those with which a reactivity group can form a covalent bond (or high affinity bond). For example, a selectivity group can cause steric hindrance, or permit specific binding to an epitope, or anything in between. It can be a substrate for a drug, lipid, peptide. It selects the environment of the groups with which the reactivity function interacts. The selectivity functionality Y, can be one whereby a capture compound forms a covalent bond with a biomolecule in a mixture or interacts with high stability such that the affinity of binding of the capture compound to the biomolecule through the reactive functionality in the presence of the selectivity functionality is at least ten-fold or 100-fold greater than in the absence of the selectivity functionality.

Q is a sorting function that can be anything that provides a means for separating each set of capture compounds from the others, such as by arraying, and includes, groups such as biotin, generally a spacer, binding to an avidin on a surface (or vice versa) array, oligonucleotides for binding oligonucleotide arrays or any molecule that has a cognate binding partner to which it binds with sufficient affinity to survive mass spectrometric analysis, such as MALDI-MS analysis, can be selected. For any collection a variety of different sorting groups can be used; each set of capture compounds should have unique Q compared to the other sets. In addition, labeling means that can be sorted by virtue of the label, such as RF tags, fluorescent tags, color-coded tags or beads, bar-coded or other symbology labeled tags and other such labels can be used. For example, the capture compounds or the X, Y, Z, W functionalities can be on a surface that is attached to an RF tag or a colored tag. These can be readily sorted after reaction so that each set can be separately analyzed to identify bound biomolecules. Thus, the collections can include capture compounds that have a variety of sorting groups.

The solubility function, W, permits alteration in properties of the capture compound components of the collection. For example, W can be selected so that the capture compounds are soluble or not in a particular reaction medium or environment, such as a hydrophobic environment, thereby permitting reactions with membrane components. The collections include sets of capture compounds, each of which set differs in Q and at least one or both X and Y.

As noted, among the capture compounds provided are those with at least three functionalities: reactivity, sorting and solubility. The sorting function can be selectively cleavable to permit its removal. These compounds also can include a selectivity function to alter the range of binding of the reactivity function, which binds either covalently or with high affinity ($k_a$ greater than $10^9$ to biomolecules, and optionally one or both of a sorting and solubility function.

More detailed description and discussion of each functionality and non-limiting exemplary embodiments follow.

1. Z, the Core

Generally all compounds include a function, even if it is one atom, such as carbon, for presenting the functional groups. In certain embodiments herein, in the capture compounds for use in the methods provided herein, Z is a moiety that is cleavable prior to or during analysis of the biomolecule, including mass spectral analysis, without altering the chemical structure of the biomolecule, including, but not limited to, a protein.

In certain embodiments, Z is a trifunctional moiety containing three functionalities that are each capable of being derivatized selectively in the presence of the other two functionalities. Non-limiting examples of such trifunctional moieties include but are not limited to trifunctionalized trityl groups and amino acids that possess a functionality on the side chain (e.g., tyrosine, cysteine, aspartic acid, glutamic acid, lysine, threonine, serine, etc.). Such amino acids include natural and non-natural amino acids.

For example, in some embodiments, the methods provided herein include a step of mass spectral analysis of biomolecules, including proteins, which are displayed in an addressable format. In certain embodiments, the compounds are then bound to an array of single oligonucleotides that include single-stranded portions (or portions that can be made single-stranded) that are complementary to the oligonucleotide portions, or oligonucleotide analog portions, (Q, the sorting function) of the capture compounds. In these embodiments, Z can be selected to be a group that is (i) stable to the reaction conditions required for reaction of the compounds provided herein with the biomolecule, such as a protein, (ii) stable to the conditions required for hybridization of the Q moiety with the single stranded oligonucleotides, and (iii) cleavable prior to or during analysis of the biomolecule.

In another embodiment, Z with the linked functional groups can be designed so that with the Q, X, W and/or Y it dissolved into lipid bilayers of a cell membrane, thereby contacting internal portions of cell membrane proteins through the X and Y functions. In this embodiment, the support captures proteins, such as membrane proteins and organelle proteins, including proteins within cell membranes. The capture compounds and functional group can be selected so that the resulting capture compounds function under selected physiological conditions. Thus, the choice of Z, Q, X, W and/or Y allows for design of surfaces and supports that mimic cell membranes and other biological membranes.

In some embodiments, a lipid bilayer, such as those used for forming liposomes and other micelles, can be provided on the surface of a support as a way of maintaining the structures of membrane proteins to make a lipid bilayer on the surface. This can be employed where the support is the "Z" function and the other functions are linked thereto, or where the compounds are linked to a support through a Q group, such as by double-stranded oligonucleotides. The resulting immobilized capture compounds can be coated with or dissolved in a lipid coating. As a result, the compounds and collections provided herein can act as an artificial membrane, dendrimer polymer chemistry can be employed for controlled synthesis of membranes having consistent pore dimensions and membrane thicknesses, through synthesis of amphiphilic dendrimeric or hyperbranched block copolymers that can be self-assembled to form ultrathin organic film membranes on porous supports. In one embodiment, an organic film membrane is composed of a linear-dendritic diblock copolymer composed of polyamidoamine (PAMAM) dendrimer attached to one end of a linear polyethylene oxide (PEO) block.

Z is Cleavable Under the Conditions of Mass Spectrometric Analysis

In one such embodiment, Z is a photocleavable group that is cleaved by a laser used in MALDI-TOF mass spectrometry. In another embodiment, Z is an acid labile group that is cleaved upon application of a matrix for mass spectrometric analysis to arrayed, such as hybridized compound-biomolecule conjugates, or by exposure to acids (e.g., trifluoroacetic or hydrochloric acids) in a vapor or liquid form, prior to analysis. In this embodiment, the matrix maintains the spacial integrity of the array, allowing for addressable analysis of the array.

Z is Not Cleavable Under the Conditions of Mass Spectrometric Analysis

In certain embodiments, the capture compounds for use in the methods provided herein have a Z moiety that is not cleavable under conditions used for analysis of biomolecules, including, but not limited to, mass spectrometry, such as matrix assisted laser desorption ionization-time of flight (MALDI-TOF) mass spectrometry. Capture compounds of these embodiments can be used, for example, in methods provided herein for identifying biomolecules in mixtures thereof, for determining biomolecule-biomolecule, including protein-protein, interactions, and for determining biomolecule-small molecule, including protein-drug or protein-drug candidate, interactions. In these embodiments, it is not necessary for the Z group to be cleaved for the analysis.

Thus, as noted, Z can be virtually any moiety that serves as a core to present the binding (the selectivity and reactivity functions) and the solubility and sorting functions. A variety are exemplified herein, but others may be substituted. The precise nature can be a matter of design choice in view of the disclosure herein and the skill of the skilled artisan a. Multivalent or Divalent Z Moieties

In one embodiment, Z is a cleavable or non-cleavable multivalent or divalent group that contains, generally 50 or fewer, or less than 20 members, and is selected from straight or branched chain alkylene, straight or branched chain alkenylene, straight or branched chain alkynylene, straight or branched chain alkylenoxy, straight or branched chain alkylenthio, straight or branched chain alkylencarbonyl, straight or branched chain alkylenamino, cycloalkylene, cycloalkenylene, cycloalkynylene, cycloalkylenoxy, cycloalkylenthio, cycloalkylencarbonyl, cycloalkylenamino, heterocyclylene, arylene, arylenoxy, arylenthio, arylencarbonyl, arylenamino, heteroarylene, heteroarylenoxy, heteroarylenthio, heteroarylencarbonyl, heteroarylenamino, oxy, thio, carbonyl, carbonyloxy, ester, amino, amido, phosphino, phosphineoxido, phosphoramidato, phosphinamidato, sulfonamido, sulfonyl, sulfoxido, carbamato, ureido, and combinations thereof, and is optionally substituted with one or more, including one, two, three or four, substituents each independently selected from Y, as described elsewhere herein.

In other embodiments, Z is a multivalent or divalent cleavable or non-cleavable group selected from straight or branched chain alkyl, straight or branched chain alkenyl, straight or branched chain alkynyl, $(C(R^{15})_2)_d$, O, S, $(CH_2)_d$, $(CH_2)_dO$, $(CH_2)_dS$, $>N(R^{15})$, $(S(O))_u$, $(S(O)_2)_w$, $>C(O)$, $(C(O))_w$, $(C(S(O)_u))_w$, $(C(O)O)_w$, $(C(R^{15})_2)_dO$, $(C(R^{15})_2)_dS(O)_u$, $O(C(R^{15})_2)_d$, $S(O)_u(C(R^{15})_2)_d$, $(C(R^{15})_2)_dO(C(R^{15})_2)_d$, $(C(R^{15})_2)_dS(O)_u(C(R^{15})_2)_d$, $N(R^{15})(C(R^{15})_2)_d$, $(C(R^{15})_2)_dNR^{15}$, $(C(R^{15})_2)_dN(R^{15})(C(R^{15})_2)_d$, $-(CH_2)_dC(O)N(CH_2)_d-$, $-(CH_2)_dC(O)N(CH_2)_dC(O)N(CH_2)_d-$, $(S(R^{15})(O_u))_w$, $(C(R^{15})_2)_d$, $(C(R^{15})_2)_dO(C(R^{15})_2)_d$, $(C(R^{15})_2)_d(C(O)O)_w(C(R^{15})_2)_d$, $(C(O)O)_w(C(R^{15})_2)_d$, $(C(R^{15})_2)_d(C(O)O)_w$, $(C(S)R^{15})_w$, $(C(O))_w(CR^{15}_2)_d$, $(CR^{15})_d(C(O))_w(CR^{15})_d$, $(C(R^{15})_2)_d(C(O))_w$, $N(R^{15})(C(R^{15})_2)_w$, $OC(R^{15})_2C(O)$, $O((R^{15})_2C(O)N(R^{15})$, $(C(R^{15})_2)_w$, $N(R^{15})(C(R^{15})_2)_w$, $(C(R^{15})_2)_wN(R^{15})$, $>P(O)_v(R^{15})_x$, $>P(O)_u(R^{15})_3$, $>P(O)_u(C(R^{15})_2)_d$, $>Si(R^{15})_2$ and combinations of any of these groups;

where u, v and x are each independently 0 to 5;

each d is independently an integer from 1 to 20, or 1 to 12, or 1-6, or 1 to 3;

each w is independently an integer selected from 1 to 6, or 1 to 3, or 1 to 2; and each $R^{15}$ is independently a monovalent group selected from straight or branched chain alkyl, straight or branched chain alkenyl, straight or branched chain alkynyl, cycloalkyl, cycloalkenyl, cycloalkynyl, heterocyclyl, straight or branched chain heterocyclylalkyl, straight or branched chain heterocyclylalkenyl, straight or branched chain heterocyclylalkynyl, aryl, straight or branched chain arylalkyl, straight or branched chain arylalkenyl, straight or branched chain arylalkynyl, heteroaryl, straight or branched chain heteroarylalkyl, straight or branched chain heteroarylalkenyl, straight or branched chain heteroarylalkynyl, halo, straight or branched chain haloalkyl, pseudohalo, azido, cyano, nitro, $OR^{60}$, $NR^{60}R^{61}$, $COOR^{60}$, $C(O)R^{60}$, $C(O)NR^{60}R^{61}$, $S(O)_qR^{60}$, $S(O)_qOR^{60}$, $S(O)_qNR^{60}R^{61}$, $NR^{60}C(O)R^{61}$, $NR^{60}C(O)NR^{60}R^{61}$, $NR^{60}S(O)_qR^{60}$, $SiR^{60}R^{61}R^{62}$, $P(R^{60})_2$, $P(O)(R^{60})_2$, $P(OR^{60})_2$, $P(O)(OR^{60})_2$, $P(O)(OR^{60})(R^{61})$ and $P(O)NR^{60}R^{61}$, where q is an integer from 0 to 2;

each $R^{60}$, $R^{61}$, and $R^{62}$ is independently hydrogen, straight or branched chain alkyl, straight or branched chain alkenyl, straight or branched chain alkynyl, aryl, straight or branched chain aralkyl, straight or branched chain aralkenyl, straight or branched chain aralkynyl, heteroaryl, straight or branched chain heteroaralkyl, straight or branched chain heteroaralkenyl, straight or branched chain heteroaralkynyl, heterocyclyl, straight or branched chain heterocyclylalkyl, straight or branched chain heterocyclylalkenyl or straight or branched chain heteorcyclylalkynyl.

In other embodiments, Z is a cleavable or non-cleavable multivalent divalent group having any combination of the following groups: arylene, heteroarylene, cycloalkylene, $>C(R^{15})_2$, $C(R^{15})=C(R^{15})$, $>C=C(R^{23})(R^{24})$, $>C(R^{23})(R^{24})$, $C\equiv C$, $O$, $>S(A)_u$, $>P(D)_v(R^{15})$, $>P(D)_v(ER^{15})$, $>N(R^{15})$, $>N^+(R^{23})(R^{24})$, $>Si(R^{15})_2$ or $>C(E)$; where u is 0, 1 or 2; v is 0, 1, 2 or 3; A is O or $NR^{15}$; D is S or O; and E is S, O or $NR^{15}$; that groups can be combined in any order;

each $R^{15}$ is a monovalent group independently selected from the group consisting of hydrogen and $VR^{18}$;

each V is a divalent group independently having any combination of the following groups: a direct link, arylene, heteroarylene, cycloalkylene, $>C(R^{17})_2$, $C(R^{17})=C(R^{17})$, $>C=C(R^{23})(R^{24})$, $>C(R^{23})(R^{24})$, $C\equiv C$, $O$, $>S(A)_u$, $>P(D)_v(R^{17})$, $>P(D)_v(ER^{17})$, $>N(R^{17})$, $>N(COR^{17})$, $>N^+(R^{23})(R^{24})$, $>Si(R^{17})_2$ and $>C(E)$; where u is 0, 1 or 2; v is 0, 1, 2 or 3; A is O or $NR^{17}$; D is S or O; and E is S, O or $NR^{17}$; that groups can be combined in any order;

$R^{17}$ and $R^{18}$ are each independently selected from the group consisting of hydrogen, halo, pseudohalo, cyano, azido, nitro, $SiR^{27}R^{28}R^{25}$, alkyl, alkenyl, alkynyl, haloalkyl, haloalkoxy, aryl, aralkyl, aralkenyl, aralkynyl, heteroaryl, heteroaralkyl, heteroaralkenyl, heteroaralkynyl, heterocyclyl, heterocyclylalkyl, heterocyclylalkenyl, heterocyclylalkynyl, hydroxy, alkoxy, aryloxy, aralkoxy, heteroaralkoxy and $NR^{19}R^{20}$;

$R^{19}$ and $R^{20}$ are each independently selected from hydrogen, alkyl, alkenyl, alkynyl, cycloalkyl, aryl, aralkyl, heteroaryl, heteroaralkyl and heterocyclyl;

$R^{23}$ and $R^{24}$ are selected from (i) or (ii) as follows:

(i) $R^{23}$ and $R^{24}$ are independently selected from the group consisting of hydrogen, alkyl, alkenyl, alkynyl, cycloalkyl, aryl and heteroaryl; or (ii) $R^{23}$ and $R^{24}$ together form alkylene, alkenylene or cycloalkylene;

$R^{25}$, $R^{27}$ and $R^{28}$ are each independently a monovalent group selected from hydrogen, alkyl, alkenyl, alkynyl, haloalkyl, haloalkoxy, aryl, aralkyl, aralkenyl, aralkynyl, heteroaryl, heteroaralkyl, heteroaralkenyl, heteroaralkynyl, heterocyclyl, heterocyclylalkyl, heterocyclylalkenyl, heterocyclylalkynyl, hydroxy, alkoxy, aryloxy, aralkoxy, heteroaralkoxy and $NR^{19}R^{20}$;

$R^{15}$, $R^{17}$, $R^{18}$, $R^{19}$, $R^{20}$, $R^{23}$, $R^{24}$, $R^{25}$, $R^{27}$ and $R^{28}$ can be substituted with one or more substituents each independently selected from $Z^2$, in that $Z^2$ is selected from alkyl, alkenyl, alkynyl, aryl, cycloalkyl, cycloalkenyl, hydroxy, $S(O)_hR^{35}$ in that h is 0, 1, or 2, $NR^{35}R^{36}$, $COOR^{35}$, $COR^{35}$, $CONR^{35}R^{36}$, $OC(O)NR^{35}R^{36}$, $N(R^{35}C(O)R^{36}$, alkoxy, aryloxy, heteroaryl, heterocyclyl, heteroaryloxy, heterocyclyloxy, aralkyl, aralkenyl, aralkynyl, heteroaralkyl, heteroaralkenyl, heteroaralkynyl, aralkoxy, heteroaralkoxy, alkoxycarbonyl, carbamoyl, thiocarbamoyl, alkoxycarbonyl, carboxyaryl, halo, pseudohalo, haloalkyl and carboxamido;

$R^{35}$ and $R^{36}$ are each independently selected from among hydrogen, halo, pseudohalo, cyano, azido, nitro, trialkylsilyl, dialkylarylsilyl, alkyldiarylsilyl, triarylsilyl, alkyl, alkenyl, alkynyl, haloalkyl, haloalkoxy, aryl, aralkyl, aralkenyl, aralkynyl, heteroaryl, heteroaralkyl, heteroaralkenyl, heteroaralkynyl, heterocyclyl, heterocyclylalkyl, heterocyclylalkenyl, heterocyclylalkynyl, hydroxy, alkoxy, aryloxy, aralkoxy, heteroaralkoxy, amino, amido, alkylamino, dialkylamino, alkylarylamino, diarylamino and arylamino.

In certain embodiments herein, the compounds are selected with the proviso that Z is cleavable prior to or during analysis, including mass spectral analysis, such as matrix assisted laser desorption ionization-time of flight (MALDI-TOF) mass spectrometry, of the biomolecule.

In certain embodiments, Z is at least a trivalent moiety selected from the divalent moieties disclosed herein absent at least one hydrogen. The capture compounds in the collections provided herein include a core Z that has a variety of valencies. Among the capture compounds are those in which Z is at least trivalent. Also among the compounds in the collections are those where Z is divalent and linked to either a Q and an X, or a Q and a Y, or an X and a Y, or other combination of the functionalities provided herein.

(i) Cleavable Multivalent or Divalent Z Moieties

In one embodiment, Z is a cleavable multivalent or divalent moiety and has the formula: $(S^1)_tM(R^{15})_a(S^2)_bL$, where $S^1$ and $S^2$ are spacer moieties; t and b are each independently 0 or 1; M is a central moiety possessing two or more points of attachment (i.e., divalent or higher valency); in certain embodiments, two to six points of attachment (i.e., divalent to hexavalent), in other embodiments, 2, 3, 4 or 5 points of attachment (i.e., divalent, trivalent, tetravalent or pentavalent); $R^{15}$ is as described above; a is 0 to 4, in certain embodiments, 0, 1 or 2; and L is a bond that is cleavable prior to or during analysis, including mass spectral analysis, of a biomolecule without altering the chemical structure of the biomolecule, such as a protein.

(a) M

In certain embodiments, M is alkylene, phenylene, biphenylene or a multivalent or divalent heterobifunctional trityl derivative. M is unsubstituted or is substituted with 1 to 4 groups, each independently selected from $R^1$.

In other embodiments, M is selected from $(CH_2)_r$, $(CH_2O)_r$, $(CH_2CH_2O)_r$, $(NH(CH_2)_rC(=O))_s$, $(NHCH(R^{52})C(=O))_s$, $(O(CH)_rC(=O))_s$,

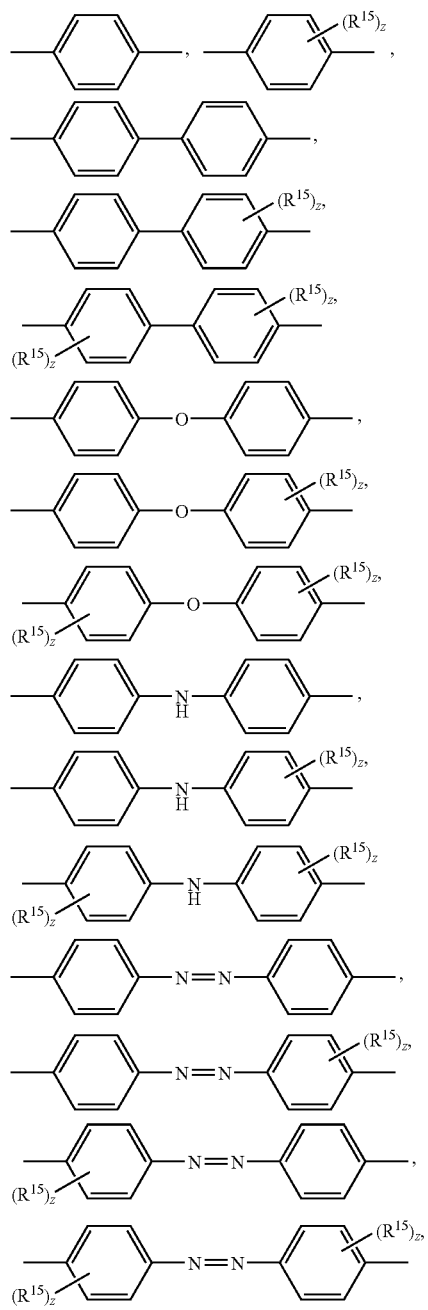

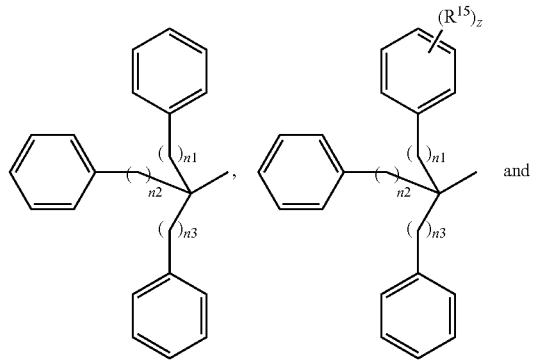

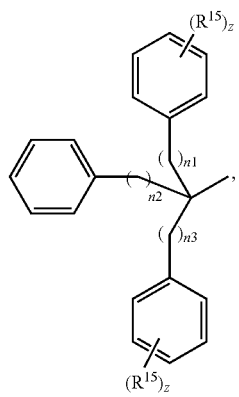

where $R^{15}$ is as defined above; r and s are each independently an integer from 1 to 10; $R^{52}$ is the side chain of a natural or unnatural α-amino acid; and z is an integer from 1 to 4. In one embodiment n1, n2, n3 are each independently integers from 0 to 4. In another embodiment, n1, n2 and n3 are selected with the proviso that n1+n2+n3≠. In another embodiment n1, n2 and n3 are 1 to 3. In another embodiment n1 and n2 are 0. In another embodiment n3 is 2. In one embodiment, z is 1.

In another embodiment M is

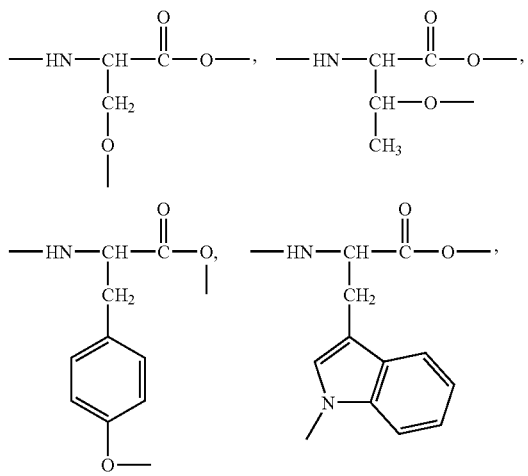

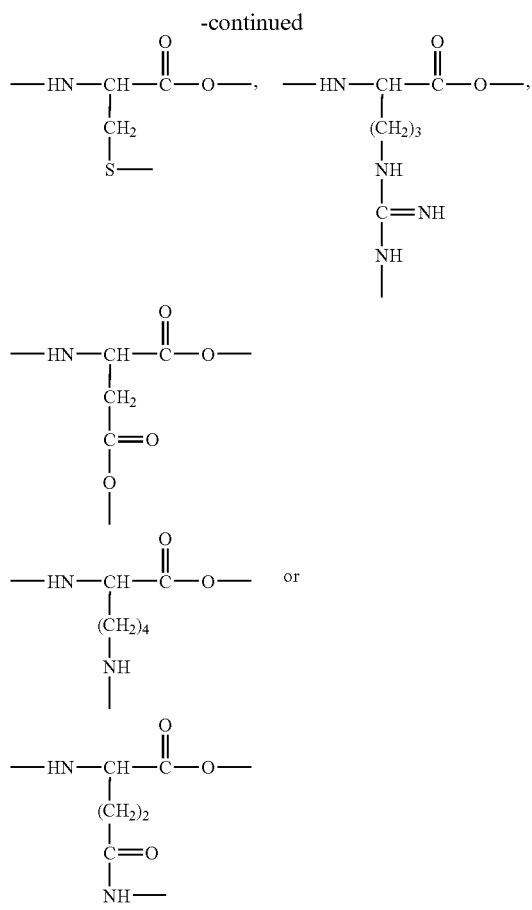

straight or branched chain alkyl, straight or branched chain alkenyl, straight or branched chain alkynyl, aryl, heteroaryl, cycloalkyl, heterocyclyl, straight or branched chain aralkyl, straight or branched chain aralkenyl, straight or branched chain aralkynyl, straight or branched chain heteroaralkyl, straight or branched chain heteroaralkenyl, straight or branched chain heteroaralkynyl, straight or branched chain cycloalkylalkyl, straight or branched chain cycloalkylalkenyl, straight or branched chain cycloalkylalkynyl, straight or branched chain heterocyclylalkyl, straight or branched chain heterocyclylalkenyl or straight or branched chain heterocyclylalkynyl.

(b) $S^1$ and $S^2$

Optionally, a spacer region $S^1$ and/or $S^2$ can be present on either or both sides of the central moiety M (linked to Z) of the compounds, for example, to reduce steric hindrance in reactions with the surface of large biomolecules and/or for facilitating sorting. These can be any groups that provide for spacing, typically without altering desired functional properties of the capture compounds and/or capture compound/biomolecule complexes. Those of skill in the art in light of the disclosure herein, can readily select suitable spacers. Exemplary spacers are set forth below.

For some embodiments, for example, where the biomolecule and the sorting function possess low steric hindrance, a spacer is optional. In certain embodiments, steric hindrance also can enhance selectivity in conjunction with Y (or in the absence of a Y). This enhanced selectivity can be achieved either by the presence of a selectivity function, Y, that is attached to M or by the selection of the appropriate spacer molecules for $S^1$ and/or $S^2$. In other embodiments, the spacer group is selected such that the selectivity function (e.g. a drug) reaches the binding pocket of a target or non-target protein. Spacer groups may be hydrophobic (e.g. PEGs or phosphodiesters) or hydrophilic; their length may be varied to achieve efficient sorting or selectivity or capture; they may be rigid (e.g. trans olefins). The spacer groups may be selected based on the properties (hydrophobic/hydrophilic, size, etc.) of the biomolecular mixture to be analyzed.

If $S^2$ is not required, the reactivity of the cleavable bond L can be influenced by one or more substituted functionalities, for example, $R^{15}$ on M. Electronic (e.g., mesomeric, inductive) and/or steric effects can be used to modulate the stability of the cleavable bond L. For example, if M is a trityl derivative, the linkage to the biomolecule, including, but not limited to, a protein, is in one embodiment a trityl ether bond. The sensitivity of this bond to mild acids, such as acetic acid or the vapor of trifluoroacetic acid, can be significantly enhanced by having as $R^{15}$ one or two electron donating groups, including, but not limited to, alkoxy groups, such as methoxy groups, in the para positions of the aryl rings. Alternatively, the trityl ether bond can be stabilized by the introduction of electron withdrawing groups, including, but not limited to, either halogen, including bromo and chloro, groups, nitro groups or ester moieties, in the para and/or ortho positions of the aromatic rings.

In certain embodiments, $S^1$ and $S^2$ are each independently selected from $(CH_2)_r$, $(CH_2O)$, $(CH_2CH_2O)_r$, $(NH(CH_2)_rC(=O))_s$, $(NHCH(R^{52})C(=O))_s$, $(O(CH)_rC(=O))_s$,

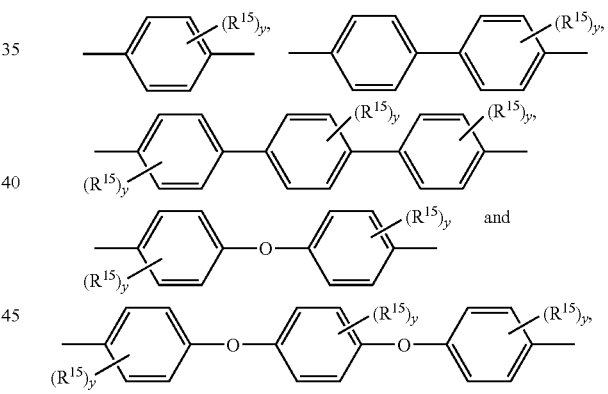

where $R^{15}$ is selected as above; r and s are each independently an integer from 1 to 10; $R^{52}$ is the side chain of a natural α-amino acid; and y is an integer from 0 to 4. In one embodiment, y is 0 or 1.

In certain embodiments, $R^{15}$ is H, OH, $OR^{51}$, SH, $SR^{51}$, $NH_2$, $NHR^{51}$, $NR^{51}_2$, F, Cl, Br, I, $SO_3H$, $PO_4$, $CH_3$, $CH_2CH_3$, $CH(CH_3)_2$ or $C(CH_3)_3$; where $R^{51}$ is straight or branched chain alkyl, straight or branched chain alkenyl, straight or branched chain alkynyl, aryl, heteroaryl, cycloalkyl, heterocyclyl, straight or branched chain aralkyl, straight or branched chain aralkenyl, straight or branched chain aralkynyl, straight or branched chain heteroaralkyl, straight or branched chain heteroaralkenyl, straight or branched chain heteroaralkynyl, straight or branched chain cycloalkylalkyl, straight or branched chain cycloalkylalkenyl, straight or branched chain cycloalkylalkynyl, straight or branched chain heterocyclylalkyl, straight or branched chain heterocyclylalkenyl or straight or branched chain heterocyclylalkynyl.

(c) L

In certain embodiments, the cleavable group L is cleaved either prior to or during analysis of the biomolecule, such as a protein. The analysis can include mass spectral analysis, for example MALDI-TOF mass spectral analysis. The cleavable group L is selected so that the group is stable during conjugation to a biomolecule, and sorting, such as hybridization of a single stranded oligonucleotide Q moiety to a complementary sequence, and washing of the hybrid; but is susceptible to cleavage under conditions of analysis of the biomolecule, including, but not limited to, mass spectral analysis, for example MALDI-TOF analysis. In certain embodiments, the cleavable group L can be a disulfide moiety, created by reaction of the compounds where X=SH, with the thiol side chain of cysteine residues on the surface of biomolecules, including, but not limited to, proteins. The resulting disulfide bond can be cleaved under various reducing conditions including, but not limited to, treatment with dithiothreitol and 2-mercaptoethanol.

In another embodiment, L is a photocleavable group, which can be cleaved by a short treatment with UV light of the appropriate wave length either prior to or during mass spectrometry. Photocleavable groups, including those bonds that can be cleaved during MALDI-TOF mass spectrometry by the action of a laser beam, can be used. For example, a trityl ether or an ortho nitro substituted aralkyl, including benzyl, group are susceptible to laser induced bond cleavage during MALDI-TOF mass spectrometry. Other useful photocleavable groups include, but are not limited to, o-nitrobenzyl, phenacyl, and nitrophenylsulfenyl groups.

Other photocleavable groups for use herein include those disclosed in International Patent Application Publication No. WO 98/2016. In one embodiment, the photocleavable groups have formula I:

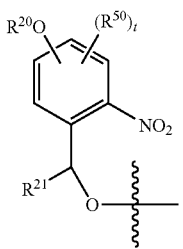

(I)

where $R^{20}$ is ωOalkylene; $R^{21}$ is selected from hydrogen, alkyl, aryl, alkoxycarbonyl, aryloxycarbonyl and carboxy; t is 0-3; and $R^{50}$ is alkyl, alkoxy, aryl or aryloxy. In one embodiment, Q is attached to $R^{20}$ through $(S^1)_t M(R^{15})_a (S^2)_b$; and the biomolecule of interest is captured onto the $R^{21}$CHO moiety via a reactive derivative of the oxygen (e.g., X).

In another embodiment, the photocleavable groups have formula II:

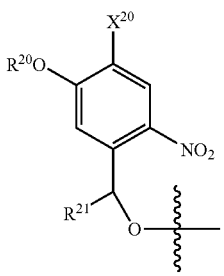

(II)

where $R^{20}$ is ωOalkylene or alkylene; $R^{21}$ is selected from hydrogen, alkyl, aryl, alkoxycarbonyl, aryloxycarbonyl and carboxy; and $X^{20}$ is hydrogen, alkyl or $OR^2$. In one embodiment, Q is attached to $R^{20}$ through $(S^1)_t M(R^{15})_a (S^2)_b$; and the biomolecule of interest is captured onto the $R^{21}$CHO moiety via a reactive derivative of the oxygen (e.g., X).

In further embodiments, $R^{20}$ is $O(CH_2)_3$ or methylene; $R^{21}$ is selected from hydrogen, methyl and carboxy; and $X^{20}$ is hydrogen, methyl or $OR^2$. In another embodiment, $R^{21}$ is methyl; and $X^{20}$ is hydrogen. In certain embodiments, $R^{20}$ is methylene; $R^{21}$ is methyl; and $X^{20}$ is 3-(4,4'-dimethoxytrityloxy)propoxy.

In another embodiment, the photocleavable groups have formula III:

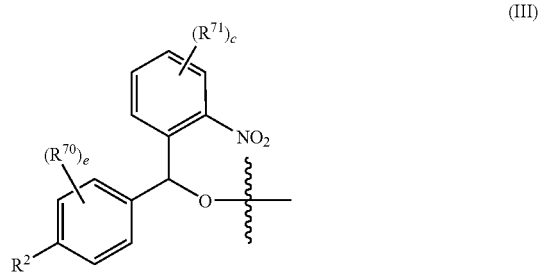

(III)

where $R^2$ is selected from ωOalkyleneO and ωOalkylene, and is unsubstituted or substituted on the alkylene chain with one or more alkyl groups; c and e are each independently 0-4; and $R^{70}$ and $R^{71}$ are each independently alkyl, alkoxy, aryl or aryloxy. In certain embodiments, $R^2$ is ωOalkylene, and is substituted on the alkylene chain with a methyl group. In one embodiment, Q is attached to $R^2$ through $(S^1)_t M(R^{15})_a (S^2)_b$; and the biomolecule of interest is captured onto the $Ar_2$CHO moiety via a reactive derivative of the oxygen (e.g., X).

In further embodiments, $R^2$ is selected from $3O(CH_2)_3O$, $4O(CH_2)_4$, $3O(CH_2)_3$, $2OCH_2CH_2$, $OCH_2$,

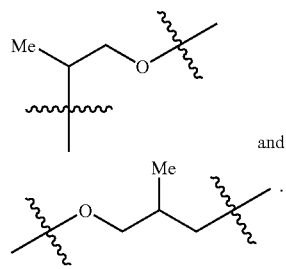

and

In other embodiments, c and e are 0.

Other cleavable groups L include acid sensitive groups, where bond cleavage is promoted by formation of a cation upon exposure to mild to strong acids. For these acid-labile groups, cleavage of the group L can be effected either prior to or during analysis, including mass spectrometric analysis, by the acidity of the matrix molecules, or by applying a short treatment of the array with an acid, such as the vapor of trifluoroacetic acid. Exposure of a trityl group to acetic or trifluoroacetic acid produces cleavage of the ether bond either before or during MALDI-TOF mass spectrometry.

The capture compound-biomolecule array can be treated by either chemical, including, but not limited to, cyanogen bromide, or enzymatic, including, but not limited to, in embodiments where the biomolecule is a protein, trypsin, chymotrypsin, an exopeptidase (e.g., aminopeptidase and carboxypeptidase) reagents to effect cleavage. For the latter, all but one peptide fragment will remain hybridized when digestion is quantitative. Partial digestion also can be of advantage to identify and characterize proteins following desorption from the array. The cleaved protein/peptide fragments are desorbed, analyzed, and characterized by their respective molecular weights.

In certain embodiments herein, L is selected from SS, OP(=O)(OR$^{51}$)NH, OC(=O),

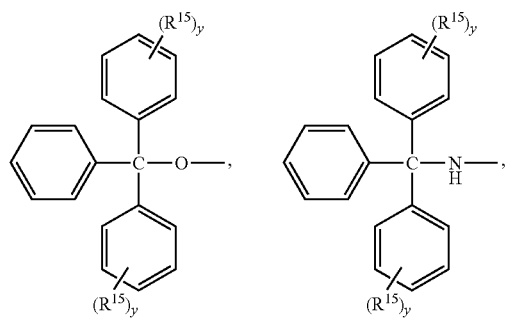

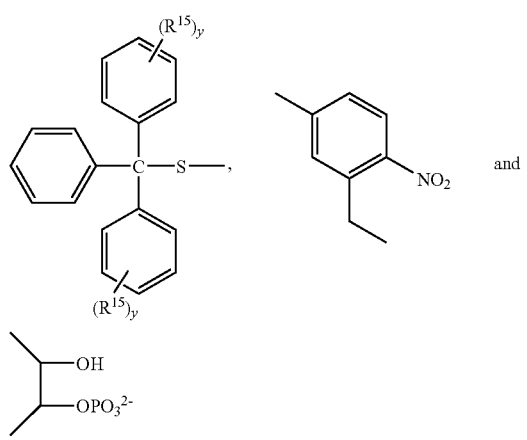

where R$^{15}$, R$^{50}$ and y are as defined above. In certain embodiments, R$^{15}$ is H, OH, OR$^{51}$, SH, SR$^{51}$, NH$_2$, NHR$^{51}$, N(R$^{51}$)$_2$, F, Cl, Br, I, SO$_3$H, PO$_4$, CH$_3$, CH$_2$CH$_3$, CH(CH$_3$)$_2$ or C(CH$_3$)$_3$; where R$^{51}$ is straight or branched chain alkyl, straight or branched chain alkenyl, straight or branched chain alkynyl, aryl, heteroaryl, cycloalkyl, heterocyclyl, straight or branched chain aralkyl, straight or branched chain aralkenyl, straight or branched chain aralkynyl, straight or branched chain heteroaralkyl, straight or branched chain heteroaralkenyl, straight or branched chain heteroaralkynyl, straight or branched chain cycloalkylalkyl, straight or branched chain cycloalkylalkenyl, straight or branched chain cycloalkylalkynyl, straight or branched chain heterocyclylalkyl, straight or branched chain heterocyclylalkenyl or straight or branched chain heterocyclylalkynyl.

(ii) Non-Cleavable Divalent Z Moieties

In another embodiment, Z is a non-cleavable divalent moiety and has the formula: $(S^1)_t M(R^{15})_a (S^2)_b$,
where $S^1$, M, $R^{15}$, $S^2$, t, a and b are as defined above.

b. Z has a Dendrimeric Structure

In another embodiment, Z has a dendritic structure (i.e., Z is a multivalent dendrimer) that is linked to a plurality of Q and X moieties. Z, in certain embodiments, has about 4 up to about 6, about 8, about 10, about 20, about 40, about 60 or more points of attachment (i.e., Z is tetravalent up to hexavalent, octavalent, decavalent, didecavalent, tetradecavalent, hexadecavalent, etc.). In these embodiments, the dendritic moiety Z is based on a multivalent core M, as defined above. The number of points of attachment on M may vary from about 2 up to about 4, about 6, about 8, or more. Thus, in one embodiment, Z has the structure:

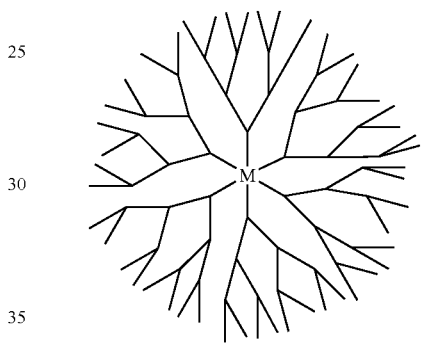

where M is as defined above, and is linked to a plurality of Q, Y, W and X moieties.

In another embodiment, Z has the structure:

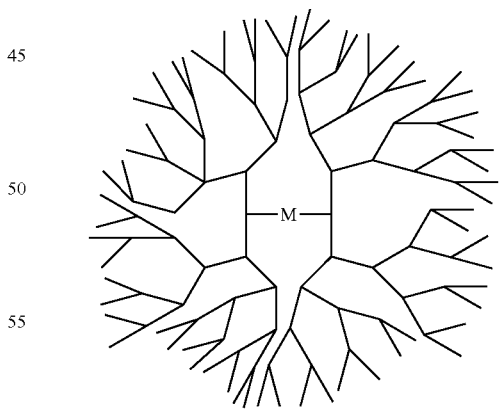

where M is as defined above, and is linked to a plurality of Q, Y, W and X moieties.

In other embodiments, the dendritic Z moieties may optionally possess a pluratlity of spacer groups S$^1$ and/or S$^2$, or for embodiments where Z is a cleavable linkage, a plurality of L groups. The S$^1$, S$^2$ and/or L moieties are attached to the end of the dendritic chain(s).

In these embodiments, the density of the biopolymer to be analyzed, and thus signal intensity of the subsequent analysis, is increased relative to embodiments where Z is a divalent group.

c. Z is an Insoluble Support or a Substrate

In other embodiments, Z can be an insoluble support or a substrate, such as a particulate solid support, such as a silicon or other "bead" or microsphere, or solid surface so that the surface presents the functional groups (X, Y, Q and, as needed W). In these embodiments, Z has bound to it one or a plurality of X moieties (typically, 1 to 100, generally 1 to 10) and optionally to at least one Q and/or Y moiety, and also optionally to one or more W moieties. Z, in these embodiments, can have tens up to hundreds, thousands, millions, or more functional moieties (groups) on its surface. For example, the capture compound can be a silicon particle or a agarose or other particle with groups presented on it. As discussed below, it further can be coated with a hydrophobic material, such as lipid bilayers or other lipids that are used, for example to produce liposomes. In such embodiments, the resulting particles with a hydrophobic surface and optional hydrophobic W groups are used in methods for probing cell membrane environments and other intracellular environments. Gentle lysis of cells, can expose the intracellular compartments and organelles, and hydrophobic capture compounds, such as these, can be reacted with them, and the bound biomolecules assessed by, for example, mass spectrometry or further treated to release the contents of the compartments and organdies and reacted with the capture compounds or other capture compounds.

In embodiments in which Z is an insoluble support, the insoluble support or substrate moiety Z can be based on a flat surface constructed, for example, of glass, silicon, metal, plastic or a composite or other suitable surface; or can be in the form of a "bead" or particle, such as a silica gel, a controlled pore glass, a magnetic or cellulose bead; or can be a pin, including an array of pins suitable for combinatorial synthesis or analysis. Substrates can be fabricated from virtually any insoluble or solid material. For example, silica gel, glass (e.g., controlled-pore glass (CPG)), nylon, Wang resin, Merrifield resin, dextran cross-linked with epichlorohydrin (e.g., Sephadex®), agarose (e.g., Sepharose®), cellulose, magnetic beads, Dynabeads, a metal surface (e.g., steel, gold, silver, aluminum, silicon and copper), a plastic material (e.g., polyethylene, polypropylene, polyamide, polyester, polyvinylidenedifluoride (PVDF)) Exemplary substrate include, but are not limited to, beads (e.g., silica gel, controlled pore glass, magnetic, dextran cross-linked with epichlorohydrin (e.g., Sephadex®), agarose (e.g., Sepharose®), cellulose, capillaries, flat supports such as glass fiber filters, glass surfaces, metal surfaces (steel, gold, silver, aluminum, copper and silicon), plastic materials including multiwell plates or membranes (e.g., of polyethylene, polypropylene, polyamide, polyvinylidenedifluoride), pins (e.g., arrays of pins suitable for combinatorial synthesis or analysis or beads in pits of flat surfaces such as wafers (e.g., silicon wafers) with or without plates. The solid support is in any desired form, including, but not limited to, a bead, capillary, plate, membrane, wafer, comb, pin, a wafer with pits, an array of pits or nanoliter wells and other geometries and forms known to those of skill in the art. Supports include flat surfaces designed to receive or link samples at discrete loci.

In one embodiment, the solid supports or substrates Z are "beads" (i.e., particles, typically in the range of less than 200 μm or less than 50 μm in their largest dimension) including, but not limited to, polymeric, magnetic, colored, $R_f$-tagged, and other such beads. The beads can be made from hydrophobic materials, including, but not limited to, polystyrene, polyethylene, polypropylene or teflon, or hydrophilic materials, including, but not limited to, cellulose, dextran cross-linked with epichlorohydrin (e.g., Sephadex®), agarose (e.g., Sepharose®), polyacrylamide, silica gel and controlled pore glass beads or particles. These types of capture compounds can be reacted in liquid phase in suspension, and the spun down or other removed from the reaction medium, and the resulting complexes analyzed, such as by mass spectrometry. They can be sorted using the Q function to bind to distinct loci on a solid support, or they can include a label to permit addressing, such as an radio frequency tag or a colored label or bar code or other symbology imprinted thereon. These can be sorted according to the label, which serves as "Q" function, and then analyzed by mass spectrometry.

In further embodiments, the insoluble support or substrate Z moieties optionally can possess spacer groups $S^1$ and/or $S^2$, or for embodiments where Z is a cleavable linkage, L. The $S^1$, $S^2$ and/or L moieties are attached to the surface of the insoluble support or substrate.

In these embodiments, the density of the biomolecule to be analyzed, and thus signal intensity of the subsequent analysis, is increased relative to embodiments where Z is a divalent group. In certain embodiments, an appropriate array of single stranded oligonucleotides or oligonucleotide analogs that are complementary to the single stranded oligonucleotide or oligonucleotide analog sorting functions Q will be employed in the methods provided herein.

d. Mass Modified Z Moieties

In other embodiments, including embodiments where Z is a cleavable moiety, Z includes a mass modifying tag. In certain embodiments, the mass modifying tag is attached to the cleavable linker L. In one embodiment, the mass modified Z moiety has the formula:
$(S^1)_t M(R^{15})_a (S^2)_b LT$, where $S^1$, t, M, $R^{15}$, a, $S^2$, b and L are selected as above; and T is a mass modifying tag. Mass modifying tags for use herein include, but are not limited to, groups of formula $X^1 R^{10}$, where $X^1$ is a divalent group such as O, OC(O)(CH$_2$)$_y$C(O)O, NHC(O), C(O)NH, NHC(O)(CH$_2$)$_y$, C(O)O, NHC(S)NH, OP(O-alkyl)O, OSO$_2$O, OC(O)CH$_2$S, S, NH and

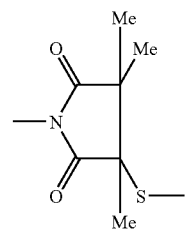

and $R^{10}$ is a divalent group including (CH$_2$CH$_2$O)$_z$ CH$_2$CH$_2$O, (CH$_2$CH$_2$O)$_z$CH$_2$CH$_2$Oalkylene, alkylene, alkenylene, alkynylene, arylene, heteroarylene, (CH$_2$)$_z$CH$_2$O, (CH$_2$)$_z$CH$_2$Oalkylene, (CH$_2$CH$_2$NH)$_z$CH$_2$CH$_2$NH, CH$_2$CH(OH)CH$_2$O, Si(R$^{12}$)(R$^{13}$), CHF and CF$_2$; where y is an integer from 1 to 20; z is an integer from 0 to 200; $R^{11}$ is the side chain of an α-amino acid; and $R^{12}$ and $R^{13}$ are each independently selected from alkyl, aryl and aralkyl.

In other embodiments, $X^1 R^{10}$ is selected from SS, S, (NH(CH$_2$)$_y$NHC(O)(CH$_2$)$_y$C(O))$_z$NH(CH$_2$)$_y$NHC(O)(CH$_2$)$_y$C (O)O, $(NH(CH_2)_yC(O))_zNH(CH_2)_yC(O)O$, $(NHCH(R^{11})C(O))_zNHCH(R^{11})C(O)O$, and $(O(CH_2)_yC(O))_zNH(CH_2)_yC(O)O$.

In the above embodiments, where $R^{10}$ is an oligo-/polyethylene glycol derivative, the mass-modifying increment is 44, i.e., five different mass-modified species can be generated by changing z from 0 to 4, thus adding mass units of 45 (z=0), 89 (z=1), 133 (z=2), 177 (z=3) and 221 (z=4) to the compounds. The oligo/polyethylene glycols also can be monoalkylated by a lower alkyl such as methyl, ethyl, propyl, isopropyl, t-butyl and the like.

Other mass modifying tags include, but are not limited to $CHF_2$, $CF_2$, $Si(CH_3)_2$, $Si(CH_3)(C_2H_5)$ and $Si(C_2H_5)_2$. In other embodiments, the mass modifying tags include homo- or heteropeptides. A non-limiting example that generates mass-modified species with a mass increment of 57 is an oligoglycine, which produce mass modifications of, e.g., 74 (y=1, z=O), 131 (y=1, z=2), 188 (y=1, z=3) or 245 (y=1, z=4). Oligoamides also can be used, e.g., mass-modifications of 74 (y=1, z=0), 88 (y=2, z=0), 102 (y=3, z=0), 116 (y=4, z=0), etc., are obtainable. Those skilled in the art will appreciate that there are numerous possibilities in addition to those exemplified herein for introducing, in a predetermined manner, many different mass modifying tags to the compounds provided herein.

In other embodiments, $R^{15}$ and/or $S^2$ can be functionalized with $X^1R^{10}H$ or $X^1R^{10}$ alkyl, where $X^1$ and $R^{10}$ are defined as above, to serve as mass modifying tags.

2. Reactivity Functions "X"

Reactivity functions ("X") confer the ability on the compounds the ability to bind either covalently or with a high affinity (greater than $10^9$, generally greater than $10^{10}$ or $10^{11}$ liters/mole, typically greater than a monoclonal antibody, and typically stable to mass spectrometric analysis, such as MALDI-MS) to a biomolecule, particularly proteins, including functional groups thereon, which include post-translationally added groups. Generally the binding is covalent or is of such affinity that it is stable under conditions of analysis, such as mass spectral, including MALDI-TOF, analysis. Exemplary groups are set forth herein (see, e.g., FIG. 16, and the discussion below). Further groups include groups that are inert toward reaction with a biomolecule, such as a protein, until activated. Such groups include photoactivatable groups, including but not limited to, azide and diazirine groups. In another embodiment, an active ester (e.g. NHS) is used as the reactivity group under acidic conditions. The active ester is inert toward reaction with amine groups under these conditions, but will react upon raising the pH.

In the compounds provided herein, X is a moiety that binds to or interacts with the surface of a biomolecule, including, but not limited to, the surface of a protein; an amino acid side chain of a protein; or an active site of an enzyme (protein) or to functional groups of other biomolecule, including lipids and polysaccharides.

Thus, for example, X is a group that reacts or interacts with functionalities on the surface of a protein to form covalent or non-covalent bonds with high affinity. A wide selection of different functional groups are available for X to interact with a protein. For example, X can act either as a nucleophile or an electrophile to form covalent bonds upon reaction with the amino acid residues on the surface of a protein. Exemplary reagents that bind covalently to amino acid side chains include, but are not limited to, protecting groups for hydroxyl, carboxyl, amino, amide, and thiol moieties, including, for example, those disclosed in T. W. Greene and P. G. M. Wuts, "Protective Groups in Organic Synthesis," 3rd ed. (1999, Wiley Interscience); photoreactive groups, Diels Alder couples (i.e., a diene on one side and a single double bond on the other side).

Hydroxyl protecting groups for use as X groups herein include, but are not limited to:

(i) ethers such as methyl, substituted methyl (methoxymethyl, methylthiomethyl, (phenyldimethylsilyl)methoxymethyl, benzyloxymethyl, p-methoxybenzyloxymethyl, p-nitrobenzyloxymethyl, o-nitrobenzyloxymethyl, (4-methoxyphenoxy)methyl, guaiacolmethyl, t-butoxymethyl, 4-pentenyloxymethyl, siloxymethyl, 2-methoxyethoxymethyl, 2,2,2,-trichloroethoxymethyl, bis(2-chloroethoxymethyl), 2-(trimethylsilyl)ethoxymethyl, menthoxymethyl, tetrahydropyranyl, 3-bromotetrahydropyranyl, tetrahydrothiopyranyl, 1-methoxycyclohexyl, 4-methoxytetrahydropyranyl, 4-methoxytetrahydrothiopyranyl, 4-methoxytetrahydrothiopyranyl S,S-dioxide, 1-[(2-chloro-4-methyl)phenyl]-4-methoxypiperidin-4-yl, 1-(2-fluorophenyl)-4-methoxypiperidin-4-yl, 1,4-dioxan-2-yl, tetrahydrofuranyl, tetrahydrothiofuranyl, 2,3,3a,4,5,6,7,7a-octahydro-7,8,8-trimethyl-4,7-methanobenzofuran-2-yl), substituted ethyl(1-ethoxyethyl, 1-(2-chloroethoxy)ethyl, 1-[2-(trimethylsilyl)ethoxy]ethyl, 1-methyl-1-methoxyethyl, 1-methyl-1-benzyloxyethyl, 1-methyl-1-benzyloxy-2-fluoroethyl, 1-methyl-1-phenoxyethyl, 2,2,2-trichloroethyl, 1,1-dianisyl-2,2,2-trichloroethyl, 1,1,1,3,3,3-hexafluoro-2-phenylisopropyl, 2-trimethylsilylethyl, 2-(benzylthio)ethyl, 2-(phenylselenyl)ethyl), t-butyl, allyl, propargyl, p-chlorophenyl, p-methoxyphenyl, p-nitrophenyl, 2,4-dinitrophenyl, 2,3,5,6-tetrafluoro-4-(trifluoromethyl)phenyl, benzyl, substituted benzyl(p-methoxybenzyl, 3,4,-dimethoxybenzyl, o-nitrobenzyl, p-nitrobenzyl, p-halobenzyl, 2,6-dichlorobenzyl, p-phenylbenzyl, p-phenylenzyl, 2,6-difluorobenzyl, p-acylaminobenzyl, p-azidobenzyl, 4-azido-3-chlorobenzyl, 2-trifluoromethylbenzyl, p-(methylsulfinyl)benzyl), 2- and 4-picolyl, 3-methyl-2-picolyl N-oxide, 2-quinolinylmethyl, 1-pyrenylmethyl, diphenylmethyl, p,p'-dinitrobenzhydryl, 5-dibenzosuberyl, triphenylmethyl, α-naphthyldiphenylmethyl, p-methoxyphenyldiphenylmethyl, di(p-methoxyphenyl)phenylmethyl, tri(p-methoxyphenyl)methyl, 4-(4-'-bromophenacyloxy)phenyldiphenylmethyl, 4,4',4"-tris(4,5-dichlorophthalimidophenyl)methyl, 4,4',4"-tris(levulinoyloxyphenyl)methyl, 4,4',4"-tris(benzoyloxyphenyl)methyl, 4,4'-dimethoxy-3"-[N-(imidazolylmethyl)]trityl, 4,4'-dimethoxy-3"-[N-(imidazolylethyl)carbamoyl]trityl, 1,1-bis(4-methoxyphenyl-1'-pyrenylmethyl, 4-(17-tetrabenzo[a,c,g,i]fluorenylmethyl)-4,4"-dimethoxytrityl, 9-Anthryl, 9-(9-phenyl)xanthenyl, 9(9-phenyl-10-oxo)anthryl, 1,3-benzodithiolan-2-yl, benzisothiazolyl s,s-dioxido, silyl ethers (trimethylsilyl, triethylsilyl, triisopropylsilyl, dimethylisopropylsilyl, diethylisopropylsilyl, dimethylthexylsilyl, t-butyldimethylsilyl, t-butyldiphenylsilyl, tribenzylsilyl, tri-p-xylylsilyl, triphenylsilyl, diphenylmethylsilyl, di-t-butylmethylsilyl, tris(trimethylsilyl)silyl(sisyl), (2-hydroxystyryl)dimethylsilyl, (2-hydroxystyryl)diisopropylsilyl, t-butylmethoxyphenylsilyl, t-butoxydiphenylsilyl);

(ii) esters such as formate, benzoylformate, acetate, substituted acetate (chloroacetate, dichloroacetate, trichloroacetate, trifluoroacetate, methoxyacetate, triphenylmethoxyacetate, phenoxyacetate, p-chlorophenoxyacetate, phenylacetate, p-P-phenylacetate, diphenylacetate), nicotinate, 3-phenylpropionate, 4-pentenoate, 4-oxopentanoate(levulinate), 4,4-(ethylenedithio)pentanoate, 5-[3-bis(4-methoxyphenyl)hydroxymethylphenoxy]levulinate, pivaloate, 1-adamantoate, crotonate, 4-methoxycrotonate, benzoate, p-phenylbenzoate, 2,4,6-trimethylbenzoate(mesitoate), carbonates (methyl, methoxymethyl, 9-fluorenylmethyl, ethyl, 2,2,2-trichloroethyl, 1,1,-dimethyl-2,2,2-trichloroethyl, 2-(trimethylsilyl)ethyl, 2-(phenylsulfonyl)ethyl, 2-(triphenylphosphonio)ethyl, isobutyl, vinyl, allyl, p-nitrophenyl, benzyl, p-methoxybenzyl, 3,4,-dimethoxybenzyl, o-nitrobenzyl, p-nitrobenzyl, 2-dansylethyl, 2-(4-nitrophenyl) ethyl, 2-(2,4-dinitrophenyl)ethyl, 2-cyano-1-phenylethyl, S-benzyl thiocarbonate, 4-ethoxy-1-naphthyl, methyl dithiocarbonate), 2-iodobenzoate, 4-azidobutyrate, 4-nitro-4-methylpentanoate, o-(dibromomethyl)benzoate, 2-formylbenzenesulfonate, 2-(methylthiomethoxy)ethyl carbonate, 4-(methylthiomethoxy)butyrate, 2-(methylthiomethoxymethyl)benzoate, 2-(chloroacetoxymethyl)benzoate, 2-[(2-chloroacetoxy)ethyl]benzoate, 2-[2-(benzyloxy)ethyl]benzoate, 2-[2-(4-methoxybenzyloxy)ethyl]benzoate, 2,6-dichloro-4-methylphenoxyacetate, 2,6-dichloro-4-(1,1,3,3-tetramethylbutyl)phenoxyacetate, 2,4-bis(1,1-dimethylpropyl)phenoxyacetate, chlorodiphenylacetate, isobutyrate, monosuccionoate, (E)-2-methyl-2-butenoate (tigloate), o-(methoxycarbonyl)benzoate, p-P-benzoate, α-naphthoate, nitrate, alkyl N,N,N',N'-tetramethylphosphorodiamidate, 2-chlorobenzoate, 4-bromobenzoate, 4-nitrobenzoate, 3'5'-dimethoxybenzoin, a wild and woolly photolabile fluorescent ester, N-phenylcarbamate, borate, dimethylphosphinothioyl, 2,4-dinitrophenylsulfenate; and (iii) sulfonates (sulfate, allylsulfonate, methanesulfonate (mesylate), benzylsulfonate, tosylate, 2-[(4-nitrophenyl) ethyl]sulfonate).

Carboxyl protecting groups for use as X groups herein include, but are not limited to:

(i) esters such as enzymatically cleavable esters (heptyl, 2-N-(morpholino)ethyl, choline, (methoxyethoxy)ethyl, methoxyethyl), methyl, substituted methyl (9-fluorenylmethyl, methoxymethyl, methylthiomethyl, tetrahydropyranyl, tetrahydrofuranyl, methoxyethoxymethyl, 2-(trimethylsilyl) ethoxymethyl, benzyloxymethyl, pivaloyloxymethyl, phenylacetoxymethyl, triisopropylsilylmethyl, cyanomethyl, acetol, phenacyl, p-bromophenacyl, α-methylphenacyl, p-methoxyphenacyl, desyl, carboxamidomethyl, p-azobenzenecarboxamidomethyl, N-phthalimidomethyl), 2-substituted ethyl(2,2,2-trichloroethyl, 2-haloethyl, ω-chloroalkyl, 2-(trimethylsilyl)ethyl, 2-methylthioethyl, 1,3-dithianyl-2-methyl, 2-(p-nitrophenylsulfenyl)ethyl, 2-(p-toluenesulfonyl)ethyl, 2-(2'-pyridyl)ethyl, 2-(p-methoxyphenyl)ethyl, 2-(diphenylphosphino)ethyl, 1-methyl-1-phenylethyl, 2-(4-acetyl-2-nitrophenyl)ethyl, 2-cyanoethyl), t-butyl, 3-methyl-3-pentyl, dicyclopropylmethyl, 2,4-dimethyl-3-pentyl, dicyclopropylmethyl, cyclopentyl, cyclohexyl, allyl, methallyl, 2-methylbut-3-en-2-yl, 3-methylbut-2-(prenyl), 3-buten-1-yl, 4-(trimethylsilyl)-2-buten-1-yl, cinnamyl, α-methylcinnamyl, prop-2-ynyl(propargyl), phenyl, 2,6-dialkylphenyl (2,6,-dimethylphenyl, 2,6,diisopropylphenyl, 2,6-di-t-butyl-4-methylphenyl, 2,6-di-t-butyl-4-methoxyphenyl, p-(methylthio)phenyl, pentafluorophenyl, benzyl, substituted benzyl (triphenylmethyl, diphenylmethyl, bis(o-nitrophenyl)methyl, 9-anthrylmethyl, 2-(9,10-dioxo)anthrylmethyl, 5-dibenzosuberyl, 1-pyrenylmethyl, 2-(trifluoromethyl)-6-chromonylmethyl, 2,4,6-trimethylbenzyl, p-bromobenzyl, o-nitrobenzyl, p-nitrobenzyl, p-methoxybenzyl, 2,6-dimethoxybenzyl, 4-(methylsulfinyl)benzyl, 4-sulfobenzyl, 4-azidomethoxybenzyl, 4-{N-[1-(4,4,-dimethyl-2,6-dioxocychlohexylidene)-3-methylbutyl]amino}benzyl, piperonyl, 4-picolyl, p-P-benzyl), silyl (trimethylsilyl, triethylsilyl, t-butyldimethylsilyl, i-propyldimethylsilyl, phenyldimethylsilyl, di-t-butylmethylsilyl, triisopropylsilyl), activated (thiol), oxazoles, 2-alkyl-1,3-oxazoline, 4-alkyl-5-oxo-1,3-oxazolidine, 2,2,-bistrifluoromethyl-4-alkyl-5-oxo-1-,3-oxazolidine, 5-alkyl-4-oxo-1,3-dioxolane, dioxanones, ortho esters, Braun ortho ester, pentaaminocobalt(iii) complex, stannyl (triethylstannyl, tri-N-butylstannyl);

(ii) amides (N,N-dimethyl, pyrrolidinyl, piperidinyl, 5,6-dihydrophenanthridinyl, o-nitroanilide, N-7-nitroindolyl, N-8-nitro-1,2,3,4-tetrahydroquinolyl, 2-(2-aminophenyl)acetaldehyde dimethyl acetal amide, p-P-benzenesulfonamide;

(iii) hydrazides (N-phenyl, N,N'-diisopropyl); and (iv) tetraalkylammonium salts.

Thiol protecting groups for use as X groups herein include, but are not limited to:

(i) thioethers (S-alkyl, S-benzyl, S-p-methoxybenzyl, S-o- or p-hydroxy- or acetoxybenzyl, S-p-nitrobenzyl, S-2,4,6-trimethylbenzyl, S-2,4,6-trimethoxybenzyl, S-4-picolyl, S-2-quinolinylmethyl, S-2-picolyl N-oxide, S-9-anthrylmethyl, S-9-fluorenylmethyl, S-xanthenyl, S-ferrocenylmethyl); S-diphenylmethyl, substituted S-diphenylmethyl and S-triphenylmethyl (S-diphenylmethyl, S-bis(4-methoxyphenyl)methyl, S-5-dibenzosuberyl, S-triphenylmethyl, S-diphenyl-4-pyridylmethyl), S-phenyl, S-2,4-dinitrophenyl, S-t-butyl, S-1-adamantyl, substituted S-methyl including monothio, dithio and aminothioacetals (S-methoxymethyl, S-isobutoxymethyl, S-benzyloxymethyl, S-2-tetrahydropyranyl, S-benzylthiomethyl, S-phenylthiomethyl, thiazolidine, S-acetamidomethyl, S-trimethylacetomidomethyl, S-benzamidomethyl, S-allyloxycarbonylaminomethyl, S-phenylacetamidomethyl, S-phthalimidomethyl, S-acetyl-, S-carboxyl-, and S-cyanomethyl), substituted S-ethyl (S-(2-nitro-1-phenyl)ethyl, S-2-(2,4-dintrophenyl)ethyl, S-2-(4'-pyridyl)ethyl, S-2-cyanoethyl, S-2-(trimethylsilyl)ethyl, S-(1-m-nitrophenyl-2-benzoyl)ethyl, S-2-phenylsulfonylethyl, S-1-(4-methylphenylsulfonyl)-2-methylprop-2-yl, silyl;

(ii) thioesters (S-acetyl, S-benzoyl, S-trifluoroacetyl, S—N-[[(p-biphenylyl)isopropoxy]carbonyl]-N-methyl-α-aminothiobutyrate, S—N-(t-butoxycarbonyl-N-methyl-α-aminothiobutyrate), thiocarbonates (S-2,2,2-trichloroethoxycarbonyl, S-t-butoxycarbonyl, S-benzyloxycarbonyl, S-p-methoxybenzyloxycarbonyl), thiocarbamates (S—(N-ethyl), S—(N-methoxymethyl));

(iii) unsymmetrical disulfides (S-ethyl, S-t-butyl, substituted S-phenyl disulfides);

(iv) sulfenyl derivatives (S-sulfonate, S-sulfenylthiocarbonate, S-3-nitro-2-pyridinesulfenyl sulfide, S-[tricarbonyl [1,2,3,4,5-ç]-2-,4-cyclohexadien-1-yl]iron(1+), oxathiolone); and (v) S-methylsulfonium salt, S-benzyl- and S-4-methoxybenzylsulfonium salt, S-1-(4-phthalimidobutyl)sulfonium salt, S-(dimethylphosphinol)thioyl, S-(diphenylphosphino) thioyl.

Amino protecting groups for use as X groups herein include, but are not limited to:

(i) carbamates (methyl, ethyl, 9-fluorenylmethyl, 9-(2-sulfo)fluorenylmethyl, 9-(2,7-dibromo)fluorenylmethyl, 17-tetrabenzo[a,c,g.i]fluorenylmethyl, 2-Chloro-3-indenylmethyl, benz[f]inden-3-ylmethyl, 2,7-di-t-butyl-[9-(10,10-dioxo-10,10,10,10-tetrahydrothiox, 1,1-dioxobenzo[b] thiophene-2-ylmethyl, substituted ethyl (2,2,2-trichloroethyl, 2-trimethylsilylethyl, 2-phenylethyl, 1-(1-adamantyl)-1-methylethyl, 2-chloroethyl, 1,1-dimethyl-2-haloethyl, 1,1-dimethyl-2,2-dibromoethyl, 1,1-dimethyl-2,2,2-trichloroethyl, 1-methyl-1-(4-biphenylyl)ethyl, 1-(3,5-di-t-butylphenyl)-1-methylethyl, 2-(2'- and 4'-pyridyl)ethyl, 2,2-bis(4'-nitrophenyl)ethyl, N-(2-pivaloylamino)-1,1-dimethylethyl, 2-[(2-nitrophenyl)dithio]-1-phenylethyl, 2-(N,N-dicyclohexylcarboxamido)ethyl), t-butyl, 1-adamantyl, 2-adamantyl, vinyl, allyl, 1-isopropylallyl, cinnamyl, 4-nitrocinnamyl, 3-(3'pyridyl)prop-2-enyl, 8-quinolyl, N-hydroxypiperidinyl, alkyldithio, benzyl, p-methoxybenzyl, p-nitrobenzyl, p-bromobenzyl, p-chlorobenzyl, 2,4-dichlorobenzyl, 4-methylsulfinylbenzyl, 9-anthrylmethyl, diphenylmethyl, 2-methylthioethyl, 2-methylsulfonylethyl, 2-(p-toluenesulfonyl)pethyl, [2-(1,3-dithianyl)methyl, 4-methylthiophenyl, 2,4-dimethylthiophenyl, 2-phosphonioethyl, 1-methyl-1-(triphenylphsophonio)ethyl, 1,1-dimethyl-2-cyanoethyl, 2-dansylethyl, 2-(4-nitrophenyl)ethyl, 4-phenylacetoxybenzyl, 4-azidobenzyl, 4-azidomethoxybenzyl, m-chloro-p-acyloxybenzyl, p-(dihydroxyboryl)benzyl, 5-benzisoxazolylmethyl, 2-(trifluoromethyl)-6-chromonylmethyl, m-nitrophenyl, 3,5-dimethoxybenzyl, 1-methyl-1-(3,5-dimethoxyphenyl)ethyl, α-methylnitropiperonyl, o-nitrobenzyl, 3,4-dimethoxy-6-nitrobenzyl, phenyl(o-nitrophenyl)methyl, 2-(2-nitrophenyl)ethyl, 6-nitroveratryl, 4-methoxyphenacyl, 3',5'-dimethoxybenzoin, ureas (phenothiazinyl-(10)-carbonyl derivative, N'-p-toluenesulfonylaminocarbonyl, N'-phenylaminothiocarbonyl), t-amyl, S-benzyl thiocarbamate, butynyl, p-cyanobenzyl, cyclobutyl, cyclohexyl, cyclopentyl, cyclopropylmethyl, p-decyloxybenzyl, diisopropylmethyl, 2,2-dimethoxycarbonylvinyl, o-(N'—N'-dimethylcarboxamido)benzyl, 1,1-dimethyl-3-(N',N'-dimethylcarboxamido)propyl, 1,1-dimethylpropynyl, di(2-pyridyl)methyl), 2-furanylmethyl, 2-Iodoethyl, isobornyl, isobutyl, isonicotinyl, p-(p'-methoxyphenylazo)benzyl, 1-methylcyclobutyl, 1-methylcyclohexyl, 1-methyl-1-cyclopropylmethyl, 1-methyl-1-(p-phenylazophenyl)ethyl, 1-methyl-1-phenylethyl, 1-methyl-1-(4'-pyridyl)ethyl, phenyl, p-(phenylazo)benzyl, 2,4,6-tri-t-butylphenyl, 4-(trimethylammonium)benzyl, 2,4,6-trimethylbenzyl);

(ii) amides (N-formyl, N-acetyl, N-chloroacetyl, N-tricholoroacetyl, N-trifluoroacetyl, N-phenylacetyl, N-3-phenylpropionyl, N-4-pentenoyl, N-picolinoyl, n-3-pyridylcarboxamido, N-benzoylphenylalanyl derivative, N-benzoyl, N-p-phenylbenzoyl, N-o-nitrophenylacetyl, N-o-nitrophenoxyacetyl, N-3-(o-nitrophenyl)propionyl, N-2-methyl-2-(o-nitrophenoxy)propionyl, N-3-methyl-3-nitrobutyryl, N-o-nitrocinnamoyl, N-o-nitrobenzoyl, N-3-(4-t-butyl-2,6-dinitrophenyl-2,2-dimethylpropionyl, N-o-(benzoyloxymethyl)benzoyl, N-(2-acetoxymethyl)benzoyl, N-2-[(t-butyldiphenylsiloxy)methyl]benzoyl, N-3-(3',6'-dioxo-2',4',5'-trimethylcyclohexa-1',4'-diene)-3,3-dimethylpropionyl, N-o-hydroxy-trans-cinnamoyl, N-2-methyl-2-(o-phenylazophenoxy)propionyl, N-4-chlorobutyryl, acetoacetyl, N-3-(p-hydroxyphenyl)propionyl, (N'-dithiobenzyloxycarbonylamino)acetyl, N-acetylmethionine derivative, 4,5-diphenyl-3-oxazolin-2-one), cyclic imides (N-phthaloyl, N-tetrachlorophthaloyl, N-4-nitrophthaloyl, N-dithiasuccinoyl, N-2,3-diphenylmaleoyl, N-2,5-dimethylpyrrolyl, N-2,5-bis(triisopropylsiloxy)pyrrolyl, N-1,1,4,4-tetramethyldisilylazacyclopentane adduct, N-1,1,3,3-tetramethyl-1,3-disilaisoindolyl, 5-substituted 1,3-dimethyl-1,3,5-triazacyclohexan-2-one, 5-substituted 1,3-dibenzyl-1,3,5-triazacyclohexan-2-one, 1-substituted 3,5-dinitro-4-pyridonyl, 1,3,5-dioxazinyl);

(iii) N-alkyl and N-aryl amines (N-methyl, N-t-butyl, N-allyl, N-[2-(trimethylsilyl)ethoxy]methyl, N-3-acetoxypropyl, N-cyanomethyl, N-(1-isopropyl-4-nitro-2-oxo-3-pyrrolin-3-yl), N-2,4-dimethoxybenzyl, N-2-azanorbornenyl, N-2,4-dinitrophenyl, quaternary ammonium salts, N-benzyl, N-4-methoxybenzyl, N-2,4-dimethoxybenzyl, N-2-hydroxybenzyl, N-diphenylmethyl, N-bis(4-methoxyphenyl)methyl, N-5-dibenzosuberyl, N-triphenylmethyl, N-(4-methoxyphenyl)diphenylmethyl, N-9-phenylfluorenyl, N-ferrocenylmethyl, N-2-picolylamine N'-oxide);

(iv) imines (N-1,1-dimethylthiomethylene, N-benzylidine, N-p-methoxybenzylidene, N-diphenylmethylene, N-[(2-pyridyl)mesityl]methylene, N—(N',N'-dimethylaminomethylene), N—(N',N'-dibenzylaminomethylene), N—(N'-t-butylaminomethylene), N,N'-isopropylidene, N-p-nitrobenzylidene, N-salicylidene, N-5-chlorosalicylidene, N-(5-chloro-2-hydroxyphenyl)phenylmethylene, N-cyclohexylidene, N-t-butylidene);

(v) enamines (N-(5,5-dimethyl-3-oxo-1-cyclohexenyl, N-2,7-dichloro-9-fluorenylmethylene, n-2-(4,4-dimethyl-2,6-dioxocyclohexylidene)ethyl, N-4,4,4-trifluoro-3-oxo-1-buteryl, N-1-isopropyl-4-nitro-2-oxo-3-pyrrolin-3-yl);

(vi) N-heteroatom derivatives (N-borane derivatives, N-diphenylborinic acid derivative, N-diethylborinic acid derivative, N-difluoroborinic acid derivative, N,N'-3,5-bis(trifluoromethyl)phenylboronic acid derivative, N-[phenyl(pentacarbonylchromium- or -tungsten)]carbenyl, N-copper or N-zinc chelate, 18-crown-6 derivative, N-nitro, N-nitroso, N-oxide, triazene derivative, N-diphenylphosphinyl, N-dimethyl- and diphenylthiophosphinyl, N-dialkyl phosphoryl, N-dibenzyl and diphenyl phosphoryl, iminotriphenylphosphorane derivative, N-benzenesulfenyl, N-o-nitrobenzenesulfenyl, N-2,4-dinitrobenzenesulfenyl, N-pentachlorobenzenesulfenyl, N-2-nitro-4-methoxybenzensulfenyl, N-triphenylmethylsulfenyl, N-1-(2,2,2-trifluoro-1,1-diphenyl)ethylsulfenyl, N-3-nitro-2-pyridinesulfenyl, N-p-toluenesulfonyl, N-benzenesulfonyl, N-2,3-6-trimethyl-4-methoxybenzenesulfonyl, N-2,4,6-trimethoxybenzesulfonyl, N-2,6-dimethyl-4-methoxybenzenesulfonyl, N-pentamethylbenzenelsulfonyl, N-2,3,5,6-tetramethyl-4-methoxybenzenesulfonyl, N-4-methoxybenzenesulfonyl, N-2,4,6-trimethylbenzenesulfonyl, N-2,6-dimethoxy-4-methylbenzenesulfonyl, N-3-methoxy-4-t-butylbenzenesulfonyl, N-2,2,5,7,8-pentamethylchroman-6-sulfonyl, N-2- and 4-nitrobenzenesulfonyl, N-2,4-dinitrobenzenesulfonyl, N-benzothiazole-2-sulfonyl, N-pyridine-2-sulfonyl, N-methanesulfonyl, N-2-(trimethylsilyl)ethanesulfonyl, N-9-anthracenesulfonyl, N-4-(4',8'-dimethoxynaphthylmethyl)benzenesulfonyl, N-benzylsulfonyl, N-trifluoromethylsulfonyl, N-phenacylsulfonyl, N-t-butylsulfonyl);

(vii) imidazole protecting groups including N-sulfonyl derivatives (N,N-dimethylsulfonyl, N-mesitylenesulfonyl, N-p-methoxyphenylsulfonyl, N-benzenesulfonyl, N-p-toluenesulfonyl); carbamates (2,2,2-trichloroethyl, 2-(trimethylsilyl)ethyl, t-butyl, 2,4-dimethylpent-3-yl, cyclohexyl, 1,1-dimethyl-2,2,2-trichloroethyl, 1-adamantyl, 2-adamantyl); N-alkyl and N-aryl derivatives (N-vinyl, N-2-chloroethyl, N-(1-ethoxy)ethyl, N-2-(2'-pyridyl)ethyl, N-2-(4'-pyridyl)ethyl, N-2-(4'-nitrophenyl)ethyl), N-trialkyl silyl derivatives (N-t-butyldimethylsilyl, N-triisopropylsilyl), N-allyl, N-benzyl, N-p-methoxybenzyl, N-3,4-dimethoxybenzyl, N-3-methoxybenzyl, N-3,5-dimethoxybenzyl, N-2-nitrobenzyl, N-4-nitrobenzyl, N-2,4-dinitrophenyl, N-pyhenacyl, N-triphenylmethyl, N-diphenylmethyl, N-(diphenyl-4-pyridylmethyl), N-(n',n'-dimethylamino)), amino acetal derivatives (N-hydroxymethyl, N-methoxymethyl, N-diethoxymethyl, N-ethoxymethyl, N-(2-chloroethoxy)methyl, N-[2-(trimethylsilyl)ethoxy]methyl, N-t-butoxymethyl, N-t-butyldimethylsiloxymethyl, N-pivaloyloxymethyl, N-benzyloxymethyl, N-dimethylaminomethyl, N-2-tetrahydropyranyl), amides (carbon dioxide adduct, N-formyl, N-(n', n'-diethylureidyl), N-dichloroacetyl, N-pivaloyl, N-diphenylthiophosphinyl); and (viii) amide NH protecting groups including amides (N-allyl, N-t-butyl, N-dicyclopropylmethyl, N-methoxymethyl, N-methylthiomethyl, N-benzyloxymethyl, N-2,2,2-trichloroethoxymethyl, N-t-butyldimethylsiloxymethyl, N-pivaloyloxymethyl, N-cyanomethyl, N-pyrrolidinomethyl, N-methoxy, N-benzyloxy, N-methylthio, N-triphenylmethylthio, N-t-butyldimethylsilyl, N-triisopropylsilyl, N-4-methoxyphenyl, N-3,4-dimethoxyphenyl, N-4-(methoxymethoxy) phenyl, N-2-methoxy-1-naphthyl, N-benzyl, N-4-methoxybenzyl, N-2,4-dimethoxybenzyl, N-3,4-dimethoxybenzyl, N-o-nitrobenzyl, N-bis(4-methoxyphenyl)methyl, N-bis(4-methoxyphenyl)phenylmethyl, N-bis(4-methylsulfinylphenyl)methyl, N-triphenylmethyl, N-9-phenylfluorenyl, N-bis (trimethylsilyl)methyl, N-t-butoxycarbonyl, N-benzyloxycarbonyl, N-methoxycarbonyl, N-ethoxycarbonyl,N-p-toluenesulfonyl, N,O-isopropylidene ketal, N,O-benzylidene acetal, N,O-formylidene acetal, N-butenyl, N-ethenyl, N-[(e)-(2-methoxycarbonyl)vinyl], N-diethoxymethyl, N-(1-methoxy-2,2-dimethylpropyl), N-2-(4-methylphenylsulfonyl)ethyl).

These protecting groups react with amino acid side chains such as hydroxyl (serine, threonine, tyrosine); amino (lysine, arginine, histadine, proline); amide (glutamine, asparagine); carboxylic acid (aspartic acid, glutamic acid); and sulfur derivatives (cysteine, methionine), and are readily adaptable for use in the capture compounds as the reactive moiety X.

It is in addition to the wide range of group-specific reagents that are known to persons of skill in the art, reagents that are known in natural product chemistry also can serve as a basis for X in forming covalent linkages. Other choices for, X include protein purification dyes, such as acridine or methylene blue, which have a strong affinity for certain proteins.

Alternatively, X can act as an electron donor or an electron acceptor to form non-covalent bonds or a complex, such as a charge-transfer complex, with a biomolecule, including, but not limited to, a protein, such that the resulting bond has a high stability (i.e., stable under conditions of mass spectrometric analysis, such as MALDI-TOF, as defined above). These reagents include those that interact strongly and with high specificity with biomolecules, including, but not limited to, proteins, without forming covalent bonds through the interaction of complementary affinity surfaces. For example, well known binding pairs, such as biotin and streptavidin, antibody and antigen, receptor and ligand, lectin and carbohydrate or other similar types of reagents are readily adaptable for use in these compounds as the reactive moiety X that will react with high affinity to biomolecules with surfaces similar to or identical to the other member of the binding pair. These moieties are selected so that the resulting conjugates (also referred to herein as complexes) have strong interactions that are sufficiently stable enough for suitable washing of the unbound biomolecules, including, but not limited to, proteins, out of the complexed biological mixtures.

The reactivity of X can be influenced by one or more selectivity functions Y on the core, i.e., M in the formula above, particularly where $S^2$ is not present.

The Y function, discussed below is employed for electronic (e.g., mesomeric, inductive) and/or steric effects to modulate the reactivity of X and the stability of the resulting X-biomolecule linkage. In these embodiments, biomolecule mixtures, including, but not limited to, protein mixtures, can react and be analyzed due to the modulation by Y, which changes the electronic or steric properties of X and, therefore, increases the selectivity of the reaction of X with the biomolecule.

In certain embodiments, X is an active ester, such as $C(=O)OPhpNO_2$, $C(=O)OC_6F_5$ or $C(=O)O(Nsuccinimidyl)$, an active halo moiety, such as an α-halo ether or an α-halo carbonyl group, including, but not limited to, $OCH_2I$, $OCH_2Br$, $OCH_2Cl$, $C(O)CH_2I$, $C(O)CH_2Br$ and $C(O)CH_2Cl$; amino acid side chain-specific functional groups, such as maleimido (for cysteine), a metal complex, including gold or mercury complexes (for cysteine or methionine), an epoxide or isothiocyanate (for arginine or lysine); reagents that bind to active sites of enzymes, including, but not limited to, transition state analogs; antibodies, e.g., against phosphorylated peptides; antigens, such as a phage display library; haptens; biotin; avidin; or streptavidin.

In certain embodiments X is an N-hydroxysuccinimidyl ester, or is

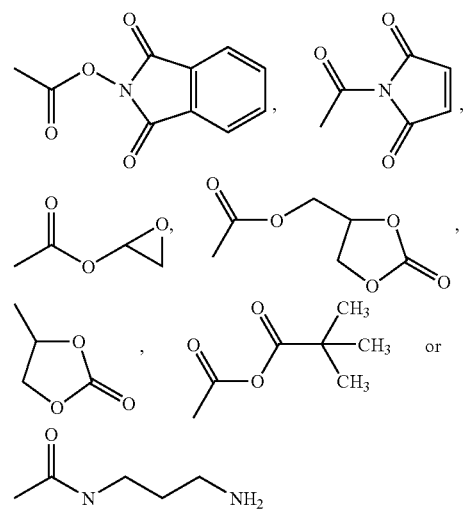

In another embodiment, X is a photoactivatable group. In these embodiment, the capture compound contains a selectivity function and is allowed to interact with a biomolecular mixture until, for example, equilibrium is reached. The X group is then activated by exposure to the appropriate wavelength of light, whereby the X group then reacts with a surface group of the biomolecule to capture it. In one embodiment, the photoactivatable group is an arylazide, such as a phenylazide. Following exposure to light, the resulting nitrene will react with, e.g., the side chain of tyrosine to capture the protein. In another embodiment, the photoactivatable group is a diazirine group, such as 3-trifluoromethyldiazirine.

In other embodiment, the reactivity functionality X, is linked to the central core Z, via a spacer S. A spacer can be any group that provides for spacing, typically without altering desired functional properties of the capture compounds and/or capture compound/biomolecule complexes. The reactive functionality X linked with the spacer can be extended from the central core Z, to reach to the active sites on the surface of the biomolecule, such as proteins. Those of skill in the art in the light of the disclosure herein, can readily select suitable spacers.

In certain embodiments, S is selected from $(CH_2)_r$, $(CH_2O)$, $(CH_2CH_2O)_r$, $(NH(CH_2)_rC(=O))_s$, $(O(CH)_rC(=O))_s$, $—((CH_2)_{r1}—C(O)NH—(CH_2)_{r2})_s—$ and $—(C(O)NH—(CH_2)_r)_s—$, where r, r1, r2 and s are each independently and integer from 1 to 10.

3. Selectivity Functions "Y"

Figure 21B:
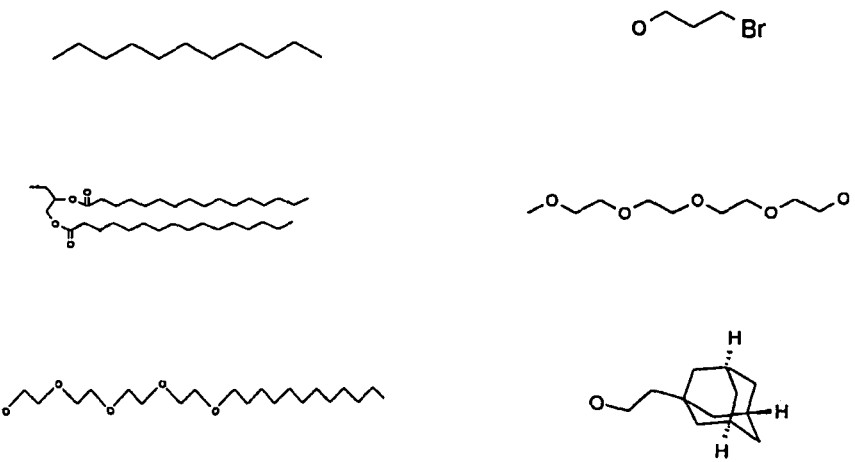
Figure 22:
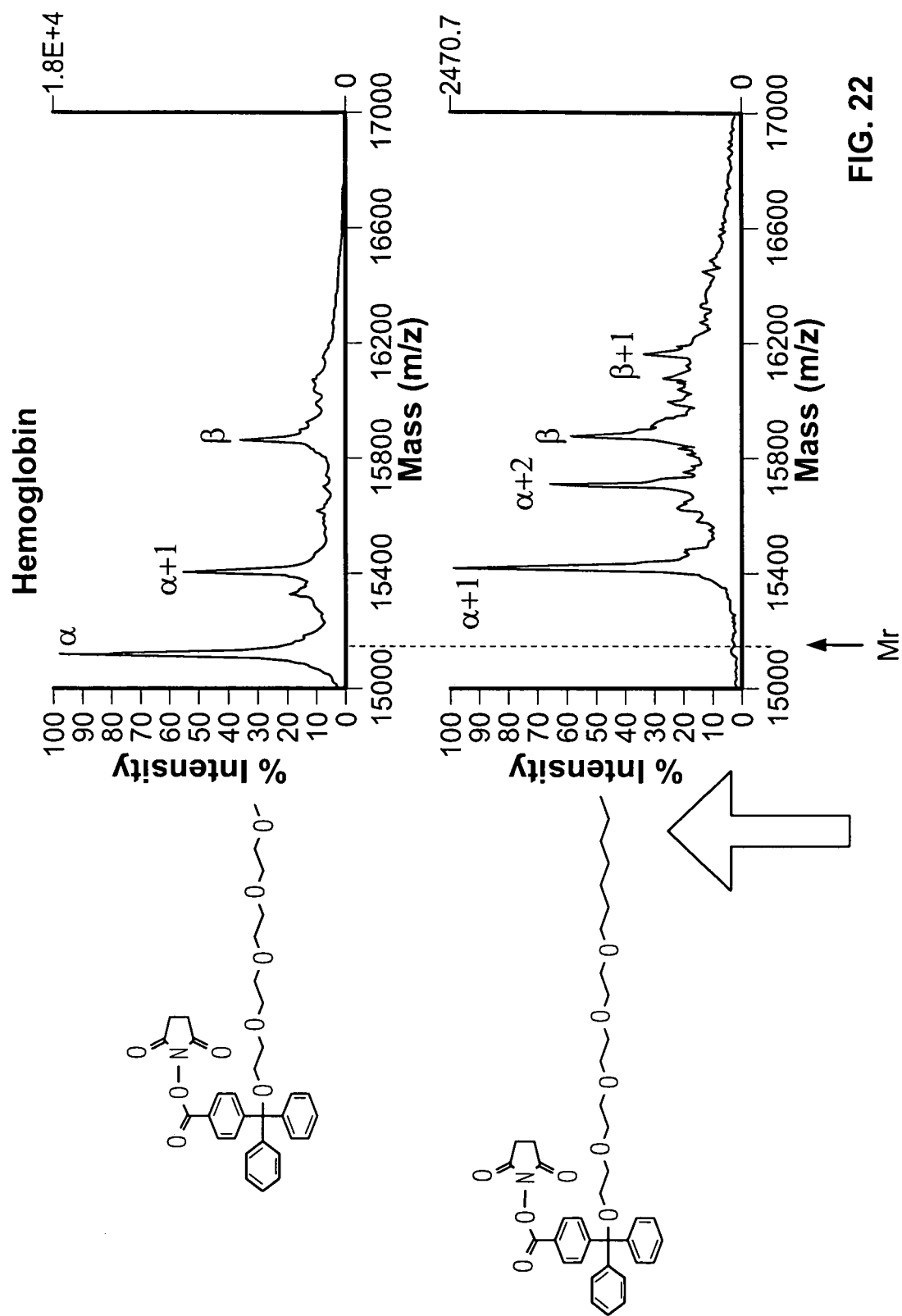
FIG. 22 shows mass spectrometric results of the reaction of hemoglobin with two of the capture compounds provided herein. As shown in the Figure, the more hydrophobic capture compound, i.e., the capture compound with a more hydrophobic selectivity function, reacts with α-hemoglobin stoichiometrically and with β-hemoglobin, while the less hydrophobic capture compound reacts incompletely with α-hemoglobin and does not react with β-hemoglobin.
Figures 1, 23A:
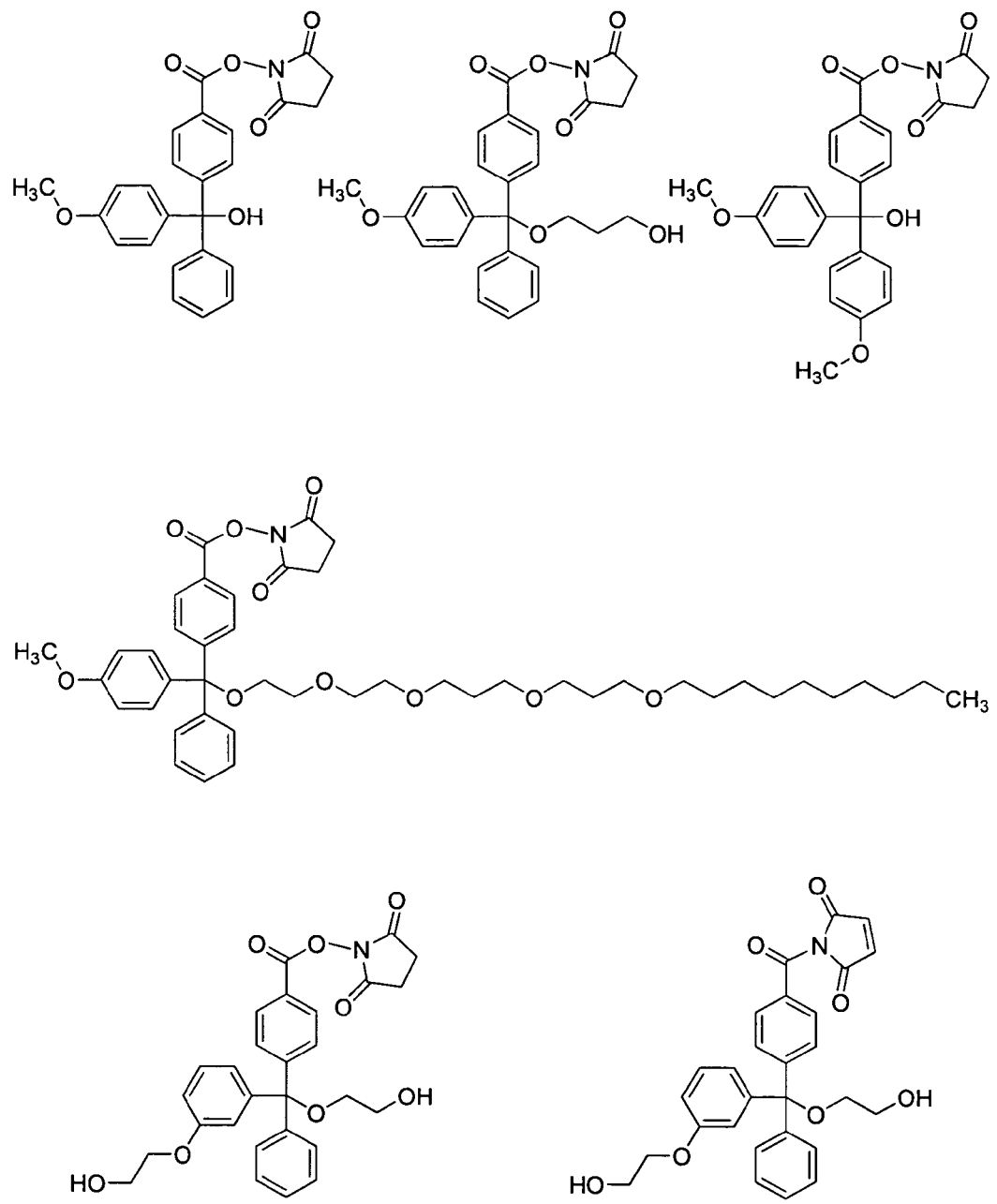
Figures 2, 23A:
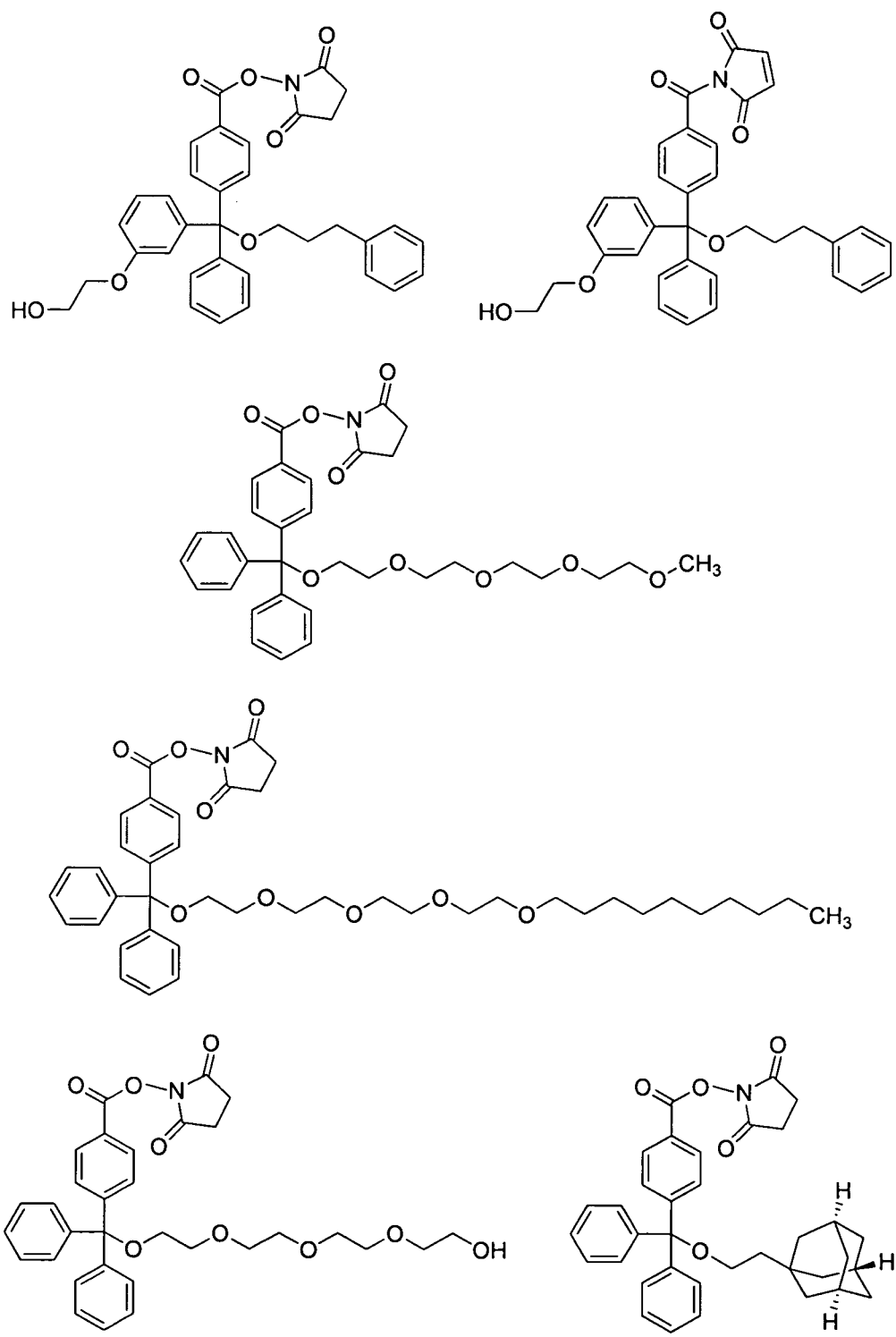
Figures 3, 23A:
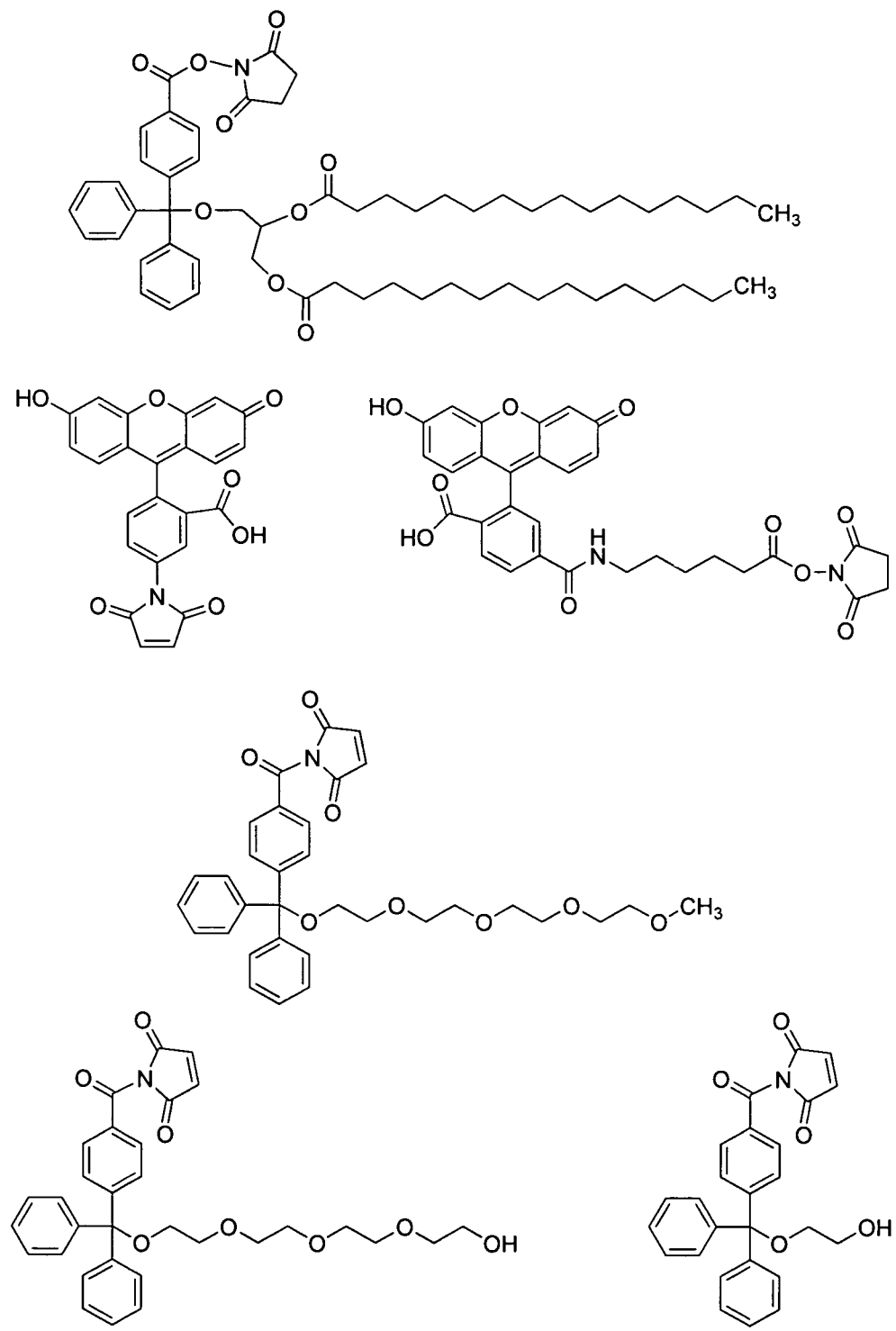
Figures 1, 23B:
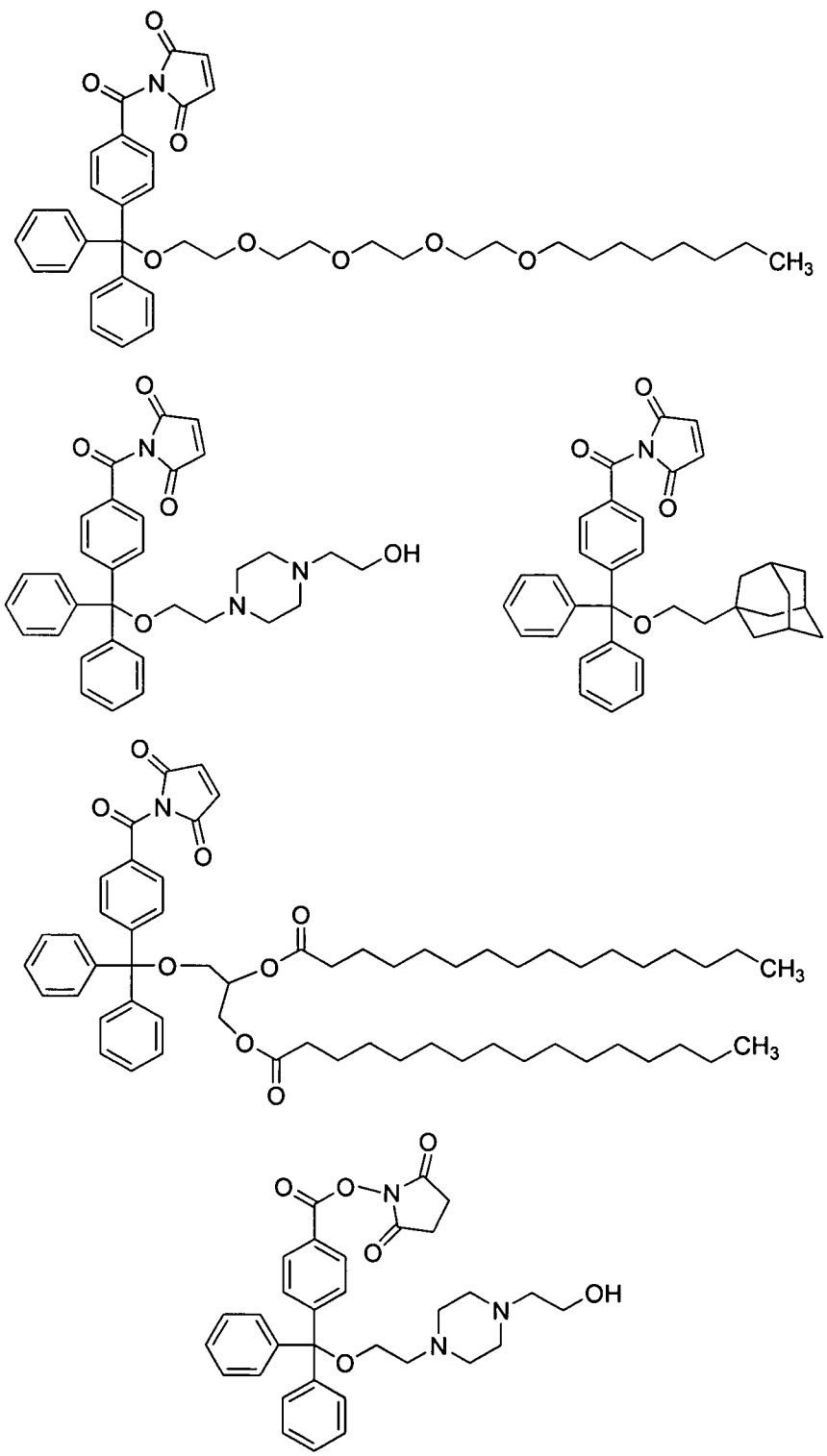
Figures 2, 23B:
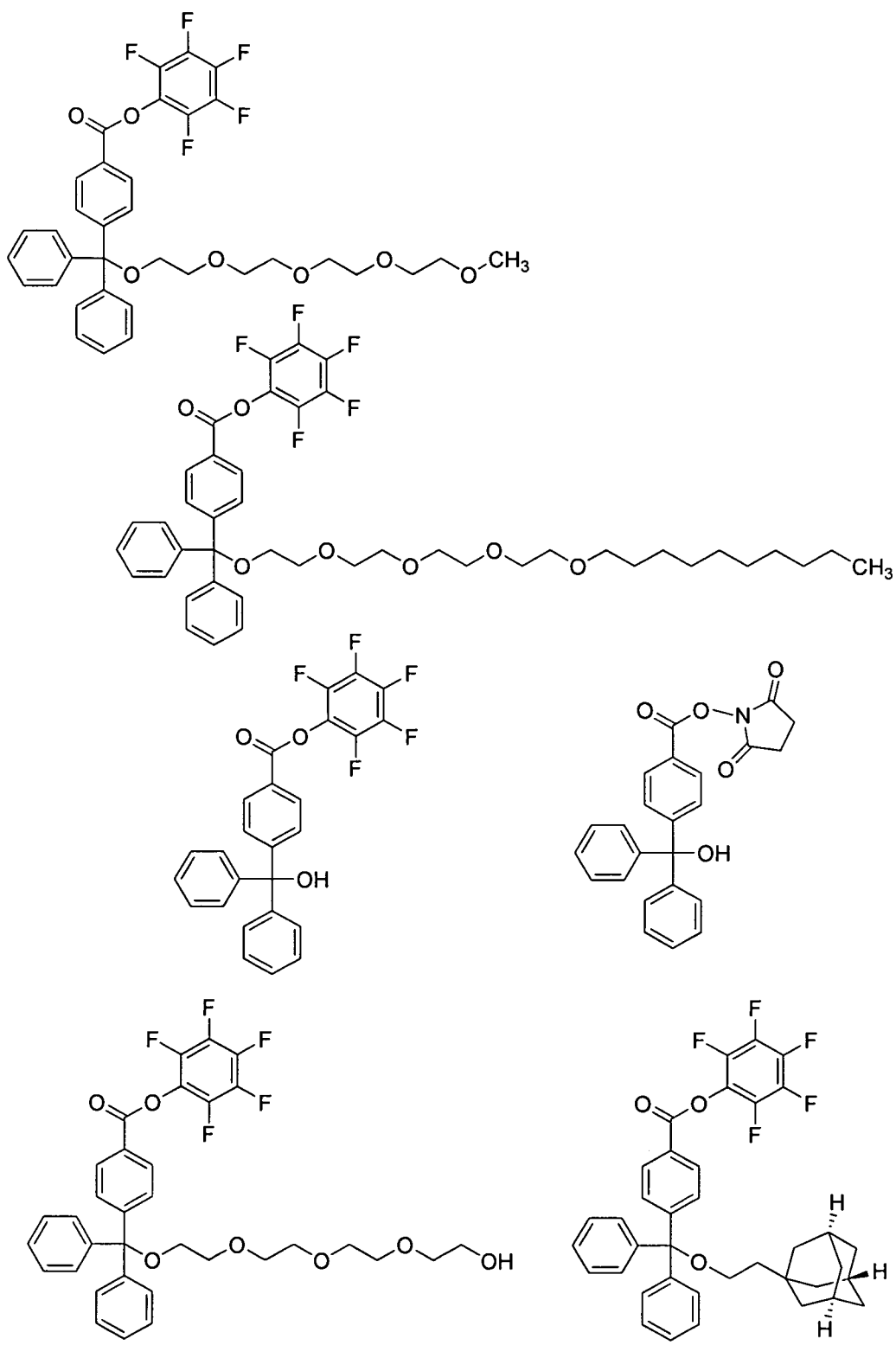
Figures 3, 23B:
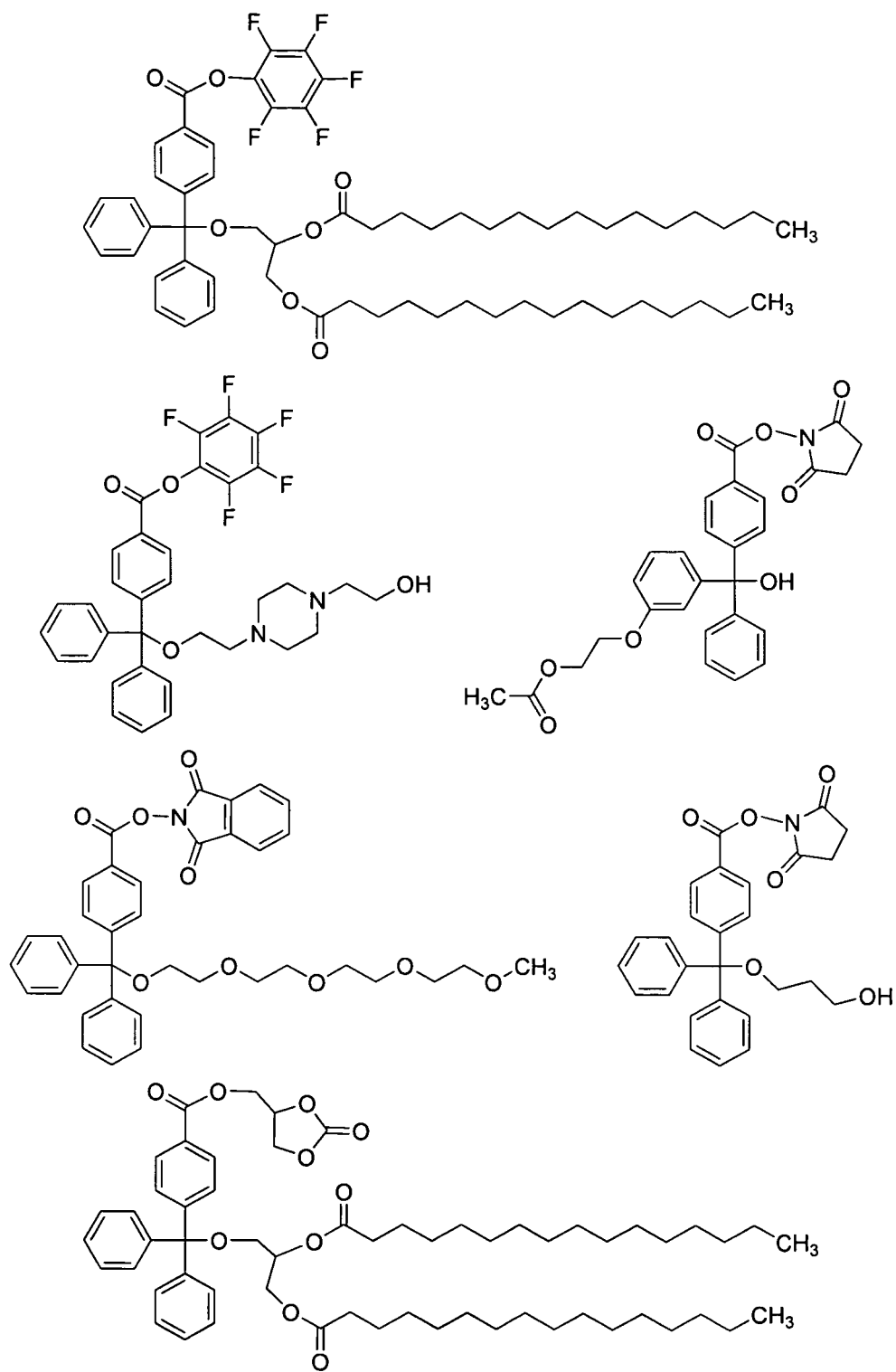
Figures 1, 23C:
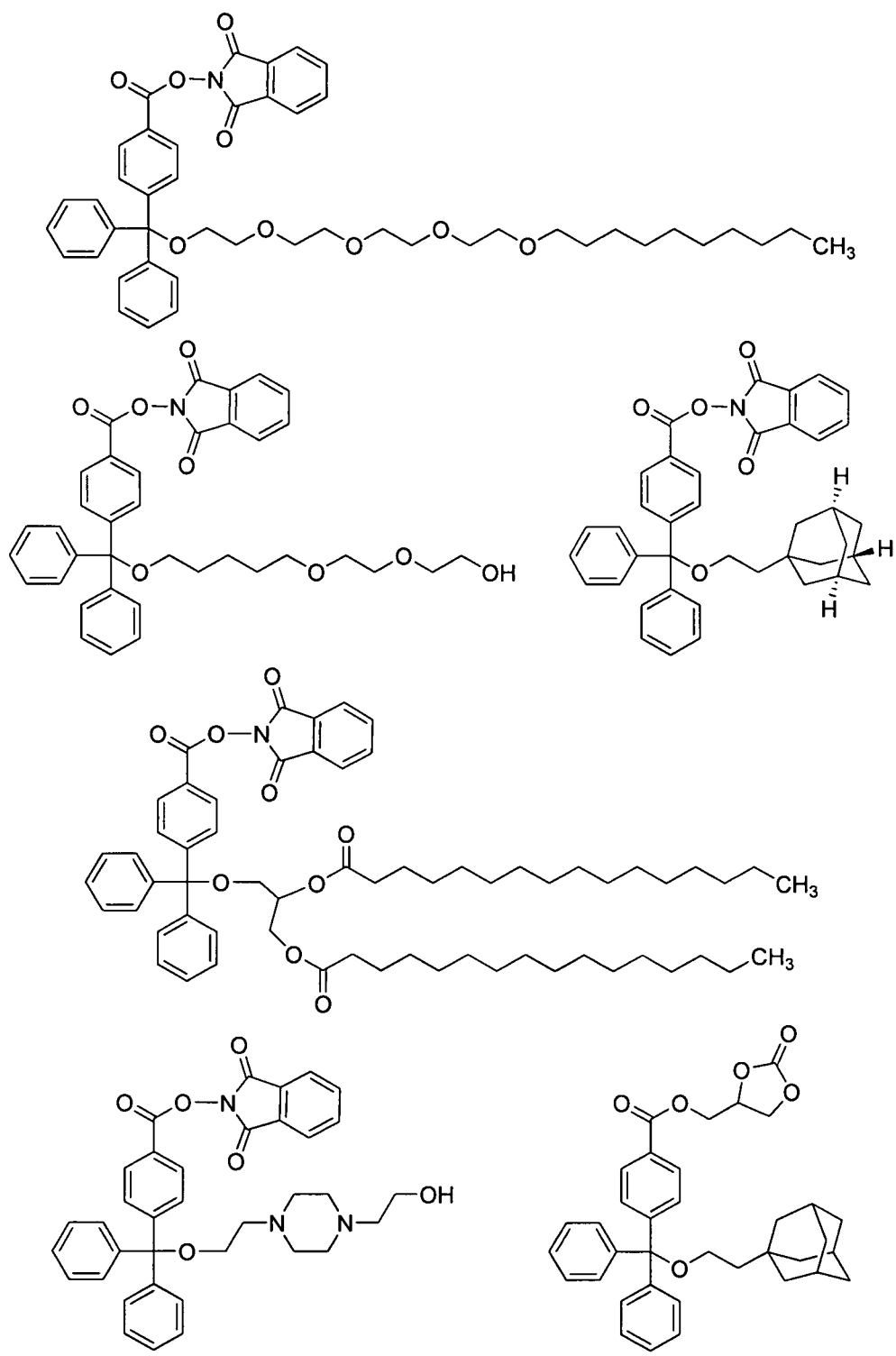
Figures 2, 23C:
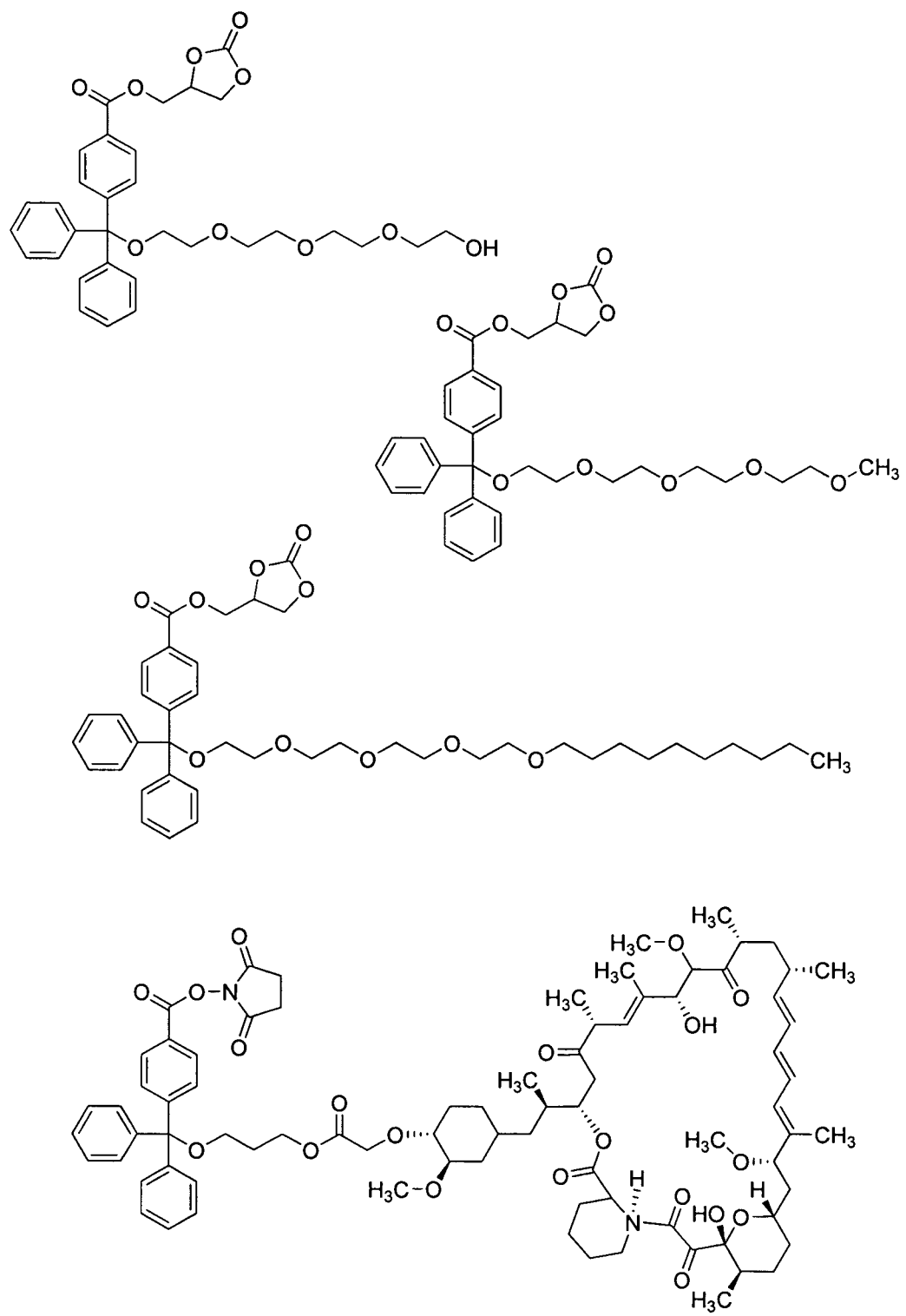
Figures 3, 23C:
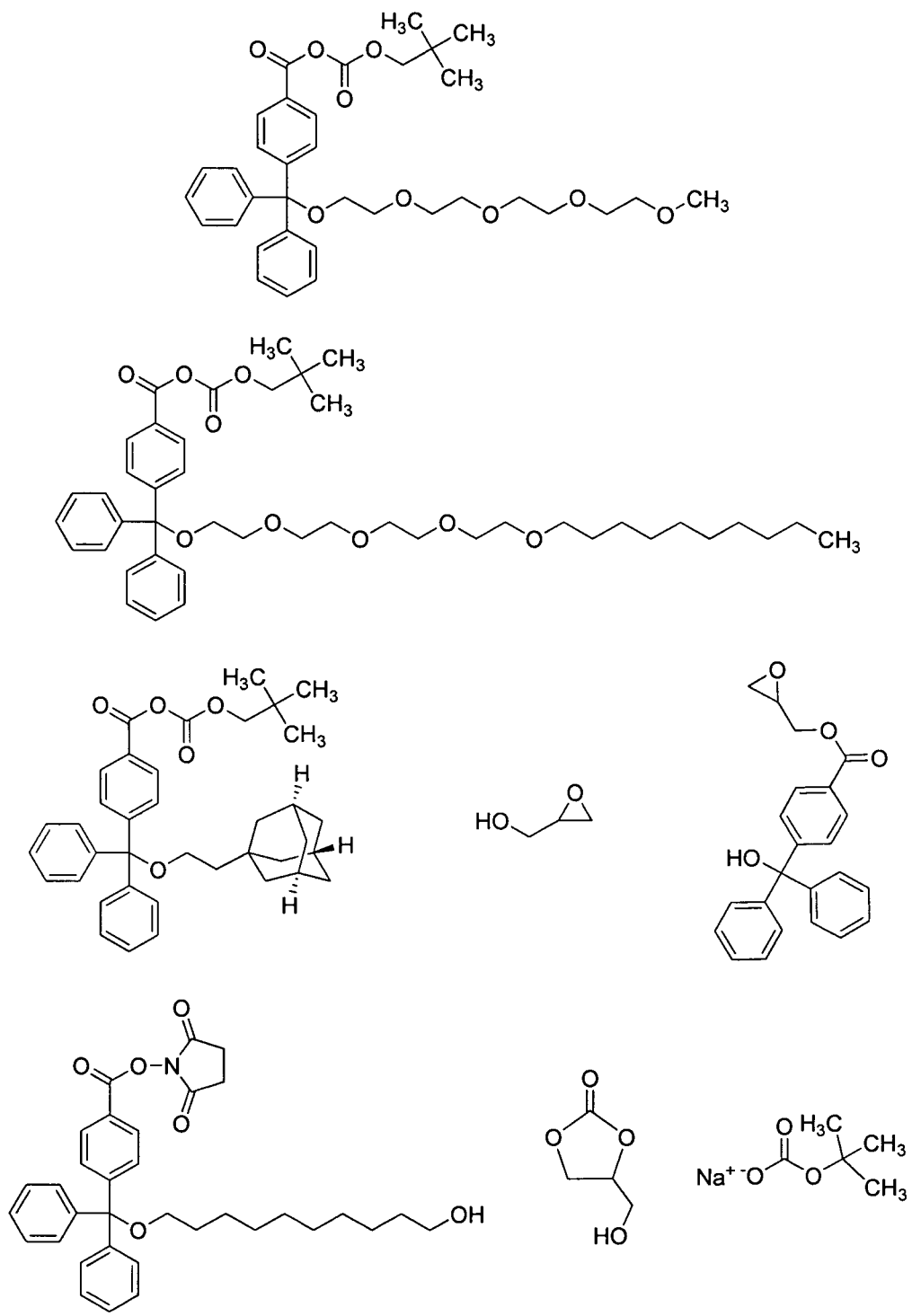
Figures 1, 23D:
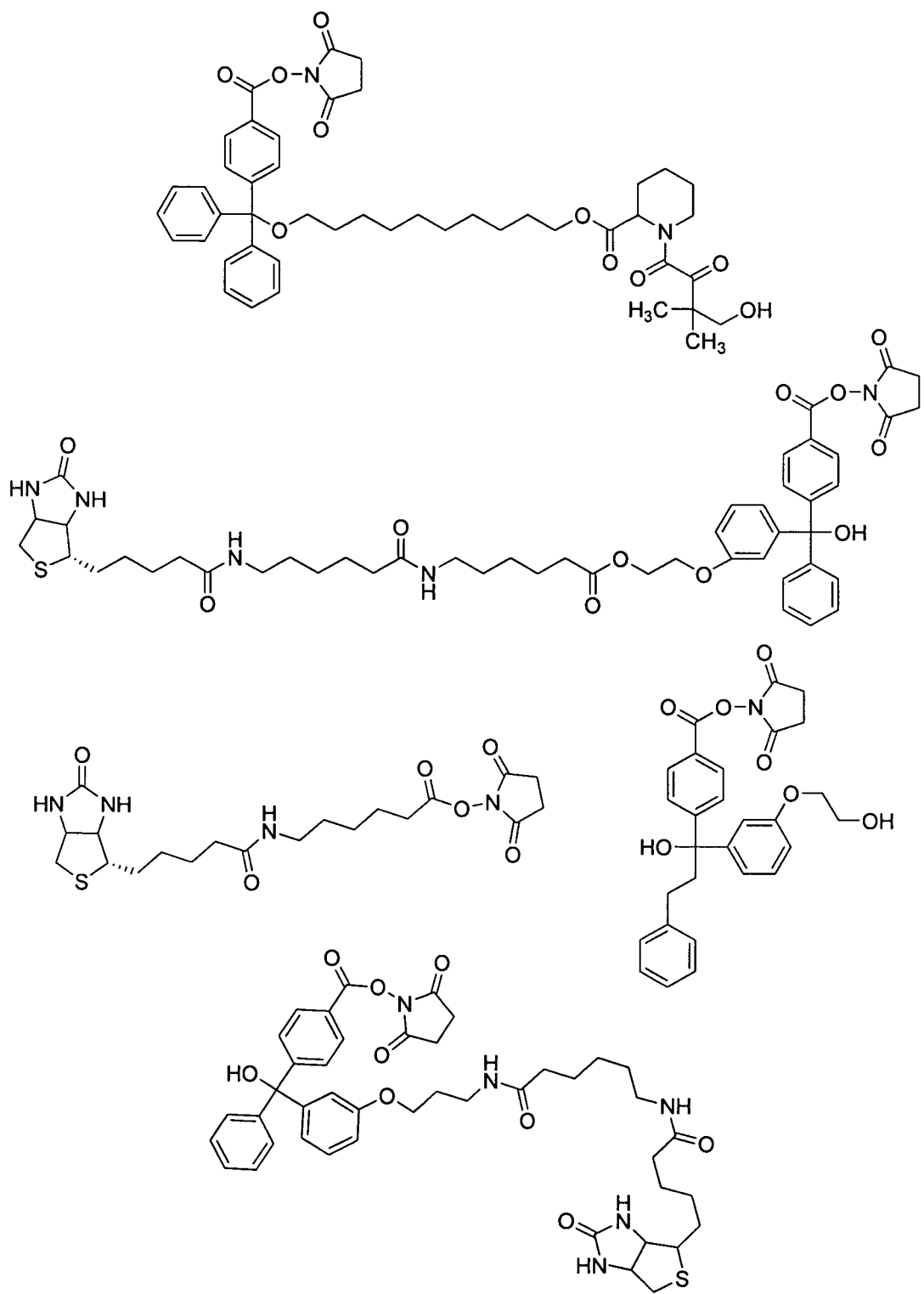
Figures 2, 23D:
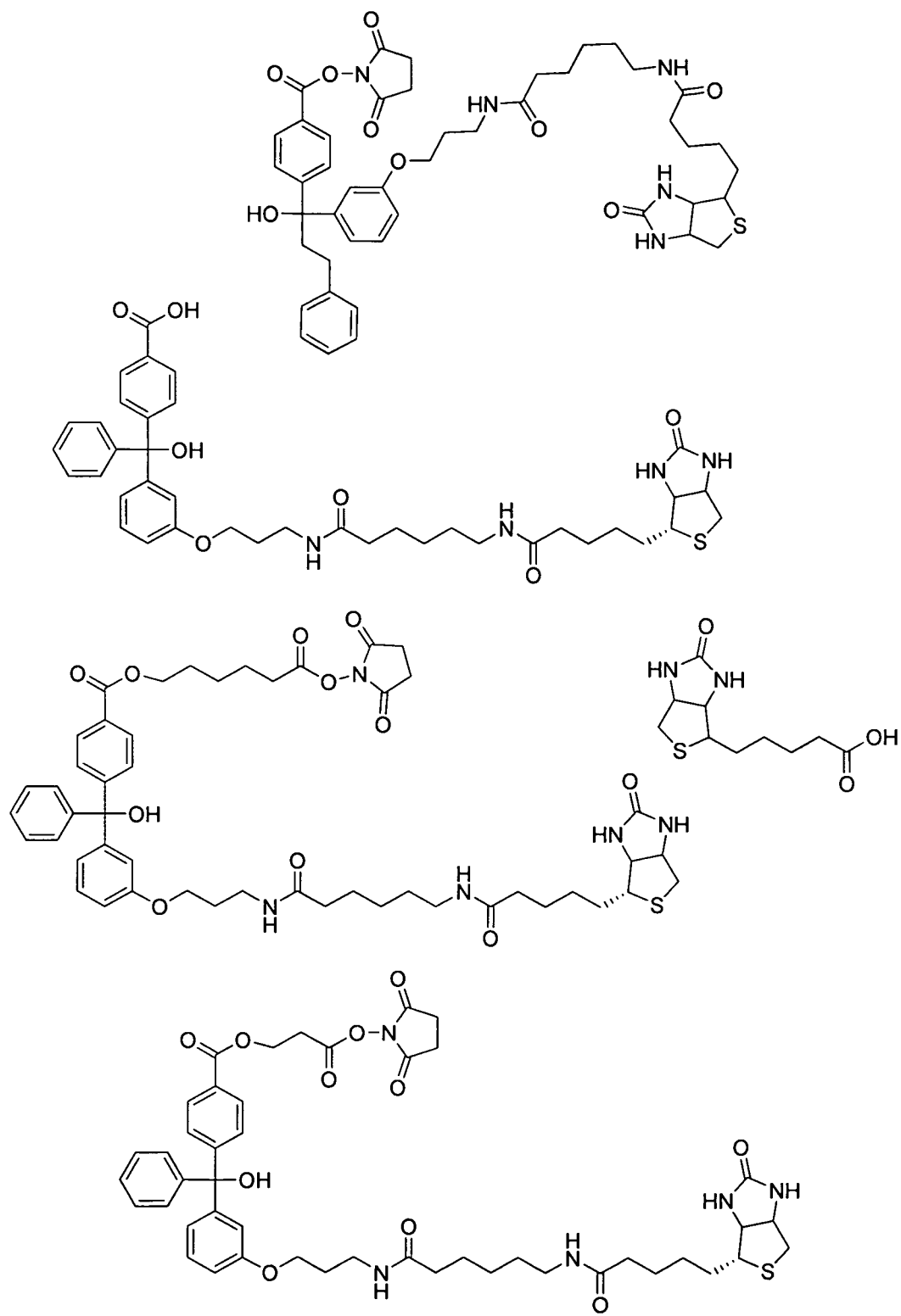
Figures 3, 23D:
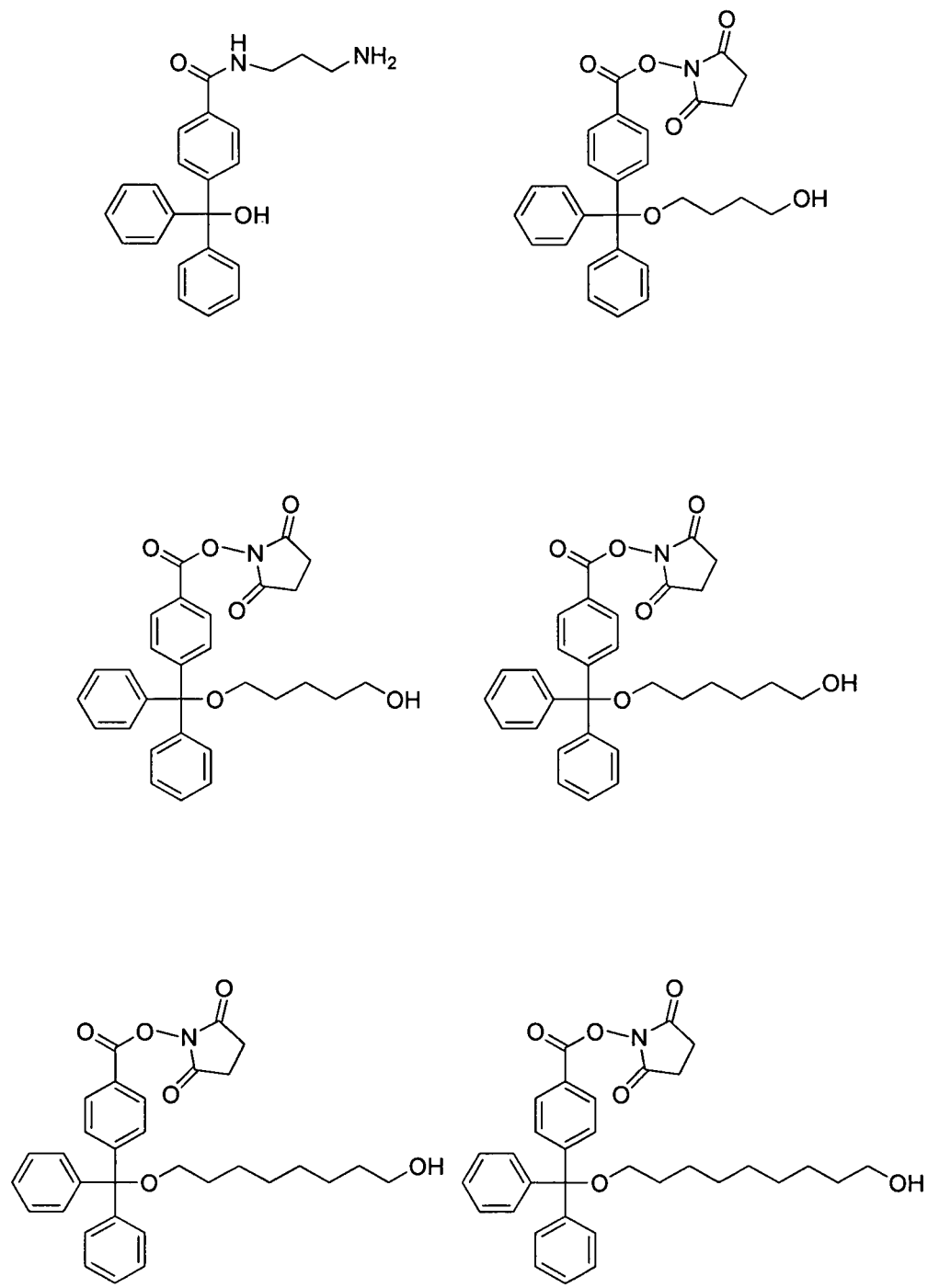
Figure 24:
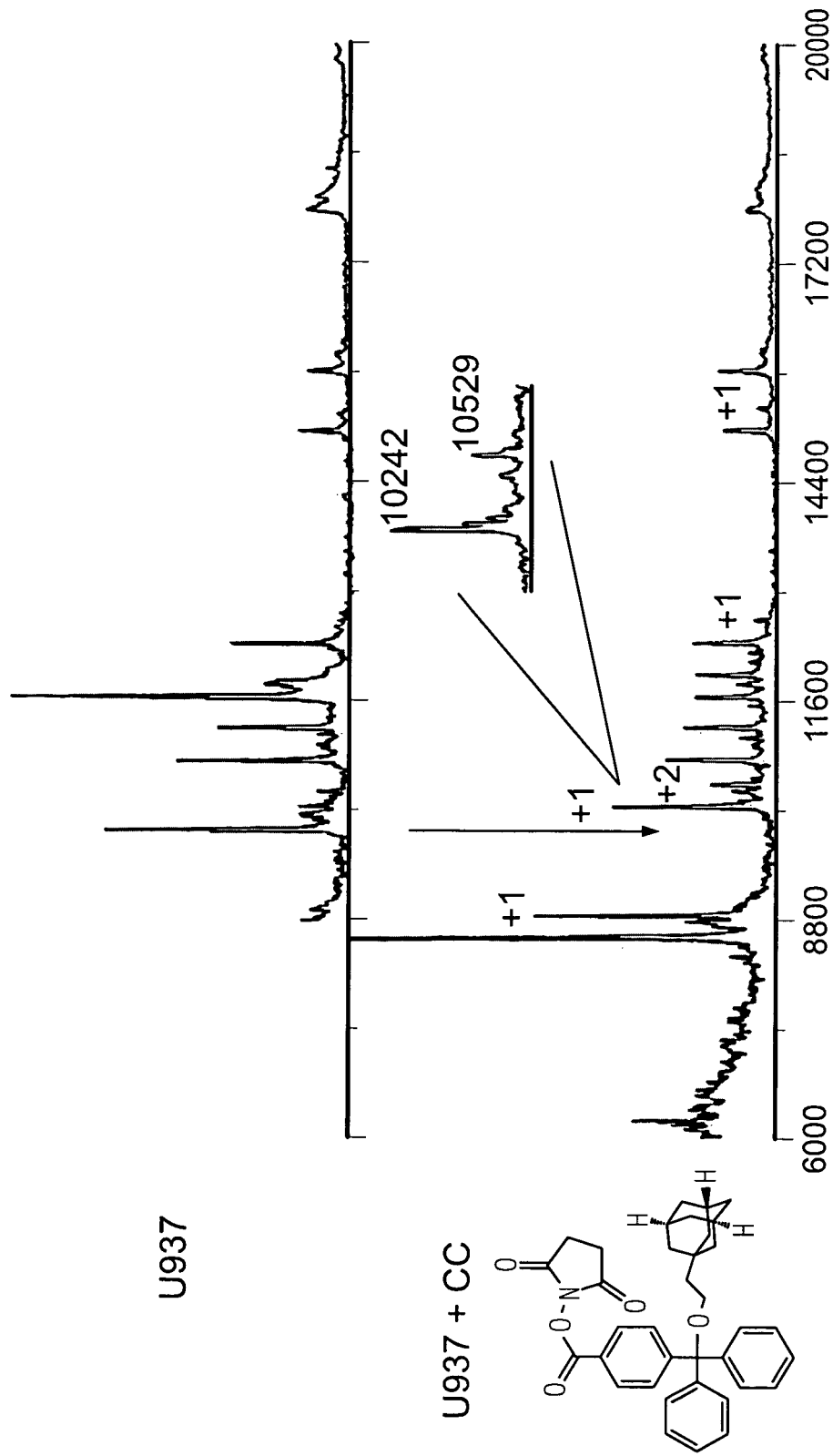
FIG. 24 shows mass spectrometric results of the reaction of a capture compound provided herein with a protein mixture obtained from U937 lymphoma blood cells. The Figure shows selective capture of the indicated protein by the capture compound.
Figure 26:
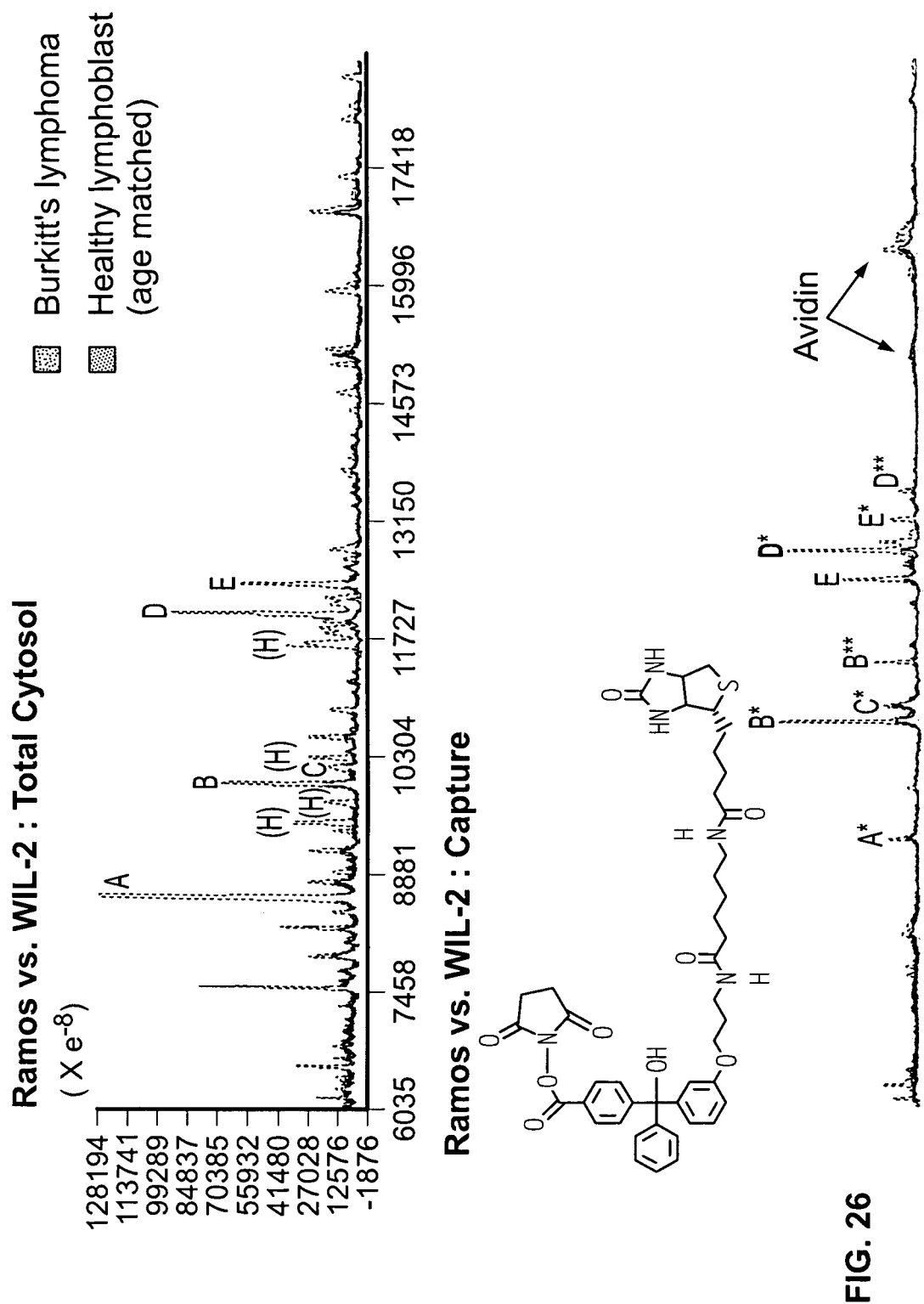
FIG. 26 shows mass spectrometric results of the reaction of a capture compound provided herein with total cytosol from Burkitt's lymphoma lymphoblast as compared to healthy age and gender matched lymphoblast. Proteins A, B, C and E are found in both samples. Protein D is expressed only in the Burkitt's lymphoma sample. Proteins labeled (H) are expressed only in the healthy sample. As shown in the Figure, reaction of the Burkitt's lymphoma sample with a capture compound provided herein results in complete capture of protein D allowing for analysis and identification of the protein.

The selectivity functions ("Y") serves to modulate the reactivity function by reducing the number of groups to which the reactivity functions bind, such as by steric hindrance and other interactions. It is a group that modifies the steric and/or electronic (e.g., mesomeric, inductive effects) properties as well as the resulting affinities of the capture compound. Selectivity functions include any functional groups that increase the selectivity of the reactivity group so that it binds to fewer different biomolecules than in the absence of the selectivity function or binds with greater affinity to biomolecules than in its absence. In the capture compounds provided herein, Y is allowed to be extensively varied depending on the goal to be achieved regarding steric hindrance and electronic factors as they relate to modulating the reactivity of the cleavable bond L, if present, and the reactive functionality X. For example, a reactivity function X can be selected to bind to amine groups on proteins; the selectivity function can be selected to ensure that only groups exposed on the surface can be accessed. The selectivity function is such that the compounds bind to or react with (via the reactivity function) fewer different biomolecules when it is part of the molecule than when it is absent and/or the compounds bind with greater specificity and higher affinity The selectivity function can be attached directly to a compound or can be attached via a linker, such as $CH_2CO_2$ or $CH_2$—O—$(CH_2)_n$—O, where n is an integer from 1 to 12, or 1 to 6, or 2 to 4. See, e.g., FIG. 17 and FIG. 21 and the discussion below for exemplary selectivity functions. In certain embodiments, the linker is chosen such that the selectivity function can reach the binding pocket of a target or non-target protein.

In certain embodiments, each Y is independently a group that modifies the affinity properties and/or steric and/or electronic (e.g., mesomeric, inductive effects) properties of the resulting capture compound. For example, Y, in certain embodiments, is selected from ATP analogs and inhibitors; peptides and peptide analogs; polyethyleneglycol (PEG); activated esters of amino acids, isolated or within a peptide; cytochrome C; and hydrophilic trityl groups.

In another embodiment, Y is a small molecule moiety, a natural product, a protein agonist or antagonist, a peptide or an antibody (see, e.g., FIG. 17). In another embodiment, Y is a hydrophilic compound or protein (e.g., PEG or trityl ether), a hydrophobic compound or protein (e.g., polar aromatics, lipids, glycolipids, phosphotriesters, oligosaccharides), a positive or negatively charged group, a small molecule, a pharmaceutical compound or a biomolecule that creates defined secondary or tertiary structures.

In certain embodiments, Y is an enzyme inhibitor, an enzyme agonist or antagonist, a pharmaceutical drug or drug fragment, a prodrug or drug metabolite that modifies the selectivity of the capture compounds or collections thereof, to interact with the biomolecules or mixtures thereof, including, but not limited to specific receptors, to form covalent or non-covalent bonds with high affinity. In one embodiment, the capture compounds/collections thereof have a selectivity function, which is a cox-2 inhibitor, and a mixture of biomolecules contains cox receptors among other biomolecules.

In certain embodiments the selectivity function is selected from pharmaceutical drugs or drug fragments set forth below, where attachment of exemplary pharmaceutical drugs to a central core is shown below. In other embodiments, the selectivity function is a drug, drug fragment, drug metabolite, or a drug synthetic intermediate.

The pharmaceutical drugs or drug fragments can be attached to the central core Z, in different orientations via different points of attachment, thereby modulating the selectivity of the capture compound. The attachment of a drug/drug fragment to the central core can be carried out by methods known to a person with skill in the art. Attachment of some exemplary pharmaceutical drugs at various points, to the central core Z is set forth below.

In another embodiment, the capture compounds provided herein include those where the selectivity function is a drug, drug fragment, drug metabolite or a prodrug. In these embodiments, the capture compounds also contain a reactivity function, as defined elsewhere herein. In further embodiments, the capture compounds also contain a sorting function, as defined elsewhere herein.

In certain embodiments, the capture compounds that contain drug, drug fragment, drug metabolite or prodrug selectivity functions contain an amino acid core. In one embodiment, the amino acid core may be an amino acid that does not have a functionality on the side chain for attachment of a third function. Such amino acid cores include, but are not limited to, glycine, alanine, phenylalanine and leucine. In these embodiments, the capture compound contains a reactivity function and a selectivity function, which are attached to the amino and carboxy groups of the amino acid.

In another embodiment, the amino acid core may be an amino acid that possesses a functionality on the side chain for attachment of a third function. Such amino acid cores include, but are not limited to, serine, threonine, lysine, tyrosine and cysteine. In these embodiments, the capture compound contains a reactivity function, a sorting function and a selectivity function, which are attached to the amino, carboxy and side chain functional groups of the amino acid.

In one embodiment, the core is tyrosine and the capture compounds have the formula:

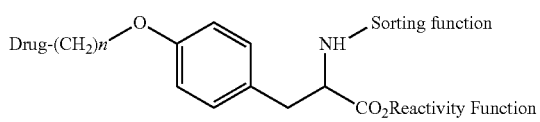

where "drug" refers to a drug, drug fragment, drug metabolite or prodrug.

In one embodiment, the drug is LIPITOR® (atorvastatin calcium) and the capture compounds have the formulae:

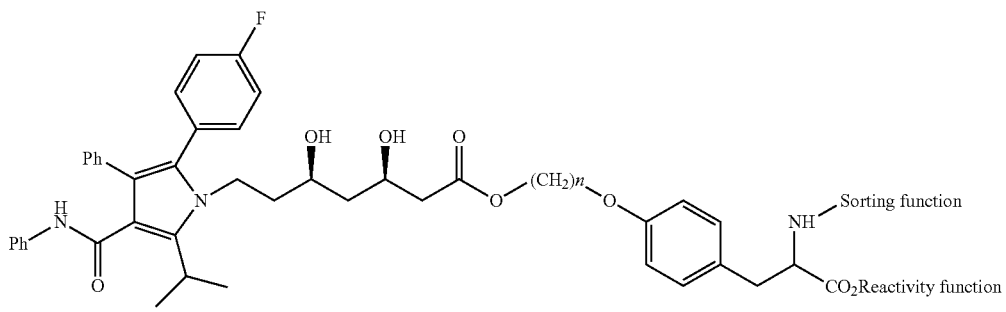

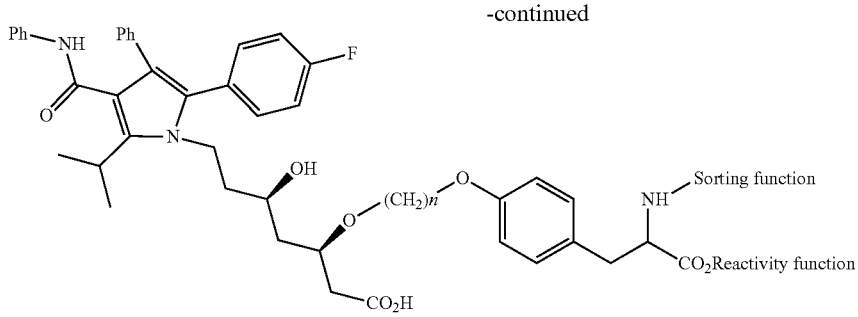
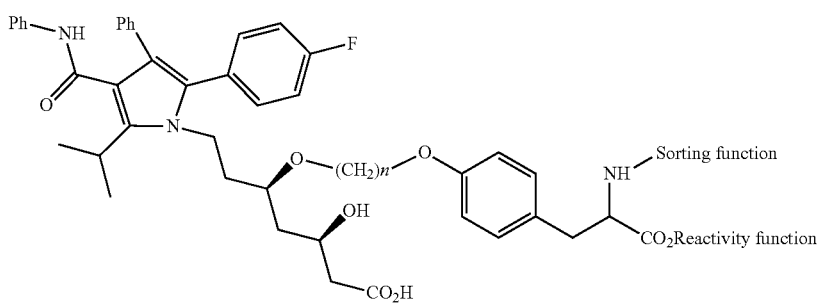
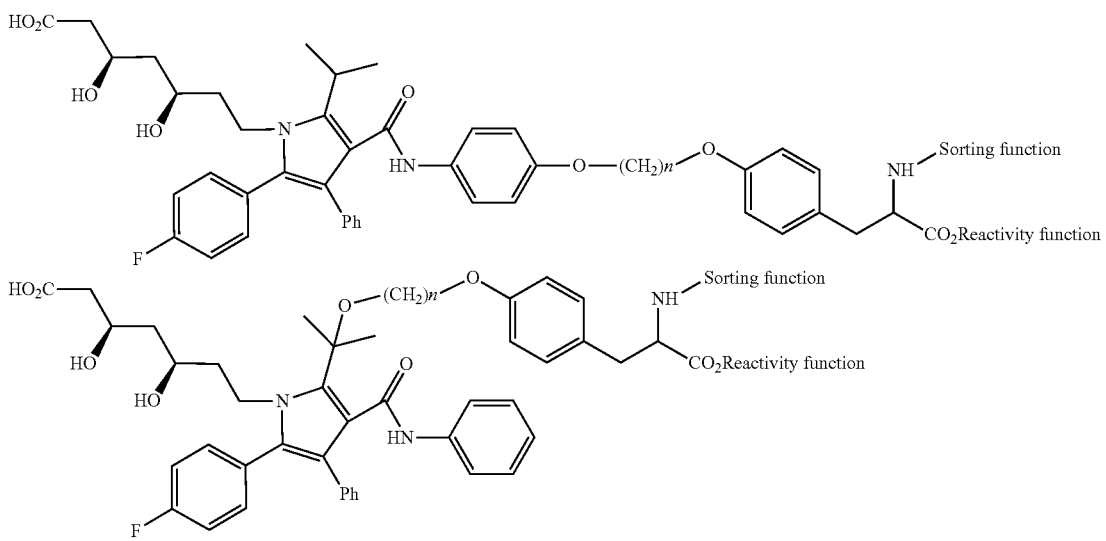
In other embodiments, the drug is CELEBREX® (celecoxib) and the capture compounds have the formulae:
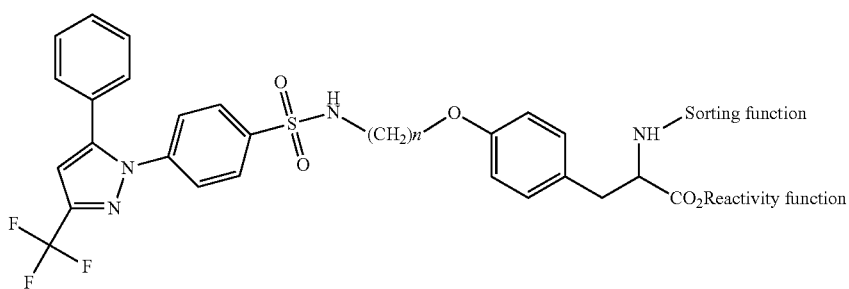

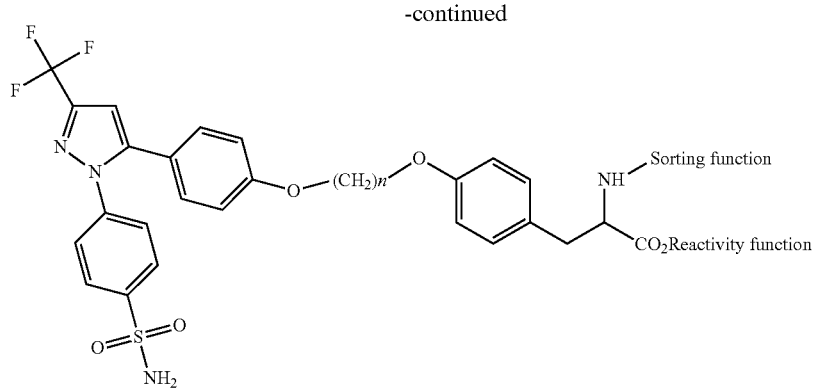
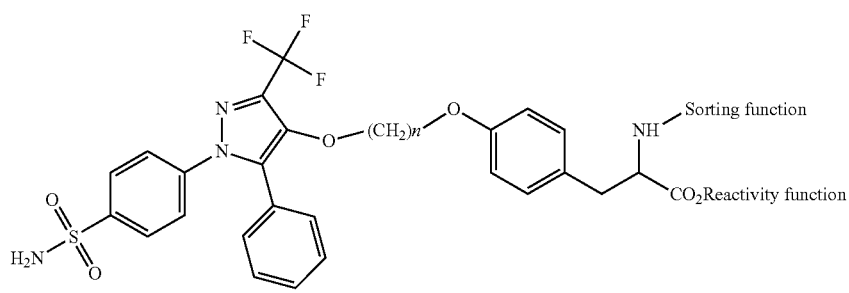
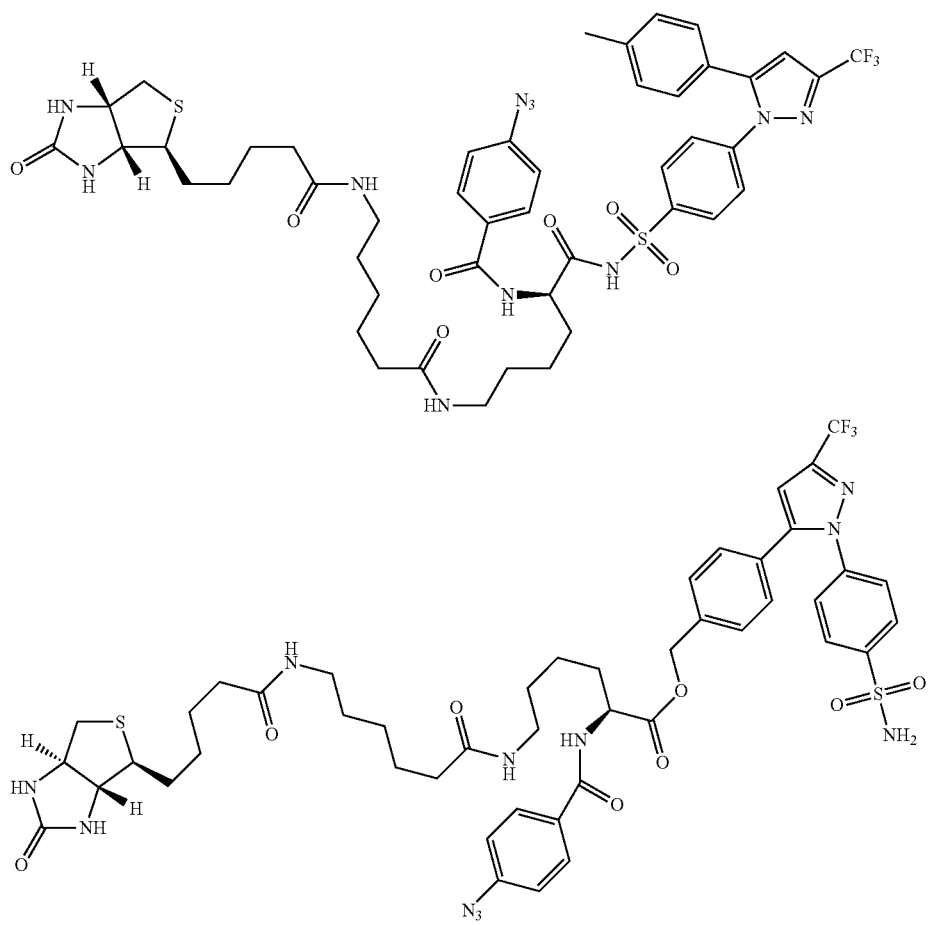

-continued
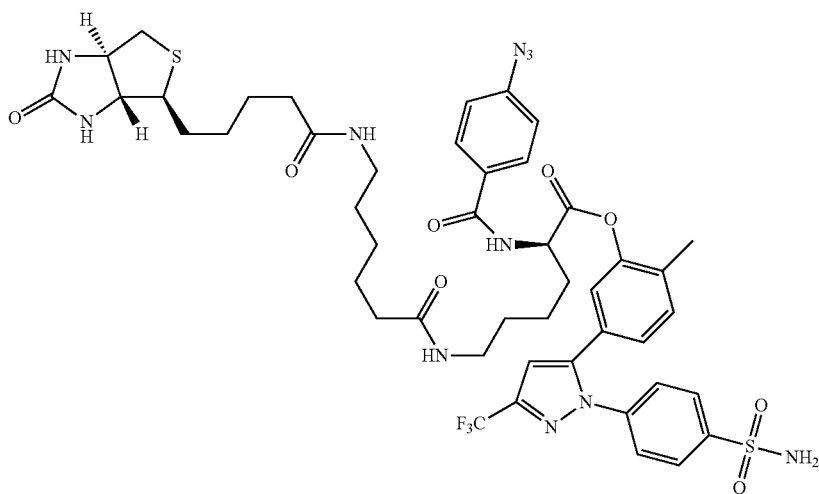
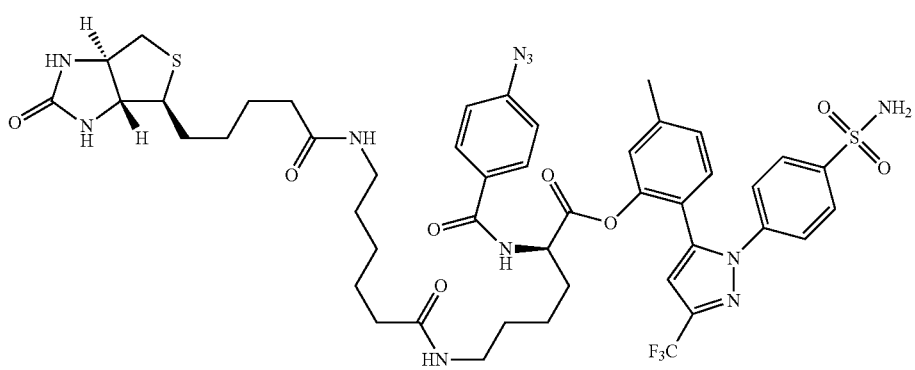
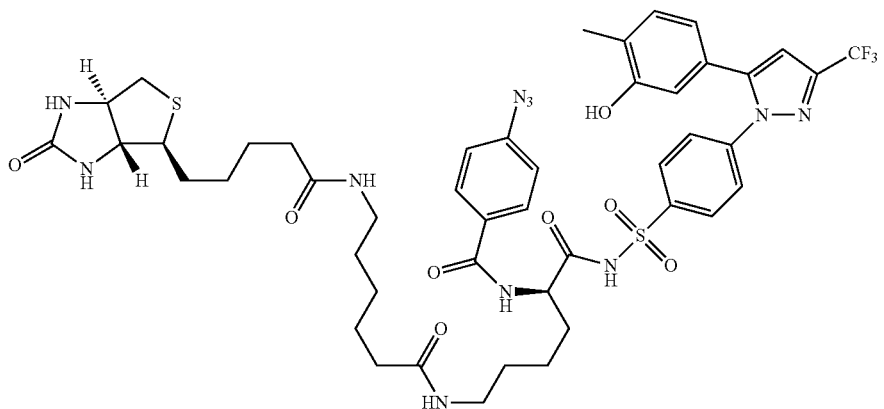

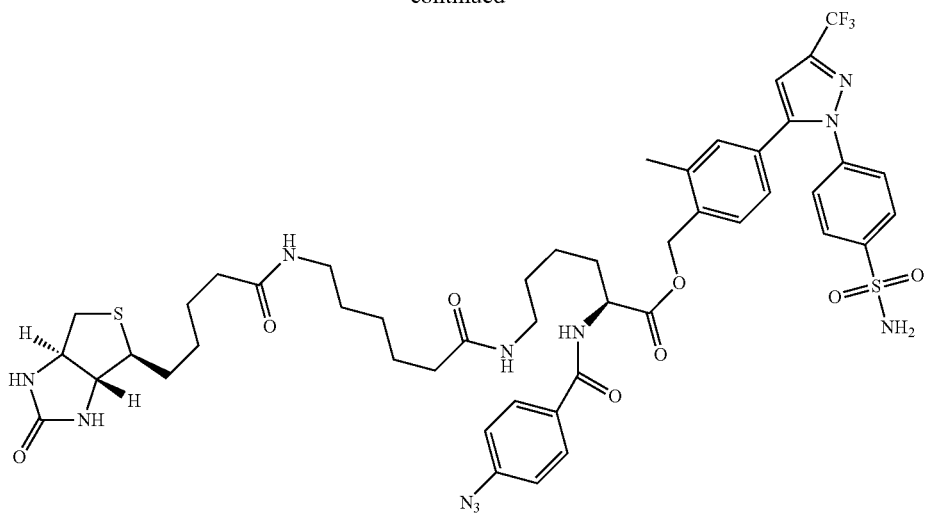
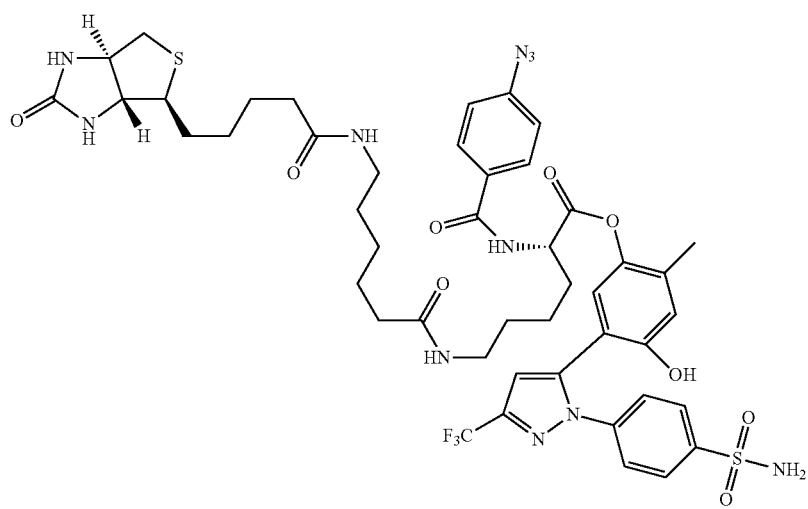
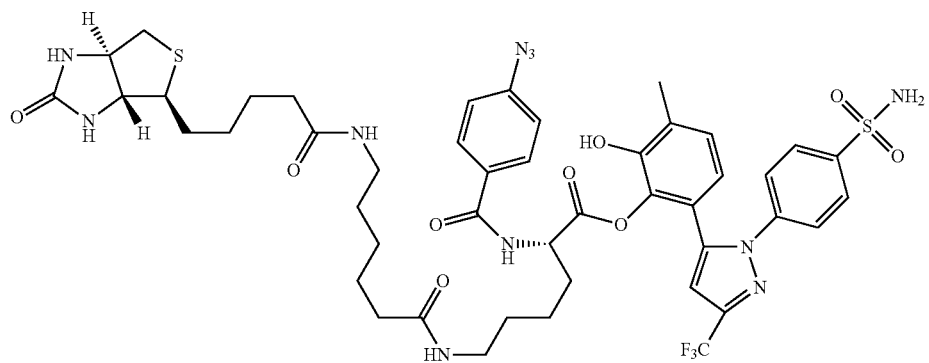

In another embodiment, the drug is VIOXX® (rofecoxib) and the capture compounds have the formulae:
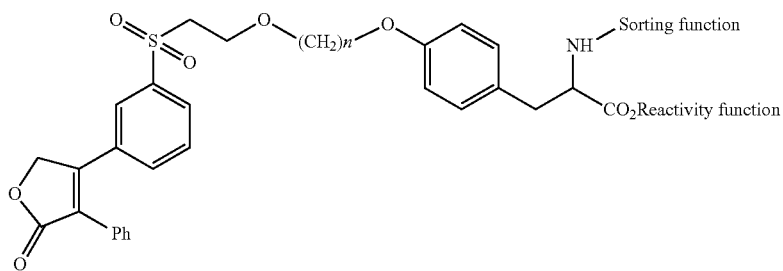
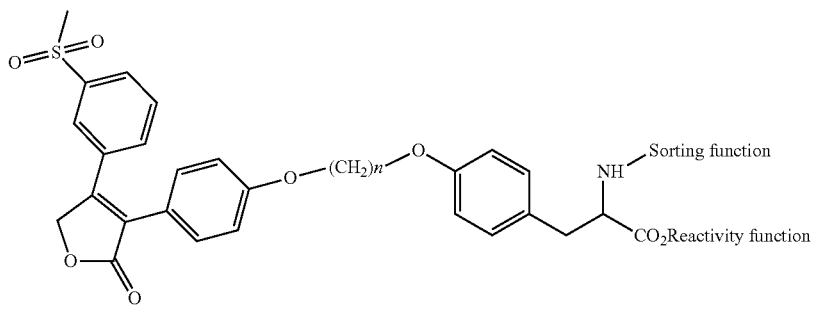
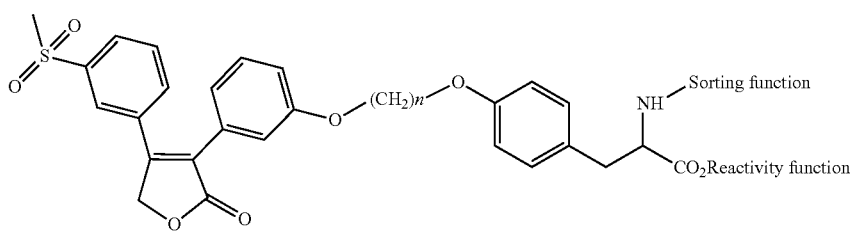
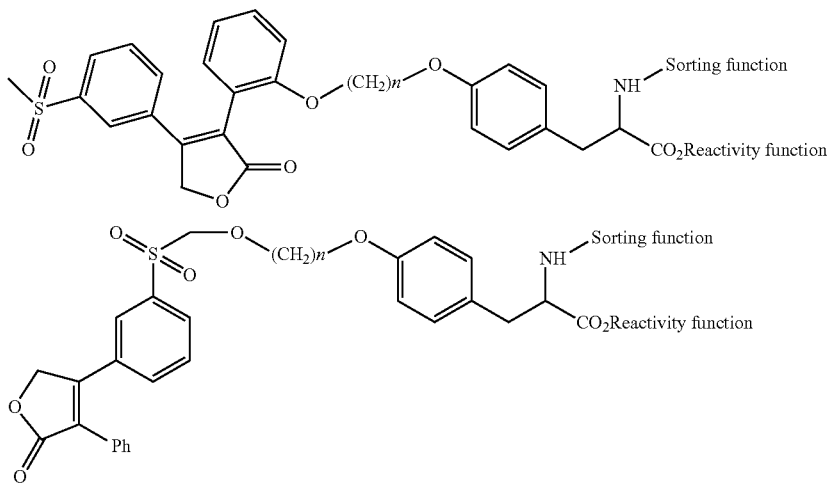

In another embodiment, the drug is BAYCOL® (cerivastatin sodium) and the capture compounds have the formula:
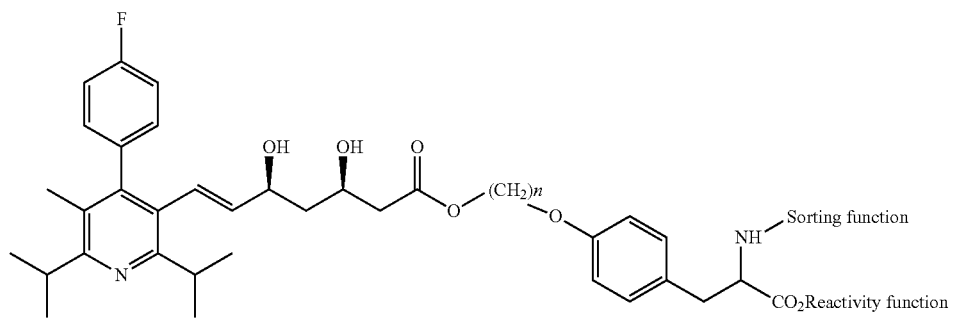
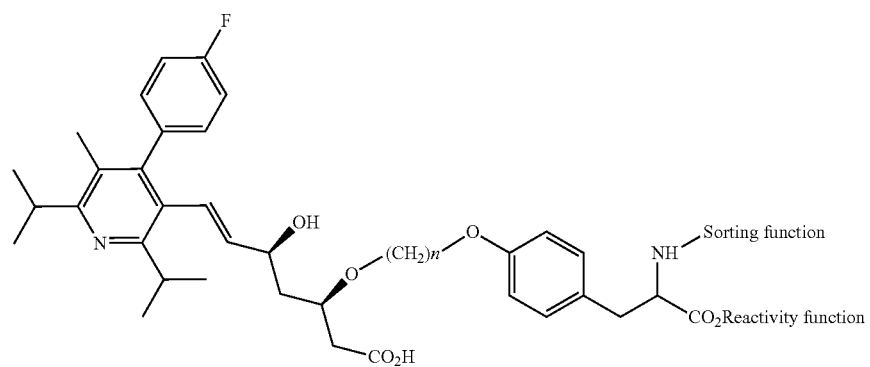
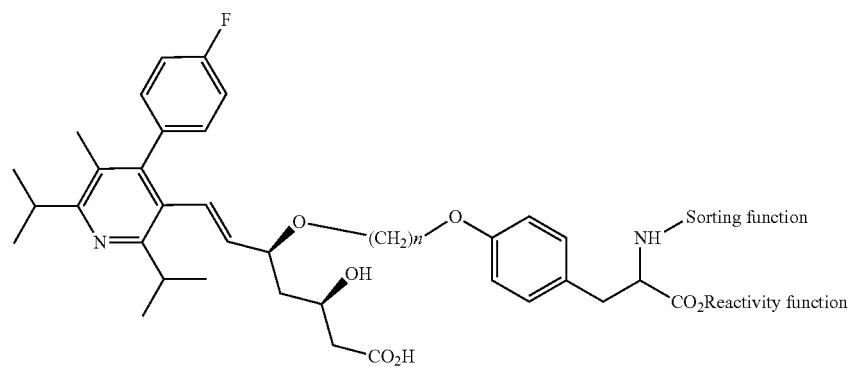
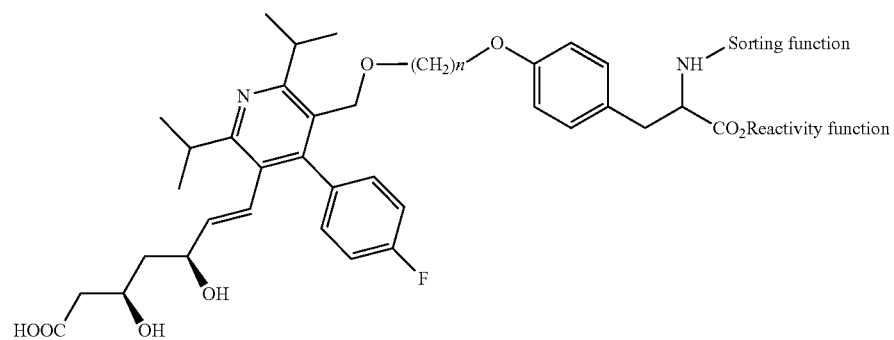

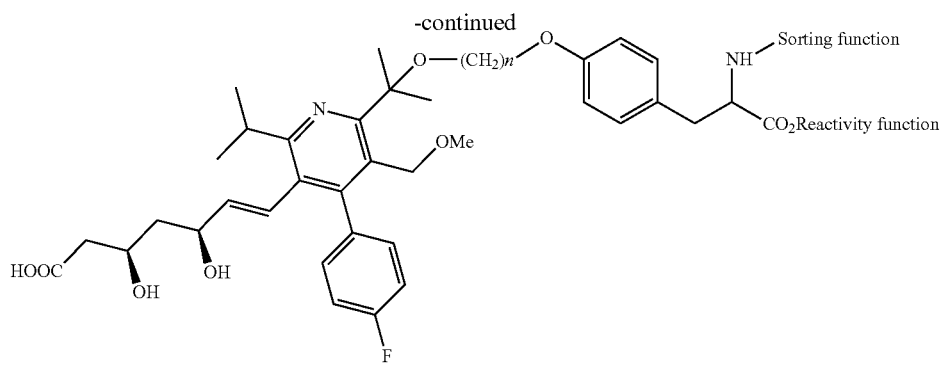
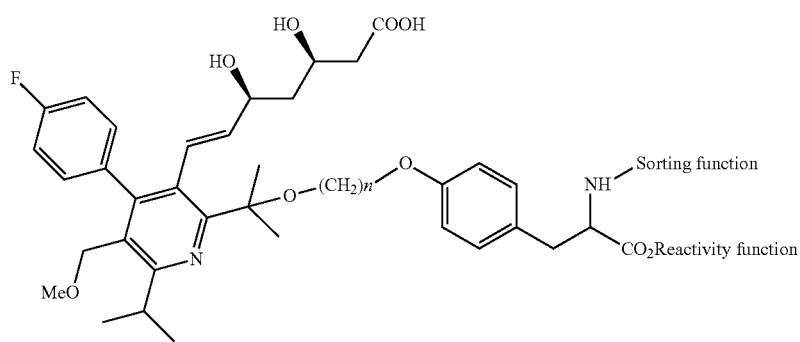
In another embodiment, the drug is methotrexate and the capture compounds have the formulae:
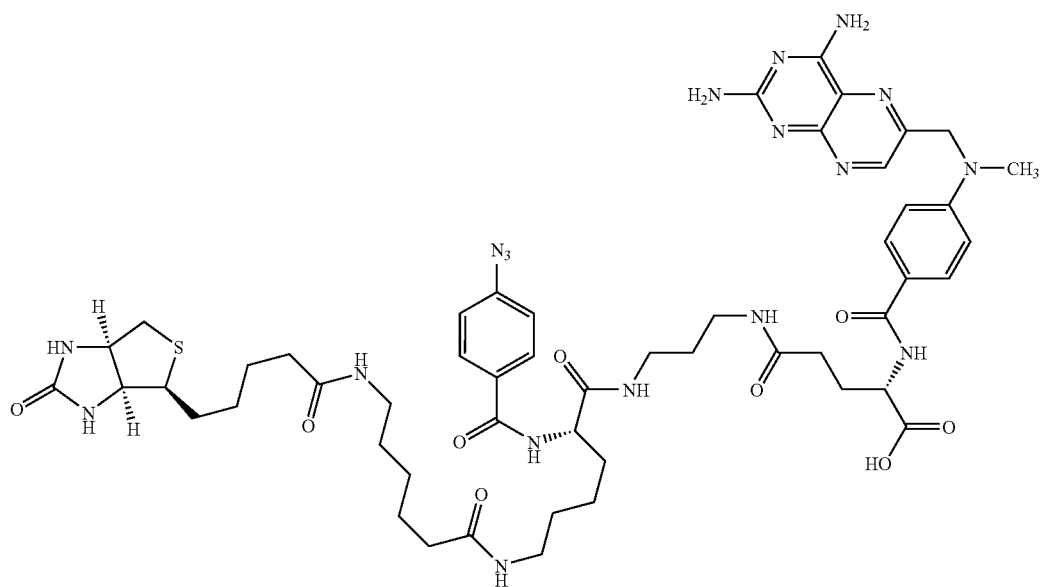

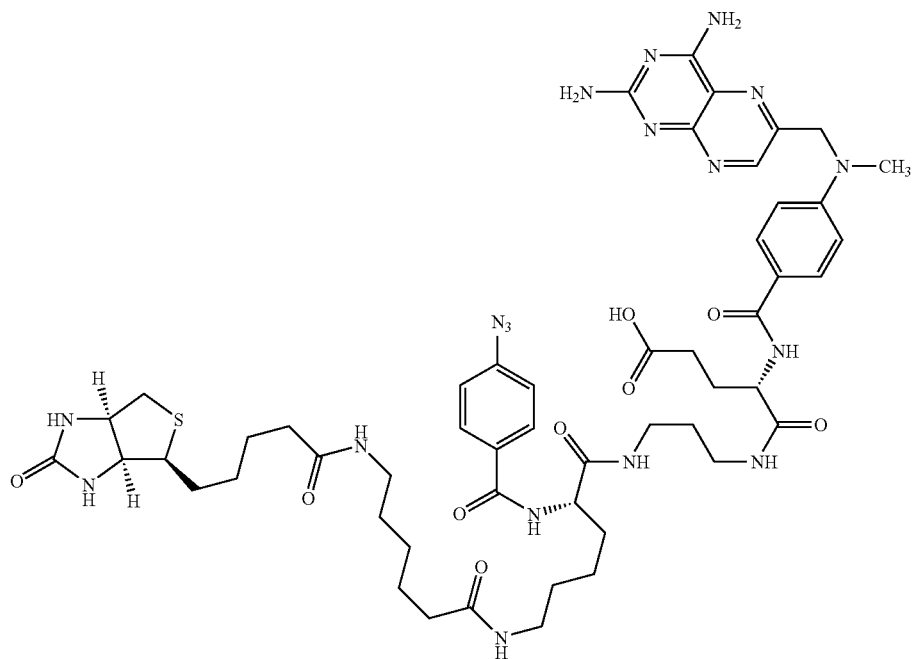
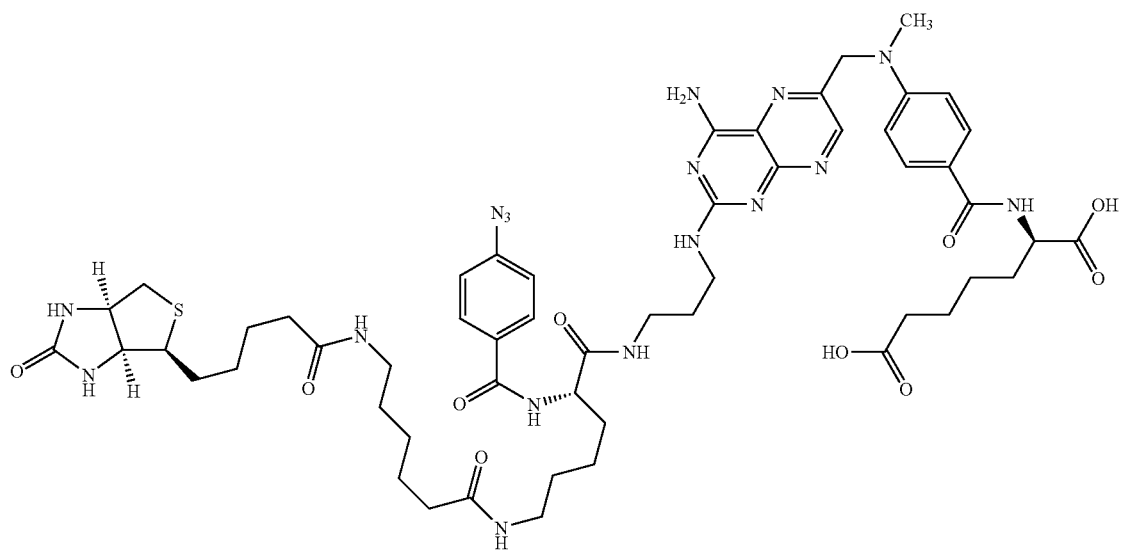

-continued

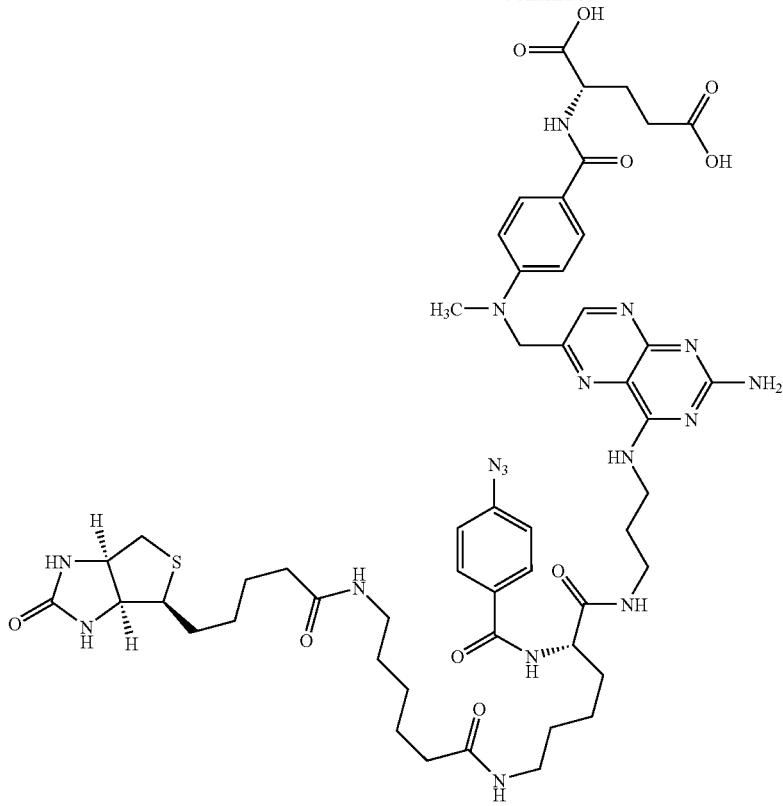 [SMILES: CN(Cc1cnc2nc(N)nc(NCCCNC(=O)[C@H](CCCCNC(=O)CCCCCNC(=O)CCCC[C@@H]3SC[C@@H]4NC(=O)N[C@@H]43)NC(=O)c3ccc(N=[N+]=[N-])cc3)c2n1)c1ccc(C(=O)N[C@@H](CCC(=O)O)C(=O)O)cc1]

In other embodiments, Y is a group that is a component of a luminescent, including fluorescent, phosphorescent, chemiluminescent and bioluminescent system, or is a group that can be detected in a colorimetric assay; in certain embodiments, Y is a monovalent group selected from straight or branched chain alkyl, straight or branched chain alkenyl, straight or branched chain alkynyl, cycloalkyl, cycloalkenyl, cycloalkynyl, heterocyclyl, straight or branched chain heterocyclylalkyl, straight or branched chain heterocyclylalkenyl, straight or branched chain heterocyclylalkynyl, aryl, straight or branched chain arylalkyl, straight or branched chain arylalkenyl, straight or branched chain arylalkynyl, heteroaryl, straight or branched chain heteroarylalkyl, straight or branched chain heteroarylalkenyl, straight or branched chain heteroarylalkynyl, halo, straight or branched chain haloalkyl, pseudohalo, azido, cyano, nitro, $OR^{60}$, $NR^{60}R^{61}$, $COOR^{60}$, $C(O)R^{60}$, $C(O)NR^{60}R^{61}$, $S(O)_qR^{60}$, $S(O)_qOR^{60}$, $S(O)_q NR^{60}R^{61}$, $NR^{60}C(O)R^{61}$, $NR^{60}C(O)NR^{60}R^{61}$, $NR^{60}S(O)_q R^{60}$, $SiR^{60}R^{61}R^{62}$, $P(R^{60})_2$, $P(O)(R^{60})_2$, $P(OR^{60})_2$, $P(O)(OR^{60})_2$, $P(O)(OR^{61})$ and $P(O)NR^{60}R^{61}$, where q is an integer from 0 to 2;

each $R^{60}$, $R^{61}$, and $R^{62}$ is independently hydrogen, straight or branched chain alkyl, straight or branched chain alkenyl, straight or branched chain alkynyl, aryl, straight or branched chain aralkyl, straight or branched chain aralkenyl, straight or branched chain aralkynyl, heteroaryl, straight or branched chain heteroaralkyl, straight or branched chain heteroaralkenyl, straight or branched chain heteroaralkynyl, heterocyclyl, straight or branched chain heterocyclylalkyl, straight or branched chain heterocyclylalkenyl or straight or branched chain heteorcyclylalkynyl.

Fluorescent, colorimetric and phosphorescent groups are known to those of skill in the art (see, e.g., U.S. Pat. No. 6,274,337; Sapan et al. (1999) Biotechnol. Appl. Biochem. 29 (Pt. 2):99-108; Sittampalam et al. (1997) Curr. Opin. Chem. Biol. 1(3):384-91; Lakowicz, J. R., Principles of Fluorescence Spectroscopy, New York: Plenum Press (1983); Herman, B., Resonance Energy Transfer Microscopy, in: Fluorescence Microscopy of Living Cells in Culture, Part B, Methods in Cell Biology, vol. 30, ed. Taylor, D. L. & Wang, Y.-L., San Diego: Academic Press (1989), pp. 219-243; Turro, N. J., Modern Molecular Photochemistry, Menlo Park: Benjamin/Cummings Publishing Col, Inc. (1978), pp. 296-361 and the Molecular Probes Catalog (1997), OR, USA). Fluorescent moieties include, but are not limited to, 1- and 2-aminonaphthalene, p,p'-diaminostilbenes, pyrenes, quaternary phenanthridine salts, 9-aminoacridines, p,p'-diaminobenzophenone imines, anthracenes, oxacarbocyanine, merocyanine, 3-aminoequilenin, perylene, bis-benzoxazole, bis-p-oxazolyl benzene, 1,2-benzophenazin, retinol, bis-3-aminopyridinium salts, hellebrigenin, tetracycline, sterophenol, benzimidazolylphenylamine, 2-oxo-3-chromen, indole, xanthen, 7-hydroxycoumarin, phenoxazine, calicylate, strophanthidin, porphyrins, triarylmethanes and flavin. Fluorescent compounds that have functionalities for linking to a compound provided herein, or that can be modified to incorporate such functionalities include, e.g., dansyl chloride; fluoresceins such as 3,6-dihydroxy-9-phenylxanthhydrol; rhodamineisothiocyanate; N-phenyl 1-amino-8-sulfonatonaphthalene; N-phenyl 2-amino-6-sulfonatonaphthalene; 4-acetamido-4-isothiocyanato-stilbene-2,2'-disulfonic acid; pyrene-3-sulfonic acid; 2-toluidinon-aphthalene-6-sulfonate; N-phenyl-N-methyl-2-aminoaphthalene-6-sulfonate; ethidium bromide; stebrine; auromine-0,2-(9'-anthroyl)palmitate; dansyl phosphatidylethanolamine; N,N'-dioctadecyl oxacarbocyanine: N,N'-dihexyl oxacarbocyanine; merocyanine, 4-(3'pyrenyl)stearate; d-3-aminodesoxy-equilenin; 12-(9'-anthroyl)stearate; 2-methylanthracene; 9-vinylanthracene; 2,2'(vinylene-p-phenylene)bisbenzoxazole; p-bis(2-(4-methyl-5-phenyl-oxazolyl))benzene; 6-dimethylamino-1,2-benzophenazin; retinol; bis(3'-aminopyridinium) 1,10-decandiyldiiodide; sulfonaphthylhydrazone of hellibrienin; chlorotetracycline; N-(7-dimethylamino4-methyl-2-oxo-3-chromenyl)maleimide; N-(p-(2-benzimidazolyl)-phenyl)maleimide; N-(4-fluoranthyl)maleimide; bis(homovanillic acid); resazarin; 4-chloro-7-nitro-2,1,3-benzooxadiazole; merocyanine 540; resorufin; rose bengal; and 2,4-diphenyl-3(2H)-furanone. Many fluorescent tags are commercially available from SIGMA chemical company (Saint Louis, Mo.), Molecular Probes, R&D systems (Minneapolis, Minn.), Pharmacia LKB Biotechnology. (Piscataway, N.J.), CLONTECH Laboratories, Inc. (Palo Alto, Calif.), Chem Genes Corp., Aldrich Chemical Company (Milwaukee, Wis.), Glen Research, Inc., GIBCO BRL Life Technologies, Inc. (Gaithersberg, Md.), Fluka Chemica-Biochemika Analytika (Fluka Chemie AG, Buchs, Switzerland), and Applied Biosystems (Foster City, Calif.) as well as other commercial sources known to one of skill in the art.

Chemiluminescent groups intended for use herein include any components of light generating systems that are catalyzed by a peroxidase and require superoxide anion (O) (and/or hydrogen peroxide ($H_2O_2$))(see, e.g., Musiani et al. (1998) *Histol. Histopathol.* 13(1):243-8). Light generating systems include, but are not limited to, luminol, isoluminol, peroxyoxalate-fluorophore, acridinium ester, lucigenin, dioxetanes, oxalate esters, acridan, hemin, indoxyl esters including 3-O-indoxyl esters, naphthalene derivatives, such as 7-dimethylamino-naphthalene-1,2-dicarbonic acid hydrazide and cypridina luciferin analogs, including 2-methyl-6-[p-methoxyphenyl]-3,7-dihyroimidazo[1,2-α]pyrazin-3-one, 2methyl-6-phenyl-3,7-dihyromidazo[1,2-α]pyrazin-3-one and 2-methyl-6-[p-[2-[sodium 3-carboxylato-4-(6-hydroxy-3-xanthenon-9-yl]phenylthioureylene]ethyleneoxy]phenyl]-3,7-dihyroimidazo[1,2-α]pyrazin-3-one. In other embodiments, the chemiluminescent moieties intended for use herein include, but are not limited to, luminol, isoluminol, N-(4-aminobutyl)-N-ethyl isoluminol (ABEI), N-(4-aminobutyl)-N-methyl isoluminol (ABMI), which have the following structures and participate in the following reactions:

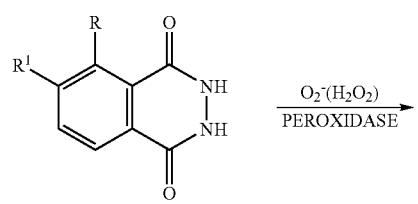

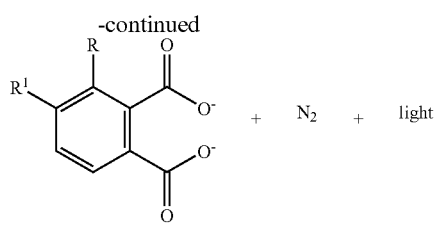

where luminol is represented, when R is $NH_2$ and $R^1$ is H; isoluminol, when R is H and $R^1$ is $NH_2$; for ABEI ((6-[N-(4-aminobutyl)-N-ethylamino]-2,3-dihyrophthalazine-1-4-dione), when R is H and $R^1$ is $C_2H_5$—N—$(CH_2)_4NH_2$; and for ABMI ((6-[N-(4-aminobutyl)-N-methylamino]-2,3-dihyrophthalazine-1-4-dione), when R is H and $R^1$ is $CH_3$—N—$(CH_2)_4NH_2$.

Bioluminescent groups for use herein include luciferase/luciferin couples, including firefly [*Photinus pyralis*] luciferase, the Aequorin system (i.e., the purified jellyfish photoprotein, aequorin). Many luciferases and substrates have been studied and well-characterized and are commercially available (e.g., firefly luciferase is available from Sigma, St. Louis, Mo., and Boehringer Mannheim Biochemicals, Indianapolis, Ind.; recombinantly produced firefly luciferase and other reagents based on this gene or for use with this protein are available from Promega Corporation, Madison, Wis.; the aequorin photoprotein luciferase from jellyfish and luciferase from *Renilla* are commercially available from Sealite Sciences, Bogart, Ga.; coelenterazine, the naturally-occurring substrate for these luciferases, is available from Molecular Probes, Eugene, Oreg.]. Other bioluminescent systems include crustacean, such as *Cyrpidina* (Vargula), systems; insect bioluminescence generating systems including fireflies, click beetles, and other insect systems; bacterial systems; dinoflagellate bioluminescence generating systems; systems from molluscs, such as Latia and Pholas; earthworms and other annelids; glow worms; marine polycheate worm systems; South American railway beetle; fish (i.e., those found in species of *Aristostomias*, such as *A. scintillans* (see, e.g., O'Day et al. (1974) *Vision Res.* 14:545-550), *Pachystomias*, and *Malacosteus*, such as *M. niger*; blue/green emmitters include cyclthone, myctophids, hatchet fish (agyropelecus), vinciguerria, howella, florenciella, and Chauliodus); and fluorescent proteins, including green (i.e., GFPs, including those from *Renilla* and from *Ptilosarcus*), red and blue (i.e., BFPs, including those from *Vibrio fischeri, Vibrio harveyi* or *Photobacterium phosphoreum*) fluorescent proteins (including *Renilla mulleri* luciferase, *Gaussia* species luciferase and *Pleuromamma* species luciferase) and phycobiliproteins.

Exemplary selectivity functions include, but are not limited to, ligands that bind to receptors such as insulin and other receptors (see, e.g., the Table of ligands below); cyclodextrins; enzyme substrates; lipid structures; prostaglandins; antibiotics; steroids; therapeutic drugs; enzyme inhibitors; transition state analogs; specific peptides that bind to biomolecule surfaces, including glue peptides; lectins (e.g., mannose type, lactose type); peptide mimetics; statins; functionalities, such as dyes and other compounds and moieties employed for protein purification and affinity chromatography. See e.g., FIG. 17, and the following table of peptide ligands:

| Exemplary peptide ligands | | |
|---|---|---|
| Designation | Sequence | SEQ ID |
| Adrenocorticotropic hormone | SYSMEHFRWG KPVGKKRRPV KVYPNGAEDE SAEAFPLEF | 1 |
| Adrenomedullin | YRQSMNNFQG LRSFGCRFGT CTVQKLAHQI YQFTDKDKDN VAPRSKISPQ GY | 2 |
| Allatostatin I-IV | APSGAQRLYGFGL | 3 |
| alpha MSH | WGKPV(ac)SYSMEHFR | 4 |
| alpha-Bag Cell Peptide | APRERFYSE | 5 |
| alpha-Neo-endorphin | YGGFLRKYPK | 6 |
| Alytesin | E*GRLGTQWAV GHLM-NH$_2$ | 7 |
| Amylin | KCNTATCATN RLANFLVHSS NNFGAILSST NVGSNTY | 8 |
| Angiotensin-1 | DRVYIHPFHL | 9 |
| Angiotensin-2 | DRVYIHPF | 10 |
| Angiotensin-3 | RVYIHPF | 11 |
| Apelin-13 | NRPRLSHLGPMPF | 12 |
| Astressin | *FHLLREVLE*IARAEQLAQEAHKNRL*IEII | 13 |
| Atrial Natriuretic Peptide | SLRRSSCFGG RMDRIGAQSG LGCNSFRY | 14 |
| Autocamtide 2 | KKALRRQETV DAL | 15 |
| BAM12 | YGGFMRRVGR PE | 16 |
| BAM18 | YGGFMRRVGR PEWW | 17 |
| BAM22 | YGGFMRRVGR PE | 18 |
| Beta Endorphins ("44") | YGGFMTSEKS QTPLVTLFKN AIIKNAYKKG E | 19 |
| beta MSH | AEKKDEGPYR MEHFRWGSPP KD | 20 |
| beta-Neo-endorphin | YGGFLRKYP | 21 |
| BetaAmyloid | DAEFRHASGYE VHHQKLVFFAE DVGSNLGAIIG LMVGGVVIAT | 22 |
| Beta-Bag Cell Peptide | RLRFH | 23 |
| BNP | SPKMVQGSGC FGRKMDRISS SSGLGCKVLR RH | 24 |
| Bradykinin | RPPGFSPFR | 25 |
| Buccalin | GMDSLAFSGG L-NH$_2$ | 26 |
| Bursin | KHG-NH$_2$ | 27 |
| C3 (undeca peptide) | ASKKPKRNIKA | 28 |
| Caerulein | *EQDY(SO3H)TGWMDF | 29 |
| Calcineurin | AIP ITSFEEAKGL DRINERMPPR RDAMP | 30 |
| Calcitonin | CGNLSTCMLG TYTQDFNKFH TFPQTAIGVG AP | 31 |
| Calpain Inhibitor ("42") | DPMSSTYIEE LGKREVTIPP KYRELLA | 32 |

Exemplary peptide ligands

| Designation | Sequence | SEQ ID |
|---|---|---|
| CAP-37 | NQGRHFCGGA EIHARFVMTA ASCFN | 33 |
| Cardiodilatin | * NPMYNAVSNA DLMDFKNLLD HLEEKMPLED | 34 |
| CD36peptideP (139-155) | CNLAVAAASH IYQNQFVQ | 35 |
| Cecropin B | KWKVFKKIEK MGRNIRNGIV KAGPAIAVLG EAKAL | 36 |
| Cerebellin | SGSAKVAFSA IRSTNH | 37 |
| CGRP-1 | ACDTATCVTH RLAGLLSRSG GVVKNNFVPT NVGSKAF | 38 |
| CGRP-2 | ACNTATCVTH RLAGLLSRSG GMVKSNFVPT NVGSKAF | 39 |
| CKS17 | LQNRRGLDLL FLKEGGL | 40 |
| Cortistatins | QEGAPPQQSA RRDRMPCRNF FWKTFSSCK | 41 |
| Crystalline | WG | 42 |
| Defensin 1 HNP1 | ACYCRIPACI AGERRYGTCI YQGRLWAFCC | 43 |
| Defensin HNP2 | CYCRIPACIA GERRYGTCIY QGRLWAFCC | 44 |
| Dermaseptin | ALWKTMLKKL GTMALHAGKA ALGAAADTIS QTQ | 45 |
| Dynorphin-A | YGGFLRRIRP KLKWDNQ | 46 |
| Dynorphin-B | YGGFLRRQFK VVT | 47 |
| Eledoisin | E*PSKDAFIGLM-NH$_2$ | 48 |
| Endomorphin-1 | YPWF | 49 |
| Endomorphin-2 | YPFF | 50 |
| Endothelin-1 | CSCSSLMDKE CVYFCHLDII W | 51 |
| Exendin-4 | HSDGTFTSDL SKQMEEEAVR LFIEWLKNGG PSSGAPPPS(NH$_2$) | 52 |
| Fibrinopeptide | AADSGEGDFLA EGGGVR | 53 |
| Fibrinopeptide | BQGVNDNEEGF FSAR | 54 |
| Fibronectin CS1 | EILDVPST | 55 |
| FMRF | FMRF | 56 |
| Galanin | GWTLNSAGYL LGPHAVGNHR SFSDKNGLTS | 57 |
| Galantide | GWTLNSAGYL LGPQQFFGLM(NH$_2$) | 58 |
| gamma-Bag Cell Peptide | RLRFD | 59 |
| Gastrin | EGPWLEEEEE AYGWMDF | 60 |
| Gastrin Releasing | VPLPAGGGTV LTKMYPRGNH WAVGHLM | 61 |
| Ghrelin | GSSFLSPEHQ RVQQRKESKK PPAKLQPR | 62 |

Exemplary peptide ligands

| Designation | Sequence | SEQ ID |
|---|---|---|
| GIP | YAEGTFISDY SIAMDKIHQQ DFVNWLLAQK GKKNDWKHNI TQ | 63 |
| Glucagon | HSQGTFTSDY SKYLDSRRAQ DFVDWLMNT | 64 |
| Grb-7 SH2 domain-1 | RRFA C DPDG YDN YFH C VPGG | 65 |
| Grb-7 SH2 domain-10 | TGSW C GLMH YDN AWL C NTQG | 66 |
| Grb-7 SH2 domain-11 | RSKW C RDGY YAN YPQ C WTQG | 67 |
| Grb-7 SH2 domain-18 | RSTL C WFEG YDN TFP C KYFR | 68 |
| Grb-7 SH2 domain-2 | RVQE C KYLY YDN DYL C KDDG | 69 |
| Grb-7 SH2 domain-23 | GLRR C LYGP YDN AWV C NIHE | 70 |
| Grb-7 SH2 domain-3 | KLFW C TYED YAN EWP C PGYS | 71 |
| Grb-7 SH2 domain-34 | FCAV C NEEL YEN CGG C SCGK | 72 |
| Grb-7 SH2 domain-46 | RTSP C GYIG YDN IFE C TYLG | 73 |
| Grb-7 SH2 domain-5 | TGEW C AQSV YAN YDN C KSAW | 74 |
| Grb-7 SH2 domain-6 | NVSR C TYIH YDN WSL C GVEV | 75 |
| Grb-7 SH2 domain-8 | GVSN C VFWG YAN DWL C SDYS | 76 |
| Growth hormone releasing factor | YADAIFTNSY RKVLGQLSAR KLLQDIMSRQ QGESNQERGA RARL | 77 |
| Guanylin | PGTCEICAYA ACTGC | 78 |
| Helodermin | HSDAIFTEEY SKLLAKLALQ KYLASILGSR TSPPP-$NH_2$ | 79 |
| Helospectin-1 | HSDATFTAEY SKLLAKLALQ KYLESILGSS TSPRPPSS | 80 |
| Helospectin-2 | HSDATFTAEY SKLLAKLALQ KYLESILGSS TSPRPPS | 81 |
| Histatin 5 | DSHAKRHHGY KRKFHEKHHS HRGY | 82 |
| ICE inhibitor(III) | ac-YVAD-fluroacyloxymethylketone | 83 |
| Immunostimulating Peptide | VEPIPY | 84 |
| Insulin (A-chain) | GIVEQCCTSI CSLYQLENYC N | 85 |
| Insulin (B-chain) | FVNQHLCGSH LVEALYLVCG ERGFFYTPKT | 86 |
| Insulin (whole molecule) | see above | 87 |
| Kinetensin | IARRHPYFL | 88 |
| Leu-Enkephalin | YGGFL | 89 |
| Litorin | E*QWAVGHFM-$NH_2$ | 90 |
| Malantide | RTKRSGSVYE PLKI | 91 |
| Met-Enkephalin | YGGFM | 92 |
| Metorphamide | YGGGFMRRV-$NH_2$ | 93 |
| Motilin | FVPIFTYGEL QRMQEKERNK GQ | 94 |
| Myomodulin | PMSMLRL-$NH_2$ | 95 |

Exemplary peptide ligands -continued

| Designation | Sequence | SEQ ID |
|---|---|---|
| Myosin Kinase | IPKKRAARATS-NH$_2$ | 96 |
| Necrofibrin | GAVSTA | 97 |
| Neurokinin A | HKTDSFVGLM-NH$_2$ | 98 |
| Neurokinin B | DMHDFFVGLM-NH$_2$ | 99 |
| Neuromedin B | GNLWATGHFM-NH$_2$ | 100 |
| Neuropeptide Y | YPSKPDNPGE DAPAEDMARY YSAKRHYINL ITRQRY-NH$_2$ | 101 |
| Neurotensin | E*LYENKPRRPUIL | 102 |
| Nociceptin | FGGFTGARKS ARKLANQ | 103 |
| Nociceptin/Orphanin FQ | FAEPLPSEEE GESYSKEVPE MEKRYGGFMR F | 104 |
| Nocistatin | EQKQLQ | 105 |
| Orexin A | E*PLPDCCRQKTCSCRLYELLHGAGN HAAGILTL-NH$_2$ | 106 |
| Orexin B | RSGPPGLQGR LQRLLQASGN HAAGILTM-NH$_2$ | 107 |
| Osteocalcin | YLYQWLGAPV PYPDPLEPRR EVCELNPDCD ELADHIGFQE AYRRFYGPV | 108 |
| Oxytocin | CYIQNCPLG-NH$_2$ | 109 |
| PACAP | HSDGIFTDSY SRYRKQMAVK KYLAAVL | 110 |
| PACAP-RP | DVAHGILNEA YRKVLDQLSA GKHLQSLVA | 111 |
| Pancreatic Polypeptide | APLEPVYPGD NATPEQMAQY AADLRRYINM LTRPRY-NH$_2$ | 112 |
| Papain Inhibitor | GGYR | 113 |
| Peptide E | YGGFMRRVGR PE | 114 |
| Peptide YY | YPIKPEAPGE DASPEELNRY YASLRHYLNL VTRQRY-NH$_2$ | 115 |
| Phosphate acceptor | RRKASGPPV | 116 |
| Physalaemin | E*ADPNKFYGLM-NH$_2$ | 117 |
| Ranatensin | E*VPQWAVGHFM-NH$_2$ | 118 |
| RGD peptides | X-RGD-X | 119 |
| Rigin | GQPR | 120 |
| RR-SRC | RRLIEDAEYA ARG | 121 |
| Schizophrenia | RPTVL | 122 |
| Secretin | HSDGTFTSEL SRLREGARLQ RLLQGLV | 123 |
| Serum Thymic Factor | E*AKSQGGSN | 124 |
| structural-site zinc ligands-alpha | PQCGKCRICK NPESNYCLK | 125 |

Exemplary peptide ligands

| Designation | Sequence | SEQ ID |
|---|---|---|
| structural-site zinc ligands-beta | PQCGKCRVCK NPESNYCLK | 126 |
| structural-site zinc ligands-gamma | PQCGKCRICK NPESNYCLK | 127 |
| structural-site-zinc ligands-pi | PLCRKCKFCLSPLTNLCGK | 128 |
| structural-site-zinc ligands-X | PQGECKFCLNPKTNLCQK | 129 |
| Substance P | RPKPQQFFGL M-NH$_2$ | 130 |
| Syntide 2 | PLARTLSVAG LPGKK | 131 |
| Systemin | AVQSKPPSKR DPPKMQTD | 132 |
| Thrombin-light chain | TFGSGEADCG LRPLFEKKSL EDKTERELLE SYIDGR | 133 |
| Thymopentin | RKDVY | 134 |
| Thymus Factor | QAKSQGGSN | 135 |
| TRH | E*HP | 136 |
| Tuftsin | TKPR | 137 |
| Uperolein | E*PDPNAFYGLM-NH$_2$ | 138 |
| Uremic Pentapeptide | DLWQK | 139 |
| Urocortin | DNPSLSIDLT FHLLRTLLEL ARTQSQRERA EQNRIIFDSV | 140 |
| Uroguanylin | NDDCELCVNV ACTGCL | 141 |
| Vasonatrin | GLSKGCFGLK LDRIGSMSGL GCNSFRY | 142 |
| Vasopressin | CYFQNCPRG | 143 |
| Vasotocin | CYIQNCPRG | 144 |
| VIP | HSDAVFTDNY TRLRKQMAVK KYLNSILN | 145 |
| Xenin | MLTKFETKSA RVKGLSFHPK RPWIL | 146 |
| YXN motif | Tyr-X-Asn | 147 |
| Zinc ligand of carbonic anhydrase I | FQFHFHWGS | 148 |
| Zinc ligand of carbonic anhydrase | IIIQFHFHWGS | 149 |

Other selections for Y are can be identified by those of skill in the art and include, for example, those disclosed in *Techniques in Protein Chemistry*, Vol. 1 (1989) T. Hugli ed. (Academic Press); *Techniques in Protein Chemistry*, Vol. 5 (1994) J. W. Crabb ed. (Academic Press); Lundblad *Techniques in Protein Modification* (1995) (CRC Press, Boca Raton, Fla.); Glazer et al. (1976) *Chemical Modification of Proteins* (North Holland (Amsterdam))(American Elsevier, New York); and Hermanson (1996) *Bioconjugate Techniques* (Academic Press, San Diego, Calif.).

4. Sorting Functions "Q"

The compounds provided herein can include a sorting function ("Q"), which permits the compounds to be addressed, such as by capture in a 2-D array. In certain embodiments, the sorting function is selected to not interact with the biomolecules (e.g. target and non-target proteins) in the sample. The sorting functions are "tags", such as oligonucleotide tags, such that when the compounds are bathed over an array of complementary oligonucleotides linked to solid supports, such as beads, chips, under suitable binding conditions, the oligonucleotides hybridize. The identity of the capture compound can be known by virtue of its position in the array. Other sorting functions can be optically coded, including as color coded or bar coded beads that can be separated, or an electronically-tagged, such as by providing microreactor supports with electronic tags or bar coded supports (see, e.g., U.S. Pat. No. 6,025,129; U.S. Pat. No. 6,017, 496; U.S. Pat. No. 5,972,639; U.S. Pat. No. 5,961,923; U.S. Pat. No. 5,925,562; U.S. Pat. No. 5,874,214; U.S. Pat. No. 5,751,629; U.S. Pat. No. 5,741,462), or chemical tags (see, e.g., U.S. Pat. No. 5,432,018; U.S. Pat. No. 5,547,839) or colored tags or other such addressing methods that can be used in place of physically addressable arrays. The sorting function is selected to permit physical arraying or other addressable separation method suitable for analysis, particularly mass spectrometric, including MALDI, analysis.

Other sorting functions for use in the compounds provided herein include biotin, $(His)_6$, BODIPY (4,4-difluoro-4-bora-3a,4a-diaza-s-indacene), oligonucleotides, nucleosides, nucleotides, antibodies, immunotoxin conjugates, adhesive peptides, lectins, liposomes, PNA (peptide nucleic acid), activated dextrans and peptides. In one embodiment, the sorting function is an oligonucleotide, particularly, either a single-stranded or partially single-stranded oligonucleotide to permit hybridization to single-stranded regions on complementary oligonucleotides on solid supports.

In one embodiment of the capture compounds provided herein, Q is a single stranded unprotected or suitably protected oligonucleotide or oligonucleotide analog (e.g., PNA) of up to 50 building blocks, which is capable of hybridizing with a base-complementary single stranded nucleic acid molecule. In certain embodiments, Q contains from about 5 up to about 10, 15, 25, 30, 35, 40, 45 or 50 building blocks.

Biomolecule mixtures, including, but not limited to, protein mixtures, can have different hydrophobicities (solubility) than the compounds provided herein. In certain embodiments, in order to achieve high reaction yields between the functionality X on the compounds provided herein and the protein surface, the reaction is performed in solution. In other embodiments, the reaction is performed at a solid/liquid or liquid/liquid interface. In certain embodiments, the solubility properties of the compounds provided herein are dominated by the Q moiety. A change in the structure of Q can, in these embodiments, accommodate different solubilities. For example, if the protein mixture is very water soluble, Q can have natural phosphodiester linkages; if the bimolecular mixture is very hydrophobic (lipids, glycolipids, membrane proteins, lipoproteins), Q can have it's phosphodiester bonds protected as phosphotriesters, or alternatively, these bonds can be methylphosphonatediesters or peptide nucleic acids (PNAs). If the biomolecule mixture is of an intermediate hydrophobicity, solubility is achieved, e.g., with phosphothioate diester bonds. Intermediate solubility also can be attained by mixing phosphodiester with phosphotriester linkages. Those skilled in the art can easily conceive of other means to achieve this goal, including, but not limited to, addition of substituents on Z, as described elsewhere herein, or use of beads for Z that are hydrophobic, including, but not limited to, polystyrene, polyethylene, polypropylene or teflon, or hydrophilic, including, but not limited to, cellulose, dextran cross-linked with epichlorohydrin (e.g., Sephadex®), agarose (e.g., Sepharose®), lectins, adhesive polypeptides, and polyacrylamides.

The flexibility of being able to change the solubility of the compounds is a significant advantage over current methods. In contrast, 2D gel electrophoresis is useful only for analysis of water soluble proteins with the result that about 30 to 35% of all cellular proteins, such as those residing in the cell membrane, cannot be analyzed by this method. This is a severe limitation of 2D gel electrophoresis since many proteins, including, but not limited to, those involved in tissue specific cell-cell contacts, signal transduction, ion channels and receptors, are localized in the cell membrane.

In one embodiment, after reaction or complexation of the compounds provided herein with a biomolecule, including, but not limited to, a protein, the compounds are brought into contact with a set of spatially resolved complementary sequences on a flat support, beads or microtiter plates under hybridization conditions.

In certain embodiments, Q is a monovalent oligonucleotide or oligonucleotide analog group that is at least partially single stranded or includes a region that can be single-stranded for hybridization to complementary oligonucleotides on a support. Q can have the formula:

where $N^1$ and $N^2$ are regions of conserved sequences; B is a region of sequence permutations; m, i and n are the number of building blocks in $N^1$, B and $N^2$, respectively; and the sum of m, n and i is a number of units able to hybridize with a complementary nucleic acid sequence to form a stable hybrid. Thus, in embodiments where B is a single stranded DNA or RNA, the number of sequence permutations is equal to $4^i$. In one embodiment, the sum of m, n and i is about 5 up to about 10, 15, 25, 30, 35, 40, 45 or 5. In certain embodiments m and n are each independently 0 to about 48, or are each independently about 1 to about 25, or about 1 to about 10 or 15, or about 1 to about 5. In other embodiments, i is about 2 to about 25, or is about 3 to about 12, or is about 3 to about 5, 6, 7 or 8.

The oligonucleotide portion, or oligonucleotide analog portion, of the compounds ($N^1_m B_i N^2_n$), can be varied to allow optimal size for binding and sequence recognition. The diversity of the sequence permutation region B can be relatively low if the biomolecule mixture, including, but not limited to, protein mixtures, is of low complexity. If the mixture is of high complexity, the sequence region B has to be of high diversity to afford sufficient resolving power to separate all the species. The flanking conserved regions $N^1_n$, and $N^2_n$, need only be long enough to provide for efficient and stable hybrid formation. There is, however, flexibility in designing these regions: $N^1_m$ and $N^2_n$ can be of the same length and same sequence, of the same length and different sequence or of different length and different sequence. In certain embodiments, including those where B is of sufficient length to provide stable hybrid formation, $N^1$ and/or $N^2$ are absent. In these embodiments, the oligonucleotide portion of the compounds, or oligonucleotide analog portion of the compounds, has the formula $N^1_m B_i$, or $B_i N^2_n$, or $B_i$.

In an exemplary embodiment (see, e.g., EXAMPLE 1.a.), B has a trinucleotide sequence embedded within a 11-mer oligonucleotide sequence, where the $N^1_m$ and $N^2_n$ tetranucleotide sequences provide flanking identical (conserved) regions. This arrangement for $N^1_m B_i N^2_n$ affords 64 different compounds where each compound carries the same reactive functionality X. In another exemplary embodiment (see, e.g., EXAMPLE 1.b.), B has a tetranucleotide sequence embedded within a 12-mer oligonucleotide sequence, where the $N^1_m$ and $N^2_n$ oligonucleotide sequences provide flanking but not identical octanucleotide sequences. This arrangement for $N^1_m B_i N^2_n$ affords 256 different compounds where each carry the same reactive functionality X. In a further exemplary embodiment (see, e.g., EXAMPLE 1.c.), B has an octanucleotide sequence embedded within a 23-mer oligonucleotide sequence, where the $N^1{}_m$ and $N^2{}_n$ oligonucleotide sequences provide flanking but not identical octanucleotide sequences. This arrangement for $N^1{}_m B_i N^2{}_n$ affords 65,536 different compounds where each carries the same reactive functionality X, and exceeds the estimated complexity of the human proteome (e.g., 30,000-35,000 different proteins). In certain embodiments, use of a B with excess permutations for the complexity of the protein mixture, as the oligonucleotides with the best hybridization properties can be used for analysis to reduce mismatching.

5. Solubility Functions "W"

The compounds provided herein can include a solubility function, W, to confer desired solubility properties, such as solubility in hydrophobic environments or hydrophilic environments to permit probing of biomolecules in physiological environments, such as in membranes. Exemplary solubility functions for use in the compounds provided herein include polyethylene glycols, sulfates, polysulfates, phosphates, sulfonates, polysulfonates, carbohydrates, dextrin, polyphosphates, poly-carboxylic acids, triethanolamine, alcohols, water soluble polymers, salts of alkyl and aryl carboxylic acids and glycols.

Amphiphilic compounds, such as quaternary ammonium salts (i.e., betain, choline, sphingomyelin, tetramethyl (or tetrabutyl) alkyl ammonium salts, cationic, ionic and neutral tensides may also be used as the solubility function W.

In other embodiments, W also can be used to modulate the solubility of the compounds to achieve homogeneous solutions, if desired, when reacting with biomolecule mixtures, including, but not limited to, protein mixtures. In certain embodiments, W is a sulfonate, a polar functionality that can be used to make the compounds more water-soluble. In other embodiments, W is a hydrophobic group, including lower alkyl, such as tert-butyl, tert-amyl, isoamyl, isopropyl, n-hexyl, sec-hexyl, isohexyl, n-butyl, sec-butyl, iso-butyl and n-amyl, or an aryl group, including phenyl or naphthyl.

6. Exemplary Embodiments

The following provides exemplary capture compounds that exhibit the above-described properties. It is understood that these are exemplary only and that any compounds that can react covalently with a biomolecule or by other highly stable interaction that is stable to analytic conditions, such as those of mass spectrometric analysis, and that can sorted or otherwise identified are contemplated for use in the collections.

a. Exemplary Embodiment 1

In one embodiment, the compounds for use in the methods provided herein have formulae:

QZX or Q-Z-Y, where Q is a sorting function that contains a single stranded unprotected or suitably protected oligonucleotide or oligonucleotide analog (e.g., peptide nucleic acid (PNA)) of up to 50 building blocks, which is capable of hybridizing with a base-complementary single-stranded nucleic acid molecule;

Z is a moiety that is cleavable prior to or during analysis of a biomolecule, including mass spectral analysis, without altering the structure of the biomolecule, including, but not limited to, a protein;

X is a reactivity functional group that interacts with and/or reacts with functionalities on the surface of a biomolecule, including, but not limited to, a protein, to form covalent bonds or bonds that are stable under conditions of mass spectrometric analysis, particularly MALDI analysis; and Y is a selectivity functional group that interacts with and/or reacts by imposing unique selectivity by introducing functionalities that interact noncovalently with target proteins.

b. Exemplary Embodiment 2

In another embodiment, the compounds for use in the methods provided herein have formula:

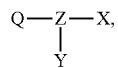

where Q is a single-stranded unprotected or suitably protected oligonucleotide or oligonucleotide analog (e.g., peptide nucleic acid (PNA)) of up to 50 building blocks, which is capable of hybridizing with a base-complementary single stranded nucleic acid molecule;

Z is a moiety that is cleavable prior to or during analysis of a biomolecule, including mass spectral analysis, without altering the structure of the biomolecule, including, but not limited to, a protein;

X is a functional group that interacts with and/or reacts with functionalities on the surface of a biomolecule, including, but not limited to, a protein, to form covalent bonds or bonds that are stable under conditions of mass spectrometric analysis, particularly MALDI analysis; and Y is a functional group that interacts with and/or reacts by imposing unique selectivity by introducing functionalities that interact noncovalently with target proteins.

c. Exemplary Embodiment 3

In another embodiment, the compounds for use in the methods provided herein have formula:

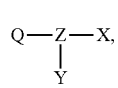

where Q is a sorting function that is a compound, or one or more biomolecules (e.g., a pharmaceutical drug preparation, a biomolecule, drug or other compound that immobilizes to the substrate and captures target biomolecules), which is(are) capable of specific noncovalent binding to a known compound to produce a tightly bound capture compound;

Z is a moiety that is cleavable prior to or during analysis of a biomolecule, including mass spectral analysis, without altering the structure of the biomolecule, including, but not limited to, a protein;

X is a functional group that interacts with and/or reacts with functionalities on the surface of a biomolecule, including, but not limited to, a protein, to form covalent bonds or bonds that are stable under conditions of mass spectrometric analysis, particularly MALDI analysis; and Y is a functional group that interacts with and/or reacts by imposing unique selectivity by introducing functionalities that interact noncovalently with target proteins.

d. Exemplary Embodiment 4

In another embodiment, the compounds for use in the methods provided herein have the formulae:

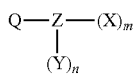

or Q-Z-(X)$_m$ or Q-Z-(Y)$_n$, where Q, Z, X and Y are as defined above; m is an integer from 1 to 100, in one embodiment 1 to 10, in another embodiment 1 to 3, 4 or 5; and n in an integer from 1 to 100, in one embodiment 1 to 10, in another embodiment 1 to 3, 4 or 5.

e. Exemplary Embodiment 5

In another embodiment, X is a pharmaceutical drug. The compounds of these embodiments can be used in drug screening by capturing biomolecules, including but not limited to proteins, which bind to the pharmaceutical drug. Mutations in the biomolecules interfering with binding to the pharmaceutical drug are identified, thereby determining possible mechanisms of drug resistance. See, e.g., Hessler et al. (Nov. 9-11, 2001) Ninth Foresight Conference on Molecular Nanotechnology (Abstract)(available online at www.foresight.org/Conferences/MNT9/Abstracts/Hessler/)

f. Other Embodiments

In certain embodiments, the compounds provided herein have the formula:

$N^1{}_m B_i N^2{}_n (S^1)_t M(R^{15})_a (S^2)_b LX$ where $N^1$, B, $N^2$, $S^1$, M, $S^2$, L, X, m, i, n, t, a and b are as defined above. In further embodiments, the compounds for use in the methods provided herein include a mass modifying tag and have the formula:

$N^1{}_m B_i N^2{}_n (S^1)_t M(R^{15})_a (S^2)_b LTX$, where $N^1$, B, $N^2$, $S^1$, M, $S^2$, L, T, X, m, i, n, t, a and b are as defined above.

In other embodiments, including those where Z is not a cleavable linker, the compounds provided herein have the formula:

$N^1{}_m B_i N^2{}_n (S^1)_t M(R^{15})_a (S^2)_b X$, where $N^1$, B, $N^2$, $S^1$, M, $S^2$, X, m, i, n, t, a and b are as defined above.

In another embodiment, the compounds for use in the methods provided herein include those of formulae:

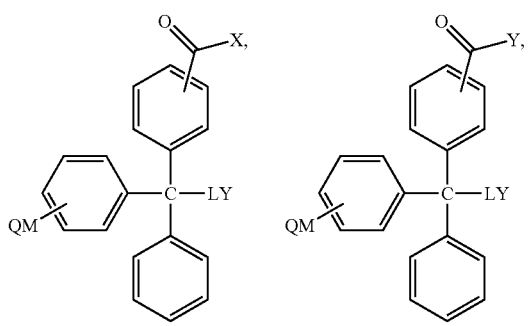

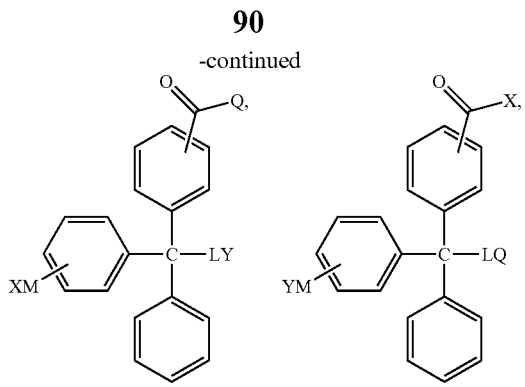

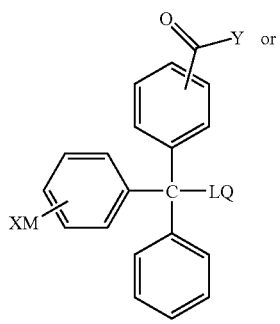

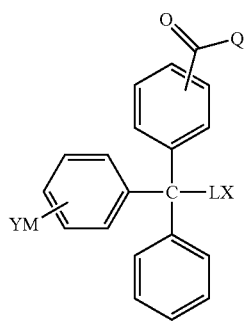

where L and M are each independently O, S or $NR^3$; X is a reactivity function, as described above; Y is a selectivity function, as described above; Q is a sorting function, as described above; and each $R^3$ is independently hydrogen, substituted or unsubstituted alkyl, substituted or unsubstituted alkenyl, substituted or unsubstituted alkynyl, substituted or unsubstituted cycloalkyl, substituted or unsubstituted heterocyclyl, substituted or unsubstituted aryl, substituted or unsubstituted heteroaryl, substituted or unsubstituted aralkyl, or substituted or unsubstituted heteroaralkyl.

In another embodiment, the capture compounds provided herein have the formula:
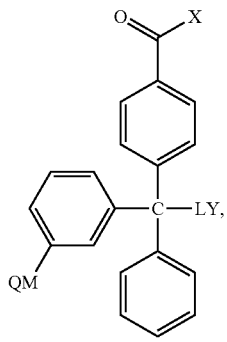
where L, M, X, Y and Q are as defined above.
In another embodiment, the capture compounds provided herein have the formula:
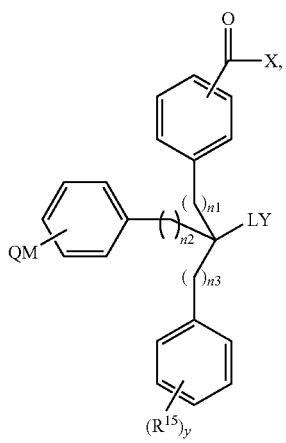
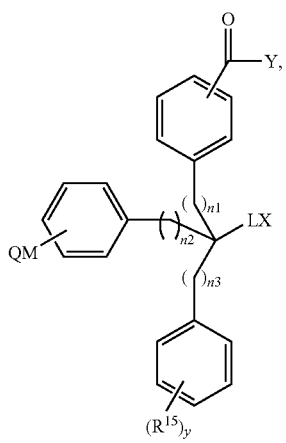
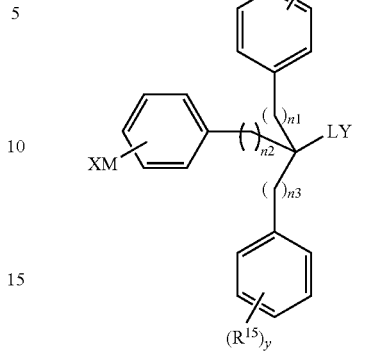
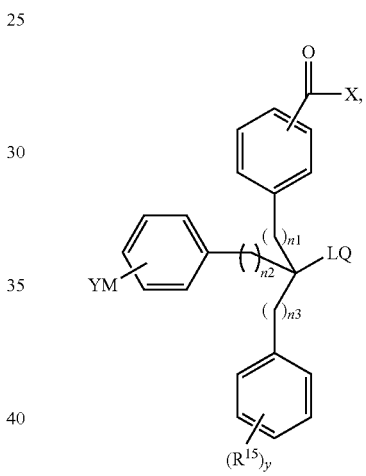
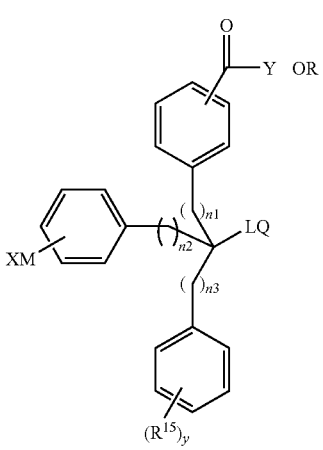

-continued

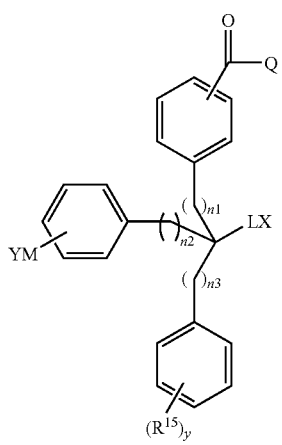

where L, M, X, Y and Q are as defined above, n1, n2 and n3 are 0 to 5. In another embodiment, n1, n2 and n3 are selected with the proviso that n1, n2 and n3 are not all 0.

In another embodiment, the capture compounds provided herein have the formula:

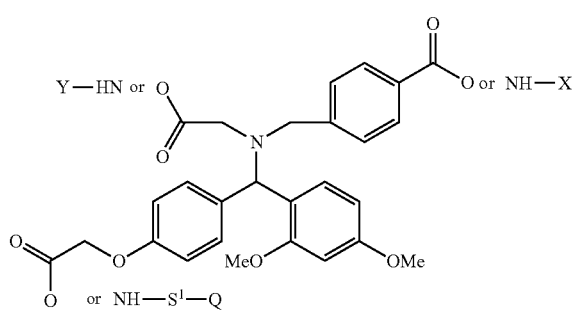

where X, Y, Q and $S^1$ are as defined above.

In another embodiment, the capture compounds provided herein have the formula:

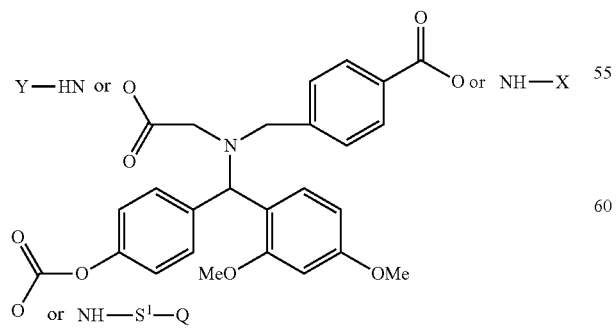

where Q, Y, X and $S^1$ are as defined above.

In another embodiment, the capture compounds provided herein have the formula:

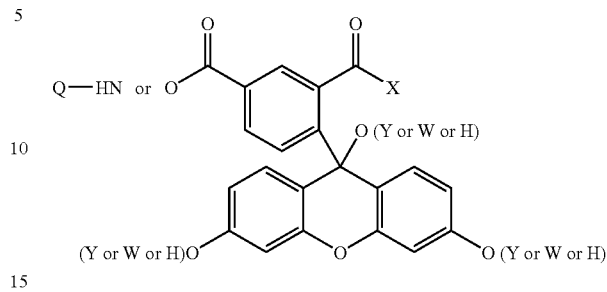

where X, Y, Q and W are as defined above.

In another embodiment, the capture compounds provided herein have the formula:

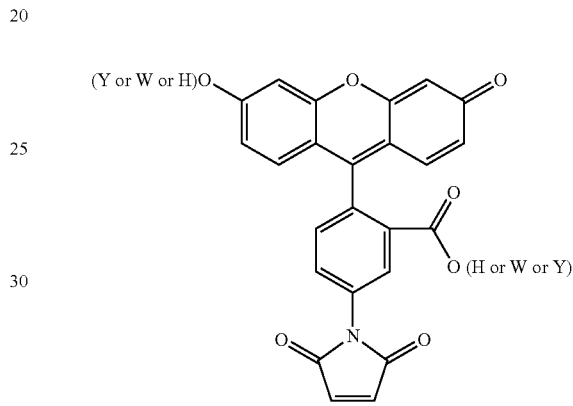

where X, Y, Q and W are as defined above.

In another embodiment, the capture compounds for use in the methods provided herein have the formulae:

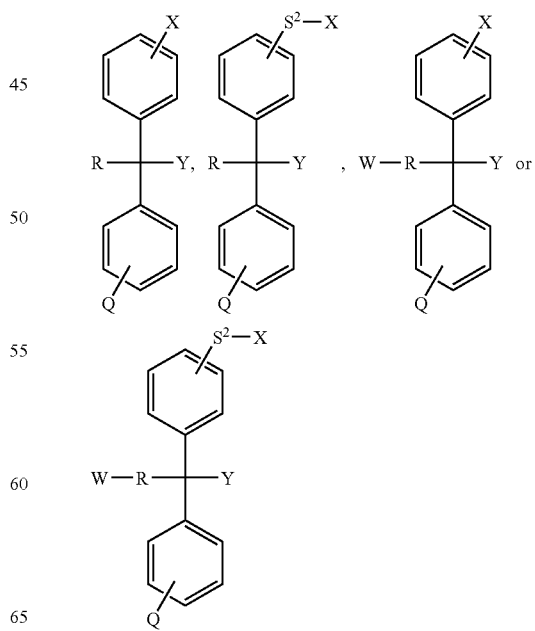

where X, Y, Q and W are selected as above; and R is substituted or unsubstituted alkyl, substituted or unsubstituted cycloalkyl, substituted or unsubstituted cycloalkylalkyl, or substituted or unsubstituted aralkyl. In another embodiment, R is selected from cyclohexyl, cyclohexyl-$(CH_2)_n$, isopropyl, and phenyl-$(CH_2)_n$, where n is 1, 2 or 3. As shown in the formulae above, R is optionally substituted with W.

In other embodiments, the compounds for use in the methods provided herein include:

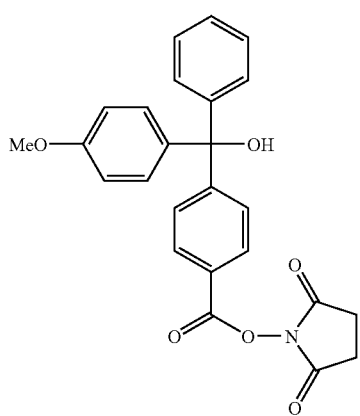
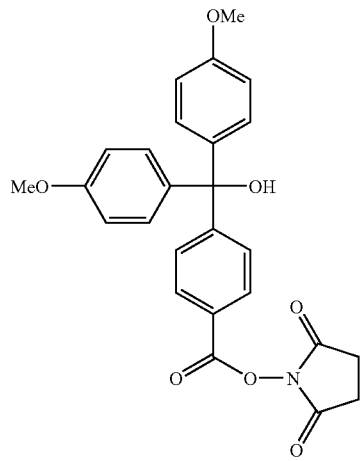
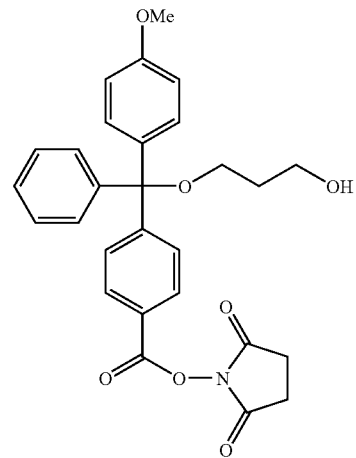
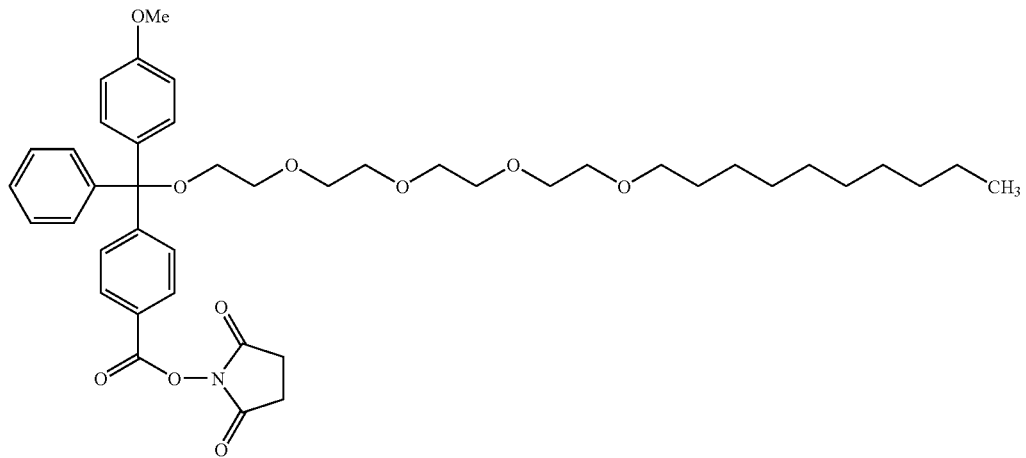
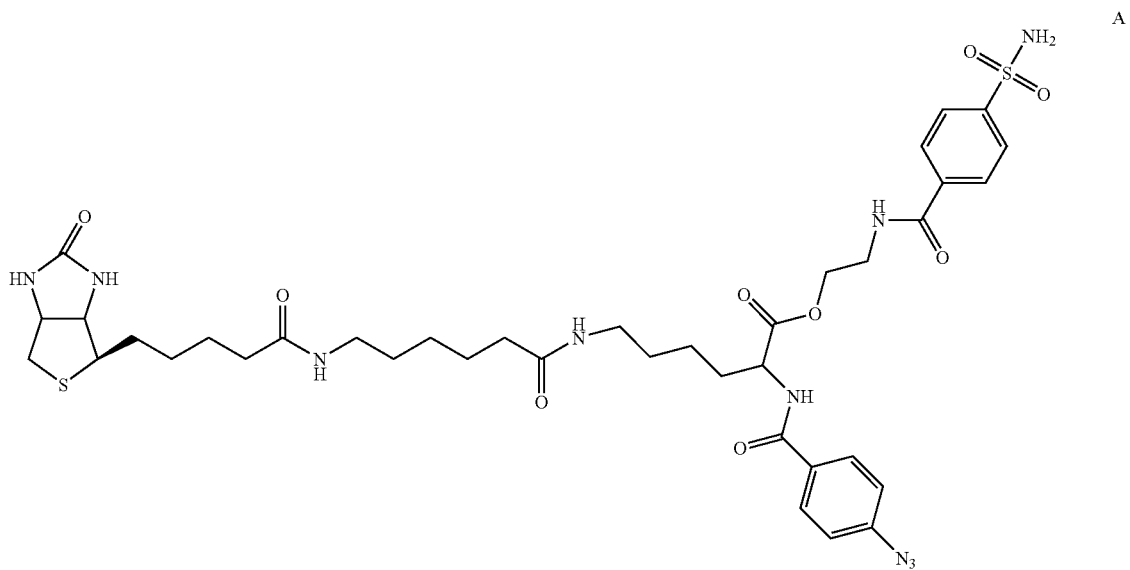

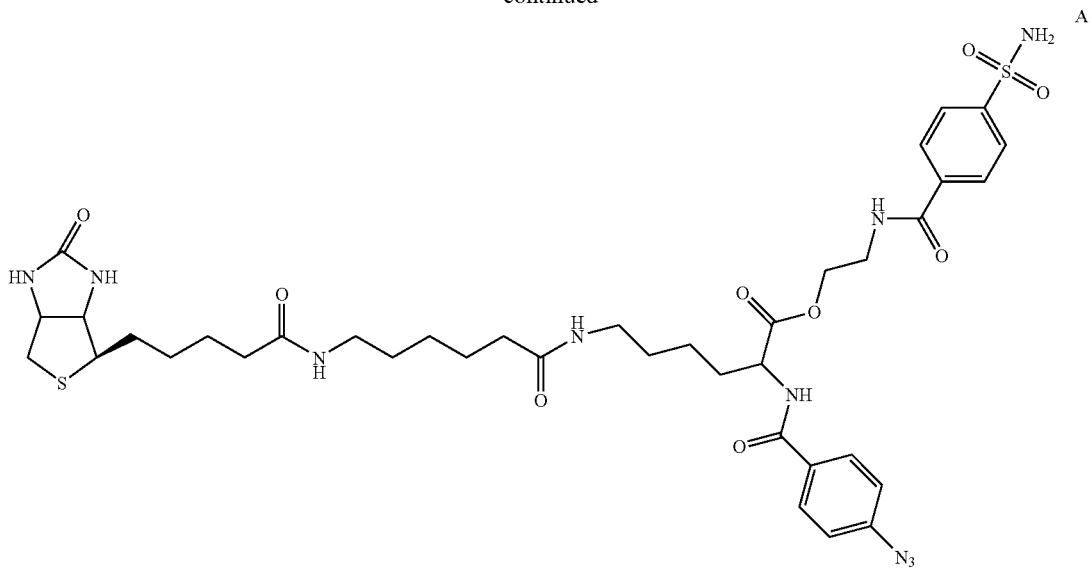

Specific compounds within these embodiments are those resulting from all combinations of the groups listed above for the variables contained in this formula and all can include Q groups. It is intended herein that each of these specific compounds is within the scope of the disclosure herein.

D. Preparation of the Capture Compounds

The capture compounds are designed by assessing the target biomolecules and reaction conditions. For example, if the target biomolecules are proteins, X functions suitable to effect covalent or binding to proteins with high affinity are selected. Y is selected according to the complexity of the target mixture and the desired specificity of binding by X. Q is selected according the number of divisions of the mixture that are desired; and W is selected based upon the environment of the biomolecules that is probed. A variety of capture compounds are designed according to such criteria.

The capture compounds once designed can be synthesized by methods available to those of skill in the art. Preparation of exemplary capture compounds is described below. Any capture compound or similar capture compound can be synthesized according to a method discussed in general below or by minor modification of the methods by selecting appropriate starting materials or by methods known to those of skill in the art.

In general, the capture compounds can prepared starting with the central moiety Z. In certain embodiments, Z is $(S^1)_t$-$M(R^{15})_a(S^2)_b$L. In these embodiments, the capture compounds can be prepared starting with an appropriately substituted (e.g., with one or more $R^{15}$ groups) M group. $M(R^{15})_a$ is optionally linked with $S^1$ and/or $S^2$, followed by linkage to the cleavable linker L. Alternatively, the L group is optionally linked to $S^2$, followed by reaction with $M(R^{15})_a$, and optionally $S^1$. This Z group is then derivatized on its $S^1$ (or $M(R^{15})_a$) terminus to have a functionality for coupling with an oligonucleotide or oligonucleotide analog Q (e.g., a phosphoramidite, H-phosphonate, or phosphoric triester group). The Q group will generally be N-protected on the bases to avoid competing reactions upon introduction of the X moiety. In one embodiment, the Z group is reacted with a mixture of all possible permutations of an oligonucleotide or oligonucleotide Q (e.g., $4^i$ permutations where i is the number of nucleotides or nucleotide analogs in B). The resulting QZ capture compound or capture compounds is(are) then derivatized through the L terminus to possess an X group for reaction with a biomolecule, such as a protein. If desired, the N-protecting groups on the Q moiety are then removed. Alternatively, the N-protecting groups can be removed following reaction of the capture compound with a biomolecule, including a protein. In other embodiments, Q can be synthesized on Z, including embodiments where Z is an insoluble support or substrate, such as a bead. In a further embodiment, Q is presynthesized by standard solid state techniques, then linked to M. Alternatively, Q can be synthesized stepwise on the M moiety.

Provided below are examples of syntheses of the capture compounds provided herein containing alkaline-labile and photocleavable linkers. One of skill in the art can prepare other capture compounds disclosure by routine modification of the methods presented herein, or by other methods known to those of skill in the art.

For synthesis of a compound provided herein containing an alkaline-labile linker, 1,4-di(hydroxymethyl)benzene (i.e., M) is mono-protected, e.g., as the corresponding mono-tert-butyldimethylsilyl ether. The remaining free alcohol is derivatized as the corresponding 2-cyano-ethyl-N,N-diisopropylphosphoramidite by reaction with 2-cyanoethyl-N,N-diisopropylchlorophosphoramidite. Reaction of this amidite with an oligonucleotide, (i.e., Q), is followed by removal of the protecting group to provide the corresponding alcohol. Reaction with, e.g., trichloromethyl chloroformate affords the illustrated chloroformate (i.e., X).

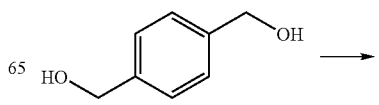

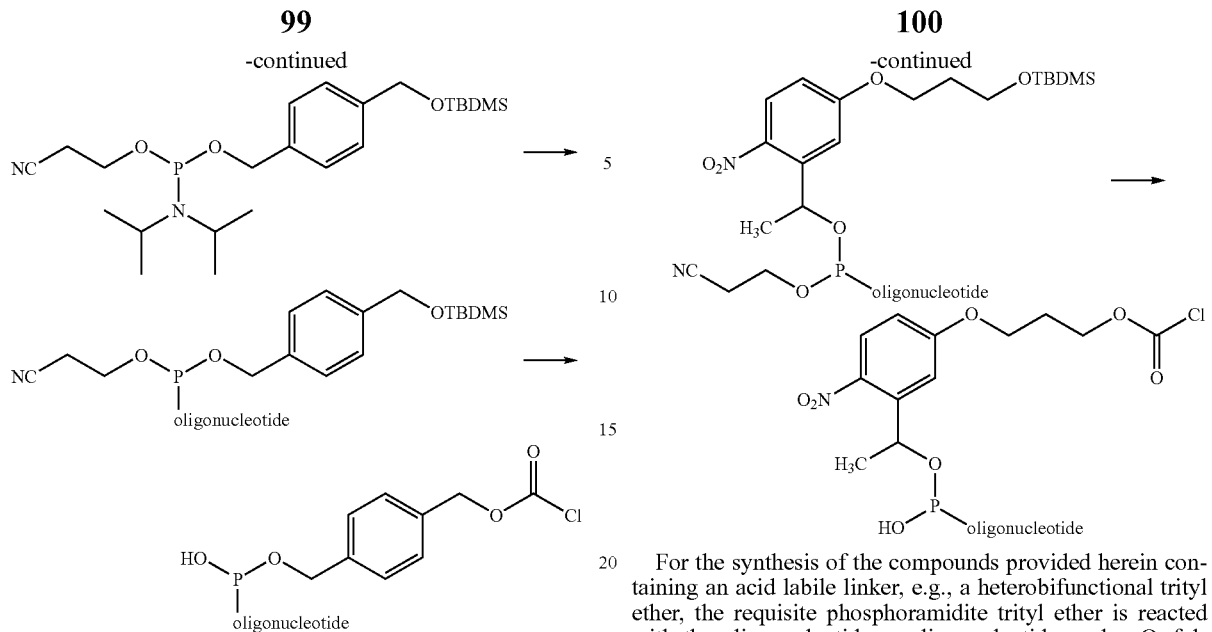

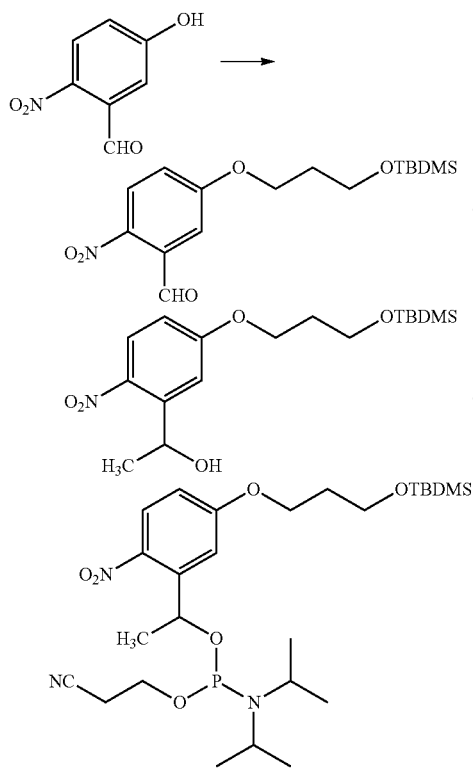

For the synthesis of a compound provided herein containing a photocleavable linker, 2-nitro-5-hydroxybenzaldehyde (i.e., a precursor of L) is reacted with, e.g., 3-bromo-1-propanol to give the corresponding ether-alcohol. The alcohol is then protected, e.g., as the corresponding tert-butyldimethylsilyl ether. Reaction of this compound with trimethylaluminum gives the corresponding benzyl alcohol, which is derivatized as its phosphoramidite using the procedure described above. The amidite is reacted with an oligonucleotide (i.e., Q), followed by removal of the protecting group and derivatization of the resulting alcohol as the corresponding chloroformate (i.e., X).

For the synthesis of the compounds provided herein containing an acid labile linker, e.g., a heterobifunctional trityl ether, the requisite phosphoramidite trityl ether is reacted with the oligonucleotide or oligonucleotide analog Q, followed by deprotection of the trityl ether and capture of a biomolecule, e.g., a protein, on the alcohol via a reactive derivative of the alcohol (X), as described above.

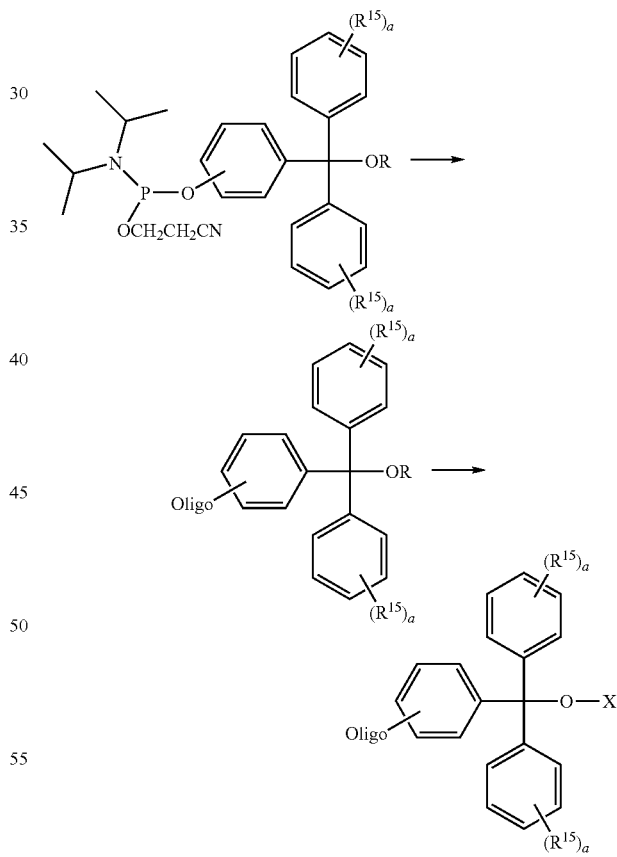

In another embodiment, the capture compounds provided herein are prepared by the method illustrated below. Briefly, reaction of cystine with a biotin-linker moiety results in derivatization of the amino functionality. Reaction of the resulting compound with N-hydroxysuccinimide and, e.g., dicyclohexylcarbodiimide (DCC) forms the corresponding di-NHS ester. Reduction of the disulfide bond followed by reaction with a drug-linker moiety forms 2 equivalents of the desired capture compound.

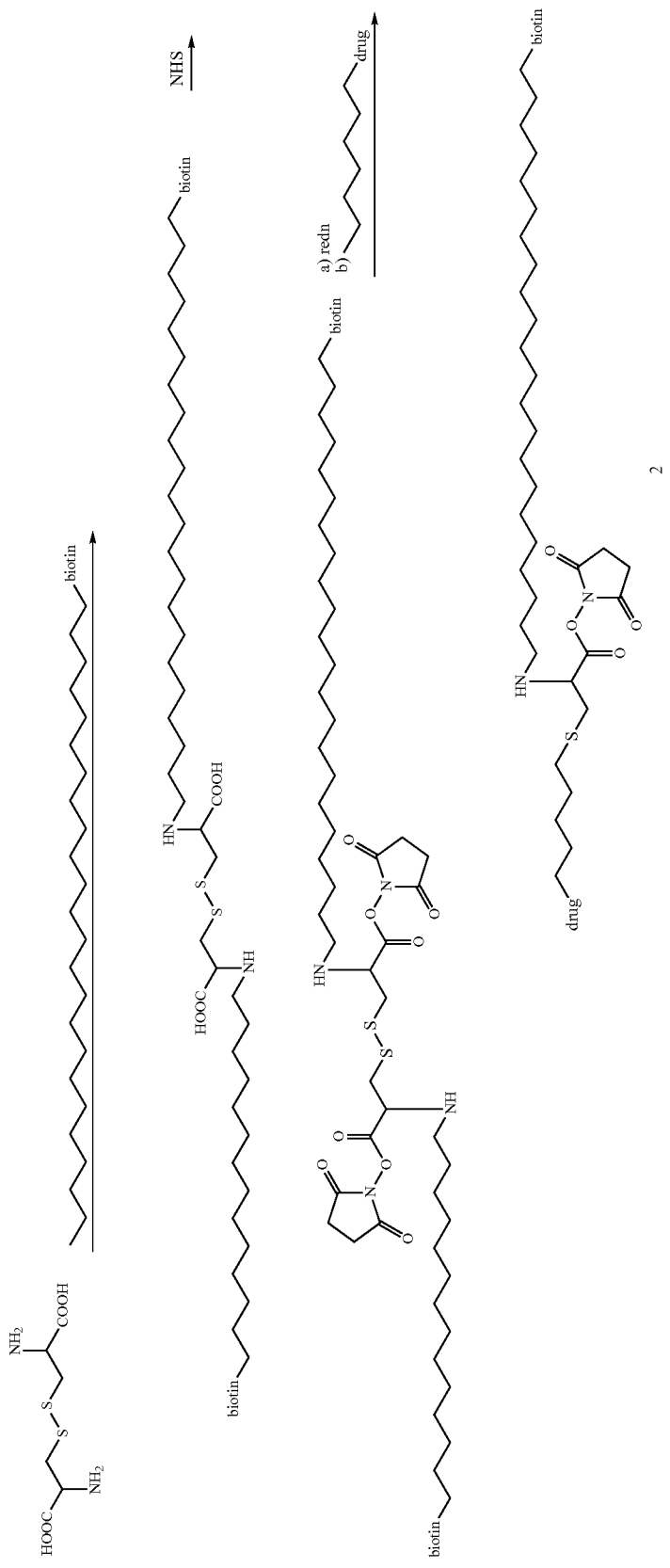

An exemplary photoactivatable capture compound may be prepared by the following method:
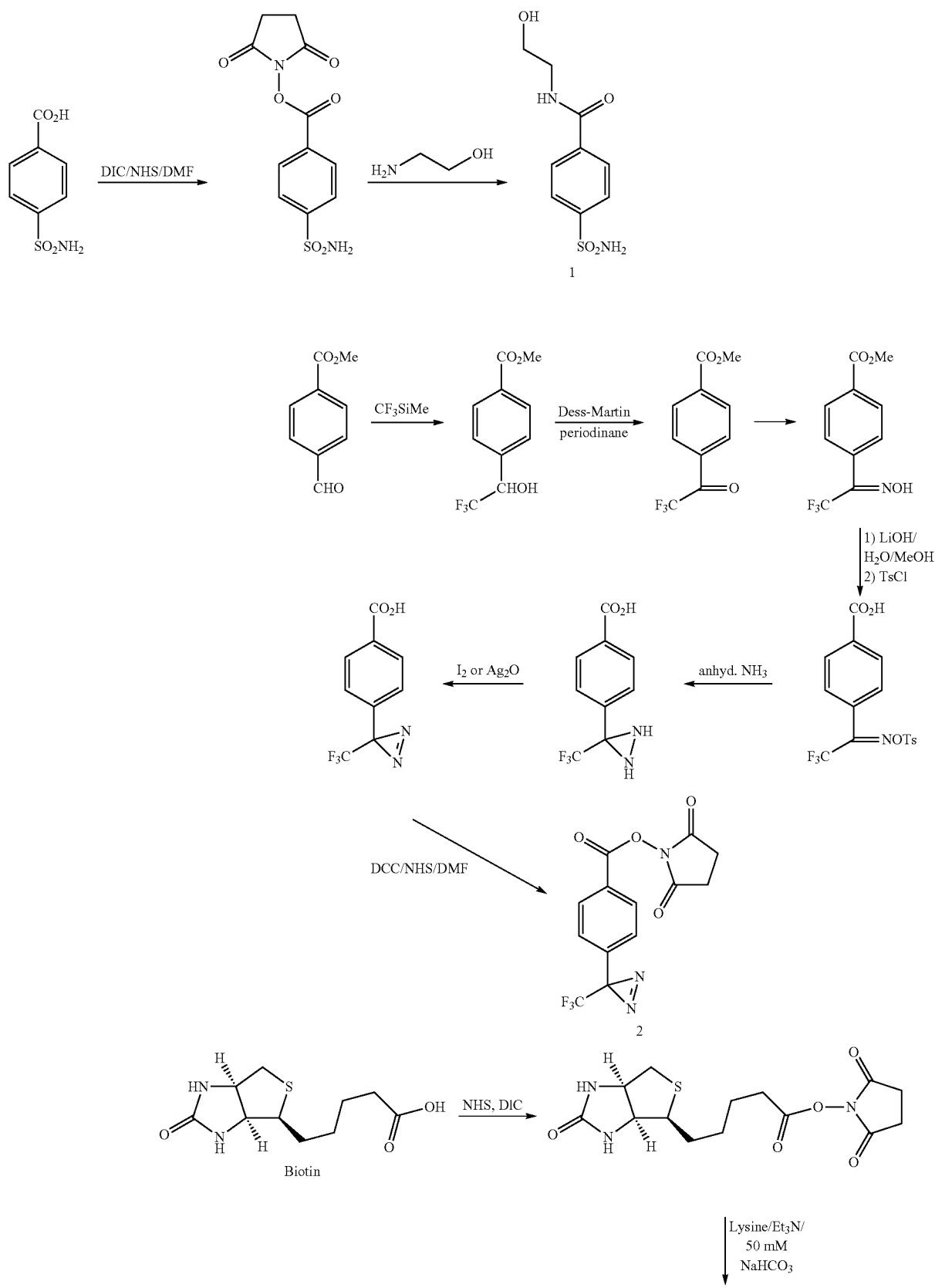

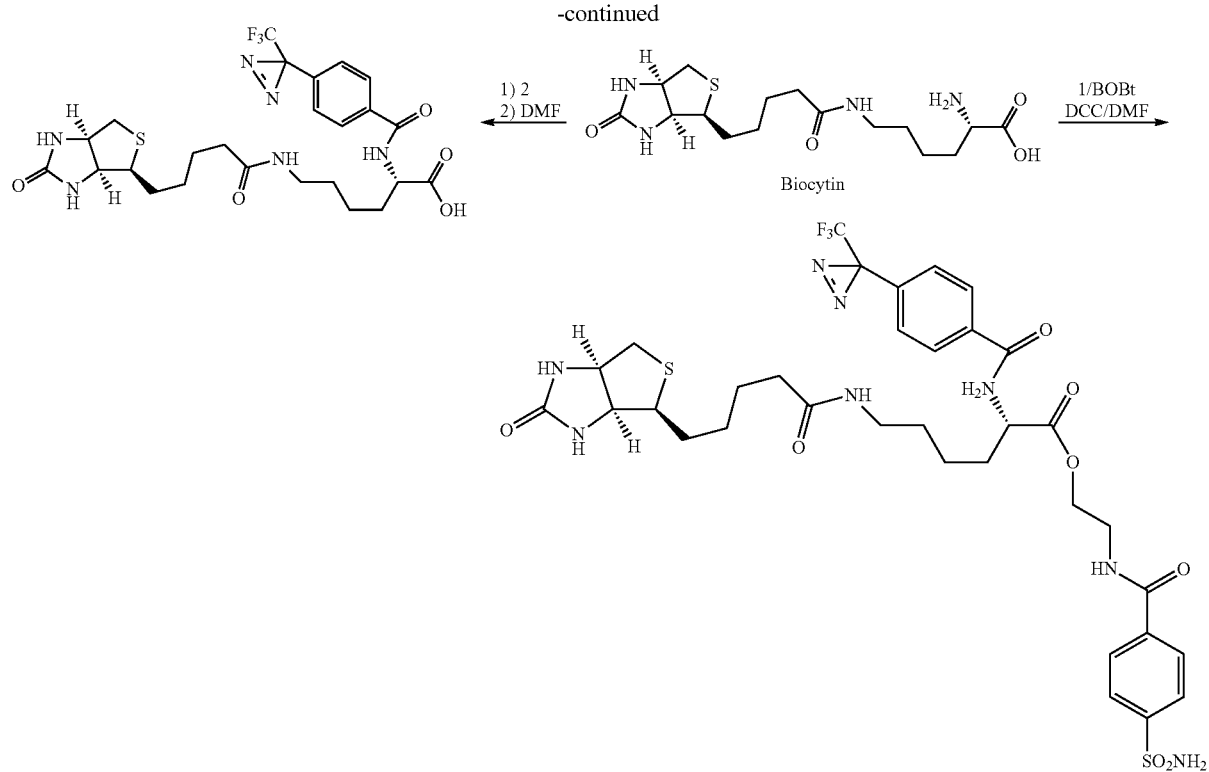
Other photoactivatable capture compounds may be prepared as follows:

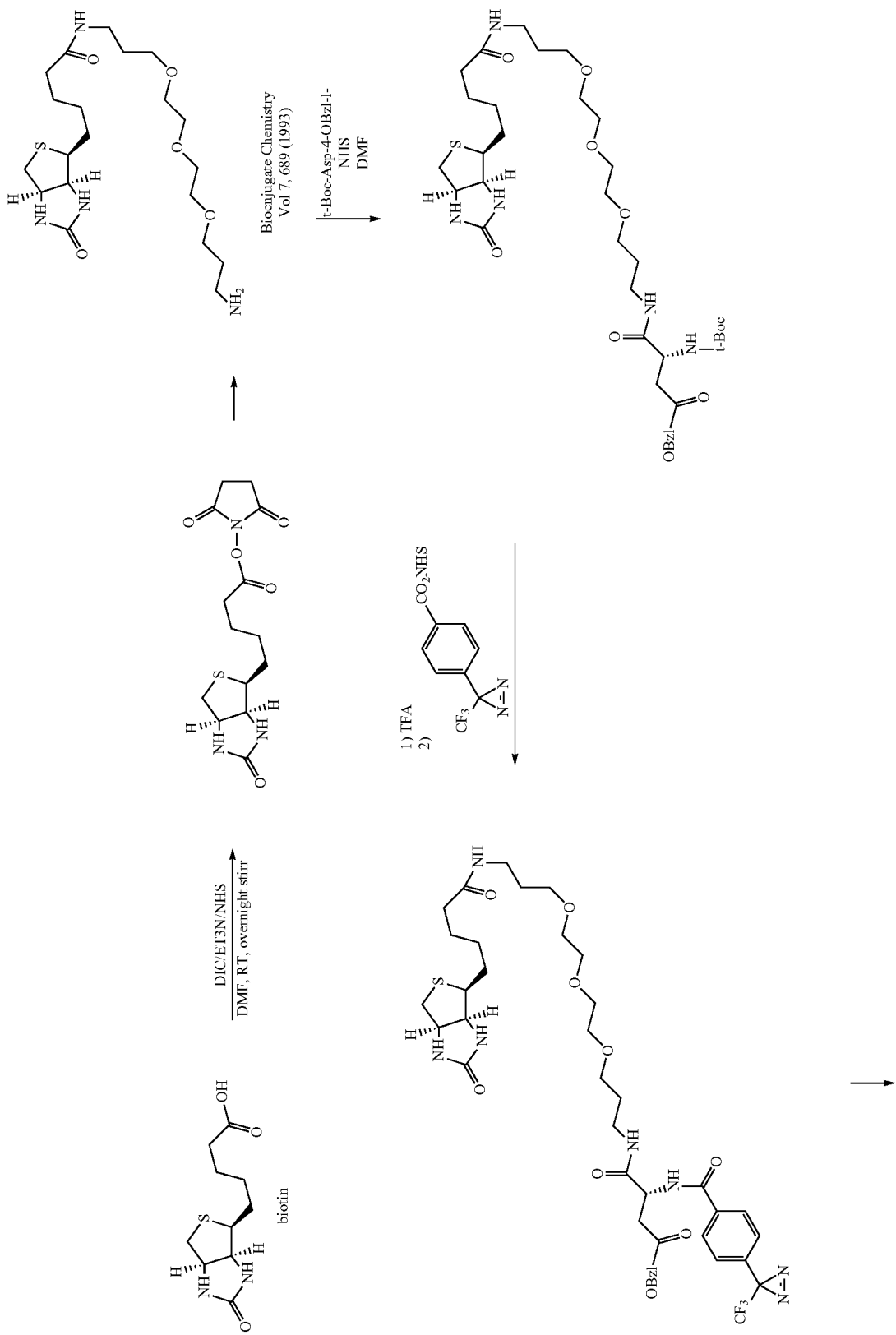

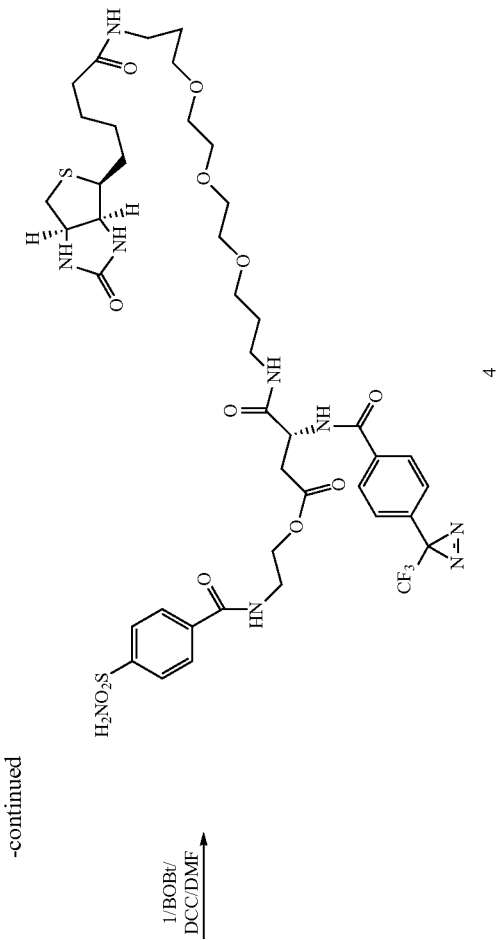
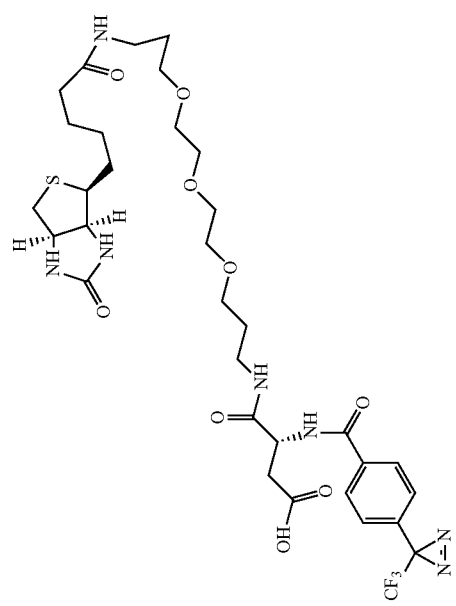
1/BOBt/
DCC/DMF

The above syntheses are exemplary only. One of skill in the art will be able to modify the above syntheses in a routine manner to synthesize other compounds within the scope of the instant disclosure. Syntheses of capture compounds as provided herein are within the skill of the skilled artisan.

E. Methods of Use of the Compounds

The capture compounds provided herein can be used for the analysis, quantification, purification and/or identification of the components of biomolecule mixtures, including, but not limited to, protein mixtures. They can be used to screen libraries of small molecules to identify drug candidates, and they can be used to assess biomolecule-biomolecule interactions and to identify biomolecule complexes and intermediates, such as those in biochemical pathways and other biological intermediates.

Figure 20A:
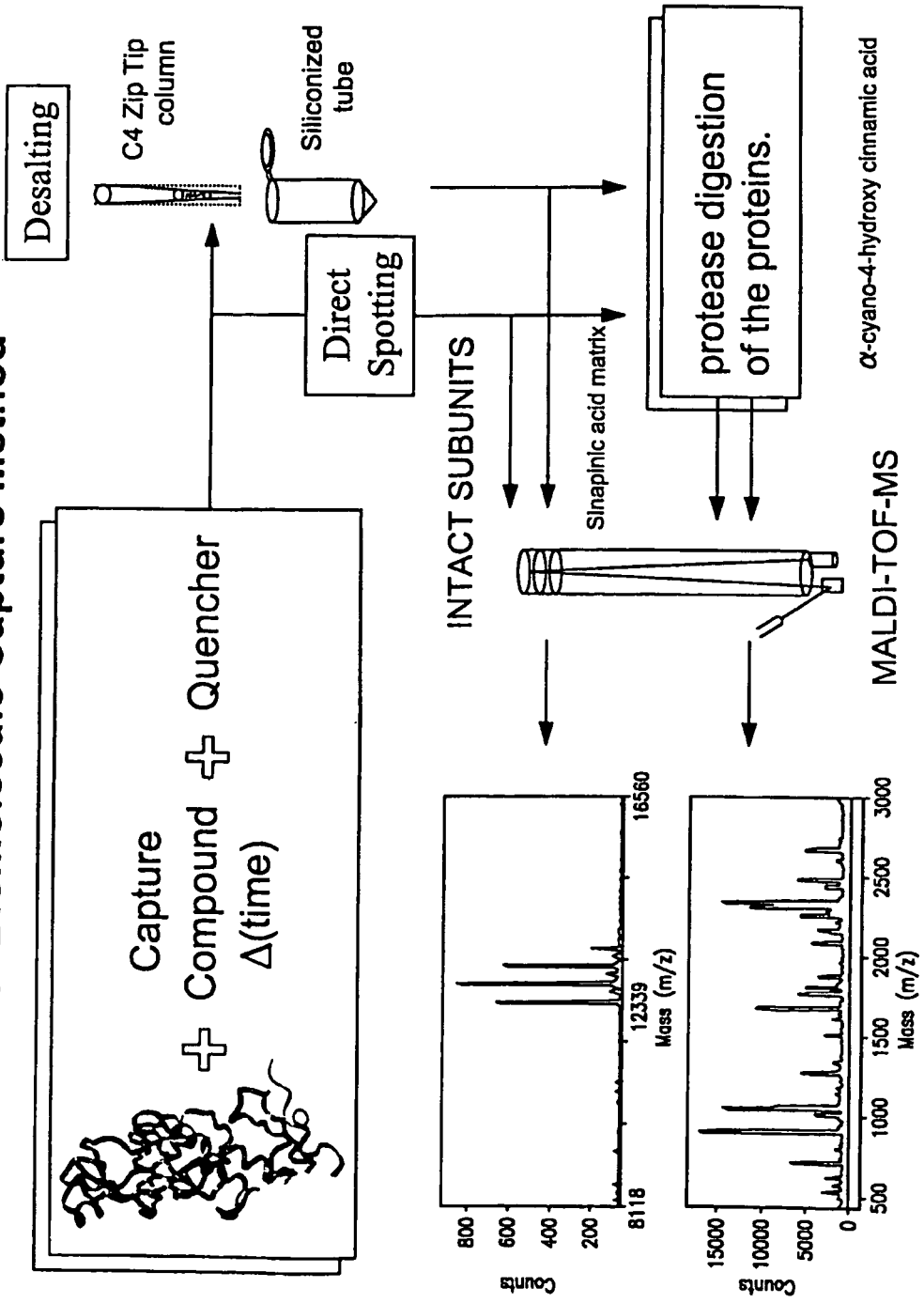

To initiate an analytical process, mixtures of biomolecules are obtained or prepared. They can then be pre-purified or partially purified as needed, according to standard procedures. Biomolecules are isolated from samples using standard methods. FIG. 20a depicts an exemplary capture assay in which capture compounds are bound to biomolecules and analyzed by MALDI-TOF MS. Example 9 and FIGS. 20b-f show results of exemplary assays using a variety of capture compounds and known proteins.

1. General Methods

The collections provided herein have a wide variety of applications, including reducing the complexity of mixtures of molecules, particularly biomolecules, by contacting the collection with the mixtures to permit covalent binding of molecules in the mixtures. The capture compounds can be arrayed by virtue of the sorting function either before, during or after the contacting. Following contacting and arraying the loci of the array each contain a subset of the molecules in the mixture. The array can then be analyzed, such as by using mass spectrometry.

For example, proteins are isolated from biological fluids and/or tissues by cell lysis followed, for example, by either precipitation methods (e.g., ammonium sulfate) or enzymatic degradation of the nucleic acids and carbohydrates (if necessary) and the low molecular weight material is removed by molecular sieving. Proteins also can be obtained from expression libraries. Aliquots of the protein mixture are reacted with the collections of capture compounds, generally members of the collection have different functionalities, such as different reactivity and/or selectivity, to separate the mixture into separate protein families according to the selected reactivity of X or the reactivity function plus the selectivity function. The diversity (number of different) selected for the sorting function Q depends on the complexity of the target mixture of biomolecules, such as proteins. Hence, for example, where there are sets of compounds differing in X and Y, solubility function and Q is an oligonucleotide, B is selected of an appropriate length to provide for sufficient number loci in the resulting array so that ultimately each "spot" on the array has about 5 to 50 or so biomolecules bound to a particular capture compound. In general, although not necessarily, all capture compounds with a particular "Q" are the same, so that each "spot" on the resulting array contains the same capture compounds. There, however, are embodiments, in which a plurality of different capture compounds can have the same Q functionality.

As noted, an array encompasses not only 2-D arrays on solid supports but any collection that is addressable or in which members are identifiable, such as by tagging with colored beads or RF tags or chemical tags or symbologies on beads. "Spots" are loci on the array, collections where capture compounds are sorted according to their "Q" function are separated.

In certain embodiments, the analysis is conducted using the smallest possible number of reactions necessary to completely analyze the mixture. Thus, in these embodiments, selection of the diversity of Q and of the number of X and X/Y groups of different reactivity will be a function of the complexity of the biomolecule mixture to be analyzed. Minimization of the diversity of B and the number of X and/or X/Y groups allows for complete analysis of the mixture with minimal complexity.

The separation of proteins from a complex mixture is achieved by virtue of the compound-protein products bound to different members of the collection. The supernatant, which contains the capture compound-protein products, is contacted with support bound or otherwise labeled or addressed recipient molecules, such as oligonucleotides on a support and allowed to bind, such as by hybridization to an array of complementary oligonucleotides. In one embodiment, a flat solid support that carries at spatially distinct locations, an array of oligonucleotides or oligonucleotide analogs that is complementary to the selected $N^1_m B_i N^2_n$ oligonucleotide or oligonucleotide analog, is hybridized to the capture compound-biomolecule products.

In embodiments where Z is an insoluble support or substrate, such as a bead, separation of the compound-protein products into an addressable array can be achieved by sorting into an array of microwell or microtiter plates, or other microcontainer arrays or by labeling with an identifiable tag. The microwell or microtiter plates, or microcontainers, can include single-stranded oligonucleotides or oligonucleotide analogs that are complementary to the oligonucleotide or oligonucleotide analog Q.

After reaction or complexation of the compounds with the proteins, any excess compounds can be removed by adding a reagent designed to act as a "capturing agent." For example, a biotinylated small molecule, which has a functionality identical or similar to that reacted with the selected X, is allowed to react with any excess compound. Exposure of this mixture to streptavidin bound to a magnetic bead, allows for removal of the excess of the compounds.

Hybridization of the compound-protein products to a complementary sequence is effected according to standard conditions (e.g., in the present of chaotropic salts to balance $T_m$ values of the various hybrids). Any non-hybridized material can be washed off and the hybridized material analyzed.

In further embodiments, the methods herein use mixtures of the compounds provided herein that have permuted Q groups to achieve sorting of the biomolecules following reaction with the compounds. These mixtures of compounds, in certain embodiments, have subsets (e.g., 64 or 256 or 1024) of different X reagents out of the 4' permutations in Q, where i is the number of nucleotides or analogs thereof contained in the B moiety of Q (e.g., 65,536 permutations for i=8). Reaction of the subsets separately with an aliquot of the biomolecule mixture to be analyzed results in conjugate mixtures that can be aligned with, e.g., a microtiter plate format (e.g., 96, 384 1536, etc.). Analysis using these subsets of compound mixtures provides further sorting of the biomolecules prior to analysis.

In other embodiments, selective pooling of the products of different X moiety-containing reagents (e.g., amino- and thiol-reactive X groups; antibody and amino-reactive X groups; antibody and lectin X groups, etc.) can be performed for combined analysis on a single assay (e.g., on a single chip).

FIG. 1 depicts an exemplary method for separation and analysis of a complex mixture of proteins by use of MALDI-TOF mass spectrometry. Exposure of a compound as described herein, to a mixture of biomolecules, including, but not limited to, proteins (P1 to P4), affords a compound-protein array (NA=oligonucleotide moiety or oligonucleotide analog moiety, L=cleavable linker, P=protein). Separation of the array is effected by hybridization of the Q portion of the array to a complementary sequence attached to a support, such as an oligonucleotide chip. The proteins (P1 to P4) are then analyzed by MALDI-TOF mass spectrometry.

When the complexity of a mixture of biomolecules, including, but not limited to, proteins, is low, affinity chromatographic or affinity filtration methods can be applied to separate the compound-protein products from the protein mixture. If the proteins to be analyzed were fluorescently labeled prior to (or after) reaction with the compound but prior to hybridization, these labeled proteins also can be detected on the array. In this way the positions that carry a hybrid can be detected prior to scanning over the array with MALDI-TOF mass spectrometry and the time to analyze the array minimized. Mass spectrometers of various kinds can be applied to analyze the proteins (e.g., linear or with reflection, with or without delayed extraction, with TOF, Q-TOFs or Fourier Transform analyzer with lasers of different wavelengths and xy sample stages).

Mass spectrometry formats for use herein, include, but are not limited to, matrix assisted laser desorption ionization (MALDI), continuous or pulsed electrospray (ES) ionization, ionspray, thermospray, or massive cluster impact mass spectrometry and a detection format such as linear time-of-flight (TOF), reflectron time-of-flight, single quadruple, multiple quadruple, single magnetic sector, multiple magnetic sector, Fourier transform, ion cyclotron resonance (ICR), ion trap, and combinations thereof such as MALDITOF spectrometry. For example, for ES, the samples, dissolved in water or in a volatile buffer, are injected either continuously or discontinuously into an atmospheric pressure ionization interface (API) and then mass analyzed by a quadrupole. The generation of multiple ion peaks that can be obtained using ES mass spectrometry can increase the accuracy of the mass determination. Even more detailed information on the specific structure can be obtained using an MS/MS quadrupole configuration.

Methods for performing MALDI are known to those of skill in the art. Numerous methods for improving resolution are also known. For example, resolution in MALDI TOF mass spectrometry can be improved by reducing the number of high energy collisions during ion extraction (see, e.g., Juhasz et al. (1996) Analysis, Anal. Chem. 68:941946, see also, e.g., U.S. Pat. No. 5,777,325, U.S. Pat. No. 5,742,049, U.S. Pat. No. 5,654,545, U.S. Pat. No. 5,641,959, U.S. Pat. No. 5,654,545, U.S. Pat. No. 5,760,393 and U.S. Pat. No. 5,760,393 for descriptions of MALDI and delayed extraction protocols). Conditioning of molecules to be analyzed or of the capture-compound bound biomolecules prior to analysis also can be employed.

In MALDI mass spectrometry (MALDI-MS), various mass analyzers can be used, e.g., magnetic sector/magnetic deflection instruments in single or triple quadrupole mode (MS/MS), Fourier transform and time-of-flight (TOF), including orthogonal time-of-flight (O-TOF), configurations as is known in the art of mass spectrometry. For the desorption/ionization process, numerous matrix/laser combinations can be used. Ion trap and reflectron configurations also can be employed.

MALDI-MS requires the biomolecule to be incorporated into a matrix. It has been performed on polypeptides and on nucleic acids mixed in a solid (i.e., crystalline) matrix. The matrix is selected so that it absorbs the laser radiation. In these methods, a laser, such as a UV or IR laser, is used to strike the biomolecule/matrix mixture, which is crystallized on a probe tip or other suitable support, thereby effecting desorption and ionization of the biomolecule. In addition, MALDI-MS has been performed on polypeptides, glycerol, and other liquids as a matrix.

A complex protein mixture can be selectively dissected, and in taking all data together, completely analyzed through the use of compounds with different functionalities X. The proteins present in a mixture of biological origin can be detected because all proteins have reactive functionalities present on their surfaces. If at each position on the compound-protein array, there is the same protein cleavable under the same conditions as L or is added without covalent attachment to the solid support and serving as an internal molecular weight standard, the relative amount of each protein (or peptide if the protein array was enzymatically digested) can be determined. This process allows for the detection of changes in expressed proteins when comparing tissues from healthy and disease individuals, or when comparing the same tissue under different physiological conditions (e.g., time dependent studies). The process also allows for the detection of changes in expressed proteins when comparing different sections of tissues (e.g., tumors), which can be obtained, e.g., by laser bioposy.

Protein-protein interactions and protein-small molecule (e.g., drug) interactions can be studied by contacting the compound-protein array with a mixture of the molecules of interest. In this case, a compound will be used that has no cleavable linkage L, or that has a linkage L that is stable under MALDI-TOF MS conditions. Subsequent scanning of the array with the mass spectrometer demonstrates that hybridized proteins of the protein array have effectively interacted with the protein or small molecule mixtures of interest.

Analysis using the well known 2-hybrid methodology is also possible and can be detected via mass spectrometry. See, e.g., U.S. Pat. Nos. 5,512,473, 5,580,721, 5,580,736, 5,955, 280, 5,695,94. See also, Brent et al. (1996) Nucleic Acids Res. 24(17):3341-3347.

In the above embodiments, including those where Z contains a cleavable linkage, the compounds can contain a mass modifying tag. In these embodiments, the mass modifying tag is used to analyze the differences in structure (e.g., side chain modification such as phosphorylation or dephosphorylation) and/or expression levels of biomolecules, including proteins. In one embodiment, two compounds (or two sets of compounds having identical permuted B moieties) are used that only differ in the presence or absence of a mass modifying tag (or have two mass tags with appropriate mass differences). One compound (or one set of compounds) is (are) reacted with "healthy" tissue and the mass modified compound(s) are reacted with the "disease" tissue under otherwise identical conditions. The two reactions are pooled and analyzed in a duplex mode. The mass differences will elucidate those proteins that are altered structurally or expressed in different quantity in the disease tissue. Three or more mass modifying tags can be used in separate reactions and pooled for multiplex analysis to follow the differences during different stages of disease development (i.e., mass modifying tag 1 at time point 1, mass modifying tag 2 at time point 2 etc.), or, alternatively, to analyze different tissue sections of a disease tissue such as a tumor sample.

Selectivity in the reaction of the compounds provided herein with a biomolecule, such as a protein mixture also can be achieved by performing the reactions under kinetic control and by withdrawing aliquots at different time intervals. Alternatively, different parallel reactions can be performed (for example, all differing in the B moiety of the Q group) and either performed with different stoichiometric ratios or stopped at different time intervals and analyzed separately.

In embodiments where the capture compounds provided herein possess a luminescent or colorimetric group, the immobilized compound-biomolecule conjugate can be viewed on the insoluble support prior to analysis. Viewing the conjugate provides information about where the conjugate has hybridized (such as for subsequent MALDI-TOF mass spectrometric analysis). In certain embodiments, with selected reagents the quantity of a given protein from separate experiments (e.g., healthy vs. disease, time point 1 vs. time point 2, etc.) can be determined by using dyes that can be spectrophotometrically differentiated.

Figure 3:
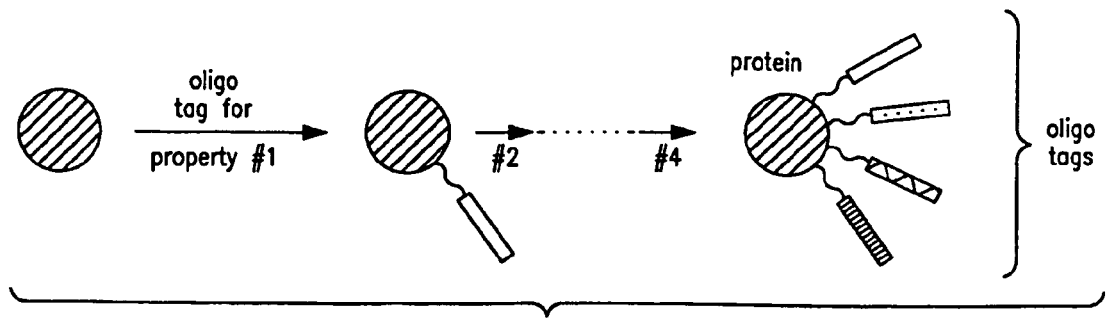
FIG. 3 illustrates a protein tagged with four compounds provided herein, thereby allowing for specific sorting of the protein.

In other embodiments, the methods are performed by tagging the biomolecules to be analyzed, including but not limited to proteins, with more than one, in one embodiment three to five, of the compounds provided herein. Such compounds possess functionality designed to target smaller chemical features of the biomolecules rather than a macromolecular feature. See, e.g., FIG. 3. Such smaller chemical features include, but are not limited to, $NH_2$, SH, SS (after capping SH, SS can be targeted by, e.g., gold), and OH. In one non-limiting example, the phenolic OH of tyrosine is selectively captured using a diazo compound, such as an aryldiazonium salt. In this embodiment, the reaction can be performed in water. For example, a functionalized diazonium salt could be used where the functionality allows for subsequent capture of a compound provided herein, thereby providing a oligonucleotide-labelled biomolecule. One such functionalized diazonium salt is:

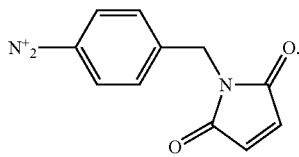

Figure 5:
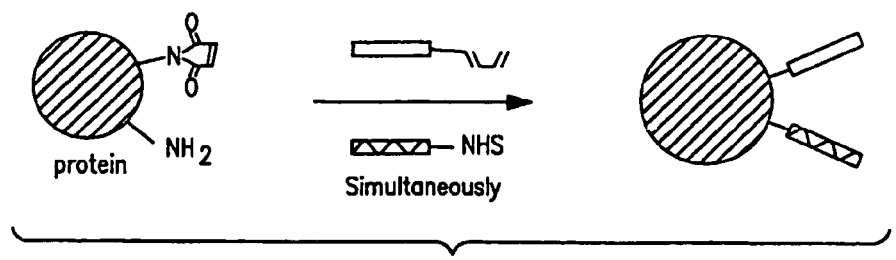
FIG. 5 shows tagging of a single protein with two different oligonucleotides in one reaction.

A biomolecule modified with this reagent is then labelled with an oligonucleotide possessing a diene residue. It is appreciated by those of skill in the art that many reagent couples other that dienophile/diene can be used in these embodiments. In the case of dienophile/diene, the reaction of the dienophile with the diene can be performed in the presence of many other functional groups, including N-hydroxysuccinimido-activated oligonucleotides reacting with an $NH_2$ group. Thus, these two labelling specific reactions can be performed in one reaction. See, e.g., FIG. 5.

Figure 4:
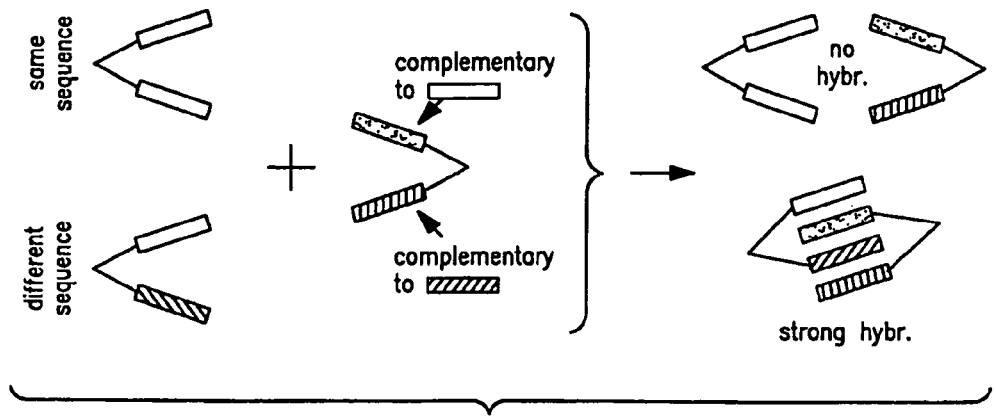
FIG. 4 shows the increased and specific hybridization resulting from use of two or more oligonucleotide tags.

Subsequently, the multiply-tagged biomolecules are hybridized on an array of antisense oligonucleotides, in one embodiment a chip containing an array of antisense oligonucleotides. Such multiply-tagged biomolecules can be sorted with greater selectivity than singly tagged biomolecules. See, e.g., FIG. 4.

In embodiments where the compounds for use in the methods provided herein are insoluble or poorly soluble in water or aqueous buffers, organic solvents are added to the buffers to improve solubility. In one embodiment, the ratio of buffer: organic solvent is such that denaturation of the biomolecule does not occur. In another embodiment, the organic solvents used include, but are not limited to, acetonitrile, formamide and pyridine. In another embodiment, the ratio of buffer: organic solvent is about 4:1. To determine if an organic co-solvent is needed, the rate of reaction of the compounds provided herein with a water-soluble amine, such as 5'-aminothymidine, is measured. For example, the following reaction is performed is a variety of solvent mixtures well known to those of skill in the art to determine optimal conditions for subsequent biomolecule tagging and analysis:

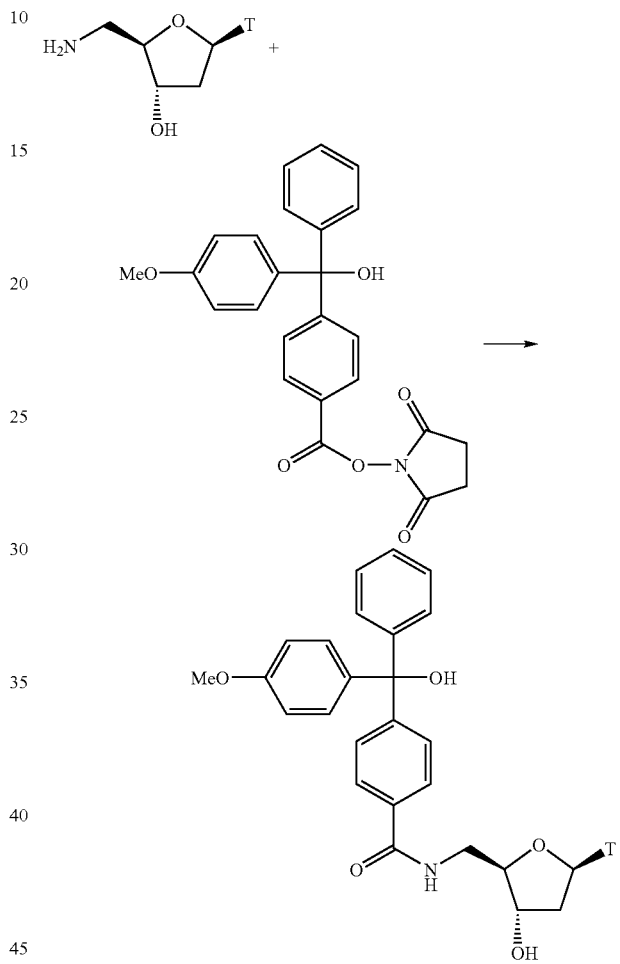

2. Phenotype Analyses

The collections of capture permit a top down holistic approach to analysis of the proteome and other biomolecules. As noted, the collections and methods of use provide an unbiased way to analyze biomolecules, since the methods do not necessarily assess specific classes of targets, but rather detect or identify changes in the samples. The changes identified include structural changes that are related to the primary sequences and modifications, including post-translational modifications. In addition, since the capture compounds can include a solubility function they can be designed for reaction in hydrophobic conditions, thereby permitting analysis of membrane-bound and membrane-associated molecules, particularly proteins.

Problems with proteome analysis arise from genetic variation that is not related to a target phenotype, proteome variation due to differences, such as gender, age, metabolic state, the complex mixtures of cells in target tissues and variations from cell cycle stage. Thus, to identify or detect changes, such as disease-related changes, among the biomolecule components of tissues and cells, homogeneity of the sample can be important. To provide homogeneity, cells, with different phenotypes, such as diseased versus healthy, from the same individual are compared. As a result, differences in patterns of biomolecules can be attributed to the differences in the phenotype rather than from differences among individuals. Hence, samples can be obtained from a single individual and cells with different phenotypes, such as healthy versus diseased and responders versus non-responders, are separated. In addition, the cells can be synchronized or frozen into a metabolic state to further reduce background differences.

Figure 19A:
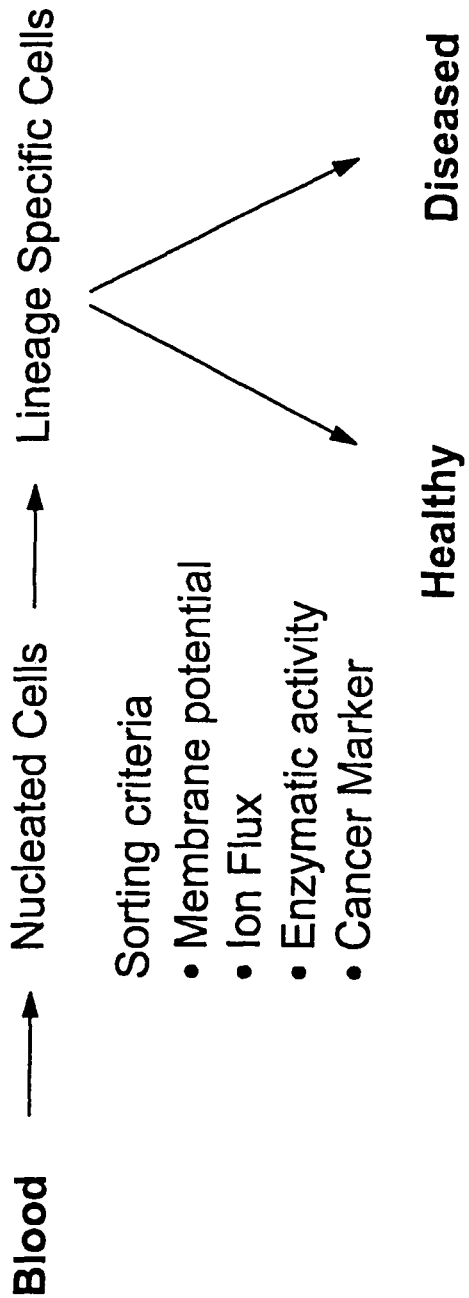
FIGS. 19a-c depict cell separation and synchronization methods.
Figure 19B:
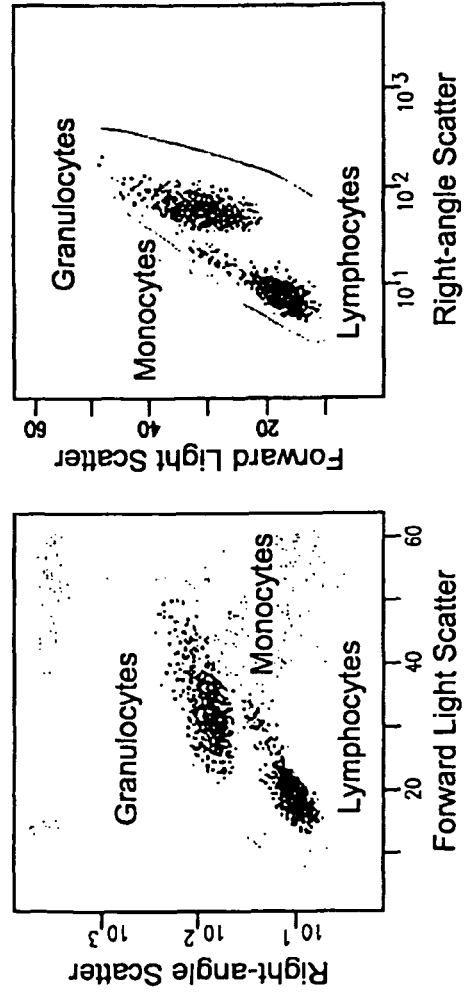
Figure 19C:
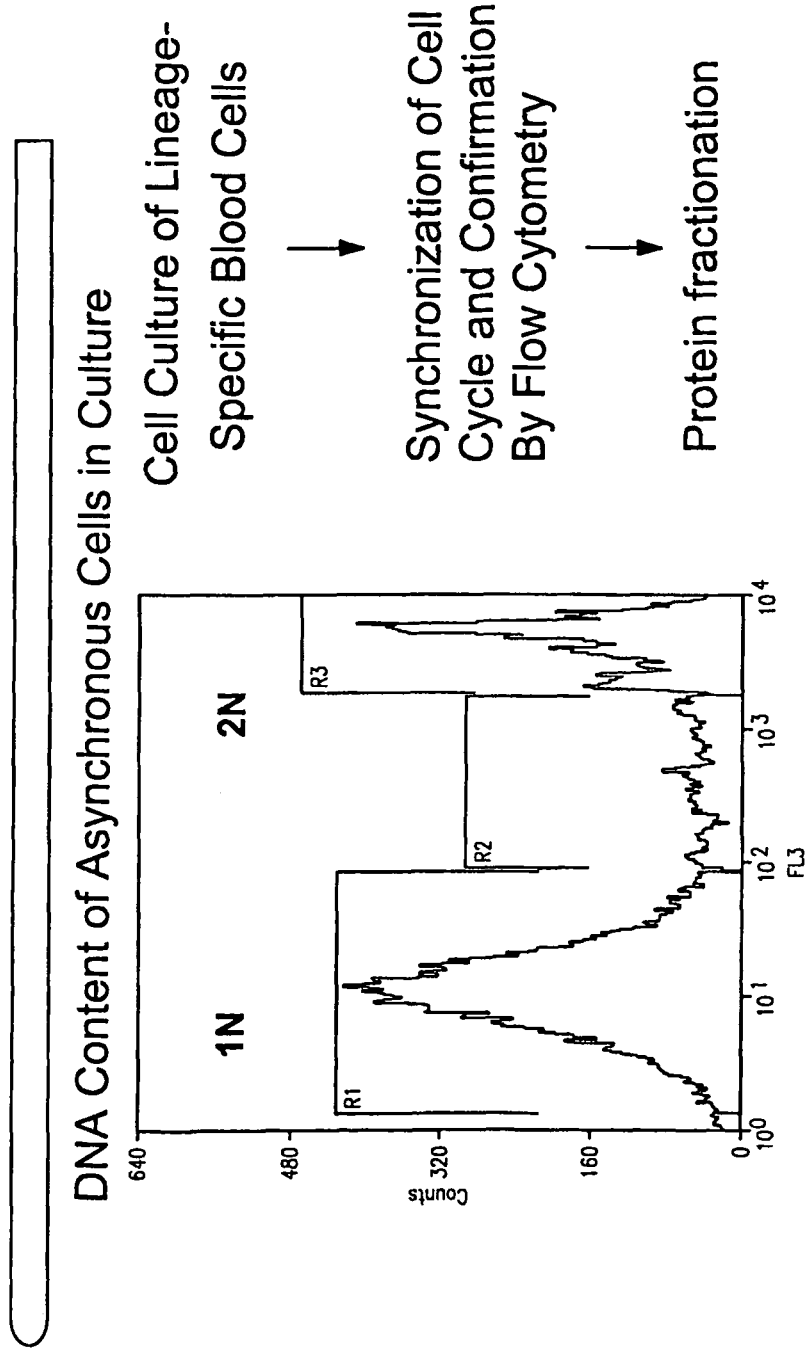

Thus, the collections of capture compounds can be used to identify phenotype-specific proteins or modifications thereof or other phenotype-specific biomolecules and patterns thereof. This can be achieved by comparing biomolecule samples from cells or tissues with one phenotype to the equivalent cells to biomolecule samples from cells or tissues with another phenotype. Phenotypes in cells from the same individual and cell type are compared. In particular, primary cells, primary cell culture and/or synchronized cells are compared. The patterns of binding of biomolecules from the cells to capture compound members of the collection can be identified and used as a signature or profile of a disease or healthy state or other phenotypes. The particular bound biomolecule, such as a protein, also can be identified and new disease-associated markers, such as particular proteins or structures thereof, can be identified. Example 6 provides an exemplary embodiment in which cells are separated. See also FIG. 19.

Phenotypes for comparison include, but are not limited to:

1) samples from diseased versus healthy cells or tissues to identify proteins or other biomolecules associated with disease or that are markers for disease;

2) samples from drug responders and non responders (i.e. on 20-30% of malignant melanoma patients respond to alpha interferon and others to do not) to identify biomolecules indicative of response;

3) samples from cells or tissues with a toxicity profile to drugs or environmental conditions to identify biomolecules associated with the response or a marker of the response; and 4) samples from cells or tissues exposed to any condition or exhibiting any phenotype in order to identify biomolecules, such as proteins, associated with the response or phenotype or that are a marker therefor.

Generally the samples for each phenotype are obtained from the same organism, such as from the same mammal so that the cells are essentially matched and any variation should reflect variation due to the phenotype and not the source of the cells. Samples can be obtained from primary cells (or tissues). In all instances, the samples can be obtained from the same individual either before exposure or treatment or from healthy non-diseased tissue in order to permit identification of phenotype-associated biomolecules.

Cells can be separated by any suitable method that permits identification of a particular phenotype and then separation of the cells based thereon. Any separation method, such as, for example, panning or negative panning (where unwanted cells are captured and the wanted cells remain in the supernatant) where the live cells are recovered can be used. These methods include, but are not limited to:

1) flow cytometry;
2) specific capture;
3) negative panning in which unwanted cells are captured and the targeted cells remain in the supernatant and live cells are recovered for analysis; and 4) Laser Capture Microdissection (LCM) (Arcturus, Inc Mountain View, Calif.).

Thus sorting criteria include, but are not limited to, membrane potential, ion flux, enzymatic activity, cell surface markers, disease markers, and other such criteria that permit separation of cells from an individual based on phenotype.

a) Exemplary Separation Methods

1) Laser Capture Microdissection

Laser Capture Microdissection (LCM) (Arcturus, Inc Mountain View, Calif.) uses a microscope platform combined with a low-energy IR laser to activate a plastic capture film onto selected cells of interest. The cells are then gently lifted from the surrounding tissue. This approach precludes any absorption of laser radiation by microdissected cells or surrounding tissue, thus ensuring the integrity of RNA, DNA, and protein prepared from the microdissected samples for downstream analysis.

2) Flow Cytometry for Separation

Flow cytometry is a method, somewhat analogous to fluorescent microscopy, in which measurements are performed on particles (cells) in liquid suspension, which flow one at a time through a focused laser beam at rates up to several thousand particles per second. Light scattered and fluorescence emitted by the particles (cells) is collected, filtered, digitized and sent to a computer for analysis. Typically flow cytometry measures the binding of a fluorochrome-labeled probe to cells and the comparison of the resultant fluorescence to the background fluorescence of unstained cells. Cells can be separated using a version of flow cytometry, flow sorting, in which the particles (cells) are separated and recovered from suspension based upon properties measured in flow. Cells that are recovered via flow sorting are viable and can be collected under sterile conditions. Typically, recovered subpopulations that are in excess of 99.5% pure (see FIGS. 19a and 19b).

Flow cytometry allows cells to be distinguished using various parameters, including physical and/or chemical characteristics associated with cells or properties of cell-associated reagents or probes, any of which are measured by instrument sensors. Separation: Live v. Dead Forward and side scatter are used for preliminary identification and gating of cell populations. Scatter parameters are used to exclude debris, dead cells, and unwanted aggregates. In a peripheral blood or bone marrow sample, lymphocyte, monocyte and granulocyte populations can be defined, and separately gated and analyzed, on the basis of forward and side scatter. Cells that are recovered via flow sorting are viable and can be collected under sterile conditions. Typically recovered subpopulations are in excess of 99.5% pure.

Common cell sorting experiments usually involve immunofluorescence assays, i.e., staining of cells with antibodies conjugated to fluorescent dyes in order to detect antigens. In addition, sorting can be performed using GFP-reporter constructs in order to isolate pure populations of cells expressing a given gene/construct.

a. Fluorescence

Fluorescent parameter measurement permits investigation of cell structures and functions based upon direct staining, reactions with fluorochrome labeled probes (e.g., antibodies), or expression of fluorescent proteins. Fluorescence signals can be measured as single or multiple parameters corresponding to different laser excitation and fluorescence emission wavelengths. When different fluorochromes are used simultaneously, signal spillover can occur between fluorescence channels. This is corrected through compensation. Certain combinations of fluorochromes cannot be used simultaneously; those of skill in the art can identify such combinations.

b. Immunofluorescence

Immunofluorescence involves the staining of cells with antibodies conjugated to fluorescent dyes such as FITC (fluorescein), PE (phycoerythrin), APC (allophycocyanin), and PE-based tandem conjugates (R670, CyChrome and others). Cell surface antigens are the usual targets of this assay, but antibodies can be directed at antigens or cytokines in the cytoplasm as well.

DNA staining is used primarily for cell cycle profiling, or as one method for measuring apoptosis. Propidium iodide (PI), the most commonly used DNA stain, cannot enter live cells and can therefore be used for viability assays. For cell cycle or apoptosis assays using PI, cells must first be fixed in order for staining to take place (see protocol). The relative quantity of PI-DNA staining corresponds to the proportion of cells in G0/G1, S, and G2/M phases, with lesser amounts of staining indicating apoptotic/necrotic cells. PI staining can be performed simultaneously with certain fluorochromes, such as FITC and GFP, in assays to further characterize apoptosis or gene expression. Gene Expression and Transfection can be measured indirectly by using a reporter gene in the construct. Green Fluorescent Protein-type constructs (EGFP, red and blue fluorescent proteins) and β-galactosidase, for example, can be used to quantify populations of those cells expressing the gene/construct. Mutants of GFP are now available that can be excited at common frequencies, but emit fluorescence at different wavelengths. This allows for measurement of co-transfection, as well as simultaneous detection of gene and antibody expression. Appropriate negative (background) controls for experiments involving GFP-type constructs should be included. Controls include, for example, the same cell type, using the gene insert minus the GFP-type construct.

3) Metabolic Studies and Other Studies

Annexin-V can be labeled with various fluorochromes in order to identify cells in early stages of apoptosis. CFSE binds to cell membranes and is equally distributed when cells divide. The number of divisions cells undergo in a period of time can then be counted. CFSE can be used in conjunction with certain fluorochromes for immunofluorescence. Calcium flux can be measured using Indo-1 markers. This can be combined with immunofluorescent staining. Intercellular conjugation assays can be performed using combinations of dyes such as calcein or hydroethidine.

b) Synchronizing Cell Cycles

Once sorted or separated cells are obtained they can be cultured, and, can be synchronized or frozen into a particular metabolic state. This enhances the ability to identify phenotype-specific biomolecules. Such cells can be separated by the above methods, including by flow cytometry. Further, cells in the same cell cycle, same metabolic state or other synchronized state can be separated into groups using flow cytometry (see, FIG. 19c).

Figure 18:
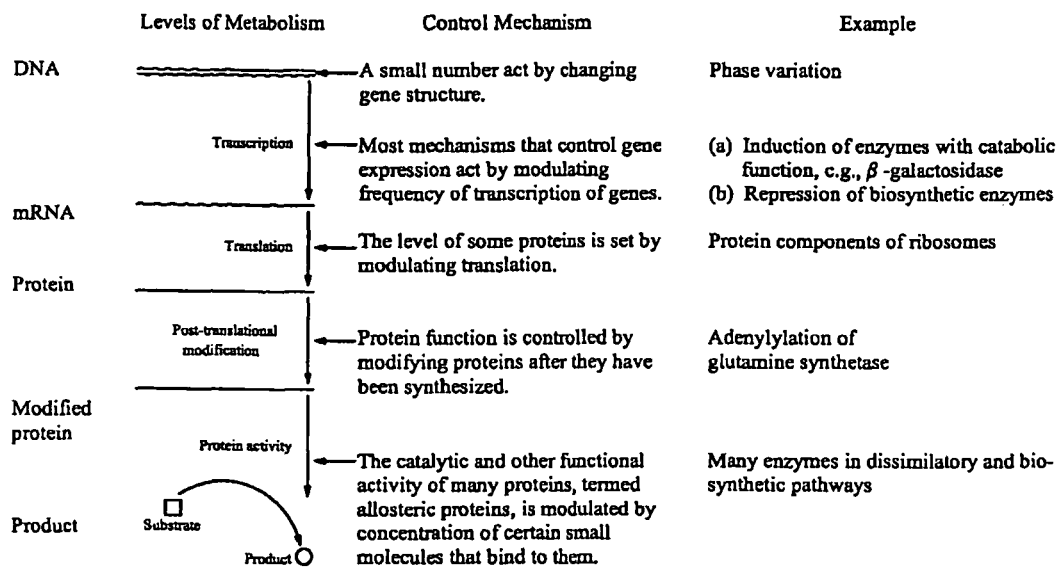
FIG. 18 depicts exemplary points for regulation of metabolic control mechanisms for cell synchronization.

Cell cycles can be synchronized or frozen by a variety of methods, including but are not limited to, cell chelation of critical ions, such as by removal of magnesium, zinc, manganese, cobalt and/or other ions that perform specific functions by EDTA or other chelators (see, e.g., EXAMPLES). Other methods include controlling various metabolic or biochemical pathways. FIG. 18 depicts exemplary points of regulation of metabolic control mechanisms for cell synchronization. Examples of synchronizing or "freezing" Metabolic Control for synchronizing cells, include, but are not limited to, the following:

1) control of gene expression;
2) regulation of enzyme reactions;
3) negative control: Feedback inhibition or End product repression and enzyme induction are mechanisms of negative control that lead to a decrease in the transcription of proteins;
4) positive control: catabolite repression is considered a form of positive control because it affects an increase in transcription of proteins.
5) Control of individual proteins translation:
   a) oligonucleotides that hybridize to the 5' cap site have inhibit protein synthesis by inhibiting the initial interaction between the mRNA and the ribosome 40S sub-unit;
   b) oligonucleotides that hybridize to the 5' UTR up to, and including, the translation initiation codon inhibit the scanning of the 40S (or 30S) subunit or assembly of the full ribosome (80S for eukaryotes or 70S for bacterial systems);
5) control of post translational modification:
6) control of allosteric enzymes, where the active site binds to the substrate of the enzyme and converts it to a product. The allosteric site is occupied by some small molecule that is not a substrate. If the protein is an enzyme, when the allosteric site is occupied, the enzyme is inactive, i.e., the effector molecule decreases the activity of the enzyme. Some multi-component allosteric enzymes have several sites occupied by various effector molecules that modulate enzyme activity over a range of conditions.

3. Analysis of Low Abundancy Proteins

Important disease-associated markers and targets could be low abundancy proteins, that might not be detected by mass spectrometry. To ensure detection, a first capture compound display experiment can be performed. The resulting array of captured proteins is reacted with a non-selective dye, such as a fluorescent dye, that will light up or render visible more proteins on the array. The dye can provide a semi-quantitative estimate of the amount of a protein. The number of different proteins detected by the dye can be determined and then compared the number detected by mass spectrometric analysis. If there are more proteins detected using the dye, the experiments can be repeated using a higher starting number of cells so that low abundance proteins can be detected and identified by the mass spectrometric analysis. For example, housekeeping proteins, such as actin and other such proteins, are present in high abundance and can mask low abundancy proteins. Capture compounds or other purification compound selected or designed to capture or remove the high abundancy proteins or biomolecules from a mixture before using a collection to assess the components of the mixture. Once the high abundancy proteins are removed, low abundancy proteins have an effectively higher concentration and can be detected. These methods, thus, have two steps: a first step to capture high abundancy components of biomolecule mixtures, such as the actins. For example, a cell lysate can be contacted with capture molecules that include a reactivity group such as biotin or other general reactivity function linked to a sorting group to remove such high abundancy proteins, and then use a suitable collection of capture compounds to identify lower abundancy compounds remaining in the lysate.

Also, as discussed above, capture compounds can be designed, such as by appropriate selection of W, to interact with intact organelles before disrupting them in cells that have been gently lysed or otherwise treated to permit access to organelles and internal membranes. Then the captured organelles can be disrupted, such as one which can include an artificial membrane, such as a lipid bilayer or micelle coating, to capture the organelle proteins and other biomolecules in an environment that retains their three-dimensional structure.

These captured proteins can be analyzed. This permits the capture compounds to interact with the captured proteins and other biomolecules in their native tertiary structure.

4. Monitoring Protein Conformation as an Indicator of Disease

The collections and/or members thereof can be used to detect or distinguish specific conformers of proteins. Hence, for example, if a particular conformation of a protein is associated with a disease (or healthy state) the collections or members thereof can detect one conformer or distinguish conformers based upon a pattern of binding to the capture compounds in a collection. Thus, the collections and/or members thereof can be used to detect conformationally altered protein diseases (or diseases of protein aggregation), where a disease-associated protein or polypeptide has a disease-associated conformation. The methods and collections provided herein permit detection of a conformer associated with a disease to be detected. These diseases include, but are not limited to, amyloid diseases and neurodegenerative diseases. Other diseases and associated proteins that exhibit two or more different conformations in which at least one conformation is associated with disease include those set forth in the following Table:

| Disease | Insoluble protein |
| --- | --- |
| Alzheimer's Disease (AD) | APP, Aα, α1-antichymotrypsin, tau, non-Aα component, presenellin 1, presenellin 2, apoE |
| Prion diseases, including but are not limited to, Creutzfeldt-Jakob disease, scrapie, bovine spongiform encephalopathy | PrP$^{Sc}$ |
| amyotrophic lateral sclerosis (ALS) | superoxide dismutase (SOD) and neurofilament |
| Pick's Disease | Pick body |
| Parkinson's disease | α-synuclein in Lewy bodies |
| Frontotemporal dementia | tau in fibrils |
| Diabetes Type II | amylin |
| Multiple myeloma Plasma cell dyscrasias | IgGL-chain |
| Familial amyloidotic polyneuropathy | Transthyretin |
| Medullary carcinoma of thyroid | Procalcitonin |
| Chronic renal failure | â$_2$-microgobulin |
| Congestive heart failure | Atrial natriuretic factor |
| Senile Cardiac and systemic amyloidosis | transthyretin |
| Chronic inflammation | Serum Amyloid A |
| Atherosclerosis | ApoAI |
| Familial amyloidosis | Gelsolin |
| Huntington's disease | Huntington |

The collections can be contacted with a mixture of the conformers and the members that bind or retain each form can be identified, and a pattern thus associated with each conformer. Alternatively, those that bind to only one conformer, such as the conformer associated with disease can be identified, and sub-collections of one or more of such capture compounds can be used as a diagnostic reagent for the disease.

5. Small Molecule Identification and Biomolecule-Biomolecule Interaction Investigation Biomolecules, such as proteins, are sorted using a covalent or noncovalent interaction with immobilized capture compounds. Collections, such as arrays of capture compounds bound to biomolecules, such as from cell lysates, then can be used to screen libraries or other mixtures of drug candidates or to further screen mixtures of biomolecules to see what binds to the bound biomolecules. The capture biomolecule-biomolecule complexes or biomolecule-drug candidate complexes can be analyzed to identify biochemical pathways and also to identify targets with the candidate drug.

For example, protein-protein or protein-biomolecule interactions are exposed to test compounds, typically small molecules, including small organic molecules, peptides, peptide mimetics, antisense molecules or dsRNA, antibodies, fragments of antibodies, recombinant and synthetic antibodies and fragments thereof and other such compounds that can serve as drug candidates or lead compounds. Bound small molecules are identified by mass spectrometry or other analytical methods.

6. Identification of Non-Target Biomolecules

Many pharmaceutical drugs have side effects that may arise from the interaction of the drugs, drug fragments, drug metabolites or prodrugs with drug non-target biomolecules under physiological conditions.

For example, aspirin reacts with the non-target Cox-1 receptor resulting in side effects such as gastrointestinal toxicity, ulceration, bleeding, perforation of the stomach, liver necrosis, hepatic failure, renal necrosis and possibly stroke and heart attack. Selective Cox-2 inhibitors such as Cox-2 inhibitors such as 4-[5-(4-methylphenyl)-3-(trifluoromethyl)-1H-pyrazol-1-yl]benzenesulfonamide, (Celebrex®) or 4-(4-(methylsulfonyl)phenyl)-3-phenyl-2(5H)-furanone (VIOXX®) have side effects that may be the result of interaction of the drug with non-target biomolecules. As another example, the thaizolidinedione (TDZ) class of antidiabetic drugs are PPAR-γ activators. The PPAR-γ protein is a receptor important in the regulation of genes involved in the metabolism of glucose and lipids. TDZs are prescribed to diabetic patients in whom blood sugar (glucose) is not properly metabolized. However, TDZ's are known to also interact with PPAR-α, a protein with a similar structure involved in the synthetic pathway of triglycerides, known to be associated with cardiovascular disease. The TDZ Rezulin was withdrawn from the market due to liver toxicity, and Actos and Avandia were recently reported in a Mayo Clinic study to have cardiovascular side effects.

Drug metabolites can also cause toxicity. There are several enzymatic systems responsible for drug metabolism. One such important system is the Cytochrome P450 family, primarily located in the liver. These proteins work by attaching functional groups to the (usually lipophilic) drug molecules. These functional groups subsequently allow other enzymes to conjugate moieties (glucuronidation, sulfation, etc.) to the metabolites rendering them water-soluble and thus facilitating excretion. Toxicity can occur if a polymorphic form of an enzyme involved in the metabolism malfunction, or a metabolite irreversibly inactivates a cytochrome p450 (suicide inhibition), compromising its excretion potentially leading to a toxic accumulation in the liver. Depending on the presence of these metabolizing enzyme systems in e.g. kidneys, lung, or heart, similar drug toxicities can be observed in those organs.

The capture compounds/collections thereof provided herein, can be used to identify the drug non-target biomolecules that interact with the pharmaceutical drugs/drug fragments, drug metabolites or prodrugs including but not limited to, receptors and enzymes. The identification and characterization of the drug interacting proteins can also lead to unexpected alternative pharmacological benefits. It is not unlikely that drug targets in other unexpected biological pathways would be found, which allow the application of the drug to treat other diseases. A failed drug that might not be efficacious (or too toxic) for one disease could be turned into a blockbuster for another disease.

In one embodiment, the capture compounds/collections thereof are designed to contain pharmaceutical drugs/drug fragments, drug metabolites or prodrugs as the selectivity function and suitable reactivity and sorting functionality. In the methods provided herein, the capture compound/collections thereof are allowed to interact with a mixture of drug target and non-target biomolecules, including but not limited to, receptor proteins. The captured biomolecules are then analyzed to identify drug target and non-target biomolecules. Screening and identification of drug non-target biomolecules can help in understanding side effects of the pharmaceutical drugs and permit modification of the drug structure to eliminate or minimize the side effects while maintaining the efficacy. Exemplary drug molecules that can be used in the methods and collections provided herein are set forth elsewhere herein, and include, but are not limited to, LIPITOR® (atorvastatin calcium), CELEBREX® (celecoxib), VIOXX® (refecoxib) and BAYCOL® (cerivastatin sodium).

Once a protein is identified to interact with the drug, public databases annotating the function of many proteins are queried to determine if that structure is likely related to the observed side effect or therapeutic response. For cases where the function of a protein is unknown, bioinformatics and functional genomic tools are available. These include in silico approaches (bioinformatics) including sequence alignment, pharmacophores, homology models and protein motif correlation; in vitro approaches including liver midrosomes metabolic pathways (e.g. P450), cDNA-expressed enzymes, signal pathways and back-mapping to yeast pathways, simulations and protein/protein interaction of pull-out proteins; in vivo approaches including native polymorphisms, knock-out/knock-in, flow cytometry, therapeutic activity of the drug (i.e. therapeutic profile and experimental toxicity, and prospective genotyping and prospective phenotyping. Using these in conjunction with cell-based assays and ribozyme-based knock-in/knock-out technology, which of the proteins identified above are associated with the therapeutic or toxic effect can be determined.

7. Drug Re-Engineering

An important goal of most drug development projects is to maximize the interaction between a drug and its target leading to positive therapeutic results, while minimizing interactions with other proteins. Interactions with proteins other than the intended target can trigger a cascade of cellular events leading to side effects. Provided herein are methods that enable design of drugs which interact with their intended target while minimizing other interactions. Here, the selectivity function of the capture compound is a drug molecule or one of its metabolites, attached in different chemically relevant orientations. Following the procedures described above, the proteins (target and non-targets) that interact with the drug and their respective putative function are identified, screening against all cell types potentially involved in the therapeutic or side-effect-related pathways. Knowledge of the therapeutic effect of the drug, as well as its side effects as previously observed in patients, facilitate the formation of a hypothesis as to which of the captured proteins lead to the desired therapeutic effect, and which are involved in its side effects.

Using these methods, one can iteratively optimize, or re-engineer, the chemical structure of the drug, maintaining or enhancing the desired target protein interactions and eliminating structural features leading to the non-target interactions. Since this process can take place even before preclinical trials, significant cost and time savings can be achieved. The result is a different and patentable new chemical entity (NCE), which can be re-introduced into clinical trials. A reduction of clinical trial time can be envisaged since efficacy data from the related parent drug molecule is already available, and the NCE has been structurally optimized for reduced side effects prior to entering the clinical trail process. An increased success rate of clinical trials would have a tremendous effect on reducing the time and especially the cost of drug development.

Using these methods, analysis is performed to identify the sets of all proteins interacting with the drug, and downstream cellular (functional) assays are used to validate which protein interactions are most likely responsible for the side effects. The drug compounds are redesigned considering data from all the drugs tested in the disease area to maintain the interaction with the protein leading to the positive therapeutic effect while minimizing other protein interactions.

Exemplary diseases that may be studies using these methods include:

(1) Diabetes. Diabetes and its major risk factor obesity will be a growing health crisis facing the western population in the coming decade. Rezulin (Troglitazone) has been withdrawn from the market, MK-767 was recently withdrawn from Phase III trials, and sales of other drugs (e.g. Actos, Avandia) have been hampered, all due to side effects.

(2) Cardiovascular. Nearly one million Americans die each year from cardiovascular diseases, many from heart attacks and strokes due to blocked arteries caused by elevated levels of cholesterol in the bloodstream. However the prescription rate of the statins, including Lipitor, is affected by side effects: patients taking these drugs must be monitored by their physician frequently to ascertain that toxic effects such as liver damage are not taking place.

(3) Arthritis/Pain/Inflammation. Reports of gastrointestinal and in some cases coronary side effects have limited sales of the anti-inflammatory COX-2 inhibitors Vioxx and Celebrex, as many doctors recommend that their patients take safer but far less effective drugs such as ibuprofen to ease inflammation symptoms.

F. Systems

In further embodiments, the compounds and the methods described herein are designed to be placed into an integrated system that standardizes and automates the following process steps:

Isolation of biomolecules from a biological source, including isolation of the proteins from cell lysates (lysis, enzymatic digestion, precipitation, washing)

Optionally, removal of low molecular weight materials

Optionally, aliquoting the biomolecule mixture, such as a protein mixture

Reaction of the biomolecule mixture, such as a protein mixture, with compounds of different chemical reactivity (X) and sequence diversity (B) provided herein; this step can be performed in parallel using aliquots of the biomolecule mixture Optionally, removal of excess compound Hybridization of the compound-biomolecule conjugate, such as a compound-protein conjugate, to single stranded oligonucleotides or oligonucleotide analogs that are complementary to the Q moiety of the compound; the single stranded oligonucleotides or oligonucleotide analogs are optionally presented in an array format and are optionally immobilized on an insoluble support Optionally, subsequent chemical or enzymatic treatment of the protein array Analysis of the biomolecule array, including, but not limited to, the steps of (i) deposition of matrix, and (ii)

spot-by-spot MALDI-TOF mass spectrometry using an array mass spectrometer (with or without internal, e.g., on-chip molecular weight standard for calibration and quantitation).

In another embodiment, the compounds and the methods described herein are designed to be placed into an integrated system that standardizes and automates the following process steps:

Isolation of biomolecules from a biological source, including isolation of the proteins from cell lysates (lysis, enzymatic digestion, precipitation, washing)

Optionally, removal of low molecular weight materials

Optionally, aliquoting the biomolecule mixture, such as a protein mixture

Reaction of the biomolecule mixture, such as a protein mixture, with compounds of different chemical reactivity (X) and sequence diversity (B) provided herein; this step can be performed in parallel using aliquots of the biomolecule mixture Optionally, removal of excess compound Chemical or enzymatic treatment of the protein array Subsequent hybridization of the compound-biomolecule conjugate, such as a compound-protein conjugate, to single stranded oligonucleotides or oligonucleotide analogs that are complementary to the Q moiety of the compound; the single stranded oligonucleotides or oligonucleotide analogs are optionally presented in an array format and are optionally immobilized on an insoluble support Analysis of the biomolecule array, including, but not limited to, the steps of (i) deposition of matrix, and (ii) spot-by-spot MALDI-TOF mass spectrometry using an array mass spectrometer (with or without internal, e.g., on-chip molecular weight standard for calibration and quantitation).

The systems include the collections provided herein, optionally arrays of such collections, software for control of the processes of sample preparation and instrumental analysis and for analysis of the resulting data, and instrumentation, such as a mass spectrometer, for analysis of the biomolecules. The systems include other devices, such as a liquid chromatographic devices so that a protein mixture is at least partially separated. The eluate is collected in a continuous series of aliquots into, e.g., microtiter plates, and each aliquot reacted with a capture compound provided.

In multiplex reactions, aliquots in each well can simultaneously react with one or more of the capture compounds provided herein that, for example each differ in X (i.e., amino, thiol, lectin specific functionality) with each having a specific and differentiating selectivity moiety Y and in the Q group. Chromatography can be done in aqueous or in organic medium. The resulting reaction mixtures are pooled and analyzed directly. Alternatively, subsequent secondary reactions or molecular interaction studies are performed prior to analysis, including mass spectrometric analysis.

Figure 2:
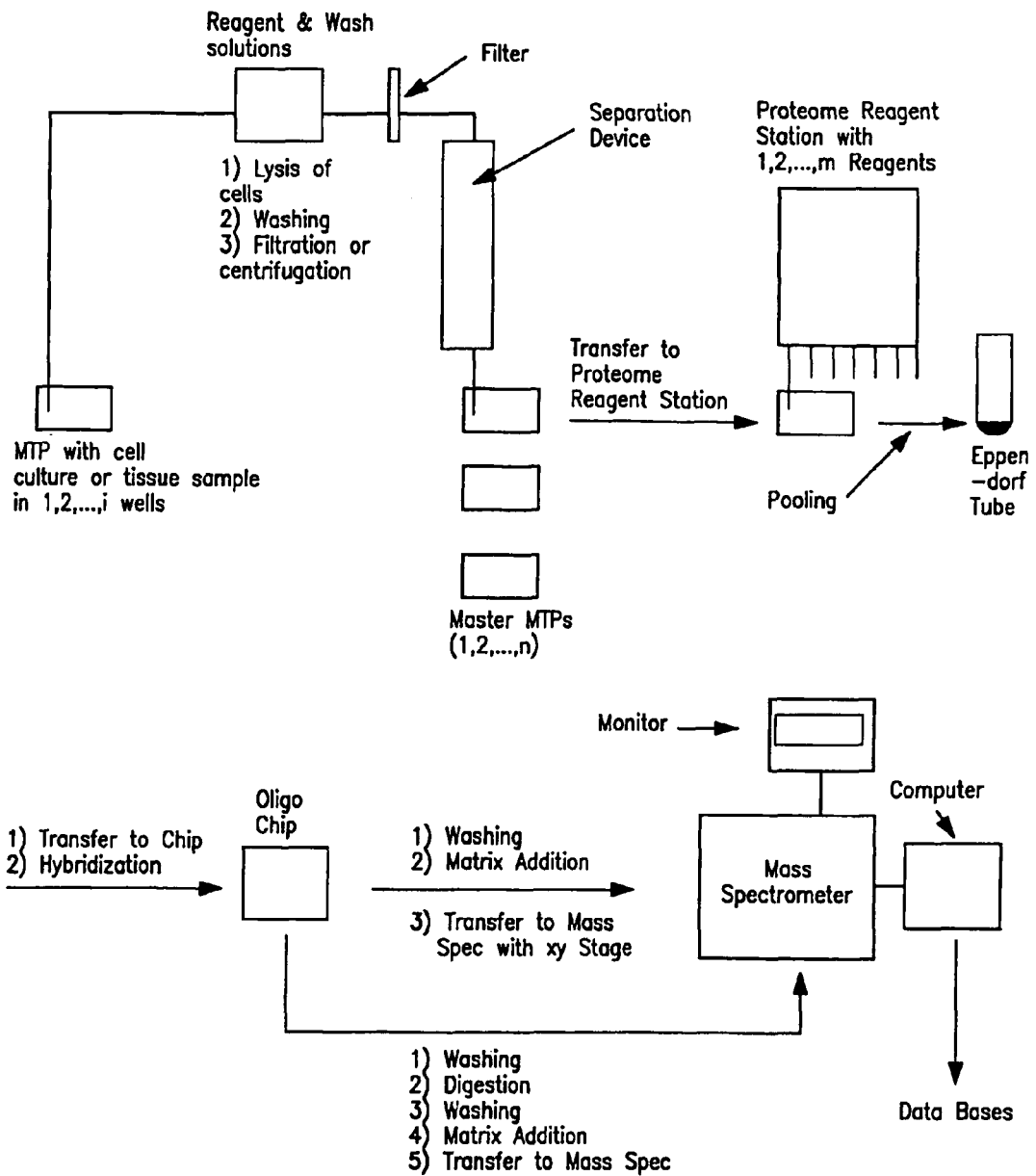
FIG. 2 provides a schematic depiction of one embodiment of the apparatus provided herein.

The systems provided herein can contain an assembly line, such as pipetting robots on xy stages and reagent supply/washing modules that are linked with a central separation device and a terminal mass spectrometer for analysis and data interpretation. The systems can be programmed to perform process steps including (see, e.g., FIG. 2), for example:

1) Cell cultures (or tissue samples) are provided in microtiter plates (MTPs) with 1, 2 . . . i wells. To each well, solutions are added for lysis of cells, thereby liberating the proteins. In some embodiments, appropriate washing steps are included, as well as addition of enzymes to digest nucleic acids and other non-protein components. In further embodiments, instead of regular MTPs, MTPs with filter plates in the bottom of wells are used. Cell debris is removed either by filtration or centrifugation. A conditioning solution for the appropriate separation process is added and the material from each well separately loaded onto the separation device.

2) Separation utilizes different separation principles such as charge, molecular sizing, adsorption, ion-exchange, and molecular exclusion principles. Depending on the sample size, suitable appropriate dimensions are utilized, such as microbore high performance liquid chromatography (HPLC). In certain embodiments, a continuous flow process is used and the effluent is continuously aliquotted into MTP 1,2 . . . n.

3) Reaction with Proteome Reagents. Each MTP in turn is transferred to a Proteome Reagent Station harboring 1, 2 . . . m reagents differing only in the oligonucleotide sequence part (i.e., Q) or/and in the chemical nature of the functionality reacting with the proteins (i.e., X). If there are more than one MTP coming from one tissue sample then reagent 1 is added to the same well of the respective MTPs 1, 2 . . . n, i.e., in well A1, reagent 2 in well A2, etc. In embodiments where the MTPs have 96 wells (i=1-96), 96 different Proteome Reagents (i.e., 96 different compounds provided herein, m=1-96) are supplied through 96 different nozzles from the Proteome Reagent Station to prevent cross-contamination.

4) Pooling: Excess Proteome Reagent is deactivated, aliquots from each well belonging to one and the same tissue samples are pooled, and the remaining material is stored at conditions that preserve the structure (and if necessary conformation) of the proteins intact, thereby serving as master MTPs for subsequent experiments.

5) Excess Proteome Reagent is removed in the pooled sample using, e.g., the biotin/streptavidin system with magnetic beads, then the supernatant is concentrated and conditioned for hybridization.

6) Transfer to an Oligonucleotide Chip. After a washing step to remove non-hybridized and other low molecular weight material, a matrix is added. Alternatively, before matrix addition, a digestion with, e.g., trypsin or/and chymotrypsin is performed. After washing out the enzyme and the digestion products, the matrix is added.

7) Transfer of chip to mass spectrometer. In one embodiment, MALDI-TOF mass spectrometry is performed. Other mass spectrometric configurations suitable for protein analysis also can be applied. The mass spectrometer has an xy stage and thereby rasters over each position on the spot for analysis. The Proteome Reagent can be designed so that most of the reagent part (including the part hybridizing with the oligonucleotide chip array) is cleaved either before or during mass spectrometry and therefore will be detected in the low molecular weight area of the spectrum and will be well separated from the peptide (in case of enzymatic digestion) or protein molecular weight signals in the mass spectrum.

8) Finally, the molecular weight signals can be processed for noise reduction, background subtraction and other such processing steps.

The data obtained can be archived and interpreted. The molecular weight values of the proteins (or the peptides obtained after enzymatic digestion) are associated with the human DNA sequence information and the derived protein sequence information from the protein coding regions. An interaction with available databases will reveal whether the proteins and their functions are already known. If the function is unknown, the protein can be expressed from the known DNA sequence in sufficient scale using standard methods to elucidate its function and subsequent location in a biochemical pathway, where it plays its metabolic role in a healthy individual or in the disease pathway for an individual with disease.

Since the master plates containing aliquots from the different proteins within a given tissue sample have been stored and are available, subsequent experiments then can be performed in a now-preselected way, e.g., the proteins are displayed on the chip surface for protein-protein (biomolecule) interaction studies for target validation or/and to study the interaction with combinatorial libraries of small molecules for drug candidate selection.

G. Bioinformatics

The raw data generated from the analysis, such as mass spectrometry analysis, of the compound-protein species is processed by background subtraction, noise reduction, molecular weight calibration and peak refinement (e.g., peak integration). The molecular weight values of the cleaved proteins or the digestion products are interpreted and compared with existing protein databases to determine whether the protein in question is known, and if so, what modifications are present (glycosylated or not glycosylated, phosphorylated or not phosphorylated, etc.). The different sets of experiments belonging to one set of compounds are composed, compared and interpreted. For example, one set of experiments uses a set of compounds with one X moiety and different Q moieties. This set of experiments provides data for a portion of the proteome, since not all proteins in the proteome will react with a given X moiety. Superposition of the data from this set of experiments with data from other sets of experiments with different X moieties provides data for the complete proteome.

Sets of experiments comparing tissues of healthy and disease individuals or from different physiological or developmental stages (e.g., tumor progression, dependence of drug treatments to monitor results of therapy, immune response to virus or bacteria infection) or different tissue areas (e.g., of a tumor) are investigated, and the final data archived.

The following examples are included for illustrative purposes only and are not intended to limit the scope of the invention.

Commercial grade solvents and reagents were used without purification unless otherwise specified, and were purchased from the following vendors: Anhydrous THF (Aldrich), $CH_2Cl_2$ (Aldrich, Acros, EM Science), $CHCl_3$ (Aldrich, Mallinckrodt), Hexanes (Acros, EM science), Ethyl acetate (Alrich, Acros), Acetone (Aldrich, EM science), Methyl alcohol (Aldrich), Diethyl ether (Fisher scientific). 4-Bromobenzoic acid (Aldrich), 2-amino-2-methyl-1-propanol (Acros), 1,3-dicyclocarbodiimide (Aldrich), N-hydroxysuccinimide (Aldrich), Maleimide (Aldrich), 1-(3-dimethylaminopropyl)-3-ethylcarbodiimide hydrochloride (Acros), Thionyl chloride (Aldrich), Pyridine (Aldrich), Magnesium turnings (Acros), 4-(Diphenylhydroxymethyl)benzoic acid (Fluka), Sodium ethoxide (Acros), Potassium carbonate, Sodium iodide, Carbon tetrachloride, methyl iodide, RED-Al (Aldrich), anhydrous $Na_2SO_4$ (Acros), Acetic acid (EM science), Sodium hydroxide (Acros), Molecular sieves $A°_4$ (Aldrich), and Acetyl chloride (Aldrich). $^1H$ NMR spectral data were obtained from a 500 MHz NMR spectrophotometer using $CDCl_3$ as a solvent. Mass spectral data were analyzed using the electrospray method.

Example 1

Examples for $N^1_m B_i N^2_n$ a. $N^1$ and $N^2$ as Identical Tetramers, B as a Trimer $N^1 = N^2$, m = n = 4, i = 3, B = 64 sequence permutations (SEQ ID. NO: 150)

GTGC ATG GTGC

AAG

ACG

AGG

TTG

CTG

GTG

. . .

. . .

. . .

GGG b. $N^1$ and $N^2$ as Non-Identical Tetramers, B as a Tetramer $N^1 \neq N^2$, m = n = 4, i = 4, B = 256 sequence permutations (SEQ ID. NO: 151)

GTCC ATCG CTAC

AACG

ACCG

AGCG

. . . .

. . . .

. . . .

GGGG c. $N^1$ as a Heptamer, $N^2$ as an Octamer, B as an Octamer $N^1 \neq N^2$, m = 7, n = 8, i = 8, B = 65,536 sequence permutations. (SEQ ID. NO: 152).

GCTGCCC ATTCGTAC GCCTGCCC
$\overline{N^1}$ $\overline{B}$ $\overline{N^2}$

Example 2

Separation of Proteins on a DNA Array $N^1{}_m B_i N^2{}_n (S^1)_t M(R^{15})_a (S^2)_b$LXProtein where B is a trimer; m = n = 4, i = 3, t = b = 1; underlined sequences are $N^1$ and $N^2$

```
         SEQ ID NO: 153
     CTGC ATG GTGC-S₁-M(R¹⁵)ₐ-S₂-L-X-Protein 1
 /   ---CACG TAC CACG
 /
 /   CTGC AAG GTGC-S₁-M(R¹⁵)ₐ-S₂-L-X-Protein 2
 /   ---CACG TTC CACG
 /
 /   CTGC ACG GTGC-S₁-M(R¹⁵)ₐ-S₂-L-X-Protein 3
 /   ---CACG TGC CACG
 /
 /           ...
 /
 /           ...
 /
 /           ...
 /
 /   CTGC GGG GTGC-S₁-M(R¹⁵)ₐ-S₂-L-X-Protein 64
 /   ---CACG CCC CACG
         SEQ ID NO: 154
```

Example 3

I. Preparation of Protein Mixtures from Cells or Via Protein Translation of a cDNA Library Prepared from Cells or Tissues The protein mixtures can be selectively divided on the physical or biochemical separation techniques 1. Preparation of Limited Complexity Protein Pools Using Cell Culture or Tissue Proteins can be isolated from cell culture or tissues according to methods well known to those of skill in the art. The isolated proteins are purified using methods well known to those of skill in the art (e.g., TPAE, differential protein precipitation (precipitation by salts, pH, and ionic polymers), differential protein crystallization bulk fractionation, electrophoresis (PAGE, isoelectric focusing, capillary), and chromatography (immunoaffinity, HPLC, LC)). Individual column fractions containing protein mixtures of limited complexity are collected for use as antigen.

Figure 6:
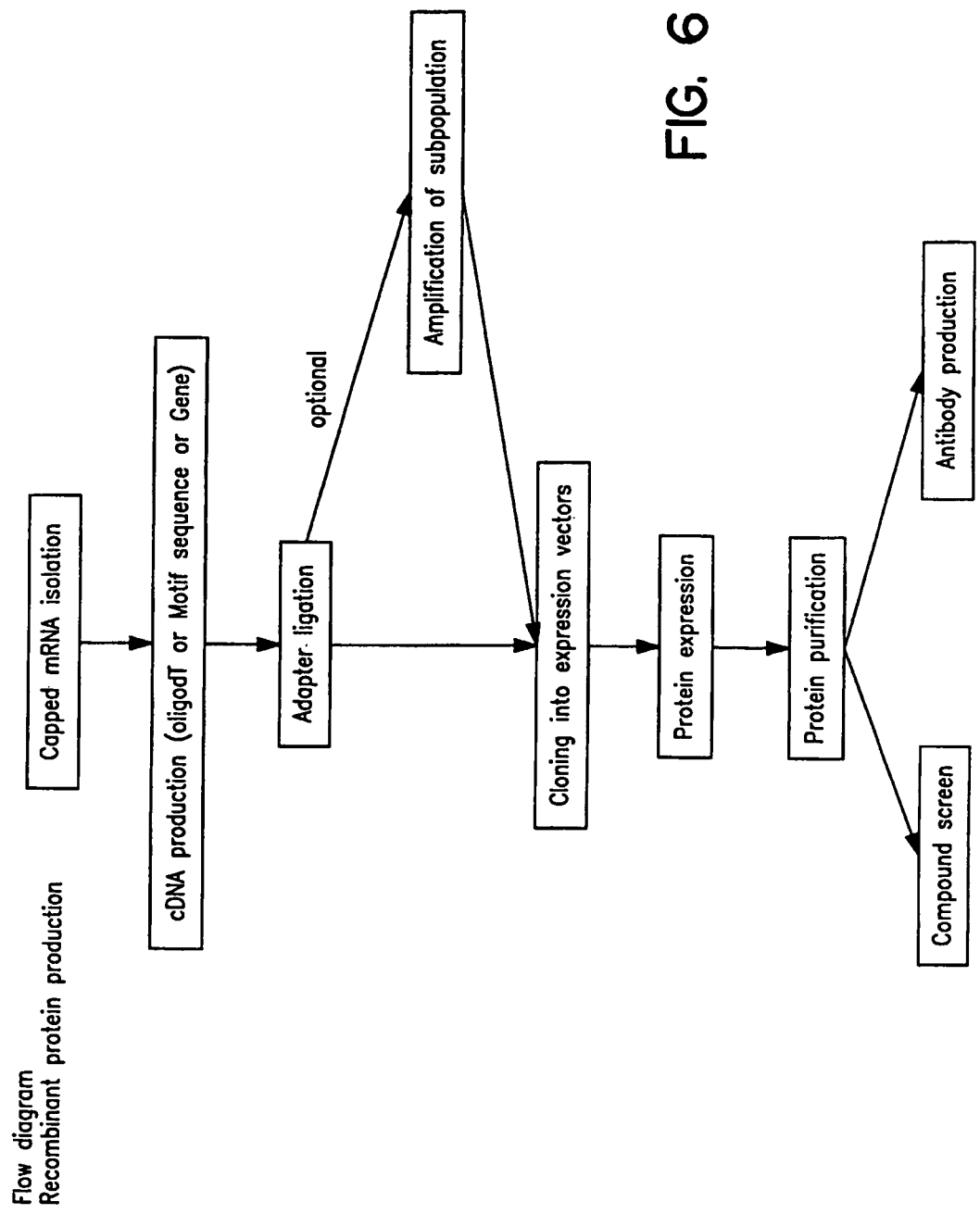
FIG. 6 is a flow diagram of recombinant protein production.

2. Preparation of Limited Complexity Protein Pools Using cDNA Expression Libraries (FIG. 6)

a. RNA Isolation i. Isolation of Total RNA

Cultured cells or tissues are homogenized in a denaturing solution containing 4 M guanidine thiocyanate. The homogenate is mixed sequentially with 2 M sodium acetate (pH 4), phenol, and finally chloroform/isoamyl alcohol or bromochloropropane. The resulting mixture is centrifuged, yielding an upper aqueous phase containing total RNA. Following isopropanol precipitation, the RNA pellet is dissolved in denaturing solution (containing 4 M guanidine thiocyanate), precipitated with isopropanol, and washed with 75% ethanol.

ii. Isolation of Cytoplasmic RNA

Cells are washed with ice-cold phosphate-buffered saline and kept on ice for all subsequent manipulations. The pellet of harvested cells is resuspended in a lysis buffer containing the nonionic detergent Nonidet P-4. Lysis of the plasma membranes occurs almost immediately. The intact nuclei are removed by a brief micro centrifuge spin, and sodium dodecyl sulfate is added to the cytoplasmic supernatant to denature protein. Protein is digested with protease and removed by extractions with phenol/chloroform and chloroform. The cytoplasmic RNA is recovered by ethanol precipitation.

b. mRNA Purification

Messenger RNA is purified from total or cytoplasmic RNA preparation using standard procedures. Poly(A)⁺ RNA can be separated from total RNA by oligo (dT) binding to the Poly (A) tail of the mRNA. Total RNA is denatured to expose the Poly(A) (polyadenylated) tails. Poly(A)-containing RNA is then bound to magnetic beads coated with oligo(dT) and spirited from the total or cytoplasmic RNA through magnetic forces. The mRNA population can be further enriched for the presence of full-length molecules through the selection of a 5'-cap containing mRNA species.

c. cDNA Synthesis

Different types of primers can be used to synthesis full length or 5'-end containing cDNA libraries from the isolated mRNA.

i. Oligo (dT) Primer, which Will Generate cDNAs for All mRNA Species (FIG. 7)

Figure 7:
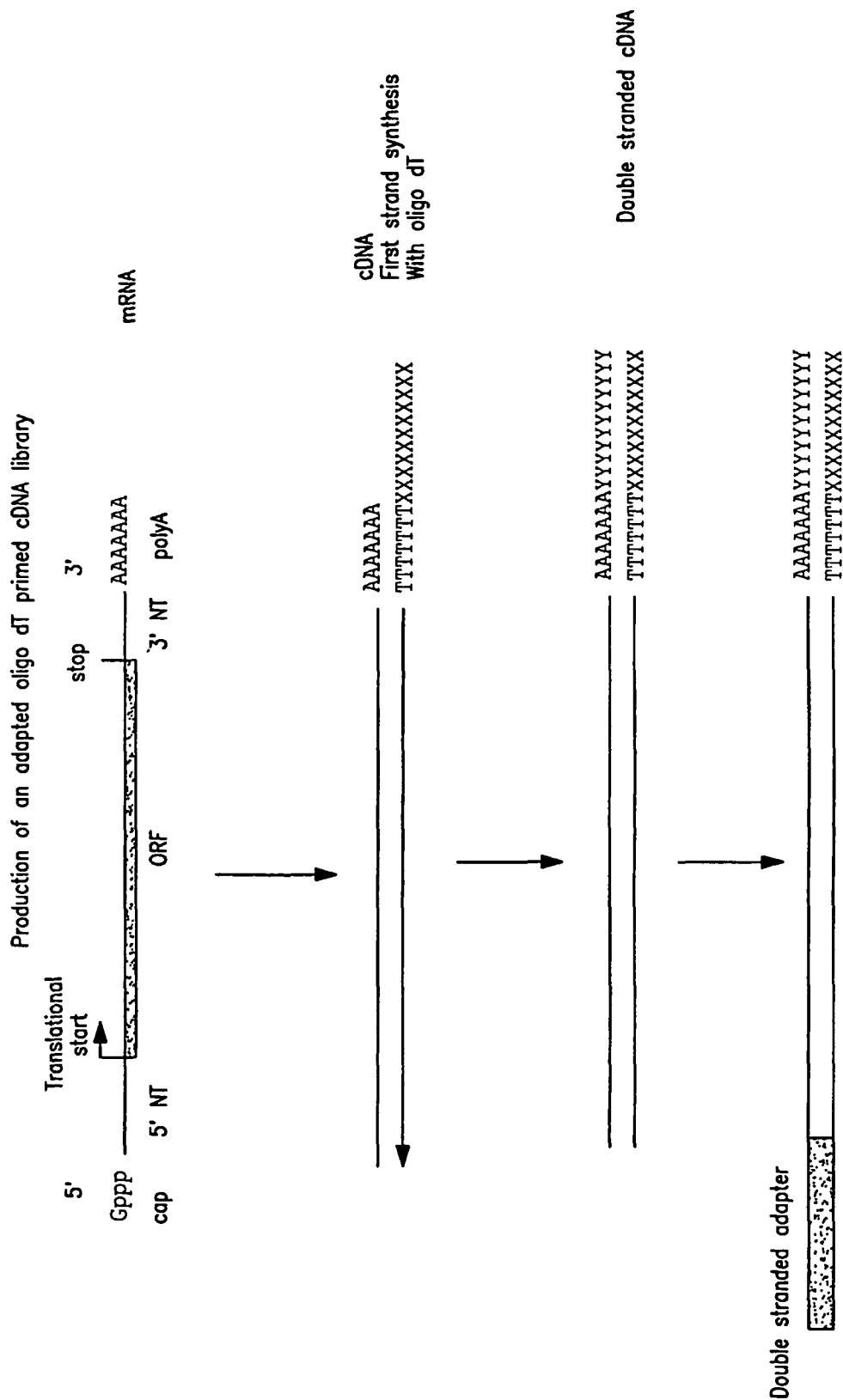
FIG. 7 illustrates production of an adapted oligonucleotide dT primed cDNA library.

An example of the production of an adapted oligo dT primed cDNA library is provided in FIG. 7.

ii. Functional Protein Motif Specific Degenerate Oligonucleotide Primers Will Generate a Limited Number of Genes Belonging to the Same Protein Family or of Functionally Related Proteins (FIG. 8)

Figure 8:
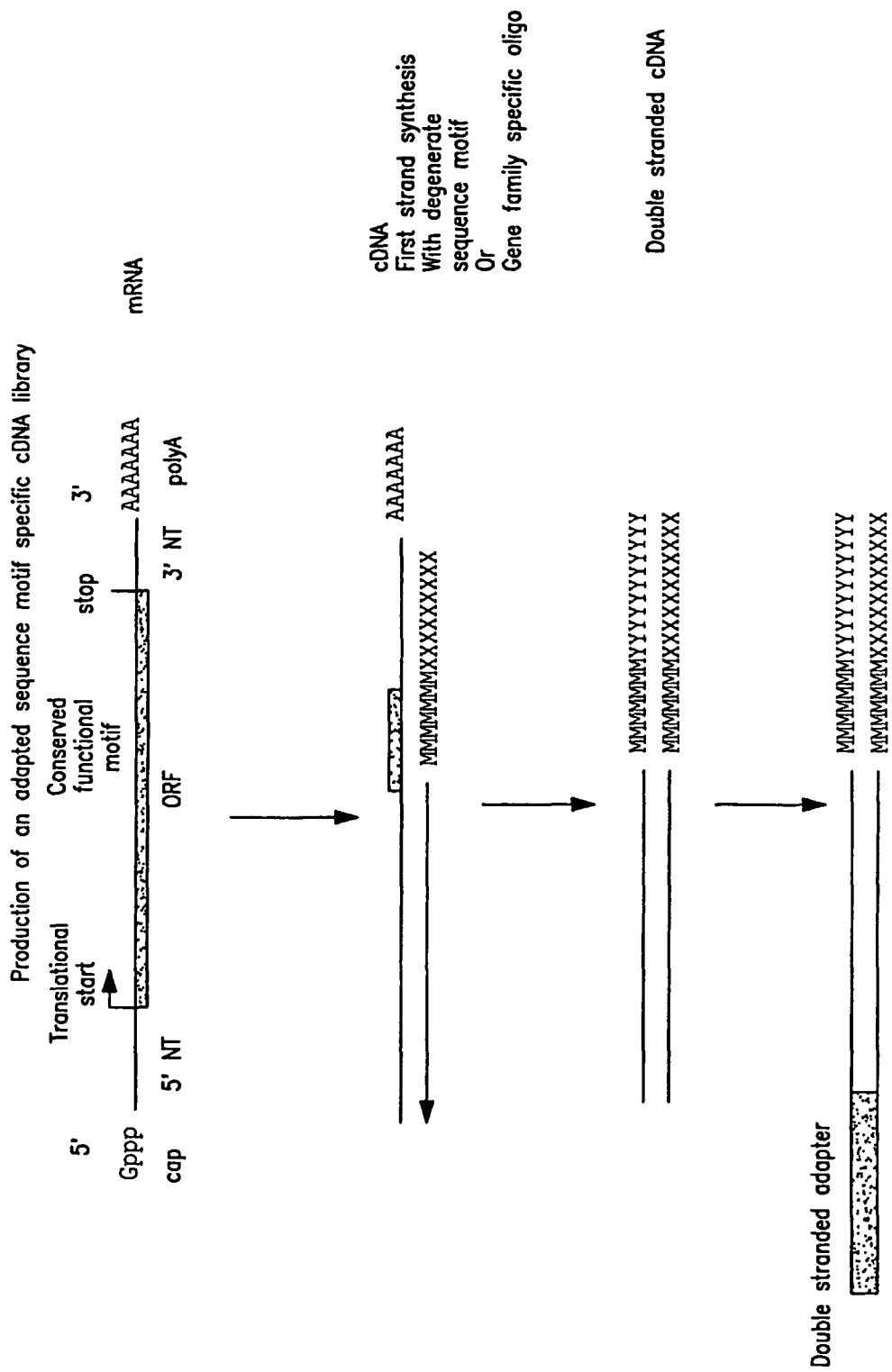
FIG. 8 shows production of an adapted sequence motif specific cDNA library.
Figure 9:
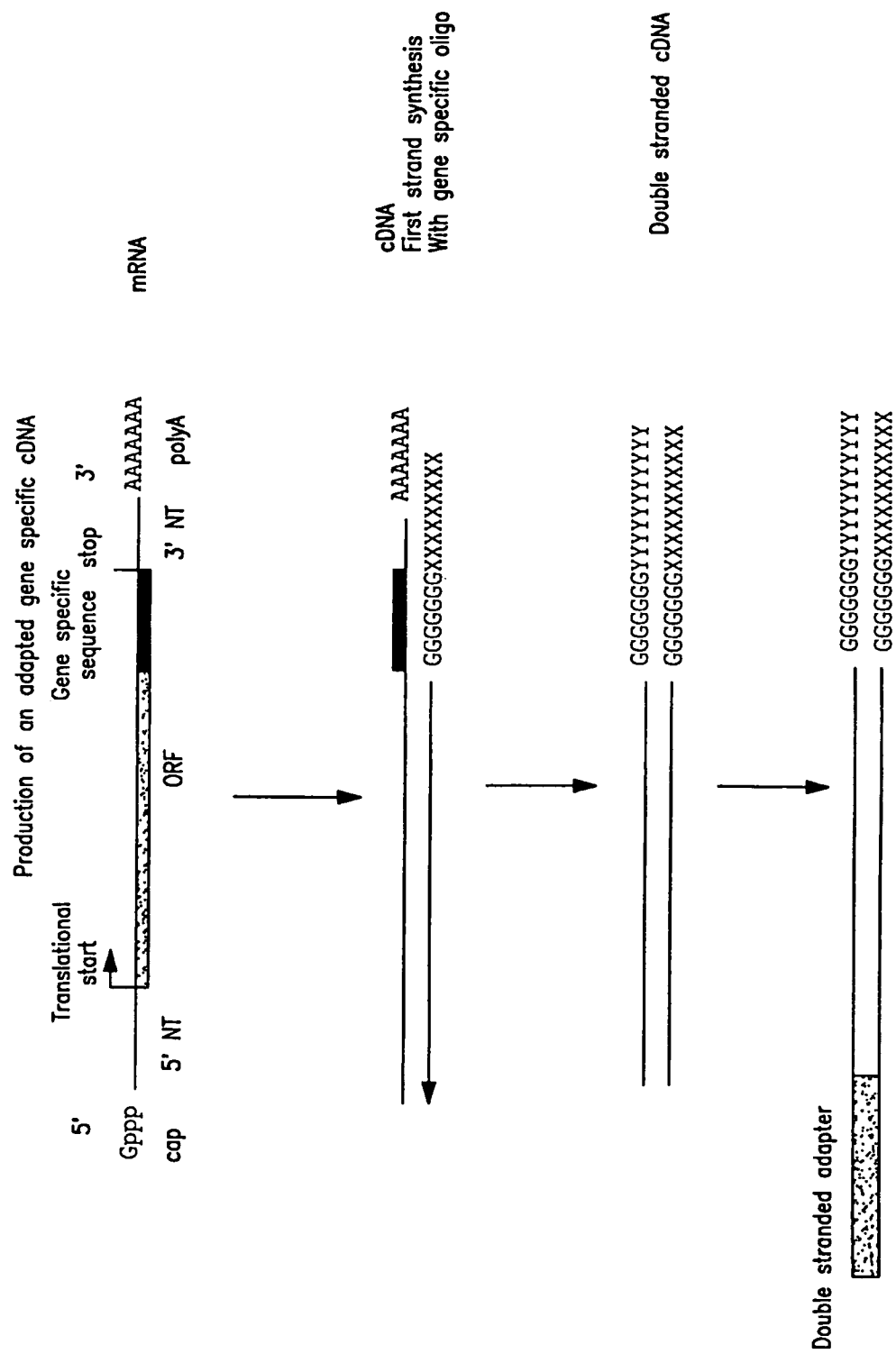
FIG. 9 shows production of an adapted gene specific cDNA.

An example of the production of an adapted sequence motif specific cDNA library is provided in FIG. 8.

iii. Gene Specific Oligonucleotide Will Produce cDNA for Only One mRNA Species (FIG. 9)

Figure 10:
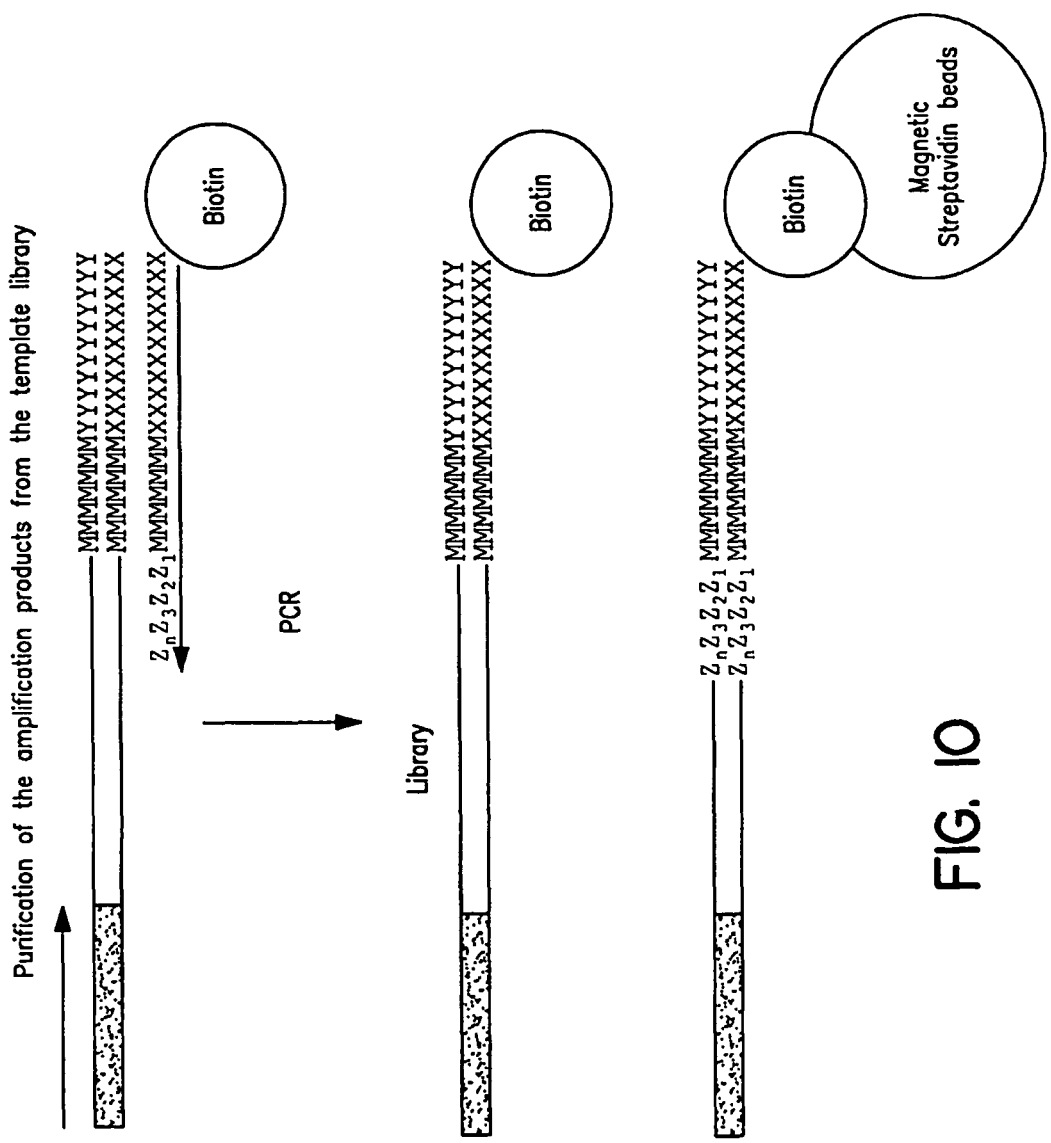
FIG. 10 illustrates purification of amplification products from a template library.

The oligonucleotides used for the cDNA production can contain additional sequences, 1) protein tag specific sequences for easier purification of the recombinant proteins (6× His), 2) restriction enzyme sites, 3) modified 5'-end for cDNA purification or DNA construction purposes (FIG. 10).

The conversion of mRNA into double-stranded cDNA for insertion into a vector is carried out in two parts. First, intact mRNA hybridized to an oligonucleotide primer, is copied by reverse transcriptase and the products isolated by phenol extraction and ethanol precipitation. The RNA in the RNA-DNA hybrid is removed with RNase H as *E. coli* DNA polymerase I fills in the gaps. The second-strand fragments thus produced are ligated by *E. coli* DNA ligase. Second-strand synthesis is completed, residual RNA degraded, and cDNA made blunt with RNase H, RNase A, T4 DNA polymerase, and *E. coli* DNA ligase.

d. Adapter Ligation

Figure 14:
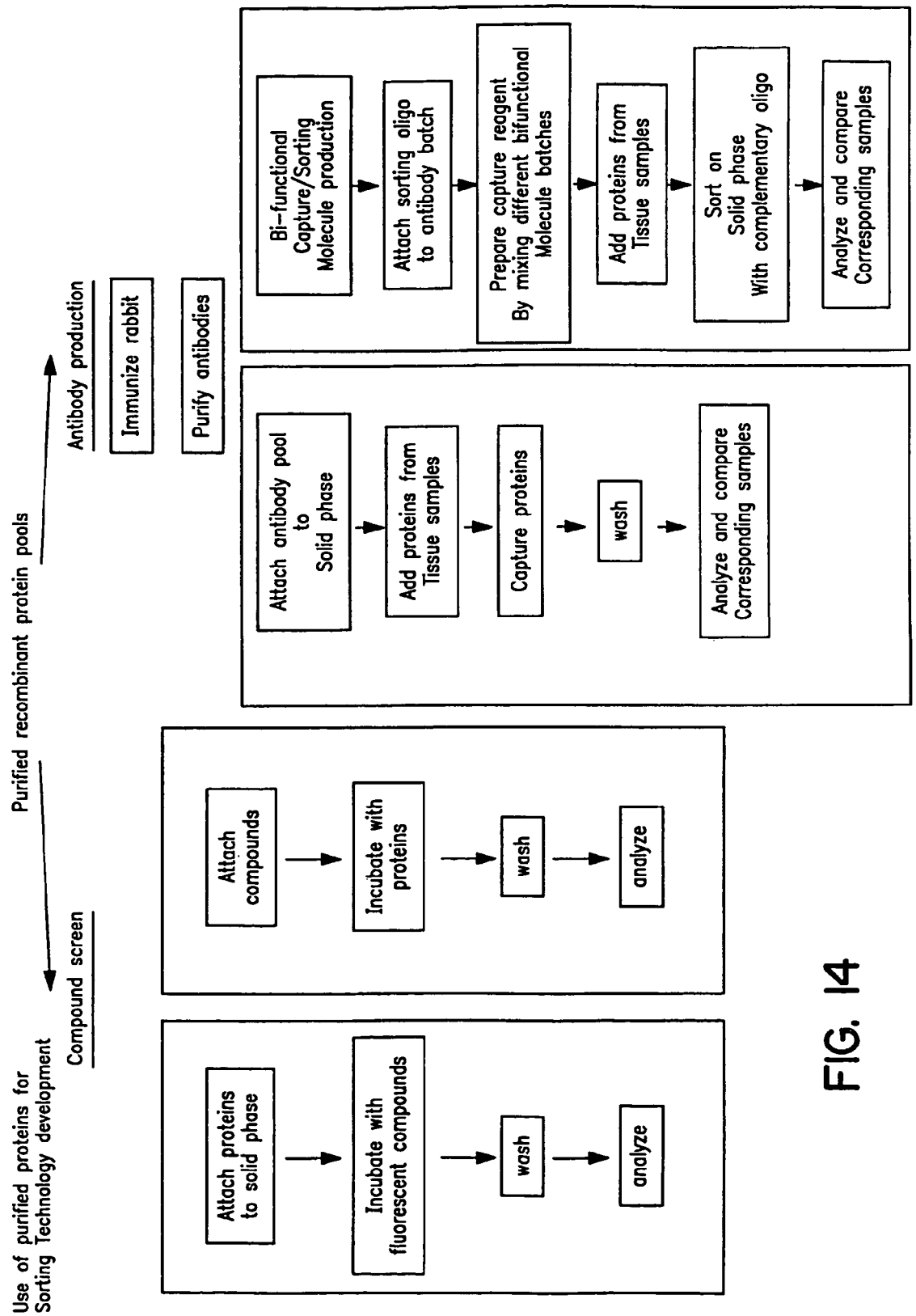
FIG. 14 shows analysis of purified proteins from compound screening and antibody production.
Figure 15A:
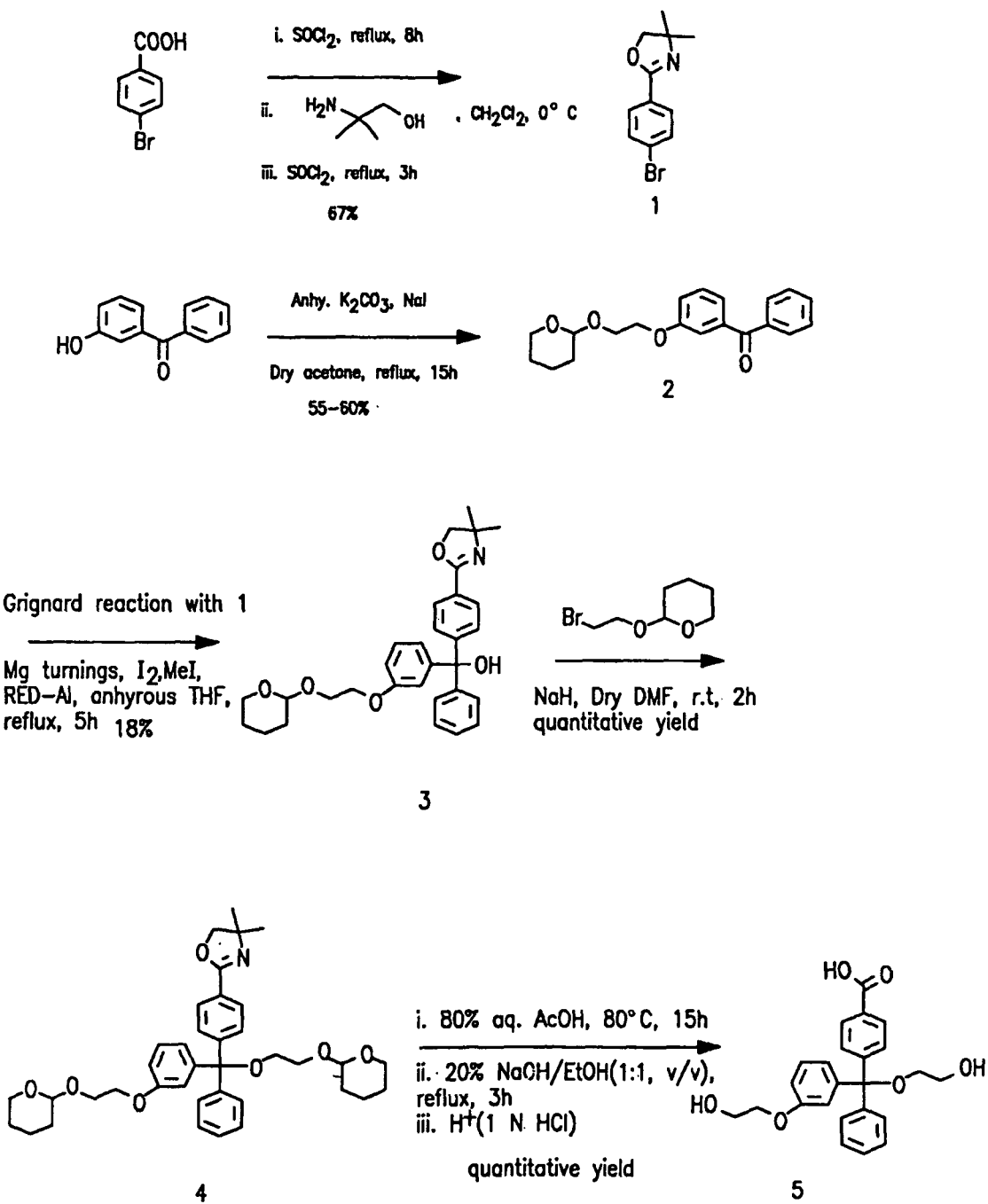
FIG. 15a-b provides synthetic schemes for synthesis of exemplary capture reagents provided herein (see, e.g., Example 4).
Figure 15B:
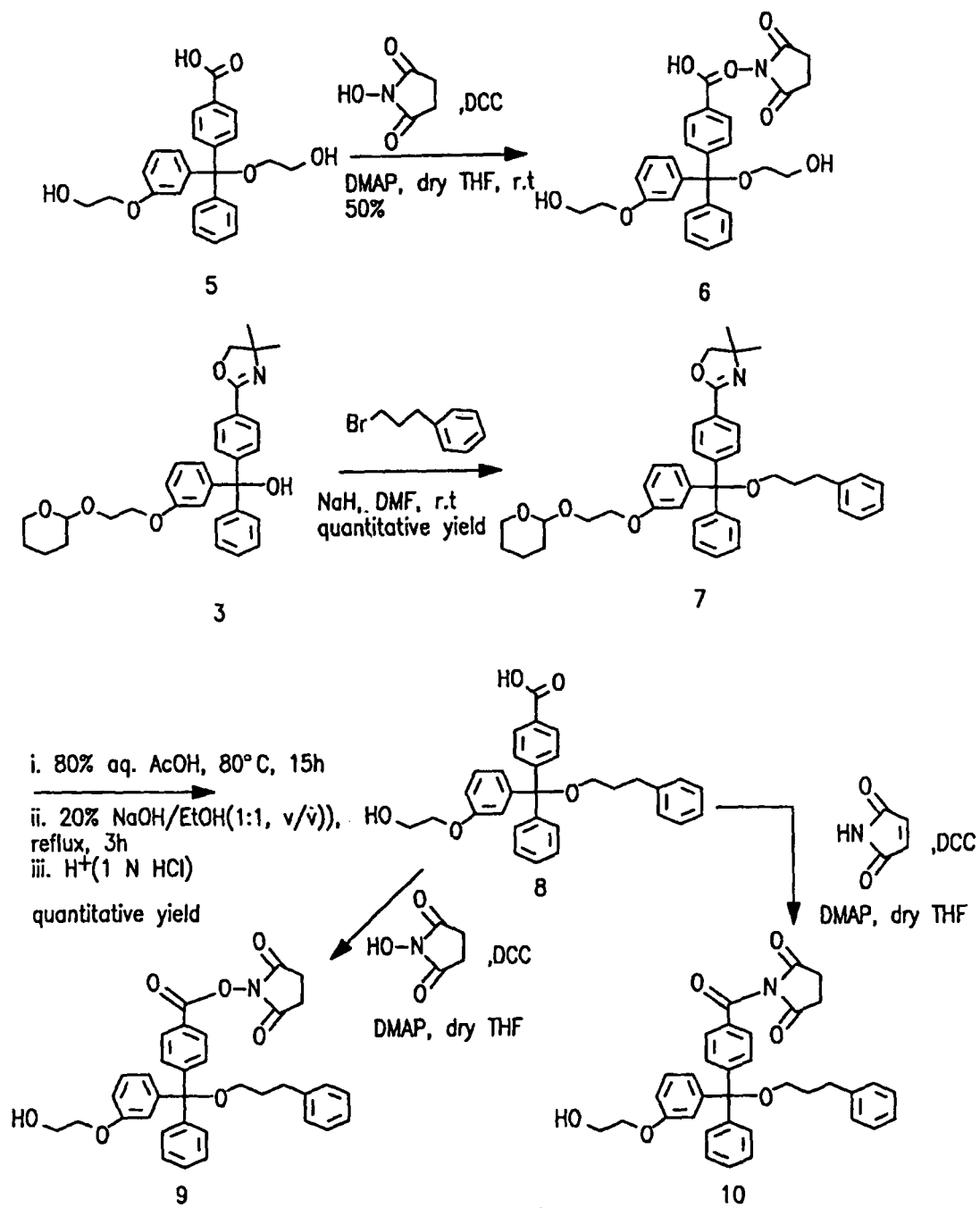
Figure 16A:
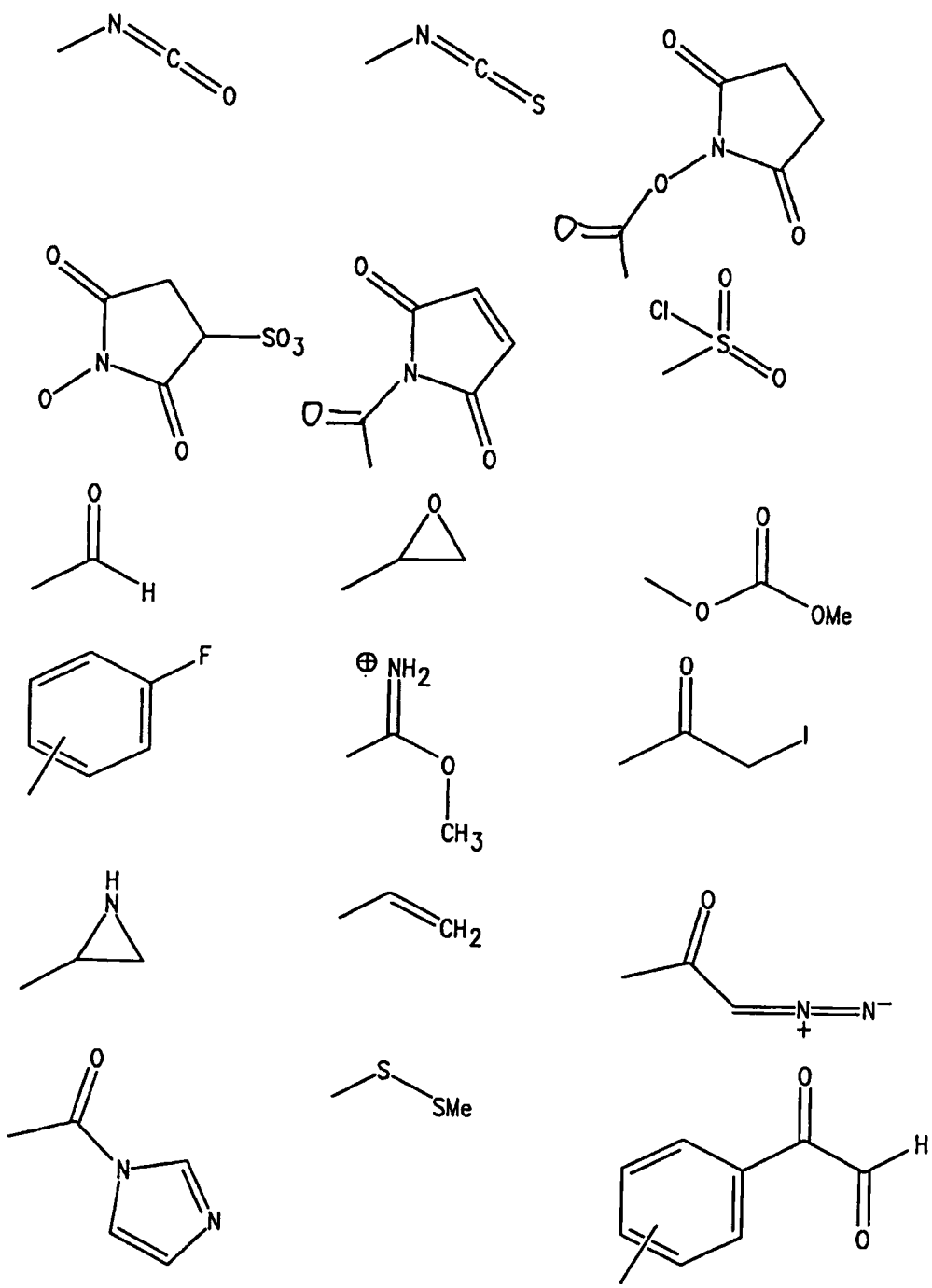
FIG. 16a-b provides exemplary reactivity functions for use in the capture reagents provided herein.
Figure 16B:
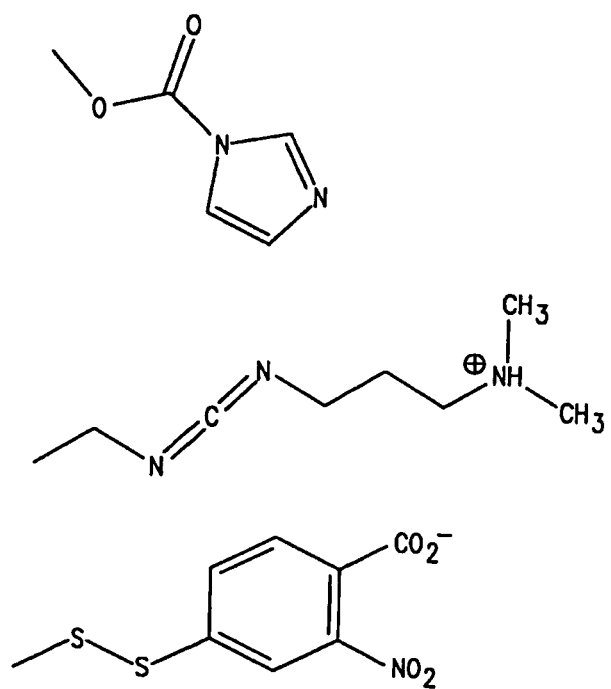
Figures 17C, 17D:
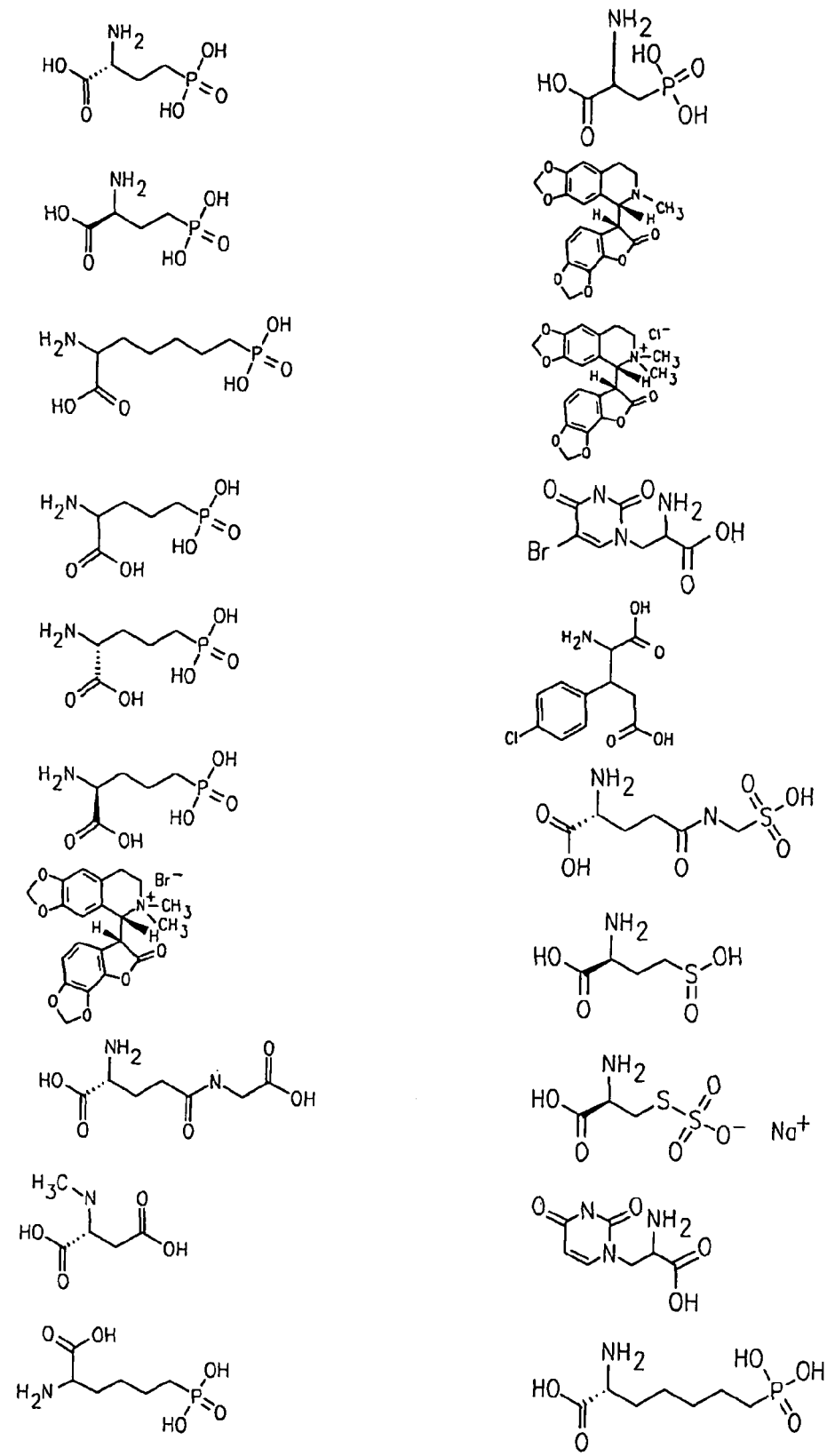
FIG. 17a-hhhh provides exemplary selectivity functions for use in the capture reagents provided herein.
Figures 17E, 17F:
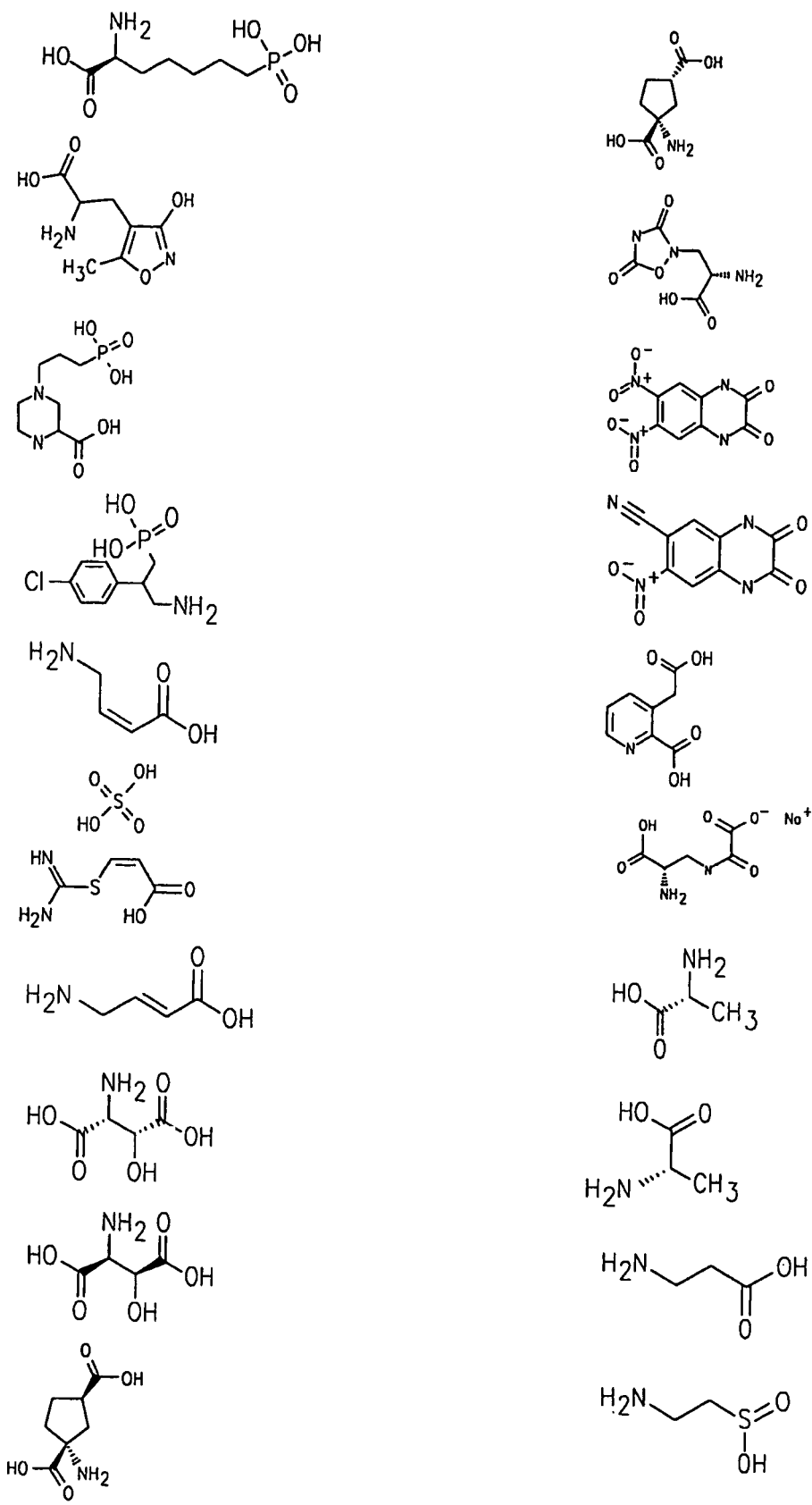
Figures 17I, 17J:
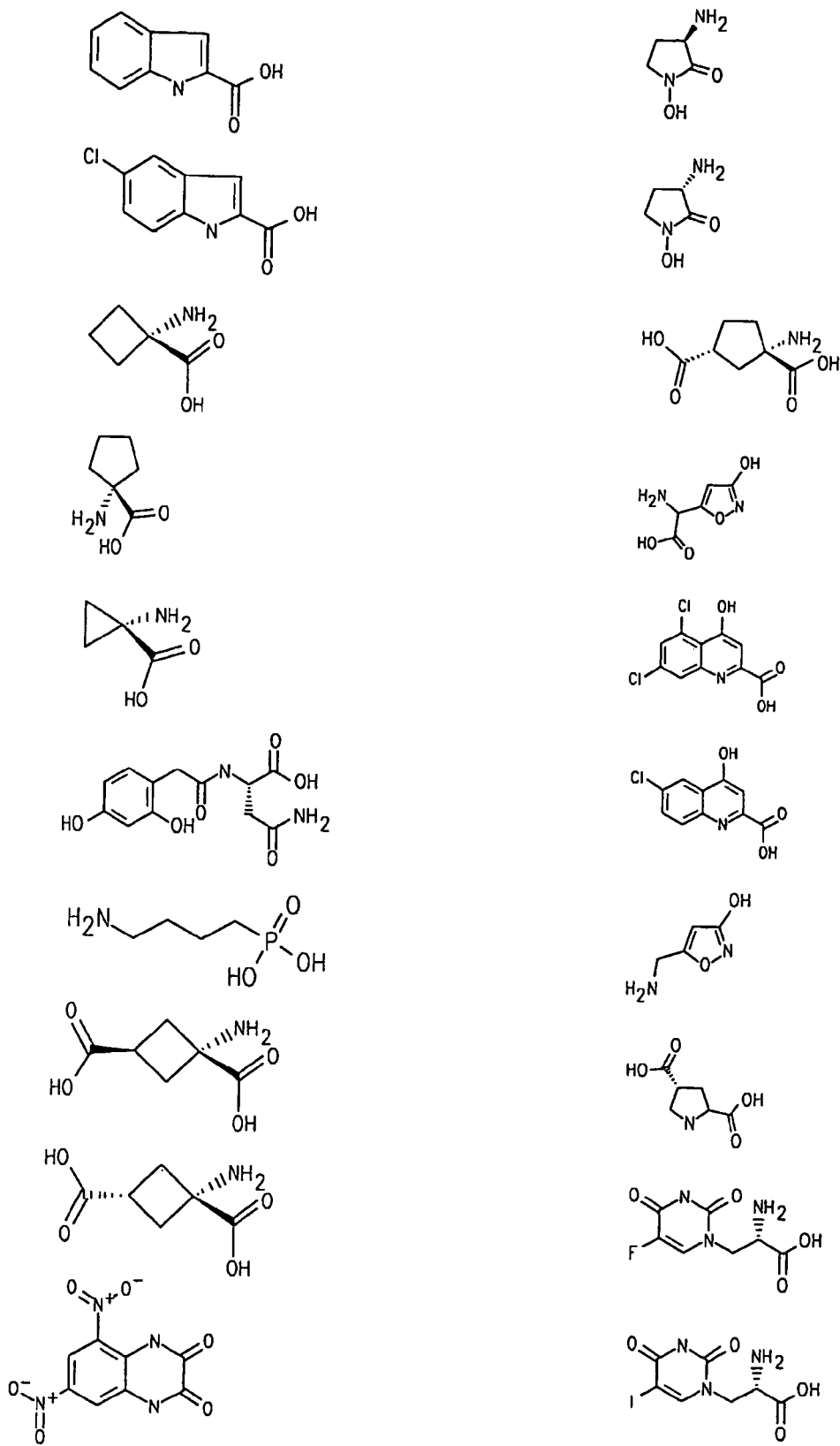
Figure 17K:
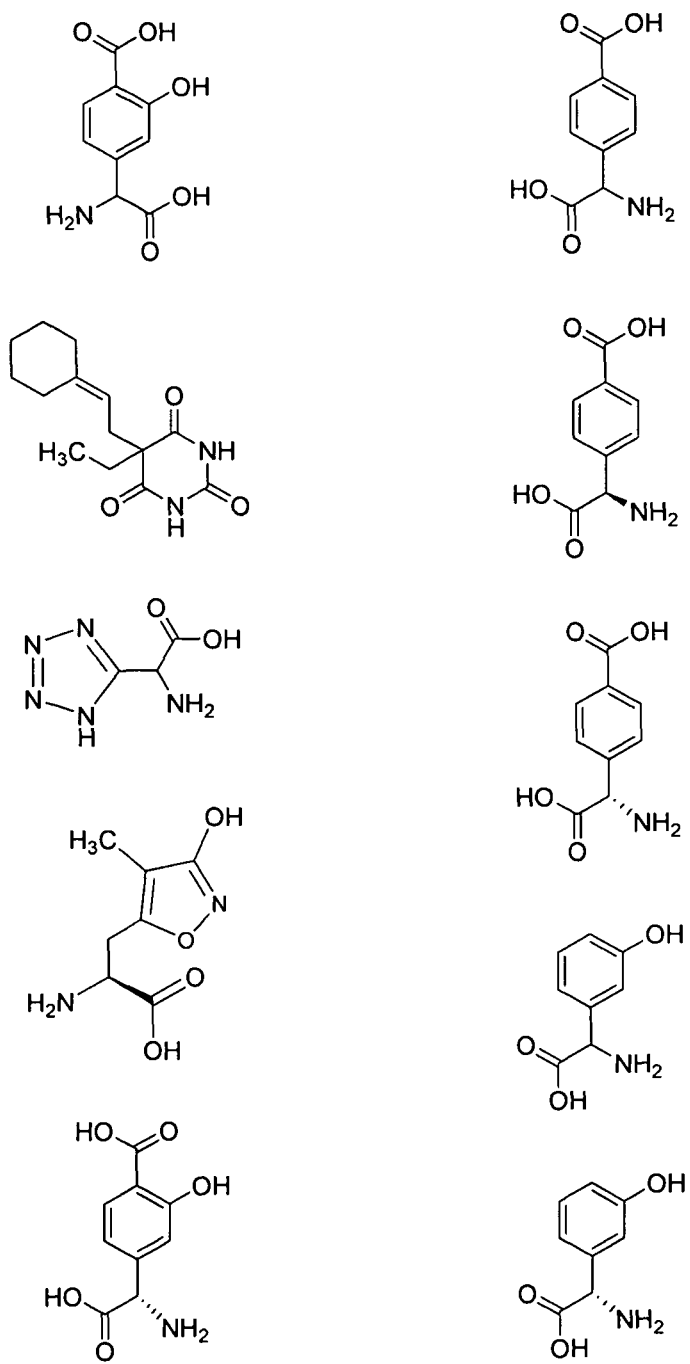
Figure 17M:
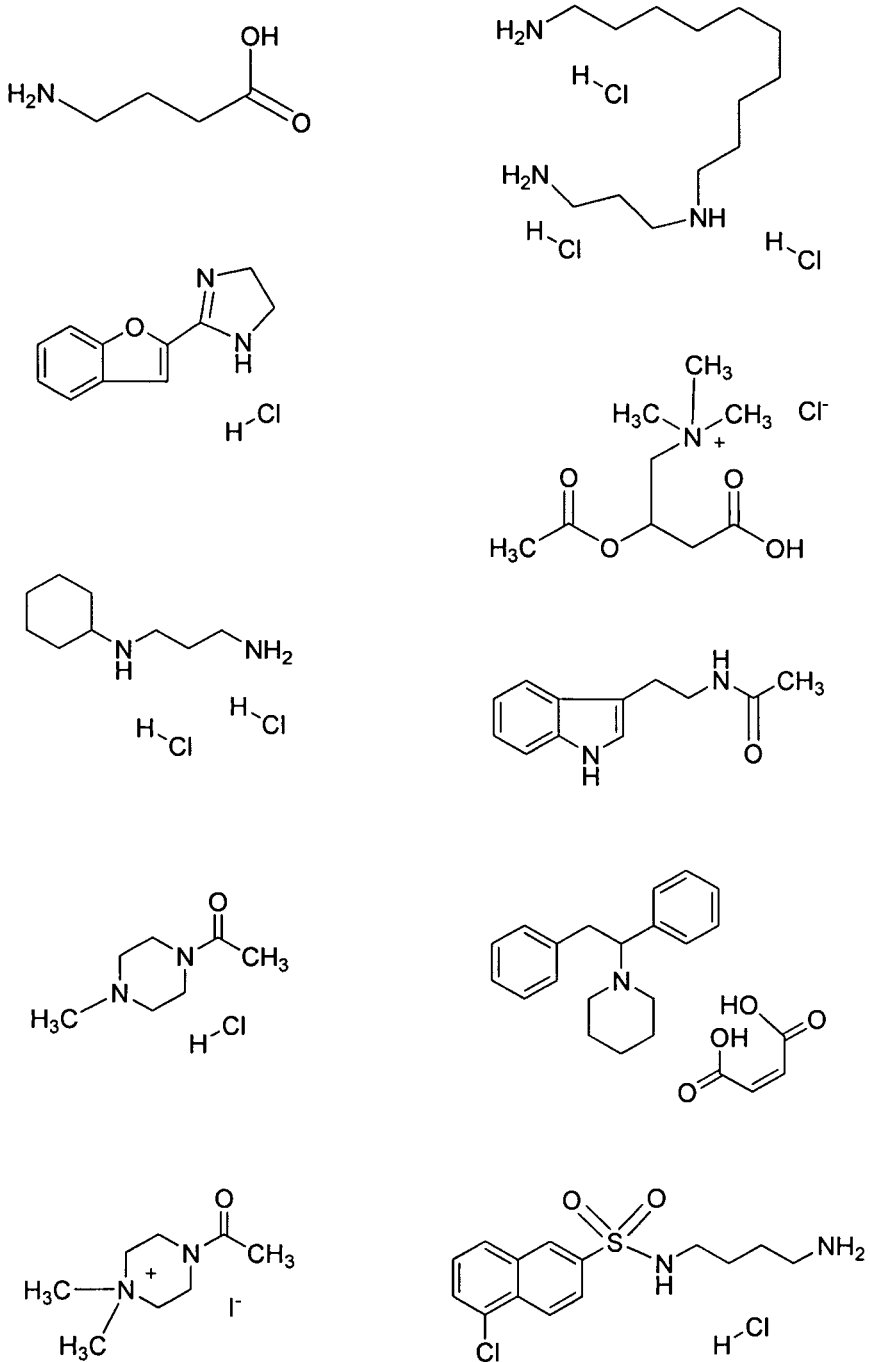
Figure 17N:
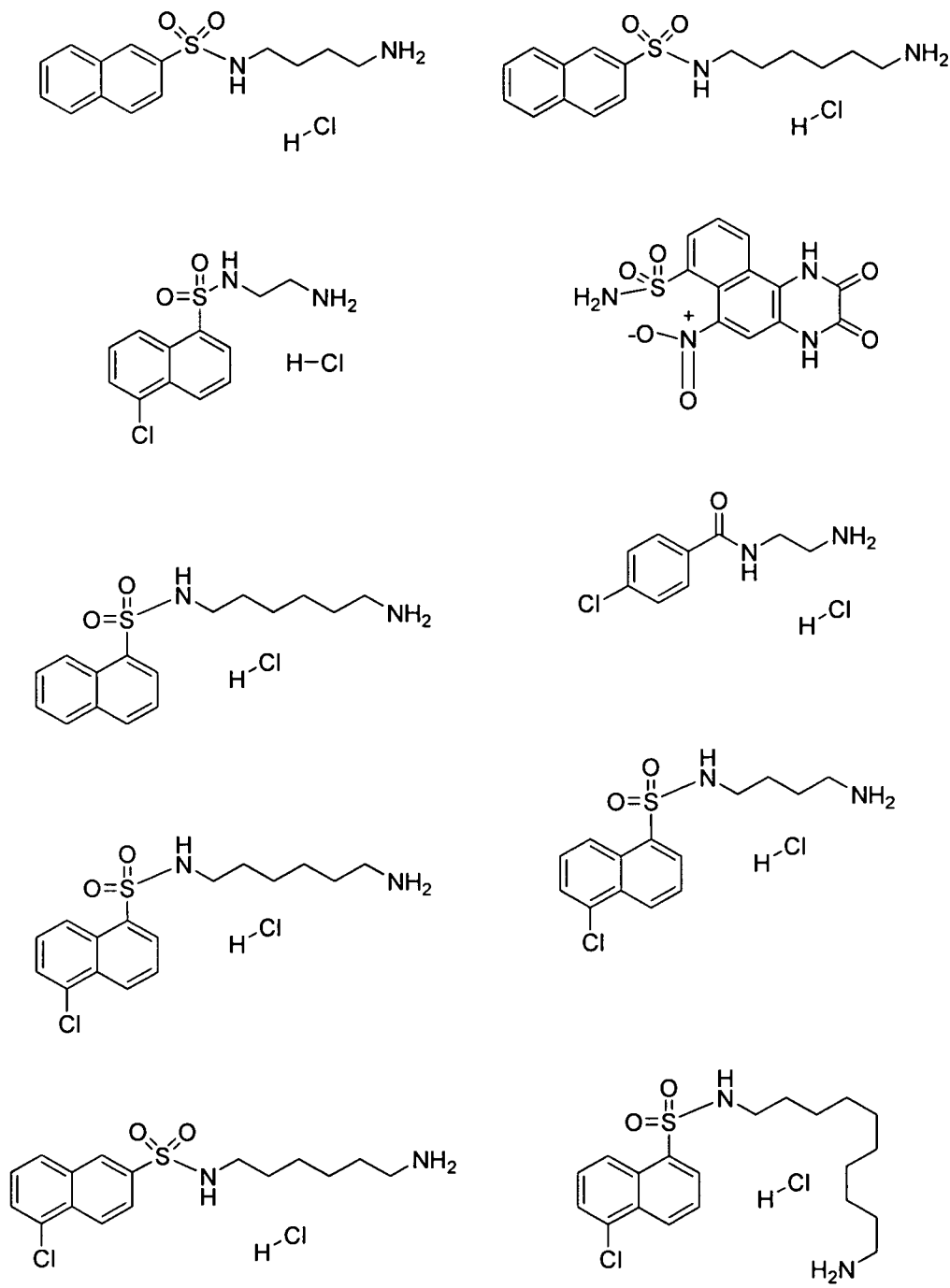
Figure 17O:
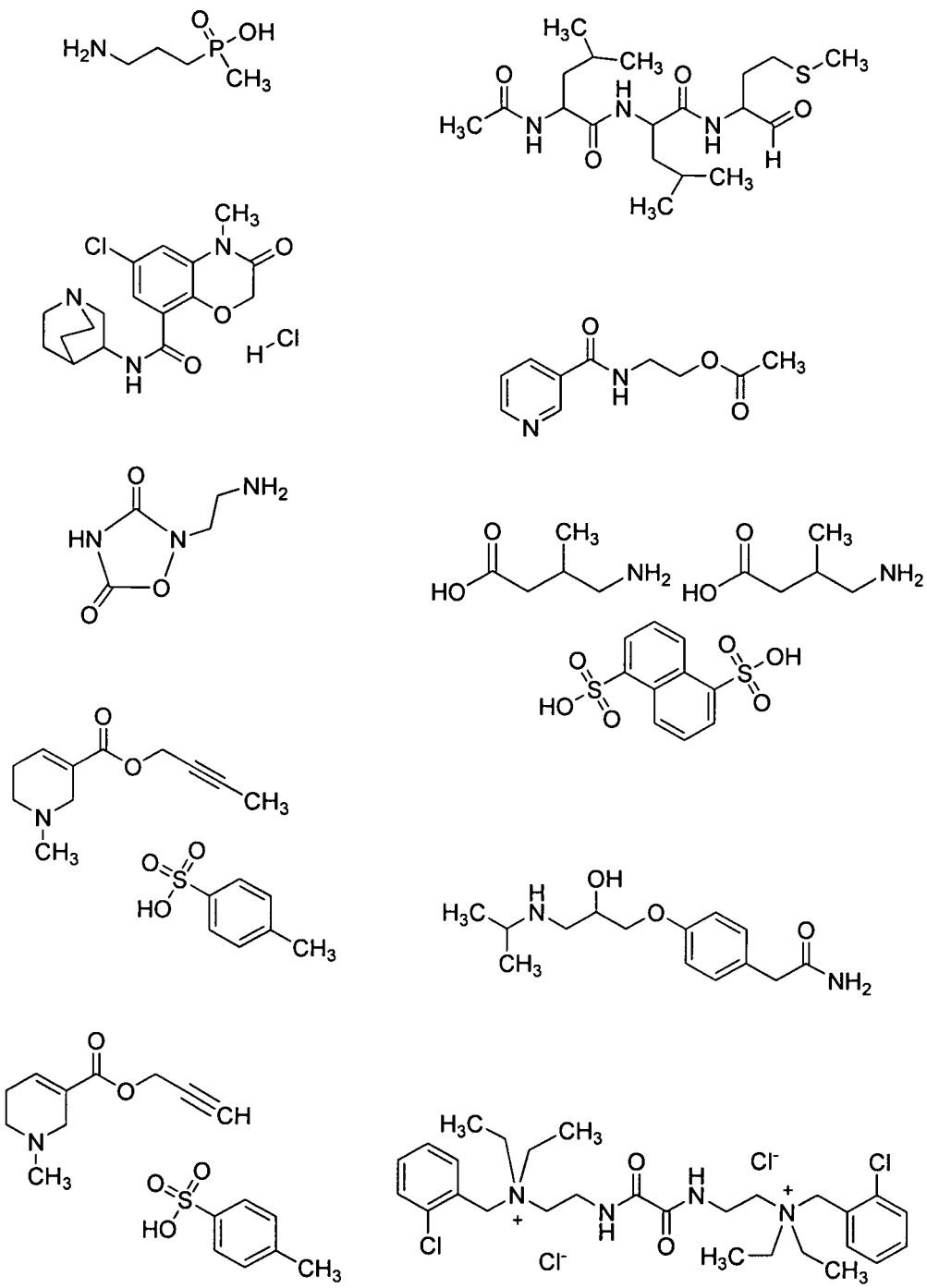
Figure 17Q:
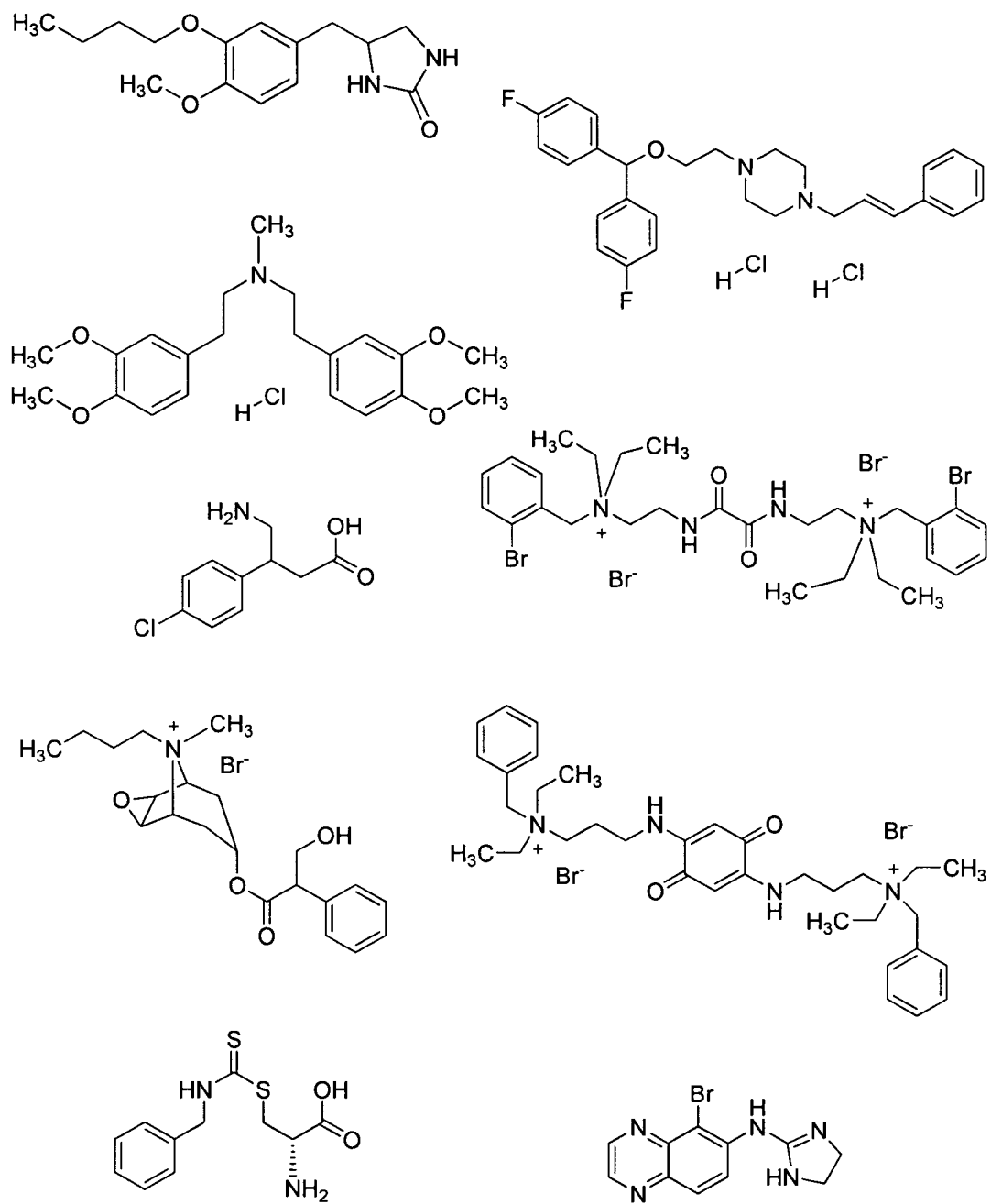
Figure 17R:
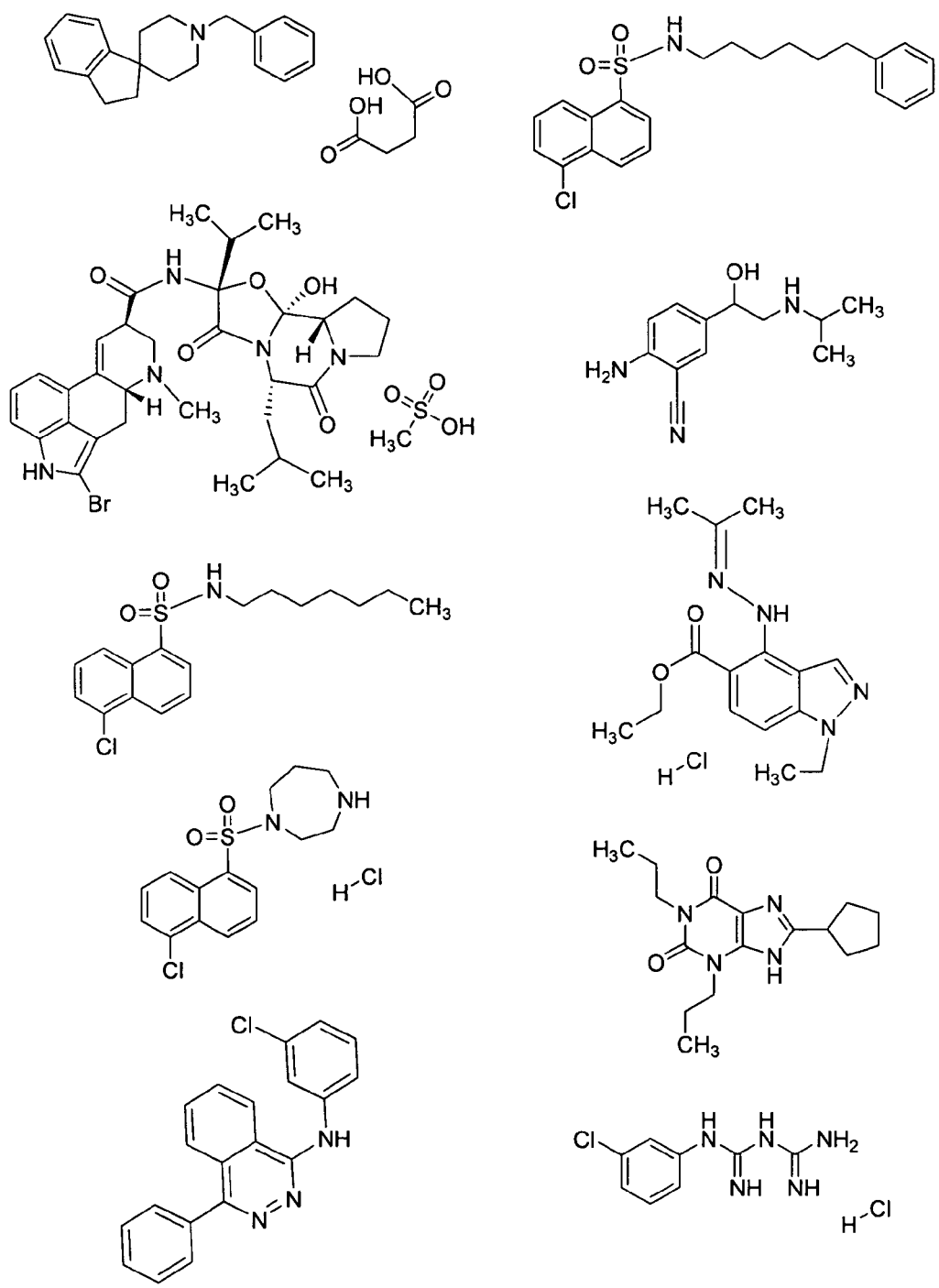
Figure 17S:
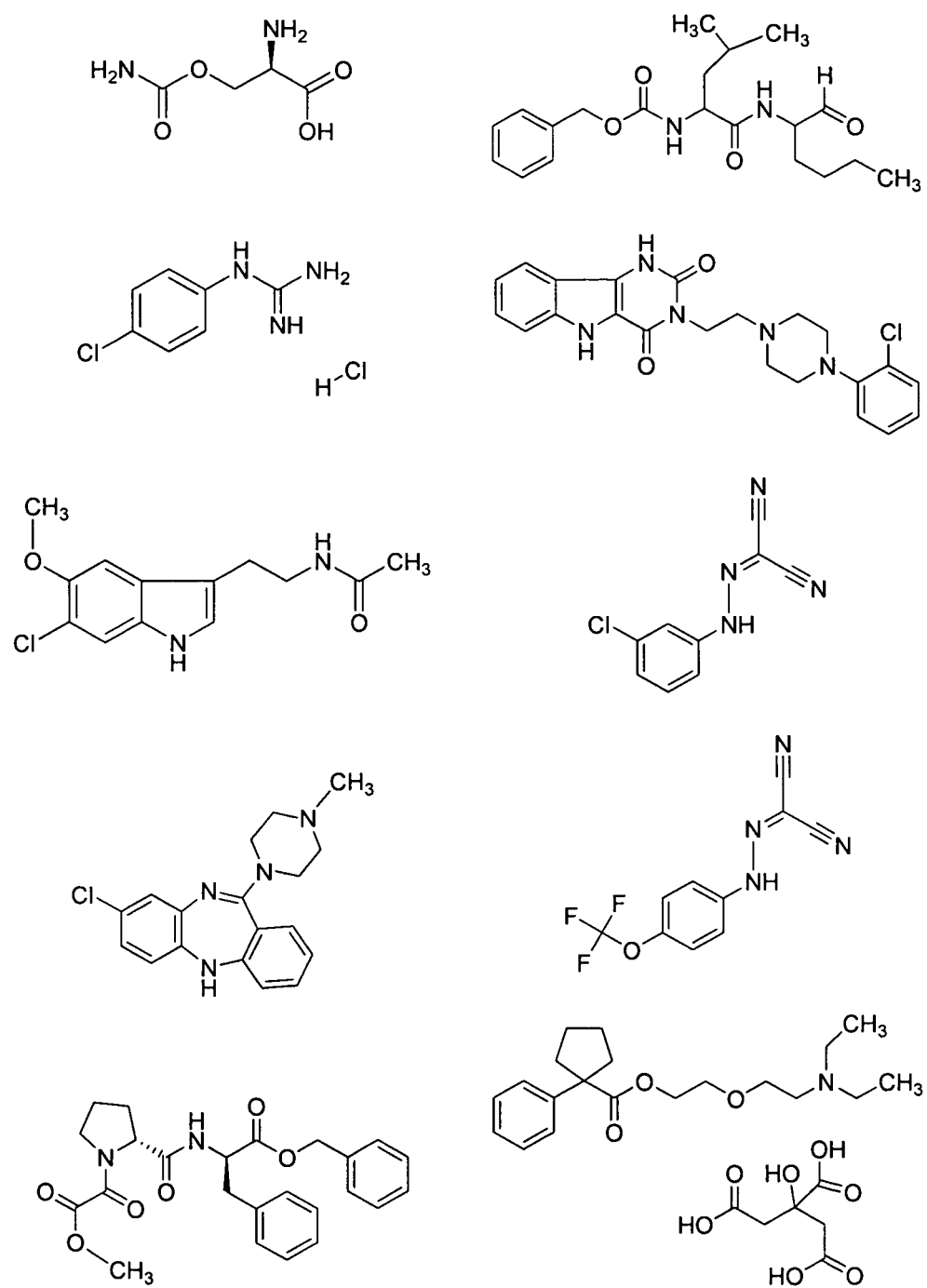
Figure 17T:
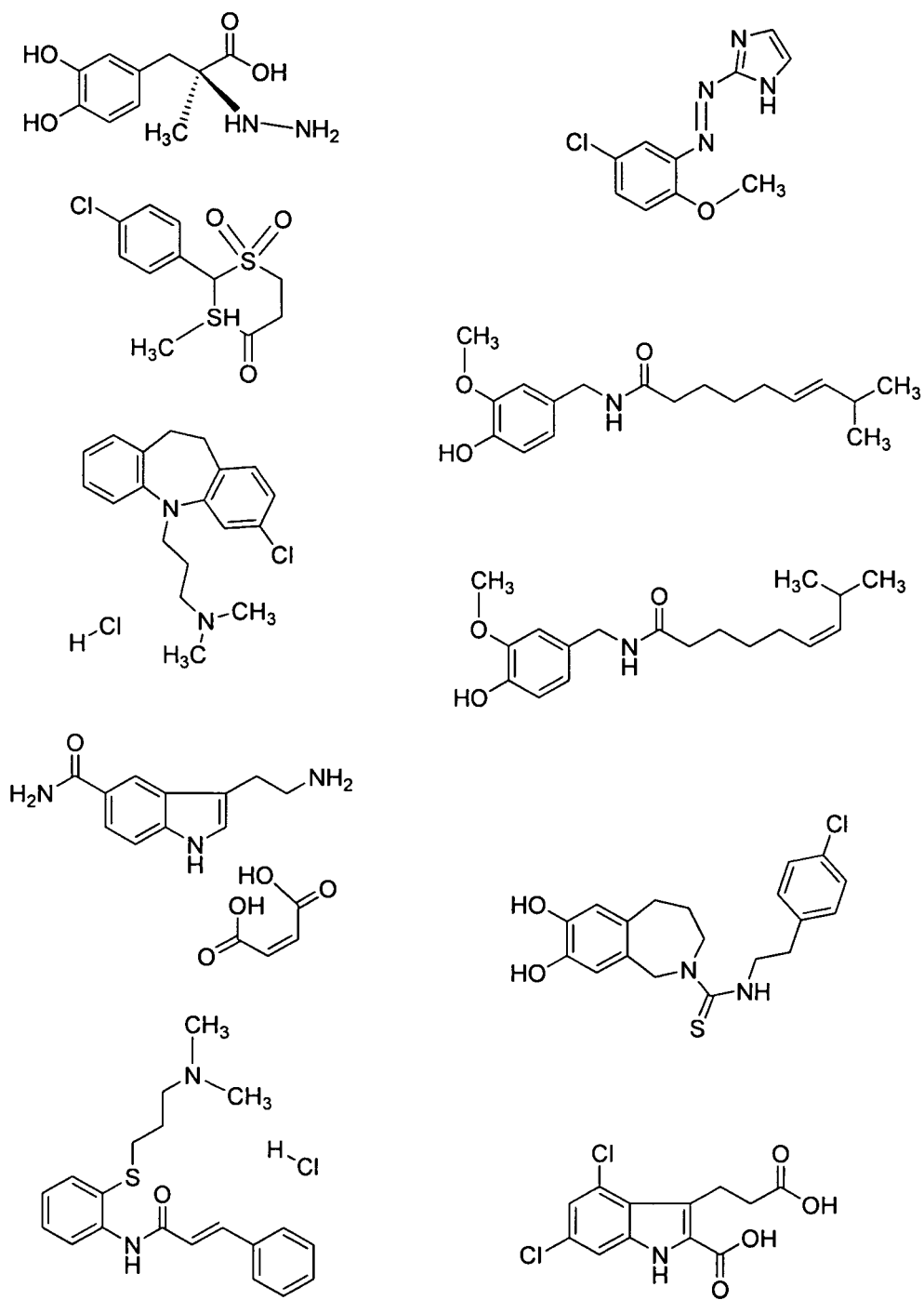
Figure 17U:
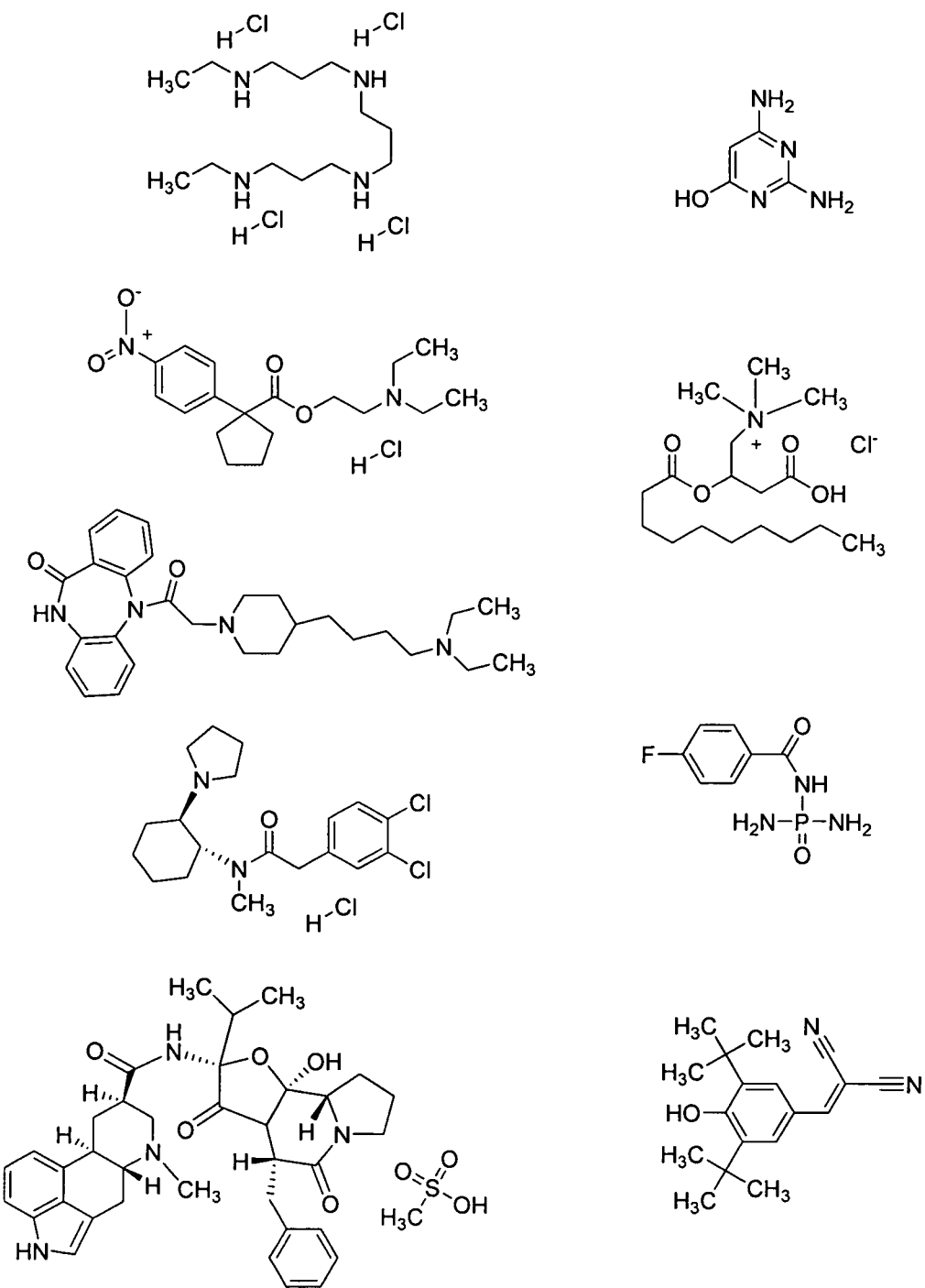
Figure 17V:
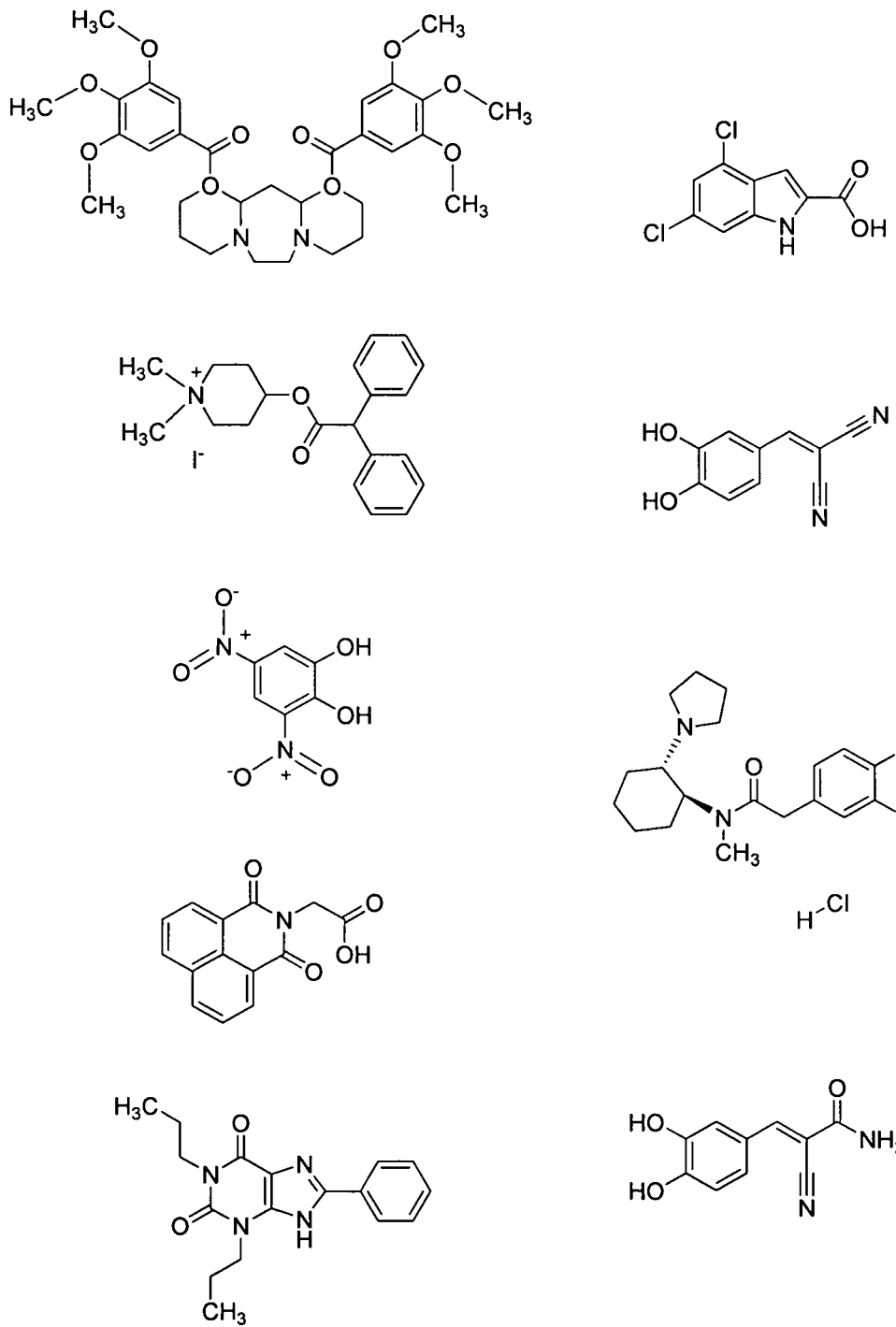
Figure 17Y:
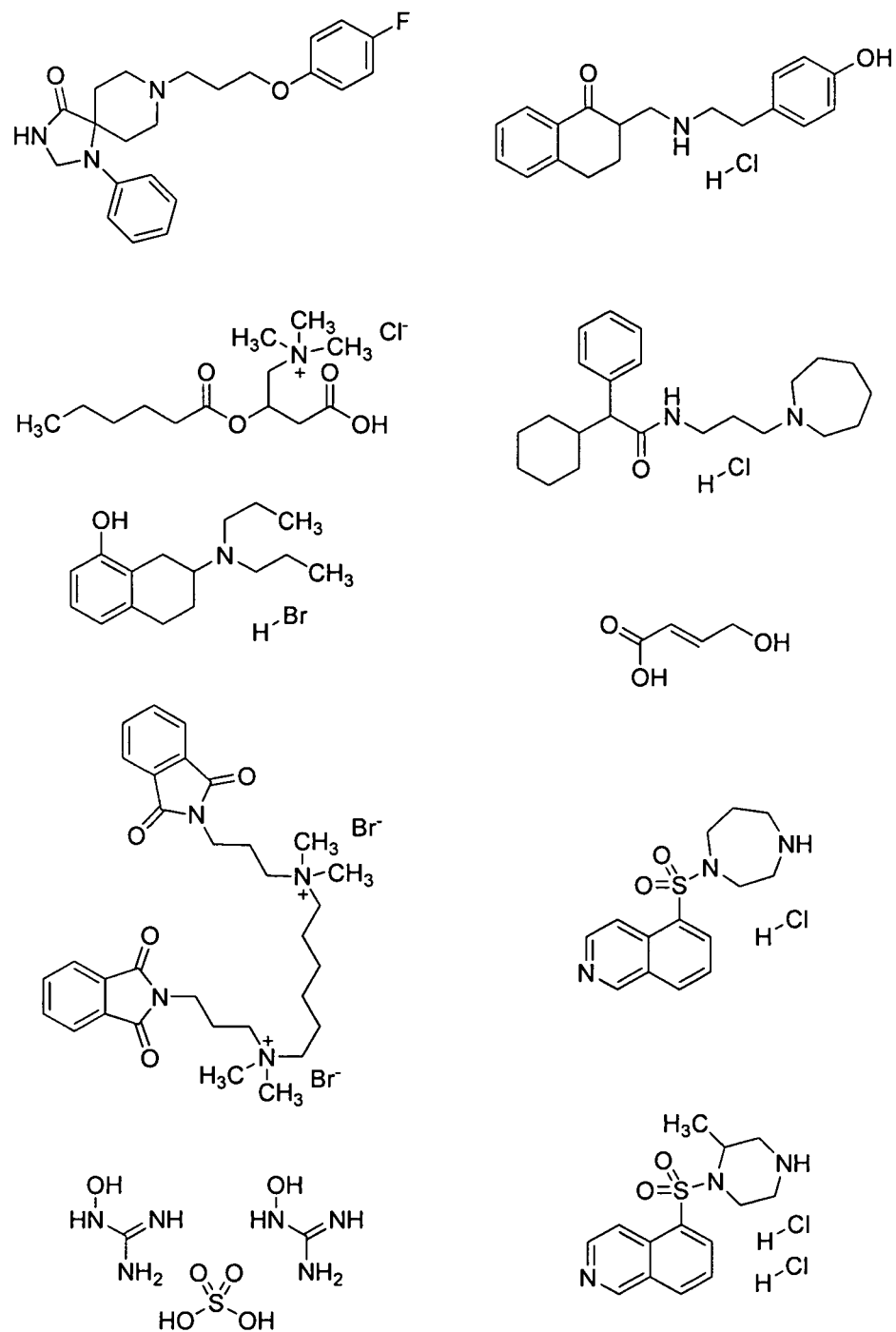
Figure 17Z:
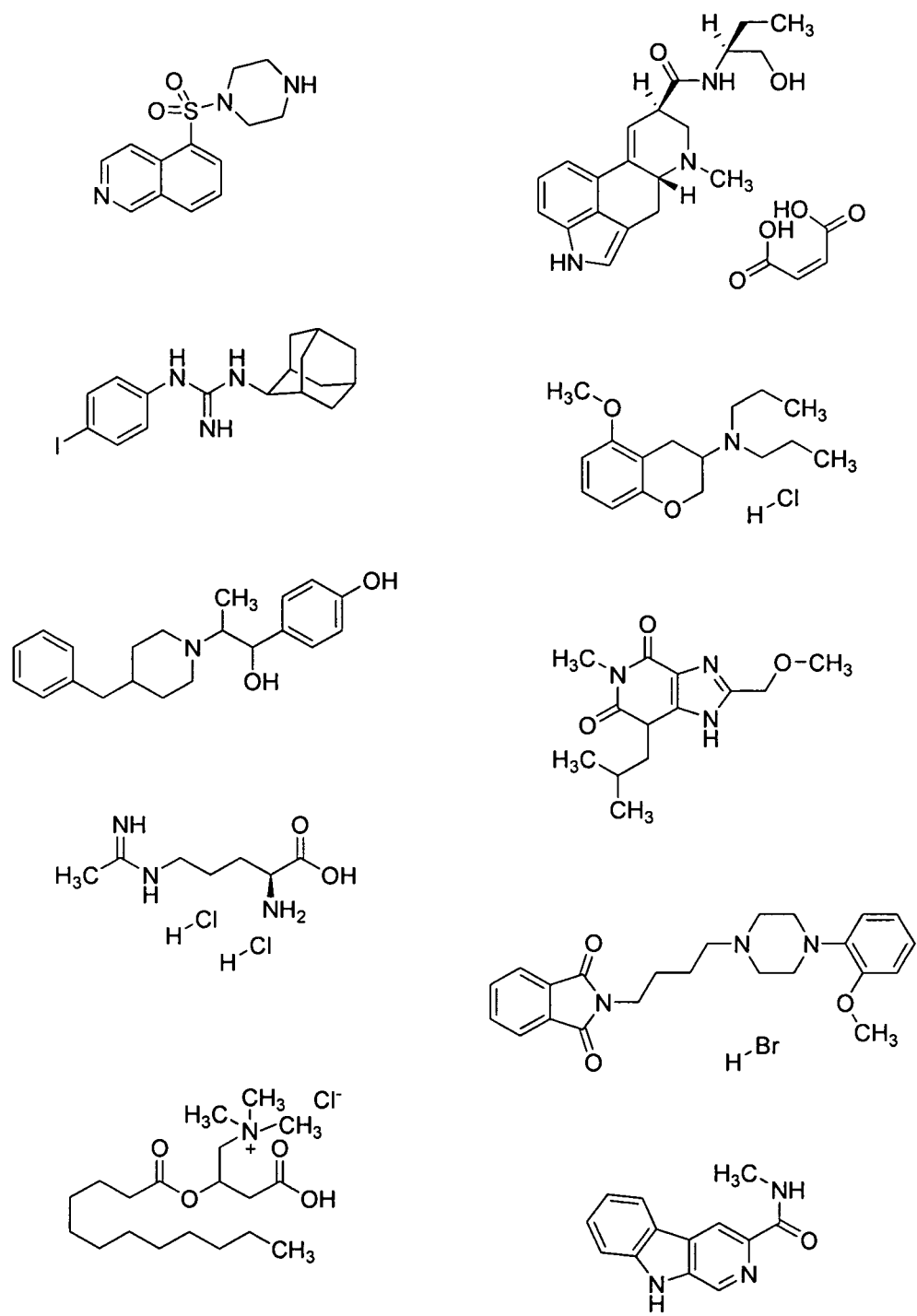
Figures 17A, 17B:
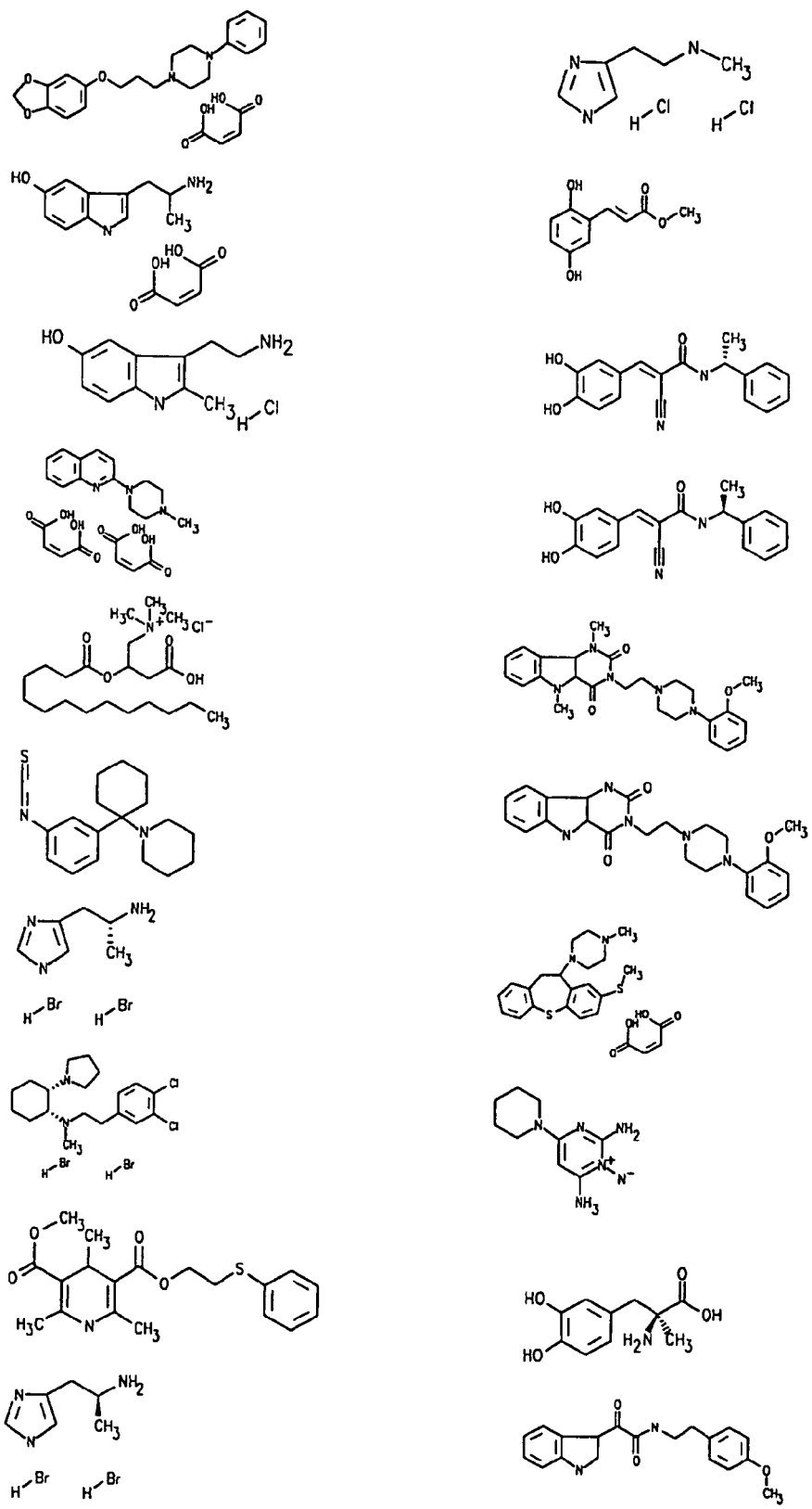
Figures 17C, 17D:
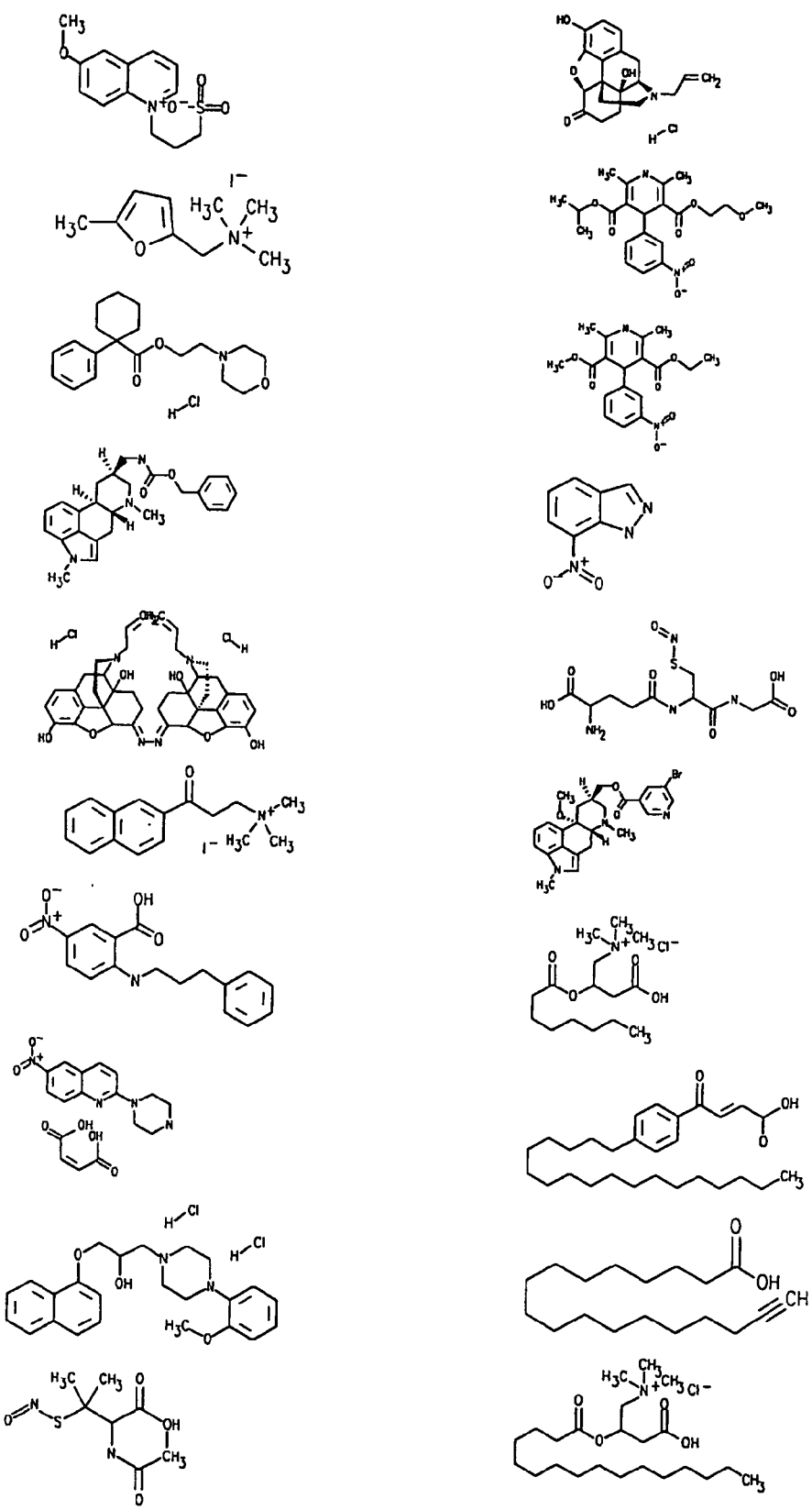
Figures 17E, 17F:
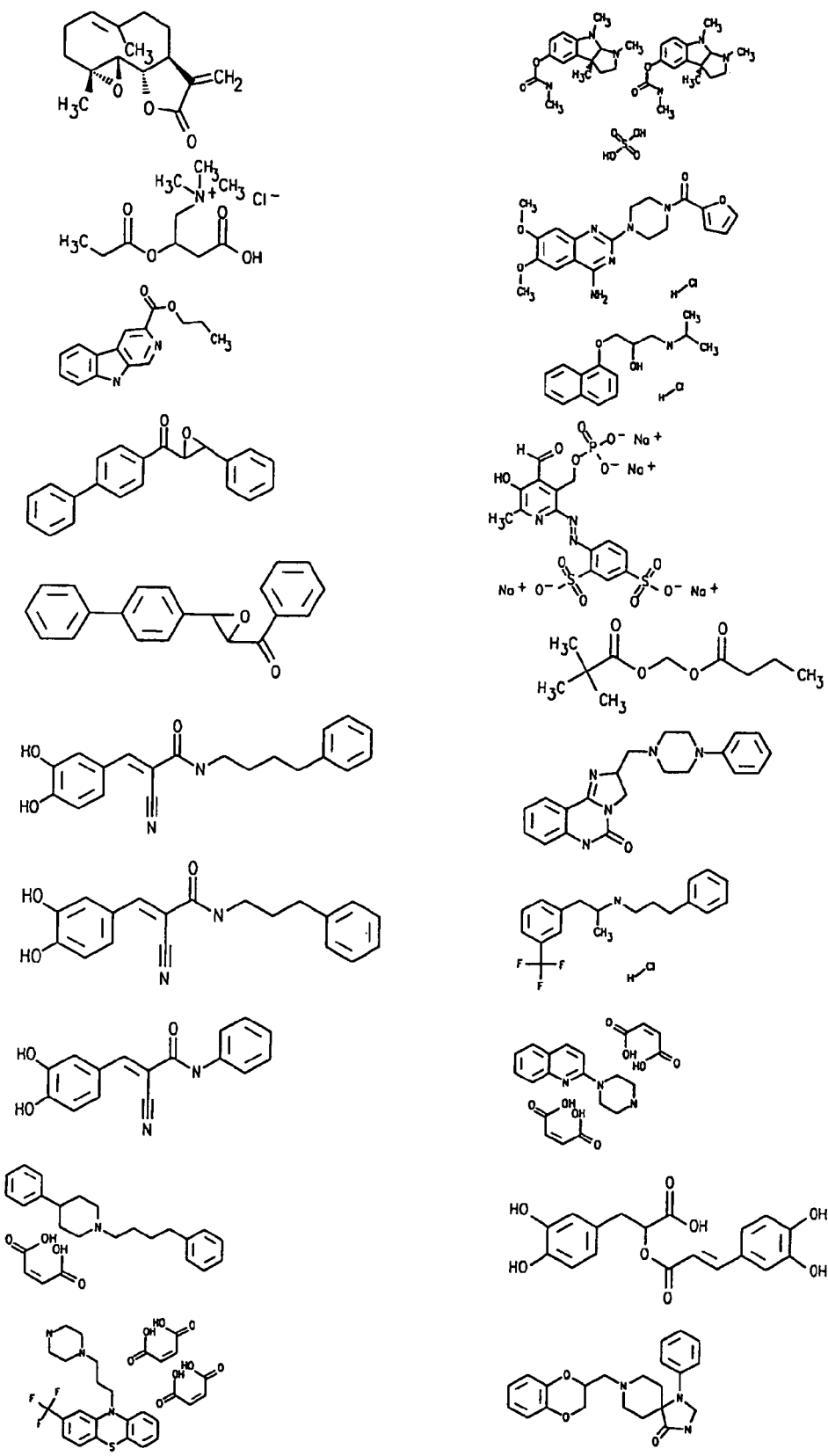
Figure 17G:
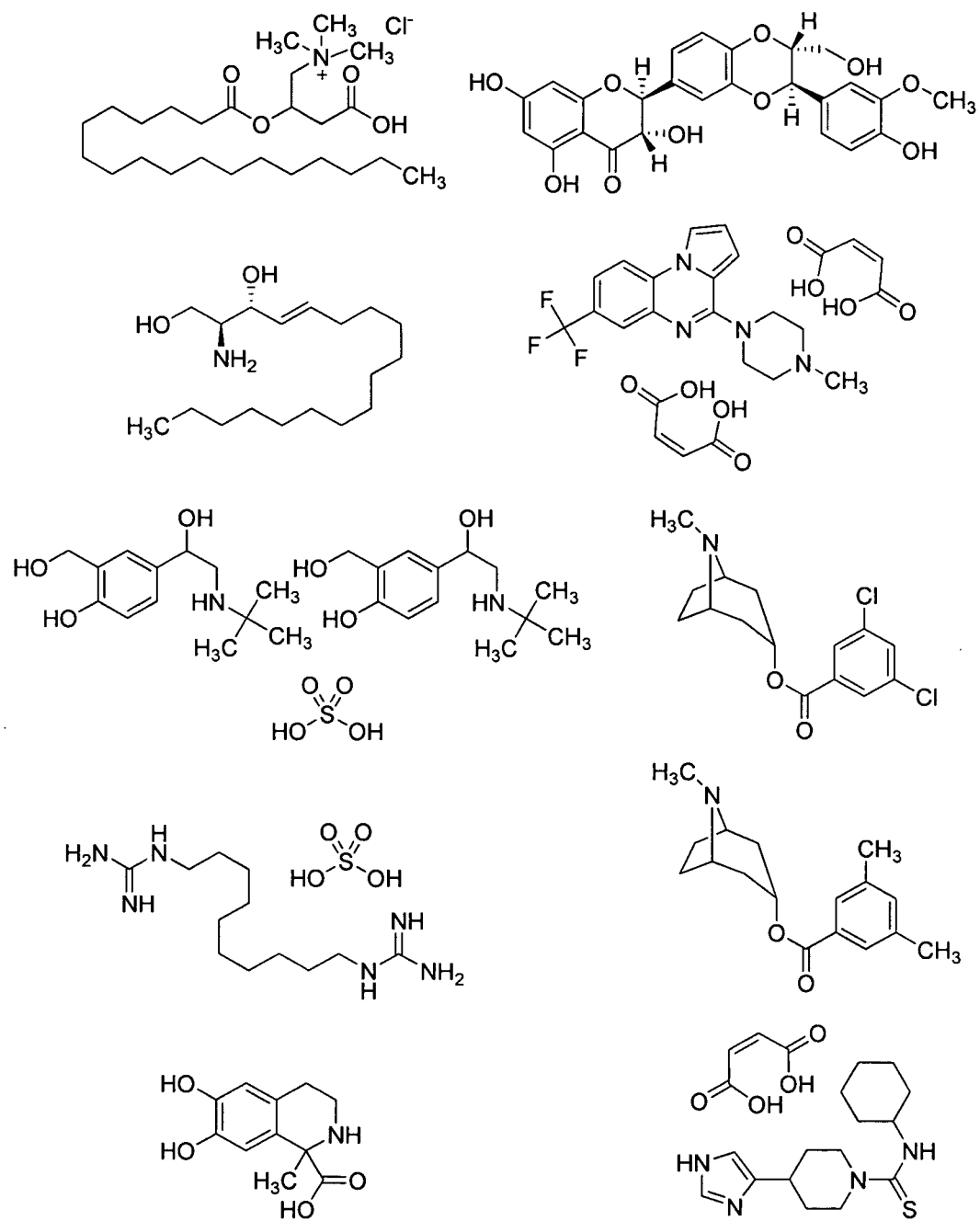
Figure 17I:
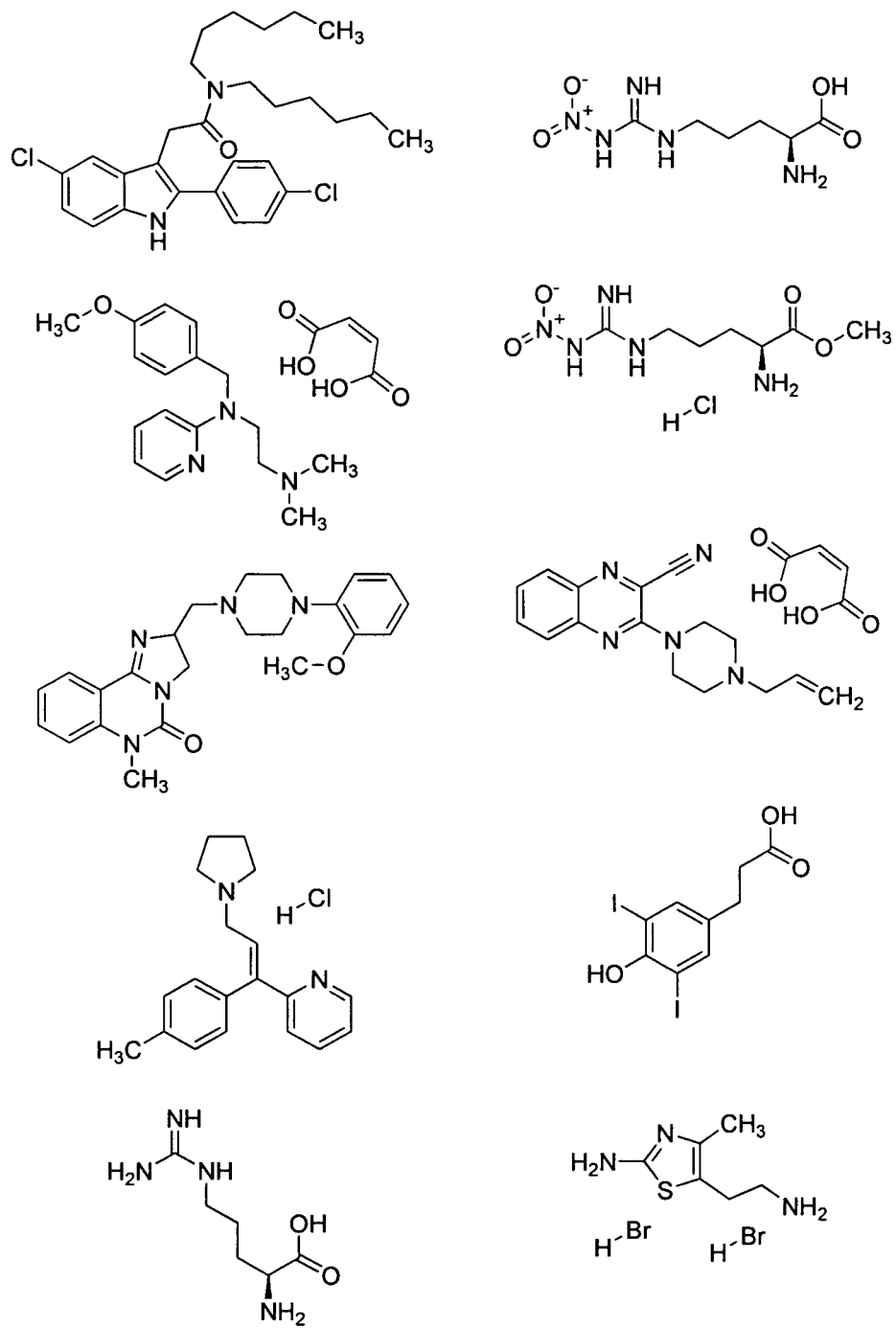
Figure 17K:
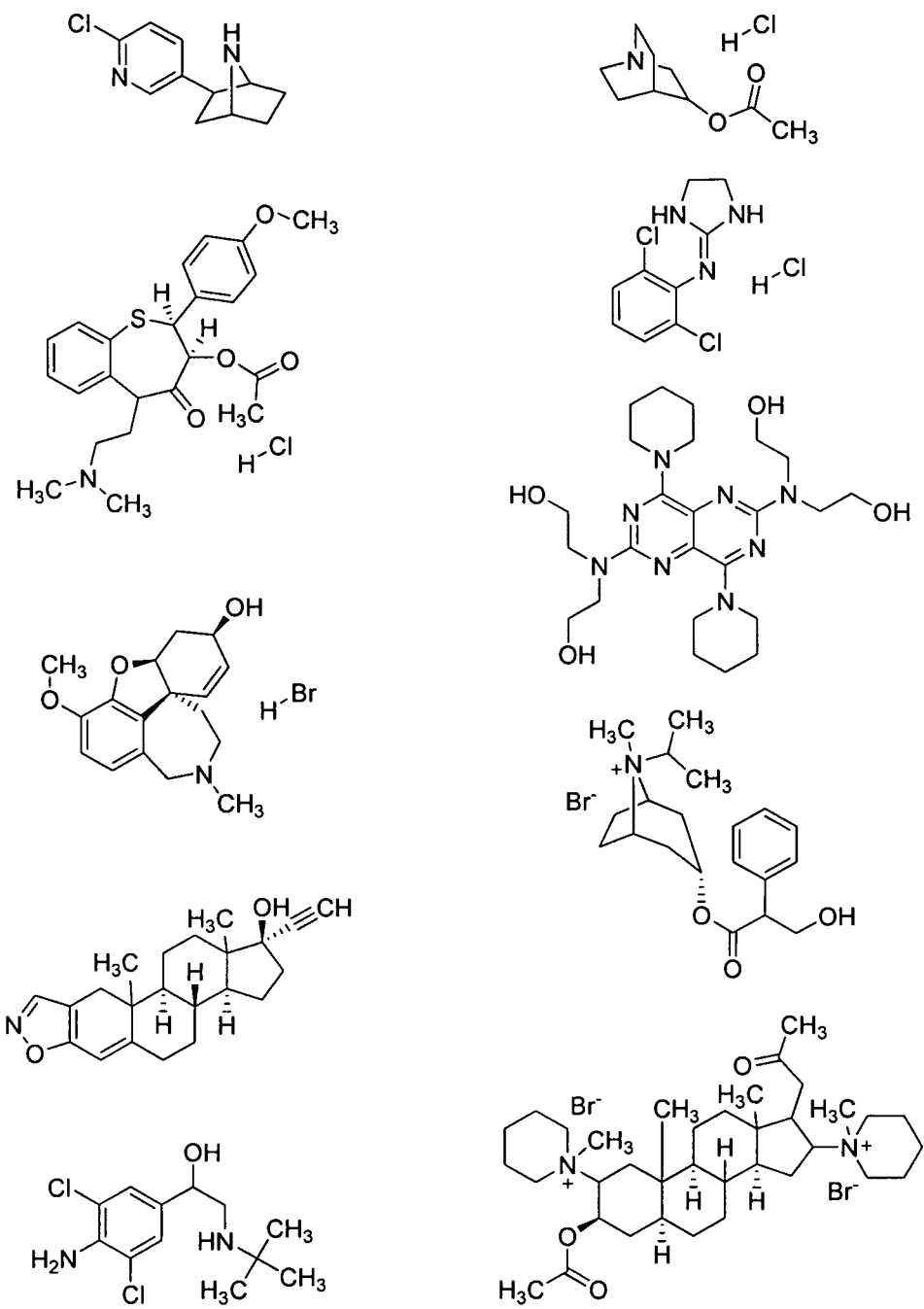
Figure 17I:
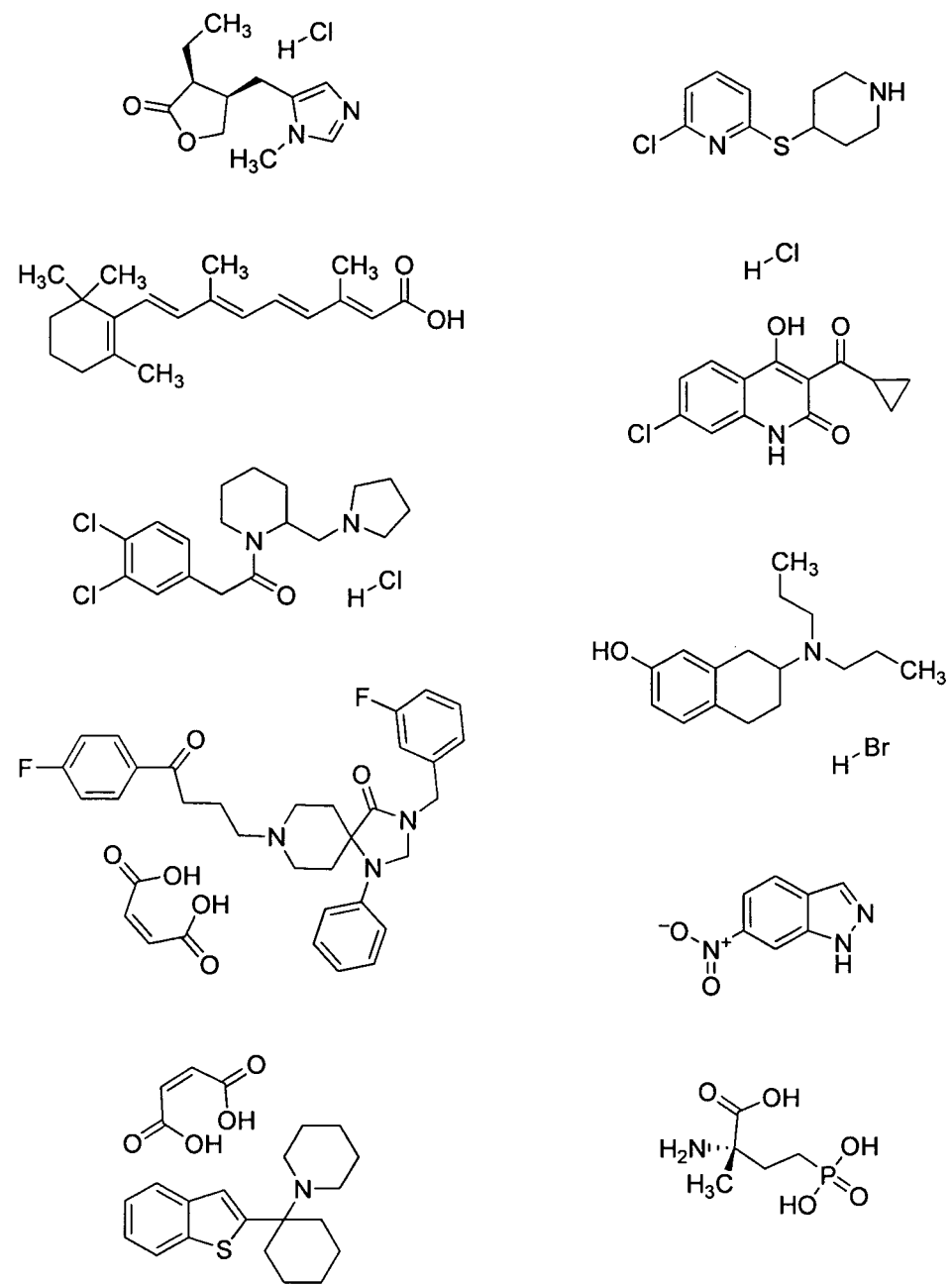
Figure 17P:
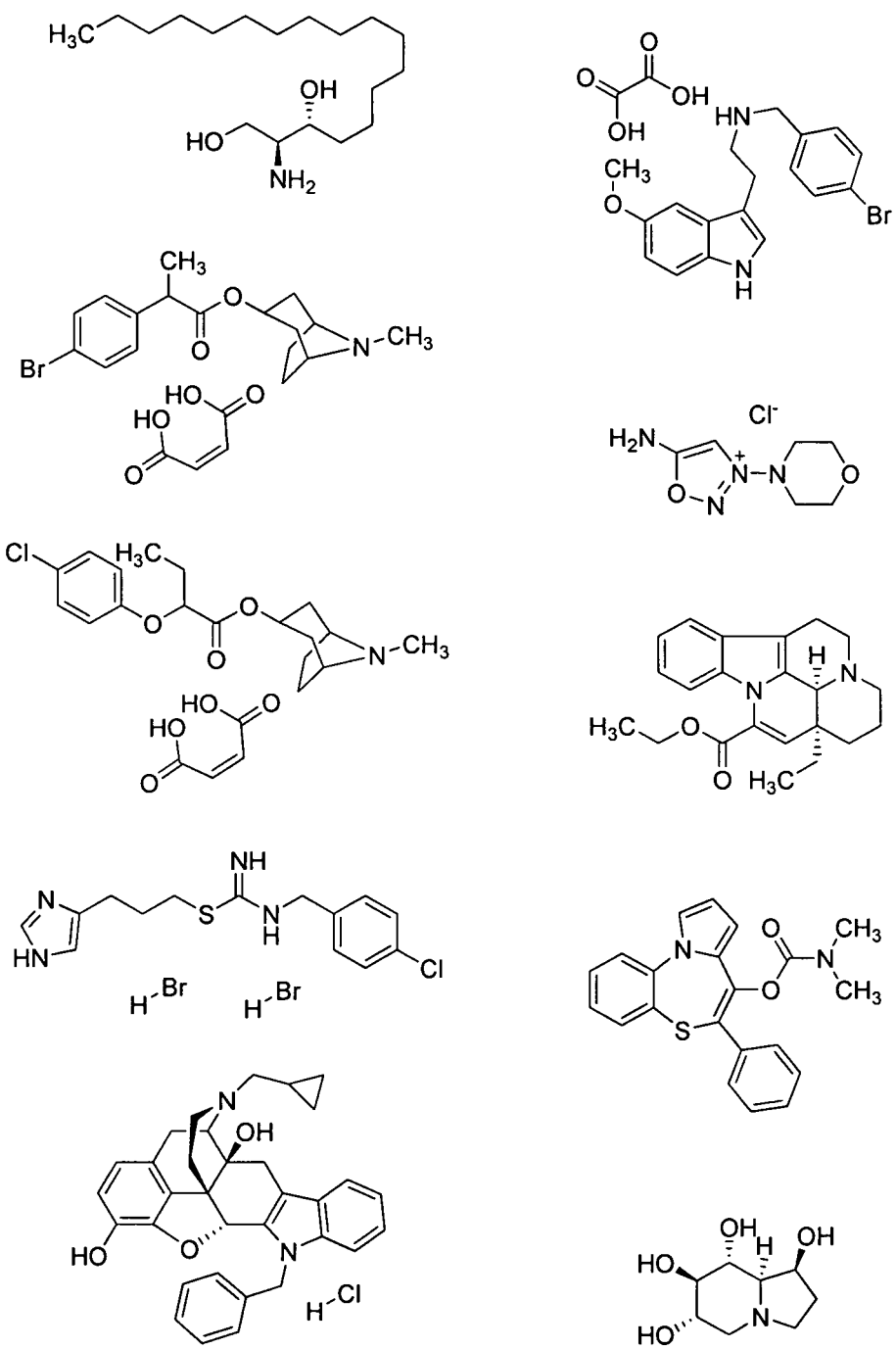
Figure 17Q:
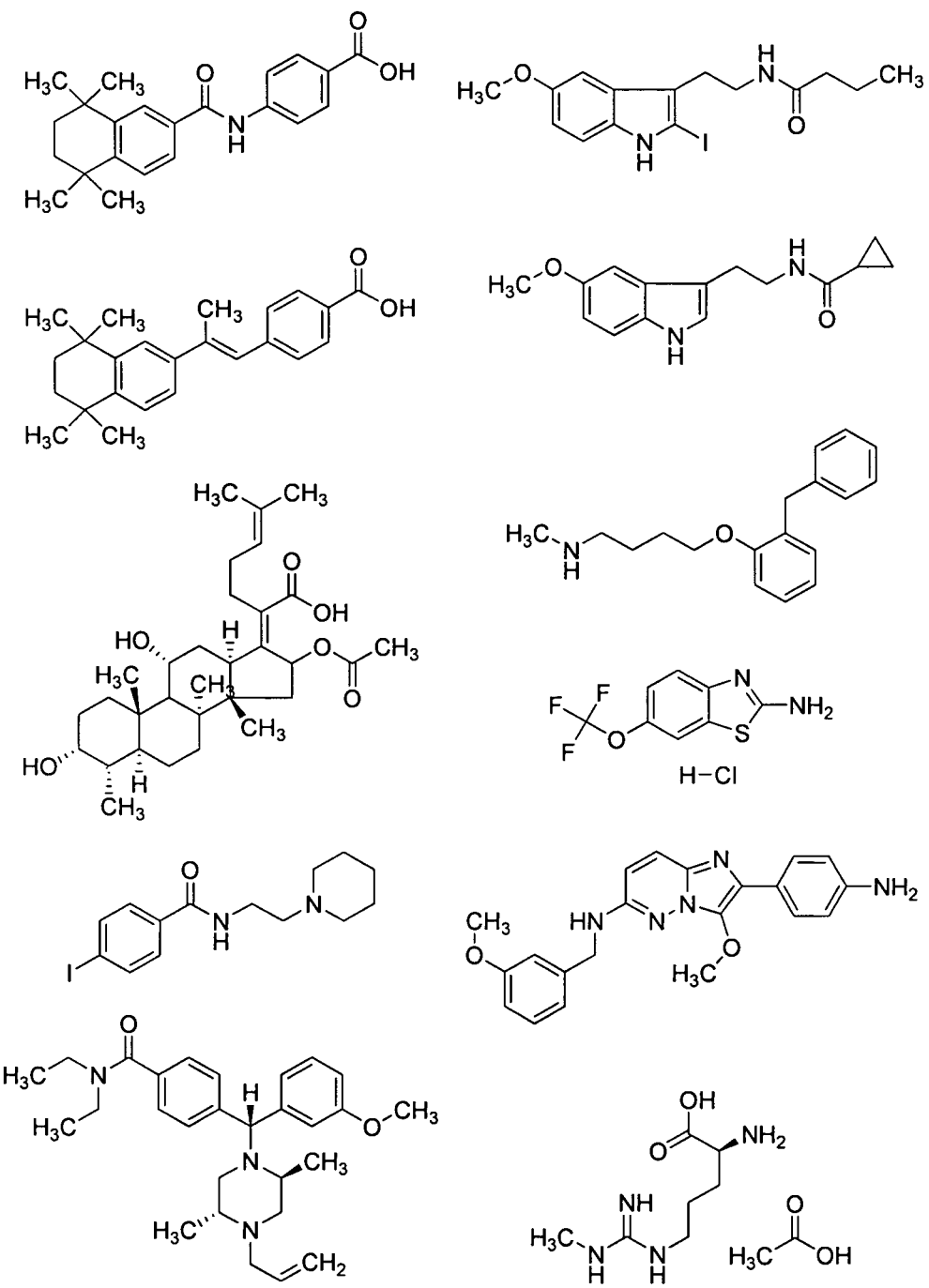
Figure 17S:
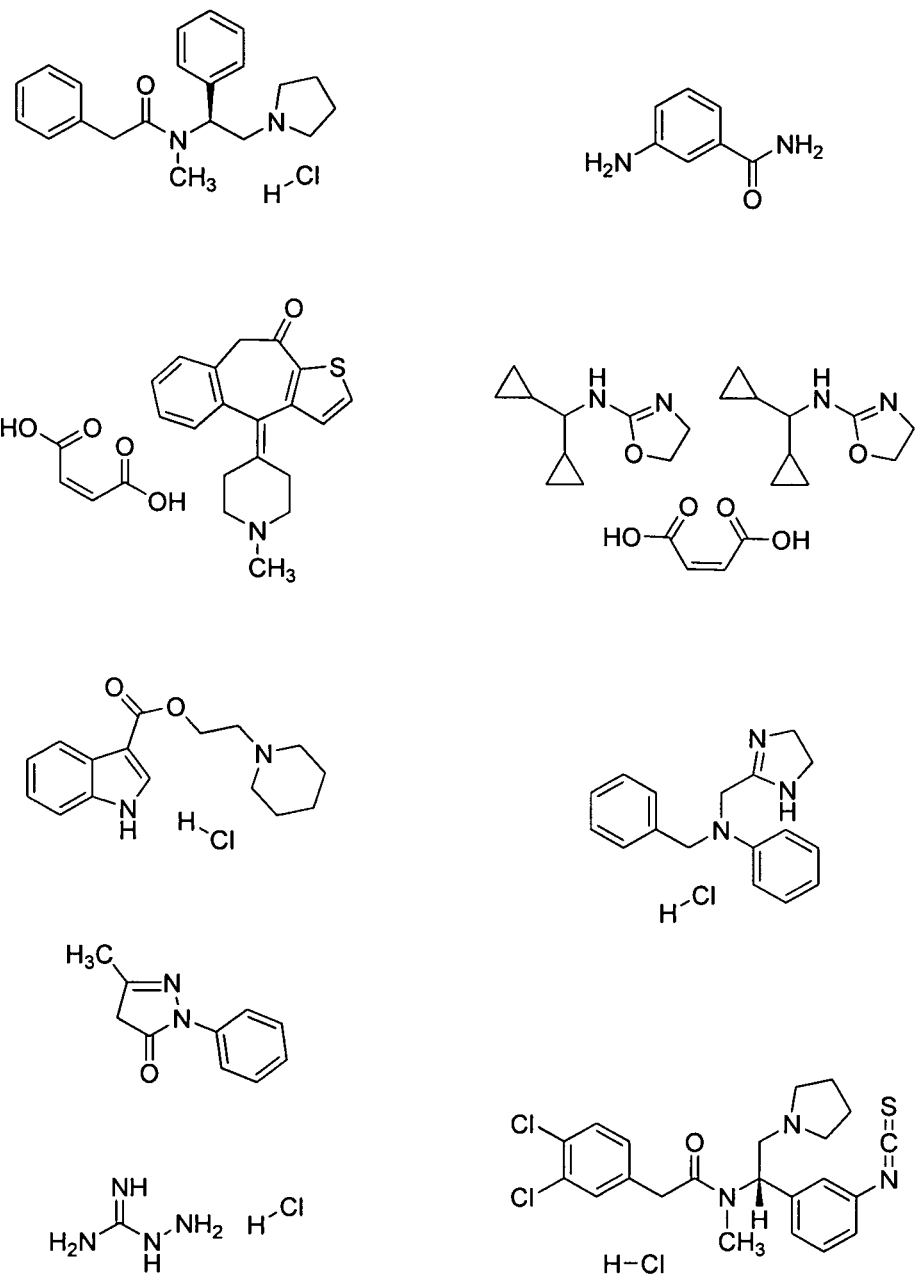
Figure 17T:
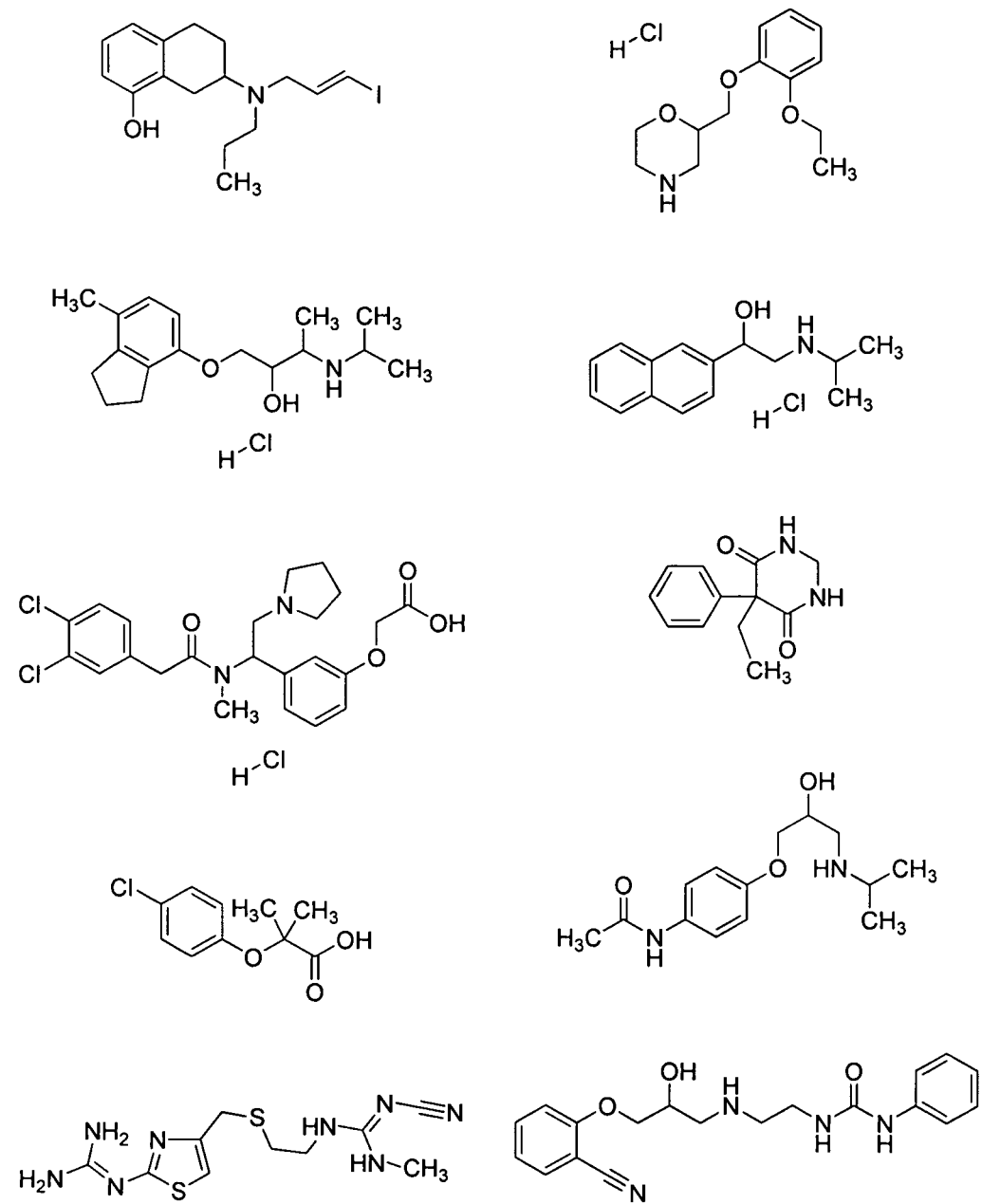
Figure 17U:
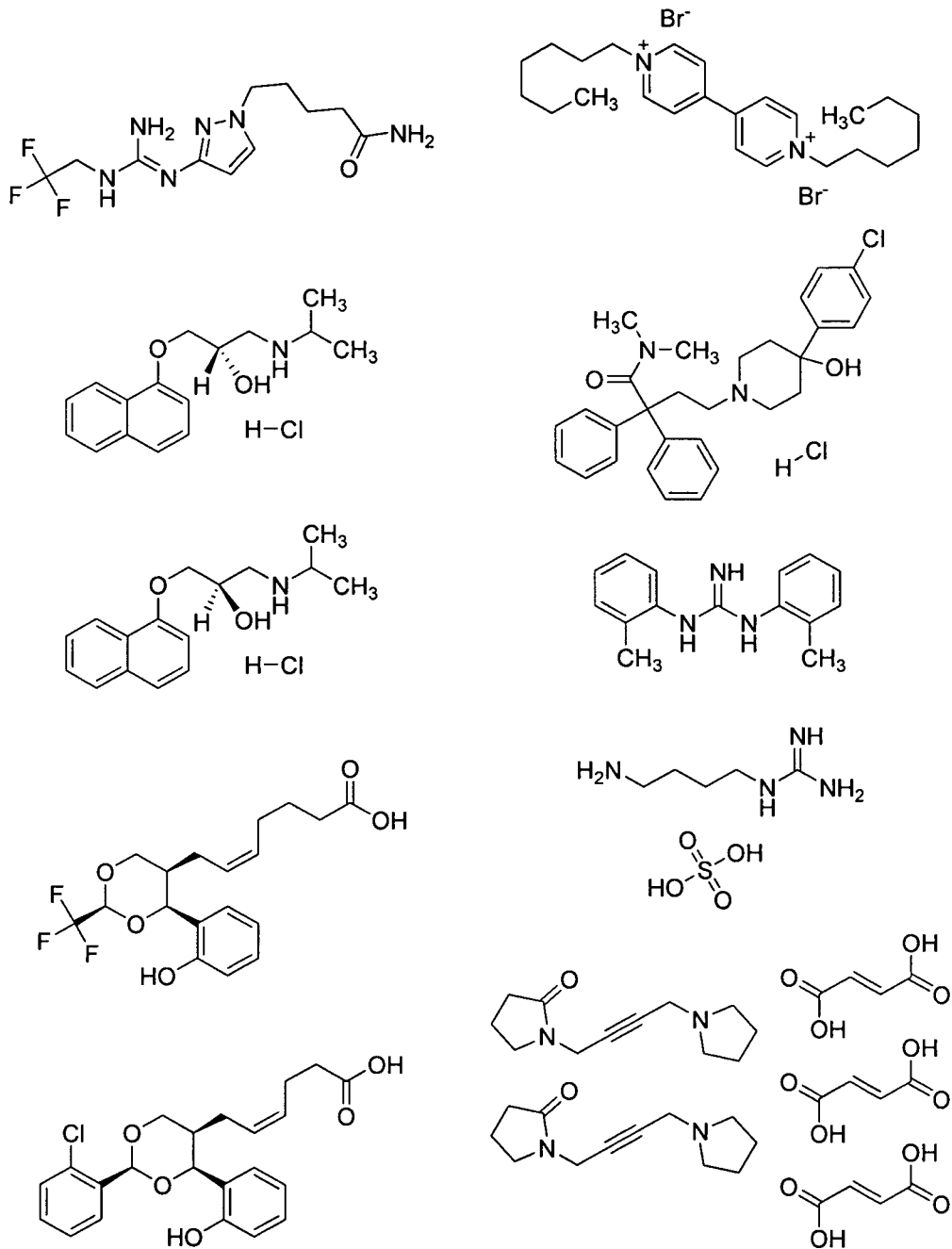
Figure 17V:
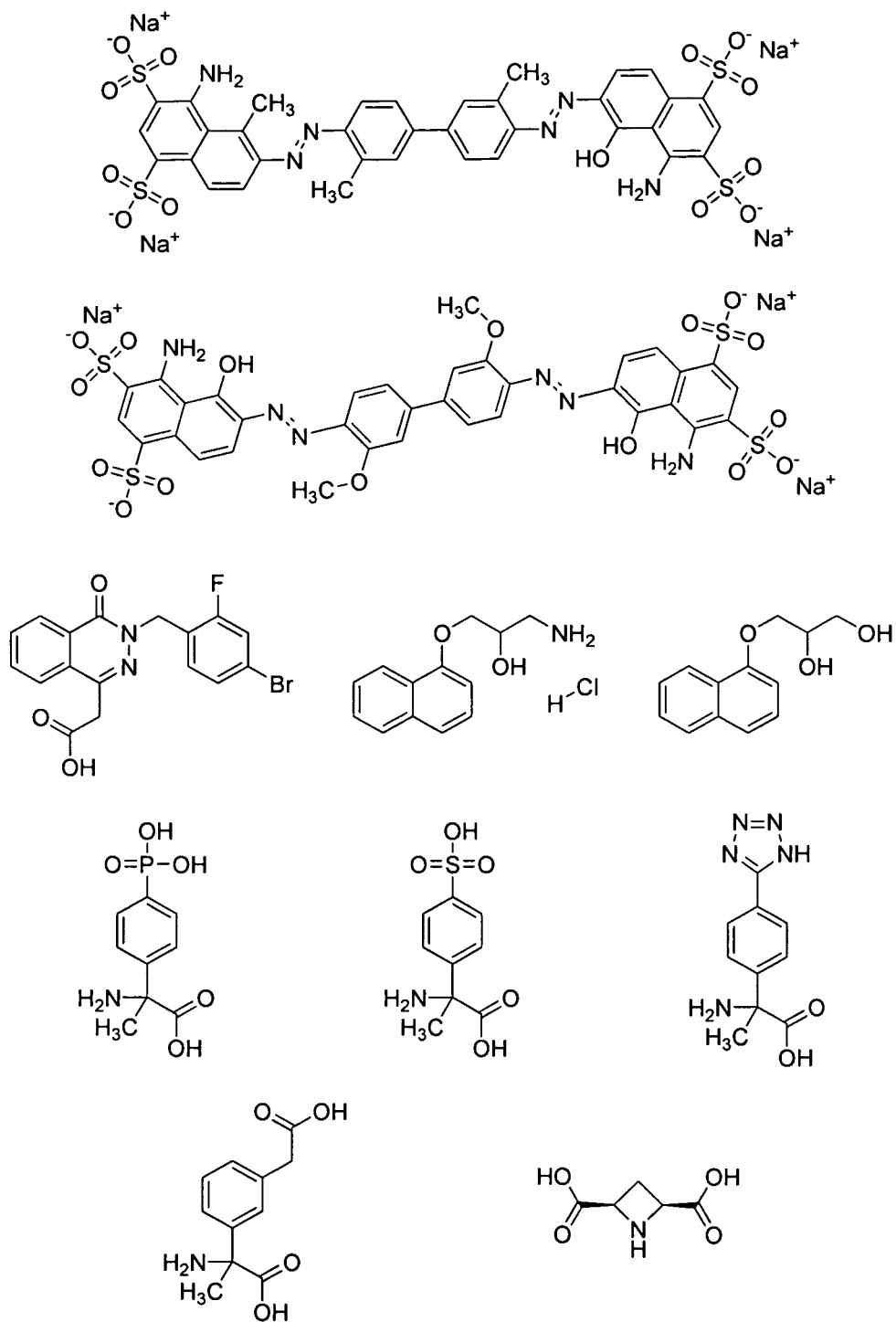
Figures 17W, 17X:
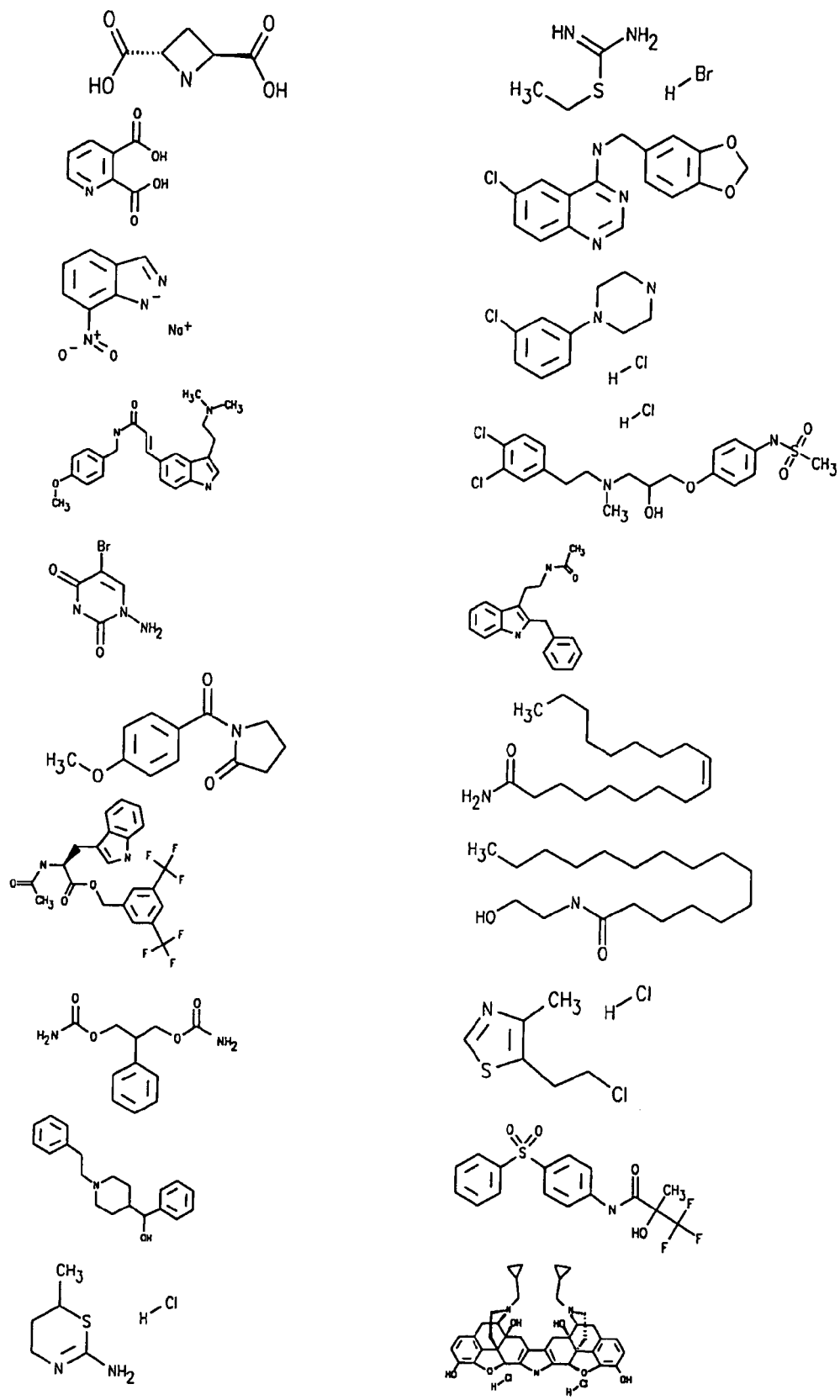
Figures 17Y, 17Z:
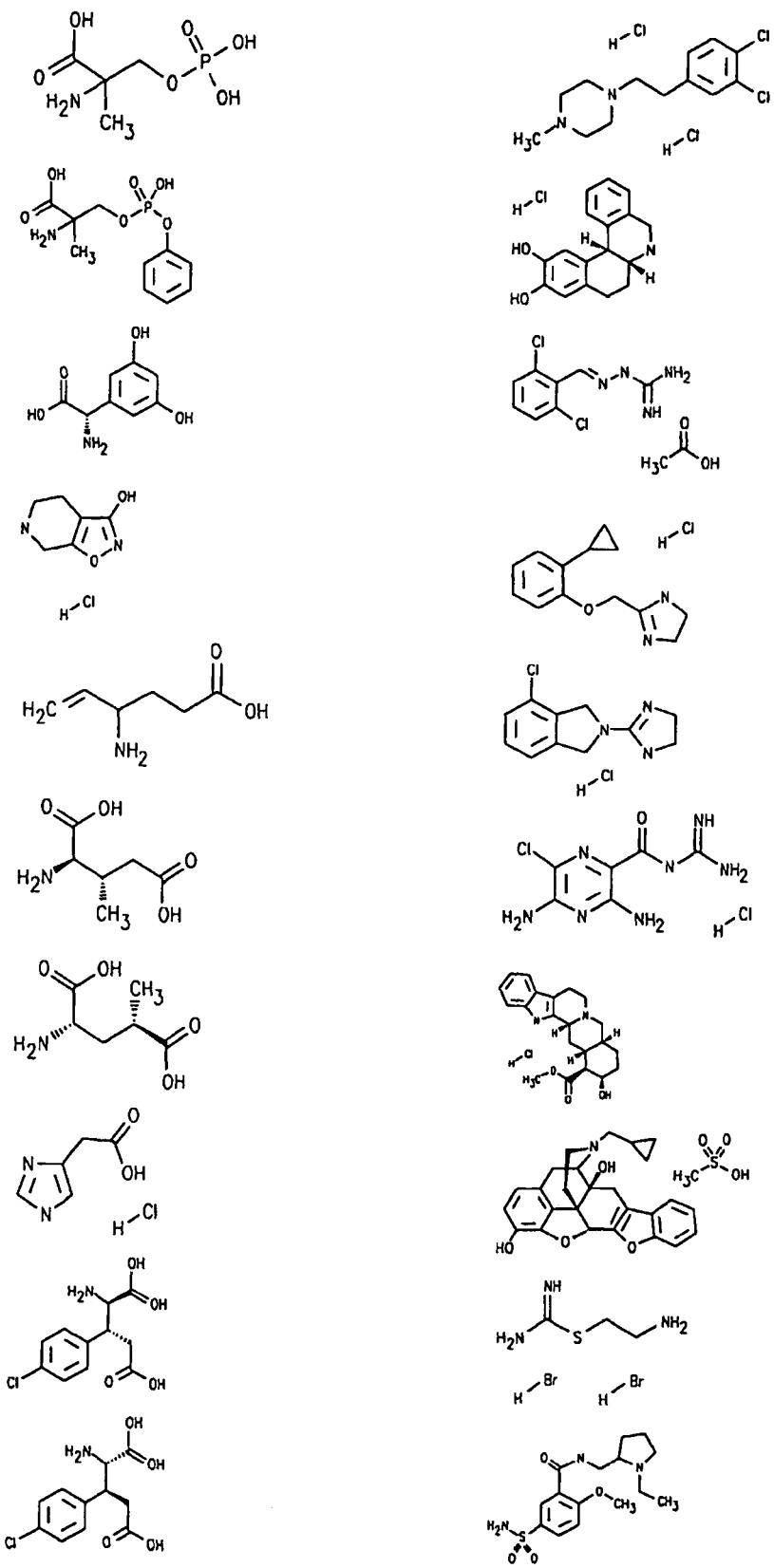

Adapter molecules can be ligated to both ends of the blunt ended double stranded cDNA or to only one end of the cDNA. Site directed adapter ligation could be achieved through the use of 5' modified oligonucleotides (for example biotinylated, aminated) during cDNA synthesis that prevents adapter ligation to the 3' end of the cDNA. The resulting cDNA molecules contain a 5'-end cDNA library comprised of the 5' non-translated region, the translational start codon AUG coding for a methionine, followed by the coding region of the gene or genes. The cDNA molecules are flanked by known DNA sequence on their 5'- and 3'-ends (FIGS. 14, 15 and 16).

e. cDNA Amplification

Figure 11:
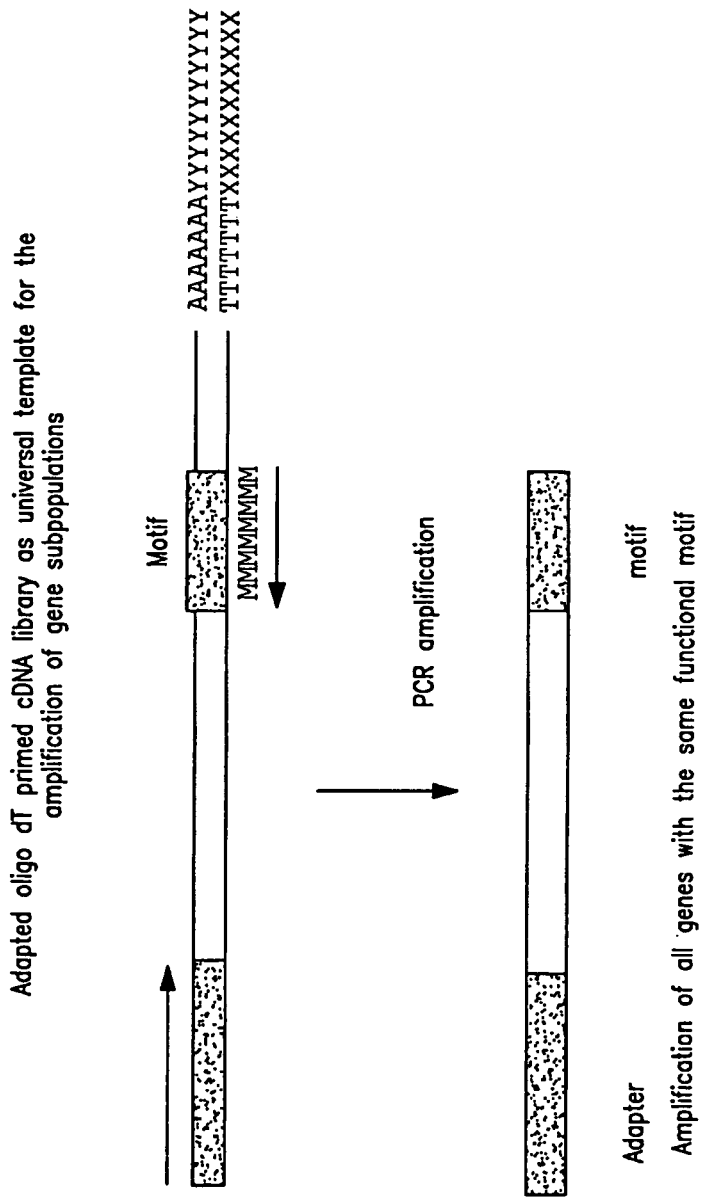
FIG. 11 shows an adapted oligonucleotide dT primed cDNA library as a universal template for the amplification of gene subpopulations.

PCR Primers to the known 5'- and 3'-end sequences or known internal sequences can be synthesized and used for the amplification of either the complete library or specific subpopulations of cDNA using an extended 5'- or 3'-amplification primer in combination with the primer located on the opposite site of the cDNA molecules (FIG. 11).

f. Primer Design for the Amplification of Gene Sub-Populations

Figure 12:
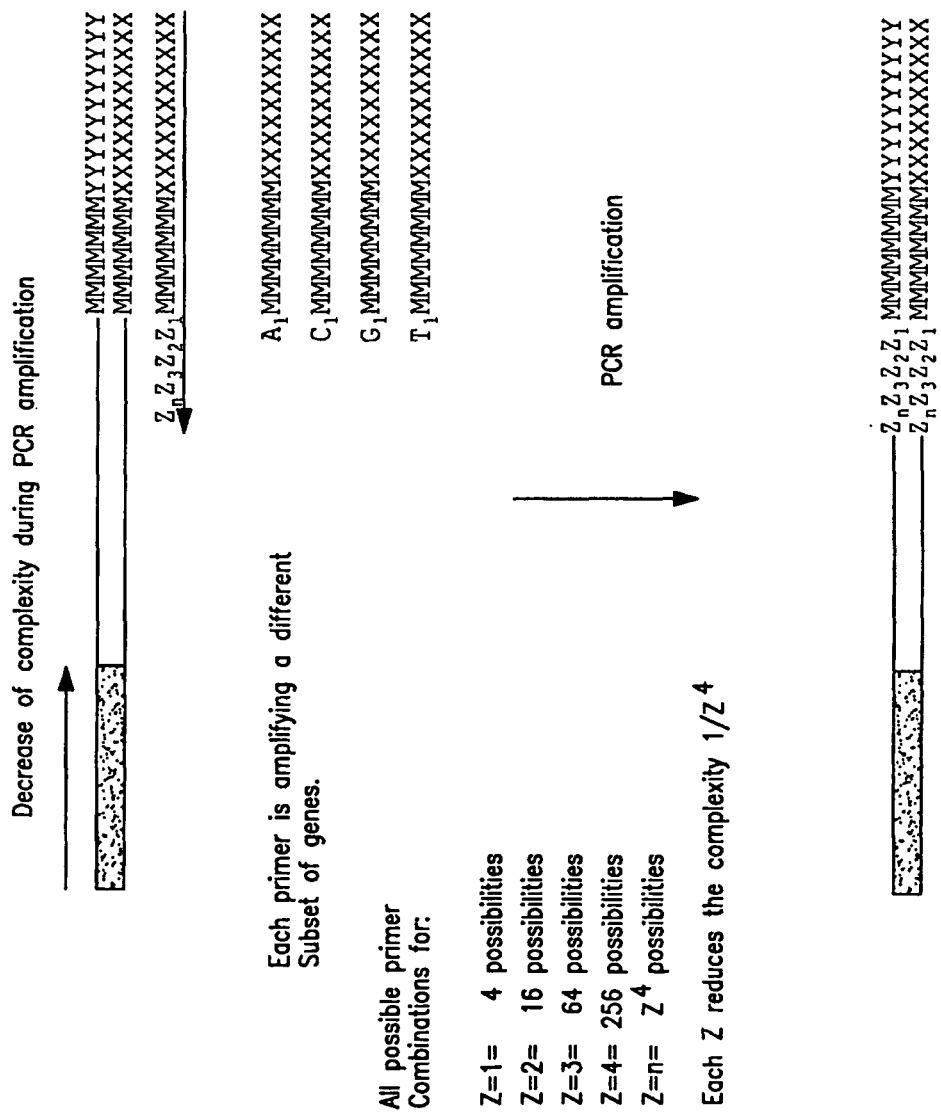
FIG. 12 illustrates decrease of complexity during PCR amplification.

The sub-population primers contain two portions (FIG. 12). The 5'-part of the primer is complementary to the sequence of a known sequence, extending with its 3'-end into the unknown cDNA sequence. Since each nucleotide in the cDNA part of the library can have an adenosine, cytidine, guanosine or thymidine residue, 4 different nucleotides possibilities exist for each nucleotide position. Four different amplification primers can be synthesized, each containing the same known sequence and extending by one nucleotide into the cDNA area of the library. The 4 primers only differ at their most 3'-nucleotide, being either A, C, G or T. If we suppose that each nucleotide (A, C, G, T) is equally represented in a stretch of DNA, each one of the 4 amplification primers will amplify one quarter of the total genes represented in the cDNA library. Extending the amplification primer sequence further and increasing the number of amplification primers, the complexity of the amplification products can be further reduced. Extending the sequence by 2 nucleotides requires the synthesis of 16 different primers decreasing the complexity by 16 fold, 3 nucleotides require 64 different primers and nucleotide extension requires $n^4$ different primers.

g. PCR Amplification

PCR amplification entails mixing template DNA, two appropriate oligonucleotide primers (5'- and 3'-end primers located in the known added sequences directed in complementary orientation), Taq or other thermostable DNA polymerases, deoxyribonucleoside triphosphates (dNTPs), and a buffer. The PCR products are analyzed after cycling on DNA gels or through analysis on an ABI 377 using the genescan analysis software. These analysis methods allow the determination of the complexity of the amplified cDNA pool.

h. Production of a Protein Expression Library

Each amplified cDNA library sub-population is cloned 5' to 3' in a bacterial (*E. coli*, etc.) or eukaryotic (Baculovirus, yeast, mammalian) protein expression system. The gene s introduced with its own translational initiation signal and a 6× His tag in all 3 frames. For example: the cDNA is restricted with two different, rare-cutting restriction enzymes (5'-end BglII and 3'-end Not I) and cloned in the 5' to 3' orientation in the Baculovirus transfer vector pVL1393 under the direct control of the polyhedra promoter.

i. Protein Expression

Linearized Baculovirus DNA and recombinant transfer-vector DNA are cotransfected into susceptible Sf9 insect cells with calcium phosphate. For cotransfection, 10 ug of purified plasmid DNA is prepared. An initial recombinant Baculovirus stock is prepared and Sf9 cells are infected for recombinant protein production.

j. Protein Purification

The expressed recombinant proteins contain an affinity tag (an example is a 6× His tag). They are purified on Ni-NTA agarose. Approximately 1 to 2 mg of 6× His recombinant fusion protein is routinely obtained per liter of insect cell culture.

k. Purification Tag Removal

If the expression vector or the amplification primer was constructed with a proteolytic cleavage site for thrombin, the purification tag can be removed from the recombinant proteins after the protein affinity purification step.

II. Antibody Generation by Immunization of Different Animals with Individual Protein Mixtures 3. Preparation of Antibody Protein Capture Reagents A purified protein preparation translated from a pool of cDNAs is injected intramuscularly, intradermally, or subcutaneously in the presence of adjuvant into an animal of the chosen species (rabbit). Booster immunizations are started 4 to 8 weeks after the priming immunization and continued at 2- to 3-week intervals. The polyclonal antiserum is purified using standards known to those skilled in the art.

The purified antibody batches can be used directly as protein capture reagents without modification. In this case the antibody batches from different animals have to be kept separate (each batch is one capture reagent).

III. Antibody Proteins are Isolated and Conjugated with Nucleic Acid Sequences that Correspond to the Original Antigen Preparation Resulting in the Antibody Capture Reagents Generation of bi-functional capture/sorting molecules for sorting of the complex protein mixture on a solid phase.

Figure 13:
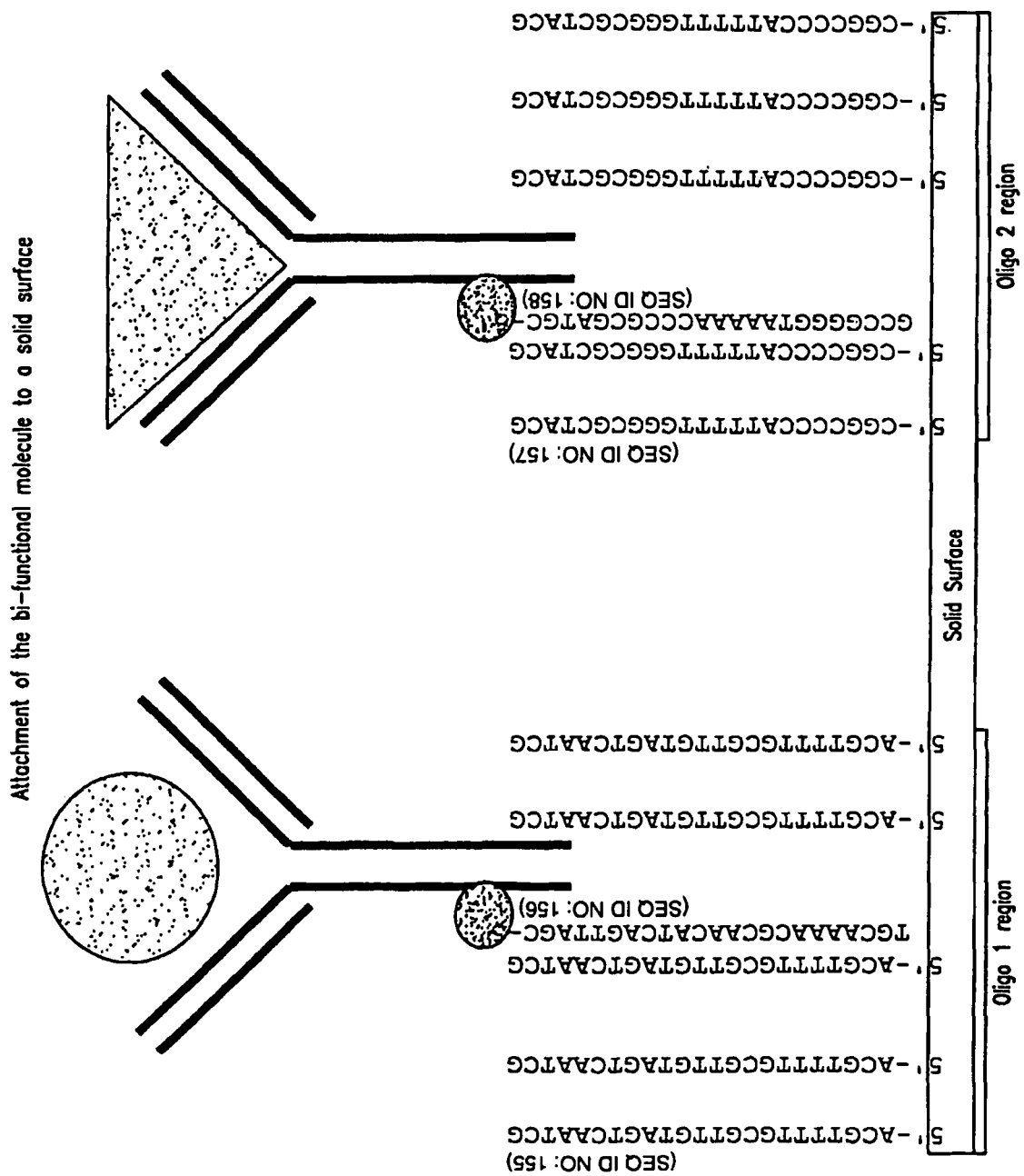
FIG. 13 shows the attachment of a bifunctional molecule to a solid surface.

The glycosylated $C_H^2$ domain of the polyclonal antibodies are conjugation to 5' modified oligonucleotides using standard conjugation methods. The resulting molecule has one protein capture moiety (antibody) and one nucleic acid moiety (oligonucleotide) (FIG. 13).

The antibody batches after immunization of an animal with a reduced complexity protein pool are conjugated with the one oligonucleotide sequence. Antibodies produced from multiple immunization events with different protein pools are conjugated to an oligonucleotide with a different sequence (FIG. 13).

4. Capture of Target Proteins Using Reactivity, Functionality and Sorting by Oligonucleotide Hybridization Two different methods have been developed for making oligonucleotides bound to a solid support: they can be synthesised in situ, or presynthesised and attached to the support. In either case, it is possible to use the support-bound oligonucleotides in a hybridization reaction with oligonucleotides in the liquid phase to form duplexes; the excess of oligonucleotide in solution can then be washed away.

The support can take the form of particles, for example, glass spheres, or magnetic beads. In this case the reactions could be carried out in tubes, or in the wells of a microtitre plate. Methods for synthesising oligonucleotides and for attaching presynthesised oligonucleotides to these materials are known (see, e.g., Stahl et al. (1988) *Nucleic Acids Research* 16(7):3025-3039).

a. Preparation of Amine-Functionalized Solid Support

Oligonucleotides of a defined sequence are synthesized on an amine-functionalized glass support. An amine function was attached at discrete locations on the glass slide using a solution of 700 μl of $H_2N(CH_2)_3 Si(OCH_2CH_3)_3$ in 10 ml of 95% ethanol at room temperature for 3 hours. The treated support is washed once with methanol and then once with ethyl ether. The support was dried at room temperature and then baked at 110° C. for 15 hours. It was then washed with water, methanol and water, and then dried.

The glass slide was reacted for 30 minutes at room temperature with 250 mg (1 millimole) of phthallic anhydride in the presence of 2 ml of anhydrous pyridine and 61 mg of 4-dimethylaminopyridine.

The product was rinsed with methylene dichloride, ethyl alcohol and ether, and then dried. The products on the slide were reacted with 330 mg of dicyclohexylcarbodiimide (DCC) for 30 minutes at room temperature. The solution was decanted and replaced with a solution of 117 mg of 6-amino-1-hexanol in 2 ml of methylene dichloride and then left at room temperature for approximately 8 hours.

b. Oligonucleotide Synthesis on a Solid Support

The amine-functionalized solid support was prepared for oligonucleotide synthesis by treatment with 400 mg of succinic anhydride and 244 mg of 4-dimethylaminopyridine in 3 ml of anhydrous pyridine for 18 hours at room temperature. The solid support was treated with 2 ml of DMF containing 3 millimoles (330 mg) of DCC and 3 millimoles (420 mg) of p-nitrophenol at room temperature overnight. The slide was washed with DMF, $CH_3CN$, $CH_2Cl_2$ and ethyl ether. A solution of 2 millimoles (234 mg) of $H_2N(CH_2)_6OH$ in 2 ml of DMF was reacted with the slide overnight. The product of this reaction was a support, $O(CH_2)_3NHCO(CH_2)_2CONH(CH_2)_5CH_2OH$. The slide was washed with DMF, $CH_3CN$, methanol and ethyl ether.

The functionalized ester resulting from the preparation of the glass support was used for the synthesis of a oligonucleotide sequence. Each nucleoside residue was added as a phosphoramidite according to known procedures (see, e.g., U.S. Pat. Nos. 4,725,677 and 5,198,540, and RE34,069, see, also Caruthers et al. U.S. Pat. No. 4,415,732).

5. Protein Analysis of the Captured Proteins and Complex Protein Sample Comparison The purified antibody batches can be either 1) directly attached to a solid surface, and incubated with protein samples, 2) incubated with the samples and subsequently bound to a solid support without using the capture compound or 3) the capture compound can be used to capture its corresponding protein in a sample and subsequently sort the captured proteins through specific nucleotide hybridization (FIG. 14).

IV. Antisense Oliogonucleotide Capture Reagents are Immobilized in Discrete and Known Locations on a Solid Surface to Create an Antibody Capture Array 6. Preparation of Capture Array Surface 5'-aminated oligonucleotides are synthesized using phosphoramidate chemistry and attached to N-oxysussinimide esters. The attached oligonucleotide sequences are complementary to the sorting oligonucleotides of the bi-functional antibody molecules (FIG. 13). Proteins are captured through nucleic acid hybridization of their sorting oligonucleotide to the complementary sequence attached to the solid surface oligonucleotide.

V. The Antibody Capture Reagents are Added to the Total Protein Mixture (Reactivity Step). The Reaction Mixture is then Added to the Solid Surface Array Under Conditions that Allow Oligonucleotide Hybridization (Sorting Step)

7. Capture Compound/Protein Capture and Sorting

The bi-functional antibodies are incubated with the protein sample under conditions that allow the antibodies to bind to their corresponding antigen. The bi-functional antibody molecule with the captured protein is added to the oligonucleotide prepared capture array. Under standard DNA annealing conditions that do not denature the antigen-antibody, binding the bi-functional antibody will hybridize with its nucleic acid moiety to the complementary oligonucleotide.

VI. The Captured Protein is Identified Using MALDI Mass Spectrometry

8. Analysis of the Capture Proteins

The attached proteins are analyzed using standard protein analysis methods, such as mass spectrometry.

Example 4

Synthesis of Trityl Based Protein Capture Compounds (see FIG. 15)

A. Synthesis of 2-(4-bromophenyl)-4,4-dimethyl-1,3-oxazoline, 1

To 4-Bromobenzoic acid (50 g, 0.25M) placed in a 500 mL round bottom flask fitted with a reflux condenser was added 150 mL of thionyl chloride and refluxed for 8 h. The excess thionyl chloride was removed under vacuum and the white solid obtained was dissolved in 100 ml of dry $CH_2Cl_2$ and kept in an ice bath. To this ice cooled solution of bromo benzoylchloride was added drop wise 45 g of 2-amino-2-methylpropan-1-ol dissolved in another 100 mL of dry $CH_2Cl_2$ with stirring for the period of 1 h. The ice bath was removed and the reaction mixture was stirred at room temperature for over night. The precipitated white solid was filtered and washed several times with $CH_2Cl_2$ (4×100 mL). The combined $CH_2Cl_2$ was removed under rotaevoporator and the solid obtained was slowly dissolved in 150 mL of thionyl chloride and refluxed for 3 h. The excess of $SOCl_2$ was evaporated to one-sixth the volume and poured in to 500 mL of dry ether cooled in ice bath and kept in the refrigerator overnight. The ether was removed and the precipitated hydrochloride was dissolved in 500 mL of cold water. The aqueous solution was carefully neutralized using 20% KOH solution on cold condition (ice bath) and the brown oily residue separated was extracted with $CH_2Cl_2$ (3×200 mL) and dried over anhydrous $Na_2SO_4$. Removal of the solvent gave 42 g (67%) of 2-(4-bromophenyl)-4,4-dimethyl-1,3-oxazoline as a yellow oil. $^1$H-NMR (500 MHz, $CDCl_3$) δ ppm: 1.36 (s, 6H), 4.08 (s, 2H), 7.52 (d, 2H), 7.79 (d, 2H). Mass: 254.3 ($M^+$).

B. Synthesis of phenyl-{3-[2-(tetrahydropyran-2-yloxy)-ethoxy]-phenyl}-methanone, 2

1. Method A: In a 100 mL two neck round bottom flask placed with 550 mg (8 mM) of NaOEt in 20 mL of dry DMF was added 3-hydroxy benzophenone (1 g, 5 mM) under argon atmosphere. The reaction was stirred at room temperature for 10 min and added 2-bromoethoxy tetrahydropyran (1 g, 5 mM) dissolved in 5 mL of dry DMF by drop wise. The reaction mixture was heated at 60° C. for overnight, cooled and poured into ice water and extracted with $CH_2Cl_2$ (2×50 mL). The combined solvent was dried over anhydrous $Na_2SO_4$ and evaporated. The crude residue obtained was purified by silica gel column chromatography using hexane/EtOAc (9:1) mixture as an eluent. Yield: 680 mg (42%).

2. Method B: To the stirred mixture of 3-hydroxy benzophenone (1 g, 5 mM), anhydrous $K_2CO_3$ (3 g, 23 mM) and NaI (500 mg) in dry acetone (40 mL) was added 2-bromoethoxytetrahydropyran (1 g, 5 mM) dissolved in 10 mL of dry acetone and refluxed for 20 h. The precipitate was filtered and washed with acetone (3×20 mL). The combined filtrate was evaporated and the yellowish residue obtained was purified by silica gel column chromatography using hexane/EtOAc (9:1) mixture as an eluent. Yield: 55-60%. $^1$H-NMR (500 MHz, $CDCl_3$) δ ppm: 1.5-1.63 (m, 4H), 1.72 (m, 1H), 1.82

(m, 1H), 3.52 (m, 1H), 3.8-3.9 (m, 2H), 4.07 (m, 1H), 4.21 (m, 2H), 4.70 (t, 1H), 7.15 (d, 1H), 7.37 (m, 3H), (7.47 (t, 2H), 7.58 (t, 1H), 7.80 (d, 1H). Mass: 327.2 (M$^+$), 349.3 (M+Na$^+$).

C. Grignard reaction: Synthesis of 2-{4'-(3-(2-tetrahydropyran-2-yloxy)ethoxy)phenyl-4"-phenyl)}-4, 4-dimethyl-1,3-oxazoline, 3

To a 100 mL two necked round-bottomed flask fitted with reflux condenser was placed activated Mg turnings (720 mg, 30 mM), a few crystals of I$_2$ and molecular sieves (A4) under argon. To this mixture 10 ml of THF was added. The mixture was heated to 50° C. and 2-(4-bromophenyl)-4,4-dimethyl-1,3-oxazoline (6.5 g, 26 mM) dissolved in 15 mL of dry THF, a catalytic amount of CH$_3$I, RED-Al and CCl$_4$ were added with stirring and refluxed for 3 h. After that the reaction mixture was cooled to room temperature and added phenyl-{3-[2-(tetrahydropyran-2-yloxy)-ethoxy]-phenyl}-methanone (5.1 g, 15.6 mM) dissolved in 15 mL of dry THF and again refluxed for 3 h, cooled and 3 mL of water added. The solvent was removed under rotaevaporator and extracted with CHCl$_3$ (3×100 mL) and dried over anhydrous Na$_2$SO$_4$. The residue obtained on removal of the solvent was separated by silica gel column chromatography using hexane/EtOAc (7:3) as an eluent. Evaporation of the column fraction yielded 2-{4'-(3-(2-tetrahydropyran-2-yloxy)ethoxy)phenyl-4"-phenyl)}-4,4-dimethyl-1,3-oxazoline (3) as a yellow crystalline solid (1.4 g, 18%). $^1$H-NMR (500 MHz, CDCl$_3$) δ ppm: 1.37 (s, 6H), 1.5-1.63 (m, 4H), 1.68 (m, 1H), 1.80 (m, 1H), 2.85 (s, 1H, —OH), 3.49 (m, 1H), 3.75 (m, 1H), 3.85 (m, 1H), 3.97 (m, 1H), 4.09 (m, 4H), 4.66 (t, 1H), 6.80 (d, 1H), 6.84 (d, 1H), 6.88 (s, 1H), 7.18-7.31 (m, 6H), 7.34 (d, 2H), 7.87 (d, 2H). Mass: 502.6 (M+1), 524.5 (M+Na$^+$)

D. 4,4-Dimethyl-2-[4-(phenyl-[2-(tetrahydro-pyran-2-yloxy)-ethoxy]-{3-[2-(tetrahydro-pyran-2-yloxy)-ethoxy]-phenyl}-methyl)-phenyl]-4,5-dihydrooxazole, 4

To the stirred mixture of 2-{4'-(3-(2-tetrahydropyran-2-yloxy)ethoxy)phenyl-4"-phenyl)}-4,4-dimethyl-1,3-oxazoline (3, 200 mg, 0.4 mM) and NaH (100 mg, 4 mM) in 3 mL of dry DMF at r.t. was added 2-(2-bromoethoxy)tetrahydro-2H-pyran (500 mg, 2.4 mM) and the reaction was allowed to stir at r.t. for 2 h. Then the reaction mixture was poured in to ice water and extracted with CH$_2$Cl$_2$ (3×20 mL) and dried over anhydrous Na$_2$SO$_4$. Evaporation of the solvent gave 4 as a yellow oily residue in quantitative yield.

E. 4-{(2-Hydroxy-ethoxy)-[3-(2-hydroxy-ethoxy)-phenyl]-phenyl-methyl}-benzoic acid, 5

A solution of 4 (360 mg) in 3 mL of 80% aqueous acetic acid was heated at 75° C. for 12 h. Then the solution was evaporated and the residue obtained was refluxed with 20% NaOH/EtOH (1:1, v/v, 3 mL) for 2 h. The solvent was removed and 10 mL of ice cooled water was added to the residue and the aqueous solution was acidified with 1N HCl. The precipitated yellow solid was filtered and washed several times with water and dried under high vacuum. Yield: 270 mg (100%, quantitative).

F. 4-{(2-Hydroxy-ethoxy)-[3-(2-hydroxy-ethoxy)-phenyl]-phenyl-methyl}-benzoic acid 2,5-dioxo-pyrrolidin-1-yl ester, 6

1. Method A: To a stirred solution of trityl acid 5 (110 mg, 0.26 mM) and N-hydroxy succinimide (80 mg, 0.7 mM) in dry 1,4-dioxane (2 mL) was added 1-Ethyl-3-(3-dimethylaminopropyl)carbodiimide hydrochloride (EDC, 105 mg, 0.5 mM) dissolved in 2 mL of water. The reaction mixture was stirred for 12 h at r.t. and the extracted with CHCl$_3$ (3×10 mL) and dried over anhydrous Na$_2$SO$_4$. The solid obtained on evaporation of the solvent was purified by preparative TLC plate. Yield: 5 mg.

2. Method B: To a stirred solution of trityl acid 5 (12 mg, 0.03 mM) in dry THF (4 mL) was added dicyclohexyl carbodiimide (DDC, 10 mg, 0.05 mM). The reaction mixture was stirred for 30 min at r.t., N-hydroxysuccinimide (11.5 mg, 0.1 mM) and a catalytic amount of DMAP was added and allowed to stir for overnight. The solvent was removed under rotaevaporator and the solid obtained was dissolved in dry ether. The precipitated DCU was filtered and the solvent ether was evaporated. The crude solid obtained was purified by preparative TLC plate. Yield 7 mg (50%). $^1$H-NMR (500 MHz, CDCl$_3$) δ ppm: 2.90 (s, 4H), 3.92 (t, 4H), 4.02 (t, 4H), 6.83 (m, 2H), 7.25 (m, 3H), 7.34 (m, 4H), 7.50 (d, 2H), 8.0 (d, 2H).

G. 4,4-Dimethyl-2-[4-(phenyl-(3-phenyl-propoxy)-{3-[2-(tetrahydro-pyran-2-yloxy)-ethoxy]-phenyl}-methyl)-phenyl]-4,5-dihydrooxazole, 7

To the stirred mixture of 2-{4'-(3-(2-tetrahydropyran-2-yloxy)ethoxy)phenyl-4"-phenyl)}-4,4-dimethyl-1,3-oxazoline (3, 300 mg, 0.6 mM) and NaH (100 mg, 4 mM) in 3 mL of dry DMF at r.t. was added 3-bromo-1-phenyl propane (250 mg, 1.2 mM) and the reaction was allowed to stir at r.t. for 2 h. Then the reaction mixture was poured into ice water and extracted with CH$_2$Cl$_2$ (3×20 mL) and dried over anhydrous Na$_2$SO$_4$. Evaporation of the solvent gave 7 as a yellow color residue in quantitative yield.

H. 4-[[3-(2-Hydroxy-ethoxy)-phenyl]-phenyl-(3-phenyl-propoxy)-methyl]-benzoic acid, 8

A solution of 7 (550 mg) in 3 mL of 80% aqueous acetic acid was heated at 75° C. for overnight. Then the solution was evaporated and the residue obtained was refluxed with 20% NaOH/EtOH (1:1, v/v, 3 mL) for 2 h. The solvent was removed, 10 mL of ice cooled water was added to the residue and the aqueous solution acidified with 1N HCl, extracted with CH$_2$Cl$_2$ (60 mL) and dried over anhydrous Na$_2$SO$_4$. Evaporation of the solvent gave yellow solid Yield: 485 mg (quantitative).

I. 4-[[3-(2-Hydroxy-ethoxy)-phenyl]-phenyl-(3-phenyl-propoxy)-methyl]-benzoic acid 2,5-dioxo-pyrrolidin-1-yl ester, 9

To a stirred solution of trityl acid 8 (200 mg, 0.42 mM) in dry THF (6 mL) was added dicyclohexyl carbodiimide (DDC, 206 mg, 1 mM). The reaction mixture was stirred for 30 min at r.t., and N-hydroxysuccinimide (70 mg, 0.6 mM) and a catalytic amount of DMAP added and was allowed to stir for overnight. The solvent was removed under rotaevaporator and the solid obtained was dissolved in dry ether. The precipitated DCU was filtered and the solvent ether was evaporated. The crude solid obtained was separated by silica column chromatography using CH$_2$Cl$_2$. Yield: about 120 mg. $^1$H-NMR (500 MHz, CDCl$_3$) δ ppm: 1.70 (m, 2H), 1.9 (t, 2H), 2.9 (s, 4H), 3.5 (m, 2H), 3.9 (t, 2H), 4.0 (t, 2H), 6.85 (m, 4H), 7.25 (m, 4H), 7.32 (m, 5H), 7.51 (m, 3H), 8.09 (d, 2H).

J. 1-{4-[[3-(2-Hydroxy-ethoxy)-phenyl]-phenyl-(3-phenyl-propoxy)-methyl]-benzoyl}-pyrrole-2,5-dione, 10

To a stirred solution of trityl acid 8 (280 mg, 0.42 mM) in dry THF (6 mL) was added dicyclohexyl carbodiimide (DDC, 400 mg, 1.95 mM). The reaction mixture was stirred for 30 min at r.t., and maleimide (100 mg, 1.1 mM) and a catalytic amount of DMAP was added and allowed to stir for overnight. The solvent was removed under rotaevaporator and the solid obtained was dissolved in dry ether. The precipitated DCU was filtered and the solvent ether was evaporated. Part of the product was purified by preparative TLC. Yield: 12 mg. $^1$H-NMR (500 MHz, CDCl$_3$) δ ppm: 1.78 (m, 2H), 1.95 (m 2H), 2.9 (s, 4H), 3.51 (m, 2H), 3.93 (t, 2H), 4.02 (t, 2H), 6.8 (m, 5H), 7.25 (m, 5H), 7.29 (m, 5H), 7.37 (m, 3H), 7.48 (d, 2H), Mass: 561.3 (M$^+$).

Example 5

This Example shows addition of a selectivity function onto a capture compound possessing a N-hydroxy succinimidyl ester reactivity function. Compounds with a sorting function can be prepared by using an appropriate analog of compound 11 below.

Procedure for Mitsunobu Reaction of Trityl Capture Reagents

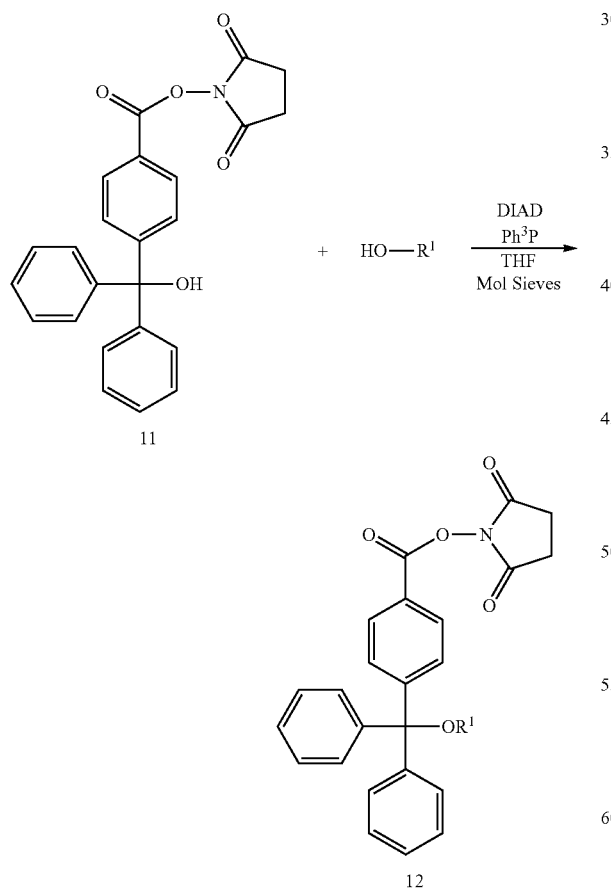

1.1 equivalents of triphenylphosphine are added to a reaction vial and dissolved in 1.0 ml THF. 1.1 equivalents of diisopropyl azidodicarboxylate are added to this solution and mixed for 5 minutes. Add 1 equivalent of 11 and stir for 5 minutes. Add nucleophile (R$_1$—OH) and stir overnight at 50° C. Preparative TLC purified the products.

Example 6

Cell Synchronization

H460 lung cancer and SW480 colon cancer cells were synchronized in Go/G1 with simvastatin and lovastatin (HMG-CoA reductase inhibitors), which can enrich a cancer cell population in Go/G1. Cells arrested in G2/M phase were obtained by treatment with nocodazole.

Cell Culture and Reagents

The SW480 cell line was cultured in Dulbecco's modified Eagle medium (DMEM), the H460 cell line (ATCC Manassas, Va.) was cultured in RPMI 1640, whereas the FK101 was cultured in serum-free medium (SFM) with 5% CO$_2$ at 37° C. The cell culture media were supplemented with 10% fetal bovine serum (FBS), 2 mM L-glutamine, penicillin (100 U/ml) and streptomycin (100 U/ml).

Synchronization of Cells

H460 and SW480 cells enriched in G$_1$ phase were obtained after incubation with serum-free medium for 48 hours, or treatment with U026, lovastatin or simvastatin. Cells in S phase were synchronized by incubating cells with medium containing no serum for 24 hours, followed by aphidicolin treatment (2 ug/ml) for 20 hours and release of cells from aphidicolin for 3 hours. Cells arrested in G2/M phase were obtained by treatment with nocodazole (0.4-0.8 mg/ml) for 16-20 hours.

Example 7

Synthesis of (4,4'-bisphenyl-hydroxymethyl)benzoyl maleimide derivatives

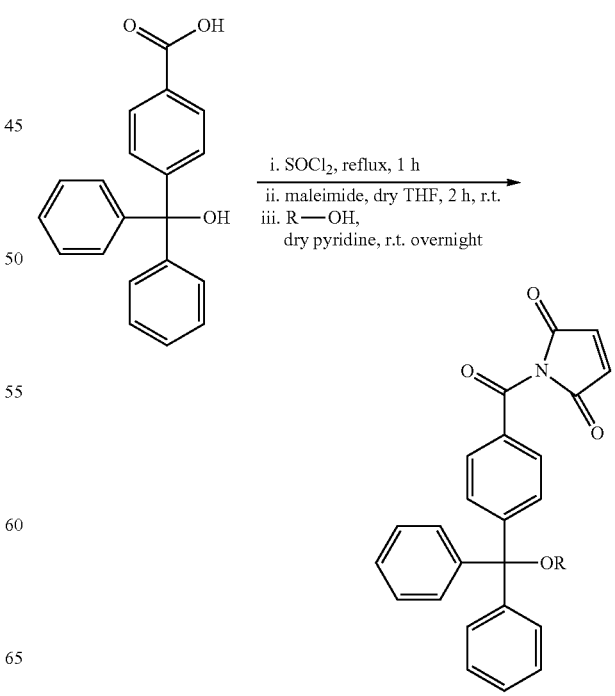

-continued

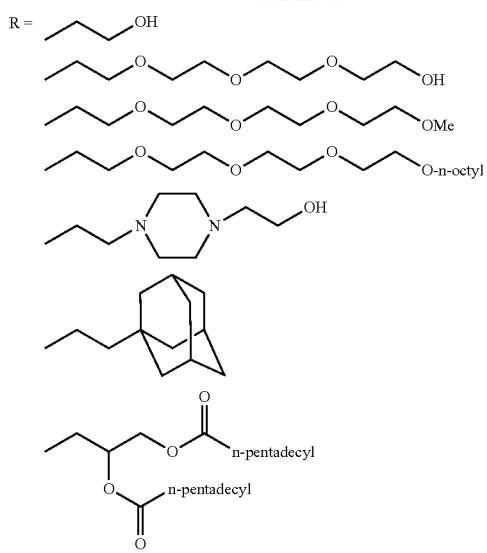

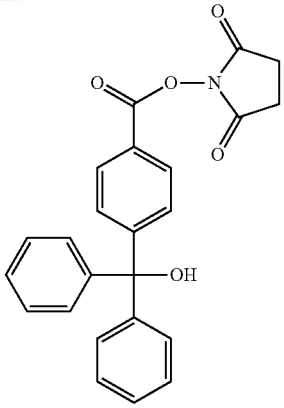

4-(Diphenylhydroxymethyl) benzoic acid was reacted with 2 equivalents of N-hydroxysuccinimide using 1.2 equivalents of Diisopropyl carbodiimide. The desired product was purified by Flash Silica chromatography and characterized by ESI mass spectrometry.

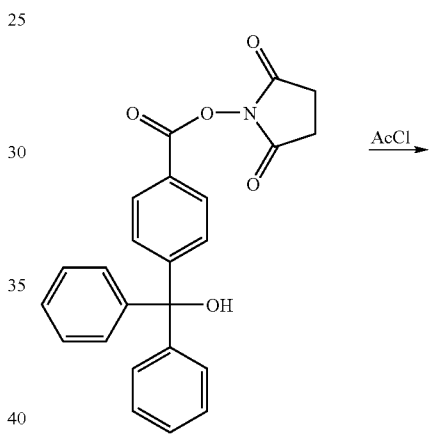

General Procedure: A solution of 4-(diphenylhydroxymethyl)benzoic acid (0.04 mM) in 1 mL of $SOCl_2$ was refluxed for 1 h and the excess $SOCl_2$ was removed under high vacuum. To this yellow solid residue obtained was added maleimide (0.045 mM) dissolved in dry freshly distilled THF (1 mL) and stirred at room temperature for 2 h. The solvent was removed and added the corresponding alcohol (ROH, 2-5 fold excess) dissolved in dry pyridine (1 mL) with stirring. After the reaction mixture stirred at room temperature for overnight the solution was extracted with $CH_2Cl_2$ (5×3 mL) and dried over anhydrous $Na_2SO_4$. The residue obtained on evaporation of the solvent was separated by preparative TLC (Silica Gel, 500 µm plate) and gave the product 1 in 50-60% yield. The trityl derivatives 1 were fully characterized by $^1H$ NMR and mass spectral data.

Example 8

Succinimidyl Ester Trityl Capture Compound Synthesis

Procedure 1

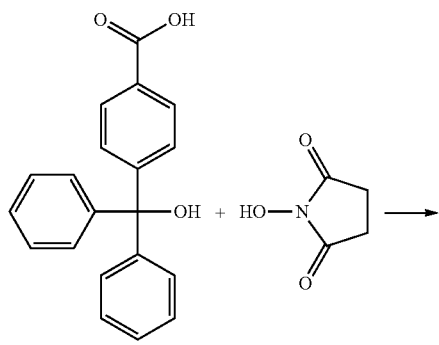

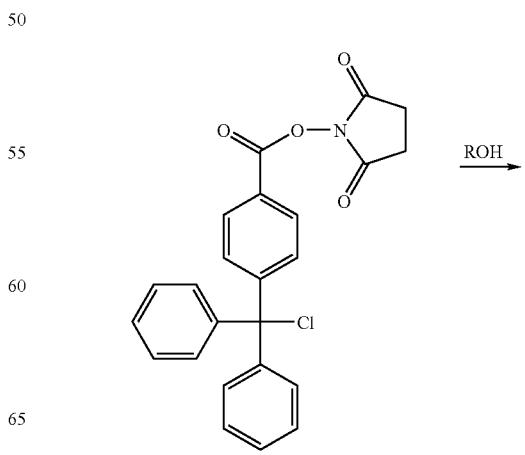

141
-continued

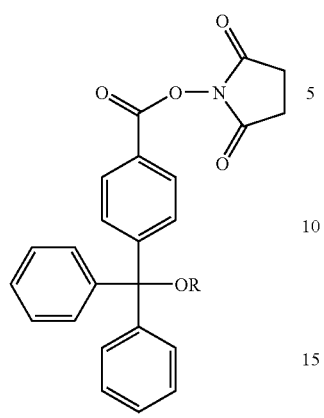

The 125 µmoles of product from above was added to 1.0 ml Acetyl Chloride. This reaction mixture was stirred at room temperature for 1 hour and evaporated three times with toluene to remove excess acetyl chloride. Equal volumes of the reaction mixture were added to nucleophiles (see below) dissolved in 1.0 M Pyridine/THF. These reaction mixtures were mixed at 60° C. for 2 hours. The resulting products were extracted from CHCl$_3$ and 10% HOAc. Products were purified by Preparative TLC (Ether). MS and NMR characterize purified products.

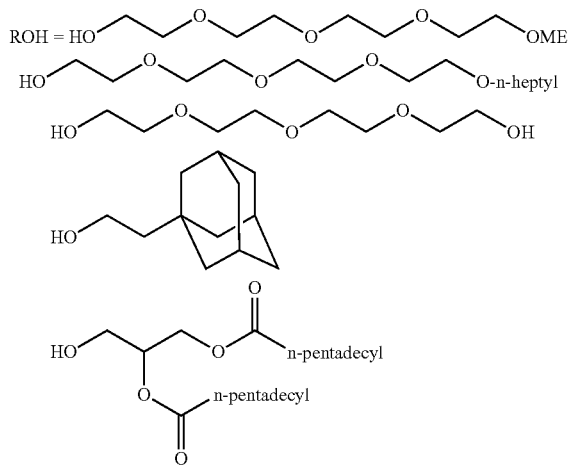

Procedure 2

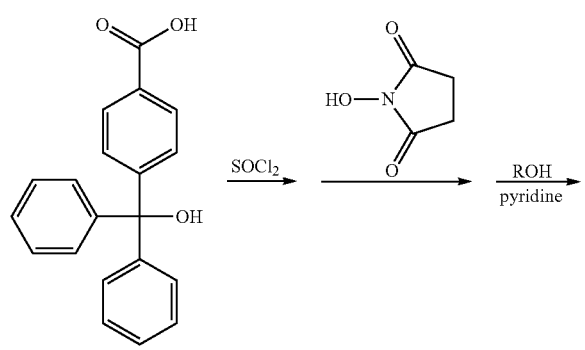

142
-continued

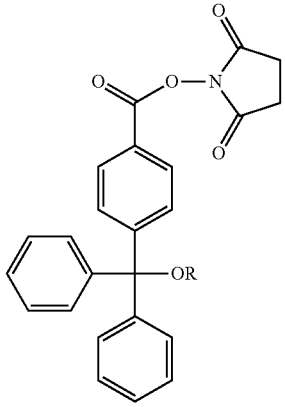

1.64 mmoles of 4-(Diphenylhydroxymethyl) benzoic acid was dissolved into 5 ml Thionyl Chloride. This reaction mixture is heated to 79° C. and stirred for 75 minutes. The Thionyl Chloride is removed under N$_2$ (g) stream. 1.3 equivalents of N-hydroxysuccinimide dissolved in dry THF is added to this dried reaction mixture and stirred for 1 hour. The THF solvent is removed under N$_2$ (g) stream. The product is dissolved into dry Pyridine. Equal volumes of this solution are added to nucleophiles dissolved in Pyridine. (See below). The resulting products are extracted from CHCl$_3$ and 10% HOAc. Products are purified by Preparative TLC (Ether). MS and NMR characterize purified products.

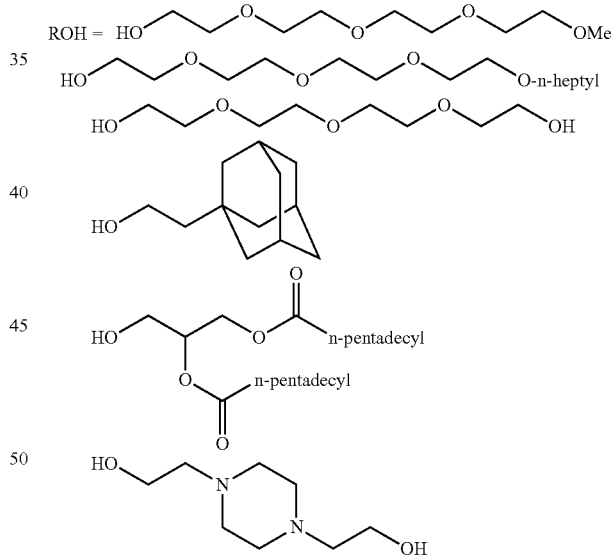

Example 9

This example shows exemplary capture binding assays and the effects of selectivity functions on binding. This example shows that changing selectivity can alter reactivity of the capture compound thereby providing a means to probe biomolecule structures and to permit sorting or diversity reduction using the collections. In this example, the core group of the capture compounds is a trityl group and the reactive group is succinimide, which interacts with a primary amine. Compound 1341 is a non-selective compound that has a reactivity group, but no selectivity group. Compound 1343 (see FIG. 20) is exemplary of such compound where the selectivity group is —OH. As the selectivity group changes there is a difference in reactivity on the target proteins (lysozyme, cytochrome C and ubiquitin).

Lysozyme

Figure 20B:
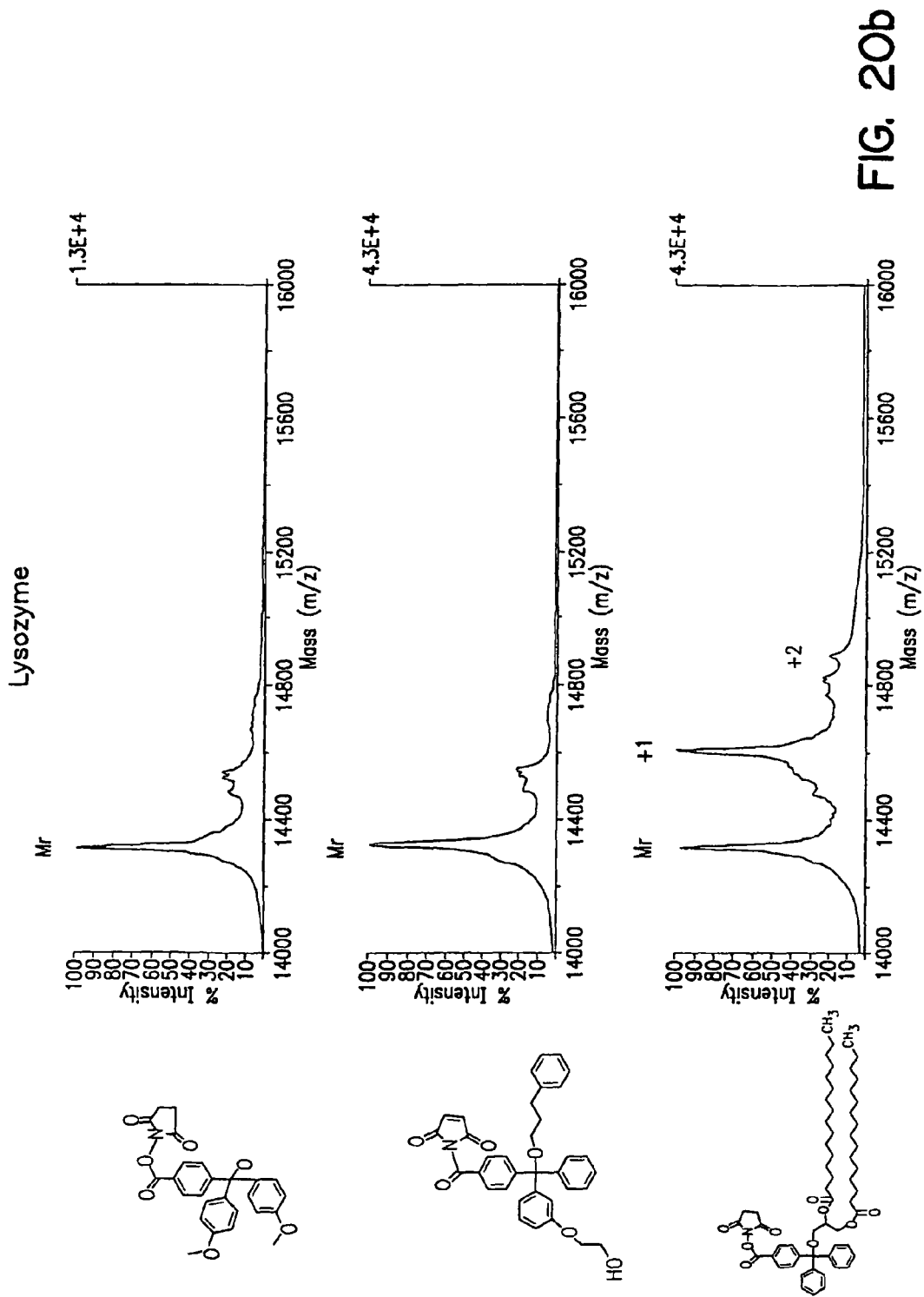
Figure 20C:
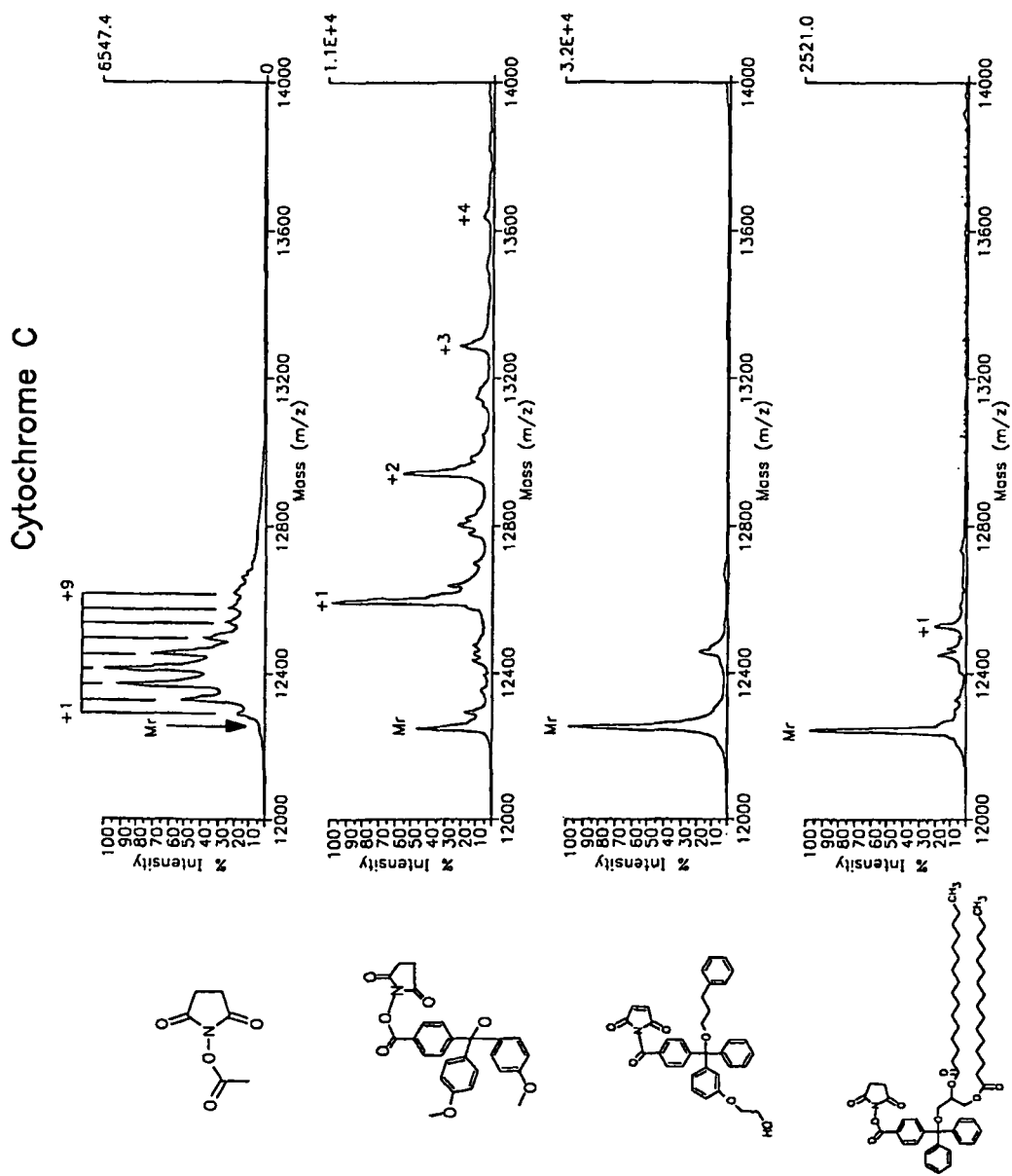

Three different capture compounds (designated HKC 1343, 1349, 1365; chemical structure of each compound is listed below the Compound name) were reacted individually with Lysozyme (Accession number P00698; FIG. 20b). The capture experiments were analyzed using MALDI-TOF Mass Spectrometry. Binding was performed in 20 µL sample volumes with a 5 µM Lysozyme concentrations in 25 mM HEPES buffer solution, pH 7.0. The trityl-based capture compounds were added to the protein solution at a 10 µM concentration. The binding reaction was incubated at room temperature for 30 minutes. The reaction was quenched using 1 µL of a 100 mM TRIZMA base solution.

The capture compound-protein binding mixture was prepared for mass spectrometry by mixing a 1 µL aliquot of a binding reaction with 1 µL of a 10 mg/mL sinapinic acid in 30% aqueous acetonitrile. The sample was deposited as a 500 nL spot on the surface of the mass target plates and air-dried before mass spectrometric analysis. The results of the mass spectrometry analysis, which are shown in FIG. 20b, demonstrate that addition of selectivity groups to compounds permits alterations in the binding specificity of capture compounds.

Cytochrome C

Four different capture compounds (designated HKC 1341, 1343, 1349, 1365; chemical structure of each compound is listed below the Compound name) were reacted individually with Cytochrome C (accession number: P00006, FIG. 20c). The capture experiments were analyzed using MALDI-TOF Mass Spectrometry. Binding was performed in 20 µL sample volumes with a 5 µM Cytochrome C concentrations in 25 mM HEPES buffer solution, pH 7.0. The trityl-based capture compounds were added to the protein solution at a 10 µM concentration. The binding reaction was incubated at room temperature for 30 minutes. The reaction was quenched using 1 µL of a 100 mM TRIZMA base solution. The capture compound-protein binding mixture was prepared for mass spectrometry analysis by mixing a 1 µL aliquot of the binding reaction with 1 µL of a 10 mg/mL sinapinic acid in 30% aqueous acetonitrile. The sample was deposited as a 500 nL spot on the surface of mass target plates and subsequently air-dried before mass spectrometric analyses. The results of the mass spectrometry analysis, which shown in FIG. 20c, demonstrate that addition of selectivity groups to compounds permits alterations in the binding specificity of capture compounds.

HKC 1343

Figure 20D:
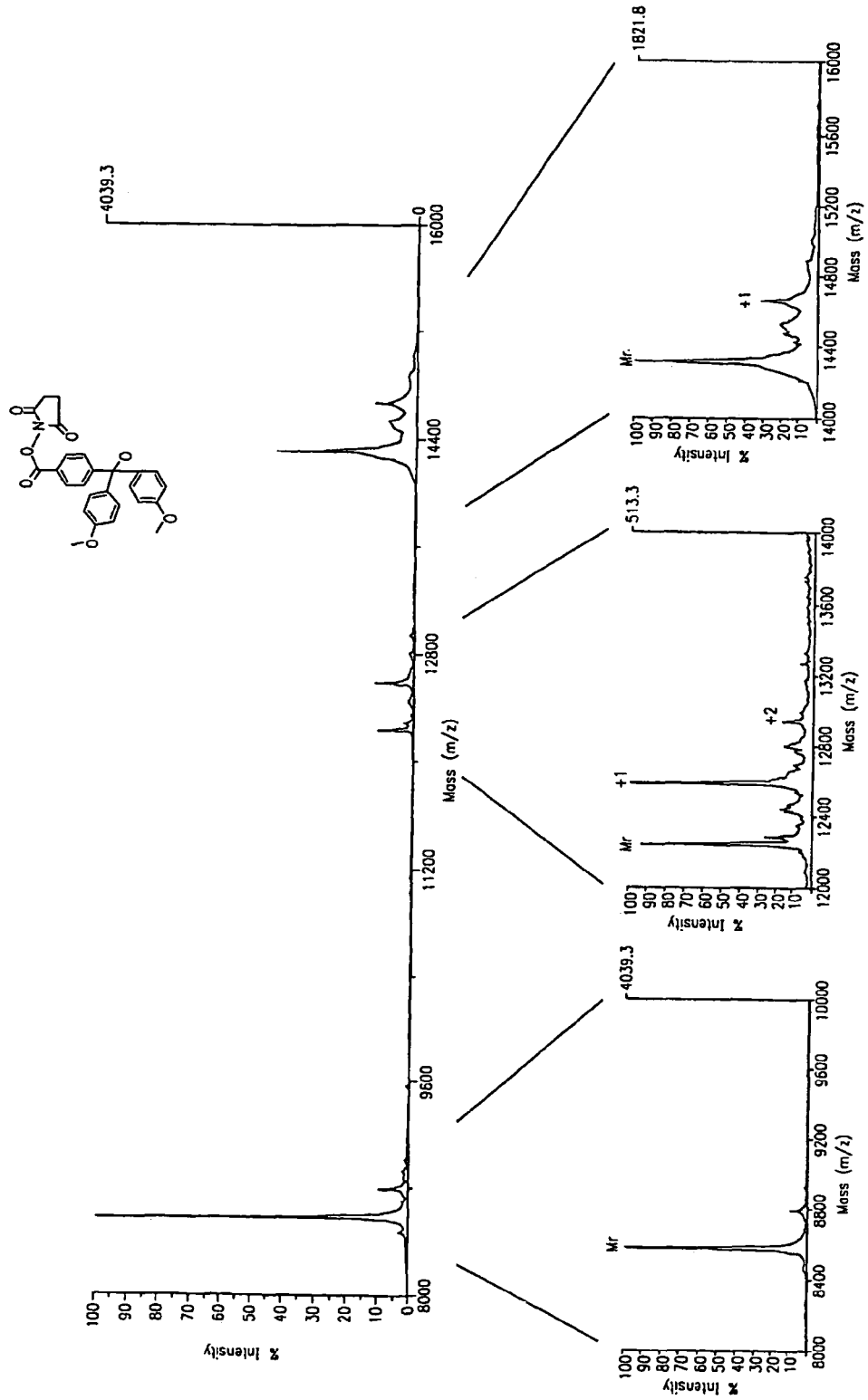

One of the exemplary capture compounds (HKC 1343) was incubated with a mixture of three different proteins (Ubiquitin, [P02248], Cytochrome C [P00006] and Lysozyme [P00698]) (see, FIG. 20d). The capture experiment was analyzed using MALDI-TOF Mass Spectrometry. The binding reactions were performed in a 20 µL sample volume with all three proteins at 5 µM concentrations in 25 mM HEPES buffer solution pH 7.0. The trityl-based capture compound was added to the protein solution at a 25 µM concentration. The binding reaction was incubated at room temperature for 30 minutes and the reaction quenched using 1 µL of a 100 mM TRIZMA base solution. The capture compound-protein binding mixture was prepared for mass spectrometry by mixing a 1 µL aliquot of the binding reaction with 1 µL of 10 mg/mL sinapinic acid in 30% aqueous acetonitrile. The sample was deposited as a 500 nL spot on the surface of mass target plates and air-dried before mass spectral analysis. The results of the mass spectrometry analysis, which are shown in FIG. 20d, demonstrate that a plurality of compounds bound to a single capture agent that is selective can be identified by mass spectrometric analysis.

HKC 1365

Figure 20E:
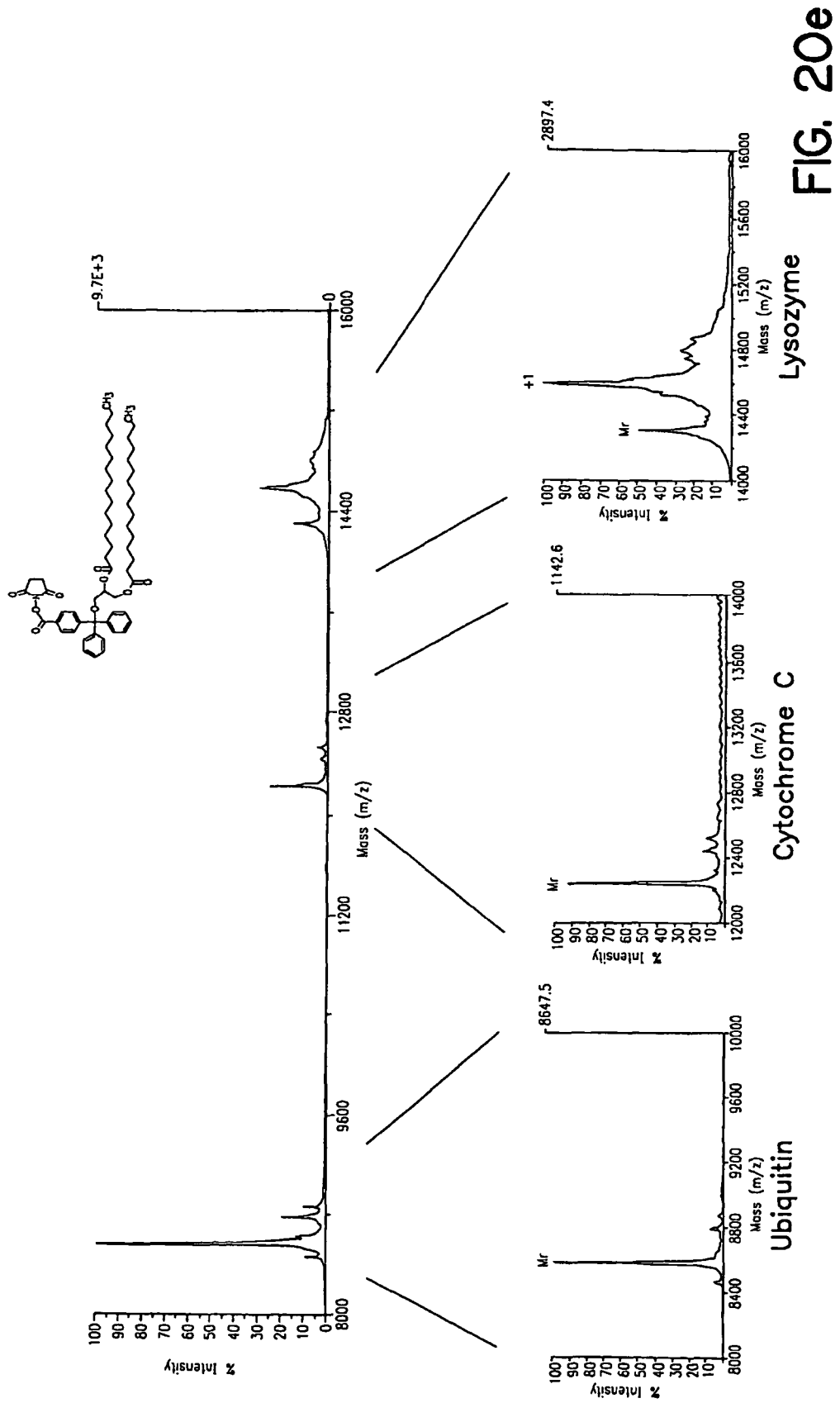

Another of the exemplary capture compounds (HKC 1365) was incubated with a mixture of three different proteins (Ubiquitin [P02248], Cytochrome C [P00006] and Lysozyme [P00698]; see FIG. 20d). The capture experiment was analyzed using MALDI-TOF Mass Spectrometry. The binding reactions were performed in a 20 µL sample volume with all three proteins at 5 µM concentrations in 25 mM HEPES buffer solution pH 7.0. The trityl-based capture compound was added to the protein solution at a 15 µM concentration. The binding reaction was incubated at room temperature for 30 minutes, and quenched using 1 µL of a 100 mM TRIZMA base solution. The capture compound-protein binding mixture was prepared for mass spectrometry by mixing a 1 µL aliquot of the binding reaction with 1 µL of a 10 mg/mL sinapinic acid in 30% aqueous acetonitrile. The sample was deposited as a 500 nL spot on the surface of the mass target plates and air-dried before mass spectral analyses. The results of the mass spectrometry analysis, which are shown in FIG. 20e, demonstrate that a plurality of compounds bound to a single capture agent that is selective can be identified by mass spectrometric analysis.

Reaction of cytochrome C with a Non-specific Compound

FIG. 20f shows mass spectra for a time course reaction of cytochrome C with a non-specific compound (HKC 1341). The succinamide reactive group shows specificity and reactivity with the lysines of cytochrome c. The top spectrum shows no modification at time 0, the middle spectrum shows 1-9 modifications resulting from binding of HKC1341 after 30 minutes, and the bottom spectrum shows, after 24 hours, 17 and 18 modifications, which correspond to the number of lysines (18) in cytochrome c.

Example 10

This example shows the selectivity of the capture compound reacting a mixture of capture compounds and a mixture of proteins Materials:
Reaction buffer: 25 mM HEPES, pH 7.0
Proteins: mixture of ubiquitin, cytochrome c and lysozyme (molar ratio is 1/5/6), the protein stock is made as 5 mg/ml (total proteins) in reaction buffer.
Capture compounds: HKC 1343 and HKC 1365, stock solution is 1 mM in acetonitrile.

Capturing Reaction

A protein dilution (mixture) is prepared in the reaction buffer at the concentration of 0.5, 2.5 and 3 µM, for ubiquitin, cytochrome c and lysozyme, respectively. 19.5 µl is used for one capturing reaction. Each reaction is started by adding 0.5 µl of 1 mM compound stock solution (final 25 µM). The reaction mixture is incubated at room temperature for 30 min before the reaction is stopped by the addition of 5 mM TRIZMA.

Three different reactions are run. The first two tubes contain HKC 1343 and HKC 1365 individually, and a third one is started by adding compounds HKC 1343 and 1365 (final concentration 25 µM for each compound). After the reaction, 1 µl of each sample is mixed with equal volume of matrix and subjected to MALDI analysis. Statistic significance of the results is ensured by triplicate each reaction sample.

Example 11
Synthesis of 4-{Hydroxy-[3-(3-{6-[5-(2-oxo-hexahydro-thieno[3,4-d]imidazol-4-yl)-pentanoylamino]-hexanoylamino}-propoxy)-phenyl]-phenyl-methyl}-benzoic acid succinimidyl ester (6)
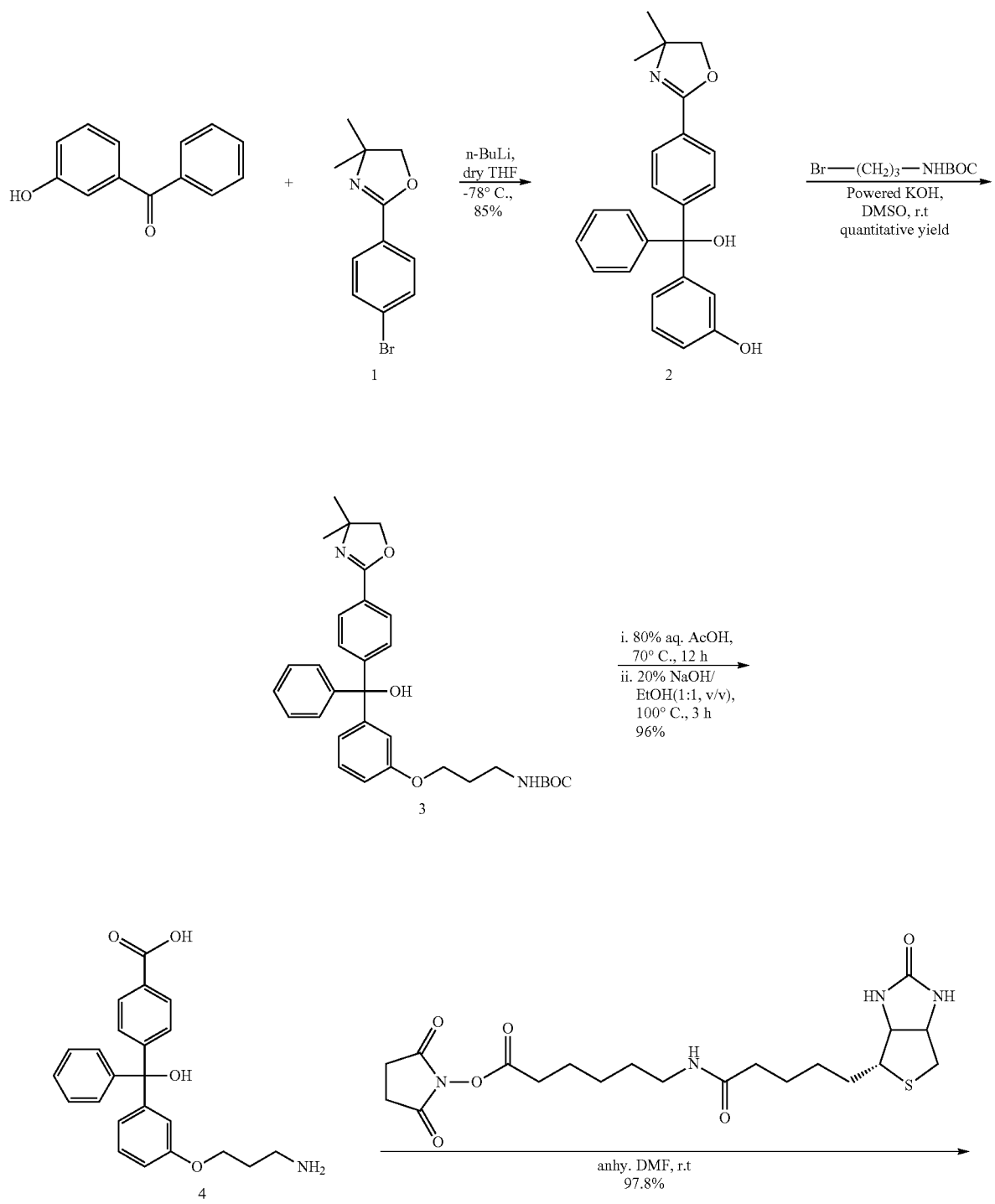

-continued

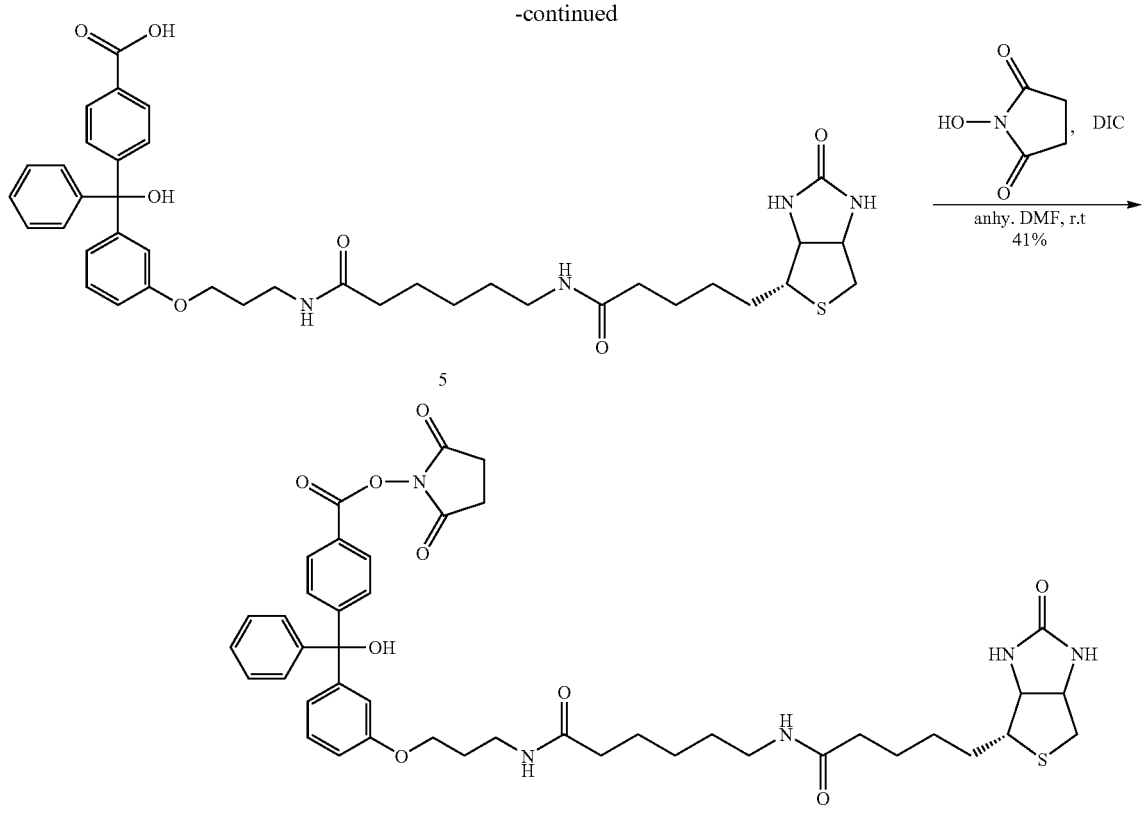

Synthesis of 3-{[4-(4,4-Dimethyl-4,5-dihydro-oxazol-2-yl)-phenyl]-hydroxy-phenyl-methyl}-phenol (2)

2-(4-Bromophenyl)-4,4-dimethyl-1,3-oxazoline 1 was prepared as described in Example 4. To a stirred solution of 2-(4-bromophenyl)-4,4-dimethyl-1,3-oxazoline (1.5 g, 6 mM) in anhydrous THF (10 mL) at −78° C. was added slowly n-BuLi (384 mg, 6 mM) in hexane over the period of 20 min. After that the reaction mixture was stirred at −78° C. for another 30 min. To this stirred solution was added 3-hydroxybenzophenone (534 mg, 2.7 mM) dissolved in anhy. THF (10 mL) by dropwise at −78° C. and allowed to stir at room temperature overnight. To this reaction mixture was added 20 mL of water to quench the reaction and extracted with $CH_2Cl_2$ (3×50 mL) and the combined extract was dried over anhydrous $Mg_2SO_4$. The oily residue obtained on evaporation of the solvent was purified by silica gel column chromatography using hexane/EtOAc (1:1) mixture gave 3-{[4-(4,4-Dimethyl-4,5-dihydro-oxazol-2-yl)-phenyl]-hydroxy-phenyl-methyl}-phenol (2) as colorless crystalline solid. Yield: 0.855 g (85%). Mass: 374 (MH+), 372 (M-H).

Synthesis of [3-(3-{[4-(4,4-Dimethyl-4,5-dihydro-oxazol-2-yl)-phenyl]-hydroxy-phenyl-methyl}-phenoxy)-propyl]-carbamic acid tert-butyl ester (3)

To a solution of powdered KOH (45 mg, 0.8 mM) in anhydrous DMSO (2.5 mL) at room temperature was added 3-{[4-(4,4-Dimethyl-4,5-dihydro-oxazol-2-yl)-phenyl]-hydroxy-phenyl-methyl}-phenol (2, 150 mg, 0.4 mM) and (3-Bromo-propyl)-carbamic acid tert-butyl ester (96 mg, 0.4 mM). The reaction mixture was stirred at room temperature for 3 h. Then the reaction mixture was extracted with ethyl acetate (3×25 mL) and the combined extract was dried over anhydrous $Mg_2SO_4$. The residue obtained on evaporation of the solvent was purified by silica gel chromatography using hexane/EtOAc (1:1) as an eluent. Evaporation of the solvent gave 3. Yield: >220 mg (quantitative yield). Mass: 531 (MH+).

Synthesis of 4-{[3-(3-Amino-propoxy)-phenyl]-hydroxy-phenyl-methyl}-benzoic acid (4)

In a 50 mL round bottomed flask placed with [3-(3-{[4-(4,4-Dimethyl-4,5-dihydro-oxazol-2-yl)-phenyl]-hydroxy-phenyl-methyl}-phenoxy)-propyl]-carbamic acid tert-butyl ester (3, 220 mg) was added 3 mL of 80% aqueous AcOH and the reaction mixture was heated 75° C. for overnight. Then the reaction mixture was concentrated and dried and added 3 mL of 20% NaOH/EtOH (1:1, v/v) and refluxed for 3 h. Residue obtained on evaporation of the solvent was dissolved in $CH_3OH/CHCl_3$ mixture and adsorbed with silica gel and dried. The dried silica gel with compound was purified by silica gel column already flashed with 1% $NH_4OH$ in $Et_2O$ solution. Elution of the column at 50% $CH_3OH/CH_2Cl_2$ gave 4-{[3-(3-Amino-propoxy)-phenyl]-hydroxy-phenyl-methyl}-benzoic acid, 4 as a colorless gelly solid. Yield: 96%. Mass: 378 (MH+), 376 (M-H), 360 (M-OH).

Synthesis of 4-{Hydroxy-[3-(3-{6-[5-(2-oxo-hexahydro-thieno[3,4-d]imidazol-4-yl)-pentanoylamino]-hexanoylamino}-propoxy)-phenyl]-phenyl-methyl}-benzoic acid (5)

A mixture of Trityl amino acid (4, 100 mg, 0.26 mM) and Biotin-X-NHS (113 mg, 0.25 mM) was stirred at room temperature in 3 mL of anhydrous DMF for overnight. After that DMF was removed under high vacuum and the residue obtained was passed through silica gel column using 50% CH$_3$OH/CHCl$_3$ as a solvent. Evaporation of the solvent yielded biotinylated trityl acid 5. (97.8%). Mass: 739 (M Na+), 715 (M-H).

Synthesis of 4-{Hydroxy-[3-(3-{6-[5-(2-oxo-hexahydro-thieno[3,4-d]imidazol-4-yl)-pentanoylamino]-hexanoylamino}-propoxy)-phenyl]-phenyl-methyl}-benzoic acid succinimidyl ester (6)

To a solution of biotinylated trityl acid (5, 175 mg, 0.244 mM) in anhydrous DMF (3 mL) was added 1,3-diisopropyl carbodiimide (4 mg, 0.35 mM) and stirred the reaction mixture for 5 min. To this reaction mixture was added N-hydroxy succinimide (40 mg, 0.32 mM) and stirred for over night at room temperature. The solvent was removed under high vacuum and the residue obtained was purified by silca gel column chromatography using CH$_3$OH/CH$_2$Cl$_2$, 3:7) mixture as a solvent system. Evaporation of the solvent gave 6 as a white crystalline solid. Yield: 80 mg (41%). $^1$H-NMR (CD$_3$OD) δ ppm:
1.29-1.71 (m, 12H), 1.90-193 (m, 2H), 2.15 (q, 4H), 2.49 (t, 1H), 2.8-2.91 (m, 2H), 2.90 (s, 4H), 3.17 (m, 4H), 3.94 (q, 3H), 4.27 (dd, 1H), 4.46 (d of d, 2H), 4.59 (br. S, 4H), 6.77 (s, 1H), 6.86 (m, 2H), 7.18-7.39 (m, 5H), 7.51 (d, 2H), 8.05 (m, 2H). Mass: 836.6 (Mna+), 812.4 (M-H).

Example 12

Synthesis of 4-[Butoxy-(3-hydroxy-phenyl)-phenyl-methyl]-benzoic acid 2,5-dioxo-pyrrolidin-1-yl ester

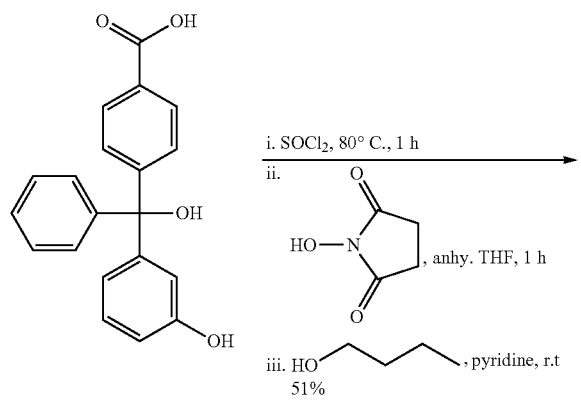

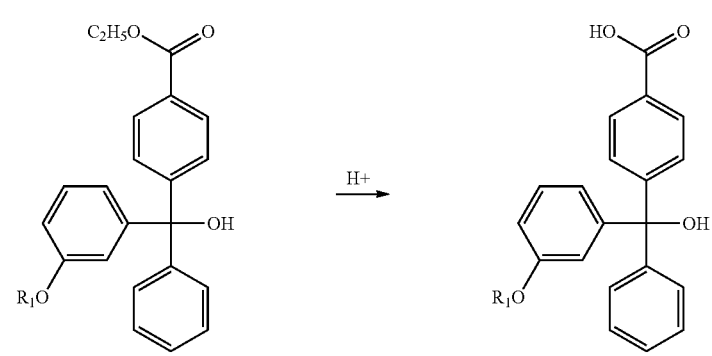

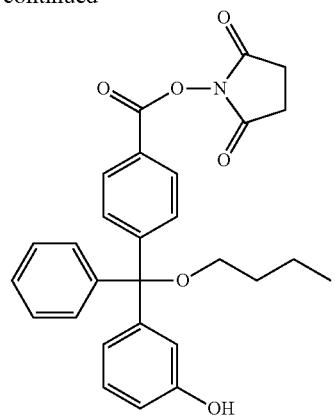

100 mg of 4-[Hydroxy-(3-hydroxy-phenyl)-phenyl-methyl]-benzoic acid (0.31 mM) placed in a 25 mL round bottomed flask was added thionyl chloride (1 mL) and refluxed at 80° C. for an hour. Then the excess of SOCl$_2$ was removed under high vacuum and dried. To this dried solid residue was added freshly distilled anhydrous THF (4 mL) under argon atmosphere followed by N-hydroxy succinimide (38 mg, 0.33 mM) and stirred at room temperature for an hour. The solvent was removed under high vacuum and dried. Then the residue obtained was dissolved in dry pyridine (1.5 mL) and added 0.2 mL of n-butanol and the reaction mixture was stirred for 3 h. The pyridine was removed under high vacuum and solid obtained was purified by silica gel column using hexane/EtOAc (7:3) as a eluent. Evaporation of the solvent afforded 4-[Butoxy-(3-hydroxy-phenyl)-phenyl-methyl]-benzoic acid 2,5-dioxo-pyrrolidin-1-yl ester (6). Yield: 50-52%). $^1$-NMR, CDCl$_3$ (δ ppm): 0.88 (t, 3H), 1.38 (m, 2H), 1.61 (m, 2H), 2.87 (br. S, 4H), 3.05 (t, 2H), 6.7 (dd, 1H), 6.9 (dd, 2H), 7.16 (t, 1H), 7.3 (m, 5H), 7.64 (d, 2H), 8.04 (d, 2H). Mass: 496 (Mna+), 472 (M-H), 400.3.

Example 13

This example shows addition of a biotin as a sorting function onto a capture compound.

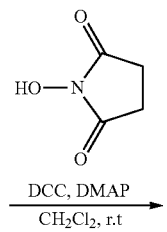

-continued

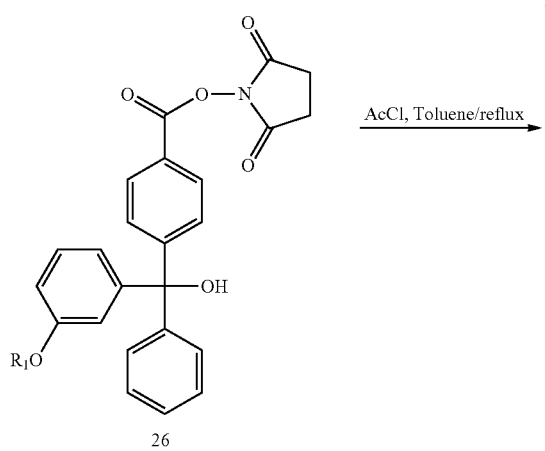

26

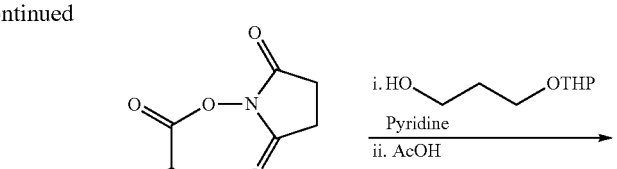

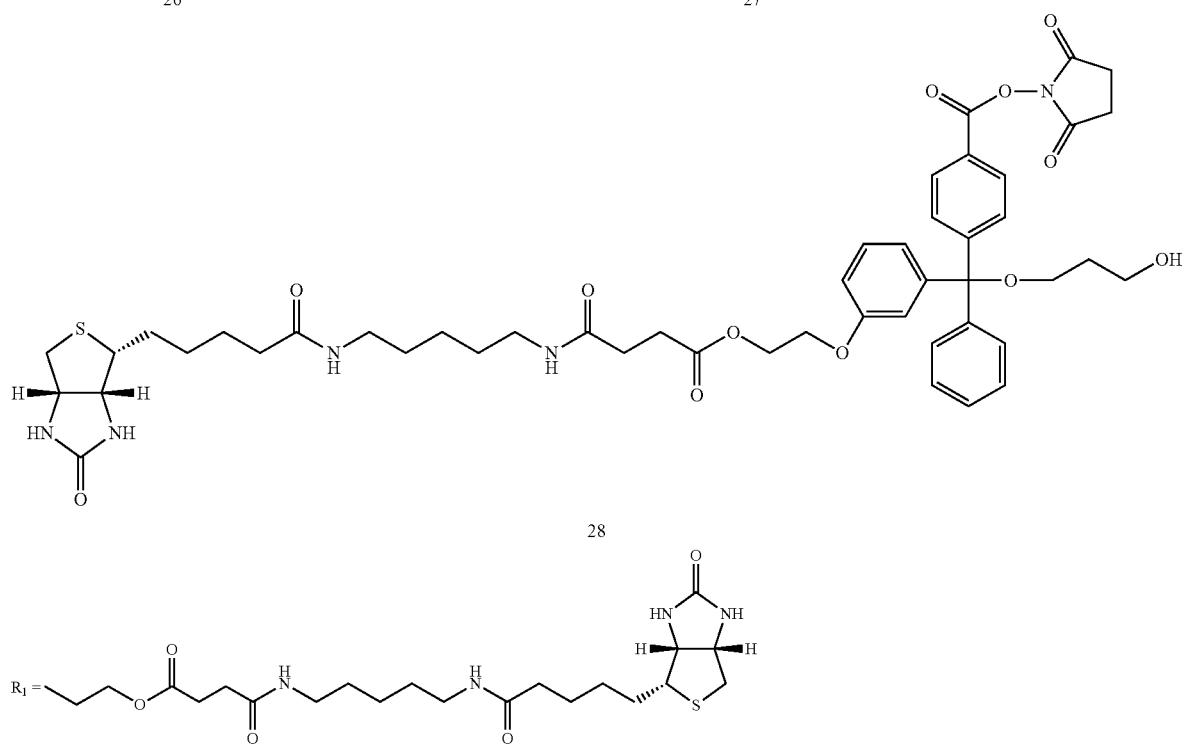

28

Example 14

Capture and pull-down for target protein from HEK293 cellular fractions with doped carbonic anhydrase II.

Materials Needed:

20 mM Hepes buffer, pH 7.2.

Add 200 μl 20 mM Hepes, pH 7.2, to reconstitute lyophilized Carbonic anhydrase II (Sigma). Transfer to an eppendorf tube. Calculate concentration of working stocks (see later in the protocol) and make the stocks using the same buffer and the master stock. Freeze master stock for long term storage.

HEK293 cellular fractions are FPLC fractionated and multiple fractions collected along the salt gradient.

Dissolve capture compound in 10 mM DMSO stock Make working stock of capture compound A in methanol. Make new stock every week and keep it on ice with aluminum foil to protect it from light.

Pierce spin columns (about 500 μl bed volume). It handles as little as 20 μl and up to 100 μl sample.

Soft-Link (avidin) resin: Wash the resin 3×1 ml (for a 100 μl resin aliquot) in 20 mM Hepes, pH 7.2. Care should be taken to maintain the right solid/liquid ratio at the end of washing in order to be consistent in the amount of resin used in pull-down experiments.

Washing buffer for pull-down: Hepes/NaCl/TX100/EDTA/DTT. Make the buffer stock with the first 4 components at the right concentration and pH first, then separately make 1M DTT stock and freeze it down in small aliquots until use. Right before the washing procedures in the pull-down experiment (step H), thaw a DTT stock tube and add DTT stock at the required final. Each pull-down tube requires ~1 ml washing buffer).

Sigma mass quality water.

Experiment Protocol:

A. In a well on a reaction plate, pipette 25 μl FT293, x μl of Carbonic Anhydrase II stock, y μl of compound stock solution, and 25-x-y μl of 20 mM Hepes buffer, pH 7.2. Keep the y value at 2.5 μl or less for a 50 μl reaction. The FT fraction in the mixture is diluted 2 fold in the final mixture. For S100, more than 3-fold dilution is required. In certain embodiments, use 15 µl for S100 in a 50 µl reaction and change the buffer volume accordingly.

B. Mix the three thoroughly by pipetting up and down 3×.

C. Incubate the reaction mixture in the dark at room temperature for 30 min.

D. Carry out photoreaction after the incubation. Care must be taken so as to not to excessively heat the microtiter plate upon flashes from high intensity broadband photography flash lamp (B1600 from Alien Bees). Use a total of ~20-40 shots.

E. Spin column processing of sample after photoreaction is not necessary for mixture that has the capture compound around 1 µM. For reactions using more than 10 µM compound, spin-column processing before binding can improve the target signal in pull-down.

F. Isolate captured protein using biotin/avidin. Wash Soft-Link resin as above; do not pre-treat with biotin. For each binding and pull-down, into one PCR tube on a strip, add 5 µl slurry of resin after mixing the resin and the liquid on top thoroughly, then add 20 µl reaction mixture after photoreaction or after spin-column. Care should be taken to make sure that the tip is at the bottom of the tube before releasing the contents, and the pipette tips should not touch the inside wall of the tube, especially the top part. Rotate the binding tube for 30 min at room temperature.

G. Spin tubes 2 min in the centrifuge. Carefully take the supernatant out. Try to take as much liquid out as possible without losing any resin.

H. Add 200 µl washing buffer into each tube, rotate for 4 min on the same setting. Make sure the resins and liquid are well mixed during the process.

I. Spin and remove supernatant as described in step G.

J. Following 4× washes by the washing buffer, switch to water, carry out another 4× washes. After the last wash in water, completely take out the supernatant, add 2 µl water on top.

K. Mix the resin and water well, take 1 µl onto a mass plate spot, give 1 or 2 minute to air dry the spot a bit (not completely dry), add 1 µl of matrix, pipette up and down 4 times.

L. If SDS-PAGE is required for the sample, silver staining (Invitrogen's Silver Quest Kit) may be used to detect proteins in the pull-down. Usually half of the pull-down resin is eluted with SDS-PAGE sample buffer for this purpose.

Example 15

Determination of Binding Strengths (Dissociation Constants)

This approach is based on the observation that photolysis acts on a very fast time scale, from activation to covalent cross linking (ns to ms, depending on the photoactive moiety). One can thus envision using photolysis to take a snap shot of a enzyme-substrate complex mixture in equilibrium. The amount of covalently crosslinked enzyme-substrate is directly proportional to that of the enzyme-bound substrate (capture compound) in equilibrium. Most importantly, this amount as a fraction of that of the starting enzyme can be very easily and reliably measured by using an off-the-shelf MALDI Machine following a pulldown step.

Equilibrium Analysis

The starting point of the analysis is the definition of the dissociation constant, $$K_d = [S][E]/[SE]$$

where [S], [E] and [SE] are the concentrations of the free substrate, free enzyme and substrate-enzyme complex respectively. To make this equation more useful, one can rewrite the equation using variables that are more immediately measurable, such as:

[$S_0$]=beginning concentration of substrate.
[$E_0$]=beginning concentration of enzyme.

Thus we have $$K_d = ([S_0] - [SE])([E_0] - [SE])/[SE].$$

This is a simple quadratic equation which yields the concentration of the complex as a simple function of $K_d$, $S_0$ and $E_0$.

$$[SE] = \tfrac{1}{2}(S_0 + E_0 + K_d - \mathrm{Sqrt}((S_0+E_0+K_d)^{**}2 - 4S_0E_0))$$

One can further simplify the equation with the assumption that the substrate concentration is much higher than the complex concentration, i.e. ([$S_0$]>>[SE]). In this case, we simply have $$[SE] = E_0/(1 + K_d/[S_0]).$$

After Photolysis

The central assumption is that the photolysis process is a very rapid process so that the amount of the covalently crosslinked substrate enzyme complex is directly proportional to the amount of the complex in equilibrium, i.e. we are indeed taking just a snap shot of the equilibrium concentrations.

Let α be the conversion efficiency of bound complex to covalently crosslinked complex, The concentration of the covalently crosslinked complex is thus α [SE].

After Pulldown

If the substrate is a biotinylated compound, then a pull down experiment will isolate the covalently captured complex. Let the pulldown efficiency be β. Then the peak area, A of this complex in a Maldi gives a direct measurement concentration of the pulldown complex $$A = \beta * \alpha * E_0/(1 + K_d/[S_0]).$$

Absolute $K_d$ Measurement

From the above equation, one can now obtain a very simple relationship between A and the initial concentration of the substrate:

$$\ln(A) = \ln(\beta) + \ln(\alpha) + \ln(E_0) - \ln(1 + K_d/[S_0]).$$

Further assuming that $K_d$<<[$S_0$], we finally have $$\ln(A) = \ln(\beta) + \ln(\alpha) + \ln(E_0) - K_d/[S_0].$$

Thus by plotting ln(A) vs 1/[$S_0$], we can obtain $K_d$ from the slope of the linear fit.

N.B. External Standard might be needed to normalize the spectra taken from samples with different values of [$S_0$].

$K_d$ Difference Measurement

In the case where the use of external standard is unavailable or undesirable, one can still obtain a measurement of the difference in $K_d$'s. Suppose that there are 2 species of enzymes that are being captured, pulled-down and mass-spected. For a very selective compound, it is reasonable to assume that their photolytic and pulldown efficiencies are also very similar. Let their dissociation constants be $K_d^1$ and $K_d^2$, their initial enzyme concentrations $E_0^1$ and $E_0^2$, their Maldi peak areas $A^1$ and $A^2$ respectively. We have $$\ln(A^1/A^2) = \ln(E_0^1/E_0^2) - (K_d^1 - K_d^2)/[S_0].$$

Thus by plotting the natural log of the relative areas against $1/[S_0]$, the difference in dissociation constants, $(K_d^1 - K_d^2)$ can be determined directly from the slope of the linear fit. The appealing feature of this analysis is that since we are dealing with relative areas, there is no need to normalize the areas from different spectra.

Example 16

Oral Hypoglycemics/Antidiabetics

Thiazolidinediones (Glitazones): Troglitazone (Rezulin™) Rosiglitazone (Avandia™) and Pioglitazone (Actos™)
I. Development and Pharmacology Troglitazone (Rezulin™) was the first thiazolidinedione marketed and was indicated for insulin-resistant patients who are receiving insulin and also as monotherapy. Troglitazone has since been removed from the market due to concerns of hepatic toxicity. However two new "glitazones" have been approved in recent years and these drugs specifically targets insulin resistance. Each of these new glitazone also have side effects.

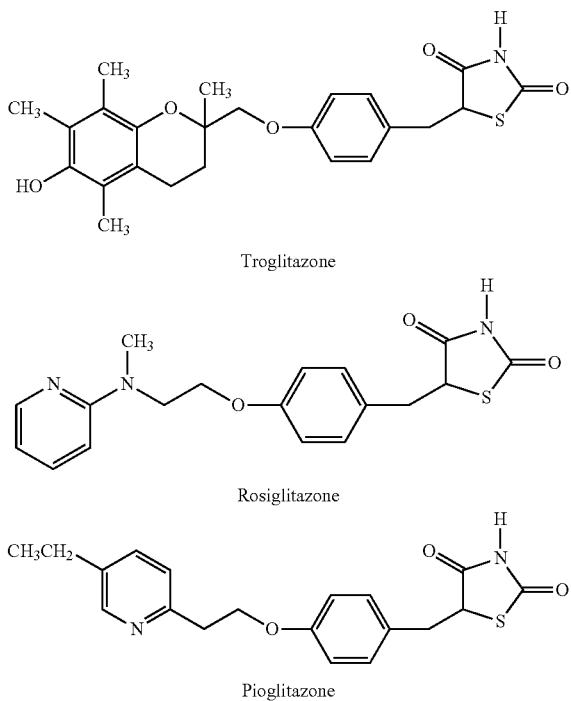

Troglitazone

Rosiglitazone

Pioglitazone

The thiazolidinediones are dependent on the presence of insulin for activity, however, they do NOT affect insulin secretion. The thiazolidinediones are highly selective and potent agonists for the peroxisome proliferator activated receptor (PPAR) gamma that regulates the transcription of a number of insulin responsive genes. PPAR receptors can be found in key target tissues for insulin action such as adipose tissue, skeletal muscle, and liver. Activation of PPAR-gamma receptors regulates the transcription of insulin-responsive genes involved in the control of glucose production, transport, and utilization. For example, stimulation of these receptors may result in increased production of GLUT1 and GLUT 4 receptors. Additionally, PPAR-gamma responsive genes also play a role in the regulation of fatty acid metabolism. Unlike oral sulfonylureas, rosiglitazone enhances tissue sensitivity to insulin rather than stimulates insulin secretion. Also, based on this mechanism, it may take several weeks for these drugs to fully express their activity (and thus to assess their potential).

Preclinical studies indicate that these drugs decrease hepatic glucose output and increase insulin-dependent glucose disposal in skeletal muscle. In animal models of diabetes, these drugs reduce the hyperglycemia, hyperinsulinemia and hypertriglyceridemia characteristic of insulin resistant states such as NIDDM.

II. Adverse Reactions:

Minimal hypoglycemia: Hypoglycemia was observed in relatively few glitazone-treated patients to date. Aggressive insulin dosing in combination with glitazone is associated with further reductions in HbA1c but with an increased risk of hypoglycemia.

In contrast to troglitazone no evidence of drug-induced hepatotoxicity was noted in clinical studies of pioglitazone or rosiglitazone. However, the FDA recommends monitoring hepatic function at the start of glitazones therapy and every two months during the first year of treatment. Patients should also be advised to monitor for signs and symptoms suggestive of hepatic dysfunction such as nausea, vomiting, abdominal pain, fatigue, anorexia, dark urine, or jaundice.

Edema, hypoglycemia, paresthesias, and elevations of creatinine phosphokinase (CPK) have occurred in some pioglitazone-treated patients. Reductions in hemoglobin and hematocrit have also been observed. Glitazone therapy is not recommended for Class III and IV CHF patients and close monitoring of the fluid status of Class I and II patients is necessary.

Glitazone-treated patients may experience weight gains in the range of 1 to 4 kg may occur perhaps improved due to glucose control. The glitazones are reported to produce increases in low-density lipoprotein-cholesterol (LDL-C), high-density lipoprotein-cholesterol (HDL-C), and total cholesterol. LDL-C is increased the least with pioglitazone. The LDL/HDL ratio is preserved, although with rosiglitazone, there is a lag time of several months before HDL-C rises relative to LDL-C. Triglycerides decrease with troglitazone and pioglitazone, whereas the effect with rosiglitazone is variable.

Avandia® and Actos® used to treat Type-II diabetes can cause fluid buildup and heart failure in some patients. U.S. doctors said on Sep. 9, 2003 (Reuters)

Avandia® and Actos® caused heart failure in six male patients with poor heart and kidney function.

studies indicate that the incidence of hypoglycemia may be increased when glitazones are used with a sulfonylurea. Currently there are no controlled published studies on the hypoglycemic effects of troglitazone with the biguanides or alpha-glucosidase inhibitors.

Oral contraceptives: Pioglitazone may induce the metabolism and reduce efficacy of OCs (some controversy over this interaction). Use additional protection or switch to rosiglitazone which does not alter OC clearance.

ToxPro Objectives

Structural classification (i.e. Thiazolidinediones) and subclassification (i.e. generation)

Identify key structural features that contribute to pharmacologic/therapeutic profile and differences in activity within a structural subclass (i.e. Thiazolidinediones)

Detailed understanding of the mechanism of action for each drug/drug class.

Pancreatic and/or extra-pancreatic mechanism(s)?

Insulin dependent or independent action

Compare drugs from different structural classes in terms of mechanism

Relative efficacy within a structural series (i.e. Thiazolidinediones) and across series.

Key disposition factors (protein binding)

Relative onset of action and relationship to mechanism or other factors

Metabolic processes and activity of metabolites (contribution to therapeutic activity)

Elimination profile: Renal and/or non-renal as parent drug and/or metabolites?

Use/cautions in renally or hepatically impaired patients due to non-target protein binding Adverse reactions:

Relative incidence of hypoglycemia and relationship to mechanism of action, duration of action, etc.

Weight gain

GI effects

Effects on renal physiology

Other key agents: i.e. lactic acidosis

Similarities and differences within a series (i.e. Thiazolidinediones) and between structural series in key adverse reactions Significant drug interactions that may compromise efficacy:

Pharmacokinetic-based interactions: Interference with Absorption, Metabolism/Cytochrome-based interactions, Competition for elimination, etc.

Pharmacologic: Use with other drugs with hypoglycemic or hyperglycemic actions.

Similarities and differences within a series (i.e. Thiazolidinediones) and between structural series for key drug interactions.

ToxPro Application

The peroxisome proliferator-activated receptor-γ (PPAR-γ): potential role for insulin resistance and β-cell function. Thiazolidinediones are pharmacological compounds that reduce insulin resistance both in prediabetic as well as diabetic individuals. Thiazolidinediones are ligands of the PPAR-γ2. PPAR-γ2 is predominantly expressed in adipocytes, intestine, and macrophages. There is some evidence that a low level expression might also occur in muscle cells. The PPAR-γ receptor is a transcription factor that controls the expression of numerous genes. It is assumed that the effect of thiazolidinediones on insulin sensitivity is mediated through altered expression of PPAR-γ2-dependent genes.

As discussed above, thiadolidinediones, as antidiabetic drugs, clearly show toxicity and undesirable side effects. Thiazolidinediones (Glitazones): Troglitazone (Rezulin™) Rosiglitazone (Avandia™) and Pioglitazone (Actos™) will be attached to the "Capture Compound (CC)." The CC-Thiazolidinediones will be incubated with kidney, liver, pancreatic, colonic epithelium and muscle cells. Rezulin, Avandia and Actos should capture PPAR-γ, PPAR-α as well as non-target proteins. These three drugs have different metabolism and pharmacokinetics, therefore it is expected that they should capture different non-target proteins. As discussed above, antidiabetic activity of thiazolidinediones is caused by binding to PPAR-γ protein. Structure Activity Relationship (SAR) of thiazolidinediones and crystal structures of and PPAR-α co-crystallized with thiazolidinediones is known in the literature.

The undesired and toxic side effects of thiazolidinediones could be due to its interaction with PPAR-α and non-target proteins. The ToxPro application of CCMS will be used to identify all proteins which bind to each drug, and their respective binding constants. After identifying non-target proteins with CCMS technology, the thiazolidinediones will be chemically re-engineered, through an iterative process, to prevent their binding to PPAR-α and non-target proteins while maintaining the interaction with the target protein PPAR-γ.

Rezulin:

Rezulin is attached to the Capture Compound as depicted below:

Structure I

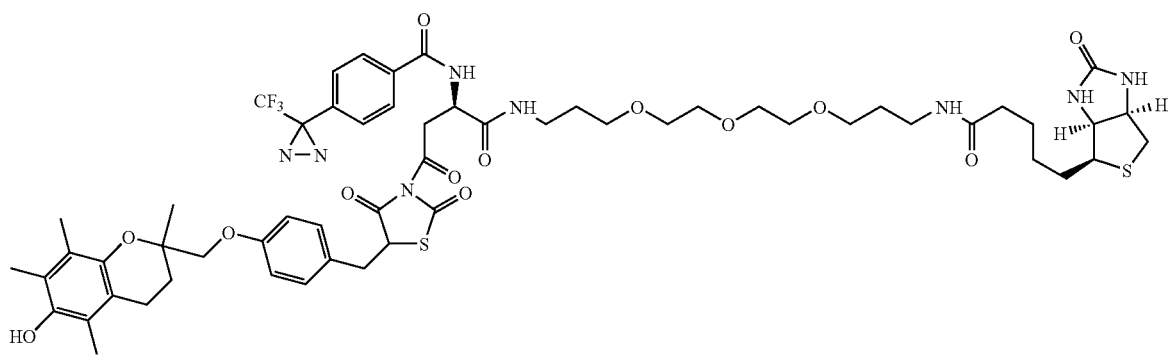

Structure II

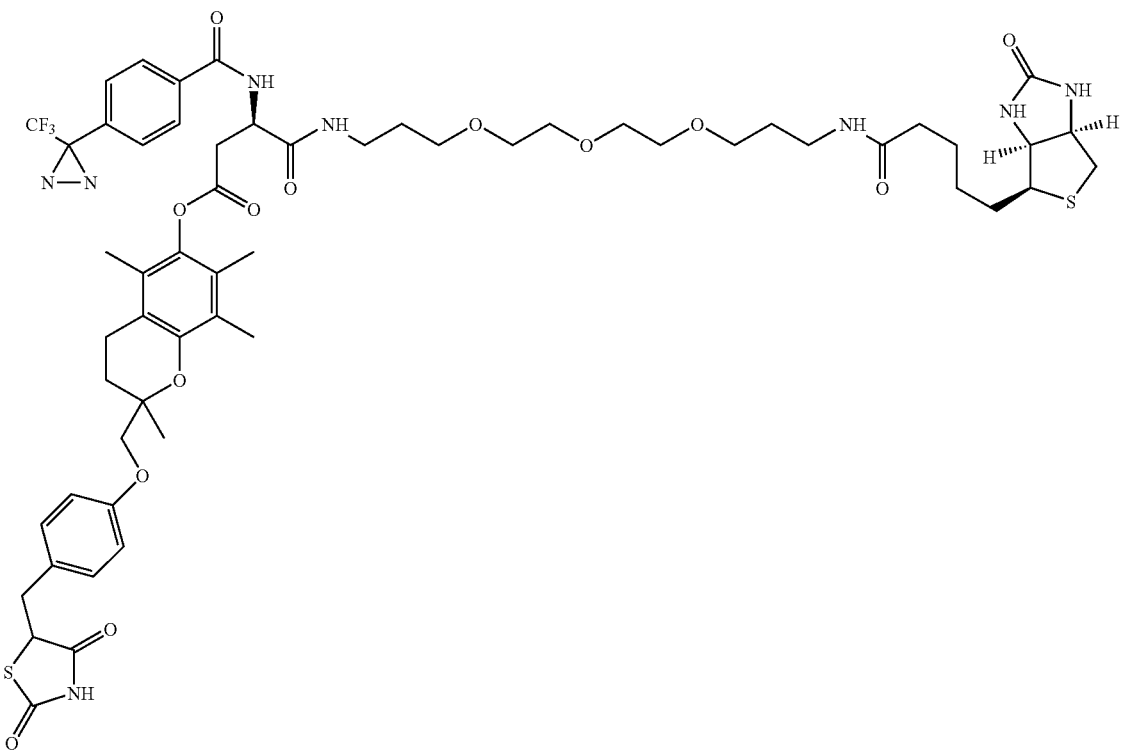

Rezulin is metabolized in the liver to its p-Hydroxy glucose and sulfate complexes. Therefore Structure II is considered.

Rezulin Capture Compound Structures I and II are incubated with kidney, liver, pancreatic, colon epithelium, and muscle cells. The target protein PPAR-γ as well as non-target protein PPAR-α and protein A, B and C are captured.

Avandia and its Metabolite:

Avandia is attached to the capture compound as depicted below:

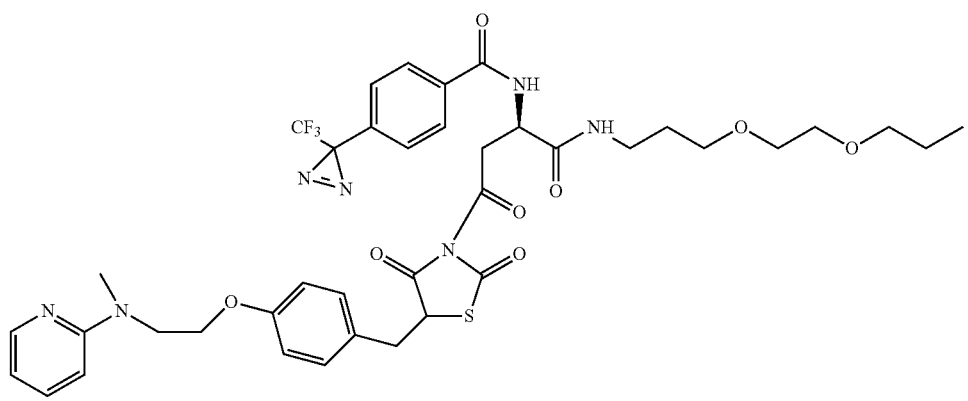

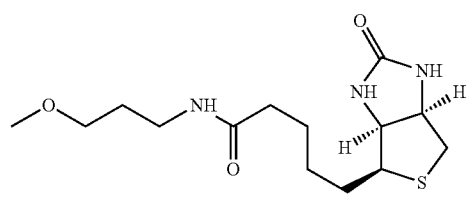

Avandia metabolizes to aromatic hydroxy metabolites. Therefore two possible metabolites are attached to the capture compound as depicted below:
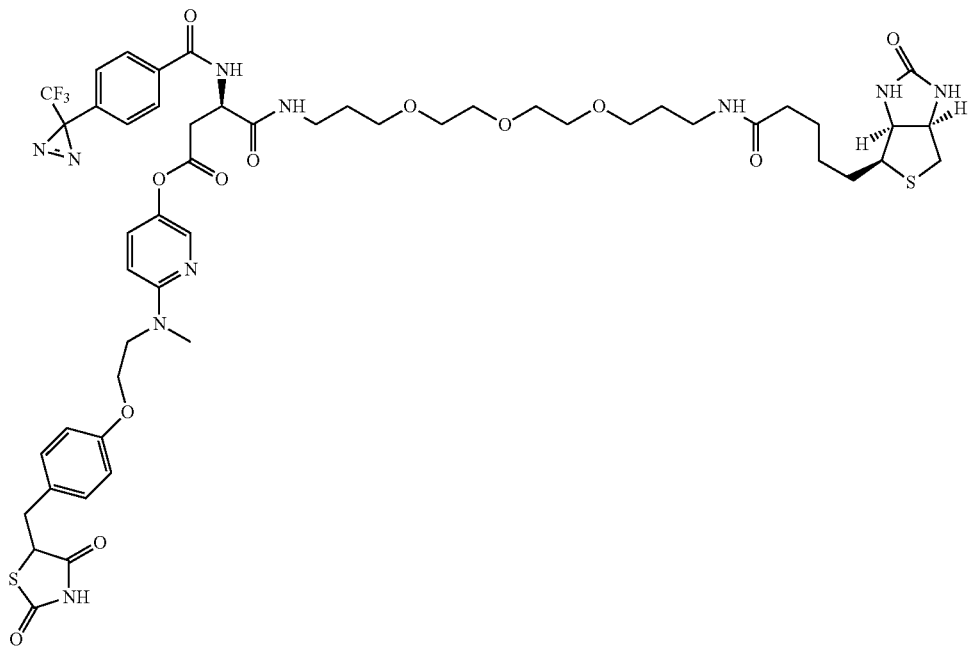
Metabolite -continued
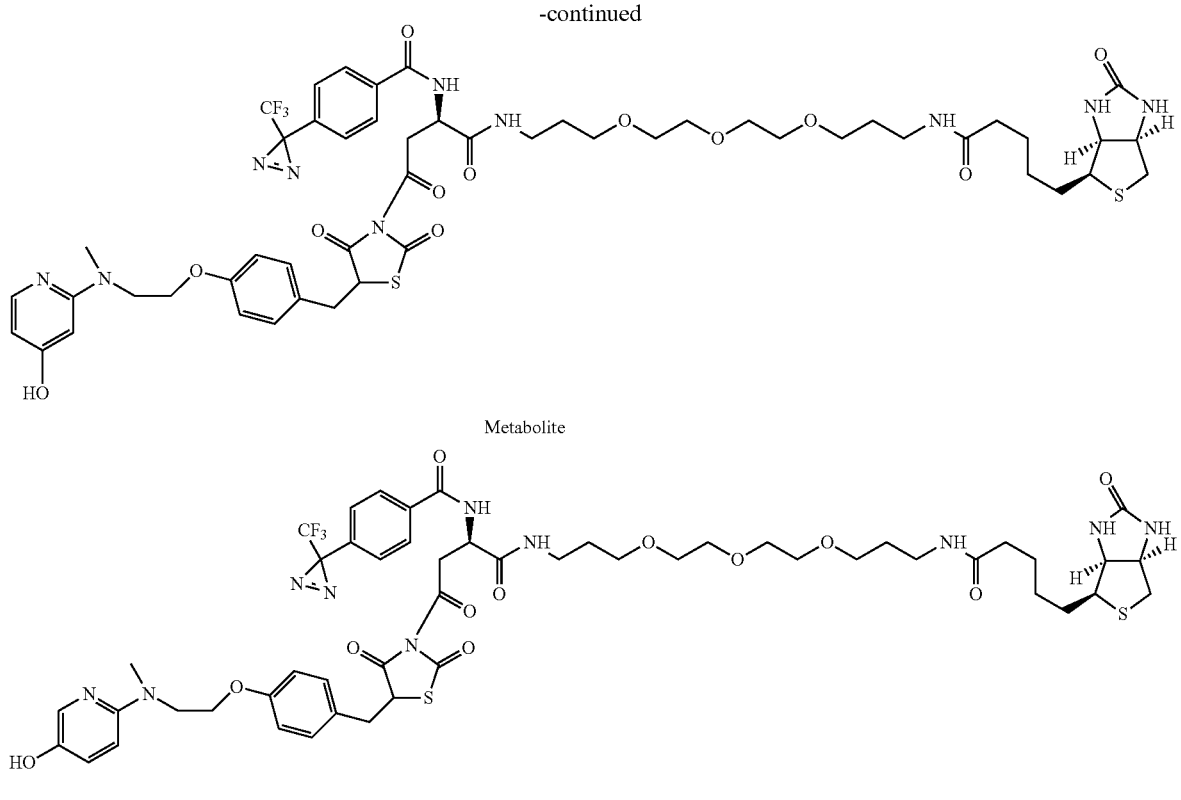
Metabolite
Avandia and its metabolites attached to the Capture Compound are incubated with kidney, liver, pancreatic, colon epithelium, and muscle cells. The target protein PPAR-γ as well as non-target protein PPAR-α and protein A, B and C are captured.
Actos and its Metabolites:
Actos is attached to the Capture Compound as depicted below:
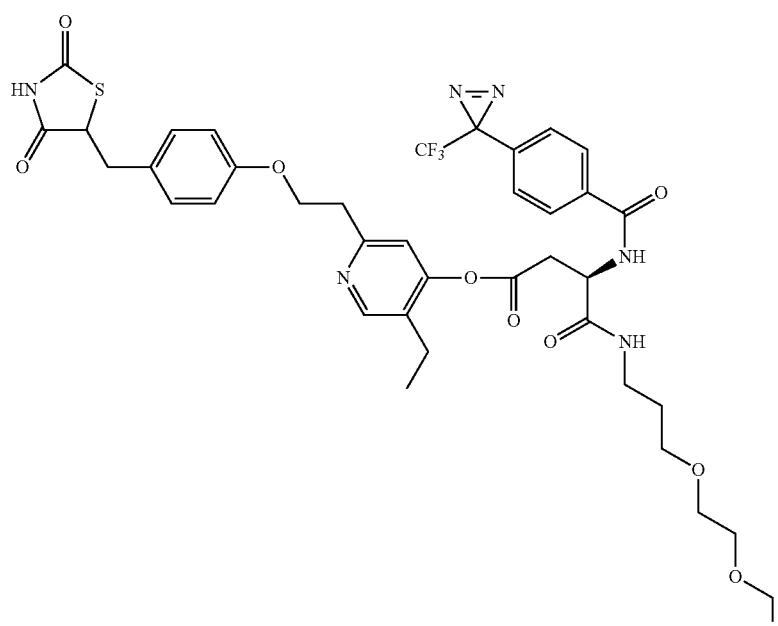

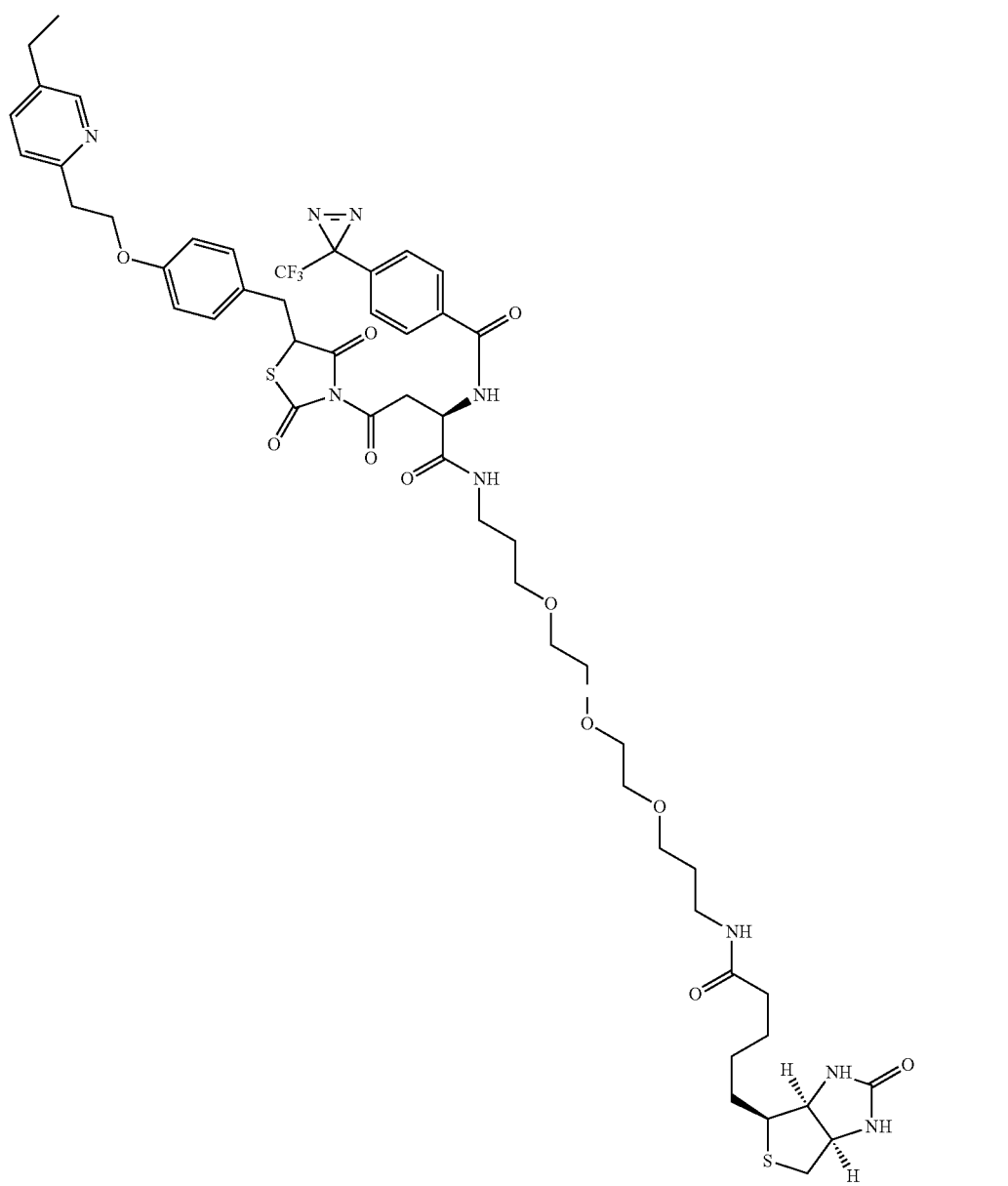 [SMILES: CCc1ccc(CCOc2ccc(CC3SC(=O)N(C(=O)C[C@@H](NC(=O)c4ccc(C5(C(F)(F)F)N=N5)cc4)C(=O)NCCCOCCOCCOCCCNC(=O)CCCC[C@@H]4SC[C@@H]5NC(=O)N[C@@H]54)C3=O)cc2)nc1]

Actos' possible metabolite is attached to the capture compound as depicted below:
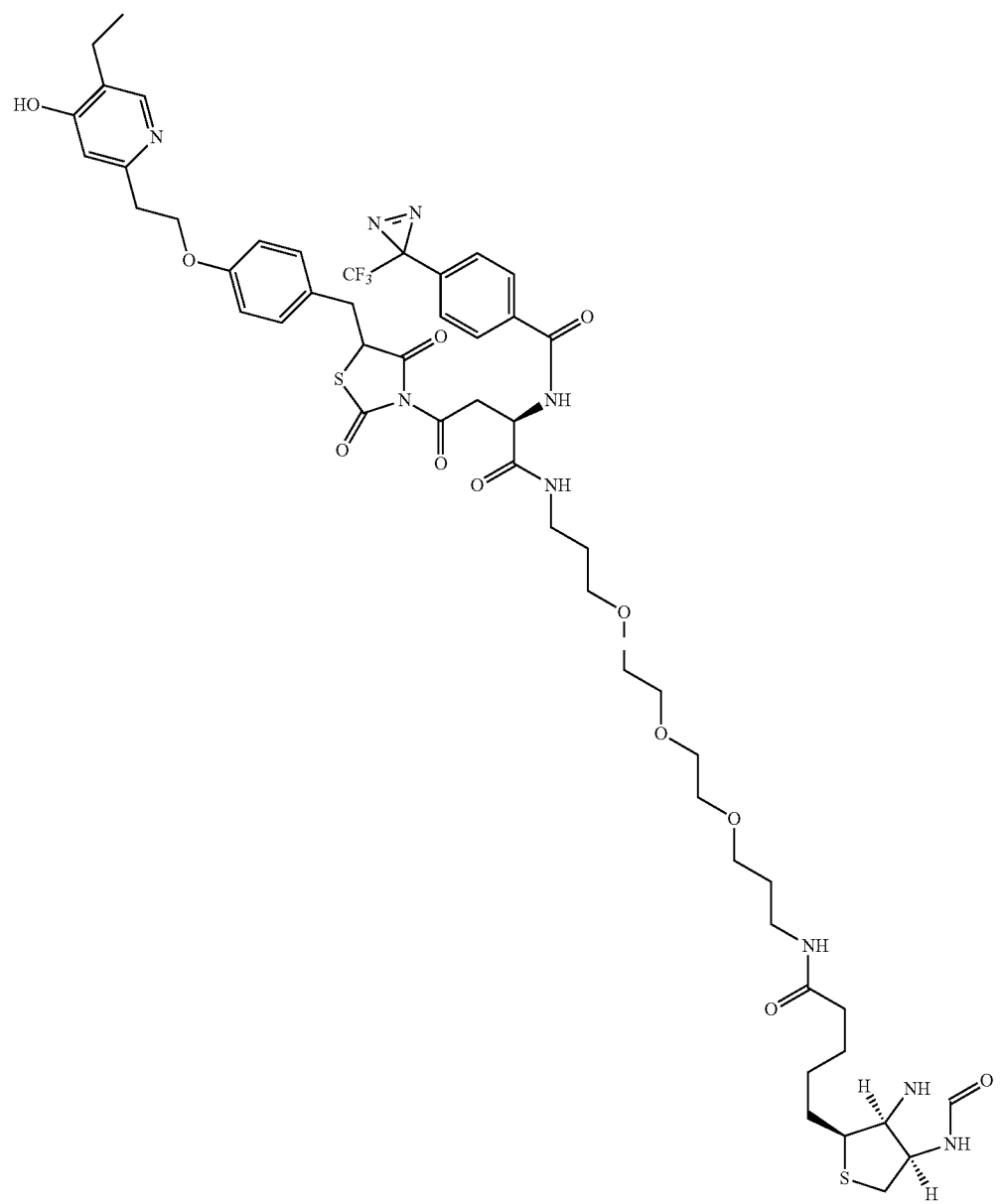 [SMILES: CCc1cnc(CCOc2ccc(CC3SC(=O)N(C(=O)C[C@@H](NC(=O)c4ccc(C5(C(F)(F)F)N=N5)cc4)C(=O)NCCCOCCOCCOCCCNC(=O)CCCC[C@@H]4SC[C@H](NC=O)[C@@H]4N)C3=O)cc2)cc1O]

Actos and its metabolites attached to the Capture Compound are incubated with kidney, liver, pancreatic, colon epithelium, and muscle cells. The target protein PPAR-γ as well as non-target protein PPAR-α and protein A, B and C are captured.

Since modifications will be apparent to those of skill in this art, it is intended that this invention be limited only by the scope of the appended claims.

What is claimed is:

1. A method for assessing interactions of a molecule Y with targets and non-targets, comprising:
   (a) selecting a molecule whose interactions with targets and non-targets are to be assessed, and providing one or more capture compound(s) that present(s) the molecule, wherein:
   the capture compound has the formula:

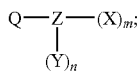

X is a photoactivable group;
   Y is a molecule whose interactions are to be assessed, and wherein Y is a small molecule drug;
   Q is a sorting function for immobilizing or separating the capture compounds;
   Z comprises the formula ML, wherein M is a trivalent moiety that presents each of X, Y and Q, and wherein M comprises an amino acid selected from the group consisting of serine, threonine, lysine, tyrosine, tryptophan, arginine, glutamine, aspartic acid, and cysteine; and wherein L is a bond that is cleavable prior to or during mass spectrometric analysis;
   m is 1; and
   n is 1;
   (b) contacting the capture compound with a cell lysate or tissue containing proteins, wherein contacting is effected under conditions in which X is not activated and for a sufficient time for interaction between the capture compounds and proteins in the cell lysate or tissue to reach equilibrium, whereby Y forms a ligand to target proteins and non-covalently binds to non-target proteins in the cell lysate or tissue;
   (c) exposing the capture compound to light that activates X forming product(s) with a covalent linkage and then immobilizing the product(s) on a solid support via Q therein affecting capture of target(s) and non-target(s) directly bound to Y;
   (d) identifying the captured proteins;
   (e) repeating steps (a)-(d) a plurality of times, wherein each repetition uses a capture compound having the moiety Y linked to the moiety Z in a different orientation via a different point of attachment on the moiety Y; and
   (f) re-designing the moiety Y to eliminate or alter the proteins captured which directly interact with Y as re-designed.

2. The method of claim 1, wherein Q is biotin or an oligonucleotide.

3. The method of claim 1, wherein:
   X is an azide; and
   Q is biotin or an oligonucleotide.

4. The method of claim 3, wherein Y is an enzyme inhibitor.

5. The method of claim 1, wherein Y is an enzyme inhibitor.

6. The method of claim 1, wherein X is

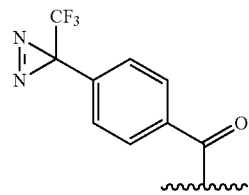 [SMILES: *C(=O)c1ccc(C2(C(F)(F)F)N=N2)cc1]

or an arylazide;
Z is selected from the group consisting of serine, threonine, lysine, tyrosine and cysteine; and
Q is biotin or an oligonucleotide.

7. The method of claim 4, wherein X is

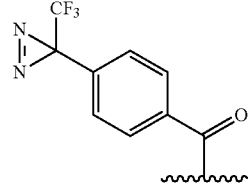 [SMILES: *C(=O)c1ccc(C2(C(F)(F)F)N=N2)cc1]

or an arylazide;
Z is selected from the group consisting of serine, threonine, lysine, tyrosine and cysteine; and
Q is biotin or an oligonucleotide.

8. The method of claim 1, wherein Q is an oligonucleotide.

9. The method of claim 1, wherein X an azide; and Q is biotin.

10. The method of claim 9, wherein Z is selected from the group consisting of among serine, threonine, lysine, tyrosine and cysteine.

11. The method of claim 1, wherein the capture compound comprises a mass modifying tag linked to Z.

12. The method of claim 1, wherein the capture compounds further comprise a solubility group W that influences the solubility properties of the capture compound.

13. The method of claim 1, further comprising identifying or detecting a captured protein by mass spectrometry.

14. The method of claim 1, further comprising identifying a function of a captured protein.

15. The method of claim 1, wherein the cell lysate or tissue is contacted with a plurality of different capture compounds.

16. The method of claim 1, wherein a concentration of capture compound is varied in a plurality of different reactions.

17. The method of claim 13, wherein the mass spectrometry is selected from among matrix assisted laser desorption ionization (MALDI), continuous or pulsed electrospray (ES) ionization, ionspray, thermo spray and massive cluster impact mass spectrometry.

18. The method of claim 17, wherein the mass spectrometry analysis is linear time-of-flight (TOF), reflectron time-of-flight, single quadruple, multiple quadruple, single magnetic sector, multiple magnetic sector, Fourier transform, ion cyclotron resonance (ICR) or ion trap.

19. The method of claim 1, wherein: redesigning the drug results in a second drug with fewer side-effects or an increased therapeutic index compared to the first drug.

20. The method of claim 6 or 7 wherein the arylazide is:

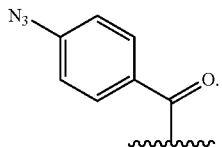 [SMILES: *C(=O)c1ccc(N=[N+]=[N-])cc1]

* * * * *